US011162080B2

(12) United States Patent
Wimmer et al.

(10) Patent No.: US 11,162,080 B2
(45) **Date of Patent: *Nov. 2, 2021**

(54) ATTENUATED VIRUSES USEFUL FOR VACCINES

(71) Applicant: The Research Foundation for The State of University New York, Albany, NY (US)

(72) Inventors: Eckard Wimmer, East Setauket, NY (US); Steve Skiena, Setauket, NY (US); Steffen Mueller, Kings Point, NY (US); Bruce Futcher, Stony Brook, NY (US); Dimitris Papamichail, Newtown, PA (US); John Robert Coleman, Blauvelt, NY (US); Jeronimo Cello, Port Jefferson, NY (US)

(73) Assignee: The Research Foundation for The State University of New York, Albany, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/036,348

(22) Filed: Jul. 16, 2018

(65) Prior Publication Data

US 2019/0010469 A1 Jan. 10, 2019

Related U.S. Application Data

(60) Continuation of application No. 15/258,584, filed on Sep. 7, 2016, now Pat. No. 10,023,845, which is a division of application No. 12/594,173, filed as application No. PCT/US2008/058952 on Mar. 31, 2008, now Pat. No. 9,476,032.

(60) Provisional application No. 60/909,389, filed on Mar. 30, 2007, provisional application No. 61/068,666, filed on Mar. 7, 2008.

(51) Int. Cl.

| | |
|---|---|
| ***C12N 7/00*** | (2006.01) |
| ***A61K 39/12*** | (2006.01) |
| ***A61K 39/13*** | (2006.01) |
| ***A61K 39/145*** | (2006.01) |
| ***C07K 14/005*** | (2006.01) |
| *A61K 39/00* | (2006.01) |

(52) U.S. Cl.

CPC ................ *C12N 7/00* (2013.01); *A61K 39/12* (2013.01); *A61K 39/13* (2013.01); *A61K 39/145* (2013.01); *C07K 14/005* (2013.01); *A61K 2039/5254* (2013.01); *C12N 2720/12361* (2013.01); *C12N 2740/15061* (2013.01); *C12N 2760/16061* (2013.01); *C12N 2760/16121* (2013.01); *C12N 2760/16134* (2013.01); *C12N 2760/16162* (2013.01); *C12N 2770/20061* (2013.01); *C12N 2770/24161* (2013.01); *C12N 2770/32061* (2013.01); *C12N 2770/32621* (2013.01); *C12N 2770/32634* (2013.01); *C12N 2770/32661* (2013.01); *C12N 2770/32662* (2013.01); *C12N 2770/32671* (2013.01); *C12N 2770/32721* (2013.01); *C12N 2770/32761* (2013.01); *C12N 2770/32762* (2013.01); *Y02A 50/30* (2018.01)

(58) Field of Classification Search

None

See application file for complete search history.

(56) References Cited

U.S. PATENT DOCUMENTS

| | | | |
|---|---|---|---|
| 5,993,824 | A | 11/1999 | Murphy et al. |
| 6,171,820 | B1 | 1/2001 | Short |
| 6,410,023 | B1 | 6/2002 | Durbin et al. |
| 6,537,776 | B1 | 3/2003 | Short |
| 6,562,594 | B1 | 5/2003 | Short |
| 6,596,539 | B1 | 7/2003 | Stemmer et al. |
| 6,696,289 | B1 | 2/2004 | Bae et al. |
| 7,585,957 | B2 | 9/2009 | Miller et al. |
| 7,704,491 | B2 | 4/2010 | Collins et al. |
| 7,820,786 | B2 | 10/2010 | Thompson et al. |
| 8,168,771 | B2 | 5/2012 | Ray et al. |
| 9,133,478 | B2 | 9/2015 | Moss et al. |
| 2002/0076415 | A1 | 6/2002 | Ou et al. |
| 2002/0119457 | A1 | 8/2002 | Short et al. |

(Continued)

FOREIGN PATENT DOCUMENTS

| | | | |
|---|---|---|---|
| WO | 1995004147 | A1 | 2/1995 |
| WO | 00/18906 | A1 | 4/2000 |

(Continued)

OTHER PUBLICATIONS

Kamps, B., et al., Influenza Report, (2006) (eds.), Flying Publisher, 225 pgs.

Kaplan, G., et al., "Construction and Characterization of Poliovirus Subgenomic Replicons", J. Virol. (1988), vol. 62, pp. 1687-1696.

Karlin, S., et al., "Why Is Cpg Suppressed In The Genomes Of Virtually Al Small Eukaryotic Viruses But Not In Those Of Large Eukaryotic Viruses?", J. Virol. (1994), vol. 68, pp. 2889-2897.

(Continued)

*Primary Examiner* — Nicole Kinsey White

(74) *Attorney, Agent, or Firm* — Fox Rothschild LLP

(57) ABSTRACT

This invention provides an attenuated virus which comprises a modified viral genome containing nucleotide substitutions engineered in multiple locations in the genome, wherein the substitutions introduce synonymous deoptimized codons into the genome. The instant attenuated virus may be used in a vaccine composition for inducing a protective immune response in a subject. The invention also provides a method of synthesizing the instant attenuated virus. Further, this invention further provides a method for preventing a subject from becoming afflicted with a virus-associated disease comprising administering to the subject a prophylactically effective dose of a vaccine composition comprising the instant attenuated virus.

6 Claims, 18 Drawing Sheets

Specification includes a Sequence Listing.

(56) References Cited

U.S. PATENT DOCUMENTS

| | | | |
|---|---|---|---|
| 2002/0137720 | A1 | 9/2002 | Ertl et al. |
| 2002/0142394 | A1 | 10/2002 | Short |
| 2003/0041354 | A1 | 2/2003 | Kjaerulff et al. |
| 2004/0023327 | A1 | 2/2004 | Short et al. |
| 2004/0097439 | A9 | 5/2004 | Nicolas et al. |
| 2004/0209241 | A1 | 10/2004 | Hermanson et al. |
| 2005/0100985 | A1 | 5/2005 | Short |
| 2005/0124010 | A1 | 6/2005 | Short et al. |
| 2006/0019301 | A1 | 1/2006 | Hansen et al. |
| 2007/0253978 | A1 | 11/2007 | Niman |
| 2008/0118530 | A1 | 5/2008 | Kew et al. |
| 2008/0274130 | A1 | 11/2008 | Rupprecht et al. |
| 2009/0136995 | A1 | 5/2009 | Nielsen et al. |
| 2009/0325244 | A1 | 12/2009 | Herold et al. |
| 2010/0041107 | A1 | 2/2010 | Herold et al. |
| 2010/0279346 | A1 | 11/2010 | Bodie et al. |
| 2018/0104326 | A1 | 4/2018 | Whitehead et al. |
| 2018/0273911 | A1 | 9/2018 | Tuller et al. |
| 2020/0123573 | A1 | 4/2020 | Kamrud et al. |
| 2021/0147832 | A1 | 5/2021 | Bloom et al. |

FOREIGN PATENT DOCUMENTS

| | | | | |
|---|---|---|---|---|
| WO | 00/53744 | A1 | 9/2000 | |
| WO | 00/58517 | A1 | 10/2000 | |
| WO | 2002008435 | A1 | 1/2002 | |
| WO | 2002032947 | A1 | 4/2002 | |
| WO | 2002/095363 | A2 | 11/2002 | |
| WO | 2005024012 | A1 | 3/2005 | |
| WO | 2006/042156 | A2 | 4/2006 | |
| WO | WO-2006042156 | A2 * | 4/2006 | ............. A61K 39/00 |
| WO | 2009049350 | A1 | 4/2009 | |

OTHER PUBLICATIONS

Kew, O., et al., "Outbreak of Poliomyelitis in Hispaniola Associated With Circulating Type 1 Vaccine-Derived Poliovirus", Science (2002) vol. 296, pp. 356-359.
Kilbourne, E.D., "Influenza pandemics of the 20th century", Emerg. Infect. Dis. (2006), vol. 12, pp. 9-14.
Koike, S., et al., "Transgenic Mice Susceptible To Poliovirus", Proc. Natl. Acad. Sci. (1991), vol. 88, pp. 951-955.
Ledford, R.M., et al., "VP1 Sequencing of All Human Rhinovirus Serotypes: Insights Into Genus Phylogeny And Susceptibility To Antiviral Capsid-Binding Compounds", J. Virol. (2004), vol. 78, pp. 3663-3674.
Molla, A., et al., "Cell-Free, De Novo Synthesis of Poliovirus", Science (1991), vol. 254, pp. 1647-1651.
Mueller, S., et al., "Poliovirus and poliomyelitis: a tale of guts, brains, and an accidental event" Virus Res. (2005), vol. 111, pp. 175-193.
Murdin, A., et al., "Construction of a poliovirus type 1/type 2 antigenic hybrid by manipulation of neutralization antigenic site II", J. Virol. (1989), vol. 63, pp. 5251-5257.
Neumann, G., et al., "Generation of Influenza A Viruses Entirely From Clone Cdnas", Proc. Natl. Acad. Sci., (1996); vol. 96, pp. 9345-9350.
Neznanov, N., et al., "Proteolytic Cleavage of The P65-Rela Subunit Of NF-Kappab During Poliovirus Infection", J. Biol. Chem. (2005), vol. 280, pp. 24153-24158.
Pfister, T., et al., "Characterization Of The Nucleoside Triphosphatase Activity Of Poliovirus Protein 2C Reveals A Mechanism By Which Guanidine Inhibits Poliovirus Replication", J. Biol. Chem. (1999), vol. 274, pp. 6992-7001.
Plotkin, J., et al., "Tissue-Specific Codon Usage and the Expression Of Human Genes", Proc. Natl. Acad. Sci. (2004), vol. 101, pp. 12588-12591.
Racaniello, V., et al., "Cloned Poliovirus Complementary DNA Is Infectious In Mammalian Cells", Science (1981), vol. 214, pp. 916-919.
Richardson, S., et al., "Genedesign: Rapid, Automated Design of Multikilobase Synthetic Genes", Genome Res. (2006), vol. 16, pp. 550-556.
Robinson, M., "Codon Usage Can Affect Efficiency Of Translation Of Genes In *Escherichia Coli.*", Nucl. Acids Res. (2006), vol. 12, pp. 6663-6671.
Sánchez, G., et al., "Genome Variability and Capsid Structural Constraints of Hepatitis A Virus", J. Virol. (2003), vol.77, pp. 452-459.
Shimizu, H., et al., "Circulation of Type 1 Vaccine-Derived Poliovirus in the Philippines In 2001", J. Virol. (2004), vol. 78, pp. 13512-13521.
Simonsen, L., "Impact Of Influenza Vaccination on Seasonal Mortality In The US Elderly Population", Arch. Intern. Med. (2005), vol. 165, pp. 265-272.
Skiena, S. "Designing Better Phages" Bioinformatics (2001), vol. 17 Suppl 1, pp. 5253-5261.
Stephenson, I., et al., "Influenza: Current Threat from Avian Influenza", Br. Med. Bull. (2005), vol. 75-76, pp. 63-80.
Talon, J., et al., "Influenza A And B Viruses Expressing Altered NS1 Proteins: A Vaccine Approach", Proc. Natl. Acad. Sci. (2000), vol. 97, pp. 4309-4314.
Thompson, W. et al., "Mortality associated with influenza and respiratory syncytial virus in the United States", JAMA. (2003), vol. 289, pp. 179-186.
Tolskaya, E., et al., "Apoptosis-Inducing and Apoptosis-Preventing Functions of Poliovirus", J. Virol. (1995), vol. 69, pp. 1181-1189.
Toyoda, H., et al., "Oncolytic Treatment and Cure of Neuroblastoma By A Novel Attenuated Poliovirus In A Novel Poliovirus-Susceptible Animal Model" Cancer Res. (2007), vol. 67, pp. 2857-2864.
Van Der Wert, S., et al., "Synthesis of infectious poliovirus RNA by purified T7 RNA polymerase", Proc. Natl. Acad. Sci. (1986), vol. 78, pp. 2330-2334.
Wahby, A., "Combined Cell Culture Enzyme-Linked Immunosorbent Assay for Quantification Of Poliovirus Neutralization-Relevant Antibodies", Clin. Diagn. Lab. Immunol. (2000) vol. 7, pp. 915-919.
Wang, B., et al., Two Proteins for the Price of One: The Design of Maximally Compressed Coding Sequences Natural Computing. Eleventh International Meeting on DNA Based Computers (DNA11), 2005. Lecture Notes in Computer Science (LNCS), (2006) vol. 3892, pp. 387-398.
Wimmer, E., et al., "Synthetic Viruses: A New Opportunity to Understand and Prevent Viral Disease", Nat. Biotech. (2009), vol. 27:12, pp. 1163-1172.
Zhao, W.D., et al, "Genetic Analysis of A Poliovirus/Hepatitis C Virus Chimera: New Structure For Domain II Of The Internal Ribosomal Entry Site Of Hepatitis C Virus", J. Virol. (2001) vol. 75, pp. 3719-3730.
Zhou, J., et al., "Papillomavirus Capsid Protein Expression Level Depends On The Match Between Codon Usage And Trna Availability", J. Virol. (1999), vol. 73, pp. 4972-4982.
Zhou, T. et al., "Analysis of Synonymous Codon Usage in H5N1 Virus and Other Influensa A Viruses", Biosystems (2005), vol. 81:1, pp. 77-86.
Zolotukhin, S., et al., "A "Humanized" Green Fluorescent Protein Cdna Adapted For High-Level Expression In Mammalian Cells", J. Virol., (1996), vol. 70, pp. 4646-4654.
Mueller, S. et al., "Reduction of the Rate of Poliovirus Protein Synthesis through Large-Scale Codon Deoptimization Causes Attenuation of Viral Virulence by lowering Specific Infectivity", Journal of Virology, (2006); vol. 80:19; pp. 9687-9696.
Burns, et al. "Modulation of Poliovirus Replicative Fitness in HeLa Cells by Deoptimization of Synonymous Codon Usage in the Capsid Region"; J. Virol. (2006); vol. 80:7; pp. 3259-3272.
Lavner, Y et al., "Codon Bias as a Factor in Regulating Expression via Translation Rate in the Human Genome", Gene (2005), vol. 345, pp. 127-138.
Cheng, L. et al., "Absence of Effect of Varying Thr-Leu Codon Pairs on Protein Synthesis in a T7 System", Biochem (2001), vol. 40, pp. 6102-6106.

(56) References Cited

OTHER PUBLICATIONS

Cohen, B. et al., "Natural Selection and Algorithmic Design of mRNA", B JCB (2003), vol. 10, pp. 3-4.
Doma, M. et al., "Endonucleolytic Cleave of Euraryotic mRNAs with Stalls and Translation Elongation", Nature (2006), vol. 440, pp. 561-564.
Garcia-Sastre, A. et al., "Genetic Manipulation of Negative-Strand RNA Virus Genomes", Annu. Rev. Microbio. (1993), vol. 47, pp. 765-790.
Greve, J. et al., "The Major Human Rhinovirus Receptor is ICAM-1", Cell (1989), vol. 56, pp. 839-847.
Gustafsson, C. et al., "Codon Bias and Heterologous Protein Expression", Trends in Biotechnology (2004), vol. 22:7, pp. 346-353.
Johansen, L. et al., "The RNA Encompassing the Internal Ribosome Entry in the Poliovirus 5' Nontranslated Region Enhances the Encapsidation of Genomic RNA", Virology (2000), vol. 273, pp. 391-399.
Luytjes, W. et al., "Amplification, Expression, and Packaging of a Foreign Gene by Influenza Virus", Cell (1989), vol. 59, pp. 1107-1113.
Mcknight, K., "The Human Rhinovirus Internal Cis-acting replication element (cre) Exhibits Disparate Properties among Stereotypes", Arch Virol. (2003), vol. 148, pp. 2397-2418.
Palease, P. et al., Orthomyxoviridae: The Viruses and Their Replication, Ch. 47, pp. 1647-1689 in Fields Virology (2007), vol. 2, 5th Edition, David M. Knipe, PHD, Editor-In-Chief, Wolters Kluwer, publisher, Philadelphia, USA.
Park, S. et al., "Advances in Computational Protein Design", COSB (2004), vol. 14, pp. 487-494.
Paul, A. et al., "Internal Ribosomal Entry Site Scanning of the Poliovirus Polyprotein: Implications for Proteolytic Processing", Virology (1998), vol. 250, 241-253.
Pelletier, J. et al., "Internal Intiiation of Translation of Eukaryotic mRNA Directed by a Sequence Derived from Poliovirus RNA", Nature (1988), vol. 334, pp. 320-325.
Rueckert, R.R., "Picornaviruses and Their Replication", Ch. 32, pp. 705-738, in Virology (1985), Bernard N. Fields, M.D., Editor-In-Chief, Raven Press, publisher, New York, USA.
Russell, C. et al., "The Genesis of a Pandemic Influenza Virus", Cell (2005), pp. 368-371.
Savolainen, C. et al., "Human Rhinoviruses", PRR (2003), vol. 4, pp. 91-98.
Tian, J. et al., "Accurate Muntiplex Gene Synthesis from Programmable DNA Microchips", Nature (2004), vol. 432, pp. 1050-1054.
Ansardi, D., et al., "Complementation Of A Poliovirus Defective Genome By A Recombinant Vaccinia Virus Which Provides Poliovirus P1 Capsid Precursor In Trans", J. Virol. (2003), vol. 67:6, pp. 3684-3690.
Belov, G. et al., "The Major Apoptotic Pathway Activated And Suppressed By Poliovirus", J. Virol. (2003), vol. 771, pp. 45-56.
Buchan, J. et al., "tRNA Properties Help Shape Codon Pair Preferences In Open Reading Frames", Nucl. Acids Res. (2006), vol. 34:3, pp. 1015-1027.
Cao, X. et al., "Replication Of Poliovirus RNA Containing Two Vpg Coding Sequences Leads To A Specific Deletion Event", J Virol. (1993), vol. 67:9, pp. 5572-5578.
Carlini, D. et al., "In Vivo Introduction of Unpreferred Synonymous Codons Into The *Drosophila* Adh Gene Results In Reduced Levels Of ADH Protein", Genetics (2003), vol. 163, pp. 239-243.
Cello, J. et al., "Chemical Synthesis of Poliovirus Cdna: Generation Of Infectious Virus In The Absence Of Natural Template", Science (2002), vol. 297, pp. 1016-1018.
Coleman, J.R. et al., "Synthetic Construct Capsid Protein P1-Min Gene, Partial Cds", (2007), retrived from EBI accession No. EM_SY: EU095953; Database accession No. EU095953.
Coleman, J.R. et al., "Virus Attenuation by Genome-Scale Changes In Condon Pair Bias", Sceicne (2008), vol. 320, pp. 1784-1787.
Corpet, F., "Multiple Sequence Alignment with Hierarchical Clustering", Nucl. Acids Res. (1988), vol. 16:22, pp. 10881-10890.
Crotty, S., et al., "RNA Virus Error Catastrophe: Direct Molecular Test By Using Ribavirin", Proc. Natl. Acad. Sci. U.S.A. (2001), vol. 98:12, pp. 6895-6900.
Curran, J., et al., "Selection of aminoacyl-tRNAs at sense codons: the size of the tRNA variable loop determines whether the immediate 3' nucleotide to the coder has a context effect", Nucl. Acids Res. (1995), vol. 23:20, pp. 4104-4108.
Dove, A., et al., "Cold-Adapted Poliovirus Mutants Bypass A Postentry Replication Block", J. Virol. (1997), vol. 71:6, pp. 4728-4735.
Enami, M. et al., "Introduction of Site-Specific Mutations into the Genome of Influenza Virus", Proc. Natl. Acad. Sci. U.S.A. (1990), vol. 87, pp. 3802-3805.
Farabaugh, P.J. Programmed Translational Frameshifting, Microbiol Rev. (1996), vol. 60:1, pp. 103-134.
Fedorov, A. et al., "Regularities of Context-Dependent Codon Bias in Eukaryotic Genes", Nucl. Acids Res. (2002), vol. 30:5, pp. 1192-1197.
Fodor, E. et al., "Rescue of Influenza a Virus From Recombinant DNA", J Virol. (1999), vol. 73:11, pp. 9679-9682.
Georgescu, M. et al., "Evolution of the Sabin Type 1 Poliovirus in Humans: Characterization of Strains Isolated From Patients with Vaccine-Associated Paralytic Poliomyelitis", J. Virol. (1997), vol. 71:10, pp. 7758-7768.
Gerber, K. et al., "Biochemical and Genetic Studies of the Initiation of Human Rhinovirus 2 RNA Replication: Identification of A Cis-Replicating Element in the Coding Sequence of 2Apro", J. Virol. (2001), vol. 75:22, pp. 10979-10990.
Girard, S. et al., "Poliovirus Induces Apoptosis in the Mouse Central Nervous System", J. Virol. (1999), vol. 73:7, pp. 6066-6072.
Goodfellow, I. et al., "Identification of A Cis-Acting Replication Element Within the Poliovirus Coding Region", J. Virol. (2000), vol. 74:10, pp. 4590-4600.
Gu, W. et al., "Analysis of Synonymous Codon Usage in SARS Coronavirus and other viruses in the Nidovirales", Virus Research (2004), vol. 101, pp. 155-161.
Gutman, G.A., et al, "Nonrandom Utilization of Codon Pairs in *Escherichia coli*", Proc. Natl. Acad. Sci. U. S. A. (1989), vol. 86, pp. 3699-3703.
He, Y. et al., "Interaction of the Poliovirus Receptor with Poliovirus", Proc. Natl. Acad. Sci. USA (2000), vol. 97:1, pp. 79-84.
Herold, J. et al., "Poliovirus Requires A Precise 5' End for Efficient Positive-Strand RNA Synthesis", J. Virol. (2001), vol. 74:14, vol. pp. 6394-6400.
Hoekema, A., et al., "Codon Replacement In The PGK1 Gene Of Saccharomyces Cerevisiae: Experimental Approach To Study The Role Of Biased Codon Usage In Gene Expression", Mol. Cell. Biol. (1987), vol. 7:8, pp. 2914-2924.
Hofer, F. et al., "Members of the Low Density Lipoprotein Receptor Family Mediate Cell Entry of a Minor-Group Common Cold Virus", Proc. Natl. Acad. Sci. U.S.A. (1994), vol. 91, pp. 1839-1842.
Hoffmann, E et al., "A DNA transfection system for generation of influenza: A virus from eight plasmids", Proc. Natl. Acad. Sci. U.S.A. (2000), vol. 97:11, pp. 6108-6113.
Hogle, J. M. "Poliovirus Cell Entry: Common Structural Themes in Viral Cell Entry Pathways", Annu. Rev. Microbiol. (2002), vol. 56, pp. 677-702.
Holland, J.J. et al. "Mutation Frequencies at Defined Single Codon Sites in Vesicular Stomatitis Virus And Poliovirus Can Be Increased Only Slightly By Chemical Mutagenesis", J. Virol. (1990), vol. 64:8, pp. 3960-3962.
Hsiao, L. L, "A Compendium of Gene Expression In Normal Human Tissues", Physiol. Genomics (2001), vol. 7, pp. 97-104.
Irwin, B., et al., "Codon Pair Utilization Biases Influence Translational Elongation Step Times" J. Biol Chem. (1995) vol. 270, pp. 22801-22806.
Jang, S., et al., "Initiation of Protein Synthesis by Internal Entry of Ribosomes into the 5' Nontranslated Region of Encephalomyocarditis Virus RNA In Vivo", J. Virol. (1989), vol. 63, pp. 1651-1660.

(56) References Cited

OTHER PUBLICATIONS

Jayaraj, S., et al., "GeMS: an advanced software package for designing synthetic genes", Nucl. Acids Res. (2005), vol. 33, pp. 3011-3016.

* cited by examiner

FIG. 4A
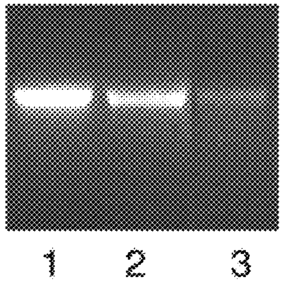
FIG. 4B
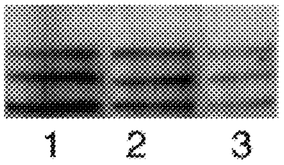
FIG. 4C
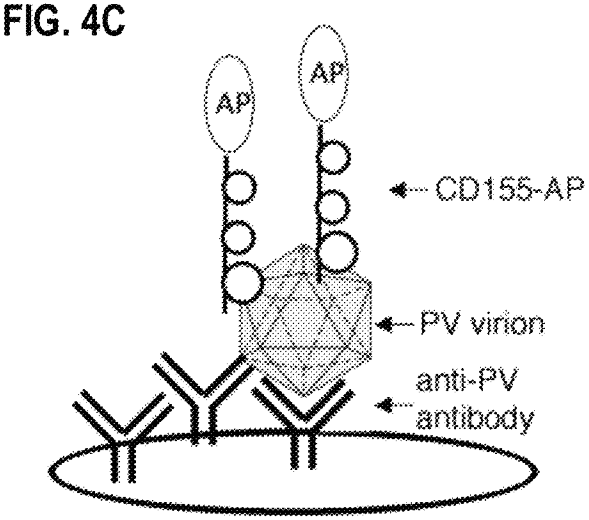
FIG. 4D
| virus | PFU(FFU) | virus particles ($OD_{260nm}$) | virus particles (ELISA) | PFU(FFU)/ particle ratio |
|---|---|---|---|---|
| PV(M) | $3.4 \times 10^{10}$ | $4.24 \times 10^{12}$ | $3.6 \times 10^{12}$ | 1/115 |
| PV-AB$^{755-1513}$ | $9.4 \times 10^{8}$ | $3.17 \times 10^{12}$ | $2.1 \times 10^{12}$ | 1/2803 |
| PV-AB$^{2470-2954}$ | $1.04 \times 10^{7}$ | $1.54 \times 10^{12}$ | $6.5 \times 10^{11}$ | 1/105000 |
FIG. 4E
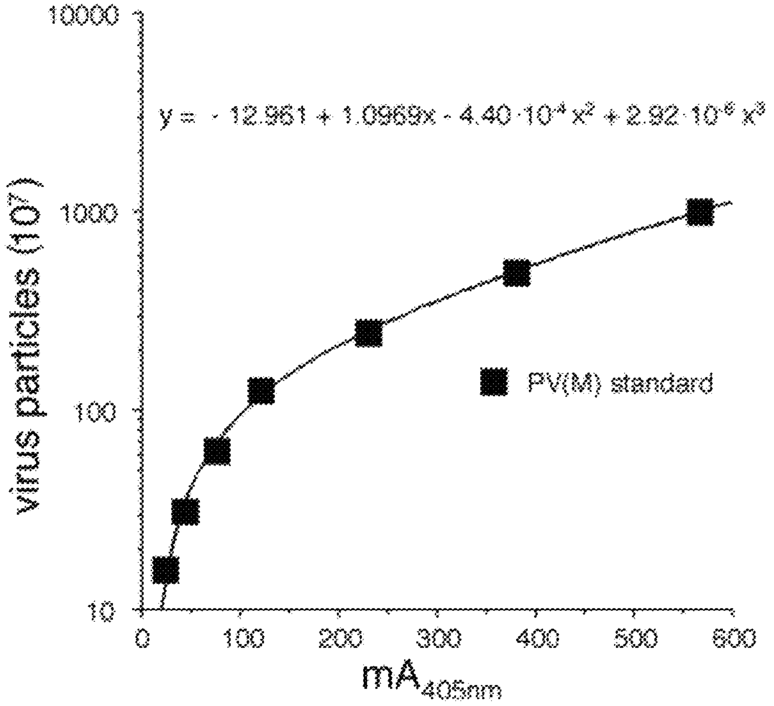
FIGS. 4A-E

| Virus | Titer PFU/ml | PFU/ Particle Ratio |
|---|---|---|
| PV(M) | $1.2 \times 10^9$ | 1/115 |
| PV-AB $^{755-1513}$ | $6.7 \times 10^7$ | 1/2803 |
| PV-AB$^{2470-2954}$ | $3 \times 10^6$ | 1/105000 |
| PV-Min$^{755-2470}$ | $2.4 \times 10^6$ | 1/71000 |
| PV-Min$^{2470-3386}$ | $1.8 \times 10^6$ | 1/17500 |
| PV-Max | $2.3 \times 10^9$ | N/D |

FIG. 18A  Reduced pathogenicity A/PR8-NP$^{Min}$ in BALB/c mice

FIG. 18B  Survival of A/PR8-NP$^{Min}$ infected mice

FIG. 18C  Protection after a lethal wt challenge of A/PR8-NP$^{Min}$ vaccinated mice

FIGS. 18A-C

ATTENUATED VIRUSES USEFUL FOR VACCINES

CROSS REFERENCE TO RELATED APPLICATIONS

This application is continuation of U.S. application Ser. No. 15/258,584, filed Sep. 7, 2016, now U.S. patent Ser. No. 10/023,845, issuing Jul. 17, 2018, which is a divisional of U.S. application Ser. No. 12/594,173, filed Mar. 29, 2010, now U.S. Pat. No. 9,476,032, issued Oct. 25, 2016, which is the national phase application of International application number PCT/US2008/058952, filed Mar. 31, 2008, which claims the benefit of priority to U.S. Application No. 60/909,389, filed Mar. 30, 2007, and U.S. Application No. 61/068,666, filed Mar. 7, 2008, which are incorporated herein by reference in their entireties.

TABLES

The patent contains table(s) that have been included at the end of the specification.

FEDERAL FUNDING

This invention was made with government support under Grant Nos. AI15122 and T32-CA009176 awarded by the National Institutes of Health, and EIA0325123 awarded by the National Science Foundation. The government has certain rights in the invention.

COPYRIGHT NOTICE

A portion of the disclosure of this patent document contains material which is subject to copyright protection. The copyright owner has no objection to the facsimile reproduction by anyone of the patent document or patent disclosure as it appears in the Patent and Trademark Office patent file or records, but otherwise reserves all copyright rights whatsoever.

FIELD OF THE INVENTION

The present invention relates to the creation of an attenuated virus comprising a modified viral genome containing a plurality of nucleotide substitutions. The nucleotide substitutions result in the exchange of codons for other synonymous codons and/or codon rearrangement and variation of codon pair bias.

BACKGROUND OF THE INVENTION

Rapid improvements in DNA synthesis technology promise to revolutionize traditional methods employed in virology. One of the approaches traditionally used to eliminate the functions of different regions of the viral genome makes extensive but laborious use of site-directed mutagenesis to explore the impact of small sequence variations in the genomes of virus strains. However, viral genomes, especially of RNA viruses, are relatively short, often less than 10,000 bases long, making them amenable to whole genome synthesis using currently available technology. Recently developed microfluidic chip-based technologies can perform de novo synthesis of new genomes designed to specification for only a few hundred dollars each. This permits the generation of entirely novel coding sequences or the modulation of existing sequences to a degree practically impossible with traditional cloning methods.

Such freedom of design provides tremendous power to perform large-scale redesign of DNA/RNA coding sequences to: (1) study the impact of changes in parameters such as codon bias, codon-pair bias, and RNA secondary structure on viral translation and replication efficiency; (2) perform efficient full genome scans for unknown regulatory elements and other signals necessary for successful viral reproduction; and (3) develop new biotechnologies for genetic engineering of viral strains and design of anti-viral vaccines.

As a result of the degeneracy of the genetic code, all but two amino acids in the protein coding sequence can be encoded by more than one codon. The frequencies with which such synonymous codons are used are unequal and have coevolved with the cell's translation machinery to avoid excessive use of suboptimal codons that often correspond to rare or otherwise disadvantaged tRNAs (Gustafsson et al., 2004). This results in a phenomenon termed "synonymous codon bias," which varies greatly between evolutionarily distant species and possibly even between different tissues in the same species (Plotkin et al., 2004).

Codon optimization by recombinant methods (that is, to bring a gene's synonymous codon use into correspondence with the host cell's codon bias) has been widely used to improve cross-species expression (see, e.g., Gustafsson et al., 2004). Though the opposite objective of reducing expression by intentional introduction of suboptimal synonymous codons has not been extensively investigated, isolated reports indicate that replacement of natural codons by rare codons can reduce the level of gene expression in different organisms. See, e.g., Robinson et al., 1984; Hoekema et al., 1987; Carlini and Stephan, 2003; Zhou et al., 1999. Accordingly, the introduction of deoptimized synonymous codons into a viral genome may adversely affect protein translation and thereby provide a method for producing attenuated viruses that would be useful for making vaccines against viral diseases.

Viral Disease and Vaccines

Viruses have always been one of the main causes of death and disease in man. Unlike bacterial diseases, viral diseases are not susceptible to antibiotics and are thus difficult to treat. Accordingly, vaccination has been humankind's main and most robust defense against viruses. Today, some of the oldest and most serious viral diseases such as smallpox and poliomyelitis (polio) have been eradicated (or nearly so) by world-wide programs of immunization. However, many other old viruses such as rhinovirus and influenza virus are poorly controlled, and still create substantial problems, though these problems vary from year to year and country to country. In addition, new viruses, such as Human Immunodeficiency Virus (HIV) and Severe Acute Respiratory Syndrome (SARS) virus, regularly appear in human populations and often cause deadly pandemics. There is also potential for lethal man-made or man-altered viruses for intentional introduction as a means of warfare or terrorism.

Effective manufacture of vaccines remains an unpredictable undertaking. There are three major kinds of vaccines: subunit vaccines, inactivated (killed) vaccines, and attenuated live vaccines. For a subunit vaccine, one or several proteins from the virus (e.g., a capsid protein made using recombinant DNA technology) are used as the vaccine. Subunit vaccines produced in *Escherichia coli* or yeast are very safe and pose no threat of viral disease. Their efficacy, however, can be low because not all of the immunogenic viral proteins are present, and those that are present may not exist in their native conformations.

Inactivated (killed) vaccines are made by growing more-or-less wild type (wt) virus and then inactivating it, for instance, with formaldehyde (as in the Salk polio vaccine). A great deal of experimentation is required to find an inactivation treatment that kills all of the virus and yet does not damage the immunogenicity of the particle. In addition, residual safety issues remain in that the facility for growing the virus may allow virulent virus to escape or the inactivation may fail.

An attenuated live vaccine comprises a virus that has been subjected to mutations rendering it less virulent and usable for immunization. Live, attenuated viruses have many advantages as vaccines: they are often easy, fast, and cheap to manufacture; they are often easy to administer (the Sabin polio vaccine, for instance, was administered orally on sugar cubes); and sometimes the residual growth of the attenuated virus allows "herd" immunization (immunization of people in close contact with the primary patient). These advantages are particularly important in an emergency, when a vaccine is rapidly needed. The major drawback of an attenuated vaccine is that it has some significant frequency of reversion to wt virulence. For this reason, the Sabin vaccine is no longer used in the United States.

Accordingly, there remains a need for a systematic approach to generating attenuated live viruses that have practically no possibility of reversion and thus provide a fast, efficient, and safe method of manufacturing a vaccine. The present invention fulfills this need by providing a systematic approach, Synthetic Attenuated Virus Engineering (SAVE), for generating attenuated live viruses that have essentially no possibility of reversion because they contain hundreds or thousands of small defects. This method is broadly applicable to a wide range of viruses and provides an effective approach for producing a wide variety of anti-viral vaccines.

SUMMARY OF THE INVENTION

The present invention provides an attenuated virus which comprises a modified viral genome containing nucleotide substitutions engineered in multiple locations in the genome, wherein the substitutions introduce a plurality of synonymous codons into the genome. This substitution of synonymous codons alters various parameters, including codon bias, codon pair bias, density of deoptimized codons and deoptimized codon pairs, RNA secondary structure, CpG dinucleotide content, C+G content, translation frameshift sites, translation pause sites, the presence or absence of tissue specific microRNA recognition sequences, or any combination thereof, in the genome. Because of the large number of defects involved, the attenuated virus of the invention provides a means of producing stably attenuated, live vaccines against a wide variety of viral diseases.

In one embodiment, an attenuated virus is provided which comprises a nucleic acid sequence encoding a viral protein or a portion thereof that is identical to the corresponding sequence of a parent virus, wherein the nucleotide sequence of the attenuated virus contains the codons of a parent sequence from which it is derived, and wherein the nucleotide sequence is less than 90% identical to the nucleotide sequence of the parent virus. In another embodiment, the nucleotide sequence is less that 80% identical to the sequence of the parent virus. The substituted nucleotide sequence which provides for attenuation is at least 100 nucleotides in length, or at least 250 nucleotides in length, or at least 500 nucleotides in length, or at least 1000 nucleotides in length. The codon pair bias of the attenuated sequence is less than the codon pair bias of the parent virus, and is reduced by at least about 0.05, or at least about 0.1, or at least about 0.2.

The virus to be attenuated can be an animal or plant virus. In certain embodiments, the virus is a human virus. In another embodiment, the virus infects multiple species. Particular embodiments include, but are not limited to, poliovirus, influenza virus, Dengue virus, HIV, rotavirus, and SARS.

This invention also provides a vaccine composition for inducing a protective immune response in a subject comprising the instant attenuated virus and a pharmaceutically acceptable carrier. The invention further provides a modified host cell line specially engineered to be permissive for an attenuated virus that is inviable in a wild type host cell.

In addition, the subject invention provides a method of synthesizing the instant attenuated virus comprising (a) identifying codons in multiple locations within at least one non-regulatory portion of the viral genome, which codons can be replaced by synonymous codons; (b) selecting a synonymous codon to be substituted for each of the identified codons; and (c) substituting a synonymous codon for each of the identified codons.

Moreover, the subject invention provides a method of synthesizing the instant attenuated virus comprising changing the order, within the coding region, of existing codons encoding the same amino acid in order to modulate codon pair bias.

Even further, the subject invention provides a method of synthesizing the instant attenuated virus that combines the previous two methods.

According to the invention, attenuated virus particles are made by transfecting viral genomes into host cells, whereby attenuated virus particles are produced. The invention further provides pharmaceutical compositions comprising attenuated virus which are suitable for immunization.

This invention further provides methods for eliciting a protective immune response in a subject, for preventing a subject from becoming afflicted with a virus-associated disease, and for delaying the onset, or slowing the rate of progression, of a virus-associated disease in a virus-infected subject, comprising administering to the subject a prophylactically or therapeutically effective dose of the instant vaccine composition.

The present invention further provides an attenuated virus which comprises a modified viral genome containing nucleotide substitutions engineered in multiple locations in the genome, wherein the substitutions introduce a plurality of synonymous codons into the genome, wherein the nucleotide substitutions are selected by a process comprising the steps of initially creating a coding sequence by randomly assigning synonymous codons in respective amino acid allowed positions, calculating a codon pair score of the coding sequence randomly selecting and exchanging either (a) pairs of codons encoding the same amino acids or (b) substituting synonymous codons in accordance with a simulated annealing optimization function and repeating the previous step until no further improvement (no change in pair score or bias) is observed for a specific or sufficient number of iterations, until the solution converges on an optima or near optimal value

BRIEF DESCRIPTION OF THE FIGURES

FIGS. 2A-2B. Sequence alignment of PV(M), PV-AB and PV-SD capsid coding regions. The nucleotide sequences of PV(M) (SEQ ID NO:1), PV-AB (SEQ ID NO:2) and PV-SD (SEQ ID NO:3) were aligned using the MultAlin online software tool (Corpet, 1988). Numbers above the sequence refer to the position within the capsid sequence. (FIG. 2A) Nucleotide 1 to nucleotide 1300; (FIG. 2B) nucleotide 1301 to nucleotide 2643. Nucleotide 1 corresponds to nucleotide 743 in the PV(M) virus genome. In the consensus sequence, the occurrence of the same nucleotide in all three sequences is indicated by an upper case letter; the occurrence of the same nucleotide in two of the three sequences is indicated by a lower case letter; and the occurrence of three different nucleotides in the three sequences is indicated by a period.

(FIG. 3A) Overview of virus constructs used in this study. (FIG. 3B) One-step growth kinetics in HeLa cell monolayers. (FIGS. 3C to H) Plaque phenotypes of codon-deoptimized viruses after 48 h (FIGS. 3C to F) or 72 h (FIGS. 3G and H) of incubation; stained with anti-3$D^{pol}$ antibody to visualize infected cells. (FIG. 3C) PV(M), (FIG. 3D) PV-SD, (FIG. 3E) PV-AB, (FIG. 3F) PV-$AB^{755-1513}$, (FIGS. 3G and H) PV-$AB^{2470-2954}$. Cleared plaque areas are outlined by a rim of infected cells (FIGS. 3C and D). (FIG. 3H) No plaques are apparent with PV-$AB^{2470-2954}$ after subsequent crystal violet staining of the well shown in panel FIG. 3G. (FIGS. 3I and J) Microphotographs of the edge of an immunostained plaque produced by PV(M) (FIG. 3I) or an infected focus produced by PV-$AB^{2470-2954}$ (FIG. 3J) after 48 h of infection.

FIGS. 4A-E. Codon deoptimization leads to a reduction of specific infectivity. (FIG. 4A) Agarose gel electrophoresis of virion genomic RNA isolated from purified virus particles of PV(M) (lane 1), PV-$AB^{755-1513}$ (lane 2), and PV-$AB^{2470-2954}$ (lane 3). (FIG. 4B) Silver-stained SDS-PAGE protein gel of purified PV(M) (lane 1), PV-$AB^{755-1513}$ (lane 2), and PV-$AB^{2470-2954}$ (lane 3) virus particles. The three larger of the four capsid proteins (VP1, VP2, and VP3) are shown, demonstrating the purity and relative amounts of virus preparations. (FIG. 4C) Development of a virus capture ELISA using a poliovirus receptor-alkaline phosphatase (CD155-AP) fusion protein probe. Virus-specific antibodies were used to coat ELISA plates, and samples containing an unknown virus concentration were applied followed by detection with CD155-AP. Virus concentrations were calculated using a standard curve prepared in parallel with known amounts of purified wt virus (FIG. 4E). (FIG. 4D) The amounts of purified virus and extracted virion RNA were spectrophotometrically quantified, and the number of particles or genome equivalents (1 genome=1 virion) was calculated. In addition, virion concentrations were determined by ELISA. The infectious titer of each virus was determined by plaque/infected-focus assay, and the specific infectivity was calculated as PFU/particle or FFU/particle.

(FIG. 5A) A standard in vitro translation in HeLa S10 extract, in the presence of exogenously added amino acids and tRNAs reveals no differences in translation capacities of codon-deoptimized genomes compared to the PV(M) wt. Shown is an autoradiograph of [$^{35}$S]methionine-labeled translation products resolved on a 12.5% SDS-PAGE gel. The identity of an aberrant band (*) is not known. (FIG. 5B) In vitro translation in nondialyzed HeLa S10 extract without the addition of exogenous amino acids and tRNA and in the presence of competing cellular mRNAs uncovers a defect in translation capacities of codon-deoptimized PV genomes. Shown is a Western blot of poliovirus 2C reactive translation products ($2C^{ATPase}$, 2BC, and P2) resolved on a 10% SDS-PAGE gel. The relative amounts of the 2BC translation products are expressed below each lane as percentages of the wt band.

(FIG. 6A) Schematic of dicistronic replicons. Various P1 capsid coding sequences were inserted upstream of the firefly luciferase gene (F-Luc). Determination of changing levels of F-Luc expression relative to an internal control (R-Luc) allows for the quantification of ribosome transit through the P1 capsid region. (FIG. 6B) Replicon RNAs were transfected into HeLa cells and incubated for 7 h in the presence of 2 mM guanidine-hydrochloride to block RNA replication. The relative rate of translation through the P1 region was inversely proportional to the extent of codon deoptimization. While the capsid coding sequences of two viable virus constructs, PV-$AB^{2470-2954}$ and PV-$AB^{2954-3386}$, allow between 60 and 80% of wt translation, translation efficiency below 20% is associated with the lethal phenotypes observed with the PV-AB, PV-$AB^{2470-3386}$, and PV-$AB^{1513-2470}$ genomes. Values represents the average of 6 assays from 3 independent experiments.

(FIG. 8A) One-step growth kinetics reveals PFU production for PV-$Min^{755-2470}$ and PV-$Min^{2470-3385}$ that is reduced on the order of 2.5 orders of magnitude by comparison to PV(M)-wt. However, all viruses produce a similar number of viral particles (not shown in this Figure). (FIG. 8B) As a result the PFU/particle ratio is reduced, similar to codon deoptimized viruses PV-$AB^{755-1513}$ and PV-$AB^{2470-2954}$ (see FIG. 3B) (PFU is "Plaque Forming Unit").

(FIG. 11A) Top, a schematic of the full-length PV(M)-wt genomic RNA. (FIG. 11B) Below, the open reading frames of PV(M)-wt, the CPB customized synthetic viruses PV-Max, PV-Min, and the PV(M)-wt:PV-Min chimera viruses. Black corresponds to PV(M)-wt sequence, Gray to PV-Min synthetic sequence, and Thatched to PV-Max. The viral constructs highlighted, PV-$Min^{755-2470}$ (PV-MinXY) and PV-$Min^{2470-3385}$ (PV-MinZ), were further characterized due to a markedly attenuated phenotype.

(FIG. 12A) An MOI of 2 was used to infect a monolayer of HeLa R19 cells, the PFU at the given time points (0, 2, 4, 7, 10, 24, 48 hrs) was measured by plaque assay. Corresponding symbols: (□) PV(M)-wt, (●) PV-Max, (◇) PV-Min755-1513, (x) PV-Min1513-2470, (▲) PV-MinXY, (Δ) PV-MinZ. (FIG. 12B) Displays the conversion of the calculated PFU/ml at each time point to particles/ml. This achieved by multiplying the PFU/ml by the respective viruses specific infectivity. Corresponding symbols as in (FIG. 12A)

(FIG. 13A) The dicistronic RNA construct used to quantify the in vivo effect CPB has on translation. The first cistron utilizes a hepatitis C virus (HCV) Internal Ribosome Entry Site (IRES) inducing the translation of *Renilla* Luciferase (R-Luc). This first cistron is the internal control used to normalize the amount of input RNA. The second cistron controlled by the PV(M)-wt IRES induces the translation of Firefly Luciferase (F-Luc). The region labeled "P1" in the construct was replaced by the cDNA of each respective viruses P1. (FIG. 13B) Each respective RNA construct was transfected, in the presence of 2 mM guanidine hydrochloride, into HeLa R19 cells and after 6 hours the R-Luc and F-Luc were measured. The F-Luc/R-Luc values were normalized relative to PV(M)-wt translation (100%).

(FIG. 16A) A/PR8-$NP^{Min}$ virus are viable and produce smaller plaques on MDCK cells compared to the A/PR8 wt. (FIG. 16B) A/PR8-$NP^{Min}$ virus display delayed growth kinetics and final titers 3-5 fold below wild type A/PR8.

(FIG. 17A) A/PR8-$PB1^{Min-RR}$ and A/PR8-$HA^{Min}$/$NP^{Min}$ virus are viable and produce smaller plaques on MDCK cells as compared to the A/PR8 wild type. (FIG. 17B) A/PR8-$PB1^{Min-RR}$ and A/PR8-$HA^{Min}$/$NP^{Min}$ virus display delayed growth kinetics and final titers about 10 fold below wild type A/PR8.

(FIG. 18A) A/PR8-$NP^{Min}$ virus has reduced pathogenicity compared to wild type A/PR8 virus as determined by weight loss upon vaccination. (FIG. 18B) All mice (eight of eight) vaccinated with A/PR8-$NP^{Min}$ virus survived, where as only 25% (two of eight) mice infected with A/PR8 were alive 13 days post vaccination. (FIG. 18C) Mice vaccinated with A/PR8-$NP^{Min}$ virus are protected from challenge with $100\times LD_{50}$ of A/PR8 wild type virus.

DETAILED DESCRIPTION OF THE INVENTION

Figure 1:
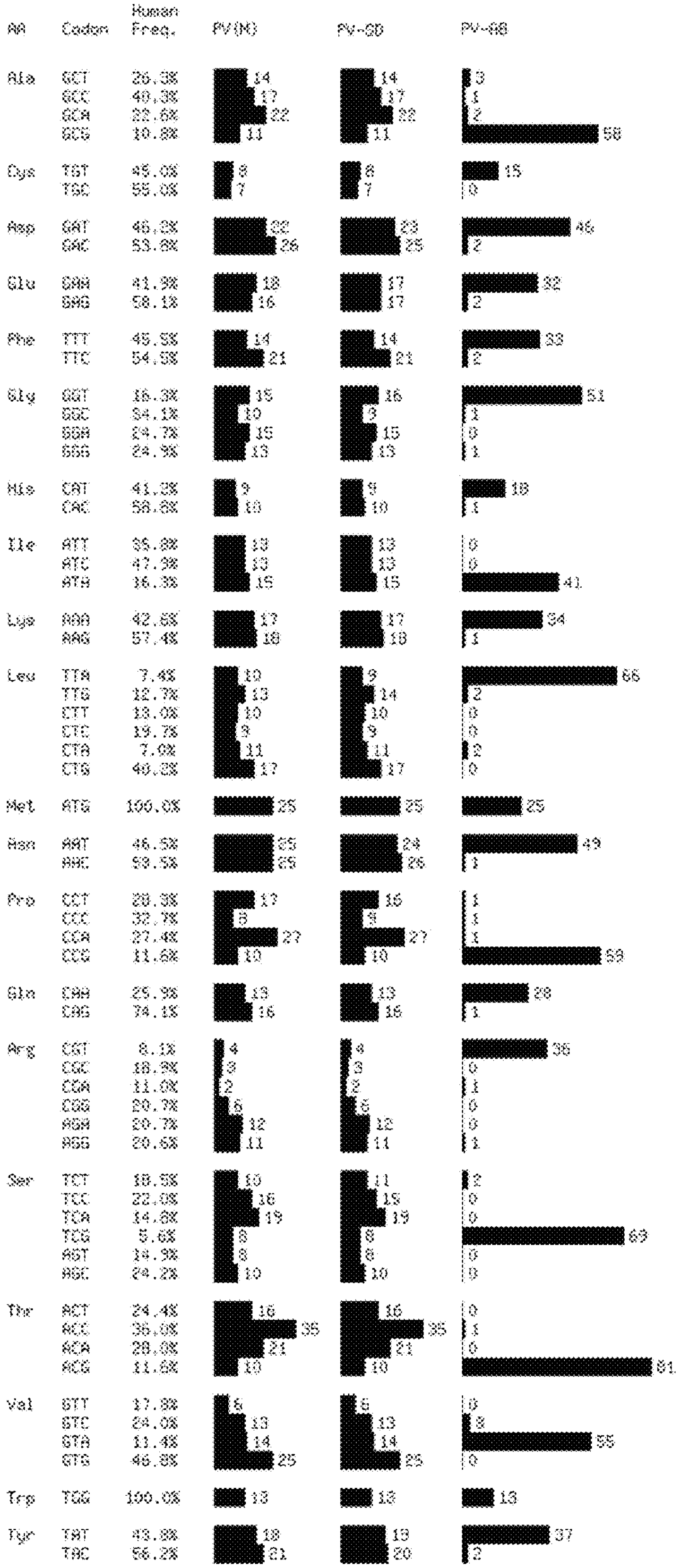
FIG. 1. Codon use statistics in synthetic P1 capsid designs. PV-SD maintains nearly identical codon frequencies compared to wt, while maximizing codon positional changes within the sequence. In PV-AB capsids, the use of nonpreferred codons was maximized. The lengths of the bars and the numbers behind each bar indicate the occurrence of each codon in the sequence. As a reference, the normal human synonymous codon frequencies ("Freq." expressed as a percentage) for each amino acid are given in the third column.

The present invention relates to the production of attenuated viruses that may be used as vaccines to protect against viral infection and disease. Accordingly, the invention provides an attenuated virus, which comprises a modified viral genome containing nucleotide substitutions engineered in multiple locations in the genome, wherein the substitutions introduce a plurality of synonymous codons into the genome and/or a change of the order of existing codons for the same amino acid (change of codon pair utilization). In both cases, the original, wild-type amino acid sequences of the viral gene products are retained.

Most amino acids are encoded by more than one codon. See the genetic code in Table 1. For instance, alanine is encoded by GCU, GCC, GCA, and GCG. Three amino acids (Leu, Ser, and Arg) are encoded by six different codons, while only Trp and Met have unique codons. "Synonymous" codons are codons that encode the same amino acid. Thus, for example, CUU, CUC, CUA, CUG, UUA, and UUG are synonymous codons that code for Leu. Synonymous codons are not used with equal frequency. In general, the most frequently used codons in a particular organism are those for which the cognate tRNA is abundant, and the use of these codons enhances the rate and/or accuracy of protein translation. Conversely, tRNAs for the rarely used codons are found at relatively low levels, and the use of rare codons is thought to reduce translation rate and/or accuracy. Thus, to replace a given codon in a nucleic acid by a synonymous but less frequently used codon is to substitute a "deoptimized" codon into the nucleic acid.

TABLE 1

Genetic Code

| | U | C | A | G | |
|---|---|---|---|---|---|
| U | Phe | Ser | Tyr | Cys | U |
| | Phe | Ser | Tyr | Cys | C |
| | Leu | Ser | STOP | STOP | A |
| | Leu | Ser | STOP | Trp | G |
| C | Leu | Pro | His | Arg | U |
| | Leu | Pro | His | Arg | C |
| | Leu | Pro | Gln | Arg | A |
| | Leu | Pro | Gln | Arg | G |
| A | Ile | Thr | Asn | Ser | U |
| | Ile | Thr | Asn | Ser | C |
| | Ile | Thr | Lys | Arg | A |
| | Met | Thr | Lys | Arg | G |
| G | Val | Ala | Asp | Gly | U |
| | Val | Ala | Asp | Gly | C |
| | Val | Ala | Glu | Gly | A |
| | Val | Ala | Glu | Gly | G |

[a] The first nucleotide in each codon encoding a particular amino acid is shown in the left-most column; the second nucleotide is shown in the top row; and the third nucleotide is shown in the right-most column.

In addition, a given organism has a preference for the nearest codon neighbor of a given codon A, referred to a bias in codon pair utilization. A change of codon pair bias, without changing the existing codons, can influence the rate of protein synthesis and production of a protein.

In various embodiments of the present invention, the virus is a DNA, RNA, double-stranded, or single-stranded virus. In further embodiments, the virus infects an animal or a plant. In preferred embodiments, the animal is a human. A large number of animal viruses are well known to cause diseases (see below). Certain medically important viruses, such as those causing rabies, severe acute respiratory syndrome (SARS), and avian flu, can also spread to humans from their normal non-human hosts.

Viruses also constitute a major group of plant pathogens, and research is ongoing to develop viral vectors for producing transgenic plants. The advantages of such vectors include the ease of transforming plants, the ability to transform mature plants which obviates the need for regeneration of a transgenic plant from a single transformed cell, and high levels of expression of foreign genes from the multiple copies of virus per cell. However, one of the main disadvantages of these vectors is that it has not been possible to separate essential viral replicative functions from pathogenic determinants of the virus. The SAVE strategy disclosed herein may afford a means of engineering non-pathogenic viral vectors for plant transformation.

Major Viral Pathogens in Humans

Viral pathogens are the causative agents of many diseases in humans and other animals. Well known examples of viral diseases in humans include the common cold (caused by human rhinoviruses, HRV), influenza (influenza virus), chickenpox (varicella-zoster virus), measles (a paramyxovirus), mumps (a paramyxovirus), poliomyelitis (poliovirus, PV), rabies (Lyssavirus), cold sores (Herpes Simplex Virus [HSV] Type 1), and genital herpes (HSV Type 2). Prior to the introduction of vaccination programs for children, many of these were common childhood diseases worldwide, and are still a significant threat to health in some developing countries. Viral diseases also include more serious diseases such as acquired immunodeficiency syndrome (AIDS) caused by Human Immunodeficiency Virus (HIV), severe acute respiratory syndrome (SARS) caused by SARS coronavirus, avian flu (H5N1 subtype of influenza A virus), Ebola (ebolavirus), Marburg haemorrhagic fever (Marburg virus), dengue fever (Flavivirus serotypes), West Nile encephalitis (a flavivirus), infectious mononucleosis (Epstein-Barr virus, EBV), hepatitis (Hepatitis C Virus, HCV; hepatitis B virus, HBV), and yellow fever (flavivirus). Certain types of cancer can also be caused by viruses. For example, although most infections by human papillomavirus (HPV) are benign, HPV has been found to be associated with cervical cancer, and Kaposi's sarcoma (KS), a tumor prevalent in AIDS patients, is caused by Kaposi's sarcoma-associated herpesvirus (KSHV).

Because viruses reside within cells and use the machinery of the host cell to reproduce, they are difficult to eliminate without killing the host cell. The most effective approach to counter viral diseases has been the vaccination of subjects at risk of infection in order to provide resistance to infection. For some diseases (e.g., chickenpox, measles, mumps, yellow fever), effective vaccines are available. However, there is a pressing need to develop vaccines for many other viral diseases. The SAVE (Synthetic Attenuated Virus Engineering) approach to making vaccines described herein is in principle applicable to all viruses for which a reverse genetics system (see below) is available. This approach is exemplified herein by focusing on the application of SAVE to develop attenuated virus vaccines for poliomyelitis, the common cold, and influenza.

Any virus can be attenuated by the methods disclosed herein. The virus can be a dsDNA virus (e.g. Adenoviruses, Herpesviruses, Poxviruses), a single stranded "plus" sense DNA virus (e.g., Parvoviruses) a double stranded RNA virus (e.g., Reoviruses), a single stranded+sense RNA virus (e.g. Picornaviruses, Togaviruses), a single stranded "minus" sense RNA virus (e.g. Orthomyxoviruses, Rhabdoviruses), a single stranded+sense RNA virus with a DNA intermediate (e.g. Retroviruses), or a double stranded reverse transcribing virus (e.g. Hepadnaviruses). In certain non-limiting embodiments of the present invention, the virus is poliovirus (PV), rhinovirus, influenza virus including avian flu (e.g. H5N1 subtype of influenza A virus), severe acute respiratory syndrome (SARS) coronavirus, Human Immunodeficiency Virus (HIV), Hepatitis B Virus (HBV), Hepatitis C Virus (HCV), infectious bronchitis virus, ebolavirus, Marburg virus, dengue fever virus (Flavivirus serotypes), West Nile disease virus, Epstein-Barr virus (EBV), yellow fever virus, Ebola (ebolavirus), chickenpox (varicella-zoster virus), measles (a paramyxovirus), mumps (a paramyxovirus), rabies (Lyssavirus), human papillomavirus, Kaposi's sarcoma-associated herpesvirus, Herpes Simplex Virus (HSV Type 1), or genital herpes (HSV Type 2).

The term "parent" virus or "parent" protein encoding sequence is used herein to refer to viral genomes and protein encoding sequences from which new sequences, which may be more or less attenuated, are derived. Parent viruses and sequences are usually "wild type" or "naturally occurring" prototypes or isolates of variants for which it is desired to obtain a more highly attenuated virus. However, parent viruses also include mutants specifically created or selected in the laboratory on the basis of real or perceived desirable properties. Accordingly, parent viruses that are candidates for attenuation include mutants of wild type or naturally occurring viruses that have deletions, insertions, amino acid substitutions and the like, and also include mutants which have codon substitutions. In one embodiment, such a parent sequence differs from a natural isolate by about 30 amino acids or fewer. In another embodiment, the parent sequence differs from a natural isolate by about 20 amino acids or fewer. In yet another embodiment, the parent sequence differs from a natural isolate by about 10 amino acids or fewer.

The attenuated PV may be derived from poliovirus type 1 (Mahoney; "PV(M)"), poliovirus type 2 (Lansing), poliovirus type 3 (Leon), monovalent oral poliovirus vaccine (OPV) virus, or trivalent OPV virus. In certain embodiments, the poliovirus is PV-AB having the genomic sequence set forth in SEQ ID NO:2, or PV-AB$^{755-1513}$, PV-AB$^{755-2470}$, PV-AB$^{1513-3386}$, PV-AB$^{2470-3386}$, PV-AB$^{1513-2470}$, PV-AB$^{2470-2954}$, or PV-AB$^{2954-3386}$. The nomenclature reflects a PV(M) genome in which portions of the genome, are substituted with nucleotides of PV-AB. The superscript provides the nucleotide numbers of PV-AB that are substituted.

In various embodiments, the attenuated rhinovirus is a human rhinovirus (HRV) derived from HRV2, HRV14, Human rhinovirus 10 Human rhinovirus 100; Human rhinovirus 11; Human rhinovirus 12; Human rhinovirus 13; Human rhinovirus 15; Human rhinovirus 16; Human rhinovirus 18; Human rhinovirus 19; Human rhinovirus 1A; Human rhinovirus 1B; Human rhinovirus 2; Human rhinovirus 20; Human rhinovirus 21; Human rhinovirus 22; Human rhinovirus 23; Human rhinovirus 24; Human rhinovirus 25; Human rhinovirus 28; Human rhinovirus 29; Human rhinovirus 30; Human rhinovirus 31 Human rhinovirus 32; Human rhinovirus 33; Human rhinovirus 34; Human rhinovirus 36; Human rhinovirus 38; Human rhinovirus 39; Human rhinovirus 40; Human rhinovirus 41; Human rhinovirus 43; Human rhinovirus 44; Human rhinovirus 45; Human rhinovirus 46; Human rhinovirus 47; Human rhinovirus 49; Human rhinovirus 50; Human rhinovirus 51; Human rhinovirus 53; Human rhinovirus 54; Human rhinovirus 55; Human rhinovirus 56; Human rhinovirus 57; Human rhinovirus 58; Human rhinovirus 59; Human rhinovirus 60; Human rhinovirus 61; Human rhinovirus 62; Human rhinovirus 63; Human rhinovirus 64; Human rhinovirus 65; Human rhinovirus 66; Human rhinovirus 67; Human rhinovirus 68; Human rhinovirus 7; Human rhinovirus 71; Human rhinovirus 73; Human rhinovirus 74; Human rhinovirus 75; Human rhinovirus 76; Human rhinovirus 77; Human rhinovirus 78; Human rhinovirus 8; Human rhinovirus 80; Human rhinovirus 81; Human rhinovirus 82; Human rhinovirus 85; Human rhinovirus 88; Human rhinovirus 89; Human rhinovirus 9; Human rhinovirus 90; Human rhinovirus 94; Human rhinovirus 95; Human rhinovirus 96 Human rhinovirus 98; Human rhinovirus 14; Human rhinovirus 17; Human rhinovirus 26; Human rhinovirus 27; Human rhinovirus 3; Human rhinovirus 8001 Finland November 1995; Human rhinovirus 35; Human rhinovirus 37;+Human rhinovirus 6253 Finland September 1994; Human rhinovirus 9166 Finland September 1995; Human rhinovirus 4; Human rhinovirus 42; Human rhinovirus 48; Human rhinovirus 9864 Finland September 1996; Human rhinovirus 5; Human rhinovirus 52; Human rhinovirus 6; Human rhinovirus 7425 Finland December 1995; Human rhinovirus 69; Human rhinovirus 5928 Finland May 1995; Human rhinovirus 70; Human rhinovirus 72; Human rhinovirus 79; Human rhinovirus 83; Human rhinovirus 84; Human rhinovirus 8317 Finland August 1996; Human rhinovirus 86; Human rhinovirus 91; Human rhinovirus 7851 Finland September 1996; Human rhinovirus 92; Human rhinovirus 93; Human rhinovirus 97; Human rhinovirus 99; Antwerp rhinovirus 98/99; Human rhinovirus 263 Berlin 2004; Human rhinovirus 3083/rhino/Hyogo/2005; Human rhinovirus NY-003; Human rhinovirus NY-028; Human rhinovirus NY-041; Human rhinovirus NY-042; Human rhinovirus NY-060; Human rhinovirus NY-063; Human rhinovirus NY-074; Human rhinovirus NY-1085; Human rhinovirus strain Hanks; Untyped human rhinovirus OK88-8162; Human enterovirus sp. ex *Amblyomma americanum*; Human rhinovirus sp. or Human rhinovirus UC.

In other embodiments, the attenuated influenza virus is derived from influenza virus A, influenza virus B, or influenza virus C. In further embodiments, the influenza virus A belongs to but is not limited to subtype H10N7, H10N1, H10N2, H10N3, H10N4, H10N5, H10N6, H10N7, H10N8, H10N9, H11N1, H11N2, H11N3, H11N4, H11N6, H11N8, H11N9, H12N1, H12N2, H12N4, H12N5, H12N6, H12N8, H12N9, H13N2, H13N3, H13N6, H13N9, H14N5, H14N6, H15N2, H15N8, H15N9, H16N3, H1N1, H1N2, H1N3, H1N5, H1N6, H1N8, H1N9, H2N1, H2N2, H2N3, H2N4, H2N5, H2N6, H2N7, H2N8, H2N9, H3N1, H3N2, H3N3, H3N4, H3N5, H3N6, H3N8, H3N9, H4N1, H4N2, H4N3, H4N4, H4N5, H4N6, H4N7, H4N8, H4N9, H5N1, H5N2, H5N3, H5N4, H5N6, H5N7, H5N8, H5N9, H6N1, H6N2, H6N3, H6N4, H6N5, H6N6, H6N7, H6N8, H6N9, H7N1, H7N2, H7N3, H7N4, H7N5, H7N7, H7N8, H7N9, H8N2, H8N4, H8N5, H9N1, H9N2, H9N3, H9N4, H9N5, H9N6, H9N7, H9N8, H9N9 and unidentified subtypes.

In further embodiments, the influenza virus B belongs to but is not limited to subtype Influenza B virus (B/Aichi/186/2005), Influenza B virus (B/Aichi/5/88), Influenza B virus (B/Akita/27/2001), Influenza B virus (B/Akita/5/2001), Influenza B virus (B/Alabama/1/2006), Influenza B virus (B/Alabama/2/2005), Influenza B virus (B/Alaska/03/1992), Influenza B virus (B/Alaska/12/1996), Influenza B virus (B/Alaska/16/2000), Influenza B virus (B/Alaska/16/2003), Influenza B virus (B/Alaska/1777/2005), Influenza B virus (B/Alaska/2/2004), Influenza B virus (B/Alaska/6/2005), Influenza B virus (B/Ann Arbor/1/1986), Influenza B virus (B/Ann Arbor/1994), Influenza B virus (B/Argentina/132/2001), Influenza B virus (B/Argentina/3640/1999), Influenza B virus (B/Argentina/69/2001), Influenza B virus (B/Arizona/1/2005), Influenza B virus (B/Arizona/12/2003), Influenza B virus (B/Arizona/13/2003), Influenza B virus (B/Arizona/135/2005), Influenza B virus (B/Arizona/14/2001), Influenza B virus (B/Arizona/14/2005), Influenza B virus (B/Arizona/140/2005), Influenza B virus (B/Arizona/146/2005), Influenza B virus (B/Arizona/148/2005), Influenza B virus (B/Arizona/15/2005), Influenza B virus (B/Arizona/16/2005), Influenza B virus (B/Arizona/162/2005), Influenza B virus (B/Arizona/163/2005), Influenza B virus (B/Arizona/164/2005), Influenza B virus (B/Arizona/2/2000), Influenza B virus (B/Arizona/2/2005), Influenza B virus (B/Arizona/2e/2006), Influenza B virus (B/Arizona/3/2006), Influenza B virus (B/Arizona/4/2002), Influenza B virus (B/Arizona/4/2006), Influenza B virus (B/Arizona/48/2005), Influenza B virus (B/Arizona/5/2000), Influenza B virus (B/Arizona/59/2005), Influenza B virus (B/Arizona/7/2000), Influenza B virus (B/Auckland/01/2000), Influenza B virus (B/Bangkok/141/1994), Influenza B virus (B/Bangkok/143/1994), Influenza B virus (B/Bangkok/153/1990), Influenza B virus (B/Bangkok/163/1990), Influenza B virus (B/Bangkok/163/90), Influenza B virus (B/Bangkok/34/99), Influenza B virus (B/Bangkok/460/03), Influenza B virus (B/Bangkok/54/99), Influenza B virus (B/Barcelona/215/03), Influenza B virus (B/Beijing/15/84), Influenza B virus (B/Beijing/184/93), Influenza B virus (B/Beijing/243/97), Influenza B virus (B/Beijing/43/75), Influenza B virus (B/Beijing/5/76), Influenza B virus (B/Beijing/76/98), Influenza B virus (B/Belgium/WV106/2002), Influenza B virus (B/Belgium/WV107/2002), Influenza B virus (B/Belgium/WV109/2002), Influenza B virus (B/Belgium/WV114/2002), Influenza B virus (B/Belgium/WV122/2002), Influenza B virus (B/Bonn/43), Influenza B virus (B/Brazil/017/00), Influenza B virus (B/Brazil/053/00), Influenza B virus (B/Brazil/055/00), Influenza B virus (B/Brazil/064/00), Influenza B virus (B/Brazil/074/00), Influenza B virus (B/Brazil/079/00), Influenza B virus (B/Brazil/110/01), Influenza B virus (B/Brazil/952/2001), Influenza B virus (B/Brazil/975/2000), Influenza B virus (B/Brisbane/32/2002), Influenza B virus (B/Bucharest/311/1998), Influenza B virus (B/Bucharest/795/03), Influenza B virus (B/Buenos Aires/161/00), Influenza B virus (B/Buenos Aires/9/95), Influenza B virus (B/Buenos Aires/SW16/97), Influenza B virus (B/Buenos Aires/VL518/99), Influenza B virus (B/California/01/1995), Influenza B virus (B/California/02/1994), Influenza B virus (B/California/02/1995), Influenza B virus (B/California/1/2000), Influenza B virus (B/California/10/2000), Influenza B virus (B/California/11/2001), Influenza B virus (B/California/14/2005), Influenza B virus (B/California/2/2002), Influenza B virus (B/California/2/2003), Influenza B virus (B/California/3/2000), Influenza B virus (B/California/3/2004), Influenza B virus (B/California/6/2000), Influenza B virus (B/California/7/2005), Influenza B virus (B/Canada/16188/2000), Influenza B virus (B/Canada/464/2001), Influenza B virus (B/Canada/464/2002), Influenza B virus (B/Chaco/366/00), Influenza B virus (B/Chaco/R113/00), Influenza B virus (B/Chantaburi/218/2003), Influenza B virus (B/Cheju/303/03), Influenza B virus (B/Chiba/447/98), Influenza B virus (B/Chile/3162/2002), Influenza B virus (B/Chongqing/3/2000), Influenza B virus (B/clinical isolate SA1 Thailand/2002), Influenza B virus (B/clinical isolate SA10 Thailand/2002), Influenza B virus (B/clinical isolate SA100 Philippines/2002), Influenza B virus (B/clinical isolate SA101 Philippines/2002), Influenza B virus (B/clinical isolate SA102 Philippines/2002), Influenza B virus (B/clinical isolate SA103 Philippines/2002), Influenza B virus (B/clinical isolate SA104 Philippines/2002), Influenza B virus (B/clinical isolate SA105 Philippines/2002), Influenza B virus (B/clinical isolate SA106 Philippines/2002), Influenza B virus (B/clinical isolate SA107 Philippines/2002), Influenza B virus (B/clinical isolate SA108 Philippines/2002), Influenza B virus (B/clinical isolate SA109 Philippines/2002), Influenza B virus (B/clinical isolate SA11 Thailand/2002), Influenza B virus (B/clinical isolate SA110 Philippines/2002), Influenza B virus (B/clinical isolate SA112 Philippines/2002), Influenza B virus (B/clinical isolate SA113 Philippines/2002), Influenza B virus (B/clinical isolate SA114 Philippines/2002), Influenza B virus (B/clinical isolate SA115 Philippines/2002), Influenza B virus (B/clinical isolate SA116 Philippines/2002), Influenza B virus (B/clinical isolate SA12 Thailand/2002), Influenza B virus (B/clinical isolate SA13 Thailand/2002), Influenza B virus (B/clinical isolate SA14 Thailand/2002), Influenza B virus (B/clinical isolate SA15 Thailand/2002), Influenza B virus (B/clinical isolate SA16 Thailand/2002), Influenza B virus (B/clinical isolate SA17 Thailand/2002), Influenza B virus (B/clinical isolate SA18 Thailand/2002), Influenza B virus (B/clinical isolate SA19 Thailand/2002), Influenza B virus (B/clinical isolate SA2 Thailand/2002), Influenza B virus (B/clinical isolate SA20 Thailand/2002), Influenza B virus (B/clinical isolate SA21 Thailand/2002), Influenza B virus (B/clinical isolate SA22 Thailand/2002), Influenza B virus (B/clinical isolate SA23 Thailand/2002), Influenza B virus (B/clinical isolate SA24 Thailand/2002), Influenza B virus (B/clinical isolate SA25 Thailand/2002), Influenza B virus (B/clinical isolate SA26 Thailand/2002), Influenza B virus (B/clinical isolate SA27 Thailand/2002), Influenza B virus (B/clinical isolate SA28 Thailand/2002), Influenza B virus (B/clinical isolate SA29 Thailand/2002), Influenza B virus (B/clinical isolate SA3 Thailand/2002), Influenza B virus (B/clinical isolate SA30 Thailand/2002), Influenza B virus (B/clinical isolate SA31 Thailand/2002), Influenza B virus (B/clinical isolate SA32 Thailand/2002), Influenza B virus (B/clinical isolate SA33 Thailand/2002), Influenza B virus (B/clinical isolate SA34 Thailand/2002), Influenza B virus (B/clinical isolate SA37 Thailand/2002), Influenza B virus (B/clinical isolate SA38 Philippines/2002), Influenza B virus (B/clinical isolate SA39 Thailand/2002), Influenza B virus (B/clinical isolate SA40 Thailand/2002), Influenza B virus (B/clinical isolate SA41 Philippines/2002), Influenza B virus (B/clinical isolate SA42 Philippines/2002), Influenza B virus (B/clinical isolate SA43 Thailand/2002), Influenza B virus (B/clinical isolate SA44 Thailand/2002), Influenza B virus (B/clinical isolate SA45 Philippines/2002), Influenza B virus (B/clinical isolate SA46 Philippines/2002), Influenza B virus (B/clinical isolate SA47 Philippines/2002), Influenza B virus (B/clinical isolate SA5 Thailand/2002), Influenza B virus (B/clinical isolate SA50 Philippines/2002), Influenza B virus (B/clinical isolate SA51 Philippines/2002), Influenza B virus (B/clinical isolate SA52 Philippines/2002), Influenza B virus (B/clinical isolate SA53 Philippines/2002), Influenza B virus (B/clinical isolate SA57 Philippines/2002), Influenza B virus (B/clinical isolate SA58 Philippines/2002), Influenza B virus (B/clinical isolate SA59 Philippines/2002), Influenza B virus (B/clinical isolate SA6 Thailand/2002), Influenza B virus (B/clinical isolate SA60 Philippines/2002), Influenza B virus (B/clinical isolate SA61 Philippines/2002), Influenza B virus (B/clinical isolate SA62 Philippines/2002), Influenza B virus (B/clinical isolate SA63 Philippines/2002), Influenza B virus (B/clinical isolate SA64 Philippines/2002), Influenza B virus (B/clinical isolate SA65 Philippines/2002), Influenza B virus (B/clinical isolate SA66 Philippines/2002), Influenza B virus (B/clinical isolate SA67 Philippines/2002), Influenza B virus (B/clinical isolate SA68 Philippines/2002), Influenza B virus (B/clinical isolate SA69 Philippines/2002), Influenza B virus (B/clinical isolate SA7 Thailand/2002), Influenza B virus (B/clinical isolate SA70 Philippines/2002), Influenza B virus (B/clinical isolate SA71 Philippines/2002), Influenza B virus (B/clinical isolate SA73 Philippines/2002), Influenza B virus (B/clinical isolate SA74 Philippines/2002), Influenza B virus (B/clinical isolate SA76 Philippines/2002), Influenza B virus (B/clinical isolate SA77 Philippines/2002), Influenza B virus (B/clinical isolate SA78 Philippines/2002), Influenza B virus (B/clinical isolate SA79 Philippines/2002), Influenza B virus (B/clinical isolate SA8 Thailand/2002), Influenza B virus (B/clinical isolate SA80 Philippines/2002), Influenza B virus (B/clinical isolate SA81 Philippines/2002), Influenza B virus (B/clinical isolate SA82 Philippines/2002), Influenza B virus (B/clinical isolate SA83

Philippines/2002), Influenza B virus (B/clinical isolate SA84 Philippines/2002), Influenza B virus (B/clinical isolate SA85 Thailand/2002), Influenza B virus (B/clinical isolate SA86 Thailand/2002), Influenza B virus (B/clinical isolate SA87 Thailand/2002), Influenza B virus (B/clinical isolate SA88 Thailand/2002), Influenza B virus (B/clinical isolate SA89 Thailand/2002), Influenza B virus (B/clinical isolate SA9 Thailand/2002), Influenza B virus (B/clinical isolate SA90 Thailand/2002), Influenza B virus (B/clinical isolate SA91 Thailand/2002), Influenza B virus (B/clinical isolate SA92 Thailand/2002), Influenza B virus (B/clinical isolate SA93 Thailand/2002), Influenza B virus (B/clinical isolate SA94 Thailand/2002), Influenza B virus (B/clinical isolate SA95 Philippines/2002), Influenza B virus (B/clinical isolate SA96 Thailand/2002), Influenza B virus (B/clinical isolate SA97 Philippines/2002), Influenza B virus (B/clinical isolate SA98 Philippines/2002), Influenza B virus (B/clinical isolate SA99 Philippines/2002), Influenza B virus (B/CNIC/27/2001), Influenza B virus (B/Colorado/04/2004), Influenza B virus (B/Colorado/11e/2004), Influenza B virus (B/Colorado/12e/2005), Influenza B virus (B/Colorado/13/2004), Influenza B virus (B/Colorado/13e/2004), Influenza B virus (B/Colorado/15/2004), Influenza B virus (B/Colorado/16e/2004), Influenza B virus (B/Colorado/17e/2004), Influenza B virus (B/Colorado/2/2004), Influenza B virus (B/Colorado/2597/2004), Influenza B virus (B/Colorado/4e/2004), Influenza B virus (B/Colorado/5/2004), Influenza B virus (B/Connecticut/02/1995), Influenza B virus (B/Connecticut/07/1993), Influenza B virus (B/Cordoba/2979/1991), Influenza B virus (B/Cordoba/VA418/99), Influenza B virus (B/Czechoslovakia/16/89), Influenza B virus (B/Czechoslovakia/69/1990), Influenza B virus (B/Czechoslovakia/69/90), Influenza B virus (B/Daeku/10/97), Influenza B virus (B/Daeku/45/97), Influenza B virus (B/Daeku/47/97), Influenza B virus (B/Daeku/9/97), Influenza B virus (B/Delaware/1/2006), Influenza B virus (B/Du/4/78), Influenza B virus (B/Durban/39/98), Influenza B virus (B/Durban/43/98), Influenza B virus (B/Durban/44/98), Influenza B virus (B/Durban/52/98), Influenza B virus (B/Durban/55/98), Influenza B virus (B/Durban/56/98), Influenza B virus (B/Egypt/2040/2004), Influenza B virus (B/England/1716/2005), Influenza B virus (B/England/2054/2005), Influenza B virus (B/England/23/04), Influenza B virus (B/EspiritoSanto/55/01), Influenza B virus (B/EspiritoSanto/79/99), Influenza B virus (B/Finland/154/2002), Influenza B virus (B/Finland/159/2002), Influenza B virus (B/Finland/160/2002), Influenza B virus (B/Finland/161/2002), Influenza B virus (B/Finland/162/03), Influenza B virus (B/Finland/162/2002), Influenza B virus (B/Finland/162/91), Influenza B virus (B/Finland/164/2003), Influenza B virus (B/Finland/172/91), Influenza B virus (B/Finland/173/2003), Influenza B virus (B/Finland/176/2003), Influenza B virus (B/Finland/184/91), Influenza B virus (B/Finland/188/2003), Influenza B virus (B/Finland/190/2003), Influenza B virus (B/Finland/191/2003), Influenza B virus (B/Finland/192/2003), Influenza B virus (B/Finland/193/2003), Influenza B virus (B/Finland/199/2003), Influenza B virus (B/Finland/202/2003), Influenza B virus (B/Finland/203/2003), Influenza B virus (B/Finland/204/2003), Influenza B virus (B/Finland/205/2003), Influenza B virus (B/Finland/206/2003), Influenza B virus (B/Finland/220/2003), Influenza B virus (B/Finland/223/2003), Influenza B virus (B/Finland/225/2003), Influenza B virus (B/Finland/227/2003), Influenza B virus (B/Finland/231/2003), Influenza B virus (B/Finland/235/2003), Influenza B virus (B/Finland/239/2003), Influenza B virus (B/Finland/244/2003), Influenza B virus (B/Finland/245/2003), Influenza B virus (B/Finland/254/2003), Influenza B virus (B/Finland/254/93), Influenza B virus (B/Finland/255/2003), Influenza B virus (B/Finland/260/93), Influenza B virus (B/Finland/268/93), Influenza B virus (B/Finland/270/2003), Influenza B virus (B/Finland/275/2003), Influenza B virus (B/Finland/767/2000), Influenza B virus (B/Finland/84/2002), Influenza B virus (B/Finland/886/2001), Influenza B virus (B/Finland/WV4/2002), Influenza B virus (B/Finland/WV5/2002), Influenza B virus (B/Florida/02/1998), Influenza B virus (B/Florida/02/2006), Influenza B virus (B/Florida/1/2000), Influenza B virus (B/Florida/1/2004), Influenza B virus (B/Florida/2/2004), Influenza B virus (B/Florida/2/2005), Influenza B virus (B/Florida/2/2006), Influenza B virus (B/Florida/7e/2004), Influenza B virus (B/Fujian/36/82), Influenza B virus (B/Geneva/5079/03), Influenza B virus (B/Genoa/11/02), Influenza B virus (B/Genoa/2/02), Influenza B virus (B/Genoa/21/02), Influenza B virus (B/Genoa/33/02), Influenza B virus (B/Genoa/41/02), Influenza B virus (B/Genoa/52/02), Influenza B virus (B/Genoa/55/02), Influenza B virus (B/Genoa/56/02), Influenza B virus (B/Genoa/7/02), Influenza B virus (B/Genoa/8/02), Influenza B virus (B/Genoa12/02), Influenza B virus (B/Genoa3/02), Influenza B virus (B/Genoa48/02), Influenza B virus (B/Genoa49/02), Influenza B virus (B/Genoa5/02), Influenza B virus (B/Genoa53/02), Influenza B virus (B/Genoa6/02), Influenza B virus (B/Genoa65/02), Influenza B virus (B/Genova/1294/03), Influenza B virus (B/Genova/1603/03), Influenza B virus (B/Genova/2/02), Influenza B virus (B/Genova/20/02), Influenza B virus (B/Genova/2059/03), Influenza B virus (B/Genova/26/02), Influenza B virus (B/Genova/30/02), Influenza B virus (B/Genova/54/02), Influenza B virus (B/Genova/55/02), Influenza B virus (B/Georgia/02/1998), Influenza B virus (B/Georgia/04/1998), Influenza B virus (B/Georgia/09/2005), Influenza B virus (B/Georgia/1/2000), Influenza B virus (B/Georgia/1/2005), Influenza B virus (B/Georgia/2/2005), Influenza B virus (B/Georgia/9/2005), Influenza B virus (B/Guangdong/05/94), Influenza B virus (B/Guangdong/08/93), Influenza B virus (B/Guangdong/5/94), Influenza B virus (B/Guangdong/55/89), Influenza B virus (B/Guangdong/8/93), Influenza B virus (B/Guangzhou/7/97), Influenza B virus (B/Guangzhou/86/92), Influenza B virus (B/Guangzhou/87/92), Influenza B virus (B/Gyeonggi/592/2005), Influenza B virus (B/Hannover/2/90), Influenza B virus (B/Harbin/07/94), Influenza B virus (B/Hawaii/1/2003), Influenza B virus (B/Hawaii/10/2001), Influenza B virus (B/Hawaii/10/2004), Influenza B virus (B/Hawaii/11/2004), Influenza B virus (B/Hawaii/11e/2004), Influenza B virus (B/Hawaii/11e/2005), Influenza B virus (B/Hawaii/12e/2005), Influenza B virus (B/Hawaii/13/2004), Influenza B virus (B/Hawaii/13e/2004), Influenza B virus (B/Hawaii/17/2001), Influenza B virus (B/Hawaii/18e/2004), Influenza B virus (B/Hawaii/1990/2004), Influenza B virus (B/Hawaii/1993/2004), Influenza B virus (B/Hawaii/19e/2004), Influenza B virus (B/Hawaii/2/2000), Influenza B virus (B/Hawaii/2/2003), Influenza B virus (B/Hawaii/20e/2004), Influenza B virus (B/Hawaii/21/2004), Influenza B virus (B/Hawaii/26/2001), Influenza B virus (B/Hawaii/31e/2004), Influenza B virus (B/Hawaii/32e/2004), Influenza B virus (B/Hawaii/33e/2004), Influenza B virus (B/Hawaii/35/2001), Influenza B virus (B/Hawaii/36/2001), Influenza B virus (B/Hawaii/37/2001), Influenza B virus (B/Hawaii/38/2001), Influenza B virus (B/Hawaii/4/2006), Influenza B virus (B/Hawaii/43/2001), Influenza B virus (B/Hawaii/44/2001), Influenza B virus (B/Hawaii/9/2001), Influenza B virus (B/Hebei/19/94), Influenza B virus (B/Hebei/3/94), Influenza B virus (B/Hebei/4/95), Influenza B virus (B/Henan/22/97), Influenza B virus (B/Hiroshima/23/2001), Influenza B virus (B/Hong Kong/02/1993), Influenza B virus (B/Hong Kong/03/1992), Influenza B virus (B/Hong Kong/05/1972), Influenza B virus (B/Hong Kong/06/2001), Influenza B virus (B/Hong Kong/110/99), Influenza B virus (B/Hong Kong/1115/2002), Influenza B virus (B/Hong Kong/112/2001), Influenza B virus (B/Hong Kong/123/2001), Influenza B virus (B/Hong Kong/1351/02), Influenza B virus (B/Hong Kong/1351/2002), Influenza B virus (B/Hong Kong/1434/2002), Influenza B virus (B/Hong Kong/147/99), Influenza B virus (B/Hong Kong/156/99), Influenza B virus (B/Hong Kong/157/99), Influenza B virus (B/Hong Kong/167/2002), Influenza B virus (B/Hong Kong/22/1989), Influenza B virus (B/Hong Kong/22/2001), Influenza B virus (B/Hong Kong/22/89), Influenza B virus (B/Hong Kong/28/2001), Influenza B virus (B/Hong Kong/293/02), Influenza B virus (B/Hong Kong/310/2004), Influenza B virus (B/Hong Kong/329/2001), Influenza B virus (B/Hong Kong/330/2001 egg adapted), Influenza B virus (B/Hong Kong/330/2001), Influenza B virus (B/Hong Kong/330/2002), Influenza B virus (B/Hong Kong/335/2001), Influenza B virus (B/Hong Kong/336/2001), Influenza B virus (B/Hong Kong/497/2001), Influenza B virus (B/Hong Kong/542/2000), Influenza B virus (B/Hong Kong/548/2000), Influenza B virus (B/Hong Kong/553a/2003), Influenza B virus (B/Hong Kong/557/2000), Influenza B virus (B/Hong Kong/6/2001), Influenza B virus (B/Hong Kong/666/2001), Influenza B virus (B/Hong Kong/692/01), Influenza B virus (B/Hong Kong/70/1996), Influenza B virus (B/Hong Kong/8/1973), Influenza B virus (B/Hong Kong/9/89), Influenza B virus (B/Houston/1/91), Influenza B virus (B/Houston/1/92), Influenza B virus (B/Houston/1/96), Influenza B virus (B/Houston/2/93), Influenza B virus (B/Houston/2/96), Influenza B virus (B/Houston/B15/1999), Influenza B virus (B/Houston/B56/1997), Influenza B virus (B/Houston/B57/1997), Influenza B virus (B/Houston/B58/1997), Influenza B virus (B/Houston/B59/1997), Influenza B virus (B/Houston/B60/1997), Influenza B virus (B/Houston/B61/1997), Influenza B virus (B/Houston/B63/1997), Influenza B virus (B/Houston/B65/1998), Influenza B virus (B/Houston/B66/2000), Influenza B virus (B/Houston/B67/2000), Influenza B virus (B/Houston/B68/2000), Influenza B virus (B/Houston/B69/2002), Influenza B virus (B/Houston/B70/2002), Influenza B virus (B/Houston/B71/2002), Influenza B virus (B/Houston/B720/2004), Influenza B virus (B/Houston/B74/2002), Influenza B virus (B/Houston/B745/2005), Influenza B virus (B/Houston/B75/2002), Influenza B virus (B/Houston/B756/2005), Influenza B virus (B/Houston/B77/2002), Influenza B virus (B/Houston/B787/2005), Influenza B virus (B/Houston/B79/2003), Influenza B virus (B/Houston/B81/2003), Influenza B virus (B/Houston/B84/2003), Influenza B virus (B/Houston/B846/2005), Influenza B virus (B/Houston/B850/2005), Influenza B virus (B/Houston/B86/2003), Influenza B virus (B/Houston/B87/2003), Influenza B virus (B/Houston/B88/2003), Influenza B virus (B/Hunan/4/72), Influenza B virus (B/Ibaraki/2/85), Influenza B virus (B/Idaho/1/2005), Influenza B virus (B/Illinois/1/2004), Influenza B virus (B/Illinois/13/2004), Influenza B virus (B/Illinois/13/2005), Influenza B virus (B/Illinois/13e/2005), Influenza B virus (B/Illinois/3/2001), Influenza B virus (B/Illinois/3/2005), Influenza B virus (B/Illinois/33/2005), Influenza B virus (B/Illinois/36/2005), Influenza B virus (B/Illinois/4/2005), Influenza B virus (B/Illinois/47/2005), Influenza B virus (B/Incheon/297/2005), Influenza B virus (B/India/3/89), Influenza B virus (B/India/7526/2001), Influenza B virus (B/India/7569/2001), Influenza B virus (B/India/7600/2001), Influenza B virus (B/India/7605/2001), Influenza B virus (B/India/77276/2001), Influenza B virus (B/Indiana/01/1995), Influenza B virus (B/Indiana/3/2006), Influenza B virus (B/Indiana/5/2006), Influenza B virus (B/Iowa/03/2002), Influenza B virus (B/Iowa/1/2001), Influenza B virus (B/Iowa/1/2005), Influenza B virus (B/Israel/95/03), Influenza B virus (B/Israel/WV124/2002), Influenza B virus (B/Israel/WV126/2002), Influenza B virus (B/Israel/WV133/2002), Influenza B virus (B/Israel/WV135/2002), Influenza B virus (B/Israel/WV137/2002), Influenza B virus (B/Israel/WV142/2002), Influenza B virus (B/Israel/WV143/2002), Influenza B virus (B/Israel/WV145/2002), Influenza B virus (B/Israel/WV146/2002), Influenza B virus (B/Israel/WV150/2002), Influenza B virus (B/Israel/WV153/2002), Influenza B virus (B/Israel/WV158/2002), Influenza B virus (B/Israel/WV161/2002), Influenza B virus (B/Israel/WV166/2002), Influenza B virus (B/Israel/WV169/2002), Influenza B virus (B/Israel/WV170/2002), Influenza B virus (B/Israel/WV174/2002), Influenza B virus (B/Israel/WV183/2002), Influenza B virus (B/Israel/WV187/2002), Influenza B virus (B/Istanbul/CTF-132/05), Influenza B virus (B/Japan/1224/2005), Influenza B virus (B/Japan/1905/2005), Influenza B virus (B/Jiangsu/10/03), Influenza B virus (B/Jiangsu/10/2003 (recomb)), Influenza B virus (B/Jiangsu/10/2003), Influenza B virus (B/Jilin/20/2003), Influenza B virus (B/Johannesburg/05/1999), Influenza B virus (B/Johannesburg/06/1994), Influenza B virus (B/Johannesburg/1/99), Influenza B virus (B/Johannesburg/113/010), Influenza B virus (B/Johannesburg/116/01), Influenza B virus (B/Johannesburg/119/01), Influenza B virus (B/Johannesburg/123/01), Influenza B virus (B/Johannesburg/163/99), Influenza B virus (B/Johannesburg/187/99), Influenza B virus (B/Johannesburg/189/99), Influenza B virus (B/Johannesburg/2/99), Influenza B virus (B/Johannesburg/27/2005), Influenza B virus (B/Johannesburg/33/01), Influenza B virus (B/Johannesburg/34/01), Influenza B virus (B/Johannesburg/35/01), Influenza B virus (B/Johannesburg/36/01), Influenza B virus (B/Johannesburg/41/99), Influenza B virus (B/Johannesburg/5/99), Influenza B virus (B/Johannesburg/69/2001), Influenza B virus (B/Johannesburg/77/01), Influenza B virus (B/Johannesburg/94/99), Influenza B virus (B/Johannesburg/96/01), Influenza B virus (B/Kadoma/1076/99), Influenza B virus (B/Kadoma/122/99), Influenza B virus (B/Kadoma/122/99-V1), Influenza B virus (B/Kadoma/122/99-V10), Influenza B virus (B/Kadoma/122/99-V11), Influenza B virus (B/Kadoma/122/99-V2), Influenza B virus (B/Kadoma/122/99-V3), Influenza B virus (B/Kadoma/122/99-V4), Influenza B virus (B/Kadoma/122/99-V5), Influenza B virus (B/Kadoma/122/99-V6), Influenza B virus (B/Kadoma/122/99-V7), Influenza B virus (B/Kadoma/122/99-V8), Influenza B virus (B/Kadoma/122/99-V9), Influenza B virus (B/Kadoma/136/99), Influenza B virus (B/Kadoma/409/2000), Influenza B virus (B/Kadoma/506/99), Influenza B virus (B/kadoma/642/99), Influenza B virus (B/Kadoma/647/99), Influenza B virus (B/Kagoshima/15/94), Influenza B virus (B/Kanagawa/73), Influenza B virus (B/Kansas/1/2005), Influenza B virus (B/Kansas/22992/99), Influenza B virus (B/Kentucky/4/2005), Influenza B virus (B/Khazkov/224/91), Influenza B virus (B/Kisumu/2036/2006), Influenza B virus (B/Kisumu/2037/2006), Influenza B virus (B/Kisumu/2038/2006), Influenza B virus (B/Kisumu/2039/2006), Influenza B virus (B/Kisumu/2040/2006), Influenza B virus (B/Kisumu/7/2005), Influenza B virus (B/Kobe/1/2002), Influenza B virus (B/Kobe/1/2002-V1), Influenza B virus (B/Kobe/1/2002-V2), Influenza B virus (B/Kobe/1/2003), Influenza B virus (B/Kobe/1/94), Influenza B virus (B/Kobe/2/2002), Influenza B virus (B/Kobe/2/2003), Influenza B virus (B/Kobe/25/2003), Influenza B virus (B/Kobe/26/2003), Influenza B virus (B/Kobe/28/2003), Influenza B virus (B/Kobe/3/2002), Influenza B virus (B/Kobe/3/2003), Influenza B virus (B/Kobe/4/2002), Influenza B virus (B/Kobe/4/2003), Influenza B virus (B/Kobe/5/2002), Influenza B virus (B/Kobe/6/2002), Influenza B virus (B/Kobe/64/2001), Influenza B virus (B/Kobe/65/2001), Influenza B virus (B/Kobe/69/2001), Influenza B virus (B/Kobe/7/2002), Influenza B virus (B/Kobe/79/2001), Influenza B virus (B/Kobe/83/2001), Influenza B virus (B/Kobe/87/2001), Influenza B virus (B/Kouchi/193/1999), Influenza B virus (B/Kouchi/193/99), Influenza B virus (B/Lazio/1/02), Influenza B virus (B/Lee/40), Influenza B virus (B/Leningrad/129/91), Influenza B virus (B/Leningrad/148/91), Influenza B virus (B/Lisbon/02/1994), Influenza B virus (B/Lissabon/2/90), Influenza B virus (B/Los Angeles/1/02), Influenza B virus (B/Lusaka/270/99), Influenza B virus (B/Lusaka/432/99), Influenza B virus (B/Lyon/1271/96), Influenza B virus (B/Malaysia/83077/2001), Influenza B virus (B/Maputo/1/99), Influenza B virus (B/Maputo/2/99), Influenza B virus (B/Mar del Plata/595/99), Influenza B virus (B/Mar del Plata/VL373/99), Influenza B virus (B/Mar del Plata/VL385/99), Influenza B virus (B/Maryland/1/01), Influenza B virus (B/Maryland/1/2002), Influenza B virus (B/Maryland/2/2001), Influenza B virus (B/Maryland/7/2003), Influenza B virus (B/Massachusetts/1/2004), Influenza B virus (B/Massachusetts/2/2004), Influenza B virus (B/Massachusetts/3/2004), Influenza B virus (B/Massachusetts/4/2001), Influenza B virus (B/Massachusetts/5/2003), Influenza B virus (B/Memphis/1/01), Influenza B virus (B/Memphis/10/97), Influenza B virus (B/Memphis/11/2006), Influenza B virus (B/Memphis/12/2006), Influenza B virus (B/Memphis/12/97), Influenza B virus (B/Memphis/12/97-MA), Influenza B virus (B/Memphis/13/03), Influenza B virus (B/Memphis/18/95), Influenza B virus (B/Memphis/19/96), Influenza B virus (B/Memphis/20/96), Influenza B virus (B/Memphis/21/96), Influenza B virus (B/Memphis/28/96), Influenza B virus (B/Memphis/3/01), Influenza B virus (B/Memphis/3/89), Influenza B virus (B/Memphis/3/93), Influenza B virus (B/Memphis/4/93), Influenza B virus (B/Memphis/5/93), Influenza B virus (B/Memphis/7/03), Influenza B virus (B/Memphis/8/99), Influenza B virus (B/Mexico/84/2000), Influenza B virus (B/Michigan/04/2006), Influenza B virus (B/Michigan/1/2005), Influenza B virus (B/Michigan/1/2006), Influenza B virus (B/Michigan/2/2004), Influenza B virus (B/Michigan/20/2005), Influenza B virus (B/Michigan/22572/99), Influenza B virus (B/Michigan/22587/99), Influenza B virus (B/Michigan/22596/99), Influenza B virus (B/Michigan/22631/99), Influenza B virus (B/Michigan/22659/99), Influenza B virus (B/Michigan/22687/99), Influenza B virus (B/Michigan/22691/99), Influenza B virus (B/Michigan/22721/99), Influenza B virus (B/Michigan/22723/99), Influenza B virus (B/Michigan/2e/2006), Influenza B virus (B/Michigan/3/2004), Influenza B virus (B/Michigan/4/2006), Influenza B virus (B/Michigan/e3/2006), Influenza B virus (B/micona/1/1989), Influenza B virus (B/Mie/01/1993), Influenza B virus (B/Mie/1/93), Influenza B virus (B/Milano/1/01), Influenza B virus (B/Milano/1/02), Influenza B virus (B/Milano/5/02), Influenza B virus (B/Milano/6/02), Influenza B virus (B/Milano/66/04), Influenza B virus (B/Milano/7/02), Influenza B virus (B/Minnesota/1/1985), Influenza B virus (B/Minnesota/14/2001), Influenza B virus (B/Minnesota/2/2001), Influenza B virus (B/Minsk/318/90), Influenza B virus (B/Mississippi/1/2001), Influenza B virus (B/Mississippi/2/2005), Influenza B virus (B/Mississippi/3/2001), Influenza B virus (B/Mississippi/3/2005), Influenza B virus (B/Mississippi/4/2003), Influenza B virus (B/Mississippi/4e/2005), Influenza B virus (B/Missouri/1/2006), Influenza B virus (B/Missouri/11/2003), Influenza B virus (B/Missouri/2/2005), Influenza B virus (B/Missouri/20/2003), Influenza B virus (B/Missouri/6/2005), Influenza B virus (B/Montana/1/2003), Influenza B virus (B/Montana/1/2006), Influenza B virus (B/Montana/1e/2004), Influenza B virus (B/Moscow/16/2002), Influenza B virus (B/Moscow/3/03), Influenza B virus (B/Nagoya/20/99), Influenza B virus (B/Nairobi/2032/2006), Influenza B virus (B/Nairobi/2033/2006), Influenza B virus (B/Nairobi/2034/2006), Influenza B virus (B/Nairobi/2035/2006), Influenza B virus (B/Nairobi/351/2005), Influenza B virus (B/Nairobi/670/2005), Influenza B virus (B/Nanchang/1/00), Influenza B virus (B/Nanchang/1/2000), Influenza B virus (B/Nanchang/12/98), Influenza B virus (B/Nanchang/15/95), Influenza B virus (B/Nanchang/15/97), Influenza B virus (B/Nanchang/195/94), Influenza B virus (B/Nanchang/2/97), Influenza B virus (B/Nanchang/20/96), Influenza B virus (B/Nanchang/26/93), Influenza B virus (B/Nanchang/3/95), Influenza B virus (B/Nanchang/4/97), Influenza B virus (B/Nanchang/480/94), Influenza B virus (B/Nanchang/5/97), Influenza B virus (B/Nanchang/560/94), Influenza B virus (B/Nanchang/560a/94), Influenza B virus (B/Nanchang/560b/94), Influenza B virus (B/Nanchang/6/96), Influenza B virus (B/Nanchang/6/98), Influenza B virus (B/Nanchang/630/94), Influenza B virus (B/Nanchang/7/98), Influenza B virus (B/Nanchang/8/95), Influenza B virus (B/Nashville/107/93), Influenza B virus (B/Nashville/3/96), Influenza B virus (B/Nashville/34/96), Influenza B virus (B/Nashville/45/91), Influenza B virus (B/Nashville/48/91), Influenza B virus (B/Nashville/6/89), Influenza B virus (B/Nebraska/1/01), Influenza B virus (B/Nebraska/1/2005), Influenza B virus (B/Nebraska/2/01), Influenza B virus (B/Nebraska/4/2001), Influenza B virus (B/Nebraska/5/2003), Influenza B virus (B/Nepal/1078/2005), Influenza B virus (B/Nepal/1079/2005), Influenza B virus (B/Nepal/1080/2005), Influenza B virus (B/Nepal/1087/2005), Influenza B virus (B/Nepal/1088/2005), Influenza B virus (B/Nepal/1089/2005), Influenza B virus (B/Nepal/1090/2005), Influenza B virus (B/Nepal/1092/2005), Influenza B virus (B/Nepal/1098/2005), Influenza B virus (B/Nepal/1101/2005), Influenza B virus (B/Nepal/1103/2005), Influenza B virus (B/Nepal/1104/2005), Influenza B virus (B/Nepal/1105/2005), Influenza B virus (B/Nepal/1106/2005), Influenza B virus (B/Nepal/1108/2005), Influenza B virus (B/Nepal/1114/2005), Influenza B virus (B/Nepal/1117/2005), Influenza B virus (B/Nepal/1118/2005), Influenza B virus (B/Nepal/1120/2005), Influenza B virus (B/Nepal/1122/2005), Influenza B virus (B/Nepal/1131/2005), Influenza B virus (B/Nepal/1132/2005), Influenza B virus (B/Nepal/1136/2005), Influenza B virus (B/Nepal/1137/2005), Influenza B virus (B/Nepal/1138/2005), Influenza B virus (B/Nepal/1139/2005), Influenza B virus (B/Nepal/1331/2005), Influenza B virus (B/Netherland/2781/90), Influenza B virus (B/Netherland/6357/90), Influenza B virus (B/Netherland/800/90), Influenza B virus (B/Netherland/801/90), Influenza B virus (B/Netherlands/1/97), Influenza B virus (B/Netherlands/13/94), Influenza B virus (B/Netherlands/2/95), Influenza B virus (B/Netherlands/31/95), Influenza B virus (B/Netherlands/32/94), Influenza B virus (B/Netherlands/384/95), Influenza B virus (B/Netherlands/429/98), Influenza B virus (B/Netherlands/580/89), Influenza B virus (B/Netherlands/6/96), Influenza B virus (B/Nevada/1/2001), Influenza B virus (B/Nevada/1/2002), Influenza B virus (B/Nevada/1/2005), Influenza B virus (B/Nevada/1/2006), Influenza B virus (B/Nevada/2/2003), Influenza B virus (B/Nevada/2/2006), Influenza B virus (B/Nevada/3/2006), Influenza B virus (B/Nevada/5/2005), Influenza B virus (B/New Jersey/1/2002), Influenza B virus (B/New Jersey/1/2004), Influenza B virus (B/New Jersey/1/2005), Influenza B virus (B/New Jersey/1/2006), Influenza B virus (B/New Jersey/3/2001), Influenza B virus (B/New Jersey/3/2005), Influenza B virus (B/New Jersey/4/2001), Influenza B virus (B/New Jersey/5/2005), Influenza B virus (B/New Jersey/6/2005), Influenza B virus (B/New Mexico/1/2001), Influenza B virus (B/New Mexico/1/2006), Influenza B virus (B/New Mexico/2/2005), Influenza B virus (B/New Mexico/9/2003), Influenza B virus (B/New York/1/2001), Influenza B virus (B/New York/1/2002), Influenza B virus (B/New York/1/2004), Influenza B virus (B/New York/1/2006), Influenza B virus (B/New York/10/2002), Influenza B virus (B/New York/11/2005), Influenza B virus (B/New York/12/2001), Influenza B virus (B/New York/12/2005), Influenza B virus (B/New York/12e/2005), Influenza B virus (B/New York/14e/2005), Influenza B virus (B/New York/17/2004), Influenza B virus (B/New York/18/2003), Influenza B virus (B/New York/19/2004), Influenza B virus (B/New York/2/2000), Influenza B virus (B/New York/2/2002), Influenza B virus (B/New York/2/2006), Influenza B virus (B/New York/20139/99), Influenza B virus (B/New York/24/1993), Influenza B virus (B/New York/2e/2005), Influenza B virus (B/New York/3/90), Influenza B virus (B/New York/39/1991), Influenza B virus (B/New York/40/2002), Influenza B virus (B/New York/47/2001), Influenza B virus (B/New York/6/2004), Influenza B virus (B/New York/7/2002), Influenza B virus (B/New York/8/2000), Influenza B virus (B/New York/9/2002), Influenza B virus (B/New York/9/2004), Influenza B virus (B/New York/C10/2004), Influenza B virus (B/NIB/48/90), Influenza B virus (B/Ningxia/45/83), Influenza B virus (B/North Carolina/1/2005), Influenza B virus (B/North Carolina/3/2005), Influenza B virus (B/North Carolina/4/2004), Influenza B virus (B/North Carolina/5/2004), Influenza B virus (B/Norway/1/84), Influenza B virus (B/Ohio/1/2005), Influenza B virus (B/Ohio/1/X-19/2005), Influenza B virus (B/Ohio/1e/2005), Influenza B virus (B/Ohio/1e4/2005), Influenza B virus (B/Ohio/2/2002), Influenza B virus (B/Ohio/2e/2005), Influenza B virus (B/Oita/15/1992), Influenza B virus (B/Oklahoma/1/2006), Influenza B virus (B/Oklahoma/2/2005), Influenza B virus (B/Oman/16291/2001), Influenza B virus (B/Oman/16296/2001), Influenza B virus (B/Oman/16299/2001), Influenza B virus (B/Oman/16305/2001), Influenza B virus (B/Oregon/1/2005), Influenza B virus (B/Oregon/1/2006), Influenza B virus (B/Oregon/5/80), Influenza B virus (B/Osaka/1036/97), Influenza B virus (B/Osaka/1058/97), Influenza B virus (B/Osaka/1059/97), Influenza B virus (B/Osaka/1146/1997), Influenza B virus (B/Osaka/1169/97), Influenza B virus (B/Osaka/1201/2000), Influenza B virus (B/Osaka/547/1997), Influenza B virus (B/Osaka/547/97), Influenza B virus (B/Osaka/710/1997), Influenza B virus (B/Osaka/711/97), Influenza B virus (B/Osaka/728/1997), Influenza B virus (B/Osaka/755/1997), Influenza B virus (B/Osaka/820/1997), Influenza B virus (B/Osaka/837/1997), Influenza B virus (B/Osaka/854/1997), Influenza B virus (B/Osaka/983/1997), Influenza B virus (B/Osaka/983/1997-M1), Influenza B virus (B/Osaka/983/1997-M2), Influenza B virus (B/Osaka/983/97-V1), Influenza B virus (B/Osaka/983/97-V2), Influenza B virus (B/Osaka/983/97-V3), Influenza B virus (B/Osaka/983/97-V4), Influenza B virus (B/Osaka/983/97-V5), Influenza B virus (B/Osaka/983/97-V6), Influenza B virus (B/Osaka/983/97-V7), Influenza B virus (B/Osaka/983/97-V8), Influenza B virus (B/Osaka/c19/93), Influenza B virus (B/Oslo/1072/2001), Influenza B virus (B/Oslo/1329/2002), Influenza B virus (B/Oslo/1510/2002), Influenza B virus (B/Oslo/1846/2002), Influenza B virus (B/Oslo/1847/2002), Influenza B virus (B/Oslo/1862/2001), Influenza B virus (B/Oslo/1864/2001), Influenza B virus (B/Oslo/1870/2002), Influenza B virus (B/Oslo/1871/2002), Influenza B virus (B/Oslo/2293/2001), Influenza B virus (B/Oslo/2295/2001), Influenza B virus (B/Oslo/2297/2001), Influenza B virus (B/Oslo/238/2001), Influenza B virus (B/Oslo/3761/2000), Influenza B virus (B/Oslo/47/2001), Influenza B virus (B/Oslo/668/2002), Influenza B virus (B/Oslo/71/04), Influenza B virus (B/Oslo/801/99), Influenza B virus (B/Oslo/805/99), Influenza B virus (B/Oslo/837/99), Influenza B virus (B/Panama/45/1990), Influenza B virus (B/Panama/45/90), Influenza B virus (B/Paraguay/636/2003), Influenza B virus (B/Paris/329/90), Influenza B virus (B/Paris/549/1999), Influenza B virus (B/Parma/1/03), Influenza B virus (B/Parma/1/04), Influenza B virus (B/Parma/13/02), Influenza B virus (B/Parma/16/02), Influenza B virus (B/Parma/2/03), Influenza B virus (B/Parma/2/04), Influenza B virus (B/Parma/23/02), Influenza B virus (B/Parma/24/02), Influenza B virus (B/Parma/25/02), Influenza B virus (B/Parma/28/02), Influenza B virus (B/Parma/3/04), Influenza B virus (B/Parma/4/04), Influenza B virus (B/Parma/5/02), Influenza B virus (B/Pennsylvania/1/2006), Influenza B virus (B/Pennsylvania/2/2001), Influenza B virus (B/Pennsylvania/2/2006), Influenza B virus (B/Pennsylvania/3/2003), Influenza B virus (B/Pennsylvania/3/2006), Influenza B virus (B/Pennsylvania/4/2004), Influenza B virus (B/Perth/211/2001), Influenza B virus (B/Perth/25/2002), Influenza B virus (B/Peru/1324/2004), Influenza B virus (B/Peru/1364/2004), Influenza B virus (B/Perugia/4/03), Influenza B virus (B/Philippines/5072/2001), Influenza B virus (B/Philippines/93079/2001), Influenza B virus (B/Pusan/250/99), Influenza B virus (B/Pusan/255/99), Influenza B virus (B/Pusan/270/99), Influenza B virus (B/Pusan/285/99), Influenza B virus (B/Quebec/1/01), Influenza B virus (B/Quebec/162/98), Influenza B virus (B/Quebec/173/98), Influenza B virus (B/Quebec/2/01), Influenza B virus (B/Quebec/3/01), Influenza B virus (B/Quebec/4/01), Influenza B virus (B/Quebec/452/98), Influenza B virus (B/Quebec/453/98), Influenza B virus (B/Quebec/465/98), Influenza B virus (B/Quebec/51/98), Influenza B virus (B/Quebec/511/98), Influenza B virus (B/Quebec/514/98), Influenza B virus (B/Quebec/517/98), Influenza B virus (B/Quebec/6/01), Influenza B virus (B/Quebec/7/01), Influenza B virus (B/Quebec/74199/99), Influenza B virus (B/Quebec/74204/99), Influenza B virus (B/Quebec/74206/99), Influenza B virus (B/Quebec/8/01), Influenza B virus (B/Quebec/9/01), Influenza B virus (B/Rabat/41/97), Influenza B virus (B/Rabat/45/97), Influenza B virus (B/Rabat/61/97), Influenza B virus (B/RiodeJaneiro/200/02), Influenza B virus (B/RiodeJaneiro/209/02), Influenza B virus (B/RiodeJaneiro/315/01), Influenza B virus (B/RiodeJaneiro/353/02), Influenza B virus (B/RiodeJaneiro/354/02), Influenza B virus (B/RioGdoSul/337/01), Influenza B virus (B/RioGdoSul/357/02), Influenza B virus (B/RioGdoSul/374/01), Influenza B virus (B/Roma/1/03), Influenza B virus (B/Roma/2/03), Influenza B virus (B/Roma/3/03), Influenza B virus (B/Roma/4/02), Influenza B virus (B/Roma/7/02), Influenza B virus (B/Romania/217/1999), Influenza B virus (B/Romania/318/1998), Influenza B virus (B/Russia/22/1995), Influenza B virus (B/Saga/S172/99), Influenza B virus (B/Seal/Netherlands/1/99), Influenza B virus (B/Seoul/1/89), Influenza B virus (B/Seoul/1163/2004), Influenza B virus (B/Seoul/12/88), Influenza B virus (B/seoul/12/95), Influenza B virus (B/Seoul/13/95), Influenza B virus (B/Seoul/16/97), Influenza B virus (B/Seoul/17/95), Influenza B virus (B/Seoul/19/97), Influenza B virus (B/Seoul/21/95), Influenza B virus (B/Seoul/232/2004), Influenza B virus (B/Seoul/28/97), Influenza B virus (B/Seoul/31/97), Influenza B virus (B/Seoul/37/91), Influenza B virus (B/Seoul/38/91), Influenza B virus (B/Seoul/40/91), Influenza B virus (B/Seoul/41/91), Influenza B virus (B/Seoul/6/88), Influenza B virus (B/Shandong/7/97), Influenza B virus (B/Shangdong/7/97), Influenza B virus (B/Shanghai/1/77), Influenza B virus (B/Shanghai/10/80), Influenza B virus (B/Shanghai/24/76), Influenza B virus (B/Shanghai/35/84), Influenza B virus (B/Shanghai/361/03), Influenza B virus (B/Shanghai/361/2002), Influenza B virus (B/Shenzhen/423/99), Influenza B virus (B/Shiga/51/98), Influenza B virus (B/Shiga/N18/98), Influenza B virus (B/Shiga/T30/98), Influenza B virus (B/Shiga/T37/98), Influenza B virus (B/Shizuoka/15/2001), Influenza B virus (B/Shizuoka/480/2000), Influenza B virus (B/Sichuan/281/96), Influenza B virus (B/Sichuan/317/2001), Influenza B virus (B/Sichuan/379/99), Influenza B virus (B/Sichuan/38/2000), Influenza B virus (B/Sichuan/8/92), Influenza B virus (B/Siena/1/02), Influenza B virus (B/Singapore/04/1991), Influenza B virus (B/Singapore/11/1994), Influenza B virus (B/Singapore/22/1998), Influenza B virus (B/Singapore/222/79), Influenza B virus (B/Singapore/31/1998), Influenza B virus (B/Singapore/35/1998), Influenza B virus (B/South Australia/5/1999), Influenza B virus (B/South Carolina/04/2003), Influenza B virus (B/South Carolina/25723/99), Influenza B virus (B/South Carolina/3/2003), Influenza B virus (B/South Carolina/4/2003), Influenza B virus (B/South Dakota/1/2000), Influenza B virus (B/South Dakota/3/2003), Influenza B virus (B/South Dakota/5/89), Influenza B virus (B/Spain/WV22/2002), Influenza B virus (B/Spain/WV26/2002), Influenza B virus (B/Spain/WV27/2002), Influenza B virus (B/Spain/WV29/2002), Influenza B virus (B/Spain/WV33/2002), Influenza B virus (B/Spain/WV34/2002), Influenza B virus (B/Spain/WV36/2002), Influenza B virus (B/Spain/WV41/2002), Influenza B virus (B/Spain/WV42/2002), Influenza B virus (B/Spain/WV43/2002), Influenza B virus (B/Spain/WV45/2002), Influenza B virus (B/Spain/WV50/2002), Influenza B virus (B/Spain/WV51/2002), Influenza B virus (B/Spain/WV56/2002), Influenza B virus (B/Spain/WV57/2002), Influenza B virus (B/Spain/WV65/2002), Influenza B virus (B/Spain/WV66/2002), Influenza B virus (B/Spain/WV67/2002), Influenza B virus (B/Spain/WV69/2002), Influenza B virus (B/Spain/WV70/2002), Influenza B virus (B/Spain/WV73/2002), Influenza B virus (B/Spain/WV78/2002), Influenza B virus (B/St. Petersburg/14/2006), Influenza B virus (B/StaCatarina/308/02), Influenza B virus (B/StaCatarina/315/02), Influenza B virus (B/StaCatarina/318/02), Influenza B virus (B/StaCatarina/345/02), Influenza B virus (B/Stockholm/10/90), Influenza B virus (B/Suzuka/18/2005), Influenza B virus (B/Suzuka/28/2005), Influenza B virus (B/Suzuka/32/2005), Influenza B virus (B/Suzuka/58/2005), Influenza B virus (B/Switzerland/4291/97), Influenza B virus (B/Switzerland/5219/90), Influenza B virus (B/Switzerland/5241/90), Influenza B virus (B/Switzerland/5441/90), Influenza B virus (B/Switzerland/5444/90), Influenza B virus (B/Switzerland/5812/90), Influenza B virus (B/Switzerland/6121/90), Influenza B virus (B/Taiwan/0002/03), Influenza B virus (B/Taiwan/0114/01), Influenza B virus (B/Taiwan/0202/01), Influenza B virus (B/Taiwan/0409/00), Influenza B virus (B/Taiwan/0409/02), Influenza B virus (B/Taiwan/0562/03), Influenza B virus (B/Taiwan/0569/03), Influenza B virus (B/Taiwan/0576/03), Influenza B virus (B/Taiwan/0600/02), Influenza B virus (B/Taiwan/0610/03), Influenza B virus (B/Taiwan/0615/03), Influenza B virus (B/Taiwan/0616/03), Influenza B virus (B/Taiwan/0654/02), Influenza B virus (B/Taiwan/0684/03), Influenza B virus (B/Taiwan/0699/03), Influenza B virus (B/Taiwan/0702/02), Influenza B virus (B/Taiwan/0722/02), Influenza B virus (B/Taiwan/0730/02), Influenza B virus (B/Taiwan/0735/03), Influenza B virus (B/Taiwan/0833/03), Influenza B virus (B/Taiwan/0874/02), Influenza B virus (B/Taiwan/0879/02), Influenza B virus (B/Taiwan/0880/02), Influenza B virus (B/Taiwan/0927/02), Influenza B virus (B/Taiwan/0932/02), Influenza B virus (B/Taiwan/0993/02), Influenza B virus (B/Taiwan/1013/02), Influenza B virus (B/Taiwan/1013/03), Influenza B virus (B/Taiwan/102/2005), Influenza B virus (B/Taiwan/103/2005), Influenza B virus (B/Taiwan/110/2005), Influenza B virus (B/Taiwan/1103/2001), Influenza B virus (B/Taiwan/114/2001), Influenza B virus (B/Taiwan/11515/2001), Influenza B virus (B/Taiwan/117/2005), Influenza B virus (B/Taiwan/1197/1994), Influenza B virus (B/Taiwan/121/2005), Influenza B virus (B/Taiwan/12192/2000), Influenza B virus (B/Taiwan/1243/99), Influenza B virus (B/Taiwan/1265/2000), Influenza B virus (B/Taiwan/1293/2000), Influenza B virus (B/Taiwan/13/2004), Influenza B virus (B/Taiwan/14/2004), Influenza B virus (B/Taiwan/1484/2001), Influenza B virus (B/Taiwan/1502/02), Influenza B virus (B/Taiwan/1503/02), Influenza B virus (B/Taiwan/1534/02), Influenza B virus (B/Taiwan/1536/02), Influenza B virus (B/Taiwan/1561/02), Influenza B virus (B/Taiwan/1574/03), Influenza B virus (B/Taiwan/1584/02), Influenza B virus (B/Taiwan/16/2004), Influenza B virus (B/Taiwan/1618/03), Influenza B virus (B/Taiwan/165/2005), Influenza B virus (B/Taiwan/166/2005), Influenza B virus (B/Taiwan/188/2005), Influenza B virus (B/Taiwan/1949/02), Influenza B virus (B/Taiwan/1950/02), Influenza B virus (B/Taiwan/202/2001), Influenza B virus (B/Taiwan/2026/99), Influenza B virus (B/Taiwan/2027/99), Influenza B virus (B/Taiwan/217/97), Influenza B virus (B/Taiwan/21706/97), Influenza B virus (B/Taiwan/2195/99), Influenza B virus (B/Taiwan/2551/03), Influenza B virus (B/Taiwan/2805/01), Influenza B virus (B/Taiwan/2805/2001), Influenza B virus (B/Taiwan/3143/97), Influenza B virus (B/Taiwan/31511/00), Influenza B virus (B/Taiwan/31511/2000), Influenza B virus (B/Taiwan/34/2004), Influenza B virus (B/Taiwan/3532/03), Influenza B virus (B/Taiwan/39/2004), Influenza B virus (B/Taiwan/41010/00), Influenza B virus (B/Taiwan/41010/2000), Influenza B virus (B/Taiwan/4119/02), Influenza B virus (B/Taiwan/4184/00), Influenza B virus (B/Taiwan/4184/2000), Influenza B virus (B/Taiwan/43/2005), Influenza B virus (B/Taiwan/4602/02), Influenza B virus (B/Taiwan/473/2005), Influenza B virus (B/Taiwan/52/2004), Influenza B virus (B/Taiwan/52/2005), Influenza B virus (B/Taiwan/54/2004), Influenza B virus (B/Taiwan/61/2004), Influenza B virus (B/Taiwan/635/2005), Influenza B virus (B/Taiwan/637/2005), Influenza B virus (B/Taiwan/68/2004), Influenza B virus (B/Taiwan/68/2005), Influenza B virus (B/Taiwan/69/2004), Influenza B virus (B/Taiwan/70/2005), Influenza B virus (B/Taiwan/74/2004), Influenza B virus (B/Taiwan/75/2004), Influenza B virus (B/Taiwan/77/2005), Influenza B virus (B/Taiwan/81/2005), Influenza B virus (B/Taiwan/872/2005), Influenza B virus (B/Taiwan/97271/2001), Influenza B virus (B/Taiwan/98/2005), Influenza B virus (B/Taiwan/H96/02), Influenza B virus (B/Taiwan/M4214/05), Influenza B virus (B/Taiwan/M227/05), Influenza B virus (B/Taiwan/M24/04), Influenza B virus (B/Taiwan/M244/05), Influenza B virus (B/Taiwan/M4251/05), Influenza B virus (B/Taiwan/M453/05), Influenza B virus (B/Taiwan/M471/01), Influenza B virus (B/Taiwan/N1013/99), Influenza B virus (B/Taiwan/N1115/02), Influenza B virus (B/Taiwan/N1207/

99), Influenza B virus (B/Taiwan/N1316/01), Influenza B virus (B/Taiwan/N1549/01), Influenza B virus (B/Taiwan/N1582/02), Influenza B virus (B/Taiwan/N16/03), Influenza B virus (B/Taiwan/N1619/04), Influenza B virus (B/Taiwan/N1848/02), Influenza B virus (B/Taiwan/N1902/04), Influenza B virus (B/Taiwan/N200/05), Influenza B virus (B/Taiwan/N2050/02), Influenza B virus (B/Taiwan/N230/01), Influenza B virus (B/Taiwan/N232/00), Influenza B virus (B/Taiwan/N2333/02), Influenza B virus (B/Taiwan/N2335/01), Influenza B virus (B/Taiwan/N253/03), Influenza B virus (B/Taiwan/N2620/04), Influenza B virus (B/Taiwan/N2986/02), Influenza B virus (B/Taiwan/N3688/04), Influenza B virus (B/Taiwan/N371/05), Influenza B virus (B/Taiwan/N376/05), Influenza B virus (B/Taiwan/N384/03), Influenza B virus (B/Taiwan/N3849/02), Influenza B virus (B/Taiwan/N404/02), Influenza B virus (B/Taiwan/N473/00), Influenza B virus (B/Taiwan/N511/01), Influenza B virus (B/Taiwan/N559/05), Influenza B virus (B/Taiwan/N612/01), Influenza B virus (B/Taiwan/N701/01), Influenza B virus (B/Taiwan/N767/01), Influenza B virus (B/Taiwan/N798/05), Influenza B virus (B/Taiwan/N860/05), Influenza B virus (B/Taiwan/N872/04), Influenza B virus (B/Taiwan/N913/04), Influenza B virus (B/Taiwan/S117/05), Influenza B virus (B/Taiwan/S141/02), Influenza B virus (B/Taiwan/S76/02), Influenza B virus (B/Taiwan/S82/02), Influenza B virus (B/Taiwan/103/2005), Influenza B virus (B/Tehran/80/02), Influenza B virus (B/Temple/B10/1999), Influenza B virus (B/Temple/B1166/2001), Influenza B virus (B/Temple/B1181/2001), Influenza B virus (B/Temple/B1182/2001), Influenza B virus (B/Temple/B1188/2001), Influenza B virus (B/Temple/B1190/2001), Influenza B virus (B/Temple/B1193/2001), Influenza B virus (B/Temple/B17/2003), Influenza B virus (B/Temple/B18/2003), Influenza B virus (B/Temple/B19/2003), Influenza B virus (B/Temple/B20/2003), Influenza B virus (B/Temple/B21/2003), Influenza B virus (B/Temple/B24/2003), Influenza B virus (B/Temple/B3/1999), Influenza B virus (B/Temple/B30/2003), Influenza B virus (B/Temple/B7/1999), Influenza B virus (B/Temple/B8/1999), Influenza B virus (B/Temple/B9/1999), Influenza B virus (B/Texas/06/2000), Influenza B virus (B/Texas/1/2000), Influenza B virus (B/Texas/1/2004), Influenza B virus (B/Texas/1/2006), Influenza B virus (B/Texas/1/91), Influenza B virus (B/Texas/10/2005), Influenza B virus (B/Texas/11/2001), Influenza B virus (B/Texas/12/2001), Influenza B virus (B/Texas/14/1991), Influenza B virus (B/Texas/14/2001), Influenza B virus (B/Texas/16/2001), Influenza B virus (B/Texas/18/2001), Influenza B virus (B/Texas/2/2006), Influenza B virus (B/Texas/22/2001), Influenza B virus (B/Texas/23/2000), Influenza B virus (B/Texas/3/2001), Influenza B virus (B/Texas/3/2002), Influenza B virus (B/Texas/3/2006), Influenza B virus (B/Texas/37/1988), Influenza B virus (B/Texas/37/88), Influenza B virus (B/Texas/4/2006), Influenza B virus (B/Texas/4/90), Influenza B virus (B/Texas/5/2002), Influenza B virus (B/Texas/57/2002), Influenza B virus (B/Texas/6/2000), Influenza B virus (B/Tokushima/101/93), Influenza B virus (B/Tokyo/6/98), Influenza B virus (B/Trento/3/02), Influenza B virus (B/Trieste/1/02), Influenza B virus (B/Trieste/1/03), Influenza B virus (B/Trieste/15/02), Influenza B virus (B/Trieste/17/02), Influenza B virus (B/Trieste/19/02), Influenza B virus (B/Trieste/2/03), Influenza B virus (B/Trieste/25/02), Influenza B virus (B/Trieste/27/02), Influenza B virus (B/Trieste/28/02), Influenza B virus (B/Trieste/34/02), Influenza B virus (B/Trieste/37/02), Influenza B virus (B/Trieste/4/02), Influenza B virus (B/Trieste/8/02), Influenza B virus (B/Trieste14/02), Influenza B virus (B/Trieste18/02), Influenza B virus (B/Trieste23/02), Influenza B virus (B/Trieste24/02), Influenza B virus (B/Trieste7/02), Influenza B virus (B/Ulan Ude/4/02), Influenza B virus (B/Ulan-Ude/6/2003), Influenza B virus (B/UlanUde/4/02), Influenza B virus (B/United Kingdom/34304/99), Influenza B virus (B/United Kingdom/34520/99), Influenza B virus (B/Uruguay/19/02), Influenza B virus (B/Uruguay/19/05), Influenza B virus (B/Uruguay/2/02), Influenza B virus (B/Uruguay/28/05), Influenza B virus (B/Uruguay/33/05), Influenza B virus (B/Uruguay/4/02), Influenza B virus (B/Uruguay/5/02), Influenza B virus (B/Uruguay/65/05), Influenza B virus (B/Uruguay/7/02), Influenza B virus (B/Uruguay/74/04), Influenza B virus (B/Uruguay/75/04), Influenza B virus (B/Uruguay/NG/02), Influenza B virus (B/Ushuaia/15732/99), Influenza B virus (B/USSR/100/83), Influenza B virus (B/Utah/1/2005), Influenza B virus (B/Utah/20139/99), Influenza B virus (B/Utah/20975/99), Influenza B virus (B/Vermont/1/2006), Influenza B virus (B/Victoria/02/1987), Influenza B virus (B/Victoria/103/89), Influenza B virus (B/Victoria/19/89), Influenza B virus (B/Victoria/2/87), Influenza B virus (B/Victoria/504/2000), Influenza B virus (B/Vienna/1/99), Influenza B virus (B/Virginia/1/2005), Influenza B virus (B/Virginia/1/2006), Influenza B virus (B/Virginia/11/2003), Influenza B virus (B/Virginia/2/2006), Influenza B virus (B/Virginia/3/2003), Influenza B virus (B/Virginia/3/2006), Influenza B virus (B/Virginia/9/2005), Influenza B virus (B/Washington/1/2004), Influenza B virus (B/Washington/2/2000), Influenza B virus (B/Washington/2/2004), Influenza B virus (B/Washington/3/2000), Influenza B virus (B/Washington/3/2003), Influenza B virus (B/Washington/5/2005), Influenza B virus (B/Wellington/01/1994), Influenza B virus (B/Wisconsin/1/2004), Influenza B virus (B/Wisconsin/1/2006), Influenza B virus (B/Wisconsin/10/2006), Influenza B virus (B/Wisconsin/15e/2005), Influenza B virus (B/Wisconsin/17/2006), Influenza B virus (B/Wisconsin/2/2004), Influenza B virus (B/Wisconsin/2/2006), Influenza B virus (B/Wisconsin/22/2006), Influenza B virus (B/Wisconsin/26/2006), Influenza B virus (B/Wisconsin/29/2006), Influenza B virus (B/Wisconsin/3/2000), Influenza B virus (B/Wisconsin/3/2004), Influenza B virus (B/Wisconsin/3/2005), Influenza B virus (B/Wisconsin/3/2006), Influenza B virus (B/Wisconsin/31/2006), Influenza B virus (B/Wisconsin/4/2006), Influenza B virus (B/Wisconsin/5/2006), Influenza B virus (B/Wisconsin/6/2006), Influenza B virus (B/Wisconsin/7/2002), Influenza B virus (B/Wuhan/2/2001), Influenza B virus (B/Wuhan/356/2000), Influenza B virus (B/WV194/2002), Influenza B virus (B/Wyoming/15/2001), Influenza B virus (B/Wyoming/16/2001), Influenza B virus (B/Wyoming/2/2003), Influenza B virus (B/Xuanwu/1/82), Influenza B virus (B/Xuanwu/23/82), Influenza B virus (B/Yamagata/1/73), Influenza B virus (B/Yamagata/115/2003), Influenza B virus (B/Yamagata/1246/2003), Influenza B virus (B/Yamagata/1311/2003), Influenza B virus (B/Yamagata/16/1988), Influenza B virus (B/Yamagata/16/88), Influenza B virus (B/Yamagata/222/2002), Influenza B virus (B/Yamagata/K198/2001), Influenza B virus (B/Yamagata/K246/2001), Influenza B virus (B/Yamagata/K270/2001), Influenza B virus (B/Yamagata/K298/2001), Influenza B virus (B/Yamagata/K320/2001), Influenza B virus (B/Yamagata/K354/2001), Influenza B virus (B/Yamagata/K386/2001), Influenza B virus (B/Yamagata/K411/2001), Influenza B virus (B/Yamagata/K461/2001), Influenza B virus (B/Yamagata/K490/2001), Influenza B virus (B/Yamagata/K500/2001), Influenza B virus (B/Yamagata/K501/2001), Influenza B virus (B/Yamagata/K508/2001), Influenza B virus (B/Yamagata/K513/2001), Influenza B virus (B/Yamagata/K515/2001), Influenza B virus (B/Yamagata/K519/2001), Influenza B virus (B/Yamagata/K520/2001), Influenza B virus (B/Yamagata/K521/2001), Influenza B virus (B/Yamagata/K535/2001), Influenza B virus (B/Yamagata/K542/2001), Influenza B virus (B/Yamanashi/166/1998), Influenza B virus (B/Yamanashi/166/98), Influenza B virus (B/Yunnan/123/2001), Influenza B virus (strain B/Alaska/12/96), Influenza B virus (STRAIN B/ANN ARBOR/1/66 [COLD-ADAPTED]), Influenza B virus (STRAIN B/ANN ARBOR/1/66 [WILD-TYPE]), Influenza B virus (STRAIN B/BA/78), Influenza B virus (STRAIN B/BEIJING/1/87), Influenza B virus (STRAIN B/ENGLAND/222/82), Influenza B virus (strain B/finland/145/90), Influenza B virus (strain B/finland/146/90), Influenza B virus (strain B/finland/147/90), Influenza B virus (strain B/finland/148/90), Influenza B virus (strain B/finland/149/90), Influenza B virus (strain B/finland/150/90), Influenza B virus (strain B/finland/151/90), Influenza B virus (strain B/finland/24/85), Influenza B virus (strain B/finland/56/88), Influenza B virus (STRAIN B/FUKUOKA/80/81), Influenza B virus (STRAIN B/GA/86), Influenza B virus (STRAIN B/GL/54), Influenza B virus (STRAIN B/HONG KONG/8/73), Influenza B virus (STRAIN B/HT/84), Influenza B virus (STRAIN B/ID/86), Influenza B virus (STRAIN B/LENINGRAD/179/86), Influenza B virus (STRAIN B/MARYLAND/59), Influenza B virus (STRAIN B/MEMPHIS/6/86), Influenza B virus (STRAIN B/NAGASAKI/1/87), Influenza B virus (strain B/Osaka/491/97), Influenza B virus (STRAIN B/PA/79), Influenza B virus (STRAIN B/RU/69), Influenza B virus (STRAIN B/SINGAPORE/64), Influenza B virus (strain B/Tokyo/942/96), Influenza B virus (STRAIN B/VICTORIA/3/85), Influenza B virus (STRAIN B/VICTORIA/87), Influenza B virus (B/Rochester/02/2001), and other subtypes. In further embodiments, the influenza virus C belongs to but is not limited to subtype Influenza C virus (C/Aichi/1/81), Influenza C virus (C/Aichi/1/99), Influenza C virus (C/Ann Arbor/1/50), Influenza C virus (C/Aomori/74), Influenza C virus (C/California/78), Influenza C virus (C/England/83), Influenza C virus (C/Fukuoka/2/2004), Influenza C virus (C/Fukuoka/3/2004), Influenza C virus (C/Fukushima/1/2004), Influenza C virus (C/Greece/79), Influenza C virus (C/Hiroshima/246/2000), Influenza C virus (C/Hiroshima/247/2000), Influenza C virus (C/Hiroshima/248/2000), Influenza C virus (C/Hiroshima/249/2000), Influenza C virus (C/Hiroshima/250/2000), Influenza C virus (C/Hiroshima/251/2000), Influenza C virus (C/Hiroshima/252/2000), Influenza C virus (C/Hiroshima/252/99), Influenza C virus (C/Hiroshima/290/99), Influenza C virus (C/Hiroshima/4/2004), Influenza C virus (C/Hyogo/1/83), Influenza C virus (C/Johannesburg/1/66), Influenza C virus (C/Johannesburg/66), Influenza C virus (C/Kanagawa/1/76), Influenza C virus (C/Kanagawa/2/2004), Influenza C virus (C/Kansas/1/79), Influenza C virus (C/Kyoto/1/79), Influenza C virus (C/Kyoto/41/82), Influenza C virus (C/Mississippi/80), Influenza C virus (C/Miyagi/1/90), Influenza C virus (C/Miyagi/1/93), Influenza C virus (C/Miyagi/1/94), Influenza C virus (C/Miyagi/1/97), Influenza C virus (C/Miyagi/1/99), Influenza C virus (C/Miyagi/12/2004), Influenza C virus (C/Miyagi/2/2000), Influenza C virus (C/Miyagi/2/92), Influenza C virus (C/Miyagi/2/93), Influenza C virus (C/Miyagi/2/94), Influenza C virus (C/Miyagi/2/96), Influenza C virus (C/Miyagi/2/98), Influenza C virus (C/Miyagi/3/2000), Influenza C virus (C/Miyagi/3/91), Influenza C virus (C/Miyagi/3/92), Influenza C virus (C/Miyagi/3/93), Influenza C virus (C/Miyagi/3/94), Influenza C virus (C/Miyagi/3/97), Influenza C virus (C/Miyagi/3/99), Influenza C virus (C/Miyagi/4/2000), Influenza C virus (C/Miyagi/4/93), Influenza C virus (C/Miyagi/4/96), Influenza C virus (C/Miyagi/4/97), Influenza C virus (C/Miyagi/4/98), Influenza C virus (C/Miyagi/42/2004), Influenza C virus (C/Miyagi/5/2000), Influenza C virus (C/Miyagi/5/91), Influenza C virus (C/Miyagi/5/93), Influenza C virus (C/Miyagi/6/93), Influenza C virus (C/Miyagi/6/96), Influenza C virus (C/Miyagi/7/91), Influenza C virus (C/Miyagi/7/93), Influenza C virus (C/Miyagi/7/96), Influenza C virus (C/Miyagi/77), Influenza C virus (C/Miyagi/8/96), Influenza C virus (C/Miyagi/9/91), Influenza C virus (C/Miyagi/9/96), Influenza C virus (C/Nara/1/85), Influenza C virus (C/Nara/2/85), Influenza C virus (C/Nara/82), Influenza C virus (C/NewJersey/76), Influenza C virus (C/Niigata/1/2004), Influenza C virus (C/Osaka/2/2004), Influenza C virus (C/pig/Beijing/115/81), Influenza C virus (C/Saitama/1/2000), Influenza C virus (C/Saitama/1/2004), Influenza C virus (C/Saitama/2/2000), Influenza C virus (C/Saitama/3/2000), Influenza C virus (C/Sapporo/71), Influenza C virus (C/Shizuoka/79), Influenza C virus (C/Yamagata/1/86), Influenza C virus (C/Yamagata/1/88), Influenza C virus (C/Yamagata/10/89), Influenza C virus (C/Yamagata/13/98), Influenza C virus (C/Yamagata/15/2004), Influenza C virus (C/Yamagata/2/2000), Influenza C virus (C/Yamagata/2/98), Influenza C virus (C/Yamagata/2/99), Influenza C virus (C/Yamagata/20/2004), Influenza C virus (C/Yamagata/20/96), Influenza C virus (C/Yamagata/21/2004), Influenza C virus (C/Yamagata/26/81), Influenza C virus (C/Yamagata/27/2004), Influenza C virus (C/Yamagata/3/2000), Influenza C virus (C/Yamagata/3/2004), Influenza C virus (C/Yamagata/3/88), Influenza C virus (C/Yamagata/3/96), Influenza C virus (C/Yamagata/4/88), Influenza C virus (C/Yamagata/4/89), Influenza C virus (C/Yamagata/5/92), Influenza C virus (C/Yamagata/6/2000), Influenza C virus (C/Yamagata/6/98), Influenza C virus (C/Yamagata/64), Influenza C virus (C/Yamagata/7/88), Influenza C virus (C/Yamagata/8/2000), Influenza C virus (C/Yamagata/8/88), Influenza C virus (C/Yamagata/8/96), Influenza C virus (C/Yamagata/9/2000), Influenza C virus (C/Yamagata/9/88), Influenza C virus (C/Yamagata/9/96), Influenza C virus (STRAIN C/BERLIN/1/85), Influenza C virus (STRAIN C/ENGLAND/892/83), Influenza C virus (STRAIN C/GREAT LAKES/1167/54), Influenza C virus (STRAIN C/JJ/50), Influenza C virus (STRAIN C/PIG/BEIJING/10/81), Influenza C virus (STRAIN C/PIG/BEIJING/439/82), Influenza C virus (STRAIN C/TAYLOR/1233/47), Influenza C virus (STRAIN C/YAMAGATA/10/81), Isavirus or Infectious salmon anemia virus, Thogotovirus or Dhori virus, Batken virus, Dhori virus (STRAIN INDIAN/1313/61) or Thogoto virus, Thogoto virus (isolate SiAr 126) or unclassified Thogotovirus, Araguari virus, unclassified Orthomyxoviridae or Fowl plague virus or Swine influenza virus or unidentified influenza virus and other subtypes.

In various embodiments, the attenuated virus belongs to the delta virus family and all related genera.

In various embodiments, the attenuated virus belongs to the Adenoviridae virus family and all related genera, strains, types and isolates for example but not limited to human adenovirus A, B C.

In various embodiments, the attenuated virus belongs to the Herpesviridae virus family and all related genera, strains, types and isolates for example but not limited to herpes simplex virus.

In various embodiments, the attenuated virus belongs to the Reoviridae virus family and all related genera, strains, types and isolates.

In various embodiments, the attenuated virus belongs to the Papillomaviridae virus family and all related genera, strains, types and isolates.

In various embodiments, the attenuated virus belongs to the Poxviridae virus family and all related genera, strains, types and isolates.

In various embodiments, the attenuated virus belongs to the Retroviridae virus family and all related genera, strains, types and isolates. For example but not limited to Human Immunodeficiency Virus.

In various embodiments, the attenuated virus belongs to the Filoviridae virus family and all related genera, strains, types and isolates.

In various embodiments, the attenuated virus belongs to the Paramyxoviridae virus family and all related genera, strains, types and isolates.

In various embodiments, the attenuated virus belongs to the Orthomyxoviridae virus family and all related genera, strains, types and isolates.

In various embodiments, the attenuated virus belongs to the Picornaviridae virus family and all related genera, strains, types and isolates.

In various embodiments, the attenuated virus belongs to the Bunyaviridae virus family and all related genera, strains, types and isolates.

In various embodiments, the attenuated virus belongs to the Nidovirales virus family and all related genera, strains, types and isolates.

In various embodiments, the attenuated virus belongs to the Caliciviridae virus family and all related genera, strains, types and isolates.

In certain embodiments, the synonymous codon substitutions alter codon bias, codon pair bias, density of deoptimized codons and deoptimized codon pairs, RNA secondary structure, CpG dinucleotide content, C+G content, translation frameshift sites, translation pause sites, the presence or absence microRNA recognition sequences or any combination thereof, in the genome. The codon substitutions may be engineered in multiple locations distributed throughout the genome, or in the multiple locations restricted to a portion of the genome. In further embodiments, the portion of the genome is the capsid coding region.

In preferred embodiments of this invention, the virus retains the ability to induce a protective immune response in an animal host. In other preferred embodiments, the virulence of the virus does not revert to wild type.

Poliovirus, Rhinovirus, and Influenza Virus

Poliovirus, a member of the Picornavirus family, is a small non-enveloped virus with a single stranded (+) sense RNA genome of 7.5 kb in length (Kitamura et al., 1981). Upon cell entry, the genomic RNA serves as an mRNA encoding a single polyprotein that after a cascade of autocatalytic cleavage events gives rise to full complement of functional poliovirus proteins. The same genomic RNA serves as a template for the synthesis of (−) sense RNA, an intermediary for the synthesis of new (+) strands that either serve as mRNA, replication template or genomic RNA destined for encapsidation into progeny virions (Mueller et al., 2005). As described herein, the well established PV system was used to address general questions of optimizing design strategies for the production of attenuated synthetic viruses. PV provides one of the most important and best understood molecular models for developing anti-viral strategies. In particular, a reverse genetics system exists whereby viral nucleic acid can be synthesized in vitro by completely synthetic methods and then converted into infectious virions (see below). Furthermore, a convenient mouse model is available (CD155tg mice, which express the human receptor for polio) for testing attenuation of synthetic PV designs as previously described (Cello et al., 2002).

Rhinoviruses are also members of the Picornavirus family, and are related to PV. Human Rhinoviruses (HRV) are the usual causative agent of the common cold, and as such they are responsible for more episodes of illness than any other infectious agent (Hendley, 1999). In addition to the common cold, HRV is also involved in ear and sinus infections, asthmatic attacks, and other diseases. Similar to PV, HRV comprises a single-stranded positive sense RNA virus, whose genome encodes a self-processing polyprotein. The RNA is translated through an internal initiation mechanism using an Internal Ribosome Entry Site (IRES) to produce structural proteins that form the capsid, as well as non-structural proteins such as the two viral proteases, 2A and 3C, and the RNA-dependent polymerase (Jang et al., 1989; Pelletier et al., 1988). Also like PV, HRV has a non-enveloped icosahedral capsid, formed by 60 copies of the four capsid proteins VP1-4 (Savolainen et al., 2003). The replication cycle of HRV is also identical to that of poliovirus. The close similarity to PV, combined with the significant, almost ubiquitous impact on human health, makes HRV an extremely attractive candidate for generating a novel attenuated virus useful for immunization.

Despite decades of research by pharmaceutical companies, no successful drug against HRV has been developed. This is partly due to the relatively low risk tolerance of federal regulators and the public for drugs that treat a mostly non-serious infection. That is, even minor side effects are unacceptable. Thus, in the absence of a drug, there is a clear desire for a safe and effective anti-rhinovirus vaccine. However, developing an anti-rhinovirus vaccine is extremely challenging, because there are over 100 serotypes of HRV, of which approximately 30 circulate widely and infect humans regularly. An effective vaccine must enable the immune system to recognize every single serotype in order to confer true immunity. The SAVE approach described herein offers a practical solution to the development of an effective rhinovirus vaccine. Based on the predictability of the SAVE design process, it would be inexpensive to design and synthesize 100 or more SAVE-attenuated rhinoviruses, which in combination would constitute a vaccine.

Influenza virus—Between 1990 and 1999, influenza viruses caused approximately 35,000 deaths each year in the U.S.A. (Thompson et al., 2003). Together with approximately 200,000 hospitalizations, the impact on the U.S. economy has been estimated to exceed $23 billion annually (Cram et al., 2001). Globally, between 300,000 to 500,000 people die each year due to influenza virus infections (Kamps et al., 2006). Although the virus causes disease amongst all age groups, the rates of serious complications are highest in children and persons over 65 years of age. Influenza has the potential to mutate or recombine into extremely deadly forms, as happened during the great influenza epidemic of 1918, in which about 30 million people died. This was possibly the single most deadly one-year epidemic in human history.

Influenza viruses are divided into three types A, B, and C. Antigenicity is determined by two glycoproteins at the surface of the enveloped virion: hemagglutinin (HA) and neuraminidase (NA). Both glycoproteins continuously change their antigenicity to escape humoral immunity. Altering the glycoproteins allows virus strains to continue infecting vaccinated individuals, which is the reason for yearly vaccination of high-risk groups. In addition, human influenza viruses can replace the HA or NA glycoproteins with those of birds and pigs, a reassortment of gene segments, known as genetic shift, leading to new viruses (H1N1 to H2N2 or H3N2, etc.) (Steinhauer and Skehel, 2002). These novel viruses, to which the global population is immunologically naive, are the cause of pandemics that kill millions of people (Kilbourne, 2006; Russell and Webster, 2005). The history of influenza virus, together with the current threat of the highly pathogenic avian influenza virus, H5N1 (Stephenson and Democratis, 2006), underscores the need for preventing influenza virus disease.

Currently, two influenza vaccines are in use: a live, attenuated vaccine (cold adapted; "FluMist") and an inactivated virus. The application of the attenuated vaccine is restricted to healthy children, adolescents and adults (excluding pregnant females), ages 5-49. This age restriction leaves out precisely those who are at highest risks of influenza. Furthermore, the attenuated FluMist virus has the possibility of reversion, which is usual for a live virus. Production of the second, more commonly administered inactivated influenza virus vaccine is complex. Further, this vaccine appears to be less effective than hoped for in preventing death in the elderly (>65-year-old) population (Simonson et al., 2005). These facts underscore the need for novel strategies to generate influenza virus vaccines.

Reverse Genetics of Picornaviruses

Reverse genetics generally refers to experimental approaches to discovering the function of a gene that proceeds in the opposite direction to the so-called forward genetic approaches of classical genetics. That is, whereas forward genetics approaches seek to determine the function of a gene by elucidating the genetic basis of a phenotypic trait, strategies based on reverse genetics begin with an isolated gene and seek to discover its function by investigating the possible phenotypes generated by expression of the wt or mutated gene. As used herein in the context of viral systems, "reverse genetics" systems refer to the availability of techniques that permit genetic manipulation of viral genomes made of RNA. Briefly, the viral genomes are isolated from virions or from infected cells, converted to DNA ("cDNA") by the enzyme reverse transcriptase, possibly modified as desired, and reverted, usually via the RNA intermediate, back into infectious viral particles. This process in picornaviruses is extremely simple; in fact, the first reverse genetics system developed for any animal RNA virus was for PV (Racaniello and Baltimore, 1981). Viral reverse genetics systems are based on the historical finding that naked viral genomic RNA is infectious when transfected into a suitable mammalian cell (Alexander et al., 1958). The discovery of reverse transcriptase and the development of molecular cloning techniques in the 1970's enabled scientists to generate and manipulate cDNA copies of RNA viral genomes. Most commonly, the entire cDNA copy of the genome is cloned immediately downstream of a phage T7 RNA polymerase promoter that allows the in vitro synthesis of genome RNA, which is then transfected into cells for generation of virus (van der Wert, et al., 1986). Alternatively, the same DNA plasmid may be transfected into cells expressing the T7 RNA polymerase in the cytoplasm. This system can be used for various viral pathogens including both PV and HRV.

Molecular Virology and Reverse Genetics of Influenza Virus

Influenza virus, like the picornaviruses, PV and HRV, is an RNA virus, but is otherwise unrelated to and quite different from PV. In contrast to the picornaviruses, influenza is a minus strand virus. Furthermore, influenza consists of eight separate gene segments ranging from 890 to 2341 nucleotides (Lamb and Krug, 2001). Partly because of the minus strand organization, and partly because of the eight separate gene segments, the reverse genetics system is more complex than for PV. Nevertheless, a reverse genetics system has been developed for influenza virus (Enami et al., 1990; Fodor et al., 1999; Garcia-Sastre and Palese, 1993; Hoffman et al., 2000; Luytjes et al., 1989; Neumann et al., 1999). Each of the eight gene segments is expressed from a separate plasmid. This reverse genetics system is extremely convenient for use in the SAVE strategy described herein, because the longest individual gene segment is less than 3 kb, and thus easy to synthesize and manipulate. Further, the different gene segments can be combined and recombined simply by mixing different plasmids. Thus, application of SAVE methods are possibly even more feasible for influenza virus than for PV.

A recent paradigm shift in viral reverse genetics occurred with the present inventors' first chemical synthesis of an infectious virus genome by assembly from synthetic DNA oligonucleotides (Cello et al., 2002). This achievement made it clear that most or all viruses for which a reverse genetics system is available can be synthesized solely from their genomic sequence information, and promises unprecedented flexibility in re-synthesizing and modifying these viruses to meet desired criteria.

De Novo Synthesis of Viral Genomes

Computer-based algorithms are used to design and synthesize viral genomes de novo. These synthesized genomes, exemplified by the synthesis of attenuated PV described herein, encode exactly the same proteins as wild type (wt) viruses, but by using alternative synonymous codons, various parameters, including codon bias, codon pair bias, RNA secondary structure, and/or dinucleotide content, are altered. The presented data show that these coding-independent changes produce highly attenuated viruses, often due to poor translation of proteins. By targeting an elementary function of all viruses, namely protein translation, a very general method has been developed for predictably, safely, quickly and cheaply producing attenuated viruses, which are useful for making vaccines. This method, dubbed "SAVE" (Synthetic Attenuated Virus Engineering), is applicable to a wide variety of viruses other than PV for which there is a medical need for new vaccines. These viruses include, but are not limited to rhinovirus, influenza virus, SARS and other coronaviruses, HIV, HCV, infectious bronchitis virus, ebolavirus, Marburg virus, dengue fever virus, West Nile disease virus, EBV, yellow fever virus, enteroviruses other than poliovirus, such as echoviruses, coxsackie viruses, and entrovirus71; hepatitis A virus, aphthoviruses, such as foot-and-mouth-disease virus, myxoviruses, such as influenza viruses, paramyxoviruses, such as measles virus, mumps virus, respiratory syncytia virus, flaviviruses such as dengue virus, yellow fever virus, St. Louis encephalitis virus and tick-born virus, alphaviruses, such as Western- and Eastern encephalitis virus, hepatitis B virus, and bovine diarrhea virus, and ebolavirus.

Both codon and codon-pair deoptimization in the PV capsid coding region are shown herein to dramatically reduce PV fitness. The present invention is not limited to any particular molecular mechanism underlying virus attenuation via substitution of synonymous codons. Nevertheless, experiments are ongoing to better understand the underlying molecular mechanisms of codon and codon pair deoptimization in producing attenuated viruses. In particular, evidence is provided in this application that indicates that codon deoptimization and codon pair deoptimization can result in inefficient translation. High throughput methods for the quick generation and screening of large numbers of viral constructs are also being developed.

Large-Scale DNA Assembly

In recent years, the plunging costs and increasing quality of oligonucleotide synthesis have made it practical to assemble large segments of DNA (at least up to about 10 kb) from synthetic oligonucleotides. Commercial vendors such as Blue Heron Biotechnology, Inc. (Bothwell, Wash.) (and also many others) currently synthesize, assemble, clone, sequence-verify, and deliver a large segment of synthetic DNA of known sequence for the relatively low price of about $1.50 per base. Thus, purchase of synthesized viral genomes from commercial suppliers is a convenient and cost-effective option, and prices continue to decrease rapidly. Furthermore, new methods of synthesizing and assembling very large DNA molecules at extremely low costs are emerging (Tian et al., 2004). The Church lab has pioneered a method that uses parallel synthesis of thousands of oligonucleotides (for instance, on photo-programmable microfluidics chips, or on microarrays available from Nimblegen Systems, Inc., Madison, Wis., or Agilent Technologies, Inc., Santa Clara, Calif.), followed by error reduction and assembly by overlap PCR. These methods have the potential to reduce the cost of synthetic large DNAs to less than 1 cent per base. The improved efficiency and accuracy, and rapidly declining cost, of large-scale DNA synthesis provides an impetus for the development and broad application of the SAVE strategy.

Alternative Encoding, Codon Bias, and Codon Pair Bias

Alternative Encoding

A given peptide can be encoded by a large number of nucleic acid sequences. For example, even a typical short 10-mer oligopeptide can be encoded by approximately $4^{10}$ (about $10^6$) different nucleic acids, and the proteins of PV can be encoded by about $10^{442}$ different nucleic acids. Natural selection has ultimately chosen one of these possible $10^{442}$ nucleic acids as the PV genome. Whereas the primary amino acid sequence is the most important level of information encoded by a given mRNA, there are additional kinds of information within different kinds of RNA sequences. These include RNA structural elements of distinct function (e.g., for PV, the cis-acting replication element, or CRE (Goodfellow et al., 2000; McKnight, 2003), translational kinetic signals (pause sites, frame shift sites, etc.), polyadenylation signals, splice signals, enzymatic functions (ribozyme) and, quite likely, other as yet unidentified information and signals).

Even with the caveat that signals such as the CRE must be preserved, $10^{442}$ possible encoding sequences provide tremendous flexibility to make drastic changes in the RNA sequence of polio while preserving the capacity to encode the same protein. Changes can be made in codon bias or codon pair bias, and nucleic acid signals and secondary structures in the RNA can be added or removed. Additional or novel proteins can even be simultaneously encoded in alternative frames (see, e.g., Wang et al., 2006).

Codon Bias

Whereas most amino acids can be encoded by several different codons, not all codons are used equally frequently: some codons are "rare" codons, whereas others are "frequent" codons. As used herein, a "rare" codon is one of at least two synonymous codons encoding a particular amino acid that is present in an mRNA at a significantly lower frequency than the most frequently used codon for that amino acid. Thus, the rare codon may be present at about a 2-fold lower frequency than the most frequently used codon. Preferably, the rare codon is present at least a 3-fold, more preferably at least a 5-fold, lower frequency than the most frequently used codon for the amino acid. Conversely, a "frequent" codon is one of at least two synonymous codons encoding a particular amino acid that is present in an mRNA at a significantly higher frequency than the least frequently used codon for that amino acid. The frequent codon may be present at about a 2-fold, preferably at least a 3-fold, more preferably at least a 5-fold, higher frequency than the least frequently used codon for the amino acid. For example, human genes use the leucine codon CTG 40% of the time, but use the synonymous CTA only 7% of the time (see Table 2). Thus, CTG is a frequent codon, whereas CTA is a rare codon. Roughly consistent with these frequencies of usage, there are 6 copies in the genome for the gene for the tRNA recognizing CTG, whereas there are only 2 copies of the gene for the tRNA recognizing CTA. Similarly, human genes use the frequent codons TCT and TCC for serine 18% and 22% of the time, respectively, but the rare codon TCG only 5% of the time. TCT and TCC are read, via wobble, by the same tRNA, which has 10 copies of its gene in the genome, while TCG is read by a tRNA with only 4 copies. It is well known that those mRNAs that are very actively translated are strongly biased to use only the most frequent codons. This includes genes for ribosomal proteins and glycolytic enzymes. On the other hand, mRNAs for relatively non-abundant proteins may use the rare codons.

TABLE 2

Codon usage in *Homo sapiens* (source: http://www.kazusa.or.jp/codon/)

| Amino Acid | Codon | Number | /1000 | Fraction |
|---|---|---|---|---|
| Gly | GGG | 636457.00 | 16.45 | 0.25 |
| Gly | GGA | 637120.00 | 16.47 | 0.25 |
| Gly | GGT | 416131.00 | 10.76 | 0.16 |
| Gly | GGC | 862557.00 | 22.29 | 0.34 |
| Glu | GAG | 1532589.00 | 39.61 | 0.58 |
| Glu | GAA | 1116000.00 | 28.84 | 0.42 |
| Asp | GAT | 842504.00 | 21.78 | 0.46 |
| Asp | GAC | 973377.00 | 25.16 | 0.54 |
| Val | GTG | 1091853.00 | 28.22 | 0.46 |
| Val | GTA | 273515.00 | 7.07 | 0.12 |
| Val | GTT | 426252.00 | 11.02 | 0.18 |
| Val | GTC | 562086.00 | 14.53 | 0.24 |
| Ala | GCG | 286975.00 | 7.42 | 0.11 |
| Ala | GCA | 614754.00 | 15.89 | 0.23 |
| Ala | GCT | 715079.00 | 18.48 | 0.27 |
| Ala | GCC | 1079491.00 | 27.90 | 0.40 |
| Arg | AGG | 461676.00 | 11.93 | 0.21 |
| Arg | AGA | 466435.00 | 12.06 | 0.21 |
| Ser | AGT | 469641.00 | 12.14 | 0.15 |
| Ser | AGC | 753597.00 | 19.48 | 0.24 |
| Lys | AAG | 1236148.00 | 31.95 | 0.57 |
| Lys | AAA | 940312.00 | 24.30 | 0.43 |
| Asn | AAT | 653566.00 | 16.89 | 0.47 |
| Asn | AAC | 739007.00 | 19.10 | 0.53 |
| Met | ATG | 853648.00 | 22.06 | 1.00 |
| Ile | ATA | 288118.00 | 7.45 | 0.17 |
| Ile | ATT | 615699.00 | 15.91 | 0.36 |
| Ile | ATC | 808306.00 | 20.89 | 0.47 |
| Thr | ACG | 234532.00 | 6.06 | 0.11 |
| Thr | ACA | 580580.00 | 15.01 | 0.28 |
| Thr | ACT | 506277.00 | 13.09 | 0.25 |

TABLE 2-continued

Codon usage in *Homo sapiens* (source: http://www.kazusa.or.jp/codon/)

| Amino Acid | Codon | Number | /1000 | Fraction |
|---|---|---|---|---|
| Thr | ACC | 732313.00 | 18.93 | 0.36 |
| Trp | TGG | 510256.00 | 13.19 | 1.00 |
| End | TGA | 59528.00 | 1.54 | 0.47 |
| Cys | TGT | 407020.00 | 10.52 | 0.45 |
| Cys | TGC | 487907.00 | 12.61 | 0.55 |
| End | TAG | 30104.00 | 0.78 | 0.24 |
| End | TAA | 38222.00 | 0.99 | 0.30 |
| Tyr | TAT | 470083.00 | 12.15 | 0.44 |
| Tyr | TAC | 592163.00 | 15.30 | 0.56 |
| Leu | TTG | 498920.00 | 12.89 | 0.13 |
| Leu | TTA | 294684.00 | 7.62 | 0.08 |
| Phe | TTT | 676381.00 | 17.48 | 0.46 |
| Phe | TTC | 789374.00 | 20.40 | 0.54 |
| Ser | TCG | 171428.00 | 4.43 | 0.05 |
| Ser | TCA | 471469.00 | 12.19 | 0.15 |
| Ser | TCT | 585967.00 | 15.14 | 0.19 |
| Ser | TCC | 684663.00 | 17.70 | 0.22 |
| Arg | CGG | 443753.00 | 11.47 | 0.20 |
| Arg | CGA | 239573.00 | 6.19 | 0.11 |
| Arg | CGT | 176691.00 | 4.57 | 0.08 |
| Arg | CGC | 405748.00 | 10.49 | 0.18 |
| Gln | CAG | 1323614.00 | 34.21 | 0.74 |
| Gln | CAA | 473648.00 | 12.24 | 0.26 |
| His | CAT | 419726.00 | 10.85 | 0.42 |
| His | CAC | 583620.00 | 15.08 | 0.58 |
| Leu | CTG | 1539118.00 | 39.78 | 0.40 |
| Leu | CTA | 276799.00 | 7.15 | 0.07 |
| Leu | CTT | 508151.00 | 13.13 | 0.13 |
| Leu | CTC | 759527.00 | 19.63 | 0.20 |
| Pro | CCG | 268884.00 | 6.95 | 0.11 |
| Pro | CCA | 653281.00 | 16.88 | 0.28 |
| Pro | CCT | 676401.00 | 17.48 | 0.29 |
| Pro | CCC | 767793.00 | 19.84 | 0.32 |

The propensity for highly expressed genes to use frequent codons is called "codon bias." A gene for a ribosomal protein might use only the 20 to 25 most frequent of the 61 codons, and have a high codon bias (a codon bias close to 1), while a poorly expressed gene might use all 61 codons, and have little or no codon bias (a codon bias close to 0). It is thought that the frequently used codons are codons where larger amounts of the cognate tRNA are expressed, and that use of these codons allows translation to proceed more rapidly, or more accurately, or both. The PV capsid protein is very actively translated, and has a high codon bias.

Codon Pair Bias

A distinct feature of coding sequences is their codon pair bias. This may be illustrated by considering the amino acid pair Ala-Glu, which can be encoded by 8 different codon pairs. If no factors other than the frequency of each individual codon (as shown in Table 2) are responsible for the frequency of the codon pair, the expected frequency of each of the 8 encodings can be calculated by multiplying the frequencies of the two relevant codons. For example, by this calculation the codon pair GCA-GAA would be expected to occur at a frequency of 0.097 out of all Ala-Glu coding pairs (0.23×0.42; based on the frequencies in Table 2). In order to relate the expected (hypothetical) frequency of each codon pair to the actually observed frequency in the human genome the Consensus CDS (CCDS) database of consistently annotated human coding regions, containing a total of 14,795 human genes, was used. This set of genes is the most comprehensive representation of human coding sequences. Using this set of genes the frequencies of codon usage were re-calculated by dividing the number of occurrences of a codon by the number of all synonymous codons coding for the same amino acid. As expected the frequencies correlated closely with previously published ones such as the ones given in Table 2. Slight frequency variations are possibly due to an oversampling effect in the data provided by the codon usage database at Kazusa DNA Research Institute (http://www.kazusa.or.jp/codon/codon.html) where 84949 human coding sequences were included in the calculation (far more than the actual number of human genes). The codon frequencies thus calculated were then used to calculate the expected codon-pair frequencies by first multiplying the frequencies of the two relevant codons with each other (see Table 3 expected frequency), and then multiplying this result with the observed frequency (in the entire CCDS data set) with which the amino acid pair encoded by the codon pair in question occurs. In the example of codon pair GCA-GAA, this second calculation gives an expected frequency of 0.098 (compared to 0.97 in the first calculation using the Kazusa dataset). Finally, the actual codon pair frequencies as observed in a set of 14,795 human genes was determined by counting the total number of occurrences of each codon pair in the set and dividing it by the number of all synonymous coding pairs in the set coding for the same amino acid pair (Table 3; observed frequency). Frequency and observed/expected values for the complete set of 3721 ($61^2$) codon pairs, based on the set of 14,795 human genes, are provided herewith as Supplemental Table 1.

TABLE 3

Codon Pair Scores Exemplified by the Amino Acid Pair Ala-Glu

| amino acid pair | codon pair | expected frequency | observed frequency | obs/exp ratio |
|---|---|---|---|---|
| AE | GCAGAA | 0.098 | 0.163 | 1.65 |
| AE | GCAGAG | 0.132 | 0.198 | 1.51 |
| AE | GCCGAA | 0.171 | 0.031 | 0.18 |
| AE | GCCGAG | 0.229 | 0.142 | 0.62 |
| AE | GCGGAA | 0.046 | 0.027 | 0.57 |
| AE | GCGGAG | 0.062 | 0.089 | 1.44 |
| AE | GCTGAA | 0.112 | 0.145 | 1.29 |
| AE | GCTGAG | 0.150 | 0.206 | 1.37 |
| Total | | 1.000 | 1.000 | |

If the ratio of observed frequency/expected frequency of the codon pair is greater than one the codon pair is said to be overrepresented. If the ratio is smaller than one, it is said to be underrepresented. In the example the codon pair GCA-GAA is overrepresented 1.65 fold while the coding pair GCC-GAA is more than 5-fold underrepresented.

Many other codon pairs show very strong bias; some pairs are under-represented, while other pairs are over-represented. For instance, the codon pairs GCCGAA (AlaGlu) and GATCTG (AspLeu) are three- to six-fold under-represented (the preferred pairs being GCAGAG and GACCTG, respectively), while the codon pairs GCCAAG (AlaLys) and AATGAA (AsnGlu) are about two-fold over-represented. It is noteworthy that codon pair bias has nothing to do with the frequency of pairs of amino acids, nor with the frequency of individual codons. For instance, the under-represented pair GATCTG (AspLeu) happens to use the most frequent Leu codon, (CTG).

Codon pair bias was discovered in prokaryotic cells (see Greve et al., 1989), but has since been seen in all other examined species, including humans. The effect has a very high statistical significance, and is certainly not just noise. However, its functional significance, if any, is a mystery.

One proposal is that some pairs of tRNAs interact well when they are brought together on the ribosome, while other pairs interact poorly. Since different codons are usually read by different tRNAs, codon pairs might be biased to avoid putting together pairs of incompatible tRNAs (Greve et al., 1989). Another idea is that many (but not all) under-represented pairs have a central CG dinucleotide (e.g., GCCGAA, encoding AlaGlu), and the CG dinucleotide is systematically under-represented in mammals (Buchan et al., 2006; Curran et al., 1995; Fedorov et al., 2002). Thus, the effects of codon pair bias could be of two kinds—one an indirect effect of the under-representation of CG in the mammalian genome, and the other having to do with the efficiency, speed and/or accuracy of translation. It is emphasized that the present invention is not limited to any particular molecular mechanism underlying codon pair bias.

As discussed more fully below, codon pair bias takes into account the score for each codon pair in a coding sequence averaged over the entire length of the coding sequence. According to the invention, codon pair bias is determined by $$CPB = \sum_{i=1}^{k} \frac{CPSi}{k-1}.$$

Accordingly, similar codon pair bias for a coding sequence can be obtained, for example, by minimized codon pair scores over a subsequence or moderately diminished codon pair scores over the full length of the coding sequence.

Since all 61 sense codons and all sense codon pairs can certainly be used, it would not be expected that substituting a single rare codon for a frequent codon, or a rare codon pair for a frequent codon pair, would have much effect. Therefore, many previous investigations of codon and codon pair bias have been done via informatics, not experimentation. One investigation of codon pair bias that was based on experimental work was the study of Irwin et al. (1995), who found, counterintuitively, that certain over-represented codon pairs caused slower translation. However, this result could not be reproduced by a second group (Cheng and Goldman, 2001), and is also in conflict with results reported below. Thus, the present results (see below) may be the first experimental evidence for a functional role of codon pair bias.

Certain experiments disclosed herein relate to re-coding viral genome sequences, such as the entire capsid region of PV, involving around 1000 codons, to separately incorporate both poor codon bias and poor codon pair bias into the genome. The rationale underlying these experiments is that if each substitution creates a small effect, then all substitutions together should create a large effect. Indeed, it turns out that both deoptimized codon bias, and deoptimized codon pair bias, separately create non-viable viruses. As discussed in more detail in the Examples, preliminary data suggest that inefficient translation is the major mechanism for reducing the viability of a virus with poor codon bias or codon pair bias. Irrespective of the precise mechanism, the data indicate that the large-scale substitution of synonymous deoptimized codons into a viral genome results in severely attenuated viruses. This procedure for producing attenuated viruses has been dubbed SAVE (Synthetic Attenuated Virus Engineering).

According to the invention, viral attenuation can be accomplished by changes in codon pair bias as well as codon bias. However, it is expected that adjusting codon pair bias is particularly advantageous. For example, attenuating a virus through codon bias generally requires elimination of common codons, and so the complexity of the nucleotide sequence is reduced. In contrast, codon pair bias reduction or minimization can be accomplished while maintaining far greater sequence diversity, and consequently greater control over nucleic acid secondary structure, annealing temperature, and other physical and biochemical properties. The work disclosed herein includes attenuated codon pair bias-reduced or-minimized sequences in which codons are shuffled, but the codon usage profile is unchanged.

Viral attenuation can be confirmed in ways that are well known to one of ordinary skill in the art. Non-limiting examples induce plaque assays, growth measurements, and reduced lethality in test animals. The instant application demonstrates that the attenuated viruses are capable of inducing protective immune responses in a host.

Synthetic Attenuated Virus Engineering (SAVE)

SAVE employs specifically designed computer software and modern methods of nucleic acid synthesis and assembly to re-code and re-synthesize the genomes of viruses. This strategy provides an efficient method of producing vaccines against various medically important viruses for which efficacious vaccines are sought.

Two effective polio vaccines, an inactivated polio vaccine (IPV) developed by Jonas Salk and an oral polio vaccine (OPV) comprising live attenuated virus developed by Albert Sabin, respectively, have been available sine the 1950's. Indeed, a global effort to eradicate poliomyelitis, begun in 1988 and led by the World Health Organization (WHO), has succeeded in eradicating polio from most of the countries in the world. The number of annual diagnosed cases has been reduced from the hundreds of thousands to less that two thousand in 2005, occurring mainly in India and in Nigeria. However, a concern regarding the wide use of the OPV is that is can revert to a virulent form, and though believed to be a rare event, outbreaks of vaccine-derived polio have been reported (Georgescu et al., 1997; Kew et al., 2002; Shimizu et al., 2004). In fact, as long as the live poliovirus vaccine strains are used, each carrying less than 7 attenuating mutations, there is a possibility that this strain will revert to wt, and such reversion poses a serious threat to the complete eradication of polio. Thus, the WHO may well need a new polio vaccine to combat the potential of reversion in the closing stages of its efforts at polio eradication, and this provides one rationale for the studies disclosed herein on the application of SAVE to PV. However, PV was selected primarily because it is an excellent model system for developing SAVE.

During re-coding, essential nucleic acid signals in the viral genome are preserved, but the efficiency of protein translation is systematically reduced by deoptimizing codon bias, codon pair bias, and other parameters such as RNA secondary structure and CpG dinucleotide content, C+G content, translation frameshift sites, translation pause sites, or any combination thereof. This deoptimization may involve hundreds or thousands of changes, each with a small effect. Generally, deoptimization is performed to a point at which the virus can still be grown in some cell lines (including lines specifically engineered to be permissive for a particular virus), but where the virus is avirulent in a normal animal or human. Such avirulent viruses are excellent candidates for either a killed or live vaccine since they encode exactly the same proteins as the fully virulent virus and accordingly provoke exactly the same immune response as the fully virulent virus. In addition, the SAVE process offers the prospect for fine tuning the level of attenuation; that is, it provides the capacity to design synthetic viruses that are deoptimized to a roughly predictable extent. Design, synthesis, and production of viral particles is achievable in a timeframe of weeks once the genome sequence is known, which has important advantages for the production of vaccines in potential emergencies. Furthermore, the attenuated viruses are expected to have virtually no potential to revert to virulence because of the extremely large numbers of deleterious nucleotide changes involved. This method may be generally applicable to a wide range of viruses, requiring only knowledge of the viral genome sequence and a reverse genetics system for any particular virus.

Viral Attenuation by Deoptimizing Codon Bias

If one uses the $IC_{50}$-ratio of control cells/test cells method as described above, then compounds with CSG values less than or equal to 1 would not generally be considered to be good clinical candidate compounds, whereas compounds with CSG values of greater than approximately 10 would be quite promising and worthy of further consideration.

As a means of engineering attenuated viruses, the capsid coding region of poliovirus type 1 Mahoney [PV(M)] was re-engineered by making changes in synonymous codon usage. The capsid region comprises about a third of the virus and is very actively translated. One mutant virus (virus PV-AB), having a very low codon bias due to replacement of the largest possible number of frequently used codons with rare synonymous codons was created. As a control, another virus (PV-SD) was created having the largest possible number of synonymous codon changes while maintaining the original codon bias. See FIGS. 1 and 2. Thus, PV-SD is a virus having essentially the same codons as the wt, but in shuffled position while encoding exactly the same proteins. In PV-SD, no attempt was made to increase or reduce codon pair bias by the shuffling procedure. See Example 1. Despite 934 nucleotide changes in the capsid-coding region, PV-SD RNA produced virus with characteristics indistinguishable from wt. In contrast, no viable virus was recovered from PV-AB carrying 680 silent mutations. See Example 2.

A trivial explanation of the inviability of PV-AB is that just one of the nucleotide changes is somehow lethal, while the other 679 are harmless. For instance, a nucleotide change could be lethal for some catastrophic but unappreciated reason, such as preventing replication. This explanation is unlikely, however. Although PV does contain important regulatory elements in its RNA, such as the CRE, it is known that no such elements exist inside the capsid coding region. This is supported by the demonstration that the entire capsid coding region can be deleted without affecting normal replication of the residual genome within the cell, though of course viral particles cannot be formed (Kaplan and Racamiello, 1988).

To address questions concerning the inviability of certain re-engineered viruses, sub-segments of the capsid region of virus PV-AB were subcloned into the wild type virus. See Example 1 and FIG. 3. Incorporating large subcloned segments (including non-overlapping segments) proved lethal, while small subcloned segments produced viable (with one exception) but sick viruses. "Sickness" is revealed by many assays: for example, segments of poor codon bias cause poor titers (FIG. 3B) and small plaques (FIGS. 3C-H). It is particularly instructive that in general, large, lethal segments can be divided into two sub-segments, both of which are alive but sick (FIG. 3). These results rule out the hypothesis that inviability is due to just one change; instead, at minimum, many changes must be contributing to the phenotype.

There is an exceptional segment from position 1513 to 2470. This segment is fairly small, but its inclusion in the PV genome causes inviability. It is not known at present whether or not this fragment can be subdivided into subfragments that merely cause sickness and do not inactivate the virus. It is conceivable that this segment does contain a highly deleterious change, possibly a translation frameshift site.

Figures 5A, 5B:
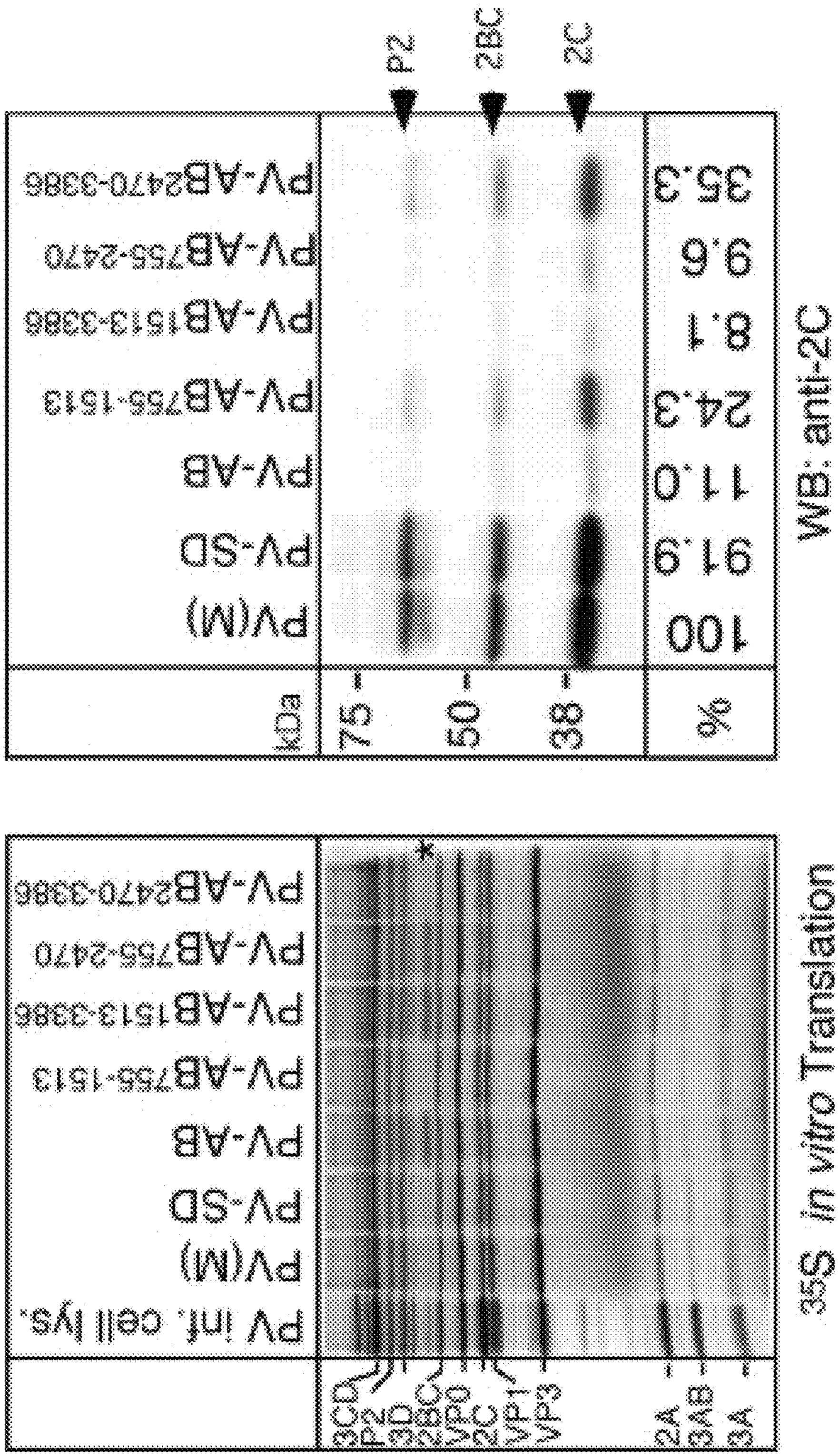
FIGS. 5A-B. In vitro translation of codon-deoptimized and wild type viruses. The PV-AB phenotype is determined at the level of genome translation.

Since poor codon bias naturally suggests an effect on translation, translation of the proteins encoded by virus PV-AB was tested. See Example 5 and FIG. 5. Indeed, all the sick viruses translated capsid protein poorly (FIG. 5B). Translation was less efficient in the sicker viruses, consistent with poor translation being the cause of the sickness. Translation was improved essentially to wt levels in reactions that were supplemented with excess tRNAs and amino acids (FIG. 5A), consistent with the rate of recognition of rare codons being limiting.

As a second test of whether deoptimized codon bias was causing inefficient translation, portions of wt and deoptimized capsid were fused to the N-terminus of firefly luciferase in a dicistronic reporter construct. See Example 5 and FIG. 6. In these fusion constructs, translation of luciferase depends on translation of the N-terminally fused capsid protein. Again, it was found that translation of the capsid proteins with deoptimized codons was poor, and was worse in the sicker viruses, suggesting a cause-and-effect relationship. Thus, the data suggest that the hundreds of rare codons in the PV-AB virus cause inviability largely because of poor translation. Further, the poor translation seen in vitro and the viral sickness seen in cultured cells are also reflected in infections of animals. Even for one of the least debilitated deoptimized viruses, $PV\text{-}AB^{2470\text{-}2954}$, the number of viral particles needed to cause disease in mice was increased by about 100-fold. See Example 4, Table 4.

Burns et al. (2006) have recently described some similar experiments with the Sabin type 2 vaccine strain of PV and reached similar conclusions. Burns et al. synthesized a completely different codon-deoptimized virus (i.e., the nucleotide sequences of the PV-AB virus described herein and their "abcd" virus are very different), and yet got a similar degree of debilitation using similar assays. Burns et al. did not test their viral constructs in host organisms for attenuation. However, their result substantiates the view that SAVE is predictable, and that the results are not greatly dependent on the exact nucleotide sequence.

Viral Attenuation by Deoptimizing Codon Pair Bias

According to the invention, codon pair bias can be altered independently of codon usage. For example, in a protein encoding sequence of interest, codon pair bias can be altered simply by directed rearrangement of its codons. In particular, the same codons that appear in the parent sequence, which can be of varying frequency in the host organism, are used in the altered sequence, but in different positions. In the simplest form, because the same codons are used as in the parent sequence, codon usage over the protein coding region being considered remains unchanged (as does the encoded amino acid sequence). Nevertheless, certain codons appear in new contexts, that is, preceded by and/or followed by codons that encode the same amino acid as in the parent sequence, but employing a different nucleotide triplet. Ideally, the rearrangement of codons results in codon pairs that are less frequent than in the parent sequence. In practice, rearranging codons often results in a less frequent codon pair at one location and a more frequent pair at a second location. By judicious rearrangement of codons, the codon pair usage bias over a given length of coding sequence can be reduced relative to the parent sequence. Alternatively, the codons could be rearranged so as to produce a sequence that makes use of codon pairs which are more frequent in the host than in the parent sequence.

Codon pair bias is evaluated by considering each codon pair in turn, scoring each pair according to the frequency that the codon pair is observed in protein coding sequences of the host, and then determining the codon pair bias for the sequence, as disclosed herein. It will be appreciated that one can create many different sequences that have the same codon pair bias. Also, codon pair bias can be altered to a greater or lesser extent, depending on the way in which codons are rearranged. The codon pair bias of a coding sequence can be altered by recoding the entire coding sequence, or by recoding one or more subsequences. As used herein, "codon pair bias" is evaluated over the length of a coding sequence, even though only a portion of the sequence may be mutated. Because codon pairs are scored in the context of codon usage of the host organism, a codon pair bias value can be assigned to wild type viral sequences and mutant viral sequences. According to the invention, a virus can be attenuated by recoding all or portions of the protein encoding sequences of the virus so a to reduce its codon pair bias.

According to the invention, codon pair bias is a quantitative property determined from codon pair usage of a host. Accordingly, absolute codon pair bias values may be determined for any given viral protein coding sequence. Alternatively, relative changes in codon pair bias values can be determined that relate a deoptimized viral protein coding sequence to a "parent" sequence from which it is derived. As viruses come in a variety of types (i.e., types I to VII by the Baltimore classification), and natural (i.e., virulent) isolates of different viruses yield different values of absolute codon pair bias, it is relative changes in codon pair bias that are usually more relevant to determining desired levels of attenuation. Accordingly, the invention provides attenuated viruses and methods of making such, wherein the attenuated viruses comprise viral genomes in which one or more protein encoding nucleotide sequences have codon pair bias reduced by mutation. In viruses that encode only a single protein (i.e., a polyprotein), all or part of the polyprotein can be mutated to a desired degree to reduce codon pair bias, and all or a portion of the mutated sequence can be provided in a recombinant viral construct. For a virus that separately encodes multiple proteins, one can reduce the codon pair bias of all of the protein encoding sequences simultaneously, or select only one or a few of the protein encoding sequences for modification. The reduction in codon pair bias is determined over the length of a protein encoding sequences, and is at least about 0.05, or at least about 0.1, or at least about 0.15, or at least about 0.2, or at least about 0.3, or at least about 0.4. Depending on the virus, the absolute codon pair bias, based on codon pair usage of the host, can be about −0.05 or less, or about −0.1 or less, or about −0.15 or less, or about −0.2 or less, or about −0.3 or less, or about −0.4 or less.

It will be apparent that codon pair bias can also be superimposed on other sequence variation. For example, a coding sequence can be altered both to encode a protein or polypeptide which contains one or more amino acid changes and also to have an altered codon pair bias. Also, in some cases, one may shuffle codons to maintain exactly the same codon usage profile in a codon-bias reduced protein encoding sequence as in a parent protein encoding sequence. This procedure highlights the power of codon pair bias changes, but need not be adhered to. Alternatively, codon selection can result in an overall change in codon usage is a coding sequence. In this regard, it is noted that in certain examples provided herein, (e.g., the design of PV-Min) even if the codon usage profile is not changed in the process of generating a codon pair bias minimized sequence, when a portion of that sequence is subcloned into an unmutated sequence (e.g., PV-MinXY or PV-MinZ), the codon usage profile over the subcloned portion, and in the hybrid produced, will not match the profile of the original unmutated protein coding sequence. However, these changes in codon usage profile have minimal effect of codon pair bias.

Similarly, it is noted that, by itself, changing a nucleotide sequence to encode a protein or polypeptide with one or many amino acid substitutions is also highly unlikely to produce a sequence with a significant change in codon pair bias. Consequently, codon pair bias alterations can be recognized even in nucleotide sequences that have been further modified to encode a mutated amino acid sequence. It is also noteworthy that mutations meant by themselves to increase codon bias are not likely to have more than a small effect on codon pair bias. For example, as disclosed herein, the codon pair bias for a poliovirus mutant recoded to maximize the use of nonpreferred codons (PV-AB) is decreased from wild type (PV-1(M)) by only about 0.05. Also noteworthy is that such a protein encoding sequence have greatly diminished sequence diversity. To the contrary, substantial sequence diversity is maintained in codon pair bias modified sequences of the invention. Moreover, the significant reduction in codon pair bias obtainable without increased use of rare codons suggests that instead of maximizing the use of nonpreferred codons, as in PV-AB, it would be beneficial to rearrange nonpreferred codons with a sufficient number of preferred codons in order to more effectively reduce codon pair bias.

The extent and intensity of mutation can be varied depending on the length of the protein encoding nucleic acid, whether all or a portion can be mutated, and the desired reduction of codon pair bias. In an embodiment of the invention, a protein encoding sequence is modified over a length of at least about 100 nucleotide, or at least about 200 nucleotides, or at least about 300 nucleotides, or at least about 500 nucleotides, or at least about 1000 nucleotides.

As discussed above, the term "parent" virus or "parent" protein encoding sequence is used herein to refer to viral genomes and protein encoding sequences from which new sequences, which may be more or less attenuated, are derived. Accordingly, a parent virus can be a "wild type" or "naturally occurring" prototypes or isolate or variant or a mutant specifically created or selected on the basis of real or perceived desirable properties.

Using de novo DNA synthesis, the capsid coding region (the P1 region from nucleotide 755 to nucleotide 3385) of PV(M) was redesigned to introduce the largest possible number of rarely used codon pairs (virus PV-Min) (SEQ ID NO:4) or the largest possible number of frequently used codon pairs (virus PV-Max) (SEQ ID NO:5), while preserving the codon bias of the wild type virus. See Example 7. That is, the designed sequences use the same codons as the parent sequence, but they appear in a different order. The PV-Max virus exhibited one-step growth kinetics and killing of infected cells essentially identical to wild type virus. (That growth kinetics are not increased for a codon pair maximized virus relative to wild type appears to hold true for other viruses as well.) Conversely, cells transfected with PV-Min mutant RNA were not killed, and no viable virus could be recovered. Subcloning of fragments (PV-Min$^{755-2470}$, PV-Min$^{2470-3386}$) of the capsid region of PV-Min into the wt background produced very debilitated, but not dead, virus. See Example 7 and FIG. 8. This result substantiates the hypothesis that deleterious codon changes are preferably widely distributed and demonstrates the simplicity and effectiveness of varying the extent of the codon pair deoptimized sequence that is substituted into a wild type parent virus genome in order to vary the codon pair bias for the overall sequence and the attenuation of the viral product. As seen with PV-AB viruses, the phenotype of PV-Min viruses is a result of reduced specific infectivity of the viral particles rather than of lower production of progeny virus.

Virus with deoptimized codon pair bias are attenuated. As exemplified below, (see Example 8, and Table 5), CD155tg mice survived challenge by intracerebral injection of attenuated virus in amounts 1000-fold higher than would be lethal for wild type virus. These findings demonstrate the power of deoptimization of codon pair bias to minimize lethality of a virus. Further, the viability of the virus can be balanced with a reduction of infectivity by choosing the degree of codon pair bias deoptimization. Further, once a degree or ranges of degrees of codon pair bias deoptimization is determined that provides desired attenuation properties, additional sequences can be designed to attain that degree of codon pair bias. For example, SEQ ID NO:6 provides a poliovirus sequence with a codon pair bias of about −0.2, and mutations distributed over the region encompassing the mutated portions of PV-MinXY and PV-MinZ (i.e., PV$^{755-3385}$).

Algorithms for Sequence Design

The inventors have developed several novel algorithms for gene design that optimize the DNA sequence for particular desired properties while simultaneously coding for the given amino acid sequence. In particular, algorithms for maximizing or minimizing the desired RNA secondary structure in the sequence (Cohen and Skiena, 2003) as well as maximally adding and/or removing specified sets of patterns (Skiena, 2001), have been developed. The former issue arises in designing viable viruses, while the latter is useful to optimally insert restriction sites for technological reasons. The extent to which overlapping genes can be designed that simultaneously encode two or more genes in alternate reading frames has also been studied (Wang et al., 2006). This property of different functional polypeptides being encoded in different reading frames of a single nucleic acid is common in viruses and can be exploited for technological purposes such as weaving in antibiotic resistance genes.

The first generation of design tools for synthetic biology has been built, as described by Jayaraj et al. (2005) and Richardson et al. (2006). These focus primarily on optimizing designs for manufacturability (i.e., oligonucleotides without local secondary structures and end repeats) instead of optimizing sequences for biological activity. These first-generation tools may be viewed as analogous to the early VLSI CAD tools built around design rule-checking, instead of supporting higher-order design principles.

As exemplified herein, a computer-based algorithm can be used to manipulate the codon pair bias of any coding region. The algorithm has the ability to shuffle existing codons and to evaluate the resulting CPB, and then to reshuffle the sequence, optionally locking in particularly "valuable" codon pairs. The algorithm also employs a for of "simulated annealing" so as not to get stuck in local minima. Other parameters, such as the free energy of folding of RNA, may optional be under the control of the algorithm as well, in order to avoid creation of undesired secondary structures. The algorithm can be used to find a sequence with a minimum codon pair bias, and in the event that such a sequence does not provide a viable virus, the algorithm can be adjusted to find sequences with reduced, but not minimized biases. Of course, a viable viral sequence could also be produced using only a subsequence of the computer minimized sequence.

Whether or not performed with the aid of a computer, using, for example, a gradient descent, or simulated annealing, or other minimization routine. An example of the procedure that rearranges codons present in a starting sequence can be represented by the following steps:

1) Obtain wildtype viral genome sequence.

2) Select protein coding sequences to target for attenuated design.

3) Lock down known or conjectured DNA segments with non-coding functions.

4) Select desired codon distribution for remaining amino acids in redesigned proteins.

5) Perform random shuffle of unlocked codon positions and calculate codon-pair score.

6) Further reduce (or increase) codon-pair score optionally employing a simulated annealing procedure.

7) Inspect resulting design for excessive secondary structure and unwanted restriction site:

if yes→go to step (5) or correct the design by replacing problematic regions with wildtype sequences and go to step (8).

8. Synthesize DNA sequence corresponding to virus design.

9. Create viral construct and assess expression:

if too attenuated, prepare subclone construct and go to 9;

if insufficiently attenuated, go to 2.

Source code (PERL script) of a computer based simulated annealing routine is provided.

Alternatively, one can devise a procedure which allows each pair of amino acids to be deoptimized by choosing a codon pair without a requirement that the codons be swapped out from elsewhere in the protein encoding sequence.

Molecular Mechanisms of Viral Attenuation: Characterization of Attenuated PV Using High-Throughput Methods As described above and in greater detail in the Examples, two synthetic, attenuated polioviruses encoding exactly the same proteins as the wildtype virus, but having altered codon bias or altered codon pair bias, were constructed. One virus uses deoptimized codons; the other virus uses deoptimized codon pairs. Each virus has many hundreds of nucleotide changes with respect to the wt virus.

The data presented herein suggest that these viruses are attenuated because of poor translation. This finding, if correct, has important consequences. First, the reduced fitness/virulence of each virus is due to small defects at hundreds of positions spread over the genome. Thus, there is essentially no chance of the virus reverting to wildtype, and so the virus is a good starting point for either a live or killed vaccine. Second, if the reduced fitness/virulence is due to additive effects of hundreds of small defects in translation, this method of reducing fitness with minimal risk of reversion should be applicable to many other viruses.

Though it is emphasized that the present invention is not limited to any particular mode of operation or underlying molecular mechanism, ongoing studies are aimed at distinguishing these alternative hypotheses. The ongoing investigations involve use of high throughput methods to scan through the genomes of various attenuated virus designs such as codon and codon pair deoptimized poliovirus and influenza virus, and to construct chimeras by placing overlapping 300-bp portions of each mutant virus into a wt context. See Example 11. The function of these chimeric viruses are then assayed. A finding that most chimeras are slightly, but not drastically, less fit than wild type, as suggested by the preliminary data disclosed herein, corroborates the "incremental loss of function" hypothesis, wherein many deleterious mutations are distributed throughout the regions covered by the chimeras. Conversely, a finding that most of the chimeras are similar or identical to wt, whereas one or only a few chimeras are attenuated like the parental mutant, suggests that there are relatively few positions in the sequence where mutation results in attenuation and that attenuation at those positions is significant.

As described in Example 12, experiments are performed to determine how codon and codon-pair deoptimization affect RNA stability and abundance, and to pinpoint the parameters that impair translation of the re-engineered viral genome. An understanding of the molecular basis of this impairment will further enhance the applicability of the SAVE approach to a broad range of viruses. Another conceivable mechanism underlying translation impairment is translational frameshifting, wherein the ribosome begins to translate a different reading frame, generating a spurious, typically truncated polypeptide up to the point where it encounters an in-frame stop codon. The PV genomes carrying the AB mutant segment from residue 1513 to 2470 are not only non-viable, but also produce a novel protein band during in vitro translation of approximately 42-44 kDa (see FIG. 5A). The ability of this $AB^{1513-2470}$ fragment to inactivate PV, as well as its ability to induce production of the novel protein, may reflect the occurrence of a frameshift event and this possibility is also being investigated. A filter for avoiding the introduction of frameshifting sites is built into the SAVE design software.

More detailed investigations of translational defects are conducted using various techniques including, but not limited to, polysome profiling, toeprinting, and luciferase assays of fusion proteins, as described in Example 12.

Molecular Biology of Poliovirus

While studies are ongoing to unravel the mechanisms underlying viral attenuation by SAVE, large-scale codon deoptimization of the PV capsid coding region revealed interesting insights into the biology of PV itself. What determines the PFU/particle ratio (specific infectivity) of a virus has been a longstanding question. In general, failure at any step during the infectious life cycle before the establishment of a productive infection will lead to an abortive infection and, therefore, to the demise of the infecting particle. In the case of PV, it has been shown that approximately 100 virions are required to result in one infectious event in cultured cells (Joklik and Darnell, 1961; Schwerdt and Fogh, 1957). That is, of 100 particles inoculated, only approximately one is likely to successfully complete all steps at the level of receptor binding (step 1), followed by internalization and uncoating (step 2), initiation of genome translation (step 3), polyprotein translation (step 4), RNA replication (step 5), and encapsidation of progeny (step 6).

In the infectious cycle of AB-type viruses described here, steps 1 and 2 should be identical to a PV(M) infection as their capsids are identical. Likewise, identical 5' nontranslated regions should perform equally well in assembly of a translation complex (step 3). Viral polyprotein translation, on the other hand (step 4), is severely debilitated due to the introduction of a great number of suboptimal synonymous codons in the capsid region (FIGS. 5 and 6). It is thought that the repeated encounter of rare codons by the translational machinery causes stalling of the ribosome as, by the laws of mass action, rare aminoacyl-tRNA will take longer to diffuse into the A site on the ribosome. As peptide elongation to a large extent is driven by the concentration of available aminoacyl-tRNA, dependence of an mRNA on many rare tRNAs consequently lengthens the time of translation (Gustafsson et al., 2004). Alternatively, excessive stalling of the ribosome may cause premature dissociation of the translation complex from the RNA and result in a truncated protein destined for degradation. Both processes lead to a lower protein synthesis rate per mRNA molecule per unit of time. While the data presented herein suggest that the phenotypes of codon-deoptimized viruses are determined by the rate of genome translation, other mechanistic explanations may be possible. For example, it has been suggested that the conserved positions of rare synonymous codons throughout the viral capsid sequence in Hepatitis A virus are of functional importance for the proper folding of the nascent polypeptide by introducing necessary translation pauses (Sánchez et al., 2003). Accordingly, large-scale alteration of the codon composition may conceivably change some of these pause sites to result in an increase of misfolded capsid proteins.

Figure 3A:
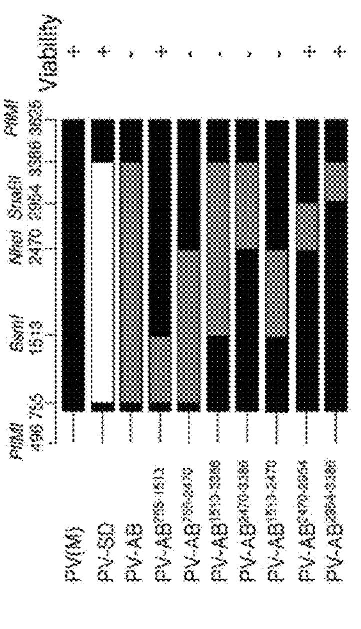
FIGS. 3A-J. Codon-deoptimized virus phenotypes.
Figure 3B:
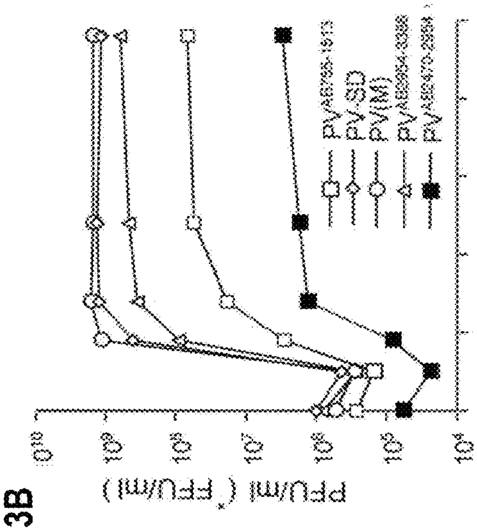

Whether these considerations also apply to the PV capsid is not clear. If so, an altered phenotype would have been expected with the PV-SD design, in which the wt codons were preserved, but their positions throughout the capsid were completely changed. That is, none of the purported pause sites would be at the appropriate position with respect to the protein sequence. No change in phenotype, however, was observed and PV-SD translated and replicated at wild type levels (FIG. 3B).

Another possibility is that the large-scale codon alterations in the tested designs may create fortuitous dominant-negative RNA elements, such as stable secondary structures, or sequences that may undergo disruptive long-range interactions with other regions of the genome.

It is assumed that all steps prior to, and including, virus uncoating should be unchanged when wt and the mutant viruses, described herein are compared. This is supported by the observation that the eclipse period for all these isolates is similar (FIG. 3B). The dramatic reduction in PFU/particle ratio is, therefore, likely to be a result of the reduced translation capacity of the deoptimized genomes, i.e., the handicap of the mutant viruses is determined intracellularly.

It is generally assumed that the relatively low PFU/particle ratio of picornaviruses of 1/100 to 1/1,000 (Rueckert, 1985) is mainly determined by structural alterations at the receptor binding step, either prior to or at the level of cell entry. The formation of 135S particles that are hardly infectious may be the major culprit behind the inefficiency of poliovirus infectivity (Hogle, 2002). However, certain virus mutants seem to sidestep A particle conversion without resulting in a higher specific infectivity, an observation suggesting that other post-entry mechanisms may be responsible for the low PFU/particle ratio (Dove and Racaniello, 1997).

The present data provide clear evidence for such post-entry interactions between virus and cell, and suggest that these, and not pre-entry events, contribute to the distinct PFU/particle ratio of poliovirus. As all replication proteins in poliovirus are located downstream of P1 on the polyprotein, they critically depend upon successful completion of P1 translation. Lowering the rate of P1 translation therefore lowers translation of all replication proteins to the same extent. This, in turn, likely leads to a reduced capacity of the virus to make the necessary modifications to the host cell required for establishment of a productive infection, such as shutdown of host cell translation or prevention of host cell innate responses. While codon deoptimization, as described herein, is likely to effect translation at the peptide elongation step, reduced initiation of translation can also be a powerful attenuating determinant as well, as has been shown for mutations in the internal ribosomal entry site in the Sabin vaccine strains of poliovirus (Svitkin et al., 1993; 1985).

On the basis of these considerations, it is predicted that many mutant phenotypes attributable to defects in genome translation or early genome replication actually manifest themselves by lowering PFU/particle ratios. This would be the case as long as the defect results in an increased chance of abortive infection. Since in almost all studies the omnipresent plaque assay is the virus detection method of choice, a reduction in the apparent virus titer is often equated with a reduction in virus production per se. This may be an inherent pitfall that can be excused with the difficulties of characterizing virus properties at the single-cell level. Instead, most assays are done on a large population of cells. A lower readout of the chosen test (protein synthesis, RNA replication, virus production as measured in PFU) is taken at face value as an indicator of lower production on a per-cell basis, without considering that virus production in a cell may be normal while the number of cells producing virus is reduced.

The near-identical production of particles per cell by codon-deoptimized viruses indicates that the total of protein produced after extended period of times is not severely affected, whereas the rate of protein production has been drastically reduced. This is reflected in the delayed appearance of CPE, which may be a sign that the virus has to go through more RNA replication cycles to build up similar intracellular virus protein concentrations. It appears that codon-deoptimized viruses are severely handicapped in establishing a productive infection because the early translation rate of the incoming infecting genome is reduced. As a result of this lower translation rate, PV proteins essential for disabling the cell's antiviral responses (most likely proteinases $2A^{pro}$ and $3C^{pro}$) are not synthesized at sufficient amounts to pass this crucial hurdle in the life cycle quickly enough. Consequently, there is a better chance for the cell to eliminate the infection before viral replication could unfold and take over the cell. Thus, the likelihood for productive infection events is reduced and the rate of abortive infection is increased. However, in the case where a codon-deoptimized virus does succeed in disabling the cell, this virus will produce nearly identical amounts of progeny to the wild type. The present data suggest that a fundamental difference may exist between early translation (from the incoming RNA genome) and late translation during the replicative phase, when the cell's own translation is largely shut down. Although this may be a general phenomenon, it might be especially important in the case of codon-deoptimized genomes. Host cell shutoff very likely results in an overabundance of free aminoacyl-tRNAs, which may overcome the imposed effect of the suboptimal codon usage as the PV genomes no longer have to compete with cellular RNAs for translation resources. This, in fact, may be analogous to observations with the modified in vitro translation system described herein (FIG. 5B). Using a translation extract that was not nuclease-treated (and thus contained cellular mRNAs) and not supplemented with exogenous amino acids or tRNAs, clear differences were observed in the translation capacity of different capsid design mutants. Under these conditions, viral genomes have to compete with cellular mRNAs in an environment where supplies are limited. In contrast, in the traditional translation extract, in which endogenous mRNAs were removed and excess tRNAs and amino acids were added, all PV RNAs translated equally well regardless of codon bias (FIG. 5A). These two different in vitro conditions may be analogous to in vivo translation during the early and late phases in the PV-infected cell.

One key finding of the present study is the realization that, besides the steps during the physical interaction and uptake of virus, the PFU/particle ratio also largely reflects the virus' capacity to overcome host cell antiviral responses. This suggests that picornaviruses are actually quite inefficient in winning this struggle, and appear to have taken the path of evolving small genomes that can quickly replicate before the cell can effectively respond. As the data show, slowing down translation rates by only 30% in PV-$AB^{2470-2954}$ (see FIG. 6) leads to a 1,000-fold higher rate of abortive infection as reflected in the lower specific infectivity (FIG. 4D). Picornaviruses apparently not only replicate at the threshold of error catastrophe (Crotty et al., 2001; Holland et al., 1990) but also at the threshold of elimination by the host cell's antiviral defenses. This effect may have profound consequences for the pathogenic phenotype of a picornavirus. The cellular antiviral processes responsible for the increased rate of aborted infections by codon-deoptimized viruses are not completely understood at present. PV has been shown to both induce and inhibit apoptosis (Belov et al., 2003; Girard et al., 1999; Tolskaya et al., 1995). Similarly PV interferes with the interferon pathway by cleaving NF-κB (Neznanov et al., 2005). It is plausible that a PV with a reduced rate of early genome translation still induces antiviral responses in the same way as a wt virus (induction of apoptosis and interferon by default) but then, due to low protein synthesis, has a reduced potential of inhibiting these processes. This scenario would increase the likelihood of the cell aborting a nascent infection and could explain the observed phenomena. At the individual cell level, PV infection is likely to be an all-or-nothing phenomenon. Viral protein and RNA syntheses likely need to be within a very close to maximal range in order to ensure productive infection.

Attenuated Virus Vaccine Compositions

The present invention provides a vaccine composition for inducing a protective immune response in a subject comprising any of the attenuated viruses described herein and a pharmaceutically acceptable carrier.

It should be understood that an attenuated virus of the invention, where used to elicit a protective immune response in a subject or to prevent a subject from becoming afflicted with a virus-associated disease, is administered to the subject in the form of a composition additionally comprising a pharmaceutically acceptable carrier. Pharmaceutically acceptable carriers are well known to those skilled in the art and include, but are not limited to, one or more of 0.01-0.1M and preferably 0.05M phosphate buffer, phosphate-buffered saline (PBS), or 0.9% saline. Such carriers also include aqueous or non-aqueous solutions, suspensions, and emulsions. Aqueous carriers include water, alcoholic/aqueous solutions, emulsions or suspensions, saline and buffered media. Examples of non-aqueous solvents are propylene glycol, polyethylene glycol, vegetable oils such as olive oil, and injectable organic esters such as ethyl oleate. Parenteral vehicles include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Solid compositions may comprise nontoxic solid carriers such as, for example, glucose, sucrose, mannitol, sorbitol, lactose, starch, magnesium stearate, cellulose or cellulose derivatives, sodium carbonate and magnesium carbonate. For administration in an aerosol, such as for pulmonary and/or intranasal delivery, an agent or composition is preferably formulated with a nontoxic surfactant, for example, esters or partial esters of C6 to C22 fatty acids or natural glycerides, and a propellant. Additional carriers such as lecithin may be included to facilitate intranasal delivery. Pharmaceutically acceptable carriers can further comprise minor amounts of auxiliary substances such as wetting or emulsifying agents, preservatives and other additives, such as, for example, antimicrobials, antioxidants and chelating agents, which enhance the shelf life and/or effectiveness of the active ingredients. The instant compositions can, as is well known in the art, be formulated so as to provide quick, sustained or delayed release of the active ingredient after administration to a subject.

In various embodiments of the instant vaccine composition, the attenuated virus (i) does not substantially alter the synthesis and processing of viral proteins in an infected cell; (ii) produces similar amounts of virions per infected cell as wt virus; and/or (iii) exhibits substantially lower virion-specific infectivity than wt virus. In further embodiments, the attenuated virus induces a substantially similar immune response in a host animal as the corresponding wt virus.

This invention also provides a modified host cell line specially isolated or engineered to be permissive for an attenuated virus that is inviable in a wild type host cell. Since the attenuated virus cannot grow in normal (wild type) host cells, it is absolutely dependent on the specific helper cell line for growth. This provides a very high level of safety for the generation of virus for vaccine production. Various embodiments of the instant modified cell line permit the growth of an attenuated virus, wherein the genome of said cell line has been altered to increase the number of genes encoding rare tRNAs.

In preferred embodiments, the rare codons are CTA (coding for Leu), TCG (Ser), and CCG (Pro). In different embodiments, one, two, or all three of these rare codons are substituted for synonymous frequent codons in the viral genome. For example, all Leu codons in the virus may be changed to CTA; all Ser codons may be changed to TCG; all Pro codons may be changed to CCG; the Leu and Ser, or Leu and Pro, or Ser and Pro codons may be replaced by the identified rare codons; or all Leu, Ser, and Pro codons may be changed to CTA, TCG, and CCG, respectively, in a single virus. Further, a fraction of the relevant codons, i.e., less than 100%, may be changed to the rare codons. Thus, the proportion of codons substituted may be about 20%, 40%, 60%, 80% or 100% of the total number of codons.

In certain embodiments, these substitutions are made only in the capsid region of the virus, where a high rate of translation is most important. In other embodiments, the substitutions are made throughout the virus. In further embodiments, the cell line overexpresses tRNAs that bind to the rare codons.

This invention further provides a method of synthesizing any of the attenuated viruses described herein, the method comprising (a) identifying codons in multiple locations within at least one non-regulatory portion of the viral genome, which codons can be replaced by synonymous codons; (b) selecting a synonymous codon to be substituted for each of the identified codons; and (c) substituting a synonymous codon for each of the identified codons.

In certain embodiments of the instant methods, steps (a) and (b) are guided by a computer-based algorithm for Synthetic Attenuated Virus Engineering (SAVE) that permits design of a viral genome by varying specified pattern sets of deoptimized codon distribution and/or deoptimized codon-pair distribution within preferred limits. The invention also provides a method wherein, the pattern sets alternatively or additionally comprise, density of deoptimized codons and deoptimized codon pairs, RNA secondary structure, CpG dinucleotide content, C+G content, overlapping coding frames, restriction site distribution, frameshift sites, or any combination thereof.

In other embodiments, step (c) is achieved by de novo synthesis of DNA containing the synonymous codons and/or codon pairs and substitution of the corresponding region of the genome with the synthesized DNA. In further embodiments, the entire genome is substituted with the synthesized DNA. In still further embodiments, a portion of the genome is substituted with the synthesized DNA. In yet other embodiments, said portion of the genome is the capsid coding region.

In addition, the present invention provides a method for eliciting a protective immune response in a subject comprising administering to the subject a prophylactically or therapeutically effective dose of any of the vaccine compositions described herein. This invention also provides a method for preventing a subject from becoming afflicted with a virus-associated disease comprising administering to the subject a prophylactically effective dose of any of the instant vaccine compositions. In embodiments of the above methods, the subject has been exposed to a pathogenic virus. "Exposed" to a pathogenic virus means contact with the virus such that infection could result.

The invention further provides a method for delaying the onset, or slowing the rate of progression, of a virus-associated disease in a virus-infected subject comprising administering to the subject a therapeutically effective dose of any of the instant vaccine compositions.

As used herein, "administering" means delivering using any of the various methods and delivery systems known to those skilled in the art. Administering can be performed, for example, intraperitoneally, intracerebrally, intravenously, orally, transmucosally, subcutaneously, transdermally, intradermally, intramuscularly, topically, parenterally, via implant, intrathecally, intralymphatically, intralesionally, pericardially, or epidurally. An agent or composition may also be administered in an aerosol, such as for pulmonary and/or intranasal delivery. Administering may be performed, for example, once, a plurality of times, and/or over one or more extended periods.

Eliciting a protective immune response in a subject can be accomplished, for example, by administering a primary dose of a vaccine to a subject, followed after a suitable period of time by one or more subsequent administrations of the vaccine. A suitable period of time between administrations of the vaccine may readily be determined by one skilled in the art, and is usually on the order of several weeks to months. The present invention is not limited, however, to any particular method, route or frequency of administration.

A "subject" means any animal or artificially modified animal. Animals include, but are not limited to, humans, non-human primates, cows, horses, sheep, pigs, dogs, cats, rabbits, ferrets, rodents such as mice, rats and guinea pigs, and birds. Artificially modified animals include, but are not limited to, SCID mice with human immune systems, and CD155tg transgenic mice expressing the human poliovirus receptor CD155. In a preferred embodiment, the subject is a human. Preferred embodiments of birds are domesticated poultry species, including, but not limited to, chickens, turkeys, ducks, and geese.

A "prophylactically effective dose" is any amount of a vaccine that, when administered to a subject prone to viral infection or prone to affliction with a virus-associated disorder, induces in the subject an immune response that protects the subject from becoming infected by the virus or afflicted with the disorder. "Protecting" the subject means either reducing the likelihood of the subject's becoming infected with the virus, or lessening the likelihood of the disorder's onset in the subject, by at least two-fold, preferably at least ten-fold. For example, if a subject has a 1% chance of becoming infected with a virus, a two-fold reduction in the likelihood of the subject becoming infected with the virus would result in the subject having a 0.5% chance of becoming infected with the virus. Most preferably, a "prophylactically effective dose" induces in the subject an immune response that completely prevents the subject from becoming infected by the virus or prevents the onset of the disorder in the subject entirely.

As used herein, a "therapeutically effective dose" is any amount of a vaccine that, when administered to a subject afflicted with a disorder against which the vaccine is effective, induces in the subject an immune response that causes the subject to experience a reduction, remission or regression of the disorder and/or its symptoms. In preferred embodiments, recurrence of the disorder and/or its symptoms is prevented. In other preferred embodiments, the subject is cured of the disorder and/or its symptoms.

Certain embodiments of any of the instant immunization and therapeutic methods further comprise administering to the subject at least one adjuvant. An "adjuvant" shall mean any agent suitable for enhancing the immunogenicity of an antigen and boosting an immune response in a subject. Numerous adjuvants, including particulate adjuvants, suitable for use with both protein- and nucleic acid-based vaccines, and methods of combining adjuvants with antigens, are well known to those skilled in the art. Suitable adjuvants for nucleic acid based vaccines include, but are not limited to, Quil A, imiquimod, resiquimod, and interleukin-12 delivered in purified protein or nucleic acid form. Adjuvants suitable for use with protein immunization include, but are not limited to, alum, Freund's incomplete adjuvant (FIA), saponin, Quil A, and QS-21.

The invention also provides a kit for immunization of a subject with an attenuated virus of the invention. The kit comprises the attenuated virus, a pharmaceutically acceptable carrier, an applicator, and an instructional material for the use thereof. In further embodiments, the attenuated virus may be one or more poliovirus, one or more rhinovirus, one or more influenza virus, etc. More than one virus may be preferred where it is desirable to immunize a host against a number of different isolates of a particular virus. The invention includes other embodiments of kits that are known to those skilled in the art. The instructions can provide any information that is useful for directing the administration of the attenuated viruses.

Of course, it is to be understood and expected that variations in the principles of invention herein disclosed can be made by one skilled in the art and it is intended that such modifications are to be included within the scope of the present invention. The following Examples further illustrate the invention, but should not be construed to limit the scope of the invention in any way. Detailed descriptions of conventional methods, such as those employed in the construction of recombinant plasmids, transfection of host cells with viral constructs, polymerase chain reaction (PCR), and immunological techniques can be obtained from numerous publications, including Sambrook et al. (1989) and Coligan et al. (1994). All references mentioned herein are incorporated in their entirety by reference into this application.

Full details for the various publications cited throughout this application are provided at the end of the specification immediately preceding the claims. The disclosures of these publications are hereby incorporated in their entireties by reference into this application. However, the citation of a reference herein should not be construed as an acknowledgement that such reference is prior art to the present invention.

Example 1

Re-Engineering of Capsid Region of Polioviruses by Altering Codon Bias

Cells, Viruses, Plasmids, and Bacteria

HeLa R19 cell monolayers were maintained in Dulbecco's modified Eagle medium (DMEM) supplemented with 10% bovine calf serum (BCS) at 37° C. All PV infectious cDNA constructs are based on PV1(M) cDNA clone pT7PVM (Cao et al., 1993; van der Werf et al., 1986). Dicistronic reporter plasmids were constructed using pHRPF-Luc (Zhao and Wimmer, 2001). *Escherichia coli* DH5a was used for plasmid transformation and propagation. Viruses were amplified by infection of HeLa R19 cell monolayers with 5 PFU per cell. Infected cells were incubated in DMEM (2% BCS) at 37° C. until complete cytopathic effect (CPE) was apparent or for at least 4 days post-infection. After three rounds of freezing and thawing, the lysate was clarified of cell debris by low-speed centrifugation and the supernatant, containing the virus, was used for further passaging or analysis.

Cloning of Synthetic Capsid Replacements and Dicistronic Reporter Replicons Two PV genome cDNA fragments spanning the genome between nucleotides 495 and 3636, named SD and AB, were synthesized using GeneMaker® technology (Blue Heron Biotechnology). pPV-SD and pPV-AB were generated by releasing the replacement cassettes from the vendor's cloning vector by PflMI digestion and insertion into the pT7PVM vector in which the corresponding PflMI fragment had been removed. pPV-$AB^{755-1513}$ and pPV-$AB^{2470-3386}$ were obtained by inserting a BsmI fragment or an NheI-EcoRI fragment, respectively, from pPV-AB into equally digested pT7PVM vector. In pPV-$AB^{1513-3386}$ and pPV-$AB^{755-2470}$, the BsmI fragment or NheI-EcoRI fragment of pT7PVM, respectively, replaces the respective fragment of the pPV-AB vector. Replacement of the NheI-EcoRI fragment of pPV-$AB^{1513-3386}$ with that of pT7PVM resulted in pPV-$AB^{2470-3386}$. Finally, replacement of the SnaBI-EcoRI fragments of pPV-$AB^{2470-3386}$ and pT7PVM with one another produced pPV-$AB^{2954-3386}$ and pPV-$AB^{2470-2954}$, respectively.

Cloning of dicistronic reporter constructs was accomplished by first introducing a silent mutation in pHRPF-Luc by site-directed mutagenesis using oligonucleotides Fluc-mutRI(+)/Fluc-mutRI(−) to mutate an EcoRI site in the firefly luciferase open reading frame and generate pdiLuc-mRI. The capsid regions of pT7PVM, pPV-$AB^{1513-2470}$, and pPV-$AB^{2470-2954}$ were PCR amplified using oligonucleotides RI-2A-P1wt(+)/P1wt-2A-RI(−). Capsid sequences of pPV-$AB^{2470-3386}$ and pPV-$AB^{2954-3386}$ or pPV-AB were amplified with RI-2A-P1wt(+)/P1AB-2A-RI(−) or RI-2A-P1AB(+)/P1AB-2A-RI(−), respectively. PCR products were digested with EcoRI and inserted into a now unique EcoRI site in pdiLuc-mRI to result in pdiLuc-PV, pdiLuc-$AB^{1513-2470}$, pdiLuc-$AB^{2470-2954}$, pdiLuc-$AB^{2470-3386}$, pdiLuc-$AB^{2954-3386}$, and pdiLuc-AB, respectively.

Oligonucleotides

The following oligonucleotides were used:

```
Fluc-mutRI(+),
                                        (SEQ ID NO: 6)
5'-GCACTGATAATGAACTCCTCTGGATCTACTGG-3';

Fluc-mutRI(-),
                                        (SEQ ID NO: 7)
5'-CCAGTAGATCCAGAGGAGTTCATTATCAGTGC-3';

RI-2A-P1wt(+),
                                        (SEQ ID NO: 8)
5'-CAAGAATTCCTGACCACATACGGTGCTCAGGTTTCATCACAGAAAGT

GGG-3';

RI-2A-P1AB(+),
                                        (SEQ ID NO: 9)
5'-CAAGAATTCCTGACCACATACGGTGCGCAAGTATCGTCGCAAAAAGT

AGG-3;

P1wt-2A-RI(-),
                                       (SEQ ID NO: 10)
5'-TTCGAATTCTCCATATGTGGTCAGATCCTTGGTGG-AGAGG-3';
and

P1AB-2A-RI(-),
                                       (SEQ ID NO: 11)
5'-TTCGAATTCTCCATACGTCGTTAAATCTTTCGTCGATAACG-3'.
```

In Vitro Transcription and RNA Transfection

Driven by the T7 promoter, 2 μg of EcoRI-linearized plasmid DNA were transcribed by T7 RNA polymerase (Stratagene) for 1 h at 37° C. One microgram of virus or dicistronic transcript RNA was used to transfect $10^6$ HeLa R19 cells on a 35-mm-diameter plate according to a modification of the DEAE-dextran method (van der Werf et al., 1986). Following a 30-min incubation at room temperature, the supernatant was removed and cells were incubated at 37° C. in 2 ml of DMEM containing 2% BCS until CPE appeared, or the cells were frozen 4 days post-transfection for further passaging. Virus titers were determined by standard plaque assay on HeLa R19 cells using a semisolid overlay of 0.6% tragacanth gum (Sigma-Aldrich) in minimal Eagle medium.

Design and Synthesis of Codon-Deoptimized Polioviruses

Two different synonymous encodings of the poliovirus P1 capsid region were produced, each governed by different design criteria. The designs were limited to the capsid, as it has been conclusively shown that the entire capsid coding sequence can be deleted from the PV genome or replaced with exogenous sequences without affecting replication of the resulting sub-genomic replicon (Johansen and Morrow, 2000; Kaplan and Racaniello, 1988). It is therefore quite certain that no unidentified crucial regulatory RNA elements are located in the capsid region, which might be affected inadvertently by modulation of the RNA sequence.

The first design (PV-SD) sought to maximize the number of RNA base changes while preserving the exact codon usage distribution of the wild type P1 region (FIG. 1). To achieve this, synonymous codon positions were exchanged for each amino acid by finding a maximum weight bipartite match (Gabow, 1973) between the positions and the codons, where the weight of each position-codon pair is the number of base changes between the original codon and the synonymous candidate codon to replace it. To avoid any positional bias from the matching algorithm, the synonymous codon locations were randomly permuted before creating the input graph and the locations were subsequently restored. Rothberg's maximum bipartite matching program (Rothberg, 1985) was used to compute the matching. A total of 11 useful restriction enzyme sites, each 6 nucleotides, were locked in the viral genome sequence so as to not participate in the codon location exchange. The codon shuffling technique potentially creates additional restriction sites that should preferably remain unique in the resulting reconstituted full-length genome. For this reason, the sequence was further processed by substituting codons to eliminate the undesired sites. This resulted in an additional nine synonymous codon changes that slightly altered the codon frequency distribution. However, no codon had its frequency changed by more than 1 over the wild type sequence. In total, there were 934 out of 2,643 nucleotides changed in the PV-SD capsid design when compared to the wt P1 sequence while maintaining the identical protein sequence of the capsid coding domain (see FIGS. 1 and 2). As the codon usage was not changed, the GC content in the PVM-SD capsid coding sequence remained identical to that in the wt at 49%.

The second design, PV-AB, sought to drastically change the codon usage distribution over the wt P1 region. This design was influenced by recent work suggesting that codon bias may impact tissue-specific expression (Plotkin et al., 2004). The desired codon usage distribution was derived from the most unfavorable codons observed in a previously described set of brain-specific genes (Hsiao et al., 2001; Plotkin et al., 2004). A capsid coding region was synthesized maximizing the usage of the rarest synonymous codon for each particular amino acid as observed in this set of genes (FIG. 1). Since for all amino acids but one (Leu) the rarest codon in brain corresponds to the rarest codons among all human genes at large, in effect this design would be expected to discriminate against expression in other human tissues as well. Altogether, the PV-AB capsid differs from the wt capsid in 680 nucleotide positions (see FIG. 2). The GC content in the PVM-AB capsid region was reduced to 43% compared to 49% in the wt.

Example 2

Effects of Codon-Deoptimization on Growth and Infectivity of Polioviruses

Determination of Virus Titer by Infected Focus Assay

Infections were done as for a standard plaque assay. After 48 or 72 h of incubation, the tragacanth gum overlay was removed and the wells were washed twice with phosphate-buffered saline (PBS) and fixed with cold methanol/acetone for 30 min. Wells were blocked in PBS containing 10% BCS followed by incubation with a 1:20 dilution of anti-3D mouse monoclonal antibody 125.2.3 (Paul et al., 1998) for 1 h at 37° C. After washing, cells were incubated with horseradish peroxidase-labeled goat anti-mouse antibody (Jackson ImmunoResearch, West Grove, Pa.) and infected cells were visualized using Vector VIP substrate kit (Vector Laboratories, Burlingame, Calif.). Stained foci, which are equivalent to plaques obtained with wt virus, were counted, and titers were calculated as in the plaque assay procedure.

Codon-Deoptimized Polioviruses Display Severe Growth Phenotypes

Figure 3C:
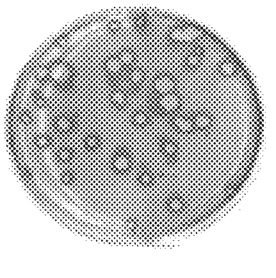

Of the two initial capsid ORF replacement designs (FIG. 3A), only PV-SD produced viable virus. In contrast, no viable virus was recovered from four independent transfections with PV-AB RNA, even after three rounds of passaging (FIG. 3E). It appeared that the codon bias introduced into the PV-AB genome was too severe. Thus, smaller portions of the PV-AB capsid coding sequence were subcloned into the PV(M) background to reduce the detrimental effects of the nonpreferred codons. Of these subclones, PV-AB$^{2954-3386}$ produced CPE 40 h after RNA transfection, while PV-AB$^{755-1513}$ and PV-AB$^{2470-2954}$ required one or two additional passages following transfection, respectively (compared to 24 h for the wild type virus). Interestingly, these chimeric viruses represent the three subclones with the smallest portions of the original AB sequence, an observation suggesting a direct correlation between the number of nonpreferred codons and the fitness of the virus.

One-step growth kinetics of all viable virus variants were determined by infecting HeLa monolayers at a multiplicity of infection (MOI) of 2 with viral cell lysates obtained after a maximum of two passages following RNA transfection (FIG. 3B). The MOI was chosen due to the low titer of PV-AB$^{2470-2954}$ and to eliminate the need for further passaging required for concentrating and purifying the inoculum. Under the conditions used, all viruses had produced complete or near complete CPE by 24 h post-infection.

Figure 2A:
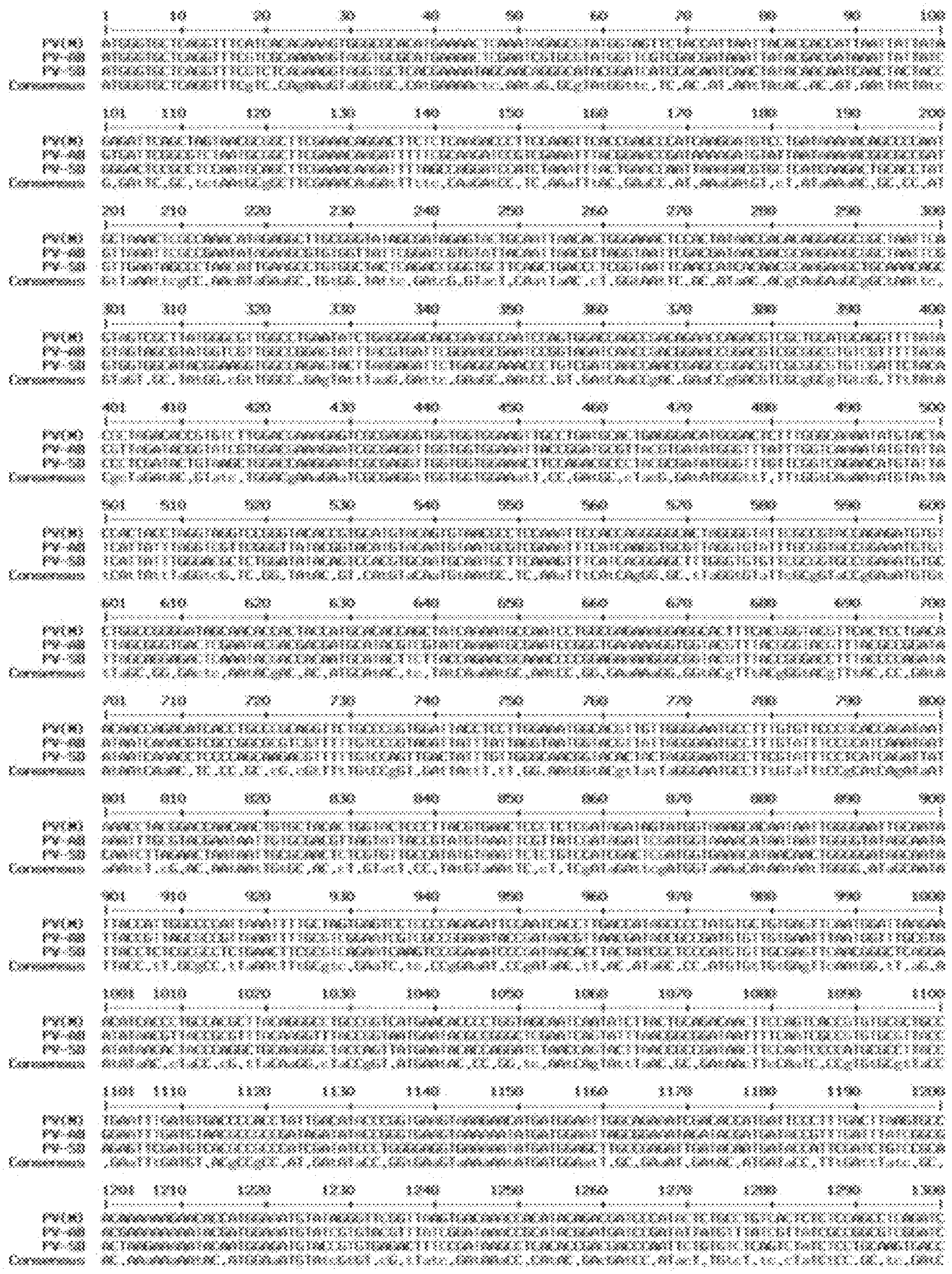
Figure 2B:
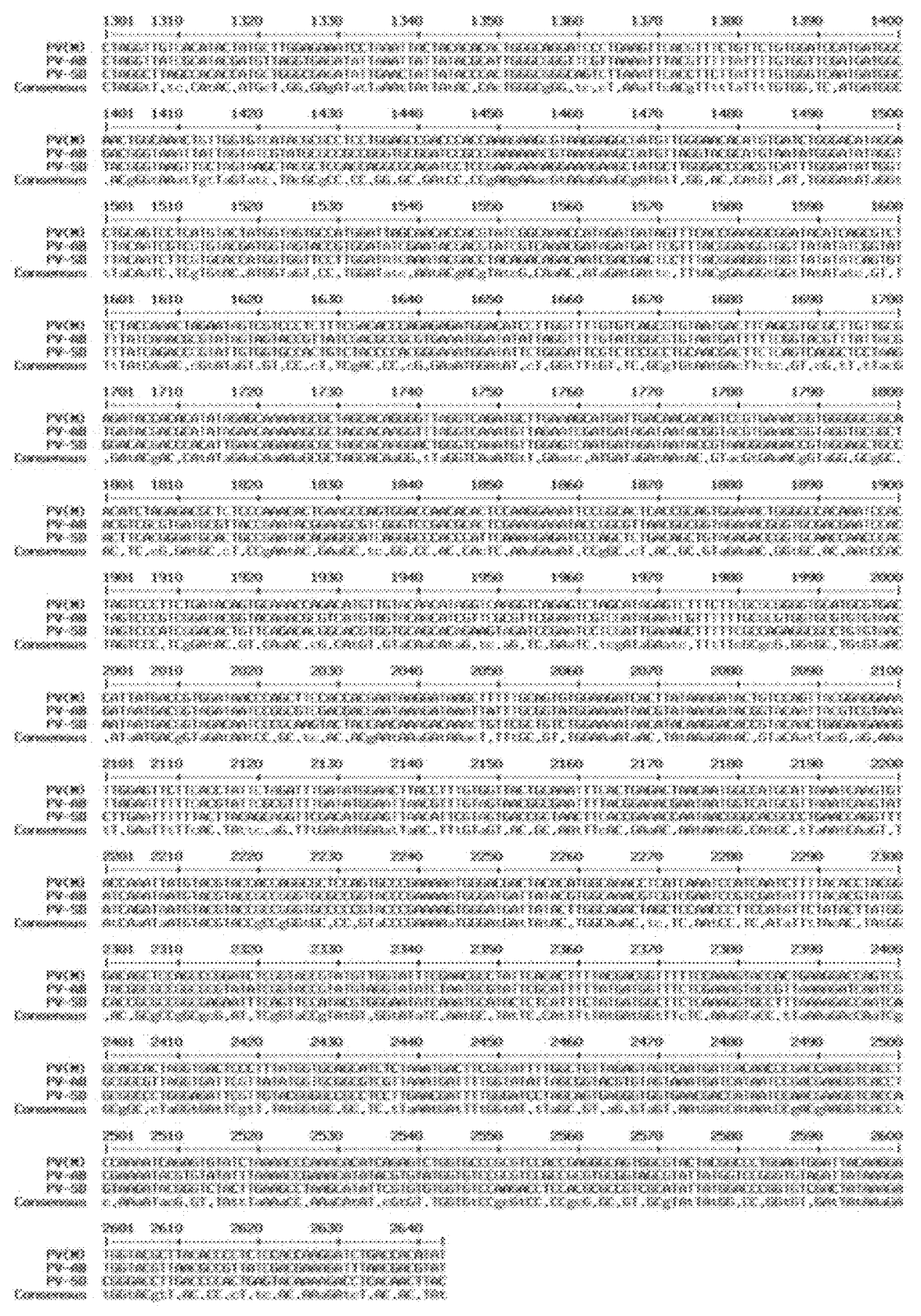
Figure 3D:
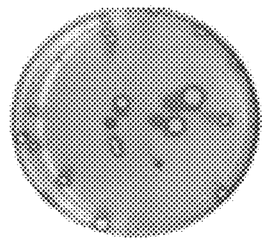
Figure 3G:
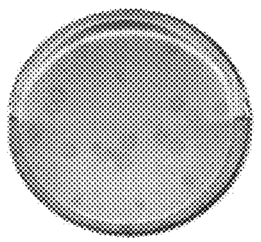
Figure 3E:
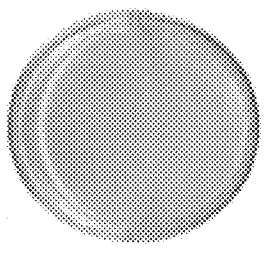
Figure 3F:
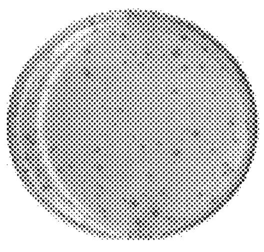
Figure 3H:
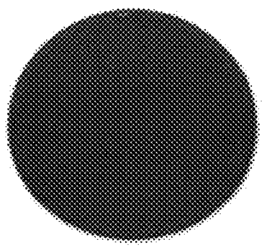
Figure 3I:
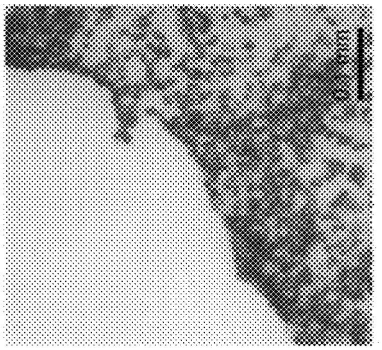
Figure 3J:
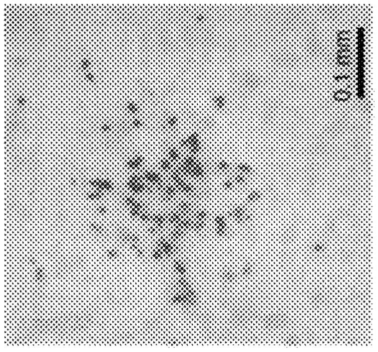

Despite 934 single-point mutations in its capsid region, PV-SD replicated at wt capacity (FIG. 3B) and produced similarly sized plaques as the wt (FIG. 3D). While PV-AB$^{2954-3386}$ grew with near-wild type kinetics (FIG. 3B), PV-AB$^{755-1513}$ produced minute plaques and approximately 22-fold less infectious virus (FIGS. 2. 3B and F, respectively). Although able to cause CPE in high-MOI infections, albeit much delayed (80 to 90% CPE after 20 to 24 h), PV-AB$^{2470-2954}$ produced no plaques at all under the conditions of the standard plaque assay (FIG. 3H). This virus was therefore quantified using a focus-forming assay, in which foci of infected cells after 72 h of incubation under plaque assay conditions were counted after they were stained immunohistochemically with antibodies to the viral polymerase 3D (FIG. 3G). After 48 h of infection, PV-AB$^{2470-2954}$-infected foci usually involved only tens to hundreds of cells (FIG. 3J) with a focus diameter of 0.2 to 0.5 mm, compared to 3-mm plaques for the wt (FIGS. 3C and D). However, after an additional 24 h, the diameter of the foci increased significantly (2 to 3 mm; FIG. 3G). When HeLa cells were infected with PV-AB$^{755-1513}$ and PV-AB$^{2470-2954}$ at an MOI of 1, the CPE appeared between 12 and 18 h and 3 and 4 days, respectively, compared to 8 h with the wt(data not shown).

In order to quantify the cumulative effect of a particular codon bias in a protein coding sequence, a relative codon deoptimization index (RCDI) was calculated, which is a comparative measure against the general codon distribution in the human genome. An RCDI of 1/codon indicates that a gene follows the normal human codon frequencies, while any deviation from the normal human codon bias results in an RCDI higher than 1. The RCDI was derived using the formula:

$$RCDI=[\Sigma(C_iF_a/C_iF_h)\cdot N_{ci}]/N\ (i=1\text{ through }64).$$

$C_iF_a$ is the observed relative frequency in the test sequence of each codon i out of all synonymous codons for the same amino acid (0 to 1); $C_iF_h$ is the normal relative frequency observed in the human genome of each codon i out of all synonymous codons for that amino acid (0.06 to 1); $N_{ci}$ is the number of occurrences of that codon i in the sequence; and N is the total number of codons (amino acids) in the sequence.

Thus, a high number of rare codons in a sequence results in a higher index. Using this formula, the RCDI values of the various capsid coding sequences were calculated to be 1.14 for PV(M) and PV-SD which is very close to a normal human distribution. The RCDI values for the AB constructs are 1.73 for PV-AB$^{755-1513}$, 1.45 for PV-AB$^{2470-2954}$, and 6.51 for the parental PV-AB. For comparison, the RCDI for probably the best known codon-optimized protein, "humanized" green fluorescent protein (GFP), was 1.31 compared to an RCDI of 1.68 for the original *Aequora victoria* gfp gene (Zolotukhin et al., 1996). According to these calculations, a capsid coding sequence with an RCDI of <2 is associated with a viable virus phenotype, while an RCDI of >2 (PV-AB=6.51, PV-AB$^{1513-3386}$=4.04, PV-AB$^{755-2470}$=3.61) results in a lethal phenotype.

Example 3

Effects of Codon-Deoptimization on Specific Infectivity of Polioviruses

Molecular Quantification of Viral Particles: Direct $OD_{260}$ Absorbance Method Fifteen-centimeter dishes of HeLa cells ($4\times10^7$ cells) were infected with PV(M), PV-AB$^{755-1513}$, or PV-AB$^{2470-2954}$ at an MOI of 0.5 until complete CPE occurred (overnight versus 4 days). Cell-associated virus was released by three successive freeze/thaw cycles. Cell lysates were cleared by 10 min of centrifugation at 2,000×g followed by a second 10-min centrifugation at 14,000×g for 10 min. Supernatants were incubated for 1 h at room temperature in the presence of 10 μg/ml RNase A (Roche) to digest any extraviral or cellular RNA. After addition of 0.5% sodium dodecyl sulfate (SDS) and 2 mM EDTA, virus-containing supernatants were overlaid on a 6-ml sucrose cushion (30% sucrose in Hanks balanced salt solution [HBSS]; Invitrogen, Carlsbad, Calif.). Virus particles were sedimented by ultracentrifugation for 4 h at 28,000 rpm using an SW28 swinging bucket rotor.

Supernatants were discarded and centrifuge tubes were rinsed twice with HBSS while leaving the sucrose cushion intact. After removal of the last wash and the sucrose cushion, virus pellets were resuspended in PBS containing 0.2% SDS and 5 mM EDTA. Virus infectious titers were determined by plaque assay/infected-focus assay (see above). Virus particle concentrations were determined with a NanoDrop spectrophotometer (NanoDrop Technologies, Inc., Wilmington, Del.) at the optical density at 260 nm ($OD_{260}$) and calculated using the formula 1 $OD_{260}$ unit=9.4×$10^{12}$ particles/ml (Rueckert, 1985). In addition, virion RNA was extracted by three rounds of phenol extraction and one round of chloroform extraction. RNA was ethanol precipitated and resuspended in ultrapure water. RNA purity was confirmed by TAE-buffered agarose gel analysis, and the concentration was determined spectrophotometrically. The total number of genome equivalents of the corresponding virus preparation was calculated via the determined RNA concentration and the molecular weight of the RNA. Thus, the relative amount of virions per infectious units could be calculated, assuming that one RNase-protected viral genome equivalent corresponds to one virus particle.

Molecular Quantification of Viral Particles: ELISA Method

Nunc Maxisorb 96-well plates were coated with 10 µs of rabbit anti-PV(M) antibody (Murdin and Wimmer, 1989) in 100 µl PBS for 2 h at 37° C. and an additional 14 h at 4° C., and then the plates were washed three times briefly with 350 µl of PBS and blocked with 350 µl of 10% bovine calf serum in PBS for 1 h at 37° C. Following three brief washes with PBS, wells were incubated with 100 µl of virus-containing cell lysates or controls in DMEM plus 2% BCS for 4 h at room temperature. Wells were washed with 350 µl of PBS three times for 5 min each. Wells were then incubated for 4 h at room temperature with 2 µg of CD155-alkaline phosphatase (AP) fusion protein (He et al., 2000) in 100 µl of DMEM-10% BCS. After the last of five washes with PBS, 100 µl of 10 mM Tris, pH 7.5, were added and plates were incubated for 1 h at 65° C. Colorimetric alkaline phosphatase determination was accomplished by addition of 100 µl of 9 mg/ml para-nitrophenylphosphate (in 2 M diethanolamine, 1 mM $MgCl_2$, pH 9.8). Alkaline phosphatase activity was determined, and virus particle concentrations were calculated in an enzyme-linked immunosorbent assay (ELISA) plate reader (Molecular Devices, Sunnyvale, Calif.) at a 405-nm wavelength on a standard curve prepared in parallel using two-fold serial dilutions of a known concentration of purified PV(M) virus stock.

The PFU/Particle Ratio is Reduced in Codon-Deoptimized Viruses

The extremely poor growth phenotype of PV-$AB^{2470-2954}$ in cell culture and its inability to form plaques suggested a defect in cell-to-cell spreading that may be consistent with a lower specific infectivity of the individual virus particles.

To test this hypothesis, PV(M), PV-$AB^{755-1513}$, and PV-$AB^{2470-2954}$ virus were purified and the amount of virus particles was determined spectrophotometrically. Purified virus preparations were quantified directly by measuring the $OD_{260}$, and particle concentrations were calculated according to the formula 1 $OD_{260}$ unit=9.4×$10^{12}$ particles/ml (FIG. 4D) (Rueckert, 1985). Additionally, genomic RNA was extracted from those virions (FIG. 4A) and quantified at $OD_{260}$ (data not shown). The number of virions (1 virion=1 genome) was then determined via the molecular size of 2.53×$10^6$ g/mol for genomic RNA. Specifically, virus was prepared from 4×$10^7$ HeLa cells that were infected with 0.5 MOI of virus until the appearance of complete CPE, as described above. Both methods of particle determinations produced similar results (FIG. 4D). Indeed, it was found that PV(M) and PV-$AB^{755-1513}$ produced roughly equal amounts of virions, while PV-$AB^{2470-2954}$ produced between ⅓ (by the direct UV method (FIG. 4D) to ⅛ of the number of virions compared to PV(M) (by genomic RNA method [data not shown]). In contrast, the wt virus sample corresponded to approximately 30 times and 3,000 times more infectious units than PV-$AB^{755-1513}$ and PV-$AB^{2470-2954}$, respectively (FIG. 4D). In addition, capsid proteins of purified virions were resolved by SDS-polyacrylamide gel electrophoresis (PAGE) and visualized by silver staining (FIG. 4B). These data also support the conclusion that on a per-cell basis, PV-$AB^{2470-2954}$ and PV-$AB^{755-1513}$ produce similar or only slightly reduced amounts of progeny per cell (FIG. 4B, lane 3), while their PFU/particle ratio is reduced. The PFU/particle ratio for a virus can vary significantly depending on the methods to determine either plaques (cell type for plaque assay and the particular plaque assay technique) or particle count (spectrophotometry or electron microscopy). A PFU/particle ratio of 1/115 for PV1(M) was determined using the method described herein, which compares well to previous determinations of 1/272 (Joklik and Darnell, 1961) (done on HeLa cells) and 1/87 (Schwerdt and Fogh, 1957) (in primary monkey kidney cells).

Development of a Virion-Specific ELISA

To confirm the reduced PFU/particle ratio observed with codon-deoptimized polioviruses, a novel virion-specific ELISA was developed (FIGS. 4C and E) as a way to determine the physical amount of intact viral particles in a sample rather than the infectious titer, which is a biological variable. The assay is based on a previous observation that the ectodomain of the PV receptor CD155 fused to heat-stable placental alkaline phosphatase (CD155-AP) binds very tightly and specifically to the intact 160S particle (He et al., 2000). Considering that PV 130S particles (A particles) lose their ability to bind CD155 efficiently (Hogle, 2002), it is expected that no other capsid intermediate or capsid subunits would interact with CD155-AP, thus ensuring specificity for intact particles. In support of this notion, lysates from cells that were infected with a vaccinia virus strain expressing the P1 capsid precursor (Ansardi et al., 1993) resulted in no quantifiable signal (data not shown).

The ELISA method allows for the quantification of virus particles in a crude sample such as the cell lysate after infection, which should minimize possible alteration of the PFU/particle ratio by other mechanisms during sample handling and purification (thermal/chemical inactivation, oxidation, degradation, etc.). Under the current conditions, the sensitivity of this assay is approximately $10^7$ viral particles, as there is no signal amplification step involved. This, in turn, resulted in an exceptionally low background. With this ELISA, PV particle concentrations could be determined in samples by back calculation on a standard curve prepared with purified PV(M) of known concentration (FIG. 4E). The particle determinations by ELISA agreed well with results obtained by the direct UV method (FIG. 4D).

Implications of Results

The present study has demonstrated the utility of large-scale codon deoptimization of PV capsid coding sequences by de novo gene synthesis for the generation of attenuated viruses. The initial goal was to explore the potential of this technology as a tool for generating live attenuated virus vaccines. Codon-deoptimized viruses were found to have very low specific infectivity (FIG. 4). The low specific infectivity (that is the chance of a single virus particle to successfully initiate an infectious cycle in a cell) results in a more slowly spreading virus infection within the host. This in turn allows the host organism more time to mount an immune response and clear the infection, which is a most desirable feature in an attenuated virus vaccine. On the other hand, codon-deoptimized viruses generated similar amounts of progeny per cell as compared the wild type virus, while being 2 to 3 orders of magnitude less infectious (FIG. 4). This allows the production of virus particles antigenically indistinguishable from the wt as effectively and cost-efficiently as the production of the wt virus itself. However due to the low specific infectivity the actual handling and processing of such a virus preparation is much safer. Since, there are increasing concerns about the production of virulent virus in sufficient quantities under high containment conditions and the associated risk of virus escape from the production facility either by accident or by malicious intent. viruses as described herein may prove very useful as safer alternatives in the production of inactivated virus vaccines. Since they are 100% identical to the wt virus at the protein level, an identical immune response in hosts who received inactivated virus is guaranteed.

Example 4

Effects of Codon-Deoptimization on Neuropathogenicity of Polioviruses

Mouse Neuropathogenicity Tests

Groups of four to five CD155tg mice (strain Tg21) (Koike et al., 1991) between 6 and 8 weeks of age were injected intracerebrally with virus dilutions between $10^2$ and $10^6$ PFU/focus-forming units (FFU) in 30 μl PBS. Fifty percent lethal dose ($LD_{50}$) values were calculated by the method of Reed and Muench (1938). Virus titers in spinal cord tissues at the time of death or paralysis were determined by plaque or infected-focus assay.

Codon-Deoptimized Polioviruses are Neuroattenuated on a Particle Basis in CD155tg Mice To test the pathogenic potential of viruses constructed in this study, CD155 transgenic mice (Koike et al., 1991) were injected intracerebrally with PV(M), PV-SD, PV-$AB^{755-1513}$ and PV-$AB^{2470-2954}$ at doses between $10^2$ and $10^5$ PFU/FFU. Initial results were perplexing, as quite counterintuitively PV-$AB^{755-1513}$ and especially PV-$AB^{2470-2954}$ were initially found to be as neuropathogenic as, or even slightly more neuropathogenic, than the wt virus. See Table 4.

TABLE 4

Neuropathogenicity in CD155tg mice.

| | $LD_{50}$ | | Spinal cord titer | |
|---|---|---|---|---|
| Construct | PFU or FFU[a] | No. of virions[b] | PFU or FFU/g[c] | No. of virions/g[d] |
| PV(M) wt | $3.2 \times 10^2$ PFU | $3.7 \times 10^4$ | $1.0 \times 10^9$ PFU | $1.15 \times 10^{11}$ |
| PV-$AB^{755-1515}$ | $2.6 \times 10^2$ PFU | $7.3 \times 10^5$ | $3.5 \times 10^7$ PFU | $9.8 \times 10^{10}$ |
| PV-$AB^{2470-2954}$ | $4.6 \times 10^2$ PFU | $4.8 \times 10^6$ | $3.4 \times 10^6$ FFU | $3.57 \times 10^{11}$ |

[a] $LD_{50}$ expressed as the number of infectious units, as determined by plaque or infectious focus assay, that results in 50% lethality after intracerebral inoculation.
[b] $LD_{50}$ expressed as the number of virus particles, as determined by $OD_{260}$ measurement, that results in 50% lethality after intracerebral inoculation.
[c] Virus recovered from the spinal cord of infected mice at the time of death or paralysis; expressed in PFU or FFU/g of tissue, as determined by plaque or infectious focus assay.
[d] Virus recovered from the spinal cord of infected mice at the time of death or paralysis, expressed in particles/g of tissue, derived by multiplying values in the third column by the particle/PFU ratio characteristic for each virus (FIG. 4D).

In addition, times of onset of paralysis following infection with PV-$AB^{755-1513}$ and PV-$AB^{2470-2954}$ were comparable to that of wt virus (data not shown). Similarly confounding was the observation that at the time of death or paralysis, the viral loads, as determined by plaque assay, in the spinal cords of mice infected with PV-$AB^{755-1513}$ and PV-$AB^{2470-2954}$ were 30- and 300-fold lower, respectively, than those in the mice infected with the wt virus (Table 4). Thus, it seemed unlikely that PV-$AB^{2470-2954}$, apparently replicating at only 0.3% of the wt virus, would have the same neuropathogenic potential as the wt. However, after having established the altered PFU/particle relationship in PV-$AB^{755-1513}$ and PV-$AB^{2470-2954}$ (see Example 3), the amount of inoculum could now be correlated with the actual number of particles inoculated. After performing this correction, it was established that on a particle basis, PV-$AB^{755-1513}$ and PV-$AB^{2470-2954}$ are 20-fold and 100-fold neuroattenuated, respectively, compared to the wt. See Table 4. Furthermore, on a particle basis the viral loads in the spinal cords of paralyzed mice were very similar with all three viruses (Table 4).

It was also concluded that it was not possible to redesign the PV capsid gene with synonymous codons that would specifically discriminated against expression in the central nervous system. This may be because tissue-specific differences in codon bias described by others (Plotkin et al., 2004) are too small to bring about a tissue-restrictive virus phenotype. In a larger set of brain-specific genes than the one used by Plotkin et al., no appreciable tissue-specific codon bias was detected (data not shown). However, this conclusion should not detract from the fact that polioviruses produced by the method of this invention are indeed neuroattenauted in mice by a factor of up to 100 fold. That is, 100 fold more of the codon or codon-pair deoptimized viral particles are needed to result in the same damage in the central nervous system as the wt virus.

Example 5

Effects of Codon Deoptimization on Genomic Translation of Polioviruses

In Vitro and In Vivo Translation

Two different HeLa cell S10 cytoplasmic extracts were used in this study. A standard extract was prepared by the method of Molla et al. (1991). [$^{35}$S]methionine-labeled translation products were analyzed by gel autoradiography. The second extract was prepared as described previously (Kaplan and Racaniello, 1988), except that it was not dialyzed and endogenous cellular mRNAs were not removed with micrococcal nuclease. Reactions with the modified extract were not supplemented with exogenous amino acids or tRNAs.

Translation products were analyzed by western blotting with anti-2C monoclonal antibody 91.23 (Pfister and Wimmer, 1999). Relative intensities of 2BC bands were determined by a pixel count of the scanned gel image using the NIH-Image 1.62 software. In all cases, translation reactions were programmed with 200 ng of the various in vitro-transcribed viral genomic RNAs.

For analysis of in vivo translation, HeLa cells were transfected with in vitro-transcribed dicistronic replicon RNA as described above. In order to assess translation isolated from RNA replication, transfections were carried out in the presence of 2 mM guanidine hydrochloride. Cells were lysed after 7 h in passive lysis buffer (Promega, Madison, Wis.) followed by a dual firefly (F-Luc) and *Renilla* (R-Luc) luciferase assay (Promega). Translation efficiency of the second cistron (P1-Fluc-P2-P3 polyprotein) was normalized through division by the *Renilla* luciferase activity of the first cistron expressed under control of the Hepatitis C Virus (HCV) internal ribosome entry site (IRES).

Codon-Deoptimized Viruses are Deficient at the Level of Genome Translation

Since the synthetic viruses and the wt PV(M) are indistinguishable in their protein makeup and no known RNA-based regulatory elements were altered in the modified RNA genomes, these designs enabled study of the effect of reduced genome translation/replication on attenuation without affecting cell and tissue tropism or immunological properties of the virus. The PV-AB genome was designed under the hypothesis that introduction of many suboptimal codons into the capsid coding sequence should lead to a reduction of genome translation. Since the P1 region is at the N-terminus of the polyprotein, synthesis of all downstream nonstructural proteins is determined by the rate of translation through the P1 region. To test whether in fact translation is affected, in vitro translations were performed (FIG. 5).

Unexpectedly, the initial translations in a standard HeLa-cell based cytoplasmic S10 extract (Molla et al., 1991) showed no difference in translation capacities for any of the genomes tested (FIG. 5A). However, as this translation system is optimized for maximal translation, it includes the exogenous addition of excess amino acids and tRNAs, which could conceivably compensate for the genetically engineered codon bias. Therefore, in vitro translations were repeated with a modified HeLa cell extract, which was not dialyzed and in which cellular mRNAs were not removed by micrococcal nuclease treatment (FIG. 5B). Translations in this extract were performed without the addition of exogenous tRNAs or amino acids. Thus, an environment was created that more closely resembles that in the infected cell, where translation of the PV genomes relies only on cellular supplies while competing for resources with cellular mRNAs. Due to the high background translation from cellular mRNA and the low [$^{35}$S]Met incorporation rate in nondialyzed extract, a set of virus-specific translation products were detected by western blotting with anti-2C antibodies (Pfister and Wimmer, 1999). These modified conditions resulted in dramatic reduction of translation efficiencies of the modified genomes which correlated with the extent of the deoptimized sequence. Whereas translation of PV-SD was comparable to that of the wt, translation of three noninfectious genomes, PV-AB, PV-AB$^{1513-3386}$, and PV-AB$^{755-2470}$ was reduced by approximately 90% (FIG. 5B).

Burns et al. (2006) recently reported experiments related to those described herein. These authors altered codon usage to a much more limited extent than in the present study, and none of their mutant viruses expressed a lethal phenotype. Interestingly, Burns et al. determined that translation did not play a major role in the altered phenotypes of their mutant viruses, a conclusion at variance with the data presented herein. It is likely that the in vitro translation assay used by Burns et al. (2006), which employed a nuclease-treated rabbit reticulocyte lysate supplemented with uninfected HeLa cell extract and excess amino acids, explains their failure to detect any significant reduction in translation. Cf. FIG. 5A.

Figures 6A, 6B:
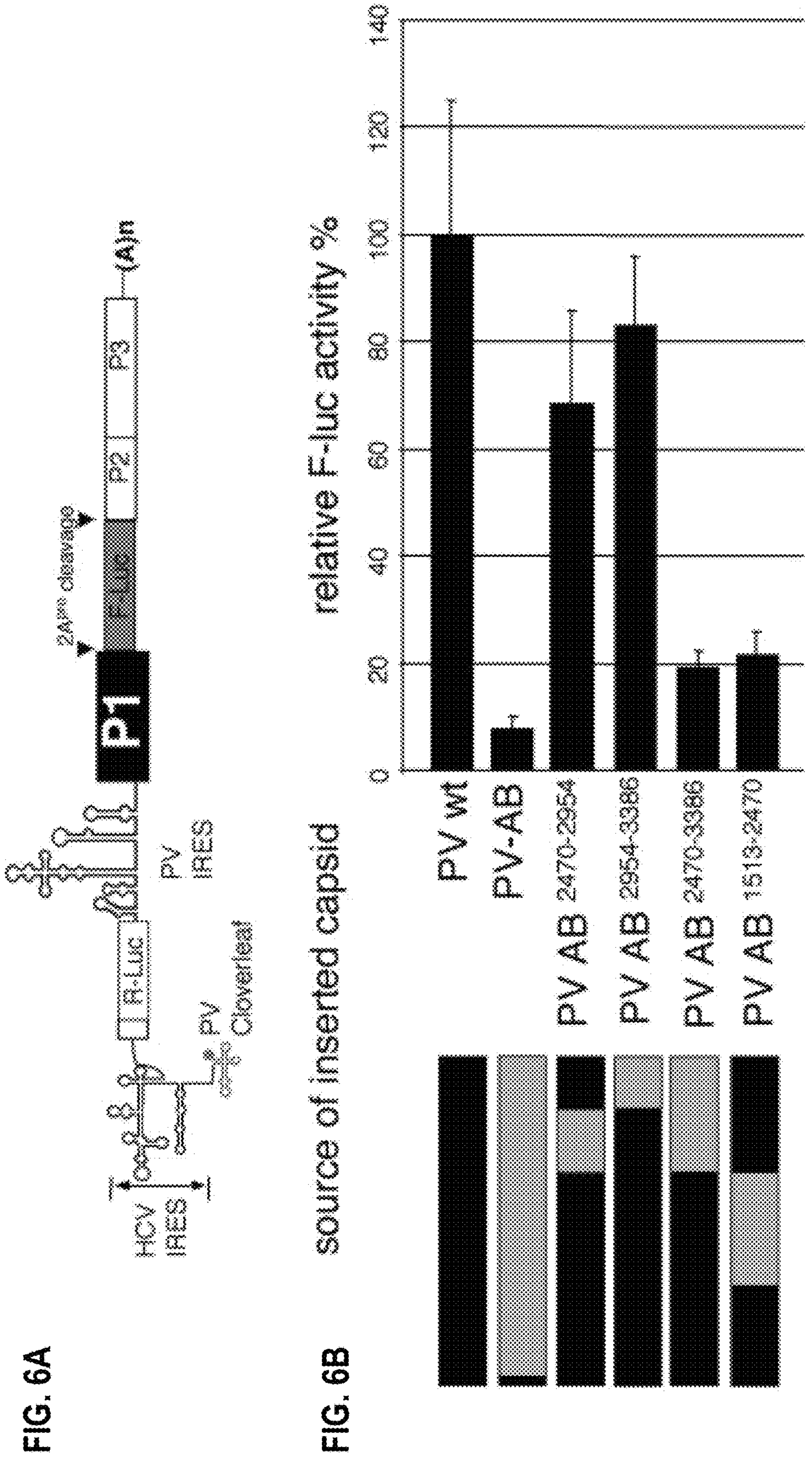
FIGS. 6A-B. Analysis of in vivo translation using dicistronic reporter replicons confirms the detrimental effect of codon deoptimization on PV translation.

Considering the ultimately artificial nature of the in vitro translation system, the effect of various capsid designs on translation in cells was also investigated. For this purpose, dicistronic poliovirus reporter replicons were constructed (FIG. 6A) based on a previously reported dicistronic replicon (Zhao and Wimmer, 2001). Various P1 cassettes were inserted immediately upstream and in-frame with the firefly luciferase (F-Luc) gene. Thus, the poliovirus IRES drives expression of a single viral polyprotein similar to the one in the viral genome, with the exception of the firefly luciferase protein between the capsid and the 2A$^{pro}$ proteinase. Expression of the *Renilla* luciferase (R-Luc) gene under the control of the HCV IRES provides an internal control. All experiments were carried out in the presence of 2 mM guanidine hydrochloride, which completely blocks genome replication (Wimmer et al., 1993). Using this type of construct allowed an accurate determination of the relative expression of the second cistron by calculating the F-Luc/R-Luc ratio. As F-Luc expression depends on successful transit of the ribosome through the upstream P1 region, it provides a measure of the effect of the inserted P1 sequence on the rate of polyprotein translation. Using this method, it was indeed found that the modified capsid coding regions, which were associated with a lethal phenotype in the virus background (e.g., PV-AB, PV-AB$^{1513-2470}$, and PV-AB$^{2470-3386}$) reduced the rate of translation by approximately 80 to 90% (FIG. 6B). Capsids from two viable virus constructs, PV-AB$^{2470-2954}$ and PV-AB$^{2954-3386}$ allowed translation at 68% and 83% of wt levels, respectively. In vivo translation rates of the first cistron remained constant in all constructs over a time period between 3 and 12 h, suggesting that RNA stability is not affected by the codon alterations (data not shown). In conclusion, the results of these experiments suggest that poliovirus is extremely dependent on very efficient translation as a relatively small drop in translation efficiency through the P1 region of 30%, as seen in PV-AB$^{2470-2954}$, resulted in a severe virus replication phenotype.

Example 6

Genetic Stability of Codon-Deoptimized Polioviruses

Due to the distributed effect of many mutations over large genome segments that contribute to the phenotype, codon deoptimized viruses should have genetically stable phenotypes. To study the genetic stability of codon deoptimized viruses, and to test the premise that these viruses are genetically stable, viruses are passaged in suitable host cells.

A benefit of the present "death by 1000 cuts" theory of vaccine design is the reduced risk of reversion to wild type. Typical vaccine strains differ by only few point mutations from the wt viruses, and only a small subset of these may actually contribute to attenuation. Viral evolution quickly works to revert such a small number of active mutations. Indeed, such reversion poses a serious threat for the World Health Organization (WHO) project to eradicate poliovirus from the globe. So long as a live vaccine strain is used, there is a very real chance that this strain will revert to wt. Such reversion has already been observed as the source of new polio outbreaks (Georgescu et al., 1997; Kew et al., 2002; Shimizu et al., 2004).

With hundreds to thousands of point mutations in the present synthetic designs, there is little risk of reversion to wt strains. However, natural selection is powerful, and upon passaging, the synthetic viruses inevitably evolve. Studies are ongoing to determine the end-point of this evolution, but a likely outcome is that they get trapped in a local optimum, not far from the original design.

To validate this theory, representative re-engineered viruses are passaged in a host cell up to 50 times. The genomes of evolved viruses are sequenced after 10, 20 and 50 passages. More specifically, at least one example chimera from each type of deoptimized virus is chosen. The starting chimera is very debilitated, but not dead. For example, for PV the chimeras could be PV-$AB^{2470-2954}$ and PV-$Min^{755-2470}$. From each starting virus ten plaques are chosen. Each of the ten plaque-derived virus populations are bulk passaged a total of 50 times. After the $10^{th}$, $20^{th}$ and $50^{th}$ passages, ten plaque-purified viruses are again chosen and their genomes are sequenced together with the genomes of the ten parent viruses. After passaging, the fitness of the 40 (30+10 per parent virus) chosen viruses is compared to that of their parents by examining plaque size, and determining plaque forming units/ml as one-step growth kinetics. Select passage isolates are tested for their pathogenicity in appropriate host organisms. For example, the pathogenicity of polioviruses is tested in CD155tg mice.

Upon sequencing of the genomes, a finding that all 10 viral lines have certain mutations in common would suggest that these changes are particularly important for viral fitness. These changes may be compared to the sites identified by toeprinting as the major pause sites (see Example 9); the combination of both kinds of assay may identify mutant codons that are most detrimental to viral fitness. Conversely, a finding that the different lines have all different mutations would support the view that many of the mutant codon changes are very similar in their effect on fitness. Thus far, after 10 passages in HeLa cells, PV-$AB^{755-1513}$ and PV-$AB^{2470-2954}$ have not undergone any perceivable gain of fitness. Viral infectious titers remained as low ($10^7$ PFU/ml and $10^6$ FFU/ml) as at the beginning of the passage experiment, and plaque phenotype did not change (data not shown). Sequence analysis of these passaged viruses is now in progress, to determine if and what kind of genetic changes occur during passaging.

Burns et al. (2006) reported that their altered codon compositions were largely conserved during 25 serial passages in HeLa cells. They found that whereas the fitness for replication in HeLa cells of both the unmodified Sabin 2 virus and the codon replacement viruses increased with higher passage numbers, the relative fitness of the modified viruses remained lower than that of the unmodified virus. Thus, all indications are that viruses redesigned by SAVE are genetically very stable. Preliminary data for codon and codon-pair deoptimized viruses of the invention suggest that less severe codon changes distributed over a larger number of codons improves the genetic stability of the individual virus phenotypes and thus improves their potential for use in vaccines.

Example 7

Re-Engineering of Capsid Region of Polioviruses by Deoptimizing Codon Pairs

Calculation of Codon Pair Bias

Every individual codon pair of the possible 3721 non-"STOP" containing codon pairs (e.g., GTT-GCT) carries an assigned "codon pair score," or "CPS" that is specific for a given "training set" of genes. The CPS of a given codon pair is defined as the log ratio of the observed number of occurrences over the number that would have been expected in this set of genes (in this example the human genome). Determining the actual number of occurrences of a particular codon pair (or in other words the likelihood of a particular amino acid pair being encoded by a particular codon pair) is simply a matter of counting the actual number of occurrences of a codon pair in a particular set of coding sequences. Determining the expected number, however, requires additional calculations. The expected number is calculated so as to be independent of both amino acid frequency and codon bias similarly to Gutman and Hatfield. That is, the expected frequency is calculated based on the relative proportion of the number of times an amino acid is encoded by a specific codon. A positive CPS value signifies that the given codon pair is statistically over-represented, and a negative CPS indicates the pair is statistically under-represented in the human genome.

To perform these calculations within the human context, the most recent Consensus CDS (CCDS) database of consistently annotated human coding regions, containing a total of 14,795 genes, was used. This data set provided codon and codon pair, and thus amino acid and amino-acid pair frequencies on a genomic scale.

The paradigm of Federov et al. (2002), was used to further enhanced the approach of Gutman and Hatfield (1989). This allowed calculation of the expected frequency of a given codon pair independent of codon frequency and non-random associations of neighboring codons encoding a particular amino acid pair.

$$S(P_{ij}) = \ln\left(\frac{N_O(P_{ij})}{N_E(P_{ij})}\right) = \ln\left(\frac{N_O(P_{ij})}{F(C_i)F(C_j)N_O(X_{ij})}\right)$$

In the calculation, $P_{ij}$ is a codon pair occurring with a frequency of $N_O(P_{ij})$ in its synonymous group. $C_i$ and $C_j$ are the two codons comprising $P_{ij}$, occurring with frequencies $F(C_i)$ and $F(C_1)$ in their synonymous groups respectively. More explicitly, $F(C_i)$ is the frequency that corresponding amino acid $X_i$ is coded by codon $C_i$ throughout all coding regions and $F(C_i)=N_O(C_i)/N_O(X_i)$, where $N_O(C_i)$ and $N_O(X_i)$ are the observed number of occurrences of codon $C_i$ and amino acid $X_i$ respectively. $F(C_j)$ is calculated accordingly. Further, $N_O(X_{ij})$ is the number of occurrences of amino acid pair $X_{ij}$ throughout all coding regions. The codon pair bias score $S(P_{ij})$ of $P_{ij}$ was calculated as the log-odds ratio of the observed frequency $N_O(P_{ij})$ over the expected number of occurrences of $N_e(P_{ij})$.

Figure 7:
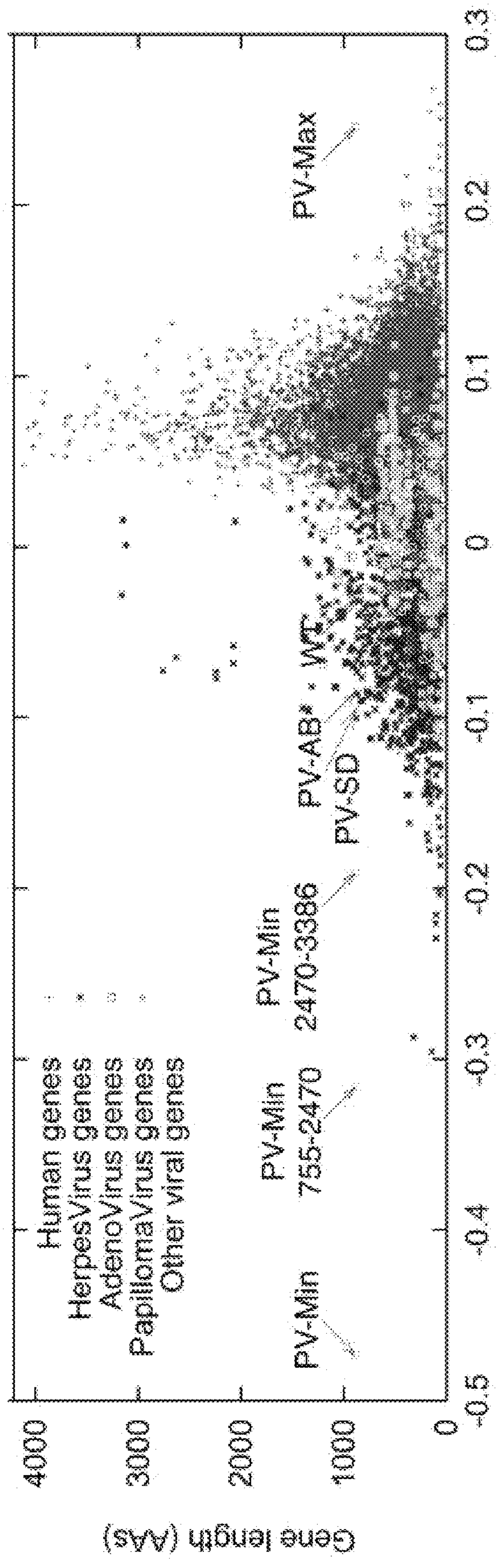
FIG. 7. Determining codon pair bias of human and viral ORFs. Dots represent the average codon-pair score per codon pair for one ORF plotted against its length. Codon pair bias (CPB) was calculated for 14,795 annotated human genes. Under-represented codon pairs yield negative scores. CPB is plotted for various poliovirus P1 constructs, represented by symbols with arrows. The figure illustrates that the bulk of human genes clusters around 0.1. CPB is shown for PV(M)-wt (labeled "WT") (−0.02), customized synthetic poliovirus capsids PV-Max (+0.25), PV-Min (−0.48), and PV(M)-wt:PV-Min chimera capsids PV-$Min^{755-2470}$ (="PV-MinXY") (−0.31) and PV-$Min^{2470-3386}$ (="PV-MinZ") (−0.20). Viruses PV-SD and PV-AB are the result of altered codon bias, but not altered codon pair bias.

Using the formula above, it was then determined whether individual codon pairs in individual coding sequences are over- or under-represented when compared to the corresponding genomic $N_e(P_{ij})$ values that were calculated by using the entire human CCDS data set. This calculation resulted in positive $S(P_{ij})$ score values for over-represented and negative values for under-represented codon pairs in the human coding regions (FIG. 7).

The "combined" codon pair bias of an individual coding sequence was calculated by averaging all codon pair scores according to the following formula:

$$S(P_{ij}) = \sum_{l=1}^{k} \frac{S(Pij)l}{k-1}.$$

The codon pair bias of an entire coding region is thus calculated by adding all of the individual codon pair scores comprising the region and dividing this sum by the length of the coding sequence.

Changing of Codon Pair Bias

The capsid-coding region of PV(M) was re-engineered to change codon pair bias. The largest possible number of rarely used codon pairs (creating virus PV-Min) or the largest possible number of widely used codon pairs (creating virus PV-Max) was introduced, while preserving the codon bias and all other features of the wt virus genome. The following explains our method in detail.

Two sequences were designed to vary the poliovirus P1 region codon pair score in the positive (PV-Max; SEQ ID NO:4) and negative (PV-Min; SEQ ID NO:5) directions. By leaving the amino acid sequence unaltered and the codon bias minimally modified, a simulated annealing algorithm was used for shuffling codons, with the optimization goal of a minimum or maximum codon pair score for the P1 capsid region. The resulting sequences were processed for elimination of splice sites and reduction of localized secondary structures. These sequences were then synthesized by a commercial vendor, Blue Heron Biotechnology, and sequence-verified. The new capsid genes were used to replace the equivalent wt sequence in an infectious cDNA clone of wt PV via two PflMI restriction sites. Virus was derived as described in Example 1.

For the PV-Max virus, death of infected cells was seen after 24 h, a result similar to that obtained with wt virus. Maximal viral titer and one-step growth kinetics of PV-Max were also identical to the wt. In contrast, no cell death resulted in cells transfected with PV-Min mutant RNA and no viable virus could be recovered. The transfections were repeated multiple times with the same result. Lysates of PV-Min transfected cells were subjected to four successive blind passages, and still no virus was obtained.

Figures 8A, 8B:
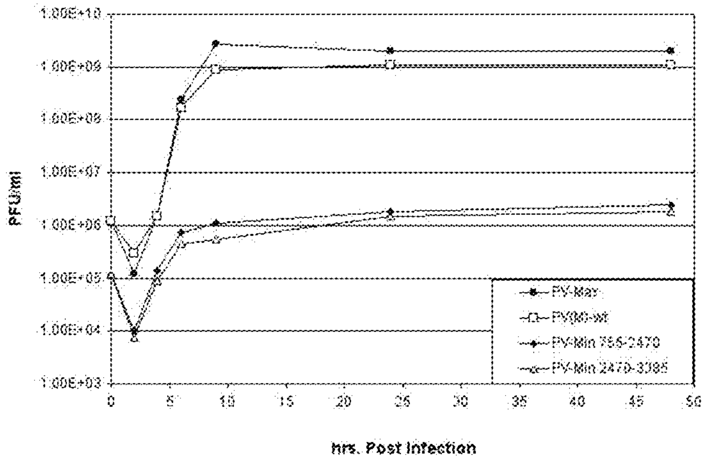
FIGS. 8A-B. Characteristics of codon-pair deoptimized polio.

The capsid region of PV-Min was divided into two smaller sub-fragments (PV-Min$^{755\text{-}247o}$ and PV-Min$^{2470\text{-}3386}$) as had been done for PV-AB (poor codon bias), and the sub-fragments were cloned into the wt background. As with the PV-AB subclones, subclones of PV-Min were very sick, but not dead (FIG. 8). As observed with PV-AB viruses, the phenotype of PV-Min viruses is a result of reduced specific infectivity of the viral particles rather than to lower production of progeny virus. Ongoing studies involve testing the codon pair-attenuated chimeras in CD155tg mice to determine their pathogenicity. Also, additional chimeric viruses comprising subclones of PV-Min cDNAs are being made, and their ability to replicate is being determined (see example 8 and 9 below). Also, the effect of distributing intermediate amounts of codon pair bias over a longer sequence are being confirmed. For example, a poliovirus derivative is designed to have a codon pair bias of about −0.2 (PV-0.2; SEQ ID NO:6), and the mutations from wild type are distributed over the full length of the P1 capsid region. This is in contrast to PV-MinZ (PV-Min$^{2470\text{-}3386}$) which has a similar codon pair bias, but with codon changes distributed over a shorter sequence.

It is worth pointing out that PV-Min and PV-0.2 are sequences in which there is little change in codon usage relative to wild type. For the most part, the sequences employ the same codons that appear in the wild type PV(M) virus. PV-MinZ is somewhat different in that it contains a portion of PV-Min subcloned into PV(M). As with PV-Min and PV-0.2, the encoded protein sequence is unchanged, but codon usage as determined in either the subcloned region, or over the entire P1 capsid region, is not identical to PV-Min (or PV-0.2), because only a portion of the codon rearranged sequence (which has identical codons over its full length, but not within smaller segments) has been substituted into the PV(M) wild type sequence. Of course, a mutated capsid sequence could be designed to have a codon pair bias over the entire P1 gene while shuffling codons only in the region from nucleotides 2470-3386.

Example 8

Viruses Constructed by a Change of Codon-Pair Bias are Attenuated in CD155 tg Mice

Mice Intracerebral Injections, Survival

To test the attenuation of PV-Min$^{755\text{-}2470}$ and PV-Min$^{2470\text{-}3385}$ in an animal model, these viruses were purified and injected intra-cerebrally into CD 155 (PVR/poliovirus receptor) transgenic mice (See Table 5). Indeed these viruses showed a significantly attenuated phenotype due to the customization of codon pair bias using our algorithm. PVM-wt was not injected at higher dose because all mice challenged at 10e5 virions died because of PVM-wt. This attenuated phenotype is due to the customization of codon pair bias using our algorithm. This reaffirms that the customization of codon-pair bias is applicable for a means to create live vaccines.

TABLE 5

Mice Intracerebral Injections, Survival.

| Virus | 10e4 Virions | 10e5 Virions | 10e6 Virions | 10e7 Virions |
|---|---|---|---|---|
| PV-Min$^{755\text{-}2470}$ | 4/4 | 3/4 | 3/5 | 3/4 |
| PV-Min$^{2470\text{-}3385}$ | 4/4 | 4/4 | 5/5 | 3/4 |
| PVM-wt | 3/4 | 0/4 | — | — |

These findings are significant in two respects. First, they are the first clear experimental evidence that codon pair bias is functionally important, i.e., that a deleterious phenotype can be generated by disturbing codon pair bias. Second, they provide an additional dimension of synonymous codon changes that can be used to attenuate a virus. The in vivo pathogenicity of these codon-pair attenuated chimeras have been tested in CD155tg and have shown an attenuated phenotype (See Table 5). Additional chimeric viruses comprising subclones of PV-Min capsid cDNAs have been assayed for replication in infected cells and have also shown an attenuated phenotype.

Example 9

Construction of Synthetic Poliovirus with Altered Codon-Pair Bias: Implications for Vaccine Development

Calculation of Codon Pair Bias, Implementation of Algorithm to Produce Codon Pair Deoptimized Sequences We developed an algorithm to quantify codon pair bias. Every possible individual codon pair was given a "codon pair score", or "CPS". We define the CPS as the natural log of the ratio of the observed over the expected number of occurrences of each codon pair over all human coding regions.

$$CPS = \ln\left(\frac{F(AB)o}{\frac{F(A)\times F(B)}{F(X)\times F(Y)}\times F(XY)}\right)$$

Although the calculation of the observed occurrences of a particular codon pair is straightforward (the actual count within the gene set), the expected number of occurrences of a codon pair requires additional calculation. We calculate This expected number is calculated to be independent both of amino acid frequency and of codon bias, similar to Gutman and Hatfield. That is, the expected frequency is calculated based on the relative proportion of the number of times an amino acid is encoded by a specific codon. A positive CPS value signifies that the given codon pair is statistically over-represented, and a negative CPS indicates the pair is statistically under-represented in the human genome Using these calculated CPSs, any coding region can then be rated as using over- or under-represented codon pairs by taking the average of the codon pair scores, thus giving a Codon Pair Bias (CPB) for the entire gene.

$$CPB = \sum_{i=1}^{k} \frac{CPSi}{k-1}$$

The CPB has been calculated for all annotated human genes using the equations shown and plotted (FIG. 7). Each point in the graph corresponds to the CPB of a single human gene. The peak of the distribution has a positive codon pair bias of 0.07, which is the mean score for all annotated human genes. Also there are very few genes with a negative codon pair bias. Equations established to define and calculate CPB were then used to manipulate this bias.

Development and Implementation of Computer-Based Algorithm to Produce Codon Pair Deoptimized Sequences Using these formulas we next developed a computer based algorithm to manipulate the CPB of any coding region while maintaining the original amino acid sequence. The algorithm has the critical ability to maintain the codon usage of a gene (i.e. preserve the frequency of use of each existing codon) but "shuffle" the existing codons so that the CPB can be increased or decreased. The algorithm uses simulated annealing, a mathematical process suitable for full-length optimization (Park, S. et al., 2004). Other parameters are also under the control of this algorithm; for instance, the free energy of the folding of the RNA. This free energy is maintained within a narrow range, to prevent large changes in secondary structure as a consequence of codon re-arrangement. The optimization process specifically excludes the creation of any regions with large secondary structures, such as hairpins or stem loops, which could otherwise arise in the customized RNA. Using this computer software the user simply needs to input the cDNA sequence of a given gene and the CPB of the gene can be customized as the experimenter sees fit.

De Novo Synthesis of P1 Encoded by Either Over-Represented or Under-Represented Codon-Pairs To obtain novel, synthetic poliovirus with its P1 encoded by either over-represented or under-represented codon pairs, we entered the DNA sequence corresponding to the P1 structural region of poliovirus type I Mahoney (PV(M)-wt) into our program yielding—PV-Max-P1 using over-represented codon pairs (566 mutations) and PV-Min-P1 using under-represented codon pairs (631 mutations). The CPB scores of these customized, novel synthetic P-1 regions are PV-Max=+0.25 and PV-Min=−0.48, whereas the CPB of PV(M)-wt is −0.02 (FIG. 7).

Figures 11A, 11B:
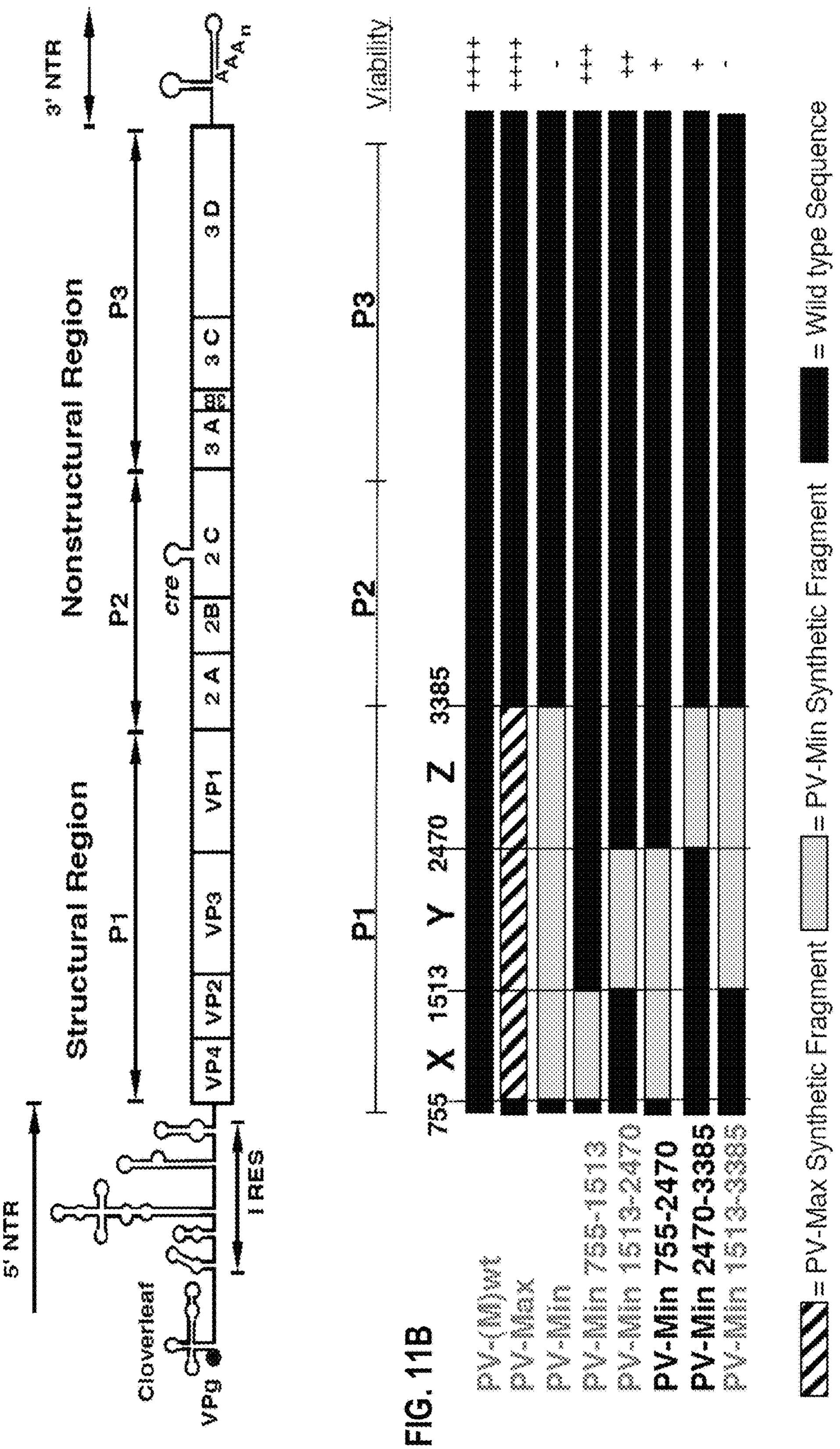
FIGS. 11A-B. Poliovirus Genome and Synthetic Viral Constructs. The poliovirus genome and open reading frames of chimeric virus constructs.

Additional customization included inclusion of restriction sites that were designed into both synthetic sequences at given intervals, to allow for sub-cloning of the P1 region. These synthetic P1 fragments were synthesized de novo by Blue Herron Corp. and incorporated into a full-length cDNA construct of poliovirus (FIG. 11) (Karlin et al., 1994). A small fragment (3 codons, 9 nucleotides) of PV(M)-wt sequence was left after the AUG start codon in both constructs to allow translation to initiate equally for all synthetic viruses; thus providing more accurate measurement of the effect of CPB on the elongation phase of translation.

DNA Synthesis, Plasmids, Sub Cloning of Synthetic Capsids and Bacteria

Large codon-pair altered PV cDNA fragments, corresponding to nucleotides 495 to 3636 of the PV genome, were synthesized by Blue Heron Corp. using their proprietary GeneMaker® system (http://www.blueheronbio.com/). All subsequent poliovirus cDNA clones/sub clones were constructed from PV1(M) cDNA clone pT7PVM using unique restriction sites (van der Wert, et al., 1986). The full-length PV-Min, PV-Max cassette was released from Blue Heron's carrier vector via PflMI digestion and insertion into the pT7PVM vector with its PflMI fragment removed. The PV-MinXY and PV-MinZ constructs were obtained by digestion with NheI and BglII simultaneously, then swapping this fragment with a pT7PVM vector digested similarly. PV-MinXY and PV-MinZ were constructed via BsmI digestion and exchanging the fragment/vector with the similarly digested pT7PVM. PV-MinY was constructed by digesting the PV-MinXY construct with BsmI and swapping this fragment with the BsmI fragment for a digested pT7PVM. Plasmid transformation and amplification were all achieved via *Escherichia coli* DH5a.

Creation of Chimeric Viruses Containing CPB-Altered Capsid Regions: Under-Represented Codon Pair Bias Throughout the P1 Results in a Null Phenotype Using the T7 RNA polymerase promoter upstream of the poliovirus genomic sequence, positive-sense RNA was transcribed. 1.5 μg of a given plasmid cDNA clone from above was linearized via an EcoRI digestion and than was transcribed into RNA via T7 RNA polymerase (Stratagene) driven by its promoter upstream of the cDNA for 2 hours at 37° C. (van der Werf et al., 1986). This RNA was transfected into $1\times10^6$ HeLa R19 cells using a modified DEAE-Dextran method (van der Werf et al., 1986). These cells were than incubate at room-temperature (RT) for 30-minutes. The transfection supernatant was removed and Dulbecco's modified Eagle medium (DMEM) containing 2% bovine calf serum (BCS) was added and the cells were incubated at 37° C. and observed (up to 4 days) for the onset of cytopathic effect (CPE).

The PV-Max RNA transfection produced 90% cytopathic effect (CPE) in 24 hours, which is comparable to the transfection of PV(M)-wt RNA. The PV-Max virus generated plaques identical in size to the wild type. In contrast, the PV-Min RNA produced no visible cytopathic effect after 96 hours, and no viable virus could be isolated even after four blind passages of the supernatant from transfected cells.

The subsequent use of the supernatant from cells subjected to PV-Max RNA transfection also produced 95% CPE in 12 hours, thus indicating that the transfected genomic material successfully produced PV-Max poliovirus virions. In contrast, the PV-Min viral RNA yielded no visible CPE after 96 hours and four blind passages of the supernatant, possibly containing extremely low levels of virus, also did not produce CPE. Therefore the full-length PV-Min synthetic sequence, utilizing under-represented codon pairs, in the P1 region cannot generate viable virus and so it would need to be sub-cloned.

HeLa R19 cells were maintained as a monolayer in DMEM containing 10% BCS. Virus amplification was achieved on ($1.0\times10^8$ cells) HeLa R19 mononlayers using 1 M.O.I. Infected cells were incubated at 37° C. in DMEM with 2% BCS for three days or until CPE was observed. After three freeze/thaw cycles cell debris was removed form the lysates via low speed centrifugation and the supernatant containing virus was used for further experiments.

One-Step growth curves were achieved by infecting a monolayer of HeLa R19 cells with 5 M.O.I of a given virus, the inoculums was removed, cells washed 2× with PBS and then incubating at 37° C. for 0, 2, 4, 7, 10, 24, and 48 hours. These time points were then analyzed via plaque assay. All Plaque assay were performed on monolayers of HeLa R19 cells. These cells were infected with serial dilution of a given growth curve time point or purified virus. These cells were then overlaid with a 0.6% tragenthum gum in Modified Eagle Medium containing 2% BCS and then incubated at 37° C. for either 2 days for PV(M)-wt and PV-Max, or 3 days for PV-Min (X, Y, XY, or Z) viruses. These were then developed via crystal violet staining and the PFU/ml titer was calculated by counting visible plaques.

Small Regions of Under-Represented Codon Pair Bias Rescues Viability, but Attenuate the Virus.

Using the restriction sites designed within the PV-Min sequence we subcloned portions of the PV-Min P1 region into an otherwise wild-type virus, producing chimeric viruses where only sub-regions of P1 had poor codon pair bias (FIG. 11) (van der Werf et al., 1986). From each of these sub-clones, RNA was produced via in vitro transcription and then transfected into HeLa R19 cells, yielding viruses with varying degrees of attenuation (Viability scores, FIG. 11). P1 fragments X and Y are each slightly attenuated; however when added together they yield a virus (PV-$Min^{755-2470}$, PV-MinXY) that is substantially attenuated (FIGS. 3, 4). Virus $PVMin^{2470-3385}$ (PV-MinZ) is about as attenuated as PV-MinXY. Construct PV-$Min^{1513-3385}$ (YZ) did not yield plaques, and so apparently is too attenuated to yield viable virus. These virus constructs, which displayed varying degrees of attenuation were further investigated to determine their actual growth kinetics.

Figure 12A:
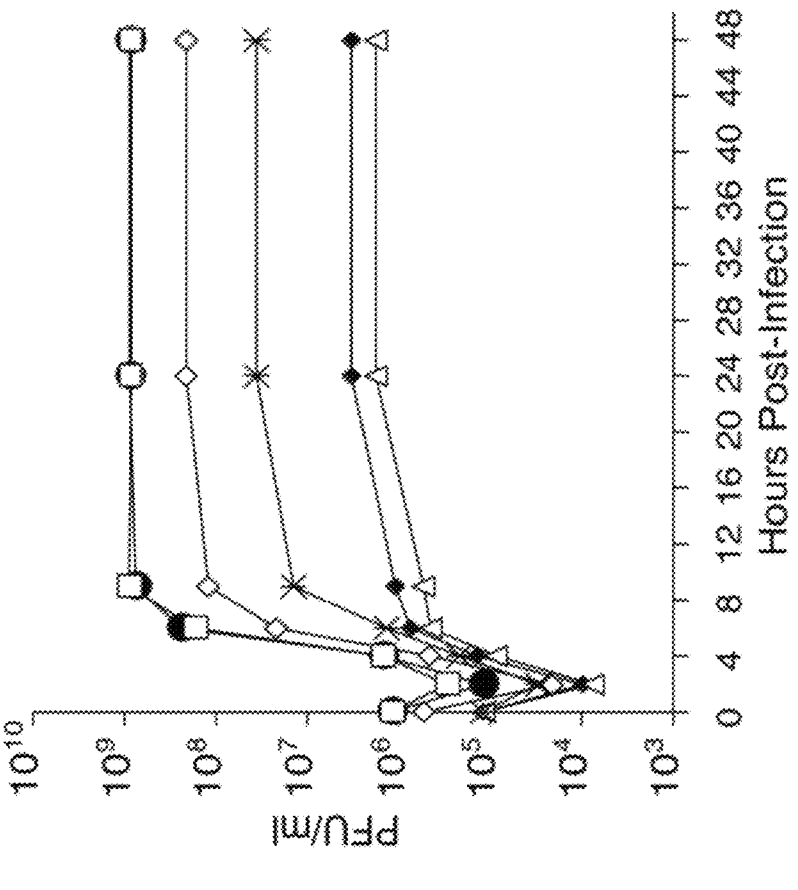
FIGS. 12A-B. On-Step growth curves display similar kinetics yielding a similar quantity of particles with decreased infectivity.

One-Step Growth Kinetics and the Mechanism of Attenuation: Specific Infectivity is Reduced For each viable construct, one step-growth kinetics were examined. These kinetics are generally similar to that of wild-type in that they proceed in the same basic manner (i.e. an eclipse phase followed by rapid, logarithmic growth). However, for all PV-Min constructs, the final titer in terms of Plaque Forming Units (PFU) was typically lower than that of wild-type viruses by one to three orders of magnitude (FIG. 12A).

Figure 12B:
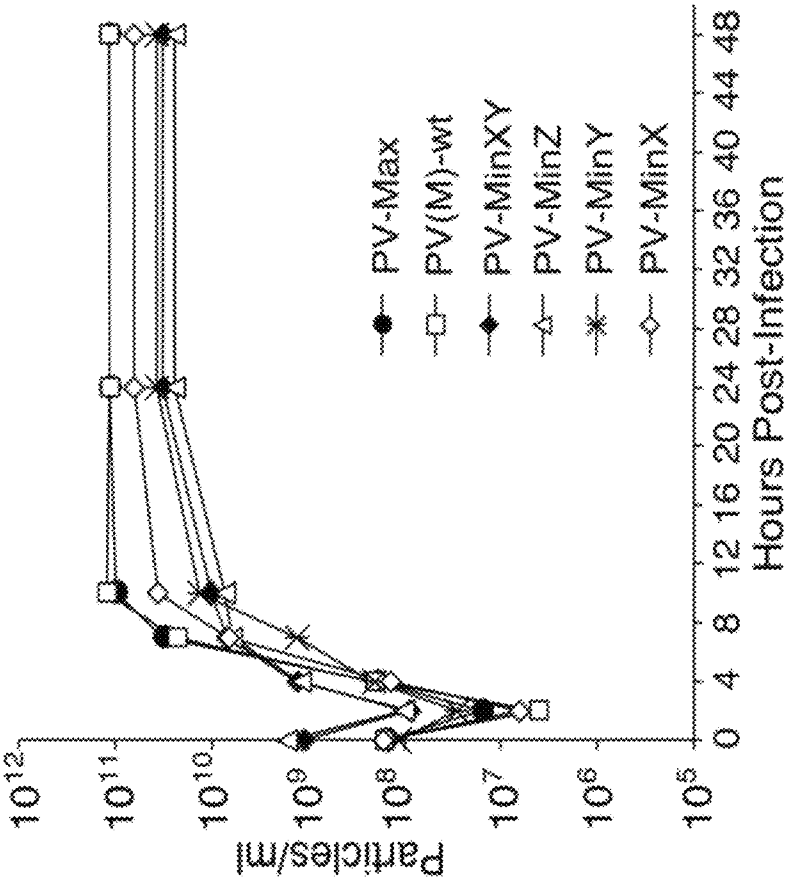

When virus is measured in viral particles per ml (FIG. 12B) instead of PFU, a slightly different result is obtained and suggests these viruses produce nearly equivalent numbers of particles per cell per cycle of infection as the wild-type virus. In terms of viral particles per ml, the most attenuated viruses are only 78% (PV-MinXY) or 82% (PV-MinZ) attenuated which on a log scale is less than one order of magnitude. Thus these viruses appear to be attenuated by about two orders of magnitude in their specific infectivity (the number of virions required to generate a plaque).

To confirm that specific infectivity was reduced, we re-measured the ratio of viral particles per PFU using highly purified virus particles. Selected viruses were amplified on $10^8$ HeLa R19 cells. Viral lysates were treated with RNAse A to destroy exposed viral genomes and any cellular RNAs, that would obscure OD values. Also the viral lysates were then incubated for 1 hour with 0.2% SDS and 2 mM EDTA to denature cellular and non-virion viral proteins. A properly folded and formed poliovirus capsid survives this harsh SDS treatment, were as alph particles do not (Mueller et al., 2005). Virions from these treated lysates were then purified via ultracentrifugation over a sucrose gradient. The virus particle concentration was measured by optical density at 260 nm using the formula $9.4\times10^{12}$ particles/ml=1 $OD_{260}$ unit (Rueckert, 1985). A similar number of particles was produced for each of the four viruses (Table 6). A plaque assay was then performed using these purified virions. Again, PV-MinXY and PV-MinZ required many more viral particles than wild-type to generate a plaque (Table 6).

For wild-type virus, the specific infectivity was calculated to be 1 PFU per 137 particles (Table 6), consistent with the literature (Mueller et al., 2006; Schwerdt and Fogh, 1957; Joklik and Darnell, 1961). The specific infectivities of viruses PV-MinXY and PV-MinZ are in the vicinity of 1 PFU per 10,000 particles (Table 6).

Additionally the heat stability of the synthetic viruses was compared to that of PV(M)-wt to reaffirm the SDS treatment data, that these particles with portions of novel RNA were equally as stable. Indeed these synthetic viruses had the same temperature profile as PV(M)-wt when incubated at 50° C. and quantified as a time course (data not shown).

Under-Represented Codon Pairs Reduce Translation Efficiency, Whereas Over-Represented Pairs Enhance Translation One hypothesis for the existence of codon pair bias is that the utilization of under-represented pairs causes poor or slow translation rates. Our synthetic viruses are, to our knowledge, the first molecules containing a high concentration of under-represented codon pairs, and as such are the first molecules suitable for a test of the translation hypothesis.

Figure 13A:
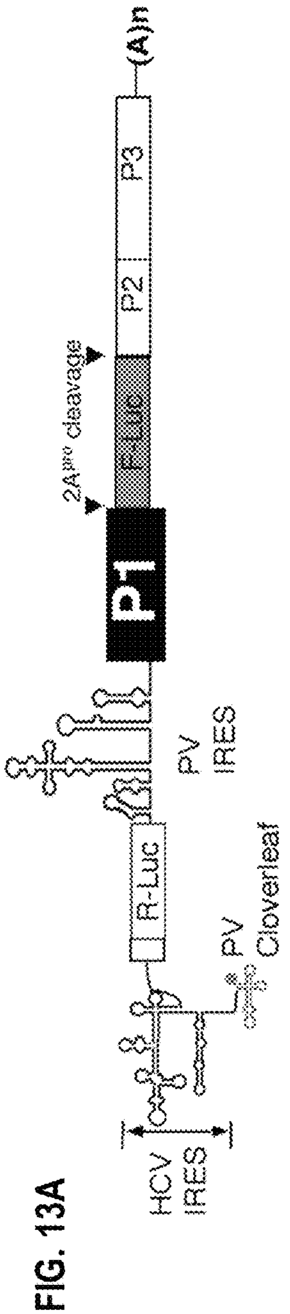
FIGS. 13A-B. In vivo modulation of translation by alteration of CPB.
Figure 13B:
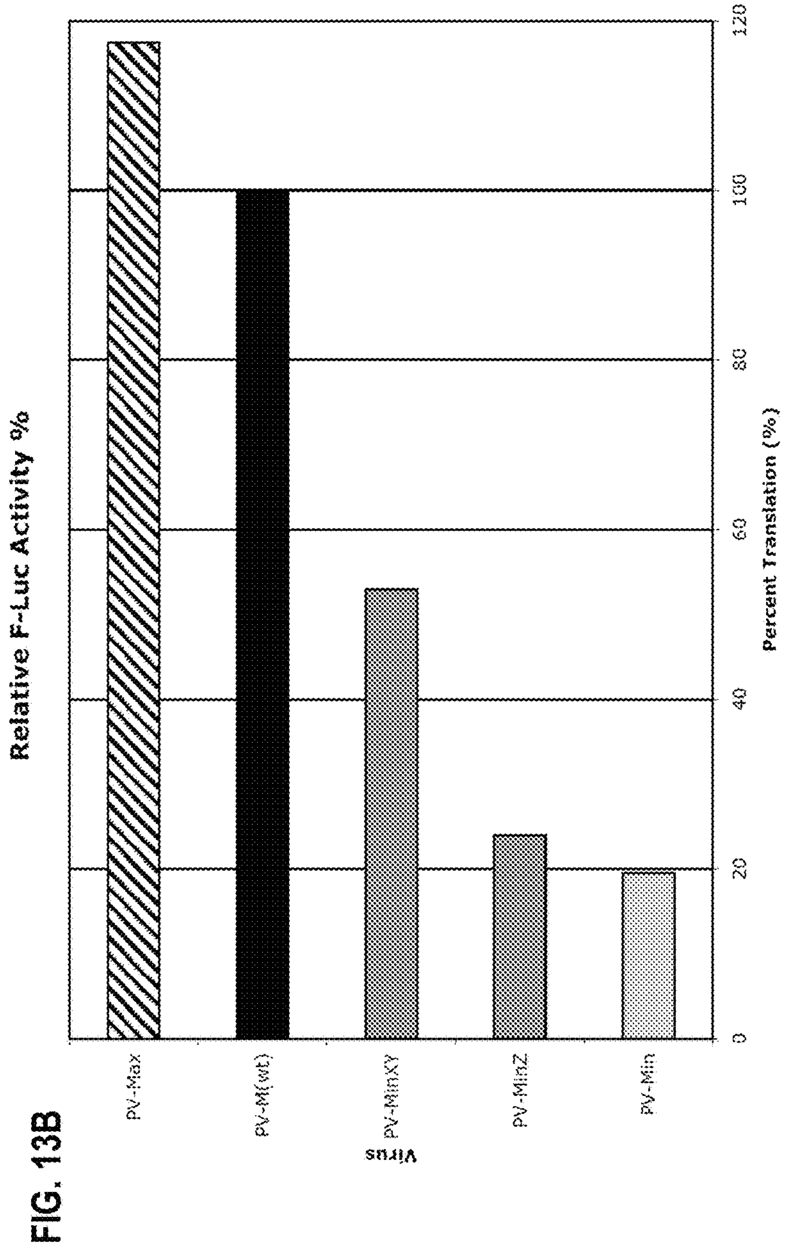

To measure the effect of codon pair bias on translation, we used a dicistronic reporter (Mueller et al., 2006) (FIG. 13). The first cistron expresses *Renilla* luciferase (R-Luc) under the control of the hepatitis C virus internal ribosome entry site (IRES) and is used as a normalization control. The second cistron expresses firefly luciferase (F-Luc) under the control of the poliovirus IRES. However, in this second cistron, the F-Luc is preceded by the P1 region of poliovirus, and this P1 region could be encoded by any of the synthetic sequence variants described here. Because F-Luc is translated as a fusion protein with the proteins of the P1 region, the translatability of the P1 region directly affects the amount of F-Luc protein produced. Thus the ratio of F-Luc luminescence to R-Luc luminescence is a measure of the translatability of the various P1 encodings.

The P1 regions of wild-type, PV-Max, PV-Min, PV-MinXY and PV-MinZ were inserted into the region labeled "P1" (FIG. 13A). PV-MinXY, PV-MinZ, and PV-Min produce much less F-Luc per unit of R-Luc than does the wild-type P1 region, strongly suggesting that the under-represented codon pairs are causing poor or slow translation rates (FIG. 13). In contrast, PV-Max P1 (which uses over-represented codon pairs) produced more F-Luc per unit of R-Luc, suggesting translation is actually better for PV-Max P1 compared to PV(M)-wt P1.

Dicistronic Reporter Construction, and In Vivo Translation

The dicistronic reporter constructs were all constructed based upon pdiLuc-PV (Mueller et al., 2006). PV-Max and PV-Min capsid regions were amplified via PCR using the oligonucleotides P1max-2A-RI (+)/P1max-2A-RI (−) or P1min-2A-RI (+)/P1min-2A-RI (−) respectively. The PCR fragment was gel purified and then inserted into an intermediate vector pCR-®-XL-TOPO® (Invitrogen). This intermediate vector was than amplified in One Shot® TOP10 chemically competent cells. After preparation of the plasmid via Quiagne miniprep the intermediate vectors containing PV-Min was digested with EcoRI and these fragments were ligated into the pdiLuc-PV vector that was equally digested with EcoRI (Mueller et al., 2006). These plasmids were also amplified in One Shot® TOP10 chemically competent cells (Invitrogen). To construct pdiLuc-PV-MinXY and pdiLuc-PV-MinZ, pdiLuc-PV and pdiLuc-PV-Min were equally digested with NheI and the resulting restriction fragments were exchanged between the respective vectors. These were than transformed into One Shot® TOP10 chemically competent cells and then amplified. From all four of these clones RNA was transcribed via the T7 polymerase method (van der Werf et al., 1986).

To analyze the in vivo translation efficiency of the synthetic capsids the RNA of the dicistronic reporter constructs were transfected into $2\times10^5$ HeLa R19 cells on 12-well dishes via Lipofectamine 2000 (Invtirogen). In order to quantify the translation of only input RNA the transfection was accomplished in the presence of 2 mM guanidine hydrochloride (GuHCL). Six hours after transfection cells were lysed via passive lysis buffer (Promega) and then these lysates were analyzed by a dual firefly (F-Luc) *Renilla* (R-Luc) luciferase assay (Promega).

Genetic Stability of PV-MinXY and PV-MinZ

Because PV-MinXY and PV-MinZ each contain hundreds of mutations (407 and 224, respectively), with each mutation causing a miniscule decrease in overall codon pair bias, we believe it should be very difficult for these viruses to revert to wild-type virulence. As a direct test of this idea, viruses PV-MinXY and PV-MinZ were serially-passaged 15 times, respectively, at an MOI of 0.5. The titer was monitored for phenotypic reversion, and the sequence of the passaged virus was monitored for reversions or mutation. After 15 passages there was no phenotypic change in the viruses (i.e. same titer, induction of CPE) and there were no fixed mutations in the synthetic region.

Heat Stability and Passaging

Figure 14:
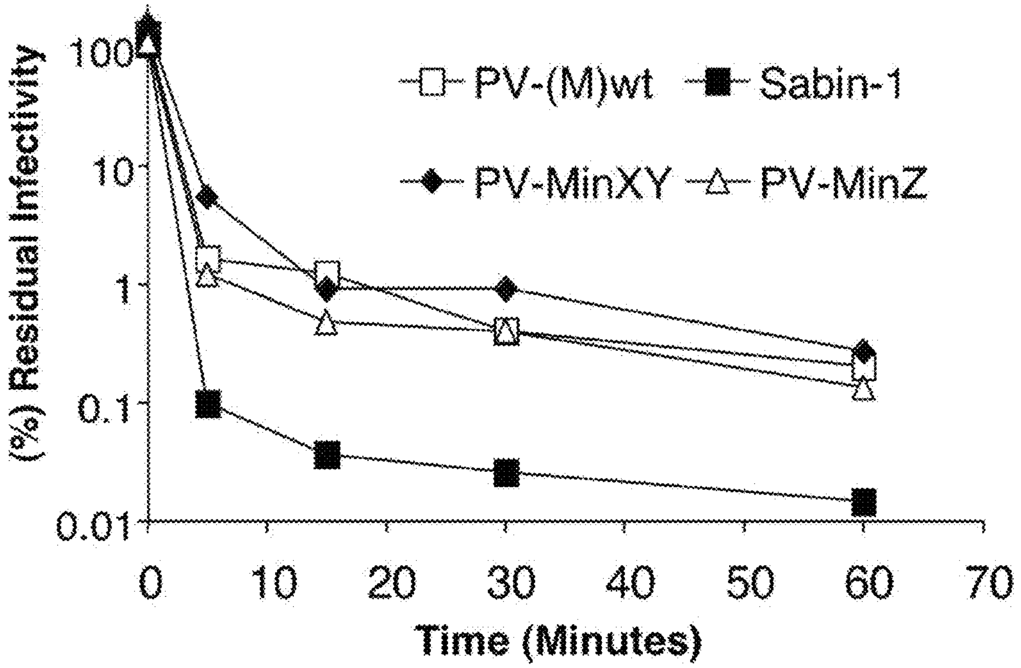
FIG. 14. The heat inactivation profile of the synthetic viruses is unchanged. To rule out that large scale codon-pair bias modification alters the gross morphology of virions, as one might expect if capsid proteins were misfolded, the thermal stability of PVMinXY and PV-MinZ was tested. An equal number of particles were incubated at 50° C. and the remaining infectivity quantified after given periods of time via plaque assay. If the capsids of the synthetic viruses were destabilized we would expect increased loss of viability at 50° C. in comparison to wt PV(M). This was not the case. The thermal inactivation kinetics of both synthetic viruses was identical to the wt. In contrast, the Sabin-1 virus carries numerous mutations in the genome region encoding the capsid, which, fittingly, rendered this virus less heat stabile as compared to wt PV1(M).
Figure 15:
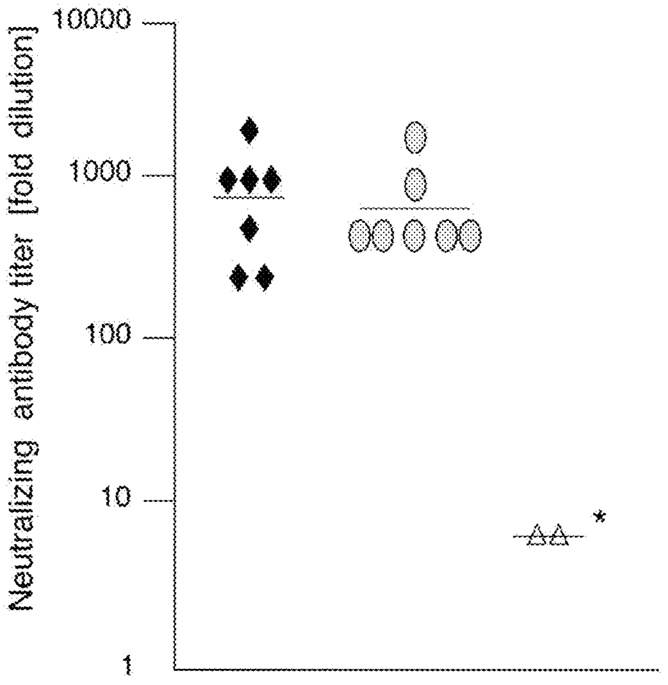
FIG. 15. Neutralizing antibody titer following vaccination. A group of eight CD155 tg mice, seven of which completed the regimen, were each inoculated by intraperitoneal injection three times at weekly intervals with $10^8$ particles of PV-MinZ (●) and PV-MinXY (♦) and the serum conversion was measured 10 days after the final vaccination. A horizontal lines across each data set marks the average neutralizing antibody titer for each virus construct. The anti-poliovirus antibody titer was measured via micro-neutralization assay. (*) No virus neutralization for mock-vaccinated animals was detected at the lowest tested 1:8.

The stability of the synthetic viruses, PV-MinXY and PV-Min Z, was tested and compared to PV(M)-wt. This was achieved by heating $1\times10^8$ particles suspended in PBS to 50° C. for 60 minutes and then measuring the decrease in intact viral particles via plaque assay at 5, 15, 30 and 60 minutes (FIG. 14). In order to test the genetic stability of the synthetic portions of the P1 region of the viruses PV-MinXY and PV-MinZ these viruses were serial passaged. This was achieved by infecting a monolayer of $1\times10^6$ HeLa R19 cells with 0.5 MOI of viruses, PV-MinXY and PV-MinZ, and then waiting for the induction of CPE. Once CPE initiated, which remained constant throughout passages, the lysates were used to infect new monolayers of HeLa R19 cells. The titer and sequence was monitored at passages 5, 9, and 15 (data not shown).

Virus Purification and Determination of Viral Particles Via $OD_{260}$ Absorbance A monolayer of HeLa R19 cells on a 15 cm dish ($1\times10^8$ cells) were infected with PV(M)-wt, PV-Max, PV-MinXY or PV-Min Z until CPE was observed. After three freeze/thaw cycles the cell lysates were subjected to two initial centrifugations at 3,000×g for 15 minutes and then 10,000×g for 15 minutes. Then 10 μg/ml of RNAse A (Roche) was added to supernatant and incubated at RT for 1 hour; Subsequently 0.5% sodium dodecyl sulfate (SDS) and 2 mM EDTA was added to the supernatant, gently mixed and incubated at RT for 30 minutes. These supernatants containing virus particles were placed above a 6 ml sucrose cushion [30% sucrose in Hank's Buffered Salt Solution (HBSS)]. Sedimentation of virus particles was achieved by ultracentrifugation through the sucrose gradient for 3.5 hours at 28,000 rpm using an SW28 swing-bucket rotor.

After centrifugation, the sucrose cushion was left intact and the supernatant was removed and the tube was washed two times with HBBS. After washing, the sucrose was removed and the virus "pearl" was re-suspended in PBS containing 0.1% SDS. Viral titers were determined via plaque assay (above). Virus particles concentration was determined via the average of three measurements of the optical density at 260 nm of the solution via the NanoDrop spectrophotometer (NanoDrop Technologies) using the formula $9.4\times10^{12}$ particles/ml=1 $OD_{260}$ unit (Mueller et al., 2006; Rueckert, 1985).

Neuroattenuation of PV-MinXY and PV-MinZ in CD155tg Mice

The primary site of infection of wild-type poliovirus is the oropharynx and gut, but this infection is relatively asymptomatic. However, when the infection spreads to motor neurons in the CNS in 1% of PV(M)-wt infections, the virus destroys these neurons, causing death or acute flaccid paralysis know as poliomyelitis (Landsteiner and Popper, 1909; Mueller et al., 2005). Since motor neurons and the CNS are the critical targets of poliovirus, we wished to know whether the synthetic viruses were attenuated in these tissues. Therefore these viruses were administered to CD155tg mice (transgenic mice expressing the poliovirus receptor) via intracerebral injection (Koike et al., 1991). The $PLD_{50}$ value was calculated for the respective viruses and the PV-MinXY and PV-MinZ viruses were attenuated either 1,000 fold based on particles or 10 fold based on PFU (Table 6) (Reed and Muench, 1938). Since these viruses did display neuroattenuation they could be used as a possible vaccine.

TABLE 6

Reduced Specific Infectivity and Neuroattenuation in CD155tg mice.

| Virus | $A_{260}$ | Purified Particles/ml[a] | Purified PFU/ml | Specific Infectivity[b] | $PLD_{50}$ (Particles)[c] | $PLD_{50}$ (PFU)[d] |
|---|---|---|---|---|---|---|
| PV-M (wt) | 0.956 | $8.97 \times 10^{12}$ | $6.0 \times 10^{10}$ | 1/137 | $10^{4.0}$ | $10^{1.9}$ |
| PV-Max | 0.842 | $7.92 \times 10^{12}$ | $6.0 \times 10^{10}$ | 1/132 | $10^{4.1}$ | $10^{1.9}$ |
| PV-MinXY | 0.944 | $8.87 \times 10^{12}$ | $9.6 \times 10^{8}$ | 1/9,200 | $10^{7.1}$ | $10^{3.2}$ |
| PV-MinZ | 0.731 | $6.87 \times 10^{12}$ | $5.1 \times 10^{8}$ | 1/13,500 | $10^{7.3}$ | $10^{3.2}$ |

[a]The $A_{260}$ was used to determine particles/ml via the formula $9.4 \times 10^{12}$ particles/ml = 1 $OD_{260}$ unit
[b]Calculated by dividing the PFU/ml of purified virus by the Particles/ml
[c,d]calculated after administration of virus via intracerebral injection to CD155tg mice at varying doses

Vaccination of CD155tg Mice Provides Immunity and Protection Against Lethal Challenge Groupings of 4-6, 6-8 week old CD155tg mice (Tg21 strain) were injected intracerebrally with purified virus dilutions from $10^2$ particles to $10^9$ particles in 30 ul PBS to determine neuropathogenicity (Koike, et al., 1991).

The lethal dose ($LD_{50}$) was calculated by the Reed and Muench method (Reed and Muench, 1938). Viral titers in the spinal chord and brain were quantified by plaque assay (data not shown).

PV-MinZ and PV-MinXY encode exactly the same proteins as wild-type virus, but are attenuated in several respects, both a reduced specific infectivity and neuroattenuation.

To test PV-Min Z, PV-MinXY as a vaccine, three sublethal dose ($10^8$ particles) of this virus was administered in 100 ul of PBS to 8, 6-8 week old CD155tg mice via intraperitoneal injection once a week for three weeks. One mouse from the vaccine cohort did not complete vaccine regimen due to illness. Also a set of control mice received three mock vaccinations with 100 ul PBS. Approximately one week after the final vaccination, 30 ul of blood was extracted from the tail vein. This blood was subjected to low speed centrifugation and serum harvested. Serum conversion against PV(M)-wt was analyzed via micro-neutralization assay with 100 plaque forming units (PFU) of challenge virus, performed according to the recommendations of WHO (Toyoda et al., 2007; Wahby, A. F., 2000). Two weeks after the final vaccination the vaccinated and control mice were challenged with a lethal dose of PV(M)-wt by intramuscular injection with a $10^6$ PFU in 100 ul of PBS (Toyoda et al., 2007). All experiments utilizing CD155tg mice were undertaken in compliance with Stony Brook University's IACUC regulations as well as federal guidelines. All 14 vaccinated mice survived and showed no signs of paralysis or parasia; in contrast, all mock-vaccinated mice died (Table 7). These data suggest that indeed the CPB virus using de-optimized codon pairs is able to immunize against the wild-type virus, providing both a robust humeral response, and also allowing complete survival following challenge.

TABLE 7

Protection Against Lethal Challenge

| Virus[a] | Mice Protected (out of 7)[b] |
|---|---|
| PV-MinZ | 7 |
| PV-MinXY | 7 |
| Mock vaccinated | 0 |

[a] CD155tg mice received three vaccination doses ($10^8$ particles) of respective virus
[b] challenged with $10^6$ PFU of PV(M)-wt via intramuscular injection.

Example 10

Application of SAVE to Influenza Virus

Influenza virus has 8 separate genomic segments. GenBank deposits disclosing the segment sequences for Influenza A virus (A/Puerto Rico/8/34/Mount Sinai(H1N1)) include AF389115 (segment 1, Polymerase PB2), AF389116 (segment 2, Polymerase PB1), AF389117 (segment 3, Polymerase PA), AF389118 (segment 4, hemagglutinin HA), AF389119 (segment 5, nucleoprotein NP), AF389120 (segment 6, neuraminidase NA), AF389121 (segment 7, matrix proteins M1 and M2), and AF389122 (segment 8, nonstructural protein NS1).

In initial studies, the genomic segment of strain A/PR/8/34 (also referred to herein as A/PR8) encoding the nucleoprotein NP, a major structural protein and the second most abundant protein of the virion (1,000 copies per particle) that binds as monomer to full-length viral RNAs to form coiled ribonucleoprotein, was chosen for deoptimization. (See Table 8, below, for parent and deoptimized sequences). Moreover, NP is involved in the crucial switch from mRNA to template and virion RNA synthesis (Palese and Shaw, 2007). Two synonymous encodings were synthesized, the first replacing frequently used codons with rare synonymous codons ($NP^{CD}$) (i.e., de-optimized codon bias) and, the second, de-optimizing codon pairs ($NP^{CPmin}$). The terminal 120 nucleotides at either end of the segment were not altered so as not to interfere with replication and encapsidation. $NP^{CD}$ contains 338 silent mutations and $NP^{CPmin}$ (SEQ ID NO:23) contains 314 silent mutations. The mutant NP segments were introduced into ambisense vectors as described (below), and together with the other seven wt influenza plasmids co-transfected into 293T/MDCK co-cultured cells. As a control, cells were transfected with all 8 wt A/PR8 plasmids. Cells transfected with the $NP^{CD}$ segment and the $NP^{CPmin}$ segment produced viable influenza virus similarly to cells transfected with wild-type NP. These new de-optimized viruses, referred to as A/PR8-$NP^{CD}$ or A/PR8-$NP^{CPmin}$, respectively, appear to be attenuated: The titer (in terms of PFU) is 3- to 10-fold lower than the wild-type virus, and the mutant viruses both make small plaques.

Although the de-optimized influenza viruses are not as severely attenuated as a poliovirus containing a similar number of de-optimized codons, there is a difference in the translational strategies of the two viruses. Poliovirus has a single long mRNA, translated into a single polyprotein. Slow translation through the beginning of this long mRNA (as in our capsid de-optimized viruses) will reduce translation of the entire message, and thus affect all proteins. In contrast, influenza has eight separate segments, and de-optimization of one will have little if any effect on translation of the others. Moreover, expression of the NP protein is particularly favored early in influenza virus infection (Palese and Shaw, 2007).

Characterization of Influenza Virus Carrying a Codon Pair Deoptimized NP Segment The growth characteristics of A/PR8-$NP^{CPmin}$ were analyzed by infecting confluent monolayers of Madin Darby Canine Kidney cells (MDCK cells) in 100 mm dishes with 0.001 multiplicities of infection (MOI). Virus inoculums were allowed to adsorb at room temperature for 30 minutes on a rocking platform, then supplemented with 10 ml of Dulbecco Modified Eagle Medium (DMEM) containing 0.2% Bovine Serum Albumin (BSA) and 2 ug/ml TPCK treated Trypsin and incubated at 37 C. After 0, 3, 6, 9, 12, 24, and 48 hours, 100 μl of virus containing medium was removed and virus titers determined by plaque assay.

Viral titers and plaque phenotypes were determined by plaque assay on confluent monolayers of MDCK cells in 35 mm six well plates. 10-fold serial dilutions of virus were prepared in Dulbecco Modified Eagle Medium (DMEM) containing 0.2% Bovine Serum Albumin (BSA) and 2 μg/ml TPCK treated Trypsin. Virus dilutions were plated out on MDCK cells and allowed to adsorb at room temperature for 30 minutes on a rocking platform, followed by a one hour incubation at 37 C in a cell culture incubator. The inoculum was then removed and 3 ml of Minimal Eagle Medium containing 0.6% tragacanth gum (Sigma-Aldrich) 0.2% BSA and 2 ug/ml TPCK treated Trypsin. After 72 hours of incubation at 37 C, plaques were visualized by staining the wells with crystal violet.

Figures 16A, 16B:
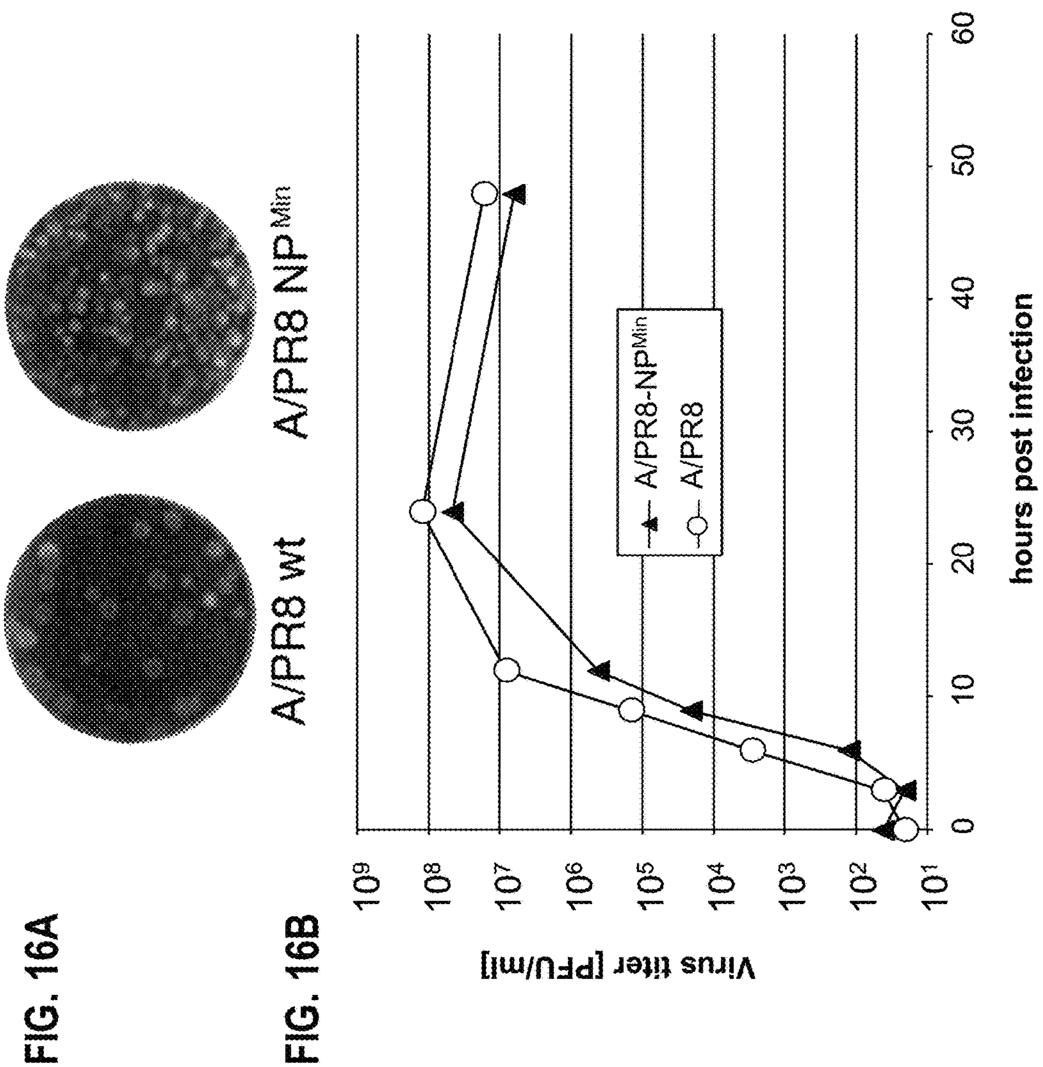
FIGS. 16A-B. Influenza virus carrying codon pair-deoptimized NP segment.

A/PR8-$NP^{Min}$ produced viable virus that produced smaller plaques on MDCK cells compared to the A/PR8 wt (FIG. 16A). Furthermore, upon low MOI infection A/PR8-$NP^{Min}$ manifests a delayed growth kinetics, between 3-12 hrs post infection, where A/PR8-$NP^{Min}$ titers lags 1.5 logs behind A/PR8 (FIG. 16B). Final titers are were 3-5 fold lower than that of A/PR8 (average of three different experiments).

Characterization of Influenza Viruses A/PR8-$PB1^{Min-RR}$, A/PR8-$HA^{Min}$ and A/PR8-$HA^{Min}$/$NP^{Min}$ Carrying Codon Pair Deoptimized PB1, HA, or HA and NP Segments Codon pair de-optimized genomic segments of strain A/PR/8/34 encoding the hemagglutinin protein HA and the polymerase subunit PB1 were produced. HA is a viral structural protein protruding from the viral surface mediating receptor attachment and virus entry. PB1 is a crucial component of the viral RNA replication machinery. Specifically a synonymous encoding of PB1 (SEQ ID NO:15) was synthesized by de-optimizing codon pairs between codons 190-488 (nucleotides 531-1488 of the PB1 segment) while retaining the wildtype codon usage ($PB1^{Min-RR}$). Segment $PB1^{Min-RR}$ contains 236 silent mutations compared the wt PB1 segment.

A second synonymous encoding of HA (SEQ ID NO:21) was synthesized by de-optimizing codon pairs between codons 50-541 (nucleotides 180-1655 of the HA segment) while retaining the wildtype codon usage ($HA^{Min}$). $HA^{Min}$ contains 355 silent mutations compared the to wt PB1 segment.

The mutant $PB1^{Min-RR}$ and $HA^{Min}$ segments were introduced into an ambisense vector as described above and together with the other seven wt influenza plasmids co-transfected into 293T/MDCK co-cultured cells. In addition the $HA^{Min}$ segment together with the $NP^{Min}$ segment and the remaining six wt plasmids were co-transfected. As a control, cells were transfected with all 8 wt A/PR8 plasmids. Cells transfected with either $PB1^{Min-RR}$ or $HA^{Min}$ segments produced viable virus as did the combination of the codon pair deoptimized segments $HA^{Min}$ and $NP^{Min}$. The new de-optimized viruses are referred to as A/PR8-$PB1^{Min-RR}$, A/PR8-$HA^{Min}$, and A/PR8-$HA^{Min}$/$NP^{Min}$, respectively.

Growth characteristics and plaque phenotypes were assessed as described above.

Figure 17A:
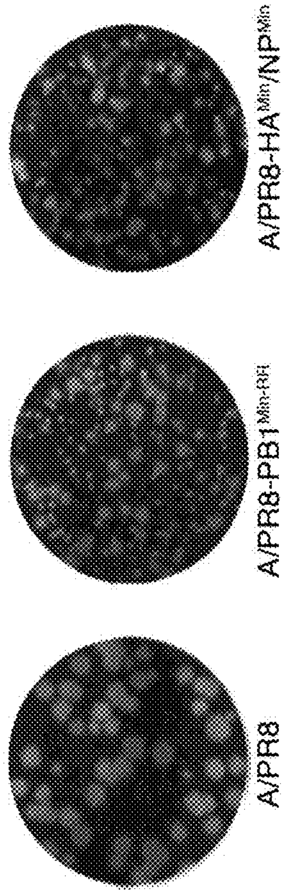
FIGS. 17A-B. Influenza virus carrying codon pair-deoptimized PB1 or HA and NP segments.
Figure 17B:
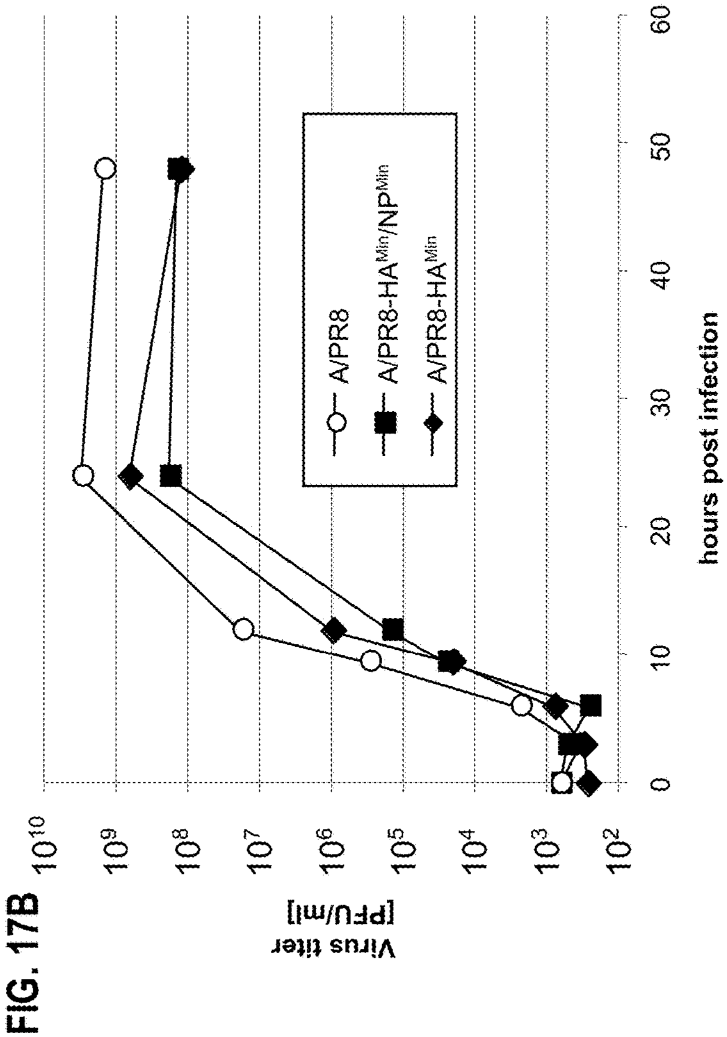

A/PR8-$PB1^{Min-RR}$, A/PR8-$HA^{Min}$, and A/PR8-$HA^{Min}$/$NP^{Min}$ all produced viable virus. A/PR8-$PB1^{Min-RR}$ and A/PR8-$HA^{Min}$/$NP^{Min}$ produced smaller plaques on MDCK cells compared to the A/PR8 wt (FIG. 17A). Furthermore, upon low MOI infection on MDCK cells A/PR8-$HA^{Min}$ and A/PR8-$HA^{Min}$/$NP^{Min}$ display much reduced growth kinetics, especially from 3-12 hrs post infection, where A/PR8-$HA^{Min}$/$NP^{Min}$ titers lag 1 to 2 orders of magnitude behind A/PR8 (FIG. 17B). Final titers for both A/PR8-$HA^{Min}$ and A/PR8-$HA^{Min}$/$NP^{Min}$ were 10 fold lower than that of A/PR8. As A/PR8-$HA^{Min}$/$NP^{Min}$ is more severely growth retarded than A/PR8-$HA^{Min}$, it can be concluded that the effect of deoptimizing two segments is additive.

Attenuation of A/PR8-$NP^{Min}$ a BALB/c Mouse Model

Groups of 6-8 anesthetized BALB/c mice 6 weeks of age were given 12.5 μl of A/PR8 or A/PR8-$NP^{Min}$ virus solution to each nostril containing 10-fold serial dilutions between $10^2$ and $10^6$ PFU of virus. Mortality and morbidity (weight loss, reduced activity, death) was monitored. The lethal dose 50, $LD_{50}$, was calculated by the method of Reed and Muench (Reed, L. J., and M. Muench. 1938. Am. J. Hyg. 27:493-497).

Eight mice were vaccinated once by intranasal inoculation with $10^2$ PFU of A/PR8-$NP^{Min}$ virus. A control group of 6 mice was not vaccinated with any virus (mock). 28 days following this initial vaccination the mice were challenged with a lethal dose of the wt virus A/PR8 corresponding to 100 times the $LD_{50}$.

Figure 18A:
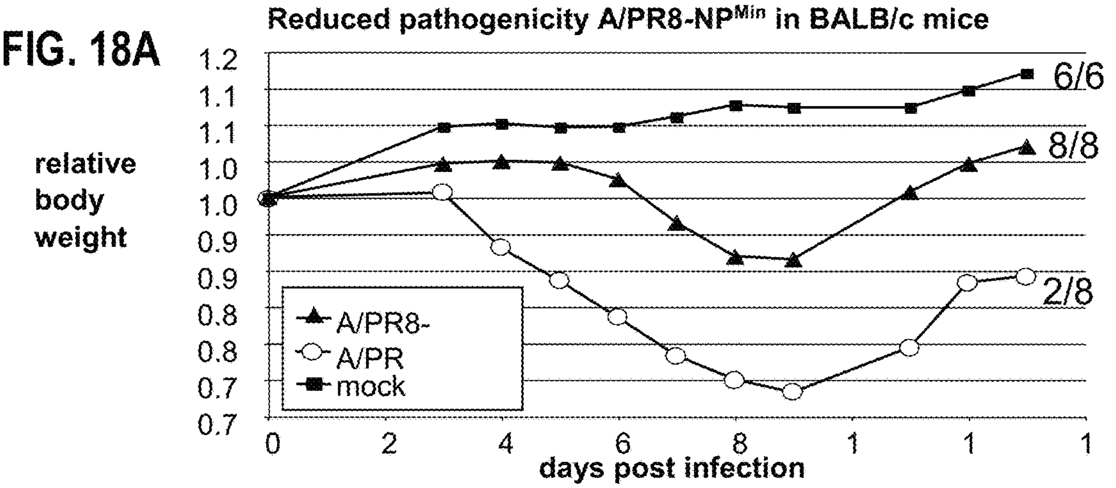
FIGS. 18A-C. Attenuation of A/PR8-$NP^{Min}$ in BALB/c mouse model.
Figure 18B:
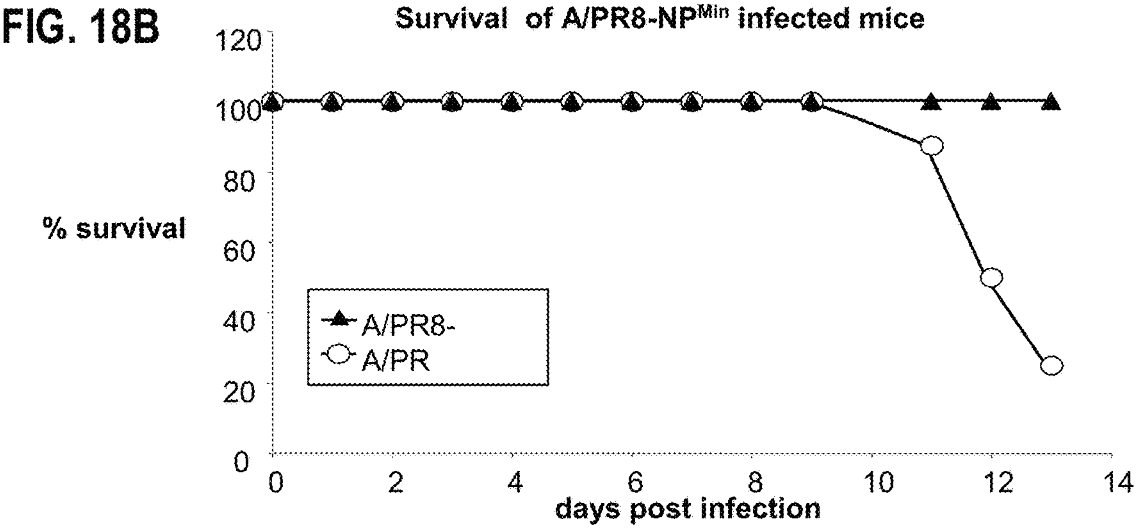

The $LD_{50}$ for A/PR8 was $4.6\times10^1$ PFU while the $LD_{50}$ for A/PR8-$NP^{Min}$ was $1\times10^3$ PFU. At a dose of $10^2$ all A/PR8-$NP^{Min}$ infected mice survived. It can be concluded that A/PR8-$NP^{Min}$ is attenuated in mice by more than 10 fold compared to the wt A/PR8 virus. This concentration was thus chosen for vaccination experiments. Vaccination of mice with $10^2$ A/PR8-$NP^{Min}$ resulted in a mild and brief illness, as indicated by a relative weight loss of less than 10% (FIG. 18A). All 8 out of 8 vaccinated mice survived. Mice infected with A/PR8 at the same dose experienced rapid weight loss with severe disease. 6 of 8 mice infected with A/PR8 died between 10 and 13 days post infection (FIG. 18B). Two mice survived and recovered from the wildtype infection.

Figure 18C:
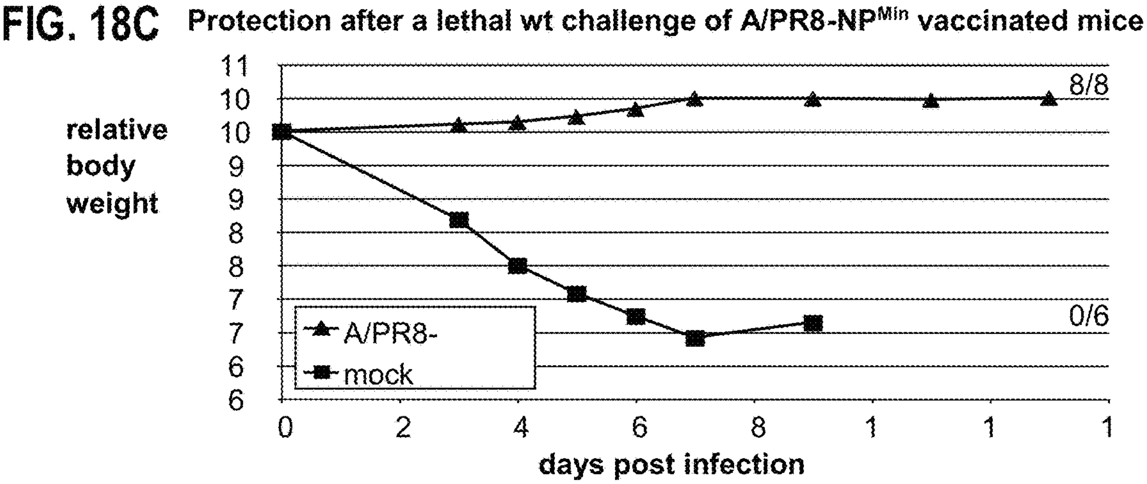

Upon challenge with 100 times $LD_{50}$ of wt virus, all A/PR8-$NP^{Min}$ vaccinated were protected, and survived the challenge without disease symptoms or weight loss (FIG. 18C). Mock vaccinated mice on the other hand showed severe symptoms, and succumbed to the infection between 9 and 11 days after challenge. It can be concluded that A/PR8-$NP^{Min}$ induced protective immunity in mice and, thus, has potential as a live attenuated influenza vaccine. Other viruses such as A/PR8-$PB1^{Min-RR}$ and A/PR8-$HA^{Min}$/$NP^{Min}$, yet to be tested in mice, may lead to improve further the beneficial properties of codon-pair deoptimized influenza viruses as vaccines.

Example 11

Development of Higher-Throughput Methods for Making and Characterizing Viral Chimeras

Constructing Chimeric Viruses by Overlapping PCR

The "scan" through each attenuated mutant virus is performed by placing approximately 300-bp fragments from each mutant virus into a wt context using overlap PCR. Any given 300-bp segment overlaps the preceding segment by ~200 bp, i.e., the scanning window is ~300 bp long, but moves forward by ~100 bp for each new chimeric virus. Thus, to scan through one mutant virus (where only the ~3000 bp of the capsid region has been altered) requires about 30 chimeric viruses. The scan is performed in 96-well dish format which has more than sufficient capacity to analyze two viruses simultaneously.

Figure 9:
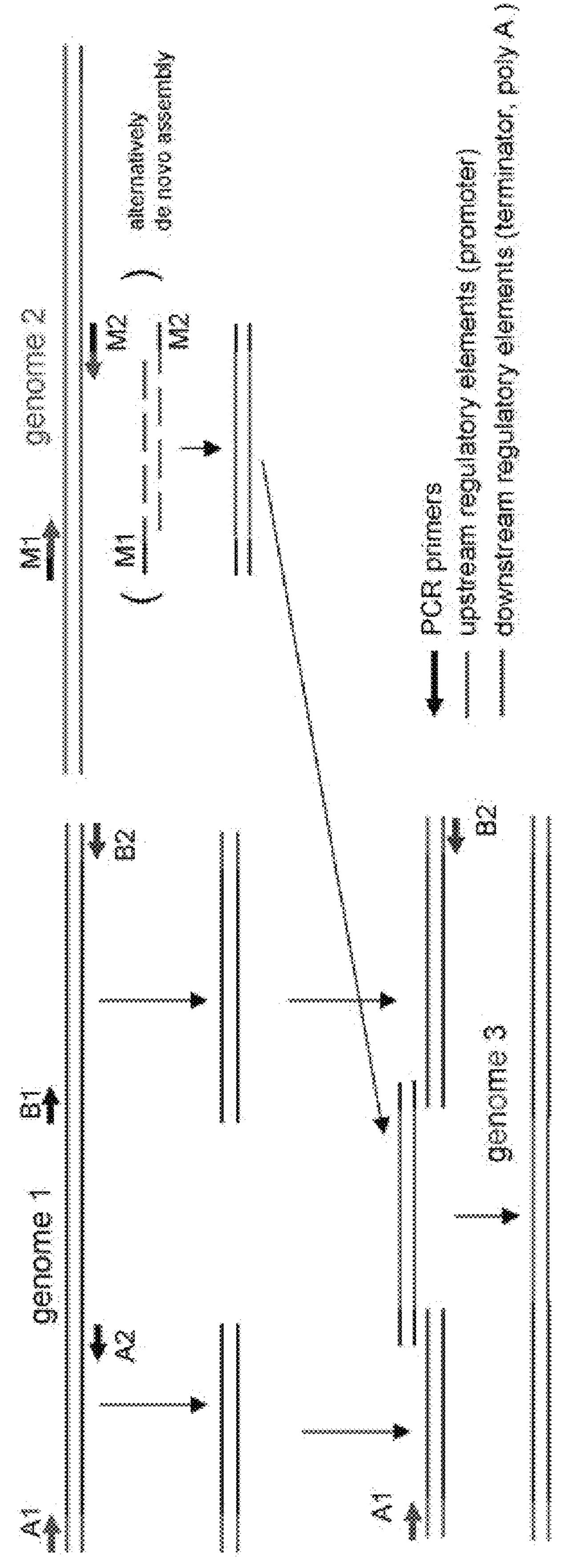
FIG. 9. Assembly of chimeric viral genomes. To "scan" through a target genome (red) small segments are amplified or synthesized and introduced into the wt genome (black) by overlapping PCR.

The starting material is picogram amounts of two plasmids, one containing the sequence of the wt virus, and the other the sequence of the mutant virus. The plasmids include all the necessary elements for the PV reverse genetics system (van der Werf et al., 1986), including the T7 RNA polymerase promoter, the hammerhead ribozyme (Herold and Aldino, 2000), and the DNA-encoded poly(A) tail. Three pairs of PCR primers are used, the A, M (for Mutant), and B pairs. See FIG. 9. The M pair amplifies the desired 300 bp segment of the mutant virus; it does not amplify wt, because the M primer pairs are designed based on sequences that have been significantly altered in the mutant. The A and B pairs amplify the desired flanks of the wt viral genome. Importantly, about 20-25 bp of overlap sequence is built into the 5' ends of each M primer as well as A2 and B1, respectively; these 20-25 bps overlap (100% complementarity) with the 3' end of the A segment and the 5' end of the B segment, respectively.

To carry out the overlapping PCR, one 96-well dish contains wt plasmid DNA, and the 30 different A and B pairs in 30 different wells. A separate but matching 96-well plate contains mutant plasmid DNA and the 30 different M primer pairs. PCR is carried out with a highly processive, low error rate, heat-stable polymerase. After the first round of PCR, each reaction is treated with DpnI, which destroys the template plasmid by cutting at methylated GmATC sites. An aliquot from each wt and matching mutant reaction is then mixed in PCR reaction buffer in a third 96-well dish. This time, primers flanking the entire construct are used (i.e., the A1 and B2 primers). Since each segment (A, M, and B) is designed to overlap each adjacent segment by at least 20 bp, and since the reaction is being driven by primers that can only amplify a full-length product, the segments anneal and mutually extend, yielding full-length product after two or three cycles. This is a "3-tube" (three 96-well dish) design that may be compacted to a "1-tube" (one 96-well dish) design.

Characterization of Chimeric Viruses

Upon incubation with T7 RNA polymerase, the full length linear chimeric DNA genomes produced above with all needed upstream and downstream regulatory elements yields active viral RNA, which produces viral particles upon incubation in HeLa S10 cell extract (Molla et al., 1991) or upon transfection into HeLa cells. Alternatively, it is possible to transfect the DNA constructs directly into HeLa cells expressing the T7 RNA polymerase in the cytoplasm.

The functionality of each chimeric virus is then assayed using a variety of relatively high-throughput assays, including visual inspection of the cells to assess virus-induced CPE in 96-well format; estimation of virus production using an ELISA; quantitative measurement of growth kinetics of equal amounts of viral particles inoculated into cells in a series of 96-well plates; and measurement of specific infectivity (infectious units/particle [IU/P] ratio).

The functionality of each chimeric virus can then be assayed. Numerous relatively high-throughput assays are available. A first assay may be to visually inspect the cells using a microscope to look for virus-induced CPE (cell death) in 96-well format. This can also be run an automated 96-well assay using a vital dye, but visual inspection of a 96-well plate for CPE requires less than an hour of hands-on time, which is fast enough for most purposes.

Second, 3 to 4 days after transfection, virus production may be assayed using the ELISA method described in Example 3. Alternatively, the particle titer is determined using sandwich ELISA with capsid-specific antibodies. These assays allow the identification of non-viable constructs (no viral particles), poorly replicating constructs (few particles), and efficiently replicating constructs (many particles), and quantification of these effects.

Third, for a more quantitative determination, equal amounts of viral particles as determined above are inoculated into a series of fresh 96-well plates for measuring growth kinetics. At various times (0, 2, 4, 6, 8, 12, 24, 48, 72 h after infection), one 96-well plate is removed and subjected to cycles of freeze-thawing to liberate cell-associated virus. The number of viral particles produced from each construct at each time is determined by ELISA as above.

Fourth, the IU/P ratio can be measured (see Example 3).

Higher Resolution Scans

If the lethality of the viruses is due to many small defects spread through the capsid region, as the preliminary data indicate, then many or most of the chimeras are sick and only a few are non-viable. If this is the case, higher-resolution scans are probably not necessary. Conversely, if one or more of the 300 bp segments do cause lethality (as is possible for the codon-deoptimized virus in the segment between 1513 and 2470 which, as described below, may carry a translation frameshift signal that contribute to the strong phenotype of this segment), the genome scan is repeated at higher resolution, for instance a 30 bp window moving 10 bp between constructs over the 300-bp segment, followed by phenotypic analysis. A 30-bp scan does not involve PCR of the mutant virus; instead, the altered 30-bp segment is designed directly into PCR primers for the wt virus. This allows the changes responsible for lethality to be pinpointed.

Example 12

Ongoing Investigations into the Molecular Mechanisms Underlying SAVE

Choice of Chimeras

Two to four example chimeras from each of the two parental inviable viruses (i.e., 4 to 8 total viruses) are used in the following experiments. Viable chimeras having relatively small segments of mutant DNA, but having strong phenotypes are selected. For instance, viruses PV-$AB^{755-1513}$, $PVAB^{2470-2954}$ and PV-$AB^{2954-3386}$ from the deoptimized codon virus (see Example 1), and PV-$Min^{755-2470}$ and PV-$Min^{2470-3386}$ (see Example 7), are suitable. Even better starting chimeras, with smaller inserts that will make analysis easier, may also be obtained from the experiments described above (Example 8).

RNA Abundance/Stability

Conceivably the altered genome sequence destabilizes the viral RNA. Such destabilization could be a direct effect of the novel sequence, or an indirect effect of a pause in translation, or other defect in translation (see, e.g., Doma and Parker, 2006). The abundance of the mutant viral RNA is therefore examined. Equal amounts of RNA from chimeric mutant virus, and wt virus are mixed and transfected into HeLa cells. Samples are taken after 2, 4, 8, and 12 h, and analyzed by Northern blotting or quantitative PCR for the two different viral RNAs, which are easily distinguishable since there are hundreds of nucleotide differences. A control with wt viral RNA compared to PV-SD (the codon-shuffled virus with a wt phenotype) is also done. A reduced ratio of mutant to wt virus RNA indicates that the chimera has a destabilized RNA.

In Vitro Translation

Translation was shown to be reduced for the codon-deoptimized virus and some of its derivatives. See Example 5. In vitro translation experiments are repeated with the codon pair-deoptimized virus (PV-Min) and its chosen chimeras. There is currently no good theory, much less any evidence, as to why deoptimized codon pairs should lead to viral inviability, and hence, investigating the effect on translation may help illuminate the underlying mechanism.

In vitro translations were performed in two kinds of extracts in Example 5. One was a "souped up" extract (Molla et al., 1991), in which even the codon-deoptimized viruses gave apparently good translation. The other was an extract more closely approximating normal in vivo conditions, in which the deoptimized-codon viruses were inefficiently translated. There were four differences between the extracts: the more "native" extract was not dialyzed; endogenous cellular mRNAs were not destroyed with micrococcal nuclease; the extract was not supplemented with exogenous amino acids; and the extract was not supplemented with exogenous tRNA. In the present study, these four parameters are altered one at a time (or in pairs, as necessary) to see which have the most significant effect on translation. For instance, a finding that it is the addition of amino acids and tRNA that allows translation of the codon-deoptimized virus strongly supports the hypothesis that translation is inefficient simply because rare aminoacyl-tRNAs are limiting. Such a finding is important from the point of view of extending the SAVE approach to other kinds of viruses.

Translational Frameshifting

Another possible defect is that codon changes could promote translational frameshifting; that is, at some codon pairs, the ribosome could shift into a different reading frame, and then arrive at an in-frame stop codon after translating a spurious peptide sequence. This type frameshifting is an important regulatory event in some viruses. The present data reveal that all PV genomes carrying the AB mutant segment from residue 1513 to 2470 are non-viable. Furthermore, all genomes carrying this mutant region produce a novel protein band during in vitro translation of approximately 42-44 kDa (see FIG. 5A, marked by asterisk). This novel protein could be the result of a frameshift.

Examination of the sequence in the 1513-2470 interval reveals three potential candidate sites that conform to the slippery heptameric consensus sequence for −1 frameshifting in eukaryotes (X-XXY-YYZ) (Farabaugh, 1996). These sites are A-AAA-AAT at positions 1885 and 1948, and T-TTA-TTT at position 2119. They are followed by stop codons in the −1 frame at 1929, 1986 or 2149, respectively. The former two seem the more likely candidates to produce a band of the observed size.

To determine whether frameshifting is occurring, each of the three candidate regions is separately mutated so that it becomes unfavorable for frameshifting. Further, each of the candidate stop codons is separately mutated to a sense codon. These six new point mutants are tested by in vitro translation. Loss of the novel 42-44 kDa protein upon mutation of the frameshifting site to an unfavorable sequence, and an increase in molecular weight of that protein band upon elimination of the stop codon, indicate that frameshifting is occurring. If frameshifting is the cause of the aberrant translation product, the viability of the new mutant that lacks the frameshift site is tested in the context of the 1513-2470 mutant segment. Clearly such a finding would be of significance for future genome designs, and if necessary, a frameshift filter may be incorporated in the software algorithm to avoid potential frameshift sites.

More detailed investigations of translational defects are conducted using various techniques including, but not limited to, polysome profiling, toeprinting, and luciferase assays of fusion proteins.

Polysome Profiling

Polysome profiling is a traditional method of examining translation. It is not high-throughput, but it is very well developed and understood. For polysome profiling, cell extracts are made in a way that arrests translation (with cycloheximide) and yet preserves the set of ribosomes that are in the act of translating their respective mRNAs (the "polysomes"). These polysomes are fractionated on a sucrose gradient, whereby messages associated with a larger number of ribosomes sediment towards the bottom. After fractionation of the gradient and analysis of RNA content using UV absorption, a polysome profile is seen where succeeding peaks of absorption correspond to mRNAs with N+1 ribosomes; typically 10 to 15 distinct peaks (representing the 40S ribosomal subunit, the 60S subunit, and 1, 2, 3, . . . 12, 13 ribosomes on a single mRNA) can be discerned before the peaks smudge together. The various fractions from the sucrose gradient are then run on a gel, blotted to a membrane, and analyzed by Northern analysis for particular mRNAs. This then shows whether that particular mRNA is primarily engaged with, say, 10 to 15 ribosomes (well translated), or 1 to 4 ribosomes (poorly translated).

In this study, for example, the wt virus, the PV-AB (codon deoptimized) virus, and its derivatives PV-$AB^{755-1513}$, and PV-$AB^{2954-3386}$, which have primarily N-terminal or C-terminal deoptimized segments, respectively, are compared. The comparison between the N-terminal and C-terminal mutant segments is particularly revealing. If codon deoptimization causes translation to be slow, or paused, then the N-terminal mutant RNA is associated with relatively few ribosomes (because the ribosomes move very slowly through the N-terminal region, preventing other ribosomes from loading, then zip through the rest of the message after traversing the deoptimized region). In contrast, the C-terminal mutant RNA are associated with a relatively large number of ribosomes, because many ribosomes are able to load, but because they are hindered near the C-terminus, they cannot get off the transcript, and the number of associated ribosomes is high.

Polysome analysis indicates how many ribosomes are actively associated with different kinds of mutant RNAs, and can, for instance, distinguish models where translation is slow from models where the ribosome actually falls off the RNA prematurely. Other kinds of models can also be tested.

Toeprinting

Toeprinting is a technique for identifying positions on an mRNA where ribosomes are slow or paused. As in polysome profiling, actively translating mRNAs are obtained, with their ribosomes frozen with cycloheximide but still associated; the mRNAs are often obtained from an in vitro translation reaction. A DNA oligonucleotide primer complementary to some relatively 3' portion of the mRNA is used, and then extended by reverse transcriptase. The reverse transcriptase extends until it collides with a ribosome. Thus, a population of translating mRNA molecules generates a population of DNA fragments extending from the site of the primer to the nearest ribosome. If there is a site or region where ribosomes tend to pause (say, 200 bases from the primer), then this site or region will give a disproportionate number of DNA fragments (in this case, fragments 200 bases long). This then shows up as a "toeprint" (a band, or dark area) on a high resolution gel. This is a standard method for mapping ribosome pause sites (to within a few nucleotides) on mRNAs.

Chimeras with segments of deoptimized codons or codon pairs, wherein in different chimeras the segments are shifted slightly 5' or 3', are analyzed. If the deoptimized segments cause ribosomes to slow or pause, the toeprint shifts 5' or 3' to match the position of the deoptimized segment. Controls include wt viral RNA and several (harmlessly) shuffled viral RNAs. Controls also include pure mutant viral RNA (i.e., not engaged in translation) to rule out ribosome-independent effects of the novel sequence on reverse transcription.

The toeprint assay has at least two advantages. First, it can provide direct evidence for a paused ribosome. Second, it has resolution of a few nucleotides, so it can identify exactly which deoptimized codons or deoptimized codon pairs are causing the pause. That is, it may be that only a few of the deoptimized codons or codon pairs are responsible for most of the effect, and toe-printing can reveal that.

Dual Luciferase Reporter Assays of Fusion Proteins

The above experiments may suggest that certain codons or codon pairs are particularly detrimental for translation. As a high-throughput way to analyze effects of particular codons and codon pairs on translation, small test peptides are designed and fused to the N-terminus of sea pansy luciferase. Luciferase activity is then measured as an assay of the translatability of the peptide. That is, if the N-terminal peptide is translated poorly, little luciferase will be produced.

A series of eight 25-mer peptides are designed based on the experiments above. Each of the eight 25-mers is encoded 12 different ways, using various permutations of rare codons and/or rare codon pairs of interest. Using assembly PCR, these 96 constructs (8 25-mers×12 encodings) are fused to the N-terminus of firefly luciferase (F-luc) in a dicistronic, dual luciferase vector described above (see Example 5 and FIG. 6). A dual luciferase system uses both the firefly luciferase (F-Luc) and the sea pansy (*Renilla*) luciferase (R-Luc); these emit light under different biochemical conditions, and so can be separately assayed from a single tube or well. A dicistronic reporter is expressed as a single mRNA, but the control luciferase (R-Luc) is translated from one internal ribosome entry site (IRES), while the experimental luciferase (F-luc) (which has the test peptides fused to its N-terminus) is independently translated from its own IRES. Thus, the ratio of F-Luc activity to R-Luc activity is an indication of the translatability of the test peptide. See FIG. 6.

The resulting 96 dicistronic reporter constructs are transfected directly from the PCR reactions into 96 wells of HEK293 or HeLa cells. The firefly luciferase of the upstream cistron serves as an internal transfection control. Codon- or codon-pair-dependent expression of the sea pansy luciferase in the second cistron can be accurately determined as the ratio between R-Luc and F-Luc. This assay is high-throughput in nature, and hundreds or even thousands of test sequences can be assayed, as necessary.

Example 13

Design and Synthesis of Attenuated Viruses Using Novel Alternative-Codon Strategy The SAVE approach to re-engineering viruses for vaccine production depends on large-scale synonymous codon substitution to reduce translation of viral proteins. This can be achieved by appropriately modulating the codon and codon pair bias, as well as other parameters such as RNA secondary structure and CpG content. Of the four de novo PV designs, two (the shuffled codon virus, PV-SD, and the favored codon pair virus, PV-Max) resulted in little phenotypic change over the wt virus. The other two de novo designs (PV-AB and PV-Min) succeeded in killing the virus employing only synonymous substitutions through two different mechanisms (drastic changes in codon bias and codon pair bias, respectively). The live-but-attenuated strains were constructed by subcloning regions from the inactivated virus strains into the wt.

A better understanding of the underlying mechanisms of viral attenuation employing large scale synonymous substitutions facilitates predictions of the phenotype and expression level of a synthetic virus. Ongoing studies address questions relating to the effect of the total number of alterations or the density of alterations on translation efficiency; the effect of the position of dense regions on translation; the interaction of codon and codon pair bias; and the effect of engineering large numbers of short-range RNA secondary structures into the genome. It is likely that there is a continuum between the wt and inactivated strains, and that any desired attenuation level can be engineered into a weakened strain. However, there may be hard limits on the attenuation level that can be achieved for any infection to be at self-sustaining and hence detectable. The $15^{442}$ encodings of PV proteins constitutes a huge sequence space to explore, and various approaches are being utilized to explore this sequence space more systematically. These approaches include, first, developing a software platform to help design novel attenuated viruses, and second, using this software to design, and then synthesize and characterize, numerous new viruses that explore more of the sequence space, and answer specific questions about how alternative encodings cause attenuation. Additionally, an important issue to consider is whether dangerous viruses might accidentally be created by apparently harmless shuffling of synonymous codons.

Development of Software for Computer-Based Design of Viral Genomes and Data Analysis Designing synthetic viruses requires substantial software support for (1) optimizing codon and codon-pair usage and monitoring RNA secondary structure while preserving, embedding, or removing sequence specific signals, and (2) partitioning the sequence into oligonucleotides that ensure accurate sequence-assembly. The prototype synthetic genome design software tools are being expanded into a full environment for synthetic genome design. In this expanded software, the gene editor is conceptually built around constraints instead of sequences. The gene designer works on the level of specifying characteristics of the desired gene (e.g., amino acid sequence, codon/codon-pair distribution, distribution of restriction sites, and RNA secondary structure constraints), and the gene editor algorithmically designs a DNA sequence realizing these constraints. There are many constraints, often interacting with each other, including, but not limited to, amino acid sequence, codon bias, codon pair bias, CG dinucleotide content, RNA secondary structure, cis-acting nucleic acid signals such as the CRE, splice sites, polyadenylation sites, and restriction enzyme recognition sites. The gene designer recognizes the existence of these constraints, and designs genes with the desired features while automatically satisfying all constraints to a pre-specified level.

The synthesis algorithms previously developed for embedding/removing patterns, secondary structures, overlapping coding frames, and adhering to codon/codon-pair distributions are implemented as part of the editor, but more important are algorithms for realizing heterogeneous combinations of such preferences. Because such combinations lead to computationally intractable (NP-complete) problems, heuristic optimization necessarily plays an important role in the editor. Simulated annealing techniques are employed to realize such designs; this is particularly appropriate as simulated annealing achieved its first practical use in the early VLSI design tools.

The full-featured gene design programming environment is platform independent, running in Linux, Windows and MacOS. The system is designed to work with genomes on a bacterial or fungal (yeast) scale, and is validated through the synthesis and evaluation of the novel attenuated viral designs described below.

Virus Designs with Extreme Codon Bias in One or a Few Amino Acids

For a live vaccine, a virus should be as debilitated as possible, short of being inactivated, in which case there is no way to grow and manufacture the virus. One way of obtaining an optimally debilitated is to engineer the substitution of rare codons for just one or a few amino acids, and to create a corresponding cell line that overexpresses the rare tRNAs that bind to those rare codons. The virus is then able to grow efficiently in the special, permissive cell line, but is inviable in normal host cell lines. Virus is grown and manufactured using the permissive cell line, which is not only very convenient, but also safer than methods used currently used for producing live attenuated vaccines.

With the sequencing of the human genome, information regarding copy number of the various tRNA genes that read rare codons is available. Based on the literature (e.g., Lavner and Kotlar, 2005), the best rare codons for present purposes are CTA (Leu), a very rare codon which has just two copies of the cognate tRNA gene; TCG (Ser), a rare codon with four copies of the cognate tRNA gene; and CCG (Pro), a rare codon with four copies of the cognate tRNA gene (Lavner and Kotlar, 2005). The median number of copies for a tRNA gene of a particular type is 9, while the range is 2 to 33 copies (Lavner and Kotlar, 2005). Thus, the CTA codon is not just a rare codon, but is also the one codon with the fewest cognate tRNA genes. These codons are not read by any other tRNA; for instance, they are not read via wobble base pairing.

Changing all the codons throughout the virus genome coding for Leu (180 codons), Ser (153), and Pro (119) to the rare synonymous codons CTA, TCG, or CCG, respectively, is expected to create severely debilitated or even non-viable viruses. Helper cells that overexpress the corresponding rare tRNAs can then be created. The corresponding virus is absolutely dependent on growing only in this artificial culture system, providing the ultimate in safety for the generation of virus for vaccine production.

Four high-priority viruses are designed and synthesized: all Leu codons switched to CTA; all Ser codons switched to TCG; all Pro codons switched to CCG; and all Leu, Ser, and Pro codons switched to CTA, TCG, and CCG, respectively, in a single virus. In one embodiment, these substitutions are made only in the capsid region of the virus, where a high rate of translation is most important. In another embodiment, the substitutions are made throughout the virus.

CG Dinucleotide Bias Viruses

With few exceptions, virus genomes under-represent the dinucleotide CpG, but not GpC (Karlin et al., 1994). This phenomenon is independent of the overall G+C content of the genome. CpG is usually methylated in the human genome, so that single-stranded DNA containing non-methylated CpG dinucleotides, as often present in bacteria and DNA viruses, are recognized as a pathogen signature by the Toll-like receptor 9. This leads to activation of the innate immune system. Although a similar system has not been shown to operate for RNA viruses, inspection of the PV genome suggests that PV has selected against synonymous codons containing CpG to an even greater extent than the significant under-representation of CpG dinucleotides in humans. This is particularly striking for arginine codons. Of the six synonymous Arg codons, the four CG containing codons (CGA, CGC CGG, CCU) together account for only 24 of all 96 Arg codons while the remaining two (AGA, AGG) account for 72. This in contrast to the average human codon usage, which would predict 65 CG containing codons and 31 AGA/AGO codons. In fact, two of the codons under-represented in PV are frequently used in human cells (CGC, CGG). There are two other hints that CG may be a disadvantageous dinucleotide in PV. First, in the codon pair-deoptimized virus, many of the introduced rare codon pairs contain CG as the central dinucleotide of the codon pair hexamer. Second, when Burns et al. (2006) passaged their codon bias-deoptimized virus and sequenced the genomes, it was observed that these viruses evolved to remove some CG dinucleotides.

Thus, in one high-priority redesigned virus, most or all Arg codons are changed to CGC or CGG (two frequent human codons). This does not negatively affect translation and allows an assessment of the effect of the CpG dinucleotide bias on virus growth. The increased C+G content of the resulting virus requires careful monitoring of secondary structure; that is, changes in Arg codons are not allowed to create pronounced secondary structures.

Modulating Codon-Bias and Codon-Pair Bias Simultaneously

Codon bias and codon-pair bias could conceivably interact with each other at the translational level. Understand this interaction may enable predictably regulation of the translatability of any given protein, possibly over an extreme range.

If we represent wild type polio codon bias and codon pair bias as 0, and the worst possible codon bias and codon pair bias as −1, then four high-priority viruses are the (−0.3, −0.3), (−0.3, −0.6), (−0.6, −0.3), and (−0.6, −0.6) viruses. These viruses reveal how moderately poor or very poor codon bias interacts with moderately poor or very poor codon pair virus. These viruses are compared to the wild type and also to the extreme PV-AB (−1, 0) and PV-Min (0, −1) designs.

Modulating RNA Secondary Structure

The above synthetic designs guard against excessive secondary structures. Two additional designs systematically avoid secondary structures. These viruses are engineered to have wt codon and codon-pair bias with (1) provably minimal secondary structure, and (2) many small secondary structures sufficient to slow translation.

Additional Viral Designs

Additional viral designs include full-genome codon bias and codon-pair bias designs; non-CG codon pair bias designs; reduced density rare codon designs; and viruses with about 150 rare codons, either spread through the capsid region, or grouped at the N-terminal end of the capsid, or grouped at the C-terminal end of the capsid.

Example 14

Testing the Potential for Accidentally Creating Viruses of Increased Virulence It is theoretically possible that redesigning of viral genomes with the aim of attenuating these viruses could accidentally make a virus more virulent than the wt virus. Because protein sequences are not altered in the SAVE procedure, this outcome is unlikely. Nevertheless, it is desirable to experimentally demonstrate that the SAVE approach is benign.

Out of the possible $10^{442}$ sequences that could possibly encode PV proteins, some reasonably fit version of PV likely arose at some point in the past, and evolved to a local optimum (as opposed to a global optimum). The creation of a new version of PV with the same protein coding capacity but a very different set of codons places this new virus in a different location on the global fitness landscape, which could conceivably be close to a different local optimum than wt PV. Conceivably, this new local optimum could be better than the wild type local optimum. Thus, it is just barely possible that shuffling synonymous codons might create a fitter virus.

To investigate this possibility, 13 PV genomes are redesigned and synthesized: one virus with the best possible codon bias; one virus with the best possible codon pair bias (i.e., PV-Max); one virus with the best possible codon and codon pair bias; and 10 additional viruses with wt codon and codon pair bias, but shuffled synonymous codons. Other parameters, such as secondary structure, C+G content, and CG dinucleotide content are held as closely as possible to wt levels.

These 13 viruses may each be in a very different location of the global fitness landscape from each other and from the wild type. But none of them is at a local optimum because they have not been subject to selection. The 13 viruses and the wt are passaged, and samples viruses are taken at the $1^{st}$, $10^{th}$, $20^{th}$, and $50^{th}$ passages. Their fitness is compared to each other and to wt by assessing plaque size, plaque-forming units/ml in one-step growth curves, and numbers of particles formed per cell. See Example 1. Five examples of each of the 13 viruses are sequenced after the $10^{th}$, $20^{th}$, and $50^{th}$ passage. Select passage isolates are tested for pathogenicity in CD155tg mice, and $LD_{50}$'s are determined. These assays reveal whether any of the viruses are fitter than wt, and provide a quantitative measure of the risk of accidental production of especially virulent viruses. The 10 viruses with wt levels of codon and codon pair bias also provide information on the variability of the fitness landscape at the encoding level.

In view of the possibility that a fitter virus could emerge, and that a fitter virus may be a more dangerous virus, these experiments are conducted in a BSL3 laboratory. After the $10^{th}$ passage, phenotypes and sequences are evaluated and the susceptibility of emerging viruses to neutralization by PV-specific antibodies is verified. The experiment is stopped and reconsidered if any evidence of evolution towards a significantly fitter virus, or of systematic evolution towards new protein sequences that evade antibody neutralization, is obtained. Phenotypes and sequences are similarly evaluated after passage 20 before proceeding to passage 50. Because the synthetic viruses are created to encode exactly the same proteins as wt virus, the scope for increased virulence seems very limited, even if evolution towards (slightly) increased fitness is observed.

Example 15

Extension of SAVE Approach to Virus Systems Other than Poliovirus

Notwithstanding the potential need for a new polio vaccine to combat the potential of reversion in the closing stages of the global effort at polio eradication, PV has been selected in the present studies primarily as a model system for developing SAVE. SAVE has, however, been developed with the expectation that this approach can be extended to other viruses where vaccines are needed. This extension of the SAVE strategy is herein exemplified by application to Rhinovirus, the causative agent of the common cold, and to influenza virus.

Adaptation of SAVE to Human Rhinovirus—a Virus Closely Related to Poliovirus

Two model rhinoviruses, HRV2 and HRV14, were selected to test the SAVE approach for several reasons: (1) HRV2 and HRV14 represent two members of the two different genetic subgroups, A and B (Ledford et al., 2004); (2) these two model viruses use different receptors, LDL-receptor and ICAM-1, respectively (Greve et al., 1989; Hofer et al., 1994); both viruses as well as their infectious cDNA clones have been used extensively, and most applicable materials and methods have been established (Altmeyer et al., 1991; Gerber et al., 2001); and (4) much of the available molecular knowledge of rhinoviruses stems from studies of these two serotypes.

The most promising SAVE strategies developed through the PV experiments are applied to the genomes of HRV2 and HRV14. For example, codons, codon pairs, secondary structures, or combinations thereof, are deoptimized. Two to three genomes with varying degrees of attenuation are synthesized for each genotype. Care is taken not to alter the CRE, a critical RNA secondary structure of about 60 nucleotides (Gerber et al., 2001; Goodfellow et al., 2000; McKnight, 2003). This element is vital to the replication of picornaviruses and thus the structure itself must be maintained when redesigning genomes. The location of the CRE within the genome varies for different picornaviruses, but is known for most families (Gerber et al., 2001; Goodfellow et al., 2000; McKnight, 2003), and can be deduced by homology modeling for others where experimental evidence is lacking. In the case of HRV2 the CRE is located in the RNA sequence corresponding to the nonstructural protein $2A^{pro}$; and the CRE of HRV14 is located in the VP1 capsid protein region (Gerber et al., 2001; McKnight, 2003).

The reverse genetics system to derive rhinoviruses from DNA genome equivalents is essentially the same as described above for PV, with the exception that transfections are done in HeLa-H1 cells at 34° C. in Hepes-buffered culture medium containing 3 mM Mg++ to stabilize the viral capsid. The resulting synthetic viruses are assayed in tissue culture to determine the PFU/IU ratio. See Example 3. Plaque size and kinetics in one-step growth curves are also assayed as described. See Example 2. Because the SAVE process can be applied relatively cheaply to all 100 or so relevant rhinoviruses, it is feasible to produce a safe and effective vaccine for the common cold using this approach.

Adaptation of SAVE to Influenza A Virus—a Virus Unrelated to Poliovirus

Figure 10:
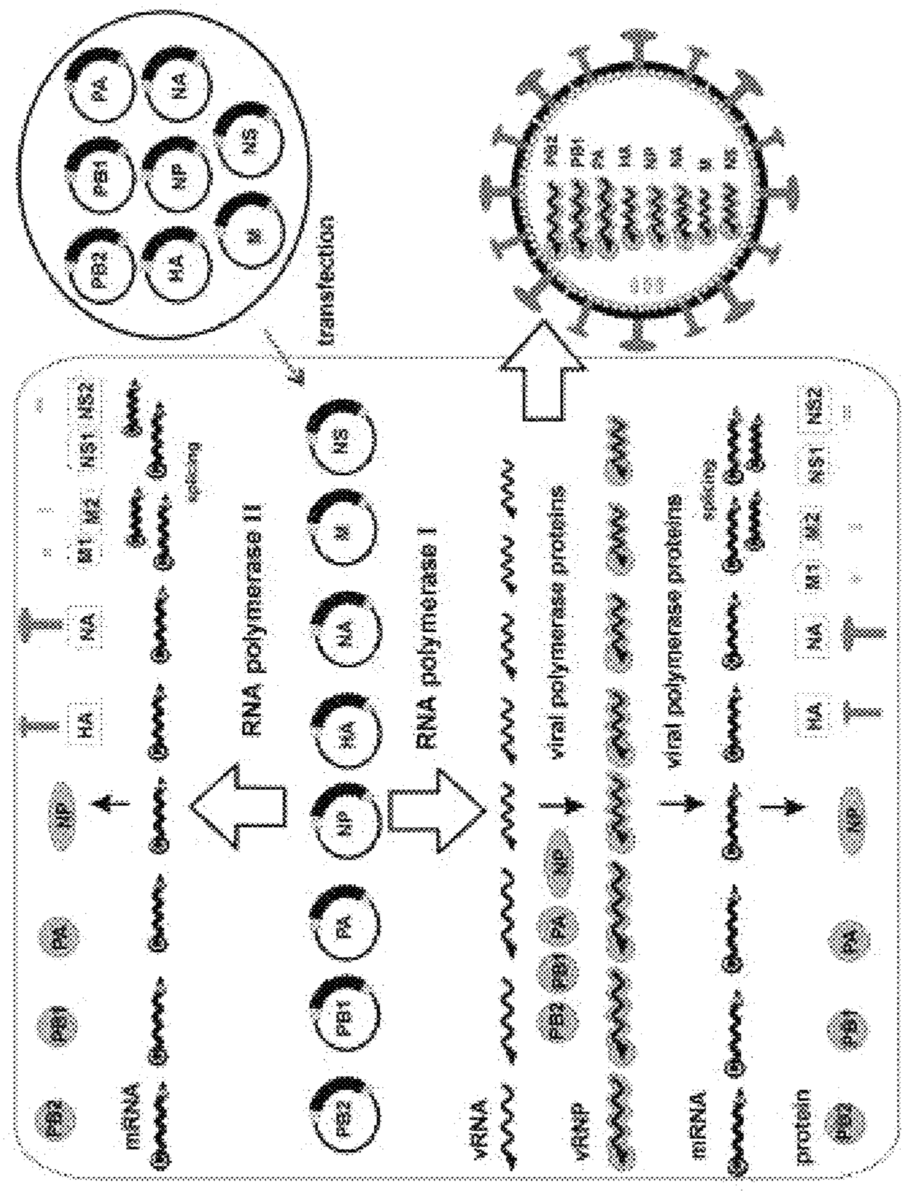
FIG. 10. The eight-plasmid pol I-pol II system for the generation of influenza A virus. Eight expression plasmids containing the eight viral cDNAs inserted between the human pol I promoter and the pol II promoter are transfected into eukaryotic cells. Because each plasmid contains two different promoters, both cellular pol I and pol II will transcribe the plasmid template, presumably in different nuclear compartments, which will result in the synthesis of viral mRNAs and vRNAs. After synthesis of the viral polymerase complex proteins (PB1, PB2, PA, nucleoproteins), the viral replication cycle is initiated. Ultimately, the assembly of all viral molecules directly (pol II transcription) or indirectly (pol I transcription and viral replication) derived from the cellular transcription and translation machinery results in the interaction of all synthesized molecules (vRNPs and the structural proteins HA, NA, M1, M2, NS2/NEP) to generate infectious influenza A virus. (Reproduced from Neumann et al., 2000.) (Note: there are other ways of synthesizing influenza de novo).

The most promising SAVE design criteria identified from PV experimentation are used to synthesize codon-deoptimized versions of influenza virus. The influenza virus is a “segmented” virus consisting of eight separate segments of RNA; each of these can be codon-modified. The well established ambisense plasmid reverse genetics system is used for generating variants of influenza virus strain A/PR/8/34. This eight-plasmid system is a variation of what has been described previously (Hoffmann et al., 2000), and has been kindly provided by Drs. P. Palese and A. Garcia-Sastre. Briefly, the eight genome segments of influenza each contained in a separate plasmid are flanked by a Pol I promoter at the 3' end and Pol I terminator at the 5' end on the antisense strand. This cassette in turn is flanked by a cytomegalovirus promoter (a Pol II promoter) at the 5' end and a polyadenylation signal at the 3' end on the forward strand (Hoffmann et al., 2000). Upon co-transfection into co-cultured 293T and MDCK cells, each ambisense expression cassette produces two kinds of RNA molecules. The Pol II transcription units on the forward strand produce all influenza mRNAs necessary for protein synthesis of viral proteins. The Pol I transcription unit on the reverse strand produces (−) sense genome RNA segments necessary for assembly of ribonucleoprotein complexes and encapsidation. Thus, infectious influenza A/PR/8/34 particles are formed (FIG. 10). This particular strain of the H1 N1 serotype is relatively benign to humans. It has been adapted for growth in tissue culture cells and is particularly useful for studying pathogenesis, as it is pathogenic in BALB/c mice.

When synthesizing segments that are alternatively spliced (NS and M), care is taken not to destroy splice sites and the alternative reading frames. In all cases the terminal 120 nt at either end of each segment are excluded, as these sequences are known to contain signals for RNA replication and virus assembly. At least two versions of each fragment are synthesized (moderate and maximal deoptimization). Viruses in which only one segment is modified are generated, the effect is assessed, and more modified segments are introduced as needed. This is easy in this system, since each segment is on a separate plasmid.

Virus infectivity is titered by plaque assay on MDCK cells in the presence of 1 ug/ml (TPCK)-trypsin. Alternatively, depending on the number of different virus constructs, a 96-well ELISA is used to determine the titer of various viruses as cell infectious units on MDCK cells essentially as described above for PV. See Example 3. The only difference is that now a HA-specific antibody is used to stain infected cells. In addition, the relative concentration of virions are determined via hemagglutination (HA) assay using chicken red blood cells (RBC) (Charles River Laboratories) using standard protocols (Kendal et al., 1982). Briefly, virus suspensions are 2-fold serially diluted in PBS in a V-bottom 96 well plates. PBS alone is used as an assay control. A standardized amount of RBCs is added to each well, and the plates are briefly agitated and incubated at room temperature for 30 minutes. HA titers are read as the reciprocal dilution of virus in the last well with complete hemagglutination. While HA-titer is a direct corollary of the amount of particles present, PFU-titer is a functional measure of infectivity. By determining both measures, a relative PFU/HA-unit ratio is calculated similar to the PFU/particle ratio described in the PV experiments. See Example 3. This addresses the question whether codon- and codon pair-deoptimized influenza viruses also display a lower PFU/particle as observed for PV.

Virulence Test

The lethal dose 50 ($LD_{50}$) of the parental NPR/8/34 virus is first determined for mice and synthetic influenza viruses are chosen for infection of BALB/c mice by intranasal infection. Methods for determining $LD_{50}$ values are well known to persons of ordinary skill in the art (see Reed and Muench, 1938, and Example 4). The ideal candidate viruses display a low infectivity (low PFU titer) with a high virion concentration (high HA-titer). Anesthetized mice are administered 25 μl of virus solution in PBS to each nostril containing 10-fold serial dilutions between $10^2$ to $10^7$ PFU of virus. Mortality and morbidity (weight loss, reduced activity) are monitored twice daily for up to three weeks. $LD_{50}$ is calculated by the method of Reed and Muench (1938). For the A/PR/8/34 wt virus the expected $LD_{50}$ is around $10^3$ PFU (Talon et al., 2000), but may vary depending on the particular laboratory conditions under which the virus is titered.

Adaptation of SAVE to Dengue, HIV, Rotavirus, and SARS

Several viruses were selected to further test the SAVE approach. Table 8 identifies the coding regions of each of Dengue, HIV, Rotavirus (two segments), and SARS, and provides nucleotide sequences for parent viruses and exemplary viral genome sequences having deoptimized codon pair bias. As described above, codon pair bias is determined for a coding sequence, even though only a portion (subsequence) may contain the deoptimizing mutations.

TABLE 8

Nucleotide sequence and codon pair bias of parent and codon pair bias-reduced coding regions

| | Parent sequence | | | Codon pair bias-reduced sequence | | |
|---|---|---|---|---|---|---|
| Virus | SEQ ID NO: | CDS | CPB | SEQ ID NO: | deoptimized segment* | CPB* |
| Flu PB1 | 13 | 25-2298 | 0.0415 | 14 | 531-2143 | −0.2582 |
| Flu PB1-RR | " | " | " | 15 | 531-1488 | −0.1266 |
| Flu PB2 | 16 | 28-2307 | 0.0054 | 17 | 33-2301 | −0.3718 |
| Flu PA | 18 | 25-2175 | 0.0247 | 19 | 30-2171 | −0.3814 |
| Flu HA | 20 | 33-1730 | 0.0184 | 21 | 180-1655 | −0.3627 |
| Flu NP | 22 | 46-1542 | 0.0069 | 23 | 126-1425 | −0.3737 |
| Flu NA | 24 | 21-1385 | 0.0037 | 25 | 123-1292 | −0.3686 |
| Flu M | 26 | | 0.0024 | | | |
| Flu NS | 27 | 27-719 | −0.0036 | 28 | 128-479 | −0.1864 |
| Rhinovirus 89 | 29 | 619-7113 | 0.051 | 30 | | −0.367 |
| Rhinovirus 14 | 31 | 629-7168 | 0.046 | 32 | | −0.418 |
| Dengue | 33 | 95-10273 | 0.0314 | 34 | | −0.4835 |
| HIV | 35 | 336-1634<br>1841-4585<br>4644-5102<br>5858-7924<br>8343-8963 | 0.0656 | 36 | | −0.3544 |
| Rotavirus Seg. 1 | 37 | 12-3284 | 0.0430 | 38 | | −0.2064 |
| Rotavirus Seg. 2 | 39 | 37-2691 | 0.0375 | 40 | | −0.2208 |
| SARS | 41 | 265-13398<br>13416-21485<br>21492-25259<br>26398-27063 | 0.0286 | 42 | | −0.4393 |

*CPB can be reduced by deoptimizing an internal segment smaller than the complete coding sequence. Nevertheless, CPB is calculated for the complete CDS.

Example 16

Assessment of Poliovirus and Influenza Virus Vaccine Candidates in Mice

The ability of deoptimized viruses to vaccinate mice against polio or influenza is tested.

Poliovirus Immunizations, Antibody Titers, and Wt Challenge Experiments

The working hypothesis is that a good vaccine candidate combines a low infectivity titer with a high virion titer. This ensures that a high amount of virus particles (i.e., antigen) can be injected while at the same time having a low risk profile. Thus, groups of five CD155tg mice will be injected intraperitoneally with $10^3$, $10^4$, $10^5$, and $10^6$ PFU of PV(Mahoney) (i.e., wild-type), PV1 Sabin vaccine strain, $PV^{AB2470-2954}$, $PV\text{-}Min^{755-2470}$ or other promising attenuated polioviruses developed during this study. For the wild-type, 1 PFU is about 100 viral particles, while for the attenuated viruses, 1 PFU is roughly 5,000 to 100,000 particles. Thus, injection with equal number of PFUs means that 50 to 1000-fold more particles of attenuated virus are being injected. For wt virus injected intraperitoneally, the $LD_{50}$ is about $10^6$ PFU, or about $10^8$ particles. Accordingly, some killing is expected with the highest doses but not with the lower doses.

Booster shots of the same dose are given one week after and four weeks after the initial inoculation. One week following the second booster, PV-neutralizing antibody titers are determined by plaque reduction assay. For this purpose, 100 PFU of wt PV(M) virus are incubated with 2-fold serial dilutions of sera from immunized mice. The residual number of PFU is determined by plaque assays. The neutralizing antibody titer is expressed as the reciprocal of the lowest serum dilution at which no plaques are observed.

Four weeks after the last booster, immunized mice and non-immunized controls are challenged with a lethal dose of PV(M) wt virus ($10^6$ PFU intraperitoneally; this equals 100 times $LD_{50}$, and survival is monitored.

Influenza Immunizations, Antibody Titers, and Wt Challenge Experiments

For vaccination experiments, groups of 5 BALB/c mice are injected with wt and attenuated influenza viruses intraperitoneally at a dose of 0.001, 0.01, 0.1, and 1.0 $LD_{50}$. Booster vaccinations are given at the same intervals described above for PV. Influenza antibody titers one week after the second booster are determined by an inhibition of hemagglutination (HI) assay following standard protocols (Kendal et al., 1982). Briefly, sera from immunized and control mice treated with receptor destroying enzyme (RDE; Sigma, St Louis, Mo.) are 2-fold serially diluted and mixed with 5 HA-units of A/PR/8/34 virus in V-bottom 96 wells. RBCs are then added and plates are processed as above for the standard HA-assay. Antibody titers are expressed as the reciprocal dilution that results in complete inhibition of hemagglutination.

Three weeks after the last booster vaccination, mice are challenged infra-nasally with 100 or 1000 $LD_{50}$ of A/PR/8/34 parental virus (approximately $10^5$ and $10^6$ PFU), and survival is monitored.

Animal Handling

Transgenic mice expressing the human poliovirus receptor CD155 (CD155tg) were obtained from Dr. Nomoto, The Tokyo University. The CD155tg mouse colony is maintained by the State University of New York (SUNY) animal facility. BALB/c mice are obtained from Taconic (Germantown, N.Y.). Anesthetized mice are inoculated using 25-gauge hypodermic needles with 30 μl of viral suspension by intravenous, intraperitoneal or intracerebral route or 50 ul by the intranasal route. Mice of both sexes between 6-24 weeks of age are used. Mice are the most economical model system for poliovirus and influenza virus research. In addition, in the case of PV, the CD155tg mouse line is the only animal model except for non-human primates. Mice also provide the safest animal model since no virus spread occurs between animals for both poliovirus and influenza virus.

All mice are housed in SUNY's state of the art animal facility under the auspices of the Department of Laboratory Animal Research (DLAR) and its veterinary staff. All animals are checked twice weekly by the veterinary staff. Virus-infected animals are checked twice daily by the investigators and daily by the veterinary staff. All infection experiments are carried out in specially designated maximum isolation rooms within the animal facility. After conclusion of an experiment, surviving mice are euthanized and cadavers are sterilized by autoclaving. No mouse leaves the virus room alive.

In the present study, mice are not subjected to any surgical procedure besides intravenous, intracerebral, intraperitoneal, intramuscular or intranasal inoculation, the injection of anesthetics, and the collection of blood samples. For vaccination experiments, blood samples are taken prior and after vaccination for detection of virus-specific antibodies. To this end, 50-100 μl are collected from mice the day before injection and one week following the second booster vaccination. A maximum of two blood samples on individual animals are collected at least four weeks apart. Animals are anesthetized and a sharp scalpel is used to cut off 2 mm of tail. Blood is collected with a capillary tube. Subsequent sampling is obtained by removing scab on the tail. If the tail is healed, a new 2-mm snip of tail is repeated.

All animal experiments are carried out following protocols approved by the SUNY Institutional Animal Care and Use Committee (IACUC). Euthanasia is performed by trained personnel in a $CO_2$ gas chamber according to the recommendation of the American Veterinary Medical Association. Infection experiments are conducted under the latest the ABSL 2/polio recommendations issued by the Centers for Disease Control and Prevention (CDC).

Example 17

Codon Pair Bias Algorithm—Codon Pair Bias and Score Matrix

In most organisms, there exists a distinct codon bias, which describes the preferences of amino acids being encoded by particular codons more often than others. It is widely believed that codon bias is connected to protein translation rates. In addition, each species has specific preferences as to whether a given pair of codons appear as neighbors in gene sequences, something that is called codon-pair bias.

To quantify codon pair bias, we define a codon pair distance as the log ratio of the observed over the expected number of occurrences (frequency) of codon pairs in the genes of an organism. Although the calculation of the observed frequency of codon pairs in a set of genes is straightforward, the expected frequency of a codon pair is calculated as in Gutman and Hatfield, Proc. Natl. Acad. Sci. USA, 86:3699-3703, 1989, and is independent of amino acid and codon bias. To achieve that, the expected frequency is calculated based on the relative proportion of the number of times an amino acid is encoded by a specific codon. In short:

$$\text{codon pair score} = \log\left(\frac{F(AB)}{\frac{F(A)\times F(B)}{F(X)\times F(Y)}\times F(XY)}\right),$$

where the codon pair AB encodes for amino acid pair XY and F denotes frequency (number of occurrences).

In this scheme we can define a 64×64 codon-pair distance matrix with all the pairwise costs as defined above. Any m-residue protein can be rated as using over-or under-represented codon pairs by the average of the codon pair scores that comprise its encoding.

Optimization of a Gene Encoding Based on Codon Pair Bias

To examine the effects of codon pair bias on the translation of specific proteins, we decided to change the codon pairs while keeping the same codon distribution. So we define the following problem: Given an amino acid sequence and a set of codon frequencies (codon distribution), change the DNA encoding of the sequence such that the codon pair score is optimized (usually minimized or maximized).

Our problem, as defined above, can be associated with the Traveling Salesman Problem (TSP). The traveling salesman problem is the most notorious NP-complete problem. This is a function of its general usefulness, and because it is easy to explain to the public at large. Imagine a traveling salesman who has to visit each of a given set of cities by car. What is the shortest route that will enable him to do so and return home, thus minimizing his total driving?

TSP Heuristics

Almost any flavor of TSP is going to be NP-complete, so the right way to proceed is with heuristics. These are often quite successful, typically coming within a few percent of the optimal solution, which is close enough for most applications and in particular for our optimized encoding.

Minimum spanning trees—A simple and popular heuristic, especially when the sites represent points in the plane, is based on the minimum spanning tree of the points. By doing a depth-first search of this tree, we walk over each edge of the tree exactly twice, once going down when we discover the new vertex and once going up when we backtrack. We can then define a tour of the vertices according to the order in which they were discovered and use the shortest path between each neighboring pair of vertices in this order to connect them. This path must be a single edge if the graph is complete and obeys the triangle inequality, as with points in the plane. The resulting tour is always at most twice the length of the minimum TSP tour. In practice, it is usually better, typically 15% to 20% over optimal. Further, the time of the algorithm is bounded by that of computing the minimum spanning tree, only O(n lg n) in the case of points in the plane.

Incremental insertion methods—A different class of heuristics inserts new points into a partial tour one at a time (starting from a single vertex) until the tour is complete. The version of this heuristic that seems to work best is furthest point insertion: of all remaining points, insert the point v into partial tour T such that $$\max_{v \in V} \min_{i=1}^{|T|} (d(v, v_i) + d(v, v_{i+1})).$$

The minimum ensures that we insert the vertex in the position that adds the smallest amount of distance to the tour, while the maximum ensures that we pick the worst such vertex first. This seems to work well because it first "roughs out" a partial tour before filling in details. Typically, such tours are only 5% to 10% longer than optimal.

k-optimal tours—Substantially more powerful are the Kernighan-Lin, or k-opt class of heuristics. Starting from an arbitrary tour, the method applies local refinements to the tour in the hopes of improving it. In particular, subsets of $k \geq 2$ edges are deleted from the tour and the k remaining subchains rewired in a different way to see if the resulting tour is an improvement. A tour is k-optimal when no subset of k edges can be deleted and rewired so as to reduce the cost of the tour. Extensive experiments suggest that 3 optimal tours are usually within a few percent of the cost of optimal tours. For $k>3$, the computation time increases considerably faster than solution quality. Two-opting a tour is a fast and effective way to improve any other heuristic. Simulated annealing provides an alternate mechanism to employ edge flips to improve heuristic tours.

Algorithm for Solving the Optimum Encoding Problem

Our problem as defined is associated with the problem of finding a traveling salesman path (not tour) under a 64-country metric. In this formulation, each of the 64 possible codons is analogous to a country, and the codon multiplicity modeled as the number of cities in the country. The codon-pair bias measure is reflected as the country distance matrix.

The real biological problem of the design of genes encoding specific proteins using a given set of codon multiplicities so as to optimize the gene/DNA sequence under a codon-pair bias measure is slightly different. What is missing in our model in the country TSP model is the need to encode specific protein sequences. The DNA triplet code partitions the 64 codons into 21 equivalence classes (coding for each of the 20 possible amino acids and a stop symbol). Any given protein/amino acid sequence can be specified by picking an arbitrary representative of the associated codon equivalence class to encode it.

Because of the special restrictions and the nature of our problem, as well as its adaptability to application of additional criteria in the optimization, we selected the Simulated annealing heuristic to optimize sequences. The technique is summarized below.

Simulated Annealing Heuristic

Simulated annealing is a heuristic search procedure that allows occasional transitions leading to more expensive (and hence inferior) solutions. This may not sound like a win, but it serves to help keep our search from getting stuck in local optima.

The inspiration for simulated annealing comes from the physical process of cooling molten materials down to the solid state. In thermodynamic theory, the energy state of a system is described by the energy state of each of the particles constituting it. The energy state of each particle jumps about randomly, with such transitions governed by the temperature of the system. In particular, the probability $P(e_i, e_j, T)$ of transition from energy $e_i$ to $e_j$ at temperature T is given by:

$$P(e_i,e_j,T)=e^{(e_i-e_j)/k_BT})$$

where kB is a constant, called Boltzmann's constant. What does this formula mean? Consider the value of the exponent under different conditions. The probability of moving from a high-energy state to a lower-energy state is very high. However, there is also a nonzero probability of accepting a transition into a high-energy state, with small energy jumps much more likely than big ones. The higher the temperature, the more likely such energy jumps will occur.

What relevance does this have for combinatorial optimization? A physical system, as it cools, seeks to go to a minimum-energy state. For any discrete set of particles, minimizing the total energy is a combinatorial optimization problem. Through random transitions generated according to the above probability distribution, we can simulate the physics to solve arbitrary combinatorial optimization problems.

As with local search, the problem representation includes both a representation of the solution space and an appropriate and easily computable cost function C(s) measuring the quality of a given solution. The new component is the cooling schedule, whose parameters govern how likely we are to accept a bad transition as a function of time.

At the beginning of the search, we are eager to use randomness to explore the search space widely, so the probability of accepting a negative transition should be high. As the search progresses, we seek to limit transitions to local improvements and optimizations. The cooling schedule can be regulated by the following parameters:

Initial system temperature—Typically $t_1=1$.

Temperature decrement function—Typically $t_k=\alpha \cdot tk-1$, where $0.8 \leq \alpha \leq 0.99$. This implies an exponential decay in the temperature, as opposed to a linear decay.

Number of iterations between temperature change—Typically, 100 to 1,000 iterations might be permitted before lowering the temperature.

Acceptance criteria—A typical criterion is to accept any transition from $s_i$ to $s_i+1$ when $C(s_i+1)<C(s_i)$ and to accept a negative transition whenever $$e^{-\frac{(C(s_i)-C(s_i+1))}{c \cdot t_i}} \geq r,$$

where r is a random number $0 \leq r<1$. The constant c normalizes this cost function, so that almost all transitions are accepted at the starting temperature.

Stop criteria—Typically, when the value of the current solution has not changed or improved within the last iteration or so, the search is terminated and the current solution reported.

In expert hands, the best problem-specific heuristics for TSP can slightly outperform simulated annealing, but the simulated annealing solution works easily and admirably.

REFERENCES

Alexander, H. E., G. Koch, I. M. Mountain, K. Sprunt, and O. Van Damme. 1958. Infectivity of ribonucleic acid of poliovirus on HeLa cell mono-layers Virology. 5:172-3.

Altmeyer, R., A. D. Murdin, J. J. Harber, and E. Wimmer. 1991. Construction and characterization of poliovirus/rhinovirus antigenic hybrid. Virology. 184:636-44.

Ansardi, D. C., D. C. Porter, and C. D. Morrow. 1993. Complementation of a poliovirus defective genome by a recombinant vaccinia virus which provides poliovirus P1 capsid precursor in trans. J. Virol. 67:3684-3690.

Belov, G. A., L. I. Romanova, E. A. Tolskaya, M. S. Kolesnikova, Y. A. Lazebnik, and V. I. Agol. 2003. The major apoptotic pathway activated and suppressed by poliovirus. J. Virol. 77:45-56.

Buchan, J. R., L. S. Aucott, and I. Stansfield. 2006. tRNA properties help shape codon pair preferences in open reading frames. Nucl. Acids Res. 34:1015-27.

Burns, C. C., J. Shaw, R. Campagnoli, J. Jorba, A. Vincent, J. Quay, and O. Kew. 2006. Modulation of poliovirus replicative fitness in HeLa cells by deoptimization of synonymous codon usage in the capsii region. J. Virol. 80:3259-72.

Cao, X., R. J. Kuhn, and E. Wimmer. 1993. Replication of poliovirus RNA containing two VPg coding sequences leads to a specific deletion event. J. Virol. 67:5572-5578.

Carlini, D. B., and W. Stephan. 2003. In vivo introduction of unpreferred synonymous codons into the *Drosophila* Adh gene results in reduced levels of ADH protein. Genetics 163:239-243.

Cello, J., A. V. Paul, and E. Wimmer. 2002. Chemical synthesis of poliovirus cDNA: generation of infectious virus in the absence of natural template Science. 297: 1016-1018.

Cheng, L., and E. Goldman. 2001. Absence of effect of varying Thr-Leu codon pairs on protein synthesis in a T7 system. Biochemistry. 40:6102-6.

Cohen, B., and S. Skiena. 2003. Natural selection and algorithmic design of mRNA. J. Comput Biol. 10:419-432.

Coligan, J., A. Kruisbeek, D. Margulies, E. Shevach, and W. Strober, eds. (1994) Current Protocols in Immunology, Wiley & Sons, Inc., New York.

Corpet, F. 1988. Multiple sequence alignment with hierarchical clustering. Nucl. Acids Res. 16:10881-90.

Cram, P., S. G. Blitz, A. Monte, and A. M. Fendrick. 2001. Influenza. Cost of illness and consideration in the economic evaluation of new and emerging therapies. Pharmacoeconomics. 19:223-30.

Crotty, S., C. E. Cameron, and R. Andino. 2001. RNA virus error catastrophe: direct molecular test by using ribavirin. Proc. Natl. Acad. Sci. U.S.A. 98:6895-6900.

Curran, J. F., E. S. Poole, W. P. Tate, and B. L. Gross. 1995. Selection of aminoacyl-tRNAs at sense codons: the size of the tRNA variable loop determines whether the immediate 3' nucleotide to the coder has a context effect. Nucl. Acids Res. 23:4104-8.

Doma, M. K., and R. Parker. 2006. Endonucleolytic cleavage of eukaryotic mRNAs with stalls in translation elongation. Nature. 440:561-4.

Dove, A. W., and V. R. Racaniello. 1997. Cold-adapted poliovirus mutants bypass a postentry replication block. J. Virol. 71:4728-4735.

Enami, M., W. Luytjes, M. Krystal, and P. Palese. 1990. Introduction of site-specific mutations into the genome of influenza virus. Proc. Natl. Acad. Sci. U.S.A. 87:3802-5.

Farabaugh, P. J. 1996. Programmed translational frameshifting Microbiol Rev. 60:103-34.

Fedorov, A., S. Saxonov, and W. Gilbert. 2002. Regularities of context-dependent codon bias in eukaryotic genes. Nucl. Acids Res. 30:1192-7.

Fodor, E., L. Devenish, O. G. Engelhardt, P. Palese, G. G. Brownlee, and A. Garcia-Sastre. 1999. Rescue of influenza A virus from recombinant DNA. J Virol. 73:9679-82.

Gabow, H. 1973. Ph.D. thesis. Stanford University, Stanford, Calif.

Garcia-Sastre, A., and P. Palese. 1993. Genetic manipulation of negative-strand RNA virus genomes. Annu. Rev. Microbiol. 47:765-90.

Georgescu, M. M., J. Balanant, A. Macadam, D. Otelea, M. Combiescu, A. A. Combiescu, R. Crainic, and F. Delpeyroux. 1997. Evolution of the Sabin type 1 poliovirus in humans: characterization of strains isolated from patients with vaccine-associated paralytic poliomyelitis. J. Virol. 71:7758-68.

Gerber, K., E. Wimmer, and A. V. Paul. 2001. Biochemical and genetic studies of the initiation of human rhinovirus 2 RNA replication: identification of a cis-replicating element in the coding sequence of 2A(pro). J. Virol. 75:10979-10990.

Girard, S., T. Couderc, J. Destombes, D. Thiesson, F. Delpeyroux, and B. Blondel. 1999. Poliovirus induces apoptosis in the mouse central nervous system. J. Virol. 73:6066-6072.

Goodfellow, I., Y. Chaudhry, A. Richardson, J. Meredith, J. W. Almond, W. Barclay, and D. J. Evans. 2000. Identification of a cis-acting replication element within the poliovirus coding region. J. Virol. 74:4590-600.

Greve, J. M., G. Davis, A. M. Meyer, C. P. Forte, S. C. Yost, C. W. Marlor, M. E. Kamarck, and A. McClelland. 1989. The major human rhinovirus receptor is ICAM-1. Cell. 56:839-47.

Gustafsson, C., S. Govindarajan, and J. Minshull. 2004. Codon bias and heterologous protein expression. Trends Biotechnol. 22:346-353.

Gutman, G. A., and G. W. Hatfield. 1989. Nonrandom utilization of codon pairs in *Escherichia coli*. Proc. Natl. Acad. Sci. U.S.A 86:3699-703.

He, Y., V. D. Bowman, S. Mueller, C. M. Bator, J. Bella, X. Peng, T. S. Baker, E. Wimmer, R. J. Kuhn, and M. G. Rossmann. 2000. Interaction of the poliovirus receptor with poliovirus. Proc. Natl. Acad. Sci. USA 97:79-84.

Hendley, J. O. 1999. Clinical virology of rhinoviruses Adv Virus Res. 54:453-66.
Herold, J., and R. Andino. 2000. Poliovirus requires a precise 5' end for efficient positive-strand RNA synthesis. J. Virol. 74:6394-400.
Hoekema, A., R. A. Kastelein, M. Vasser, and H. A. de Boer. 1987. Codon replacement in the PGK1 gene of *Saccharomyces cerevisiae*: experimental approach to study the role of biased codon usage in gene expression. Mol. Cell. Biol. 7:2914-2924.
Hofer, F., M. Gruenberger, H. Kowalski, H. Machat, M. Huettinger, E. Kuechler, and D. Blaas. 1994 Members of the low density lipoprotein receptor family mediate cell entry of a minor-group common cold virus. Proc. Natl. Acad. Sci. U.S.A. 91:1839-42.
Hoffmann, E., G. Neumann, Y. Kawaoka, G. Hobom, and R. G. Webster. 2000. A DNA transfection system for generation of influenza: A virus from eight plasmids. Proc. Natl. Acad. Sci. U.S.A. 97:6108-13.
Hogle, J. M. 2002. Poliovirus cell entry: common structural themes in viral cell entry pathways. Annu. Rev. Microbiol. 56:677-702.
Holland, J. J., E. Domingo, J. C. de la Torre, and D. A. Steinhauer. 1990. Mutation frequencies at defined single codon sites in vesicular stomatitis virus and poliovirus can be increased only slightly by chemical mutagenesis. J. Virol. 64:3960-3962.
Hsiao, L. L., F. Dangond, T. Yoshida, R. Hong, R. V. Jensen et al. 2001. A compendium of gene expression in normal human tissues. Physiol. Genomics 7:97-104.
Irwin, B., J. D. Heck, and G. W. Hatfield. 1995. Codon pair utilization biases influence translational elongation step times. J. Biol Chem. 270:22801-6.
Jang, S. K., M. V. Davies, R. J. Kaufman, and E. Wimmer. 1989. Initiation of protein synthesis by internal entry of ribosomes into the 5' nontranslated region of encephalomyocarditis virus RNA in vitro. J. Virol. 63:1651-1660.
Jayaraj, S., R. Reid, and D. V. Santi. 2005. GeMS: an advanced software package for designing synthetic genes. Nucl. Acids Res. 33:3011-3016.
Johansen, L. K., and C. D. Morrow. 2000. The RNA encompassing the internal ribosome entry site in the poliovirus 5' nontranslated region enhances the encapsidation of genomic RNA. Virology 273:391-399.
Joklik, W., and J. Darnell. 1961. The adsorption and early fate of purified poliovirus in HeLa cells. Virology 13:439-447.
Kamps, B. S., C. Hoffmann, and W. Preiser (eds.) 2006. Influenza Report, 2006. Flying Publisher.
Kaplan, G., and V. R. Racaniello. 1988. Construction and characterization of poliovirus subgenomic replicons. J. Virol. 62:1687-96.
Karlin, S., W. Doerfler, and L. R. Cardon. 1994. Why is CpG suppressed in the genomes of virtually al small eukaryotic viruses but not in those of large eukaryotic viruses? J Virol. 68:2889-97.
Kendal, A. P., J. J. Skehel, and M. S. Pereira (eds.) 1982 Concepts and procedures for laboratory-based influenza surveillance. World Health Organization Collaborating Centers for Reference and Research on Influenza, Geneva.
Kew, O., V. Morris-Glasgow, M. Landaverde, C. Burns, J. Shaw, Z. Garib, J. Andre, E. Blackman, C. J. Freeman, J. Jorba, R. Sutter, G. Tambini, L. Venczel, C. Pedreira, F. Laender, H. Shimizu, T. Yoneyama, T. Miyamura, H. van Der Avoort, M. S. Oberste, D. Kilpatrick, S. Cochi, M. Pallansch, and C. de Quadros. 2002. Outbreak of poliomyelitis in Hispaniola associated with circulating type 1 vaccine-derived poliovirus. Science. 296:356-9.
Kilbourne, E. D. 2006. Influenza pandemics of the 20th century. Emerg. Infect. Dis. 12:9-14.
Kitamura, N., B. L. Semler, P. G. Rothberg, G. R. Larsen, C. J. Adler, A. J. Dorner, E. A. Emini, R. Hanecak, J. Lee, S. van der Well, C. W. Anderson, and E. Wimmer. 1981. Primary structure, gene organization and polypeptide expression of poliovirus RNA. Nature. 291:547-553.
Koike, S., C. Taya, T. Kurata, S. Abe, I. Ise, H. Yonekawa, and A. Nomoto. 1991. Transgenic mice susceptible to poliovirus. Proc. Natl. Acad. Sci. U.S.A. 88:951-955.
Landsteiner, K. and E. Popper. 1909. Ubertragung der Poliomyelitis acuta auf Affen. Z. ImmunnitatsForsch Orig. 2:377-90.
Lavner, Y., and D. Kotlar. 2005. Codon bias as a factor in regulating expression via translation rate in the human genome. Gene. 345:127-38.
Ledford, R. M., N. R. Patel, T. M. Demenczuk, A. Watanyar, T. Herbertz, M. S. Collett, and D. C. Pevear. 2004. VP1 sequencing of all human rhinovirus serotypes: insights into genus phylogeny and susceptibility to antiviral capsid-binding compounds. J. Virol. 78:3663-74.
Luytjes, W., M. Krystal, M. Enami, J. D. Pavin, and P. Palese. 1989. Amplification, expression, and packaging of foreign gene by influenza virus. Cell. 59:1107-13.
McKnight, K. L. 2003. The human rhinovirus internal cis-acting replication element (cre) exhibits disparate properties among serotypes. Arch. Virol. 148:2397-418.
Molla, A., A. V. Paul, and E. Wimmer. 1991. Cell-free, de novo synthesis of poliovirus. Science 254:1647-1651.
Mueller, S., D. Papamichail, J. R. Coleman, S. Skiena, and E. Wimmer. 2006. Reduction of the Rate of Poliovirus Protein Synthesis through Large-Scale Codon Deoptimization Causes Attenuation of Viral Virulence by lowering specific infectivity. J. Virol. 80:9687-9696.
Mueller, S., E. Wimmer, and J. Cello. 2005. Poliovirus and poliomyelitis: a tale of guts, brains, and an accidental event. Virus Res. 111:175-193.
Murdin, A. D., and E. Wimmer. 1989. Construction of a poliovirus type 1/type 2 antigenic hybrid by manipulation of neutralization antigenic site II. J. Virol. 63:5251-5257.
Neumann, G., T. Watanabe, H. Ito, S. Watanabe, H. Goto, P. Gao, M. Hughes, D. R. Perez, R. Donis E. Hoffmann, G. Hobom, and Y. Kawaoka. 1999. Generation of influenza A viruses entirely from clone cDNAs. Proc. Natl. Acad. Sci. U.S.A. 96:9345-50.
Neznanov, N., K. M. Chumakov, L. Neznanova, A. Almasan, A. K. Banerjee, and A. V. Gudkov. 2005. Proteolytic cleavage of the p65-RelA subunit of NF-kappaB during poliovirus infection. J. Biol. Chem. 280: 24153-24158.
Palese, P., and M. L. Shaw. 2007. Orthomyxoviridae: the viruses and their replication, p. 1647-1689. In D. M. Knipe and P. M. Howley (ed.), Fields virology. Lippincott Williams & Wilkins, Philadelphia, Pa.
Park, S., X. Yang, and J. G. Saven. 2004. Advances in computational protein design. Curr Opin Struct Biol 14:487-94.
Paul, A. V., J. A. Mugavero, A. Molla, and E. Wimmer. 1998. Internal ribosomal entry site scanning of the poliovirus polyprotein: implications for proteolytic processing. Virology 250:241-253.
Pelletier, J., and N. Sonenberg. 1988. Internal initiation of translation of eukaryotic mRNA directed by; sequence derived from poliovirus RNA. Nature. 334:320-325.

Pfister, T., and E. Wimmer. 1999. Characterization of the nucleoside triphosphatase activity of poliovirus protein 2C reveals a mechanism by which guanidine inhibits poliovirus replication. J. Biol. Chem. 274:6992-7001.

Plotkin, J. B., H. Robins, and A. J. Levine. 2004. Tissue-specific codon usage and the expression of human genes. Proc. Natl. Acad. Sci. U.S.A. 101:12588-12591.

Racaniello, V. R., and D. Baltimore. 1981. Cloned poliovirus complementary DNA is infectious in mammalian cells. Science. 214:916-9.

Reed, L. J., and M. Muench. 1938. A simple method for estimating fifty percent endpoints. Am. J. Hyg. 27:493-497.

Richardson, S. M., S. J. Wheelan, R. M. Yarrington, and J. D. Boeke. 2006. GeneDesign: rapid, automated design of multikilobase synthetic genes. Genome Res. 16:550-556.

Robinson, M., R. Lilley, S. Little, J. S. Emtage, G. Yarronton, P. Stephens, A. Millican, M. Eaton, and G. Humphreys. 1984. Codon usage can affect efficiency of translation of genes in *Escherichia coli*. Nucl. Acids Res. 12:6663-6671.

Rothberg, E. 1985. wmatch: a C program to solve maximum-weight matching. [Online.]

Rueckert, R. R. 1985. Picornaviruses and their replication, p. 705-738. In B. N. Fields, D. M. Knipe, R. M. Chanock, J. L. Melnick, B. Roizman, and R. E. Shope (ed.), Fields virology, vol. 1: Raven Press, New York, N.Y.

Russell, C. J., and R. G. Webster. 2005. The genesis of a pandemic influenza virus. Cell. 123:368-371.

Sambrook, J., E. F. Fritsch, and T. Maniatis. (1989) Molecular Cloning: A Laboratory Manual, $2^{nd}$ ed., Cold Spring Harbor Laboratory Press, Cold Spring Harbor, N.Y.

Sánchez, G., A. Bosch, and R. M. Pinto. 2003. Genome variability and capsid structural constraints of hepatitis A virus. J. Virol. 77:452-459.

Savolainen, C., S. Blomqvist, and T. Novi. 2003. Human rhinoviruses. Paediatr. Respir. Rev. 4:91-98.

Schwerdt, C., and J. Fogh. 1957. The ratio of physical particles per infectious unit observed for poliomyelitis viruses. Virology 4:41-52.

Shimizu, H., B. Thorley, F. J. Paladin, K. A. Brussen, and V. Stambos et al. 2004. Circulation of type 1 vaccine-derived poliovirus in the Philippines in 2001. J. Virol. 78:13512-13521.

Simonsen, L., T. A. Reichert, C. Viboud, W. C. Blackwelder, R. J. Taylor, and M. A. Miller. 2005. Impact of influenza vaccination on seasonal mortality in the US elderly population. Arch. Intern. Med. 165:265-272.

Skiena, S. S. 2001. Designing better phages Bioinformatics. 17 Suppl 1:5253-61.

Steinhauer, D. A., and J. J. Skehel. 2002. Genetics of influenza viruses. Annu. Rev. Genet. 36:305-332.

Stephenson, I., and J. Democratis. 2006. Influenza: current threat from avian influenza. Br. Med. Bull. 75-76:63-80.

Svitkin, Y. V., G. A. Alpatova, G. A. Lipskaya, S. V. Maslova, V. I. Agol, O. Kew, K. Meerovitch, and N. Sonenberg. 1993. Towards development of an in vitro translation test for poliovirus neurovirulence. Dev. Biol. Stand. 78:27-32.

Svitkin, Y. V., S. V. Maslova, and V. I. Agol. 1985. The genomes of attenuated and virulent poliovirus strains differ in their in vitro translation efficiencies. Virology 147:243-252.

Talon, J., M. Salvatore, R. E. O'Neill, Y. Nakaya, H. Zheng, T. Muster, A. Garcia-Sastre, and P. Palese. 2000. Influenza A and B viruses expressing altered NS1 proteins: A vaccine approach. Proc. Natl. Acad. Sci. U.S.A. 97:4309-4314.

Thompson, W. W., D. K. Shay, E. Weintraub, L. Brammer, N. Cox, L. J. Anderson, and K. Fukuda. 2003. Mortality associated with influenza and respiratory syncytial virus in the United States. JAMA. 289:179-186.

Tian, J., H. Gong, N. Shang, X. Zhou, E. Gulari, X. Gao, and G. Church. 2004. Accurate multiplex gene synthesis from programmable DNA microchips. Nature. 432:1050-1054.

Tolskaya, E. A., L. I. Romanova, M. S. Kolesnikova, T. A. Ivannikova, E. A. Smirnova, N. T. Raikhlin, and V. I. Agol. 1995. Apoptosis-inducing and apoptosis-preventing functions of poliovirus. J. Virol. 69:1181-1189.

Toyoda, H., J. Yin, S. Mueller, E. Wimmer, and J. Cello. 2007. Oncolytic treatment and cure of neuroblastoma by a novel attenuated poliovirus in a novel poliovirus-susceptible animal model. Cancer Res. 67:2857-64.

van der Wert, S., J. Bradley, E. Wimmer, F. W. Studier, and J. J. Dunn. 1986. Synthesis of infectious poliovirus RNA by purified T7 RNA polymerase. Proc. Natl. Acad. Sci. U.S.A. 78:2330-2334.

Wahby, A. F. 2000. Combined cell culture enzyme-linked immunosorbent assay for quantification of poliovirus neutralization-relevant antibodies. Clin. Diagn. Lab. Immunol. 7:915-9.

Wang, B., D. Papamichail, S. Mueller, and S. Skiena. 2006. Two Proteins for the Price of One: The Design of Maximally Compressed Coding Sequences Natural Computing. Eleventh International Meeting on DNA Based Computers (DNA11), 2005. Lecture Notes in Computer Science (LNCS), 3892:387-398.

Zhao, W. D., and E. Wimmer. 2001. Genetic analysis of a poliovirus/hepatitis C virus chimera: new structure for domain II of the internal ribosomal entry site of hepatitis C virus. J. Virol. 75:3719-3730.

Zhou, J., W. J. Liu, S. W. Peng, X. Y. Sun, and I. Frazer. 1999. Papillomavirus capsid protein expression level depends on the match between codon usage and tRNA availability. J. Virol. 73:4972-4982.

Zolotukhin, S., M. Potter, W. W. Hauswirth, J. Guy, and N. Muzyczka. 1996. A "humanized" green fluorescent protein cDNA adapted for high-level expression in mammalian cells. J. Virol. 70:4646-4654.

| AA pair | Codon pair | Expected | Observed | Observed/ Expected | CPS |
|---|---|---|---|---|---|
| AA | GCGGCG | 630.04 | 2870 | 4.555 | 1.516 |
| AA | GCGGCC | 2330.20 | 4032 | 1.730 | 0.548 |
| AA | GCTGCT | 3727.41 | 5562 | 1.492 | 0.400 |
| AA | GCAGCA | 2856.40 | 4196 | 1.469 | 0.385 |
| AA | GCAGCT | 3262.97 | 4711 | 1.444 | 0.367 |
| AA | GCTGCA | 3262.97 | 4357 | 1.335 | 0.289 |
| AA | GCTGCC | 5667.77 | 7014 | 1.238 | 0.213 |
| AA | GCAGCC | 4961.56 | 6033 | 1.216 | 0.196 |
| AA | GCAGCG | 1341.51 | 1420 | 1.059 | 0.057 |
| AA | GCTGCG | 1532.46 | 1533 | 1.000 | 0.000 |
| AA | GCGGCT | 1532.46 | 1472 | 0.961 | −0.040 |
| AA | GCCGCG | 2330.20 | 2042 | 0.876 | −0.132 |
| AA | GCGGCA | 1341.51 | 1142 | 0.851 | −0.161 |
| AA | GCCGCC | 8618.21 | 5141 | 0.597 | −0.517 |
| AA | GCCGCT | 5667.77 | 1378 | 0.243 | −1.414 |
| AA | GCCGCA | 4961.56 | 1122 | 0.226 | −1.487 |
| AC | GCCTGC | 2333.61 | 3975 | 1.703 | 0.533 |
| AC | GCCTGT | 1965.56 | 2436 | 1.239 | 0.215 |
| AC | GCGTGC | 630.96 | 560 | 0.888 | −0.119 |
| AC | GCTTGT | 1292.65 | 1142 | 0.883 | −0.124 |
| AC | GCATGT | 1131.59 | 881 | 0.779 | −0.250 |
| AC | GCGTGT | 531.45 | 322 | 0.606 | −0.501 |

-continued

| AA pair | Codon pair | Expected | Observed | Observed/ Expected | CPS |
|---|---|---|---|---|---|
| AC | GCTTGC | 1534.70 | 894 | 0.583 | −0.540 |
| AC | GCATGC | 1343.47 | 554 | 0.412 | −0.886 |
| AD | GCAGAT | 2373.33 | 4215 | 1.776 | 0.574 |
| AD | GCTGAT | 2711.15 | 3887 | 1.434 | 0.360 |
| AD | GCTGAC | 3062.55 | 4374 | 1.428 | 0.356 |
| AD | GCGGAC | 1259.11 | 1625 | 1.291 | 0.255 |
| AD | GCAGAC | 2680.95 | 3395 | 1.266 | 0.236 |
| AD | GCGGAT | 1114.64 | 839 | 0.753 | −0.284 |
| AD | GCCGAC | 4656.80 | 2726 | 0.585 | −0.535 |
| AD | GCCGAT | 4122.47 | 920 | 0.223 | −1.500 |
| AE | GCAGAA | 3517.48 | 5814 | 1.653 | 0.503 |
| AE | GCAGAG | 4703.98 | 7094 | 1.508 | 0.411 |
| AE | GCGGAG | 2209.23 | 3171 | 1.435 | 0.361 |
| AE | GCTGAG | 5373.53 | 7362 | 1.370 | 0.315 |
| AE | GCTGAA | 4018.14 | 5186 | 1.291 | 0.255 |
| AE | GCCGAG | 8170.80 | 5082 | 0.622 | −0.475 |
| AE | GCGGAA | 1651.99 | 949 | 0.574 | −0.554 |
| AE | GCCGAA | 6109.85 | 1097 | 0.180 | −1.717 |
| AF | GCCTTC | 4447.90 | 7382 | 1.660 | 0.507 |
| AF | GCATTT | 2237.22 | 2332 | 1.042 | 0.041 |
| AF | GCTTTT | 2555.66 | 2580 | 1.010 | 0.009 |
| AF | GCCTTT | 3886.04 | 3842 | 0.989 | −0.011 |
| AF | GCTTTC | 2925.16 | 2315 | 0.791 | −0.234 |
| AF | GCGTTC | 1202.63 | 636 | 0.529 | −0.637 |
| AF | GCGTTT | 1050.71 | 518 | 0.493 | −0.707 |
| AF | GCATTC | 2560.68 | 1261 | 0.492 | −0.708 |
| AG | GCGGGC | 1369.64 | 2638 | 1.926 | 0.655 |
| AG | GCGGGG | 986.17 | 1738 | 1.762 | 0.567 |
| AG | GCTGGG | 2398.67 | 3855 | 1.607 | 0.474 |
| AG | GCTGGT | 1590.73 | 2524 | 1.587 | 0.462 |
| AG | GCTGGA | 2457.02 | 3783 | 1.540 | 0.432 |
| AG | GCAGGA | 2150.87 | 3074 | 1.429 | 0.357 |
| AG | GCAGGG | 2099.79 | 2782 | 1.325 | 0.281 |
| AG | GCAGGT | 1392.52 | 1748 | 1.255 | 0.227 |
| AG | GCTGGC | 3331.38 | 3961 | 1.189 | 0.173 |
| AG | GCAGGC | 2916.28 | 3119 | 1.070 | 0.067 |
| AG | GCGGGT | 654.00 | 617 | 0.943 | −0.058 |
| AG | GCGGGA | 1010.16 | 793 | 0.785 | −0.242 |
| AG | GCCGGG | 3647.33 | 2240 | 0.614 | −0.488 |
| AG | GCCGGC | 5065.58 | 2977 | 0.588 | −0.532 |
| AG | GCCGGT | 2418.80 | 581 | 0.240 | −1.426 |
| AG | GCCGGA | 3736.06 | 795 | 0.213 | −1.547 |
| AH | GCGCAC | 748.29 | 983 | 1.314 | 0.273 |
| AH | GCCCAC | 2767.53 | 3465 | 1.252 | 0.225 |
| AH | GCTCAT | 1319.86 | 1471 | 1.115 | 0.108 |
| AH | GCACAT | 1155.40 | 1122 | 0.971 | −0.029 |
| AH | GCCCAT | 2006.93 | 1827 | 0.910 | −0.094 |
| AH | GCTCAC | 1820.07 | 1526 | 0.838 | −0.176 |
| AH | GCACAC | 1593.29 | 1312 | 0.823 | −0.194 |
| AH | GCGCAT | 542.64 | 248 | 0.457 | −0.783 |
| AI | GCCATC | 3894.51 | 7798 | 2.002 | 0.694 |
| AI | GCCATT | 3079.73 | 3761 | 1.221 | 0.200 |
| AI | GCAATA | 815.43 | 924 | 1.133 | 0.125 |
| AI | GCAATT | 1773.02 | 1684 | 0.950 | −0.052 |
| AI | GCCATA | 1416.41 | 1257 | 0.887 | −0.119 |
| AI | GCTATT | 2025.39 | 1709 | 0.844 | −0.170 |
| AI | GCTATA | 931.50 | 771 | 0.828 | −0.189 |
| AI | GCTATC | 2561.23 | 1194 | 0.466 | −0.763 |
| AI | GCGATT | 832.70 | 373 | 0.448 | −0.803 |
| AI | GCAATC | 2242.09 | 984 | 0.439 | −0.824 |
| AI | GCGATA | 382.97 | 149 | 0.389 | −0.944 |
| AI | GCGATC | 1053.00 | 404 | 0.384 | −0.958 |
| AK | GCCAAG | 5767.01 | 9818 | 1.702 | 0.532 |
| AK | GCAAAA | 2563.57 | 3011 | 1.175 | 0.161 |
| AK | GCCAAA | 4452.91 | 4794 | 1.077 | 0.074 |
| AK | GCAAAG | 3320.10 | 3044 | 0.917 | −0.087 |
| AK | GCTAAA | 2928.46 | 2022 | 0.690 | −0.370 |
| AK | GCGAAG | 1559.29 | 765 | 0.491 | −0.712 |
| AK | GCTAAG | 3792.68 | 1725 | 0.455 | −0.788 |
| AK | GCGAAA | 1203.98 | 409 | 0.340 | −1.080 |
| AL | GCGCTG | 2369.16 | 4619 | 1.950 | 0.668 |
| AL | GCGCTC | 1140.05 | 1765 | 1.548 | 0.437 |
| AL | GCTTTG | 1873.51 | 2601 | 1.388 | 0.328 |
| AL | GCCCTG | 8762.30 | 11409 | 1.302 | 0.264 |
| AL | GCCTTG | 2848.79 | 3695 | 1.297 | 0.260 |
| AL | GCTTTA | 1115.24 | 1385 | 1.242 | 0.217 |
| AL | GCCCTC | 4216.45 | 4499 | 1.067 | 0.065 |
| AL | GCTCTT | 1912.07 | 2038 | 1.066 | 0.064 |
| AL | GCATTA | 976.28 | 986 | 1.010 | 0.010 |
| AL | GCTCTA | 1031.16 | 940 | 0.912 | −0.093 |
| AL | GCACTT | 1673.82 | 1444 | 0.863 | −0.148 |
| AL | GCATTG | 1640.07 | 1364 | 0.832 | −0.184 |
| AL | GCACTA | 902.68 | 747 | 0.828 | −0.189 |
| AL | GCGCTA | 423.94 | 342 | 0.807 | −0.215 |
| AL | GCCCTA | 1567.95 | 1228 | 0.783 | −0.244 |
| AL | GCTCTG | 5762.53 | 4505 | 0.782 | −0.246 |
| AL | GCCCTT | 2907.42 | 2230 | 0.767 | −0.265 |
| AL | GCTCTC | 2772.95 | 2036 | 0.734 | −0.309 |
| AL | GCCTTA | 1695.80 | 1205 | 0.711 | −0.342 |
| AL | GCACTG | 5044.51 | 3522 | 0.698 | −0.359 |
| AL | GCGTTG | 770.26 | 476 | 0.618 | −0.481 |
| AL | GCGCTT | 786.11 | 459 | 0.584 | −0.538 |
| AL | GCACTC | 2427.43 | 1415 | 0.583 | −0.540 |
| AL | GCGTTA | 458.51 | 169 | 0.369 | −0.998 |
| AM | GCCATG | 4236.47 | 6521 | 1.539 | 0.431 |
| AM | GCAATG | 2438.96 | 1900 | 0.779 | −0.250 |
| AM | GCTATG | 2786.11 | 1561 | 0.560 | −0.579 |
| AM | GCGATG | 1145.46 | 625 | 0.546 | −0.606 |
| AN | GCCAAC | 3190.28 | 5452 | 1.709 | 0.536 |
| AN | GCAAAT | 1667.60 | 2282 | 1.368 | 0.314 |
| AN | GCCAAT | 2896.62 | 3122 | 1.078 | 0.075 |
| AN | GCAAAC | 1836.66 | 1512 | 0.823 | −0.195 |
| AN | GCTAAT | 1904.97 | 1356 | 0.712 | −0.340 |
| AN | GCTAAC | 2098.09 | 925 | 0.441 | −0.819 |
| AN | GCGAAC | 862.59 | 331 | 0.384 | −0.958 |
| AN | GCGAAT | 783.19 | 260 | 0.332 | −1.103 |
| AP | GCGCCG | 406.74 | 1172 | 2.881 | 1.058 |
| AP | GCGCCC | 1122.56 | 2271 | 2.023 | 0.705 |
| AP | GCCCCG | 1504.34 | 2335 | 1.552 | 0.440 |
| AP | GCTCCA | 2360.19 | 2463 | 1.044 | 0.043 |
| AP | GCTCCT | 2445.47 | 2548 | 1.042 | 0.041 |
| AP | GCCCCC | 4151.78 | 3957 | 0.953 | −0.048 |
| AP | GCACCT | 2140.76 | 2028 | 0.947 | −0.054 |
| AP | GCCCCA | 3588.82 | 3371 | 0.939 | −0.063 |
| AP | GCACCA | 2066.10 | 1831 | 0.886 | −0.121 |
| AP | GCACCC | 2390.20 | 2111 | 0.883 | −0.124 |
| AP | GCCCCT | 3718.49 | 3269 | 0.879 | −0.129 |
| AP | GCTCCC | 2730.42 | 2384 | 0.873 | −0.136 |
| AP | GCTCCG | 989.33 | 773 | 0.781 | −0.247 |
| AP | GCGCCT | 1005.41 | 778 | 0.774 | −0.256 |
| AP | GCACCG | 866.06 | 571 | 0.659 | −0.417 |
| AP | GCGCCA | 970.35 | 595 | 0.613 | −0.489 |
| AQ | GCCCAG | 7143.67 | 9550 | 1.337 | 0.290 |
| AQ | GCGCAG | 1931.51 | 2101 | 1.088 | 0.084 |
| AQ | GCACAA | 1472.79 | 1416 | 0.961 | −0.039 |
| AQ | GCTCAA | 1682.42 | 1522 | 0.905 | −0.100 |
| AQ | GCTCAG | 4698.04 | 4141 | 0.881 | −0.126 |
| AQ | GCACAG | 4112.65 | 3374 | 0.820 | −0.198 |
| AQ | GCCCAA | 2558.23 | 1943 | 0.760 | −0.275 |
| AQ | GCGCAA | 691.70 | 244 | 0.353 | −1.042 |
| AR | GCGCGC | 580.17 | 1255 | 2.163 | 0.772 |
| AR | GCGCGG | 634.54 | 1175 | 1.852 | 0.616 |
| AR | GCCCGG | 2346.82 | 3946 | 1.681 | 0.520 |
| AR | GCCCGC | 2145.76 | 3135 | 1.461 | 0.379 |
| AR | GCCAGG | 2323.57 | 3242 | 1.395 | 0.333 |
| AR | GCAAGA | 1362.59 | 1559 | 1.144 | 0.135 |
| AR | GCTCGA | 836.64 | 943 | 1.127 | 0.120 |
| AR | GCCCGA | 1272.16 | 1418 | 1.115 | 0.109 |
| AR | GCCCGT | 918.67 | 935 | 1.018 | 0.018 |
| AR | GCTCGT | 604.17 | 595 | 0.985 | −0.015 |
| AR | GCCAGA | 2366.81 | 2219 | 0.938 | −0.064 |
| AR | GCTCGG | 1543.39 | 1295 | 0.839 | −0.175 |
| AR | GCGCGT | 248.39 | 205 | 0.825 | −0.192 |
| AR | GCAAGG | 1337.69 | 1089 | 0.814 | −0.206 |
| AR | GCGAGG | 628.25 | 486 | 0.774 | −0.257 |
| AR | GCACGA | 732.39 | 533 | 0.728 | −0.318 |
| AR | GCTCGC | 1411.16 | 941 | 0.667 | −0.405 |
| AR | GCGCGA | 343.97 | 226 | 0.657 | −0.420 |
| AR | GCACGT | 528.89 | 338 | 0.639 | −0.448 |
| AR | GCACGG | 1351.08 | 859 | 0.636 | −0.453 |
| AR | GCACGC | 1235.33 | 619 | 0.501 | −0.691 |
| AR | GCTAGA | 1556.53 | 714 | 0.459 | −0.779 |

-continued

| AA pair | Codon pair | Expected | Observed | Observed/ Expected | CPS |
|---|---|---|---|---|---|
| AR | GCGAGA | 639.94 | 263 | 0.411 | −0.889 |
| AR | GCTAGG | 1528.10 | 487 | 0.319 | −1.144 |
| AS | GCCTCG | 963.41 | 1977 | 2.052 | 0.719 |
| AS | GCGTCG | 260.49 | 465 | 1.785 | 0.579 |
| AS | GCCAGC | 4127.58 | 6466 | 1.567 | 0.449 |
| AS | GCCTCC | 3643.21 | 5443 | 1.494 | 0.401 |
| AS | GCTTCT | 2084.25 | 2488 | 1.194 | 0.177 |
| AS | GCCAGT | 2604.12 | 3085 | 1.185 | 0.169 |
| AS | GCATCT | 1824.55 | 2154 | 1.181 | 0.166 |
| AS | GCTTCA | 1684.99 | 1932 | 1.147 | 0.137 |
| AS | GCGTCC | 985.05 | 1079 | 1.095 | 0.091 |
| AS | GCATCA | 1475.04 | 1531 | 1.038 | 0.037 |
| AS | GCCTCT | 3169.23 | 3235 | 1.021 | 0.021 |
| AS | GCCTCA | 2562.14 | 2514 | 0.981 | −0.019 |
| AS | GCTTCC | 2395.96 | 2295 | 0.958 | −0.043 |
| AS | GCAAGT | 1499.21 | 1307 | 0.872 | −0.137 |
| AS | GCTTCG | 633.59 | 516 | 0.814 | −0.205 |
| AS | GCATCC | 2097.42 | 1658 | 0.790 | −0.235 |
| AS | GCATCG | 554.64 | 403 | 0.727 | −0.319 |
| AS | GCGTCT | 856.90 | 521 | 0.608 | −0.498 |
| AS | GCGAGC | 1116.02 | 595 | 0.533 | −0.629 |
| AS | GCGTCA | 692.75 | 319 | 0.460 | −0.775 |
| AS | GCAAGC | 2376.27 | 1080 | 0.454 | −0.789 |
| AS | GCTAGT | 1712.60 | 737 | 0.430 | −0.843 |
| AS | GCGAGT | 704.10 | 265 | 0.376 | −0.977 |
| AS | GCTAGC | 2714.51 | 673 | 0.248 | −1.395 |
| AT | GCCACG | 1262.40 | 2478 | 1.963 | 0.674 |
| AT | GCCACC | 3842.98 | 6598 | 1.717 | 0.541 |
| AT | GCCACA | 3111.04 | 4031 | 1.296 | 0.259 |
| AT | GCCACT | 2751.18 | 3205 | 1.165 | 0.153 |
| AT | GCAACA | 1791.05 | 1761 | 0.983 | −0.017 |
| AT | GCGACG | 341.33 | 329 | 0.964 | −0.037 |
| AT | GCAACT | 1583.87 | 1509 | 0.953 | −0.048 |
| AT | GCTACT | 1809.31 | 1395 | 0.771 | −0.260 |
| AT | GCTACA | 2045.98 | 1528 | 0.747 | −0.292 |
| AT | GCGACC | 1039.07 | 601 | 0.578 | −0.547 |
| AT | GCAACC | 2212.43 | 1259 | 0.569 | −0.564 |
| AT | GCTACC | 2527.34 | 1364 | 0.540 | −0.617 |
| AT | GCAACG | 726.77 | 384 | 0.528 | −0.638 |
| AT | GCTACG | 830.22 | 363 | 0.437 | −0.827 |
| AT | GCGACT | 743.87 | 308 | 0.414 | −0.882 |
| AT | GCGACA | 841.17 | 347 | 0.413 | −0.885 |
| AV | GCTGTT | 1736.99 | 3025 | 1.742 | 0.555 |
| AV | GCTGTG | 4399.56 | 7279 | 1.654 | 0.503 |
| AV | GCTGTA | 1127.89 | 1750 | 1.552 | 0.439 |
| AV | GCTGTC | 2223.90 | 3351 | 1.507 | 0.410 |
| AV | GCAGTA | 987.35 | 1401 | 1.419 | 0.350 |
| AV | GCGGTG | 1808.80 | 2487 | 1.375 | 0.318 |
| AV | GCAGTT | 1520.56 | 2087 | 1.373 | 0.317 |
| AV | GCAGTG | 3851.36 | 4349 | 1.129 | 0.122 |
| AV | GCGGTC | 914.32 | 883 | 0.966 | −0.035 |
| AV | GCAGTC | 1946.80 | 1806 | 0.928 | −0.075 |
| AV | GCCGTG | 6689.81 | 4322 | 0.646 | −0.437 |
| AV | GCGGTT | 714.13 | 423 | 0.592 | −0.524 |
| AV | GCGGTA | 463.71 | 270 | 0.582 | −0.541 |
| AV | GCCGTC | 3381.59 | 1798 | 0.532 | −0.632 |
| AV | GCCGTT | 2641.21 | 563 | 0.213 | −1.546 |
| AV | GCCGTA | 1715.03 | 329 | 0.192 | −1.651 |
| AW | GCCTGG | 2528.22 | 3848 | 1.522 | 0.420 |
| AW | GCGTGG | 683.58 | 558 | 0.816 | −0.203 |
| AW | GCTTGG | 1662.69 | 1066 | 0.641 | −0.445 |
| AW | GCATGG | 1455.51 | 858 | 0.589 | −0.529 |
| AY | GCCTAC | 2643.77 | 4073 | 1.541 | 0.432 |
| AY | GCCTAT | 2148.26 | 2457 | 1.144 | 0.134 |
| AY | GCTTAT | 1412.81 | 1478 | 1.046 | 0.045 |
| AY | GCATAT | 1236.77 | 1244 | 1.006 | 0.006 |
| AY | GCTTAC | 1738.68 | 1139 | 0.655 | −0.423 |
| AY | GCGTAC | 714.83 | 429 | 0.600 | −0.511 |
| AY | GCATAC | 1522.04 | 868 | 0.570 | −0.562 |
| AY | GCGTAT | 580.85 | 310 | 0.534 | −0.628 |
| CA | TGTGCT | 1164.04 | 2021 | 1.736 | 0.552 |
| CA | TGTGCC | 1769.99 | 2992 | 1.690 | 0.525 |
| CA | TGTGCA | 1019.00 | 1708 | 1.676 | 0.517 |
| CA | TGTGCG | 478.57 | 477 | 0.997 | −0.003 |
| CA | TGCGCG | 568.18 | 502 | 0.884 | −0.124 |
| CA | TGCGCC | 2101.42 | 1313 | 0.625 | −0.470 |

-continued

| AA pair | Codon pair | Expected | Observed | Observed/ Expected | CPS |
|---|---|---|---|---|---|
| CA | TGCGCT | 1382.00 | 368 | 0.266 | −1.323 |
| CA | TGCGCA | 1209.80 | 312 | 0.258 | −1.355 |
| CC | TGCTGC | 1534.17 | 2610 | 1.701 | 0.531 |
| CC | TGCTGT | 1292.21 | 1571 | 1.216 | 0.195 |
| CC | TGTTGT | 1088.41 | 529 | 0.486 | −0.721 |
| CC | TGTTGC | 1292.21 | 497 | 0.385 | −0.956 |
| CD | TGTGAC | 1920.20 | 3470 | 1.807 | 0.592 |
| CD | TGTGAT | 1699.87 | 2853 | 1.678 | 0.518 |
| CD | TGCGAC | 2279.75 | 1134 | 0.497 | −0.698 |
| CD | TGCGAT | 2018.17 | 461 | 0.228 | −1.477 |
| CE | TGTGAA | 1901.69 | 3636 | 1.912 | 0.648 |
| CE | TGTGAG | 2543.16 | 3935 | 1.547 | 0.437 |
| CE | TGCGAG | 3019.37 | 1709 | 0.566 | −0.569 |
| CE | TGCGAA | 2257.78 | 442 | 0.196 | −1.631 |
| CF | TGCTTC | 1891.74 | 2684 | 1.419 | 0.350 |
| CF | TGCTTT | 1652.78 | 1685 | 1.019 | 0.019 |
| CF | TGTTTT | 1392.11 | 1096 | 0.787 | −0.239 |
| CF | TGTTTC | 1593.38 | 1065 | 0.668 | −0.403 |
| CG | TGTGGG | 1594.78 | 3240 | 2.032 | 0.709 |
| CG | TGTGGA | 1633.57 | 2846 | 1.742 | 0.555 |
| CG | TGTGGT | 1057.61 | 1627 | 1.538 | 0.431 |
| CG | TGTGGC | 2214.90 | 3133 | 1.415 | 0.347 |
| CG | TGCGGG | 1893.40 | 1137 | 0.601 | −0.510 |
| CG | TGCGGC | 2629.63 | 1461 | 0.556 | −0.588 |
| CG | TGCGGT | 1255.64 | 344 | 0.274 | −1.295 |
| CG | TGCGGA | 1939.46 | 431 | 0.222 | −1.504 |
| CH | TGCCAC | 1618.50 | 2144 | 1.325 | 0.281 |
| CH | TGCCAT | 1173.68 | 1253 | 1.068 | 0.065 |
| CH | TGTCAT | 988.58 | 831 | 0.841 | −0.174 |
| CH | TGTCAC | 1363.24 | 916 | 0.672 | −0.398 |
| CI | TGCATC | 1821.04 | 2813 | 1.545 | 0.435 |
| CI | TGCATT | 1440.05 | 1579 | 1.096 | 0.092 |
| CI | TGCATA | 662.30 | 576 | 0.870 | −0.140 |
| CI | TGTATA | 557.84 | 474 | 0.850 | −0.163 |
| CI | TGTATT | 1212.94 | 927 | 0.764 | −0.269 |
| CI | TGTATC | 1533.83 | 859 | 0.560 | −0.580 |
| CK | TGCAAG | 2777.53 | 3348 | 1.205 | 0.187 |
| CK | TGCAAA | 2144.62 | 2441 | 1.138 | 0.129 |
| CK | TGTAAA | 1806.38 | 1770 | 0.980 | −0.020 |
| CK | TGTAAG | 2339.47 | 1509 | 0.645 | −0.438 |
| CL | TGCCTC | 1722.14 | 2468 | 1.433 | 0.360 |
| CL | TGCCTG | 3578.83 | 4525 | 1.264 | 0.235 |
| CL | TGTTTA | 583.38 | 704 | 1.207 | 0.188 |
| CL | TGCCTT | 1187.49 | 1384 | 1.165 | 0.153 |
| CL | TGTTTG | 980.04 | 1079 | 1.101 | 0.096 |
| CL | TGCTTG | 1163.55 | 1179 | 1.013 | 0.013 |
| CL | TGTCTT | 1000.21 | 940 | 0.940 | −0.062 |
| CL | TGCCTA | 640.41 | 585 | 0.913 | −0.090 |
| CL | TGTCTA | 539.40 | 481 | 0.892 | −0.115 |
| CL | TGCTTA | 692.62 | 565 | 0.816 | −0.204 |
| CL | TGTCTC | 1450.53 | 1010 | 0.696 | −0.362 |
| CL | TGTCTG | 3014.39 | 1633 | 0.542 | −0.613 |
| CM | TGCATG | 1518.22 | 1979 | 1.304 | 0.265 |
| CM | TGTATG | 1278.78 | 818 | 0.640 | −0.447 |
| CN | TGCAAC | 1825.04 | 2351 | 1.288 | 0.253 |
| CN | TGCAAT | 1657.05 | 1636 | 0.987 | −0.013 |
| CN | TGTAAT | 1395.71 | 1349 | 0.967 | −0.034 |
| CN | TGTAAC | 1537.20 | 1079 | 0.702 | −0.354 |
| CP | TGCCCG | 687.28 | 978 | 1.423 | 0.353 |
| CP | TGCCCC | 1896.80 | 2279 | 1.201 | 0.184 |
| CP | TGCCCA | 1639.61 | 1728 | 1.054 | 0.053 |
| CP | TGCCCT | 1698.85 | 1690 | 0.995 | −0.005 |
| CP | TGTCCT | 1430.91 | 1333 | 0.932 | −0.071 |
| CP | TGTCCA | 1381.01 | 1263 | 0.915 | −0.089 |
| CP | TGTCCC | 1597.65 | 1369 | 0.857 | −0.154 |
| CP | TGTCCG | 578.88 | 271 | 0.468 | −0.759 |
| CQ | TGCCAG | 3338.89 | 4321 | 1.294 | 0.258 |
| CQ | TGCCAA | 1195.69 | 1319 | 1.103 | 0.098 |
| CQ | TGTCAA | 1007.11 | 905 | 0.899 | −0.107 |
| CQ | TGTCAG | 2812.30 | 1809 | 0.643 | −0.441 |
| CR | TGCCGC | 1031.52 | 1860 | 1.803 | 0.590 |
| CR | TGCCGG | 1128.18 | 1543 | 1.368 | 0.313 |
| CR | TGCAGG | 1117.00 | 1450 | 1.298 | 0.261 |
| CR | TGCCGT | 441.63 | 541 | 1.225 | 0.203 |
| CR | TGCCGA | 611.56 | 742 | 1.213 | 0.193 |
| CR | TGCAGA | 1137.78 | 1252 | 1.100 | 0.096 |

-continued

| AA pair | Codon pair | Expected | Observed | Observed/ Expected | CPS |
|---|---|---|---|---|---|
| CR | TGTCGA | 515.11 | 458 | 0.889 | −0.118 |
| CR | TGTCGT | 371.98 | 308 | 0.828 | −0.189 |
| CR | TGTAGA | 958.34 | 570 | 0.595 | −0.520 |
| CR | TGTCGC | 868.83 | 497 | 0.572 | −0.559 |
| CR | TGTCGG | 950.24 | 463 | 0.487 | −0.719 |
| CR | TGTAGG | 940.83 | 389 | 0.413 | −0.883 |
| CS | TGCAGC | 1990.73 | 3150 | 1.582 | 0.459 |
| CS | TGCTCC | 1757.12 | 2397 | 1.364 | 0.311 |
| CS | TGCAGT | 1255.97 | 1701 | 1.354 | 0.303 |
| CS | TGCTCG | 464.65 | 571 | 1.229 | 0.206 |
| CS | TGTTCT | 1287.45 | 1184 | 0.920 | −0.084 |
| CS | TGCTCT | 1528.52 | 1393 | 0.911 | −0.093 |
| CS | TGTTCA | 1040.83 | 932 | 0.895 | −0.110 |
| CS | TGCTCA | 1235.72 | 1079 | 0.873 | −0.136 |
| CS | TGTTCC | 1479.99 | 1102 | 0.745 | −0.295 |
| CS | TGTAGT | 1057.88 | 699 | 0.661 | −0.414 |
| CS | TGTTCG | 391.37 | 192 | 0.491 | −0.712 |
| CS | TGTAGC | 1676.76 | 767 | 0.457 | −0.782 |
| CT | TGCACG | 535.88 | 829 | 1.547 | 0.436 |
| CT | TGCACC | 1631.31 | 2321 | 1.423 | 0.353 |
| CT | TGCACA | 1320.60 | 1508 | 1.142 | 0.133 |
| CT | TGCACT | 1167.85 | 1185 | 1.015 | 0.015 |
| CT | TGTACT | 983.66 | 802 | 0.815 | −0.204 |
| CT | TGTACA | 1112.32 | 830 | 0.746 | −0.293 |
| CT | TGTACC | 1374.02 | 942 | 0.686 | −0.377 |
| CT | TGTACG | 451.36 | 160 | 0.354 | −1.037 |
| CV | TGTGTC | 1064.94 | 1821 | 1.710 | 0.536 |
| CV | TGTGTT | 831.78 | 1383 | 1.663 | 0.508 |
| CV | TGTGTA | 540.10 | 866 | 1.603 | 0.472 |
| CV | TGTGTG | 2106.78 | 3241 | 1.538 | 0.431 |
| CV | TGCGTG | 2501.27 | 1537 | 0.614 | −0.487 |
| CV | TGCGTC | 1264.35 | 734 | 0.581 | −0.544 |
| CV | TGCGTT | 987.53 | 219 | 0.222 | −1.506 |
| CV | TGCGTA | 641.24 | 137 | 0.214 | −1.543 |
| CW | TGCTGG | 1275.05 | 1842 | 1.445 | 0.368 |
| CW | TGTTGG | 1073.95 | 507 | 0.472 | −0.751 |
| CY | TGCTAC | 1379.34 | 1995 | 1.446 | 0.369 |
| CY | TGCTAT | 1120.82 | 1170 | 1.044 | 0.043 |
| CY | TGTTAT | 944.05 | 653 | 0.692 | −0.369 |
| CY | TGTTAC | 1161.80 | 788 | 0.678 | −0.388 |
| DA | GATGCT | 2675.13 | 5292 | 1.978 | 0.682 |
| DA | GATGCA | 2341.80 | 3898 | 1.665 | 0.510 |
| DA | GATGCC | 4067.71 | 5983 | 1.471 | 0.386 |
| DA | GACGCG | 1242.39 | 1116 | 0.898 | −0.107 |
| DA | GATGCG | 1099.83 | 972 | 0.884 | −0.124 |
| DA | GACGCC | 4594.94 | 2668 | 0.581 | −0.544 |
| DA | GACGCA | 2645.34 | 852 | 0.322 | −1.133 |
| DA | GACGCT | 3021.87 | 908 | 0.300 | −1.202 |
| DC | GACTGC | 2386.86 | 3465 | 1.452 | 0.373 |
| DC | GACTGT | 2010.41 | 2804 | 1.395 | 0.333 |
| DC | GATTGT | 1779.74 | 1163 | 0.653 | −0.425 |
| DC | GATTGC | 2112.99 | 858 | 0.406 | −0.901 |
| DD | GATGAT | 4271.42 | 7846 | 1.837 | 0.608 |
| DD | GATGAC | 4825.06 | 7181 | 1.488 | 0.398 |
| DD | GACGAC | 5450.46 | 2965 | 0.544 | −0.609 |
| DD | GACGAT | 4825.06 | 1380 | 0.286 | −1.252 |
| DE | GATGAA | 5114.33 | 10045 | 1.964 | 0.675 |
| DE | GATGAG | 6839.48 | 9573 | 1.400 | 0.336 |
| DE | GACGAG | 7725.97 | 4498 | 0.582 | −0.541 |
| DE | GACGAA | 5777.22 | 1341 | 0.232 | −1.461 |
| DF | GACTTC | 4696.28 | 6094 | 1.298 | 0.261 |
| DF | GACTTT | 4103.05 | 4250 | 1.036 | 0.035 |
| DF | GATTTT | 3632.26 | 3485 | 0.959 | −0.041 |
| DF | GATTTC | 4157.42 | 2760 | 0.664 | −0.410 |
| DG | GATGGT | 1910.36 | 3443 | 1.802 | 0.589 |
| DG | GATGGA | 2950.72 | 5133 | 1.740 | 0.554 |
| DG | GATGGG | 2880.65 | 4437 | 1.540 | 0.432 |
| DG | GATGGC | 4000.77 | 5419 | 1.354 | 0.303 |
| DG | GACGGC | 4519.33 | 2987 | 0.661 | −0.414 |
| DG | GACGGG | 3254.02 | 1979 | 0.608 | −0.497 |
| DG | GACGGT | 2157.97 | 723 | 0.335 | −1.094 |
| DG | GACGGA | 3333.18 | 886 | 0.266 | −1.325 |
| DH | GACCAC | 2653.74 | 3480 | 1.311 | 0.271 |
| DH | GACCAT | 1924.41 | 2014 | 1.047 | 0.046 |
| DH | GATCAT | 1703.60 | 1623 | 0.953 | −0.048 |
| DH | GATCAC | 2349.25 | 1514 | 0.644 | −0.439 |

-continued

| AA pair | Codon pair | Expected | Observed | Observed/ Expected | CPS |
|---|---|---|---|---|---|
| DI | GACATC | 4715.94 | 6532 | 1.385 | 0.326 |
| DI | GACATT | 3729.31 | 4087 | 1.096 | 0.092 |
| DI | GATATT | 3301.40 | 3271 | 0.991 | −0.009 |
| DI | GATATA | 1518.36 | 1495 | 0.985 | −0.016 |
| DI | GACATA | 1715.16 | 1565 | 0.912 | −0.092 |
| DI | GATATC | 4174.83 | 2205 | 0.528 | −0.638 |
| DK | GACAAG | 5562.52 | 7324 | 1.317 | 0.275 |
| DK | GACAAA | 4295.02 | 4794 | 1.116 | 0.110 |
| DK | GATAAA | 3802.20 | 3855 | 1.014 | 0.014 |
| DK | GATAAG | 4924.27 | 2611 | 0.530 | −0.634 |
| DL | GACCTC | 3785.97 | 5029 | 1.328 | 0.284 |
| DL | GACTTG | 2557.95 | 3396 | 1.328 | 0.283 |
| DL | GATTTA | 1347.95 | 1740 | 1.291 | 0.255 |
| DL | GACCTG | 7867.71 | 9796 | 1.245 | 0.219 |
| DL | GATTTG | 2264.44 | 2687 | 1.187 | 0.171 |
| DL | GACCTT | 2610.58 | 2774 | 1.063 | 0.061 |
| DL | GATCTT | 2311.04 | 2416 | 1.045 | 0.044 |
| DL | GACCTA | 1407.87 | 1416 | 1.006 | 0.006 |
| DL | GACTTA | 1522.66 | 1403 | 0.921 | −0.082 |
| DL | GATCTA | 1246.33 | 1020 | 0.818 | −0.200 |
| DL | GATCTC | 3351.56 | 2214 | 0.661 | −0.415 |
| DL | GATCTG | 6964.95 | 3348 | 0.481 | −0.733 |
| DM | GACATG | 4089.63 | 5411 | 1.323 | 0.280 |
| DM | GATATG | 3620.37 | 2299 | 0.635 | −0.454 |
| DN | GACAAC | 3511.00 | 4849 | 1.381 | 0.323 |
| DN | GACAAT | 3187.82 | 3349 | 1.051 | 0.049 |
| DN | GATAAT | 2822.05 | 2549 | 0.903 | −0.102 |
| DN | GATAAC | 3108.14 | 1882 | 0.606 | −0.502 |
| DP | GACCCC | 3732.11 | 5119 | 1.372 | 0.316 |
| DP | GACCCG | 1352.28 | 1692 | 1.251 | 0.224 |
| DP | GACCCT | 3342.62 | 3700 | 1.107 | 0.102 |
| DP | GATCCT | 2959.08 | 3111 | 1.051 | 0.050 |
| DP | GACCCA | 3226.05 | 3205 | 0.993 | −0.007 |
| DP | GATCCA | 2855.89 | 2349 | 0.823 | −0.195 |
| DP | GATCCC | 3303.88 | 2338 | 0.708 | −0.346 |
| DP | GATCCG | 1197.11 | 455 | 0.380 | −0.967 |
| DQ | GACCAG | 5250.37 | 6524 | 1.243 | 0.217 |
| DQ | GACCAA | 1880.22 | 2169 | 1.154 | 0.143 |
| DQ | GATCAA | 1664.48 | 1808 | 1.086 | 0.083 |
| DQ | GATCAG | 4647.93 | 2942 | 0.633 | −0.457 |
| DR | GACCGC | 1807.77 | 2634 | 1.457 | 0.376 |
| DR | GACAGA | 1994.00 | 2869 | 1.439 | 0.364 |
| DR | GACAGG | 1957.57 | 2730 | 1.395 | 0.333 |
| DR | GACCGT | 773.97 | 1029 | 1.330 | 0.285 |
| DR | GACCGG | 1977.16 | 2568 | 1.299 | 0.261 |
| DR | GACCGA | 1071.78 | 1292 | 1.205 | 0.187 |
| DR | GATCGA | 948.80 | 923 | 0.973 | −0.028 |
| DR | GATCGT | 685.16 | 626 | 0.914 | −0.090 |
| DR | GATAGA | 1765.20 | 1123 | 0.636 | −0.452 |
| DR | GATCGG | 1750.30 | 859 | 0.491 | −0.712 |
| DR | GATCGC | 1600.34 | 754 | 0.471 | −0.753 |
| DR | GATAGG | 1732.96 | 658 | 0.380 | −0.968 |
| DS | GACTCG | 918.57 | 1527 | 1.662 | 0.508 |
| DS | GACAGC | 3935.48 | 6143 | 1.561 | 0.445 |
| DS | GACAGT | 2482.92 | 3657 | 1.473 | 0.387 |
| DS | GATTCT | 2675.01 | 2968 | 1.110 | 0.104 |
| DS | GACTCC | 3473.65 | 3800 | 1.094 | 0.090 |
| DS | GATTCA | 2162.59 | 2129 | 0.984 | −0.016 |
| DS | GACTCA | 2442.89 | 2382 | 0.975 | −0.025 |
| DS | GACTCT | 3021.73 | 2910 | 0.963 | −0.038 |
| DS | GATTCC | 3075.07 | 2186 | 0.711 | −0.341 |
| DS | GATAGT | 2198.02 | 1355 | 0.616 | −0.484 |
| DS | GATTCG | 813.17 | 414 | 0.509 | −0.675 |
| DS | GATAGC | 3483.91 | 1212 | 0.348 | −1.056 |
| DT | GACACG | 1110.58 | 1842 | 1.659 | 0.506 |
| DT | GACACC | 3380.79 | 4666 | 1.380 | 0.322 |
| DT | GACACA | 2736.88 | 3538 | 1.293 | 0.257 |
| DT | GACACT | 2420.30 | 2688 | 1.111 | 0.105 |
| DT | GATACT | 2142.59 | 1731 | 0.808 | −0.213 |
| DT | GATACA | 2422.85 | 1788 | 0.738 | −0.304 |
| DT | GATACC | 2992.87 | 1586 | 0.530 | −0.635 |
| DT | GATACG | 983.15 | 351 | 0.357 | −1.030 |
| DV | GATGTT | 1957.96 | 3699 | 1.889 | 0.636 |
| DV | GATGTA | 1271.37 | 2214 | 1.741 | 0.555 |
| DV | GATGTC | 2506.81 | 3869 | 1.543 | 0.434 |
| DV | GATGTG | 4959.23 | 6668 | 1.345 | 0.296 |

-continued

| AA pair | Codon pair | Expected | Observed | Observed/ Expected | CPS |
|---|---|---|---|---|---|
| DV | GACGTG | 5602.02 | 3616 | 0.645 | −0.438 |
| DV | GACGTC | 2831.73 | 1654 | 0.584 | −0.538 |
| DV | GACGTT | 2211.73 | 672 | 0.304 | −1.191 |
| DV | GACGTA | 1436.16 | 385 | 0.268 | −1.316 |
| DW | GACTGG | 2619.27 | 3853 | 1.471 | 0.386 |
| DW | GATTGG | 2318.73 | 1085 | 0.468 | −0.759 |
| DY | GACTAC | 3307.71 | 3930 | 1.188 | 0.172 |
| DY | GATTAT | 2379.36 | 2608 | 1.096 | 0.092 |
| DY | GACTAT | 2687.76 | 2853 | 1.061 | 0.060 |
| DY | GATTAC | 2928.18 | 1912 | 0.653 | −0.426 |
| EA | GAGGCG | 2437.29 | 3179 | 1.304 | 0.266 |
| EA | GAAGCA | 3880.59 | 4844 | 1.248 | 0.222 |
| EA | GAAGCT | 4432.94 | 5143 | 1.160 | 0.149 |
| EA | GAGGCC | 9014.27 | 9805 | 1.088 | 0.084 |
| EA | GAGGCT | 5928.25 | 5314 | 0.896 | −0.109 |
| EA | GAGGCA | 5189.57 | 4530 | 0.873 | −0.136 |
| EA | GAAGCC | 6740.57 | 5649 | 0.838 | −0.177 |
| EA | GAAGCG | 1822.52 | 982 | 0.539 | −0.618 |
| EC | GAATGT | 2182.58 | 3541 | 1.622 | 0.484 |
| EC | GAGTGT | 2918.80 | 2792 | 0.957 | −0.044 |
| EC | GAGTGC | 3465.35 | 2987 | 0.862 | −0.149 |
| EC | GAATGC | 2591.27 | 1838 | 0.709 | −0.343 |
| ED | GAAGAT | 6605.82 | 9691 | 1.467 | 0.383 |
| ED | GAGGAC | 9979.09 | 9684 | 0.970 | −0.030 |
| ED | GAAGAC | 7462.02 | 6820 | 0.914 | −0.090 |
| ED | GAGGAT | 8834.07 | 6686 | 0.757 | −0.279 |
| EE | GAAGAA | 10747.11 | 14461 | 1.346 | 0.297 |
| EE | GAGGAG | 19220.31 | 21731 | 1.131 | 0.123 |
| EE | GAAGAG | 14372.29 | 11875 | 0.826 | −0.191 |
| EE | GAGGAA | 14372.29 | 10645 | 0.741 | −0.300 |
| EF | GAATTT | 3136.91 | 4237 | 1.351 | 0.301 |
| EF | GAGTTC | 4801.58 | 4739 | 0.987 | −0.013 |
| EF | GAGTTT | 4195.05 | 4095 | 0.976 | −0.024 |
| EF | GAATTC | 3590.46 | 2653 | 0.739 | −0.303 |
| EG | GAAGGA | 3358.73 | 5032 | 1.498 | 0.404 |
| EG | GAAGGT | 2174.51 | 2839 | 1.306 | 0.267 |
| EG | GAAGGG | 3278.97 | 3559 | 1.085 | 0.082 |
| EG | GAGGGC | 6090.10 | 6505 | 1.068 | 0.066 |
| EG | GAAGGC | 4553.97 | 4340 | 0.953 | −0.048 |
| EG | GAGGGG | 4385.02 | 3795 | 0.865 | −0.145 |
| EG | GAGGGT | 2908.01 | 2378 | 0.818 | −0.201 |
| EG | GAGGGA | 4491.69 | 2793 | 0.622 | −0.475 |
| EH | GAACAT | 2017.28 | 2539 | 1.259 | 0.230 |
| EH | GAGCAC | 3720.16 | 4190 | 1.126 | 0.119 |
| EH | GAGCAT | 2697.74 | 2448 | 0.907 | −0.097 |
| EH | GAACAC | 2781.81 | 2040 | 0.733 | −0.310 |
| EI | GAAATA | 1687.78 | 3007 | 1.782 | 0.578 |
| EI | GAAATT | 3669.78 | 4788 | 1.305 | 0.266 |
| EI | GAGATC | 6206.03 | 6191 | 0.998 | −0.002 |
| EI | GAGATT | 4907.66 | 3978 | 0.811 | −0.210 |
| EI | GAGATA | 2257.09 | 1785 | 0.791 | −0.235 |
| EI | GAAATC | 4640.66 | 3620 | 0.780 | −0.248 |
| EK | GAGAAG | 12729.57 | 15133 | 1.189 | 0.173 |
| EK | GAAAAA | 7349.75 | 7522 | 1.023 | 0.023 |
| EK | GAGAAA | 9828.94 | 9127 | 0.929 | −0.074 |
| EK | GAAAAG | 9518.74 | 7645 | 0.803 | −0.219 |
| EL | GAGCTG | 10945.64 | 15625 | 1.428 | 0.356 |
| EL | GAATTA | 1584.03 | 2256 | 1.424 | 0.354 |
| EL | GAACTA | 1464.61 | 1830 | 1.249 | 0.223 |
| EL | GAACTT | 2715.79 | 3371 | 1.241 | 0.216 |
| EL | GAGCTC | 5267.08 | 5877 | 1.116 | 0.110 |
| EL | GAGCTA | 1958.64 | 2049 | 1.046 | 0.045 |
| EL | GAATTG | 2661.03 | 2335 | 0.877 | −0.131 |
| EL | GAGCTT | 3631.87 | 3084 | 0.849 | −0.164 |
| EL | GAGTTG | 3558.64 | 2719 | 0.764 | −0.269 |
| EL | GAACTC | 3938.54 | 2632 | 0.668 | −0.403 |
| EL | GAGTTA | 2118.35 | 1357 | 0.641 | −0.445 |
| EL | GAACTG | 8184.78 | 4894 | 0.598 | −0.514 |
| EM | GAAATG | 4983.92 | 5010 | 1.005 | 0.005 |
| EM | GAGATG | 6665.08 | 6639 | 0.996 | −0.004 |
| EN | GAAAAT | 4791.73 | 6977 | 1.456 | 0.376 |
| EN | GAGAAC | 7057.70 | 6756 | 0.957 | −0.044 |
| EN | GAAAAC | 5277.51 | 4930 | 0.934 | −0.068 |
| EN | GAGAAT | 6408.07 | 4872 | 0.760 | −0.274 |
| EP | GAGCCG | 1650.94 | 2438 | 1.477 | 0.390 |
| EP | GAGCCC | 4556.38 | 6270 | 1.376 | 0.319 |

-continued

| AA pair | Codon pair | Expected | Observed | Observed/ Expected | CPS |
|---|---|---|---|---|---|
| EP | GAGCCT | 4080.86 | 4236 | 1.038 | 0.037 |
| EP | GAGCCA | 3938.55 | 4067 | 1.033 | 0.032 |
| EP | GAACCA | 2945.12 | 2684 | 0.911 | −0.093 |
| EP | GAACCT | 3051.53 | 2547 | 0.835 | −0.181 |
| EP | GAACCC | 3407.10 | 2106 | 0.618 | −0.481 |
| EP | GAACCG | 1234.52 | 517 | 0.419 | −0.870 |
| EQ | GAACAA | 2579.50 | 3396 | 1.317 | 0.275 |
| EQ | GAGCAG | 9632.80 | 11185 | 1.161 | 0.149 |
| EQ | GAGCAA | 3449.61 | 3185 | 0.923 | −0.080 |
| EQ | GAACAG | 7203.08 | 5099 | 0.708 | −0.345 |
| ER | GAAAGA | 2650.27 | 3769 | 1.422 | 0.352 |
| ER | GAGAGG | 3479.50 | 4315 | 1.240 | 0.215 |
| ER | GAGCGG | 3514.32 | 4356 | 1.240 | 0.215 |
| ER | GAGCGC | 3213.23 | 3682 | 1.146 | 0.136 |
| ER | GAAAGG | 2601.85 | 2679 | 1.030 | 0.029 |
| ER | GAGAGA | 3544.25 | 3633 | 1.025 | 0.025 |
| ER | GAGCGT | 1375.70 | 1286 | 0.935 | −0.067 |
| ER | GAACGT | 1028.70 | 894 | 0.869 | −0.140 |
| ER | GAACGA | 1424.52 | 1188 | 0.834 | −0.182 |
| ER | GAGCGA | 1905.04 | 1562 | 0.820 | −0.199 |
| ER | GAACGG | 2627.88 | 1333 | 0.507 | −0.679 |
| ER | GAACGC | 2402.74 | 1071 | 0.446 | −0.808 |
| ES | GAAAGT | 2081.93 | 3138 | 1.507 | 0.410 |
| ES | GAGAGC | 4413.03 | 5786 | 1.311 | 0.271 |
| ES | GAGAGT | 2784.21 | 3237 | 1.163 | 0.151 |
| ES | GAGTCG | 1030.03 | 1174 | 1.140 | 0.131 |
| ES | GAATCT | 2533.73 | 2812 | 1.110 | 0.104 |
| ES | GAATCA | 2048.37 | 2131 | 1.040 | 0.040 |
| ES | GAAAGC | 3299.91 | 2880 | 0.873 | −0.136 |
| ES | GAGTCC | 3895.16 | 3392 | 0.871 | −0.138 |
| ES | GAGTCT | 3388.40 | 2799 | 0.826 | −0.191 |
| ES | GAGTCA | 2739.33 | 2198 | 0.802 | −0.220 |
| ES | GAATCC | 2912.67 | 1943 | 0.667 | −0.405 |
| ES | GAATCG | 770.22 | 407 | 0.528 | −0.638 |
| ET | GAGACG | 1658.42 | 2190 | 1.321 | 0.278 |
| ET | GAAACA | 3056.09 | 3851 | 1.260 | 0.231 |
| ET | GAAACT | 2702.59 | 3224 | 1.193 | 0.176 |
| ET | GAGACC | 5048.51 | 5514 | 1.092 | 0.088 |
| ET | GAGACA | 4086.97 | 3619 | 0.885 | −0.122 |
| ET | GAGACT | 3614.21 | 3028 | 0.838 | −0.177 |
| ET | GAAACC | 3775.11 | 2950 | 0.781 | −0.247 |
| ET | GAAACG | 1240.11 | 806 | 0.650 | −0.431 |
| EV | GAAGTA | 1580.16 | 2675 | 1.693 | 0.526 |
| EV | GAAGTT | 2433.50 | 3724 | 1.530 | 0.425 |
| EV | GAGGTG | 8242.83 | 9074 | 1.101 | 0.096 |
| EV | GAAGTC | 3115.66 | 2860 | 0.918 | −0.086 |
| EV | GAGGTC | 4166.62 | 3741 | 0.898 | −0.108 |
| EV | GAAGTG | 6163.71 | 5122 | 0.831 | −0.185 |
| EV | GAGGTT | 3254.36 | 2359 | 0.725 | −0.322 |
| EV | GAGGTA | 2113.17 | 1515 | 0.717 | −0.333 |
| EW | GAGTGG | 3085.08 | 3238 | 1.050 | 0.048 |
| EW | GAATGG | 2306.92 | 2154 | 0.934 | −0.069 |
| EY | GAATAT | 2307.55 | 3428 | 1.486 | 0.396 |
| EY | GAGTAC | 3797.72 | 3796 | 1.000 | 0.000 |
| EY | GAGTAT | 3085.93 | 2596 | 0.841 | −0.173 |
| EY | GAATAC | 2839.80 | 2211 | 0.779 | −0.250 |
| FA | TTTGCA | 1643.98 | 3299 | 2.007 | 0.696 |
| FA | TTTGCT | 1877.98 | 3746 | 1.995 | 0.690 |
| FA | TTTGCC | 2855.59 | 4348 | 1.523 | 0.420 |
| FA | TTTGCG | 772.10 | 622 | 0.806 | −0.216 |
| FA | TTCGCG | 883.73 | 598 | 0.677 | −0.391 |
| FA | TTCGCC | 3268.46 | 1802 | 0.551 | −0.595 |
| FA | TTCGCT | 2149.50 | 516 | 0.240 | −1.427 |
| FA | TTCGCA | 1881.67 | 402 | 0.214 | −1.543 |
| FC | TTCTGC | 2058.60 | 3045 | 1.479 | 0.391 |
| FC | TTCTGT | 1733.93 | 2055 | 1.185 | 0.170 |
| FC | TTTTGT | 1514.90 | 1159 | 0.765 | −0.268 |
| FC | TTTTGC | 1798.56 | 847 | 0.471 | −0.753 |
| FD | TTTGAT | 2786.65 | 5380 | 1.931 | 0.658 |
| FD | TTTGAC | 3147.84 | 4737 | 1.505 | 0.409 |
| FD | TTCGAC | 3602.96 | 1746 | 0.485 | −0.724 |
| FD | TTCGAT | 3189.55 | 864 | 0.271 | −1.306 |
| FE | TTTGAA | 3016.02 | 6247 | 2.071 | 0.728 |
| FE | TTTGAG | 4033.37 | 6066 | 1.504 | 0.408 |
| FE | TTCGAG | 4616.53 | 2165 | 0.469 | −0.757 |
| FE | TTCGAA | 3452.08 | 640 | 0.185 | −1.685 |

-continued

| AA pair | Codon pair | Expected | Observed | Observed/ Expected | CPS |
|---|---|---|---|---|---|
| FF | TTCTTC | 3429.53 | 5168 | 1.507 | 0.410 |
| FF | TTCTTT | 2996.32 | 2989 | 0.998 | −0.002 |
| FF | TTTTTT | 2617.83 | 1937 | 0.740 | −0.301 |
| FF | TTTTTC | 2996.32 | 1946 | 0.649 | −0.432 |
| FG | TTTGGA | 2068.21 | 4271 | 2.065 | 0.725 |
| FG | TTTGGT | 1339.00 | 2552 | 1.906 | 0.645 |
| FG | TTTGGG | 2019.09 | 3449 | 1.708 | 0.535 |
| FG | TTTGGC | 2804.20 | 3462 | 1.235 | 0.211 |
| FG | TTCGGG | 2311.02 | 1292 | 0.559 | −0.581 |
| FG | TTCGGC | 3209.64 | 1648 | 0.513 | −0.667 |
| FG | TTCGGT | 1532.60 | 419 | 0.273 | −1.297 |
| FG | TTCGGA | 2367.24 | 558 | 0.236 | −1.445 |
| FH | TTCCAC | 2463.48 | 3200 | 1.299 | 0.262 |
| FH | TTTCAT | 1560.78 | 1697 | 1.087 | 0.084 |
| FH | TTCCAT | 1786.44 | 1866 | 1.045 | 0.044 |
| FH | TTTCAC | 2152.30 | 1200 | 0.558 | −0.584 |
| FI | TTCATC | 3454.46 | 5156 | 1.493 | 0.400 |
| FI | TTCATT | 2731.75 | 2953 | 1.081 | 0.078 |
| FI | TTTATT | 2386.67 | 2296 | 0.962 | −0.039 |
| FI | TTTATA | 1097.66 | 950 | 0.865 | −0.144 |
| FI | TTCATA | 1256.36 | 1035 | 0.824 | −0.194 |
| FI | TTTATC | 3018.10 | 1555 | 0.515 | −0.663 |
| FK | TTCAAG | 4090.45 | 5137 | 1.256 | 0.228 |
| FK | TTCAAA | 3158.38 | 3245 | 1.027 | 0.027 |
| FK | TTTAAA | 2759.42 | 2762 | 1.001 | 0.001 |
| FK | TTTAAG | 3573.75 | 2438 | 0.682 | −0.382 |
| FL | TTCCTC | 3228.53 | 4426 | 1.371 | 0.315 |
| FL | TTCCTG | 6709.28 | 8734 | 1.302 | 0.264 |
| FL | TTTTTA | 1134.45 | 1334 | 1.176 | 0.162 |
| FL | TTTCTT | 1945.00 | 2267 | 1.166 | 0.153 |
| FL | TTCCTA | 1200.58 | 1280 | 1.066 | 0.064 |
| FL | TTTCTA | 1048.92 | 1087 | 1.036 | 0.036 |
| FL | TTCTTG | 2181.32 | 2239 | 1.026 | 0.026 |
| FL | TTCCTT | 2226.21 | 2150 | 0.966 | −0.035 |
| FL | TTTTTG | 1905.78 | 1799 | 0.944 | −0.058 |
| FL | TTCTTA | 1298.47 | 1144 | 0.881 | −0.127 |
| FL | TTTCTC | 2820.70 | 1904 | 0.675 | −0.393 |
| FL | TTTCTG | 5861.77 | 3197 | 0.545 | −0.606 |
| FM | TTCATG | 2804.11 | 3662 | 1.306 | 0.267 |
| FM | TTTATG | 2449.89 | 1592 | 0.650 | −0.431 |
| FN | TTCAAC | 2855.47 | 3919 | 1.372 | 0.317 |
| FN | TTTAAT | 2265.13 | 2185 | 0.965 | −0.036 |
| FN | TTCAAT | 2592.63 | 2456 | 0.947 | −0.054 |
| FN | TTTAAC | 2494.77 | 1648 | 0.661 | −0.415 |
| FP | TTCCCG | 961.40 | 1205 | 1.253 | 0.226 |
| FP | TTTCCT | 2076.25 | 2539 | 1.223 | 0.201 |
| FP | TTCCCC | 2653.35 | 3099 | 1.168 | 0.155 |
| FP | TTTCCA | 2003.85 | 2141 | 1.068 | 0.066 |
| FP | TTCCCA | 2293.57 | 2310 | 1.007 | 0.007 |
| FP | TTCCCT | 2376.44 | 2379 | 1.001 | 0.001 |
| FP | TTTCCC | 2318.18 | 1529 | 0.660 | −0.416 |
| FP | TTTCCG | 839.96 | 321 | 0.382 | −0.962 |
| FQ | TTCCAG | 5468.69 | 7069 | 1.293 | 0.257 |
| FQ | TTTCAA | 1711.02 | 1803 | 1.054 | 0.052 |
| FQ | TTCCAA | 1958.40 | 1980 | 1.011 | 0.011 |
| FQ | TTTCAG | 4777.89 | 3064 | 0.641 | −0.444 |
| FR | TTCCGC | 1531.47 | 2588 | 1.690 | 0.525 |
| FR | TTCCGA | 907.97 | 1410 | 1.553 | 0.440 |
| FR | TTCCGG | 1674.97 | 2451 | 1.463 | 0.381 |
| FR | TTCCGT | 655.68 | 893 | 1.362 | 0.309 |
| FR | TTCAGA | 1689.24 | 1852 | 1.096 | 0.092 |
| FR | TTCAGG | 1658.38 | 1810 | 1.091 | 0.087 |
| FR | TTTCGA | 793.28 | 850 | 1.072 | 0.069 |
| FR | TTTCGT | 572.85 | 490 | 0.855 | −0.156 |
| FR | TTTAGA | 1475.86 | 947 | 0.642 | −0.444 |
| FR | TTTAGG | 1448.90 | 691 | 0.477 | −0.740 |
| FR | TTTCGG | 1463.39 | 688 | 0.470 | −0.755 |
| FR | TTTCGC | 1338.02 | 540 | 0.404 | −0.907 |
| FS | TTCTCC | 2990.83 | 4507 | 1.507 | 0.410 |
| FS | TTCAGC | 3388.47 | 4577 | 1.351 | 0.301 |
| FS | TTCAGT | 2137.80 | 2692 | 1.259 | 0.231 |
| FS | TTCTCG | 790.89 | 910 | 1.151 | 0.140 |
| FS | TTTTCT | 2273.08 | 2536 | 1.116 | 0.109 |
| FS | TTCTCT | 2601.73 | 2741 | 1.054 | 0.052 |
| FS | TTTTCA | 1837.65 | 1903 | 1.036 | 0.035 |
| FS | TTCTCA | 2103.34 | 1997 | 0.949 | −0.052 |
| FS | TTTTCC | 2613.03 | 1872 | 0.716 | −0.334 |
| FS | TTTAGT | 1867.76 | 1201 | 0.643 | −0.442 |
| FS | TTTTCG | 690.99 | 258 | 0.373 | −0.985 |
| FS | TTTAGC | 2960.44 | 1062 | 0.359 | −1.025 |
| FT | TTCACC | 2909.29 | 4513 | 1.551 | 0.439 |
| FT | TTCACG | 955.69 | 1315 | 1.376 | 0.319 |
| FT | TTCACT | 2082.75 | 2494 | 1.197 | 0.180 |
| FT | TTCACA | 2355.18 | 2372 | 1.007 | 0.007 |
| FT | TTTACT | 1819.66 | 1622 | 0.891 | −0.115 |
| FT | TTTACA | 2057.68 | 1485 | 0.722 | −0.326 |
| FT | TTTACC | 2541.79 | 1495 | 0.588 | −0.531 |
| FT | TTTACG | 834.97 | 261 | 0.313 | −1.163 |
| FV | TTTGTA | 912.19 | 1711 | 1.876 | 0.629 |
| FV | TTTGTT | 1404.80 | 2620 | 1.865 | 0.623 |
| FV | TTTGTC | 1798.60 | 2635 | 1.465 | 0.382 |
| FV | TTTGTG | 3558.17 | 5206 | 1.463 | 0.381 |
| FV | TTCGTG | 4072.62 | 2589 | 0.636 | −0.453 |
| FV | TTCGTC | 2058.64 | 1086 | 0.528 | −0.640 |
| FV | TTCGTT | 1607.91 | 386 | 0.240 | −1.427 |
| FV | TTCGTA | 1044.07 | 224 | 0.215 | −1.539 |
| FW | TTCTGG | 2126.30 | 2834 | 1.333 | 0.287 |
| FW | TTTTGG | 1857.70 | 1150 | 0.619 | −0.480 |
| FY | TTCTAC | 2720.70 | 3710 | 1.364 | 0.310 |
| FY | TTTTAT | 1931.51 | 2003 | 1.037 | 0.036 |
| FY | TTCTAT | 2210.77 | 2145 | 0.970 | −0.030 |
| FY | TTTTAC | 2377.02 | 1382 | 0.581 | −0.542 |
| GA | GGTGCT | 1531.20 | 2505 | 1.636 | 0.492 |
| GA | GGGGCG | 949.27 | 1433 | 1.510 | 0.412 |
| GA | GGGGCC | 3510.85 | 5061 | 1.442 | 0.366 |
| GA | GGTGCC | 2328.29 | 3109 | 1.335 | 0.289 |
| GA | GGAGCA | 2070.38 | 2678 | 1.293 | 0.257 |
| GA | GGTGCA | 1340.41 | 1715 | 1.279 | 0.246 |
| GA | GGCGCG | 1318.38 | 1659 | 1.258 | 0.230 |
| GA | GGAGCT | 2365.08 | 2975 | 1.258 | 0.229 |
| GA | GGGGCT | 2308.91 | 2850 | 1.234 | 0.211 |
| GA | GGAGCC | 3596.25 | 3845 | 1.069 | 0.067 |
| GA | GGGGCA | 2021.22 | 2074 | 1.026 | 0.026 |
| GA | GGTGCG | 629.52 | 501 | 0.796 | −0.228 |
| GA | GGAGCG | 972.36 | 712 | 0.732 | −0.312 |
| GA | GGCGCC | 4876.02 | 3121 | 0.640 | −0.446 |
| GA | GGCGCT | 3206.72 | 906 | 0.283 | −1.264 |
| GA | GGCGCA | 2807.15 | 688 | 0.245 | −1.406 |
| GC | GGCTGC | 1888.96 | 4102 | 2.172 | 0.775 |
| GC | GGCTGT | 1591.04 | 2360 | 1.483 | 0.394 |
| GC | GGTTGT | 759.72 | 658 | 0.866 | −0.144 |
| GC | GGATGT | 1173.45 | 793 | 0.676 | −0.392 |
| GC | GGTTGC | 901.97 | 523 | 0.580 | −0.545 |
| GC | GGATGC | 1393.18 | 655 | 0.470 | −0.755 |
| GC | GGGTGC | 1360.09 | 628 | 0.462 | −0.773 |
| GC | GGGTGT | 1145.59 | 495 | 0.432 | −0.839 |
| GD | GGGGAC | 3126.50 | 4967 | 1.589 | 0.463 |
| GD | GGTGAT | 1835.49 | 2621 | 1.428 | 0.356 |
| GD | GGTGAC | 2073.40 | 2960 | 1.428 | 0.356 |
| GD | GGAGAT | 2835.09 | 3829 | 1.351 | 0.301 |
| GD | GGAGAC | 3202.56 | 4240 | 1.324 | 0.281 |
| GD | GGGGAT | 2767.76 | 2575 | 0.930 | −0.072 |
| GD | GGCGAC | 4342.22 | 1955 | 0.450 | −0.798 |
| GD | GGCGAT | 3843.98 | 880 | 0.229 | −1.474 |
| GE | GGAGAA | 3433.99 | 5903 | 1.719 | 0.542 |
| GE | GGGGAG | 4483.27 | 6552 | 1.461 | 0.379 |
| GE | GGTGAA | 2223.23 | 3248 | 1.461 | 0.379 |
| GE | GGAGAG | 4592.33 | 5961 | 1.298 | 0.261 |
| GE | GGTGAG | 2973.17 | 2988 | 1.005 | 0.005 |
| GE | GGGGAA | 3352.44 | 3041 | 0.907 | −0.098 |
| GE | GGCGAG | 6226.56 | 3530 | 0.567 | −0.568 |
| GE | GGCGAA | 4656.01 | 718 | 0.154 | −1.869 |
| GF | GGCTTC | 3466.22 | 6121 | 1.766 | 0.569 |
| GF | GGATTT | 2233.54 | 2666 | 1.194 | 0.177 |
| GF | GGTTTT | 1446.04 | 1665 | 1.151 | 0.141 |
| GF | GGCTTT | 3028.37 | 3201 | 1.057 | 0.055 |
| GF | GGTTTC | 1655.11 | 1548 | 0.935 | −0.067 |
| GF | GGATTC | 2556.47 | 1534 | 0.600 | −0.511 |
| GF | GGGTTT | 2180.50 | 1244 | 0.571 | −0.561 |
| GF | GGGTTC | 2495.76 | 1083 | 0.434 | −0.835 |
| GG | GGTGGT | 1061.28 | 2286 | 2.154 | 0.767 |
| GG | GGTGGC | 2222.59 | 3657 | 1.645 | 0.498 |

-continued

| AA pair | Codon pair | Expected | Observed | Observed/ Expected | CPS |
|---|---|---|---|---|---|
| GG | GGTGGA | 1639.25 | 2618 | 1.597 | 0.468 |
| GG | GGAGGA | 2531.97 | 3609 | 1.425 | 0.354 |
| GG | GGTGGG | 1600.32 | 2267 | 1.417 | 0.348 |
| GG | GGGGGC | 3351.47 | 4673 | 1.394 | 0.332 |
| GG | GGAGGT | 1639.25 | 2152 | 1.313 | 0.272 |
| GG | GGAGGC | 3433.00 | 3776 | 1.100 | 0.095 |
| GG | GGCGGC | 4654.67 | 4787 | 1.028 | 0.028 |
| GG | GGGGGT | 1600.32 | 1543 | 0.964 | −0.036 |
| GG | GGAGGG | 2471.84 | 2351 | 0.951 | −0.050 |
| GG | GGGGGA | 2471.84 | 1517 | 0.614 | −0.488 |
| GG | GGCGGG | 3351.47 | 2001 | 0.597 | −0.516 |
| GG | GGGGGG | 2413.14 | 1080 | 0.448 | −0.804 |
| GG | GGCGGT | 2222.59 | 936 | 0.421 | −0.865 |
| GG | GGCGGA | 3433.00 | 845 | 0.246 | −1.402 |
| GH | GGCCAC | 2540.15 | 3679 | 1.448 | 0.370 |
| GH | GGTCAT | 879.57 | 1022 | 1.162 | 0.150 |
| GH | GGACAT | 1358.57 | 1438 | 1.058 | 0.057 |
| GH | GGCCAT | 1842.04 | 1679 | 0.911 | −0.093 |
| GH | GGGCAC | 1828.97 | 1629 | 0.891 | −0.116 |
| GH | GGTCAC | 1212.92 | 1008 | 0.831 | −0.185 |
| GH | GGACAC | 1873.46 | 1479 | 0.789 | −0.236 |
| GH | GGGCAT | 1326.31 | 928 | 0.700 | −0.357 |
| GI | GGCATC | 3372.48 | 5474 | 1.623 | 0.484 |
| GI | GGAATA | 904.63 | 1338 | 1.479 | 0.391 |
| GI | GGAATT | 1966.96 | 2560 | 1.302 | 0.264 |
| GI | GGCATT | 2666.92 | 2670 | 1.001 | 0.001 |
| GI | GGTATT | 1273.45 | 1052 | 0.826 | −0.191 |
| GI | GGGATC | 2428.27 | 1958 | 0.806 | −0.215 |
| GI | GGTATA | 585.67 | 461 | 0.787 | −0.239 |
| GI | GGAATC | 2487.34 | 1910 | 0.768 | −0.264 |
| GI | GGGATA | 883.14 | 666 | 0.754 | −0.282 |
| GI | GGGATT | 1920.24 | 1421 | 0.740 | −0.301 |
| GI | GGCATA | 1226.55 | 885 | 0.722 | −0.326 |
| GI | GGTATC | 1610.35 | 931 | 0.578 | −0.548 |
| GK | GGAAAA | 3199.11 | 4553 | 1.423 | 0.353 |
| GK | GGGAAG | 4044.81 | 5674 | 1.403 | 0.338 |
| GK | GGGAAA | 3123.14 | 4119 | 1.319 | 0.277 |
| GK | GGCAAG | 5617.61 | 5712 | 1.017 | 0.017 |
| GK | GGAAAG | 4143.21 | 3706 | 0.894 | −0.112 |
| GK | GGCAAA | 4337.55 | 3581 | 0.826 | −0.192 |
| GK | GGTAAA | 2071.17 | 1334 | 0.644 | −0.440 |
| GK | GGTAAG | 2682.40 | 540 | 0.201 | −1.603 |
| GL | GGCCTC | 3017.19 | 4559 | 1.511 | 0.413 |
| GL | GGTTTA | 579.43 | 820 | 1.415 | 0.347 |
| GL | GGTTTG | 973.39 | 1294 | 1.329 | 0.285 |
| GL | GGGCTG | 4514.62 | 5878 | 1.302 | 0.264 |
| GL | GGTCTT | 993.42 | 1258 | 1.266 | 0.236 |
| GL | GGCCTG | 6270.10 | 7822 | 1.248 | 0.221 |
| GL | GGGCTC | 2172.45 | 2563 | 1.180 | 0.165 |
| GL | GGATTA | 894.98 | 991 | 1.107 | 0.102 |
| GL | GGACTT | 1534.44 | 1613 | 1.051 | 0.050 |
| GL | GGCTTG | 2038.53 | 2109 | 1.035 | 0.034 |
| GL | GGCCTT | 2080.48 | 2098 | 1.008 | 0.008 |
| GL | GGACTA | 827.51 | 799 | 0.966 | −0.035 |
| GL | GGGCTT | 1497.99 | 1445 | 0.965 | −0.036 |
| GL | GGTCTC | 1440.70 | 1365 | 0.947 | −0.054 |
| GL | GGTCTA | 535.75 | 487 | 0.909 | −0.095 |
| GL | GGGCTA | 807.86 | 726 | 0.899 | −0.107 |
| GL | GGCCTA | 1121.99 | 968 | 0.863 | −0.148 |
| GL | GGCTTA | 1213.47 | 935 | 0.771 | −0.261 |
| GL | GGACTC | 2225.29 | 1656 | 0.744 | −0.295 |
| GL | GGATTG | 1503.50 | 1062 | 0.706 | −0.348 |
| GL | GGTCTG | 2993.96 | 2034 | 0.679 | −0.387 |
| GL | GGGTTG | 1467.79 | 870 | 0.593 | −0.523 |
| GL | GGGTTA | 873.73 | 467 | 0.534 | −0.626 |
| GL | GGACTG | 4624.44 | 2384 | 0.516 | −0.663 |
| GM | GGCATG | 3177.11 | 3953 | 1.244 | 0.219 |
| GM | GGAATG | 2343.24 | 2482 | 1.059 | 0.058 |
| GM | GGGATG | 2287.59 | 2247 | 0.982 | −0.018 |
| GM | GGTATG | 1517.06 | 643 | 0.424 | −0.858 |
| GN | GGAAAT | 2150.19 | 3332 | 1.550 | 0.438 |
| GN | GGGAAC | 2311.93 | 2816 | 1.218 | 0.197 |
| GN | GGCAAC | 3210.92 | 3701 | 1.153 | 0.142 |
| GN | GGAAAC | 2368.18 | 2679 | 1.131 | 0.123 |
| GN | GGGAAT | 2099.13 | 1823 | 0.868 | −0.141 |
| GN | GGCAAT | 2915.36 | 2061 | 0.707 | −0.347 |
| GN | GGTAAT | 1392.08 | 784 | 0.563 | −0.574 |
| GN | GGTAAC | 1533.21 | 785 | 0.512 | −0.669 |
| GP | GGGCCC | 2634.22 | 3947 | 1.498 | 0.404 |
| GP | GGGCCG | 954.47 | 1417 | 1.485 | 0.395 |
| GP | GGCCCC | 3658.52 | 4576 | 1.251 | 0.224 |
| GP | GGCCCG | 1325.61 | 1623 | 1.224 | 0.202 |
| GP | GGTCCT | 1564.62 | 1910 | 1.221 | 0.199 |
| GP | GGGCCT | 2359.31 | 2542 | 1.077 | 0.075 |
| GP | GGTCCC | 1746.93 | 1827 | 1.046 | 0.045 |
| GP | GGCCCT | 3276.71 | 2994 | 0.914 | −0.090 |
| GP | GGGCCA | 2277.03 | 2003 | 0.880 | −0.128 |
| GP | GGTCCA | 1510.06 | 1264 | 0.837 | −0.178 |
| GP | GGACCC | 2698.30 | 2240 | 0.830 | −0.186 |
| GP | GGACCA | 2332.42 | 1908 | 0.818 | −0.201 |
| GP | GGACCT | 2416.70 | 1957 | 0.810 | −0.211 |
| GP | GGCCCA | 3162.44 | 2548 | 0.806 | −0.216 |
| GP | GGTCCG | 632.98 | 351 | 0.555 | −0.590 |
| GP | GGACCG | 977.69 | 421 | 0.431 | −0.843 |
| GQ | GGACAA | 1382.58 | 1677 | 1.213 | 0.193 |
| GQ | GGGCAG | 3769.06 | 4425 | 1.174 | 0.160 |
| GQ | GGCCAG | 5234.64 | 6081 | 1.162 | 0.150 |
| GQ | GGTCAA | 895.11 | 953 | 1.065 | 0.063 |
| GQ | GGCCAA | 1874.58 | 1593 | 0.850 | −0.163 |
| GQ | GGGCAA | 1349.74 | 1124 | 0.833 | −0.183 |
| GQ | GGACAG | 3860.75 | 3134 | 0.812 | −0.209 |
| GQ | GGTCAG | 2499.53 | 1879 | 0.752 | −0.285 |
| GR | GGCCGC | 1832.29 | 3615 | 1.973 | 0.680 |
| GR | GGAAGA | 1490.60 | 2294 | 1.539 | 0.431 |
| GR | GGCCGG | 2003.98 | 2892 | 1.443 | 0.367 |
| GR | GGCCGT | 784.47 | 1022 | 1.303 | 0.265 |
| GR | GGTCGT | 374.58 | 450 | 1.201 | 0.183 |
| GR | GGCCGA | 1086.32 | 1252 | 1.153 | 0.142 |
| GR | GGGCGC | 1319.29 | 1471 | 1.115 | 0.109 |
| GR | GGTCGA | 518.71 | 546 | 1.053 | 0.051 |
| GR | GGCAGG | 1984.13 | 2022 | 1.019 | 0.019 |
| GR | GGGAGG | 1428.62 | 1435 | 1.004 | 0.004 |
| GR | GGGCGG | 1442.91 | 1437 | 0.996 | −0.004 |
| GR | GGAAGG | 1463.37 | 1370 | 0.936 | −0.066 |
| GR | GGGAGA | 1455.20 | 1344 | 0.924 | −0.079 |
| GR | GGACGT | 578.58 | 514 | 0.888 | −0.118 |
| GR | GGACGA | 801.20 | 671 | 0.837 | −0.177 |
| GR | GGGCGT | 564.84 | 471 | 0.834 | −0.182 |
| GR | GGCAGA | 2021.05 | 1684 | 0.833 | −0.182 |
| GR | GGGCGA | 782.17 | 626 | 0.800 | −0.223 |
| GR | GGTCGC | 874.92 | 596 | 0.681 | −0.384 |
| GR | GGTCGG | 956.90 | 555 | 0.580 | −0.545 |
| GR | GGTAGA | 965.05 | 529 | 0.548 | −0.601 |
| GR | GGACGC | 1351.39 | 729 | 0.539 | −0.617 |
| GR | GGACGG | 1478.01 | 737 | 0.499 | −0.696 |
| GR | GGTAGG | 947.42 | 244 | 0.258 | -1.357 |
| GS | GGCAGC | 3581.32 | 6542 | 1.827 | 0.603 |
| GS | GGCTCC | 3161.05 | 5376 | 1.701 | 0.531 |
| GS | GGCTCG | 835.91 | 1323 | 1.583 | 0.459 |
| GS | GGCAGT | 2259.47 | 2875 | 1.272 | 0.241 |
| GS | GGAAGT | 1666.45 | 2085 | 1.251 | 0.224 |
| GS | GGTTCT | 1313.02 | 1563 | 1.190 | 0.174 |
| GS | GGCTCT | 2749.80 | 3087 | 1.123 | 0.116 |
| GS | GGGAGC | 2578.63 | 2566 | 0.995 | −0.005 |
| GS | GGTTCC | 1509.39 | 1428 | 0.946 | −0.055 |
| GS | GGCTCA | 2223.05 | 2101 | 0.945 | −0.056 |
| GS | GGTTCA | 1061.50 | 981 | 0.924 | −0.079 |
| GS | GGAAGC | 2641.36 | 2137 | 0.809 | −0.212 |
| GS | GGATCA | 1639.59 | 1281 | 0.781 | −0.247 |
| GS | GGGAGT | 1626.88 | 1267 | 0.779 | −0.250 |
| GS | GGATCT | 2028.08 | 1470 | 0.725 | −0.322 |
| GS | GGGTCC | 2276.03 | 1646 | 0.723 | −0.324 |
| GS | GGGTCT | 1979.92 | 1280 | 0.646 | −0.436 |
| GS | GGGTCG | 601.87 | 379 | 0.630 | −0.463 |
| GS | GGTAGT | 1078.89 | 646 | 0.599 | −0.513 |
| GS | GGATCC | 2331.40 | 1342 | 0.576 | −0.552 |
| GS | GGGTCA | 1600.65 | 887 | 0.554 | −0.590 |
| GS | GGTTCG | 399.14 | 209 | 0.524 | −0.647 |
| GS | GGATCG | 616.51 | 276 | 0.448 | −0.804 |
| GS | GGTAGC | 1710.07 | 723 | 0.423 | −0.861 |
| GT | GGCACC | 3271.07 | 4870 | 1.489 | 0.398 |
| GT | GGCACG | 1074.53 | 1368 | 1.273 | 0.241 |

-continued

| AA pair | Codon pair | Expected | Observed | Observed/ Expected | CPS |
|---|---|---|---|---|---|
| GT | GGGACC | 2355.25 | 2817 | 1.196 | 0.179 |
| GT | GGAACA | 1953.05 | 2290 | 1.173 | 0.159 |
| GT | GGAACT | 1727.13 | 1900 | 1.100 | 0.095 |
| GT | GGGACG | 773.69 | 838 | 1.083 | 0.080 |
| GT | GGGACA | 1906.66 | 1903 | 0.998 | −0.002 |
| GT | GGCACT | 2341.75 | 2331 | 0.995 | −0.005 |
| GT | GGCACA | 2648.06 | 2499 | 0.944 | −0.058 |
| GT | GGGACT | 1686.11 | 1534 | 0.910 | −0.095 |
| GT | GGAACC | 2412.54 | 1841 | 0.763 | −0.270 |
| GT | GGTACT | 1118.18 | 840 | 0.751 | −0.286 |
| GT | GGTACC | 1561.93 | 994 | 0.636 | −0.452 |
| GT | GGTACA | 1264.44 | 780 | 0.617 | −0.483 |
| GT | GGAACG | 792.51 | 445 | 0.562 | −0.577 |
| GT | GGTACG | 513.09 | 150 | 0.292 | −1.230 |
| GV | GGTGTT | 816.93 | 1802 | 2.206 | 0.791 |
| GV | GGTGTC | 1045.94 | 2070 | 1.979 | 0.683 |
| GV | GGTGTA | 530.46 | 957 | 1.804 | 0.590 |
| GV | GGTGTG | 2069.18 | 3207 | 1.550 | 0.438 |
| GV | GGAGTA | 819.35 | 1225 | 1.495 | 0.402 |
| GV | GGAGTT | 1261.83 | 1841 | 1.459 | 0.378 |
| GV | GGGGTC | 1577.18 | 2150 | 1.363 | 0.310 |
| GV | GGAGTC | 1615.55 | 1839 | 1.138 | 0.130 |
| GV | GGGGTT | 1231.86 | 1123 | 0.912 | −0.093 |
| GV | GGGGTG | 3120.14 | 2770 | 0.888 | −0.119 |
| GV | GGAGTG | 3196.04 | 2641 | 0.826 | −0.191 |
| GV | GGGGTA | 799.89 | 631 | 0.789 | −0.237 |
| GV | GGCGTC | 2190.46 | 1653 | 0.755 | −0.282 |
| GV | GGCGTG | 4333.39 | 2790 | 0.644 | −0.440 |
| GV | GGCGTT | 1710.87 | 499 | 0.292 | −1.232 |
| GV | GGCGTA | 1110.93 | 232 | 0.209 | −1.566 |
| GW | GGCTGG | 2102.85 | 3748 | 1.782 | 0.578 |
| GW | GGTTGG | 1004.11 | 690 | 0.687 | −0.375 |
| GW | GGATGG | 1550.94 | 1012 | 0.653 | −0.427 |
| GW | GGGTGG | 1514.10 | 722 | 0.477 | −0.741 |
| GY | GGCTAC | 2577.81 | 4581 | 1.777 | 0.575 |
| GY | GGTTAT | 1000.20 | 1309 | 1.309 | 0.269 |
| GY | GGCTAT | 2094.66 | 2528 | 1.207 | 0.188 |
| GY | GGATAT | 1544.90 | 1478 | 0.957 | −0.044 |
| GY | GGTTAC | 1230.90 | 1074 | 0.873 | −0.136 |
| GY | GGATAC | 1901.24 | 1052 | 0.553 | −0.592 |
| GY | GGGTAC | 1856.09 | 982 | 0.529 | −0.637 |
| GY | GGGTAT | 1508.21 | 710 | 0.471 | −0.753 |
| HA | CATGCT | 1101.90 | 1959 | 1.778 | 0.575 |
| HA | CATGCA | 964.61 | 1670 | 1.731 | 0.549 |
| HA | CATGCC | 1675.52 | 2408 | 1.437 | 0.363 |
| HA | CACGCG | 624.72 | 681 | 1.090 | 0.086 |
| HA | CATGCG | 453.03 | 447 | 0.987 | −0.013 |
| HA | CACGCC | 2310.52 | 1649 | 0.714 | −0.337 |
| HA | CACGCA | 1330.18 | 617 | 0.464 | −0.768 |
| HA | CACGCT | 1519.52 | 549 | 0.361 | −1.018 |
| HC | CACTGC | 1778.65 | 2629 | 1.478 | 0.391 |
| HC | CACTGT | 1498.13 | 1717 | 1.146 | 0.136 |
| HC | CATTGT | 1086.40 | 673 | 0.619 | −0.479 |
| HC | CATTGC | 1289.82 | 634 | 0.492 | −0.710 |
| HD | CATGAT | 1329.76 | 2349 | 1.766 | 0.569 |
| HD | CATGAC | 1502.11 | 2329 | 1.550 | 0.439 |
| HD | CACGAC | 2071.40 | 1343 | 0.648 | −0.433 |
| HD | CACGAT | 1833.73 | 716 | 0.390 | −0.940 |
| HE | CATGAA | 1769.46 | 3512 | 1.985 | 0.686 |
| HE | CATGAG | 2366.33 | 3307 | 1.398 | 0.335 |
| HE | CACGAG | 3263.15 | 2230 | 0.683 | −0.381 |
| HE | CACGAA | 2440.07 | 790 | 0.324 | −1.128 |
| HF | CACTTC | 2538.66 | 3116 | 1.227 | 0.205 |
| HF | CATTTT | 1608.41 | 1806 | 1.123 | 0.116 |
| HF | CACTTT | 2217.98 | 1884 | 0.849 | −0.163 |
| HF | CATTTC | 1840.95 | 1400 | 0.760 | −0.274 |
| HG | CATGGA | 1246.72 | 2238 | 1.795 | 0.585 |
| HG | CATGGT | 807.15 | 1426 | 1.767 | 0.569 |
| HG | CATGGG | 1217.11 | 1849 | 1.519 | 0.418 |
| HG | CATGGC | 1690.37 | 2320 | 1.372 | 0.317 |
| HG | CACGGC | 2331.01 | 1680 | 0.721 | −0.328 |
| HG | CACGGG | 1678.38 | 1184 | 0.705 | −0.349 |
| HG | CACGGT | 1113.05 | 468 | 0.420 | −0.866 |
| HG | CACGGA | 1719.21 | 638 | 0.371 | −0.991 |
| HH | CACCAC | 2269.33 | 2795 | 1.232 | 0.208 |
| HH | CATCAT | 1193.37 | 1250 | 1.047 | 0.046 |

-continued

| AA pair | Codon pair | Expected | Observed | Observed/ Expected | CPS |
|---|---|---|---|---|---|
| HH | CACCAT | 1645.65 | 1453 | 0.883 | −0.125 |
| HH | CATCAC | 1645.65 | 1256 | 0.763 | −0.270 |
| HI | CACATC | 2433.52 | 3538 | 1.454 | 0.374 |
| HI | CACATT | 1924.40 | 1924 | 1.000 | 0.000 |
| HI | CACATA | 885.05 | 867 | 0.980 | −0.021 |
| HI | CATATT | 1395.51 | 1260 | 0.903 | −0.102 |
| HI | CATATA | 641.81 | 552 | 0.860 | −0.151 |
| HI | CATATC | 1764.71 | 904 | 0.512 | −0.669 |
| HK | CACAAG | 3102.81 | 3928 | 1.266 | 0.236 |
| HK | CACAAA | 2395.79 | 2432 | 1.015 | 0.015 |
| HK | CATAAA | 1737.35 | 1690 | 0.973 | −0.028 |
| HK | CATAAG | 2250.06 | 1436 | 0.638 | −0.449 |
| HL | CATTTA | 707.71 | 1053 | 1.488 | 0.397 |
| HL | CATTTG | 1188.90 | 1485 | 1.249 | 0.222 |
| HL | CACCTG | 5042.69 | 6030 | 1.196 | 0.179 |
| HL | CACCTC | 2426.56 | 2850 | 1.175 | 0.161 |
| HL | CATCTT | 1213.36 | 1409 | 1.161 | 0.149 |
| HL | CACTTG | 1639.48 | 1700 | 1.037 | 0.036 |
| HL | CATCTA | 654.36 | 649 | 0.992 | −0.008 |
| HL | CACCTT | 1673.21 | 1499 | 0.896 | −0.110 |
| HL | CACCTA | 902.35 | 761 | 0.843 | −0.170 |
| HL | CATCTC | 1759.66 | 1422 | 0.808 | −0.213 |
| HL | CACTTA | 975.93 | 781 | 0.800 | −0.223 |
| HL | CATCTG | 3656.80 | 2202 | 0.602 | −0.507 |
| HM | CACATG | 2348.18 | 3023 | 1.287 | 0.253 |
| HM | CATATG | 1702.82 | 1028 | 0.604 | −0.505 |
| HN | CACAAC | 2031.88 | 2762 | 1.359 | 0.307 |
| HN | CACAAT | 1844.85 | 1832 | 0.993 | −0.007 |
| HN | CATAAT | 1337.83 | 1225 | 0.916 | −0.088 |
| HN | CATAAC | 1473.45 | 869 | 0.590 | −0.528 |
| HP | CACCCG | 846.94 | 1341 | 1.583 | 0.460 |
| HP | CATCCT | 1518.15 | 1770 | 1.166 | 0.153 |
| HP | CACCCC | 2337.46 | 2530 | 1.082 | 0.079 |
| HP | CATCCA | 1465.21 | 1577 | 1.076 | 0.074 |
| HP | CACCCA | 2020.51 | 1919 | 0.950 | −0.052 |
| HP | CACCCT | 2093.51 | 1859 | 0.888 | −0.119 |
| HP | CATCCC | 1695.05 | 1265 | 0.746 | −0.293 |
| HP | CATCCG | 614.18 | 330 | 0.537 | −0.621 |
| HQ | CATCAA | 1143.96 | 1358 | 1.187 | 0.172 |
| HQ | CACCAG | 4405.09 | 4761 | 1.081 | 0.078 |
| HQ | CATCAG | 3194.43 | 2957 | 0.926 | −0.077 |
| HQ | CACCAA | 1577.51 | 1245 | 0.789 | −0.237 |
| HR | CACAGG | 1447.19 | 1936 | 1.338 | 0.291 |
| HR | CACCGC | 1336.44 | 1772 | 1.326 | 0.282 |
| HR | CACAGA | 1474.12 | 1788 | 1.213 | 0.193 |
| HR | CACCGG | 1461.67 | 1772 | 1.212 | 0.193 |
| HR | CACCGT | 572.18 | 667 | 1.166 | 0.153 |
| HR | CATCGA | 574.58 | 627 | 1.091 | 0.087 |
| HR | CATCGT | 414.93 | 452 | 1.089 | 0.086 |
| HR | CACCGA | 792.34 | 855 | 1.079 | 0.076 |
| HR | CATCGG | 1059.96 | 729 | 0.688 | −0.374 |
| HR | CATAGA | 1068.98 | 635 | 0.594 | −0.521 |
| HR | CATCGC | 969.15 | 565 | 0.583 | −0.540 |
| HR | CATAGG | 1049.46 | 423 | 0.403 | −0.909 |
| HS | CACTCG | 551.81 | 880 | 1.595 | 0.467 |
| HS | CACAGC | 2364.16 | 3726 | 1.576 | 0.455 |
| HS | CACAGT | 1491.56 | 1957 | 1.312 | 0.272 |
| HS | CATTCA | 1064.20 | 1307 | 1.228 | 0.206 |
| HS | CATTCT | 1316.36 | 1517 | 1.152 | 0.142 |
| HS | CACTCC | 2086.72 | 1964 | 0.941 | −0.061 |
| HS | CACTCA | 1467.52 | 1318 | 0.898 | −0.107 |
| HS | CATTCC | 1513.23 | 1219 | 0.806 | −0.216 |
| HS | CACTCT | 1815.24 | 1231 | 0.678 | −0.388 |
| HS | CATAGT | 1081.63 | 710 | 0.656 | −0.421 |
| HS | CATTCG | 400.16 | 256 | 0.640 | −0.447 |
| HS | CATAGC | 1714.41 | 782 | 0.456 | −0.785 |
| HT | CACACG | 778.62 | 1526 | 1.960 | 0.673 |
| HT | CACACT | 1696.86 | 2036 | 1.200 | 0.182 |
| HT | CACACA | 1918.82 | 2255 | 1.175 | 0.161 |
| HT | CACACC | 2370.26 | 2537 | 1.070 | 0.068 |
| HT | CATACT | 1230.51 | 1306 | 1.061 | 0.060 |
| HT | CATACA | 1391.46 | 979 | 0.704 | −0.352 |
| HT | CATACC | 1718.84 | 806 | 0.469 | −0.757 |
| HT | CATACG | 564.63 | 225 | 0.398 | −0.920 |
| HV | CATGTT | 869.32 | 1563 | 1.798 | 0.587 |
| HV | CATGTA | 564.48 | 880 | 1.559 | 0.444 |

-continued

| AA pair | Codon pair | Expected | Observed | Observed/ Expected | CPS |
|---|---|---|---|---|---|
| HV | CATGTC | 1113.00 | 1607 | 1.444 | 0.367 |
| HV | CATGTG | 2201.86 | 2797 | 1.270 | 0.239 |
| HV | CACGTG | 3036.34 | 2579 | 0.849 | −0.163 |
| HV | CACGTC | 1534.82 | 1158 | 0.754 | −0.282 |
| HV | CACGTT | 1198.78 | 434 | 0.362 | −1.016 |
| HV | CACGTA | 778.41 | 279 | 0.358 | −1.026 |
| HW | CACTGG | 1602.74 | 2197 | 1.371 | 0.315 |
| HW | CATTGG | 1162.26 | 568 | 0.489 | −0.716 |
| HY | CACTAC | 1943.40 | 2385 | 1.227 | 0.205 |
| HY | CATTAT | 1145.15 | 1240 | 1.083 | 0.080 |
| HY | CACTAT | 1579.16 | 1378 | 0.873 | −0.136 |
| HY | CATTAC | 1409.29 | 1074 | 0.762 | −0.272 |
| IA | ATTGCT | 1886.56 | 3678 | 1.950 | 0.668 |
| IA | ATAGCA | 759.54 | 1446 | 1.904 | 0.644 |
| IA | ATTGCA | 1651.49 | 2818 | 1.706 | 0.534 |
| IA | ATAGCT | 867.65 | 1289 | 1.486 | 0.396 |
| IA | ATTGCC | 2868.63 | 3435 | 1.197 | 0.180 |
| IA | ATAGCC | 1319.32 | 1191 | 0.903 | −0.102 |
| IA | ATCGCG | 980.82 | 708 | 0.722 | −0.326 |
| IA | ATCGCC | 3627.56 | 2570 | 0.708 | −0.345 |
| IA | ATTGCG | 775.62 | 494 | 0.637 | −0.451 |
| IA | ATAGCG | 356.72 | 198 | 0.555 | −0.589 |
| IA | ATCGCA | 2088.41 | 831 | 0.398 | −0.922 |
| IA | ATCGCT | 2385.67 | 910 | 0.381 | −0.964 |
| IC | ATCTGC | 2115.05 | 3055 | 1.444 | 0.368 |
| IC | ATCTGT | 1781.48 | 2074 | 1.164 | 0.152 |
| IC | ATATGT | 647.91 | 731 | 1.128 | 0.121 |
| IC | ATTTGT | 1408.77 | 1197 | 0.850 | −0.163 |
| IC | ATATGC | 769.23 | 470 | 0.611 | −0.493 |
| IC | ATTTGC | 1672.56 | 868 | 0.519 | −0.656 |
| ID | ATTGAT | 2604.76 | 4341 | 1.667 | 0.511 |
| ID | ATAGAT | 1197.96 | 1947 | 1.625 | 0.486 |
| ID | ATTGAC | 2942.37 | 3938 | 1.338 | 0.291 |
| ID | ATAGAC | 1353.23 | 1476 | 1.091 | 0.087 |
| ID | ATCGAC | 3720.81 | 2270 | 0.610 | −0.494 |
| ID | ATCGAT | 3293.87 | 1141 | 0.346 | −1.060 |
| IE | ATAGAA | 1371.51 | 2939 | 2.143 | 0.762 |
| IE | ATTGAA | 2982.12 | 5518 | 1.850 | 0.615 |
| IE | ATTGAG | 3988.04 | 4634 | 1.162 | 0.150 |
| IE | ATAGAG | 1834.15 | 1898 | 1.035 | 0.034 |
| IE | ATCGAG | 5043.12 | 3007 | 0.596 | −0.517 |
| IE | ATCGAA | 3771.07 | 994 | 0.264 | −1.333 |
| IF | ATATTT | 1144.73 | 1929 | 1.685 | 0.522 |
| IF | ATCTTC | 3602.60 | 4836 | 1.342 | 0.294 |
| IF | ATTTTT | 2489.02 | 2226 | 0.894 | −0.112 |
| IF | ATCTTT | 3147.52 | 2779 | 0.883 | −0.125 |
| IF | ATATTC | 1310.24 | 886 | 0.676 | −0.391 |
| IF | ATTTTC | 2848.89 | 1887 | 0.662 | −0.412 |
| IG | ATTGGT | 1013.16 | 2102 | 2.075 | 0.730 |
| IG | ATTGGA | 1564.91 | 3151 | 2.014 | 0.700 |
| IG | ATAGGA | 719.72 | 1054 | 1.464 | 0.381 |
| IG | ATTGGG | 1527.75 | 2144 | 1.403 | 0.339 |
| IG | ATAGGT | 465.96 | 596 | 1.279 | 0.246 |
| IG | ATTGGC | 2121.81 | 2706 | 1.275 | 0.243 |
| IG | ATAGGG | 702.63 | 549 | 0.781 | −0.247 |
| IG | ATAGGC | 975.84 | 700 | 0.717 | −0.332 |
| IG | ATCGGG | 1931.93 | 1244 | 0.644 | −0.440 |
| IG | ATCGGC | 2683.15 | 1619 | 0.603 | −0.505 |
| IG | ATCGGT | 1281.20 | 498 | 0.389 | −0.945 |
| IG | ATCGGA | 1978.93 | 604 | 0.305 | −1.187 |
| IH | ATTCAT | 1622.93 | 2242 | 1.381 | 0.323 |
| IH | ATCCAC | 2830.09 | 3367 | 1.190 | 0.174 |
| IH | ATACAT | 746.40 | 760 | 1.018 | 0.018 |
| IH | ATCCAT | 2052.29 | 1814 | 0.884 | −0.123 |
| IH | ATTCAC | 2238.00 | 1778 | 0.794 | −0.230 |
| IH | ATACAC | 1029.28 | 558 | 0.542 | −0.612 |
| II | ATCATC | 3797.03 | 5979 | 1.575 | 0.454 |
| II | ATAATA | 502.24 | 700 | 1.394 | 0.332 |
| II | ATAATT | 1092.04 | 1309 | 1.199 | 0.181 |
| II | ATCATT | 3002.64 | 3321 | 1.106 | 0.101 |
| II | ATTATT | 2374.46 | 2157 | 0.908 | −0.096 |
| II | ATCATA | 1380.95 | 1183 | 0.857 | −0.155 |
| II | ATTATA | 1092.04 | 921 | 0.843 | −0.170 |
| II | ATAATC | 1380.95 | 715 | 0.518 | −0.658 |
| II | ATTATC | 3002.64 | 1340 | 0.446 | −0.807 |
| IK | ATAAAA | 1419.09 | 2244 | 1.581 | 0.458 |
| IK | ATCAAG | 5053.39 | 5884 | 1.164 | 0.152 |
| IK | ATAAAG | 1837.88 | 1943 | 1.057 | 0.056 |
| IK | ATTAAA | 3085.58 | 3107 | 1.007 | 0.007 |
| IK | ATCAAA | 3901.90 | 3830 | 0.982 | −0.019 |
| IK | ATTAAG | 3996.16 | 2286 | 0.572 | −0.559 |
| IL | ATTTTA | 977.08 | 1679 | 1.718 | 0.541 |
| IL | ATATTA | 449.37 | 723 | 1.609 | 0.476 |
| IL | ATTTTG | 1641.41 | 2339 | 1.425 | 0.354 |
| IL | ATTCTT | 1675.18 | 2271 | 1.356 | 0.304 |
| IL | ATCCTC | 3072.14 | 4017 | 1.308 | 0.268 |
| IL | ATCCTG | 6384.29 | 7754 | 1.215 | 0.194 |
| IL | ATTCTA | 903.41 | 1021 | 1.130 | 0.122 |
| IL | ATCTTG | 2075.66 | 2250 | 1.084 | 0.081 |
| IL | ATCCTA | 1142.42 | 1170 | 1.024 | 0.024 |
| IL | ATACTA | 415.49 | 416 | 1.001 | 0.001 |
| IL | ATCCTT | 2118.37 | 2058 | 0.972 | −0.029 |
| IL | ATATTG | 754.90 | 717 | 0.950 | −0.052 |
| IL | ATACTT | 770.44 | 726 | 0.942 | −0.059 |
| IL | ATCTTA | 1235.57 | 1077 | 0.872 | −0.137 |
| IL | ATTCTC | 2429.41 | 1918 | 0.789 | −0.236 |
| IL | ATTCTG | 5048.62 | 3005 | 0.595 | −0.519 |
| IL | ATACTC | 1117.32 | 458 | 0.410 | −0.892 |
| IL | ATACTG | 2321.92 | 934 | 0.402 | −0.911 |
| IM | ATCATG | 3206.80 | 4314 | 1.345 | 0.297 |
| IM | ATAATG | 1166.29 | 1196 | 1.025 | 0.025 |
| IM | ATTATG | 2535.90 | 1399 | 0.552 | −0.595 |
| IN | ATAAAT | 1088.42 | 1649 | 1.515 | 0.415 |
| IN | ATCAAC | 3296.07 | 4599 | 1.395 | 0.333 |
| IN | ATCAAT | 2992.68 | 2890 | 0.966 | −0.035 |
| IN | ATAAAC | 1198.76 | 1113 | 0.928 | −0.074 |
| IN | ATTAAT | 2366.58 | 1967 | 0.831 | −0.185 |
| IN | ATTAAC | 2606.49 | 1331 | 0.511 | −0.672 |
| IP | ATTCCT | 2051.78 | 2787 | 1.358 | 0.306 |
| IP | ATTCCA | 1980.23 | 2644 | 1.335 | 0.289 |
| IP | ATACCA | 910.73 | 1047 | 1.150 | 0.139 |
| IP | ATCCCC | 2896.94 | 3229 | 1.115 | 0.109 |
| IP | ATACCT | 943.64 | 995 | 1.054 | 0.053 |
| IP | ATCCCG | 1049.66 | 1073 | 1.022 | 0.022 |
| IP | ATCCCA | 2504.13 | 2366 | 0.945 | −0.057 |
| IP | ATCCCT | 2594.61 | 2451 | 0.945 | −0.057 |
| IP | ATTCCC | 2290.86 | 1775 | 0.775 | −0.255 |
| IP | ATACCC | 1053.60 | 610 | 0.579 | −0.547 |
| IP | ATTCCG | 830.06 | 386 | 0.465 | −0.766 |
| IP | ATACCG | 381.76 | 125 | 0.327 | −1.116 |
| IQ | ATACAA | 765.47 | 950 | 1.241 | 0.216 |
| IQ | ATTCAA | 1664.38 | 2045 | 1.229 | 0.206 |
| IQ | ATCCAG | 5877.26 | 6881 | 1.171 | 0.158 |
| IQ | ATTCAG | 4647.67 | 3987 | 0.858 | −0.153 |
| IQ | ATCCAA | 2104.71 | 1765 | 0.839 | −0.176 |
| IQ | ATACAG | 2137.52 | 1569 | 0.734 | −0.309 |
| IR | ATCCGC | 1552.18 | 2623 | 1.690 | 0.525 |
| IR | ATTCGA | 727.72 | 1142 | 1.569 | 0.451 |
| IR | ATCCGA | 920.25 | 1434 | 1.558 | 0.444 |
| IR | ATCCGT | 664.55 | 943 | 1.419 | 0.350 |
| IR | ATAAGA | 622.67 | 877 | 1.408 | 0.342 |
| IR | ATCCGG | 1697.63 | 2265 | 1.334 | 0.288 |
| IR | ATTCGT | 525.51 | 677 | 1.288 | 0.253 |
| IR | ATCAGA | 1712.09 | 1680 | 0.981 | −0.019 |
| IR | ATCAGG | 1680.81 | 1513 | 0.900 | −0.105 |
| IR | ATAAGG | 611.30 | 547 | 0.895 | −0.111 |
| IR | ATACGT | 241.69 | 213 | 0.881 | −0.126 |
| IR | ATACGA | 334.69 | 292 | 0.872 | −0.136 |
| IR | ATTCGG | 1342.46 | 907 | 0.676 | −0.392 |
| IR | ATTAGA | 1353.90 | 900 | 0.665 | −0.408 |
| IR | ATTCGC | 1227.45 | 780 | 0.635 | −0.453 |
| IR | ATACGG | 617.42 | 260 | 0.421 | −0.865 |
| IR | ATTAGG | 1329.16 | 503 | 0.378 | −0.972 |
| IR | ATACGC | 564.52 | 170 | 0.301 | −1.200 |
| IS | ATCTCC | 2689.59 | 3743 | 1.392 | 0.330 |
| IS | ATATCA | 687.92 | 954 | 1.387 | 0.327 |
| IS | ATCAGC | 3047.17 | 3998 | 1.312 | 0.272 |
| IS | ATTTCT | 1850.19 | 2423 | 1.310 | 0.270 |
| IS | ATTTCA | 1495.77 | 1957 | 1.308 | 0.269 |
| IS | ATCAGT | 1922.48 | 2287 | 1.190 | 0.174 |
| IS | ATATCT | 850.92 | 1012 | 1.189 | 0.173 |
| IS | ATCTCG | 711.23 | 773 | 1.087 | 0.083 |

-continued

| AA pair | Codon pair | Expected | Observed | Observed/ Expected | CPS |
|---|---|---|---|---|---|
| IS | ATAAGT | 699.19 | 695 | 0.994 | −0.006 |
| IS | ATCTCT | 2339.68 | 2317 | 0.990 | −0.010 |
| IS | ATCTCA | 1891.49 | 1767 | 0.934 | −0.068 |
| IS | ATTTCC | 2126.89 | 1795 | 0.844 | −0.170 |
| IS | ATATCC | 978.18 | 703 | 0.719 | −0.330 |
| IS | ATTAGT | 1520.28 | 906 | 0.596 | −0.518 |
| IS | ATAAGC | 1108.24 | 636 | 0.574 | −0.555 |
| IS | ATATCG | 258.67 | 132 | 0.510 | −0.673 |
| IS | ATTTCG | 562.43 | 255 | 0.453 | −0.791 |
| IS | ATTAGC | 2409.67 | 797 | 0.331 | −1.106 |
| IT | ATCACC | 3094.94 | 4722 | 1.526 | 0.422 |
| IT | ATCACG | 1016.68 | 1306 | 1.285 | 0.250 |
| IT | ATAACT | 805.82 | 1009 | 1.252 | 0.225 |
| IT | ATCACT | 2215.66 | 2751 | 1.242 | 0.216 |
| IT | ATCACA | 2505.48 | 2989 | 1.193 | 0.176 |
| IT | ATAACA | 911.22 | 1079 | 1.184 | 0.169 |
| IT | ATTACT | 1752.12 | 1369 | 0.781 | −0.247 |
| IT | ATTACA | 1981.30 | 1531 | 0.773 | −0.258 |
| IT | ATAACC | 1125.61 | 741 | 0.658 | −0.418 |
| IT | ATAACG | 369.76 | 204 | 0.552 | −0.595 |
| IT | ATTACC | 2447.44 | 1083 | 0.443 | −0.815 |
| IT | ATTACG | 803.98 | 246 | 0.306 | −1.184 |
| IV | ATTGTT | 1261.28 | 2414 | 1.914 | 0.649 |
| IV | ATTGTA | 819.00 | 1478 | 1.805 | 0.590 |
| IV | ATAGTA | 376.67 | 645 | 1.712 | 0.538 |
| IV | ATAGTT | 580.08 | 877 | 1.512 | 0.413 |
| IV | ATTGTC | 1614.84 | 2315 | 1.434 | 0.360 |
| IV | ATTGTG | 3194.65 | 3762 | 1.178 | 0.163 |
| IV | ATCGTC | 2042.07 | 1679 | 0.822 | −0.196 |
| IV | ATAGTG | 1469.26 | 1196 | 0.814 | −0.206 |
| IV | ATAGTC | 742.69 | 575 | 0.774 | −0.256 |
| IV | ATCGTG | 4039.83 | 2922 | 0.723 | −0.324 |
| IV | ATCGTA | 1035.67 | 361 | 0.349 | −1.054 |
| IV | ATCGTT | 1594.97 | 547 | 0.343 | −1.070 |
| IW | ATCTGG | 1887.23 | 2427 | 1.286 | 0.252 |
| IW | ATATGG | 686.37 | 622 | 0.906 | −0.098 |
| IW | ATTTGG | 1492.40 | 1017 | 0.681 | −0.384 |
| IY | ATCTAC | 2708.47 | 3486 | 1.287 | 0.252 |
| IY | ATATAT | 800.43 | 953 | 1.191 | 0.174 |
| IY | ATTTAT | 1740.39 | 1984 | 1.140 | 0.131 |
| IY | ATCTAT | 2200.83 | 2196 | 0.998 | −0.002 |
| IY | ATTTAC | 2141.83 | 1403 | 0.655 | −0.423 |
| IY | ATATAC | 985.05 | 555 | 0.563 | −0.574 |
| KA | AAAGCA | 3029.93 | 4322 | 1.426 | 0.355 |
| KA | AAAGCT | 3461.21 | 4262 | 1.231 | 0.208 |
| KA | AAGGCC | 6816.15 | 6676 | 0.979 | −0.021 |
| KA | AAGGCG | 1842.96 | 1790 | 0.971 | −0.029 |
| KA | AAGGCA | 3924.10 | 3654 | 0.931 | −0.071 |
| KA | AAAGCC | 5262.99 | 4742 | 0.901 | −0.104 |
| KA | AAGGCT | 4482.65 | 4032 | 0.899 | −0.106 |
| KA | AAAGCG | 1423.01 | 765 | 0.538 | −0.621 |
| KC | AAATGT | 1815.55 | 2671 | 1.471 | 0.386 |
| KC | AAGTGT | 2351.33 | 2267 | 0.964 | −0.037 |
| KC | AAGTGC | 2791.62 | 2498 | 0.895 | −0.111 |
| KC | AAATGC | 2155.50 | 1678 | 0.778 | −0.250 |
| KD | AAAGAT | 4684.00 | 6115 | 1.306 | 0.267 |
| KD | AAGGAC | 6852.58 | 6836 | 0.998 | −0.002 |
| KD | AAGGAT | 6066.30 | 5379 | 0.887 | −0.120 |
| KD | AAAGAC | 5291.12 | 4564 | 0.863 | −0.148 |
| KE | AAAGAA | 6989.41 | 9895 | 1.416 | 0.348 |
| KE | AAGGAG | 12105.47 | 12287 | 1.015 | 0.015 |
| KE | AAGGAA | 9052.06 | 8366 | 0.924 | −0.079 |
| KE | AAAGAG | 9347.06 | 6946 | 0.743 | −0.297 |
| KF | AAATTT | 2631.62 | 3140 | 1.193 | 0.177 |
| KF | AAGTTT | 3408.25 | 3638 | 1.067 | 0.065 |
| KF | AAGTTC | 3901.02 | 3950 | 1.013 | 0.012 |
| KF | AAATTC | 3012.11 | 2225 | 0.739 | −0.303 |
| KG | AAAGGA | 2672.15 | 4509 | 1.687 | 0.523 |
| KG | AAAGGT | 1730.00 | 2402 | 1.388 | 0.328 |
| KG | AAAGGC | 3623.06 | 3435 | 0.948 | −0.053 |
| KG | AAAGGG | 2608.69 | 2465 | 0.945 | −0.057 |
| KG | AAGGGC | 4692.27 | 4309 | 0.918 | −0.085 |
| KG | AAGGGT | 2240.55 | 1978 | 0.883 | −0.125 |
| KG | AAGGGG | 3378.54 | 2740 | 0.811 | −0.209 |
| KG | AAGGGA | 3460.73 | 2568 | 0.742 | −0.298 |
| KH | AAACAT | 1929.29 | 2356 | 1.221 | 0.200 |
| KH | AAGCAC | 3445.60 | 3583 | 1.040 | 0.039 |
| KH | AAGCAT | 2498.64 | 2430 | 0.973 | −0.028 |
| KH | AAACAC | 2660.47 | 2165 | 0.814 | −0.206 |
| KI | AAAATA | 1547.96 | 2667 | 1.723 | 0.544 |
| KI | AAAATT | 3365.76 | 3894 | 1.157 | 0.146 |
| KI | AAGATC | 5512.26 | 5523 | 1.002 | 0.002 |
| KI | AAGATA | 2004.77 | 1943 | 0.969 | −0.031 |
| KI | AAGATT | 4359.03 | 3732 | 0.856 | −0.155 |
| KI | AAAATC | 4256.21 | 3287 | 0.772 | −0.258 |
| KK | AAGAAG | 11070.03 | 13815 | 1.248 | 0.222 |
| KK | AAGAAA | 8547.55 | 10129 | 1.185 | 0.170 |
| KK | AAAAAG | 8547.55 | 6145 | 0.719 | −0.330 |
| KK | AAAAAA | 6599.86 | 4676 | 0.708 | −0.345 |
| KL | AAATTA | 1273.72 | 2084 | 1.636 | 0.492 |
| KL | AAACTA | 1177.70 | 1750 | 1.486 | 0.396 |
| KL | AAACTT | 2183.78 | 3014 | 1.380 | 0.322 |
| KL | AAGCTG | 8523.68 | 9600 | 1.126 | 0.119 |
| KL | AAGCTA | 1525.25 | 1660 | 1.088 | 0.085 |
| KL | AAGCTC | 4101.62 | 4076 | 0.994 | −0.006 |
| KL | AAATTG | 2139.75 | 2113 | 0.987 | −0.013 |
| KL | AAGCTT | 2828.24 | 2772 | 0.980 | −0.020 |
| KL | AAGTTA | 1649.61 | 1459 | 0.884 | −0.123 |
| KL | AAACTC | 3167.00 | 2653 | 0.838 | −0.177 |
| KL | AAGTTG | 2771.21 | 2280 | 0.823 | −0.195 |
| KL | AAACTG | 6581.43 | 4462 | 0.678 | −0.389 |
| KM | AAGATG | 5479.27 | 5650 | 1.031 | 0.031 |
| KM | AAAATG | 4230.73 | 4060 | 0.960 | −0.041 |
| KN | AAAAAT | 3683.47 | 4378 | 1.189 | 0.173 |
| KN | AAGAAC | 5254.13 | 5515 | 1.050 | 0.048 |
| KN | AAGAAT | 4770.51 | 4618 | 0.968 | −0.032 |
| KN | AAAAAC | 4056.89 | 3254 | 0.802 | −0.221 |
| KP | AAACCA | 2803.51 | 3370 | 1.202 | 0.184 |
| KP | AAGCCC | 4200.41 | 4673 | 1.113 | 0.107 |
| KP | AAGCCA | 3630.85 | 4035 | 1.111 | 0.106 |
| KP | AAACCT | 2904.80 | 3118 | 1.073 | 0.071 |
| KP | AAGCCG | 1521.96 | 1544 | 1.014 | 0.014 |
| KP | AAGCCT | 3762.04 | 3396 | 0.903 | −0.102 |
| KP | AAACCC | 3243.28 | 2624 | 0.809 | −0.212 |
| KP | AAACCG | 1175.16 | 482 | 0.410 | −0.891 |
| KQ | AAACAA | 2178.87 | 3274 | 1.503 | 0.407 |
| KQ | AAGCAA | 2821.88 | 3177 | 1.126 | 0.119 |
| KQ | AAGCAG | 7879.90 | 8081 | 1.026 | 0.025 |
| KQ | AAACAG | 6084.35 | 4433 | 0.729 | −0.317 |
| KR | AAAAGA | 2247.57 | 3147 | 1.400 | 0.337 |
| KR | AAGAGG | 2857.67 | 3975 | 1.391 | 0.330 |
| KR | AAGAGA | 2910.85 | 3511 | 1.206 | 0.187 |
| KR | AAAAGG | 2206.51 | 2325 | 1.054 | 0.052 |
| KR | AAACGT | 872.39 | 862 | 0.988 | −0.012 |
| KR | AAGCGG | 2886.27 | 2828 | 0.980 | −0.020 |
| KR | AAGCGC | 2638.99 | 2532 | 0.959 | −0.041 |
| KR | AAACGA | 1208.07 | 1087 | 0.900 | −0.106 |
| KR | AAGCGT | 1129.84 | 978 | 0.866 | −0.144 |
| KR | AAGCGA | 1564.59 | 1325 | 0.847 | −0.166 |
| KR | AAACGG | 2228.59 | 1178 | 0.529 | −0.638 |
| KR | AAACGC | 2037.65 | 1041 | 0.511 | −0.672 |
| KS | AAATCA | 1871.14 | 2533 | 1.354 | 0.303 |
| KS | AAAAGT | 1901.80 | 2389 | 1.256 | 0.228 |
| KS | AAATCT | 2314.50 | 2793 | 1.207 | 0.188 |
| KS | AAGTCA | 2423.33 | 2566 | 1.059 | 0.057 |
| KS | AAGAGC | 3903.97 | 4045 | 1.036 | 0.035 |
| KS | AAGAGT | 2463.04 | 2459 | 0.998 | −0.002 |
| KS | AAGTCG | 911.22 | 904 | 0.992 | −0.008 |
| KS | AAGTCC | 3445.84 | 3100 | 0.900 | −0.106 |
| KS | AAGTCT | 2997.54 | 2675 | 0.892 | −0.114 |
| KS | AAATCC | 2660.65 | 2304 | 0.866 | −0.144 |
| KS | AAAAGC | 3014.39 | 2381 | 0.790 | −0.236 |
| KS | AAATCG | 703.58 | 462 | 0.657 | −0.421 |
| KT | AAAACA | 2831.74 | 3611 | 1.275 | 0.243 |
| KT | AAGACG | 1488.17 | 1790 | 1.203 | 0.185 |
| KT | AAAACT | 2504.18 | 2969 | 1.186 | 0.170 |
| KT | AAGACC | 4530.26 | 4475 | 0.988 | −0.012 |
| KT | AAGACA | 3667.42 | 3574 | 0.975 | −0.026 |
| KT | AAGACT | 3243.20 | 2876 | 0.887 | −0.120 |
| KT | AAAACC | 3497.97 | 2854 | 0.816 | −0.203 |
| KT | AAAACG | 1149.07 | 763 | 0.664 | −0.409 |
| KV | AAAGTA | 1317.00 | 2214 | 1.681 | 0.519 |

-continued

| AA pair | Codon pair | Expected | Observed | Observed/ Expected | CPS |
|---|---|---|---|---|---|
| KV | AAAGTT | 2028.22 | 3042 | 1.500 | 0.405 |
| KV | AAAGTC | 2596.78 | 2642 | 1.017 | 0.017 |
| KV | AAGGTG | 6653.25 | 6512 | 0.979 | −0.021 |
| KV | AAGGTC | 3363.11 | 3016 | 0.897 | −0.109 |
| KV | AAGGTT | 2626.77 | 2294 | 0.873 | −0.135 |
| KV | AAAGTG | 5137.21 | 4417 | 0.860 | −0.151 |
| KV | AAGGTA | 1705.66 | 1291 | 0.757 | −0.279 |
| KW | AAGTGG | 2598.56 | 2701 | 1.039 | 0.039 |
| KW | AAATGG | 2006.44 | 1904 | 0.949 | −0.052 |
| KY | AAATAT | 2319.32 | 2982 | 1.286 | 0.251 |
| KY | AAGTAC | 3696.62 | 3603 | 0.975 | −0.026 |
| KY | AAATAC | 2854.29 | 2763 | 0.968 | −0.033 |
| KY | AAGTAT | 3003.78 | 2526 | 0.841 | −0.173 |
| LA | CTGGCG | 2275.39 | 3643 | 1.601 | 0.471 |
| LA | TTGGCA | 1575.16 | 2350 | 1.492 | 0.400 |
| LA | CTGGCC | 8415.49 | 12456 | 1.480 | 0.392 |
| LA | TTGGCT | 1799.36 | 2643 | 1.469 | 0.384 |
| LA | TTAGCA | 937.64 | 1314 | 1.401 | 0.337 |
| LA | CTTGCT | 1836.39 | 2345 | 1.277 | 0.244 |
| LA | CTAGCA | 866.95 | 1107 | 1.277 | 0.244 |
| LA | CTTGCA | 1607.57 | 1861 | 1.158 | 0.146 |
| LA | TTAGCT | 1071.10 | 1239 | 1.157 | 0.146 |
| LA | CTGGCT | 5534.46 | 6333 | 1.144 | 0.135 |
| LA | CTAGCT | 990.35 | 1099 | 1.110 | 0.104 |
| LA | CTGGCA | 4844.85 | 5013 | 1.035 | 0.034 |
| LA | TTGGCC | 2736.04 | 2824 | 1.032 | 0.032 |
| LA | TTGGCG | 739.77 | 623 | 0.842 | −0.172 |
| LA | CTTGCC | 2792.34 | 2201 | 0.788 | −0.238 |
| LA | CTAGCC | 1505.89 | 1159 | 0.770 | −0.262 |
| LA | CTAGCG | 407.16 | 253 | 0.621 | −0.476 |
| LA | TTAGCC | 1628.68 | 941 | 0.578 | −0.549 |
| LA | CTTGCG | 755.00 | 346 | 0.458 | −0.780 |
| LA | TTAGCG | 440.36 | 198 | 0.450 | −0.799 |
| LA | CTCGCC | 4049.56 | 1527 | 0.377 | −0.975 |
| LA | CTCGCG | 1094.93 | 390 | 0.356 | −1.032 |
| LA | CTCGCT | 2663.20 | 605 | 0.227 | −1.482 |
| LA | CTCGCA | 2331.36 | 429 | 0.184 | −1.693 |
| LC | CTCTGC | 1769.27 | 3523 | 1.991 | 0.689 |
| LC | CTCTGT | 1490.23 | 2145 | 1.439 | 0.364 |
| LC | CTTTGT | 1027.58 | 1155 | 1.124 | 0.117 |
| LC | TTATGT | 599.35 | 627 | 1.046 | 0.045 |
| LC | CTGTGC | 3676.77 | 3517 | 0.957 | −0.044 |
| LC | TTGTGT | 1006.86 | 856 | 0.850 | −0.162 |
| LC | CTTTGC | 1219.99 | 974 | 0.798 | −0.225 |
| LC | CTGTGT | 3096.89 | 2370 | 0.765 | −0.268 |
| LC | CTATGT | 554.17 | 417 | 0.752 | −0.284 |
| LC | TTGTGC | 1195.39 | 722 | 0.604 | −0.504 |
| LC | TTATGC | 711.58 | 368 | 0.517 | −0.659 |
| LC | CTATGC | 657.93 | 332 | 0.505 | −0.684 |
| LD | TTGGAT | 2174.51 | 3688 | 1.696 | 0.528 |
| LD | TTAGAT | 1294.41 | 1977 | 1.527 | 0.424 |
| LD | CTGGAC | 7555.23 | 10531 | 1.394 | 0.332 |
| LD | CTAGAT | 1196.83 | 1584 | 1.323 | 0.280 |
| LD | TTGGAC | 2456.35 | 2775 | 1.130 | 0.122 |
| LD | CTTGAT | 2219.25 | 2463 | 1.110 | 0.104 |
| LD | CTGGAT | 6688.33 | 6912 | 1.033 | 0.033 |
| LD | CTAGAC | 1351.95 | 1390 | 1.028 | 0.028 |
| LD | CTTGAC | 2506.90 | 1832 | 0.731 | −0.314 |
| LD | TTAGAC | 1462.19 | 969 | 0.663 | −0.411 |
| LD | CTCGAC | 3635.60 | 981 | 0.270 | −1.310 |
| LD | CTCGAT | 3218.44 | 658 | 0.204 | −1.587 |
| LE | TTAGAA | 1739.66 | 3085 | 1.773 | 0.573 |
| LE | CTAGAA | 1608.51 | 2701 | 1.679 | 0.518 |
| LE | TTGGAA | 2922.49 | 4652 | 1.592 | 0.465 |
| LE | CTGGAG | 12021.09 | 18044 | 1.501 | 0.406 |
| LE | TTGGAG | 3908.29 | 4774 | 1.222 | 0.200 |
| LE | CTAGAG | 2151.09 | 2515 | 1.169 | 0.156 |
| LE | CTTGAA | 2982.63 | 3161 | 1.060 | 0.058 |
| LE | CTGGAA | 8988.96 | 7642 | 0.850 | −0.162 |
| LE | TTAGAG | 2326.48 | 1873 | 0.805 | −0.217 |
| LE | CTTGAG | 3988.72 | 2484 | 0.623 | −0.474 |
| LE | CTCGAG | 5784.58 | 1305 | 0.226 | −1.489 |
| LE | CTCGAA | 4325.51 | 512 | 0.118 | −2.134 |
| LF | CTCTTC | 2629.18 | 6495 | 2.470 | 0.904 |
| LF | TTATTT | 923.85 | 1405 | 1.521 | 0.419 |
| LF | CTCTTT | 2297.07 | 3446 | 1.500 | 0.406 |

-continued

| AA pair | Codon pair | Expected | Observed | Observed/ Expected | CPS |
|---|---|---|---|---|---|
| LF | CTTTTT | 1583.93 | 1937 | 1.223 | 0.201 |
| LF | CTTTTC | 1812.93 | 1936 | 1.068 | 0.066 |
| LF | CTATTT | 854.20 | 876 | 1.026 | 0.025 |
| LF | TTGTTT | 1551.99 | 1544 | 0.995 | −0.005 |
| LF | CTGTTT | 4773.59 | 2957 | 0.619 | −0.479 |
| LF | CTGTTC | 5463.77 | 3119 | 0.571 | −0.561 |
| LF | TTATTC | 1057.42 | 583 | 0.551 | −0.595 |
| LF | TTGTTC | 1776.38 | 940 | 0.529 | −0.636 |
| LF | CTATTC | 977.70 | 464 | 0.475 | −0.745 |
| LG | CTTGGA | 1534.14 | 2667 | 1.738 | 0.553 |
| LG | CTTGGT | 993.23 | 1579 | 1.590 | 0.464 |
| LG | CTGGGC | 6268.87 | 9794 | 1.562 | 0.446 |
| LG | CTAGGA | 827.35 | 1087 | 1.314 | 0.273 |
| LG | CTTGGG | 1497.70 | 1881 | 1.256 | 0.228 |
| LG | TTAGGA | 894.81 | 1114 | 1.245 | 0.219 |
| LG | CTGGGG | 4513.74 | 5602 | 1.241 | 0.216 |
| LG | TTGGGT | 973.20 | 1194 | 1.227 | 0.204 |
| LG | TTGGGA | 1503.20 | 1820 | 1.211 | 0.191 |
| LG | CTAGGT | 535.64 | 611 | 1.141 | 0.132 |
| LG | TTAGGT | 579.32 | 611 | 1.055 | 0.053 |
| LG | TTGGGG | 1467.50 | 1452 | 0.989 | −0.011 |
| LG | CTGGGT | 2993.37 | 2947 | 0.985 | −0.016 |
| LG | CTTGGC | 2080.08 | 2009 | 0.966 | −0.035 |
| LG | CTAGGG | 807.70 | 766 | 0.948 | −0.053 |
| LG | TTGGGC | 2038.13 | 1786 | 0.876 | −0.132 |
| LG | CTGGGA | 4623.54 | 4034 | 0.872 | −0.136 |
| LG | CTAGGC | 1121.77 | 940 | 0.838 | −0.177 |
| LG | TTAGGG | 873.56 | 529 | 0.606 | −0.502 |
| LG | CTCGGG | 2172.02 | 1076 | 0.495 | −0.702 |
| LG | CTCGGC | 3016.60 | 1313 | 0.435 | −0.832 |
| LG | TTAGGC | 1213.24 | 507 | 0.418 | −0.873 |
| LG | CTCGGT | 1440.42 | 365 | 0.253 | −1.373 |
| LG | CTCGGA | 2224.86 | 510 | 0.229 | −1.473 |
| LH | CTTCAT | 1127.31 | 1980 | 1.756 | 0.563 |
| LH | TTACAT | 657.52 | 935 | 1.422 | 0.352 |
| LH | CTACAT | 607.95 | 741 | 1.219 | 0.198 |
| LH | CTGCAC | 4685.05 | 5459 | 1.165 | 0.153 |
| LH | CTCCAC | 2254.46 | 2204 | 0.978 | −0.023 |
| LH | CTTCAC | 1554.55 | 1490 | 0.958 | −0.042 |
| LH | CTCCAT | 1634.86 | 1521 | 0.930 | −0.072 |
| LH | CTACAC | 838.36 | 777 | 0.927 | −0.076 |
| LH | TTGCAT | 1104.58 | 1017 | 0.921 | −0.083 |
| LH | TTGCAC | 1523.20 | 1140 | 0.748 | −0.290 |
| LH | CTGCAT | 3397.45 | 2394 | 0.705 | −0.350 |
| LH | TTACAC | 906.71 | 634 | 0.699 | −0.358 |
| LI | CTCATC | 2602.42 | 6250 | 2.402 | 0.876 |
| LI | TTAATA | 380.66 | 798 | 2.096 | 0.740 |
| LI | TTAATT | 827.68 | 1290 | 1.559 | 0.444 |
| LI | CTCATT | 2057.96 | 3117 | 1.515 | 0.415 |
| LI | CTAATA | 351.96 | 516 | 1.466 | 0.383 |
| LI | CTAATT | 765.28 | 952 | 1.244 | 0.218 |
| LI | CTTATT | 1419.05 | 1761 | 1.241 | 0.216 |
| LI | TTGATA | 639.48 | 791 | 1.237 | 0.213 |
| LI | TTGATT | 1390.44 | 1468 | 1.056 | 0.054 |
| LI | CTTATA | 652.64 | 683 | 1.047 | 0.045 |
| LI | CTCATA | 946.48 | 919 | 0.971 | −0.029 |
| LI | CTTATC | 1794.48 | 1189 | 0.663 | −0.412 |
| LI | TTGATC | 1758.29 | 1135 | 0.646 | −0.438 |
| LI | CTGATC | 5408.15 | 3356 | 0.621 | −0.477 |
| LI | CTGATT | 4276.70 | 2639 | 0.617 | −0.483 |
| LI | CTGATA | 1966.91 | 1193 | 0.607 | −0.500 |
| LI | TTAATC | 1046.66 | 633 | 0.605 | −0.503 |
| LI | CTAATC | 967.75 | 563 | 0.582 | −0.542 |
| LK | TTAAAA | 1429.91 | 2557 | 1.788 | 0.581 |
| LK | CTAAAA | 1322.10 | 1842 | 1.393 | 0.332 |
| LK | TTGAAA | 2402.12 | 3193 | 1.329 | 0.285 |
| LK | CTCAAG | 4604.55 | 6048 | 1.313 | 0.273 |
| LK | CTAAAG | 1712.27 | 2078 | 1.214 | 0.194 |
| LK | TTAAAG | 1851.89 | 2128 | 1.149 | 0.139 |
| LK | CTGAAG | 9568.82 | 10212 | 1.067 | 0.065 |
| LK | TTGAAG | 3111.01 | 3222 | 1.036 | 0.035 |
| LK | CTCAAA | 3555.33 | 2768 | 0.779 | −0.250 |
| LK | CTTAAA | 2451.55 | 1850 | 0.755 | −0.282 |
| LK | CTGAAA | 7388.42 | 5227 | 0.707 | −0.346 |
| LK | CTTAAG | 3175.03 | 1448 | 0.456 | −0.785 |
| LL | TTATTA | 500.55 | 802 | 1.602 | 0.471 |

-continued

| AA pair | Codon pair | Expected | Observed | Observed/ Expected | CPS |
|---|---|---|---|---|---|
| LL | CTTCTA | 793.49 | 1132 | 1.427 | 0.355 |
| LL | CTTCTT | 1471.36 | 2099 | 1.427 | 0.355 |
| LL | CTTTTA | 858.19 | 1203 | 1.402 | 0.338 |
| LL | CTGCTG | 13364.10 | 18236 | 1.365 | 0.311 |
| LL | CTTTTG | 1441.69 | 1945 | 1.349 | 0.299 |
| LL | TTACTA | 462.82 | 608 | 1.314 | 0.273 |
| LL | CTCCTC | 3094.54 | 3800 | 1.228 | 0.205 |
| LL | CTCCTG | 6430.85 | 7786 | 1.211 | 0.191 |
| LL | TTACTT | 858.19 | 1039 | 1.211 | 0.191 |
| LL | TTGCTA | 777.49 | 929 | 1.195 | 0.178 |
| LL | CTGCTC | 6430.85 | 7550 | 1.174 | 0.160 |
| LL | CTACTA | 427.93 | 474 | 1.108 | 0.102 |
| LL | CTTCTC | 2133.82 | 2292 | 1.074 | 0.072 |
| LL | CTACTT | 793.49 | 839 | 1.057 | 0.056 |
| LL | CTCTTG | 2090.79 | 2131 | 1.019 | 0.019 |
| LL | TTGCTT | 1441.69 | 1464 | 1.015 | 0.015 |
| LL | TTATTG | 840.89 | 818 | 0.973 | −0.028 |
| LL | CTCCTT | 2133.82 | 2034 | 0.953 | −0.048 |
| LL | TTGTTA | 840.89 | 771 | 0.917 | −0.087 |
| LL | TTGTTG | 1412.62 | 1289 | 0.912 | −0.092 |
| LL | CTCCTA | 1150.75 | 1034 | 0.899 | −0.107 |
| LL | TTGCTG | 4344.93 | 3820 | 0.879 | −0.129 |
| LL | CTTCTG | 4434.34 | 3837 | 0.865 | −0.145 |
| LL | CTGCTA | 2391.41 | 1913 | 0.800 | −0.223 |
| LL | CTCTTA | 1244.58 | 959 | 0.771 | −0.261 |
| LL | CTATTA | 462.82 | 354 | 0.765 | −0.268 |
| LL | CTGCTT | 4434.34 | 3148 | 0.710 | −0.343 |
| LL | TTGCTC | 2090.79 | 1440 | 0.689 | −0.373 |
| LL | CTACTC | 1150.75 | 792 | 0.688 | −0.374 |
| LL | CTATTG | 777.49 | 532 | 0.684 | −0.379 |
| LL | CTACTG | 2391.41 | 1583 | 0.662 | −0.413 |
| LL | CTGTTG | 4344.93 | 2615 | 0.602 | −0.508 |
| LL | TTACTC | 1244.58 | 657 | 0.528 | −0.639 |
| LL | TTACTG | 2586.40 | 1358 | 0.525 | −0.644 |
| LL | CTGTTA | 2586.40 | 953 | 0.368 | −0.998 |
| LM | CTCATG | 2631.41 | 4030 | 1.531 | 0.426 |
| LM | TTAATG | 1058.32 | 1228 | 1.160 | 0.149 |
| LM | CTAATG | 978.53 | 1101 | 1.125 | 0.118 |
| LM | TTGATG | 1777.88 | 1763 | 0.992 | −0.008 |
| LM | CTGATG | 5468.39 | 4470 | 0.817 | −0.202 |
| LM | CTTATG | 1814.47 | 1137 | 0.627 | −0.467 |
| LN | TTAAAT | 962.36 | 1926 | 2.001 | 0.694 |
| LN | CTCAAC | 2635.40 | 4681 | 1.776 | 0.574 |
| LN | CTAAAT | 889.81 | 1446 | 1.625 | 0.486 |
| LN | TTGAAT | 1616.68 | 2048 | 1.267 | 0.236 |
| LN | CTCAAT | 2392.82 | 2652 | 1.108 | 0.103 |
| LN | CTAAAC | 980.01 | 922 | 0.941 | −0.061 |
| LN | TTAAAC | 1059.92 | 965 | 0.910 | −0.094 |
| LN | CTTAAT | 1649.95 | 1441 | 0.873 | −0.135 |
| LN | TTGAAC | 1780.58 | 1541 | 0.865 | −0.145 |
| LN | CTGAAC | 5476.68 | 4308 | 0.787 | −0.240 |
| LN | CTGAAT | 4972.58 | 3413 | 0.686 | −0.376 |
| LN | CTTAAC | 1817.22 | 891 | 0.490 | −0.713 |
| LP | CTTCCT | 1728.14 | 2795 | 1.617 | 0.481 |
| LP | CTTCCA | 1667.88 | 2369 | 1.420 | 0.351 |
| LP | CTGCCC | 5815.10 | 7856 | 1.351 | 0.301 |
| LP | TTACCT | 1007.96 | 1244 | 1.234 | 0.210 |
| LP | CTGCCG | 2107.02 | 2489 | 1.181 | 0.167 |
| LP | TTACCA | 972.81 | 1140 | 1.172 | 0.159 |
| LP | CTCCCG | 1013.90 | 1184 | 1.168 | 0.155 |
| LP | TTGCCA | 1634.25 | 1897 | 1.161 | 0.149 |
| LP | CTACCT | 931.97 | 1045 | 1.121 | 0.114 |
| LP | TTGCCT | 1693.30 | 1800 | 1.063 | 0.061 |
| LP | CTTCCC | 1929.51 | 1889 | 0.979 | −0.021 |
| LP | CTACCA | 899.47 | 850 | 0.945 | −0.057 |
| LP | CTCCCA | 2418.82 | 2126 | 0.879 | −0.129 |
| LP | CTGCCT | 5208.23 | 4563 | 0.876 | −0.132 |
| LP | CTCCCT | 2506.21 | 2192 | 0.875 | −0.134 |
| LP | CTACCC | 1040.57 | 888 | 0.853 | −0.159 |
| LP | CTCCCC | 2798.25 | 2369 | 0.847 | −0.167 |
| LP | TTGCCC | 1890.60 | 1560 | 0.825 | −0.192 |
| LP | TTGCCG | 685.03 | 478 | 0.698 | −0.360 |
| LP | CTGCCA | 5026.60 | 3348 | 0.666 | −0.406 |
| LP | CTTCCG | 699.13 | 451 | 0.645 | −0.438 |
| LP | TTACCC | 1125.42 | 666 | 0.592 | −0.525 |
| LP | CTACCG | 377.04 | 211 | 0.560 | −0.580 |
| LP | TTACCG | 407.78 | 175 | 0.429 | −0.846 |
| LQ | TTACAA | 864.28 | 1290 | 1.493 | 0.401 |
| LQ | CTACAA | 799.12 | 1188 | 1.487 | 0.397 |
| LQ | CTTCAA | 1481.79 | 2098 | 1.416 | 0.348 |
| LQ | CTACAG | 2231.48 | 2674 | 1.198 | 0.181 |
| LQ | CTGCAG | 12470.36 | 14508 | 1.163 | 0.151 |
| LQ | CTTCAG | 4137.79 | 4363 | 1.054 | 0.053 |
| LQ | TTGCAA | 1451.91 | 1467 | 1.010 | 0.010 |
| LQ | CTCCAG | 6000.78 | 5430 | 0.905 | −0.100 |
| LQ | TTACAG | 2413.43 | 2107 | 0.873 | −0.136 |
| LQ | TTGCAG | 4054.36 | 3177 | 0.784 | −0.244 |
| LQ | CTCCAA | 2148.94 | 1524 | 0.709 | −0.344 |
| LQ | CTGCAA | 4465.77 | 2694 | 0.603 | −0.505 |
| LR | CTTCGA | 661.43 | 1365 | 2.064 | 0.725 |
| LR | CTTCGT | 477.64 | 784 | 1.641 | 0.496 |
| LR | CTGCGG | 3677.31 | 5467 | 1.487 | 0.397 |
| LR | TTAAGA | 717.74 | 1026 | 1.429 | 0.357 |
| LR | CTGCGC | 3362.26 | 4574 | 1.360 | 0.308 |
| LR | CTCCGA | 959.23 | 1289 | 1.344 | 0.295 |
| LR | CTCCGG | 1769.53 | 2229 | 1.260 | 0.231 |
| LR | CTAAGA | 663.63 | 821 | 1.237 | 0.213 |
| LR | CTCAGG | 1752.00 | 2047 | 1.168 | 0.156 |
| LR | CTTCGG | 1220.17 | 1415 | 1.160 | 0.148 |
| LR | CTCCGT | 692.69 | 771 | 1.113 | 0.107 |
| LR | TTACGA | 385.79 | 427 | 1.107 | 0.101 |
| LR | CTAAGG | 651.51 | 721 | 1.107 | 0.101 |
| LR | CTCCGC | 1617.93 | 1790 | 1.106 | 0.101 |
| LR | TTGAGA | 1205.75 | 1290 | 1.070 | 0.068 |
| LR | CTACGT | 257.59 | 275 | 1.068 | 0.065 |
| LR | CTACGA | 356.70 | 378 | 1.060 | 0.058 |
| LR | CTGAGG | 3640.88 | 3637 | 0.999 | −0.001 |
| LR | TTAAGG | 704.63 | 678 | 0.962 | −0.039 |
| LR | TTACGT | 278.59 | 264 | 0.948 | −0.054 |
| LR | CTGCGT | 1439.50 | 1363 | 0.947 | −0.055 |
| LR | TTGAGG | 1183.72 | 1080 | 0.912 | −0.092 |
| LR | CTACGG | 658.03 | 577 | 0.877 | −0.131 |
| LR | CTCAGA | 1784.60 | 1469 | 0.823 | −0.195 |
| LR | CTTCGC | 1115.63 | 819 | 0.734 | −0.309 |
| LR | CTACGC | 601.65 | 438 | 0.728 | −0.317 |
| LR | CTGCGA | 1993.40 | 1399 | 0.702 | −0.354 |
| LR | TTGCGT | 468.01 | 321 | 0.686 | −0.377 |
| LR | CTGAGA | 3708.63 | 2486 | 0.670 | −0.400 |
| LR | TTGCGG | 1195.56 | 772 | 0.646 | −0.437 |
| LR | TTGCGA | 648.09 | 418 | 0.645 | −0.439 |
| LR | CTTAGA | 1230.56 | 694 | 0.564 | −0.573 |
| LR | TTACGG | 711.68 | 383 | 0.538 | −0.620 |
| LR | TTGCGC | 1093.14 | 542 | 0.496 | −0.702 |
| LR | CTTAGG | 1208.08 | 503 | 0.416 | −0.876 |
| LR | TTACGC | 650.71 | 232 | 0.357 | -1.031 |
| LS | CTCAGC | 2740.30 | 5167 | 1.886 | 0.634 |
| LS | CTTTCT | 1450.83 | 2502 | 1.725 | 0.545 |
| LS | CTCTCC | 2418.72 | 4070 | 1.683 | 0.520 |
| LS | CTCTCG | 639.61 | 1016 | 1.588 | 0.463 |
| LS | CTCAGT | 1728.87 | 2589 | 1.498 | 0.404 |
| LS | TTATCA | 684.12 | 963 | 1.408 | 0.342 |
| LS | TTATCT | 846.22 | 1175 | 1.389 | 0.328 |
| LS | CTTTCA | 1172.91 | 1626 | 1.386 | 0.327 |
| LS | TTAAGT | 695.33 | 886 | 1.274 | 0.242 |
| LS | CTCTCT | 2104.05 | 2553 | 1.213 | 0.193 |
| LS | CTAAGT | 642.91 | 770 | 1.198 | 0.180 |
| LS | CTCTCA | 1701.00 | 2003 | 1.178 | 0.163 |
| LS | CTTTCC | 1667.81 | 1819 | 1.091 | 0.087 |
| LS | TTGTCA | 1149.26 | 1210 | 1.053 | 0.052 |
| LS | CTGTCG | 1329.18 | 1392 | 1.047 | 0.046 |
| LS | TTGTCT | 1421.58 | 1461 | 1.028 | 0.027 |
| LS | CTGAGC | 5694.68 | 5805 | 1.019 | 0.019 |
| LS | CTGTCC | 5026.41 | 4628 | 0.921 | −0.083 |
| LS | TTGAGT | 1168.09 | 1035 | 0.886 | −0.121 |
| LS | TTGTCC | 1634.18 | 1334 | 0.816 | −0.203 |
| LS | CTATCA | 632.54 | 512 | 0.809 | −0.211 |
| LS | CTAAGC | 1019.02 | 791 | 0.776 | −0.253 |
| LS | TTATCC | 972.78 | 727 | 0.747 | −0.291 |
| LS | CTGAGT | 3592.81 | 2665 | 0.742 | −0.299 |
| LS | CTTAGT | 1192.13 | 856 | 0.718 | −0.331 |
| LS | CTATCT | 782.42 | 557 | 0.712 | −0.340 |
| LS | CTGTCT | 4372.48 | 2950 | 0.675 | −0.394 |

-continued

| AA pair | Codon pair | Expected | Observed | Observed/ Expected | CPS |
|---|---|---|---|---|---|
| LS | CTTTCG | 441.04 | 291 | 0.660 | −0.416 |
| LS | TTGTCG | 432.14 | 278 | 0.643 | −0.441 |
| LS | CTGTCA | 3534.89 | 2228 | 0.630 | −0.462 |
| LS | TTGAGC | 1851.45 | 1128 | 0.609 | −0.496 |
| LS | CTATCC | 899.44 | 541 | 0.601 | −0.508 |
| LS | TTATCG | 257.24 | 152 | 0.591 | −0.526 |
| LS | TTAAGC | 1102.11 | 551 | 0.500 | −0.693 |
| LS | CTATCG | 237.85 | 102 | 0.429 | −0.847 |
| LS | CTTAGC | 1889.55 | 793 | 0.420 | −0.868 |
| LT | CTCACC | 2534.19 | 4959 | 1.957 | 0.671 |
| LT | CTCACG | 832.47 | 1510 | 1.814 | 0.595 |
| LT | TTAACA | 825.09 | 1163 | 1.410 | 0.343 |
| LT | CTCACT | 1814.22 | 2521 | 1.390 | 0.329 |
| LT | TTAACT | 729.65 | 969 | 1.328 | 0.284 |
| LT | CTAACT | 674.64 | 817 | 1.211 | 0.191 |
| LT | CTAACA | 762.89 | 898 | 1.177 | 0.163 |
| LT | CTCACA | 2051.52 | 2374 | 1.157 | 0.146 |
| LT | CTGACG | 1729.98 | 1795 | 1.038 | 0.037 |
| LT | TTGACT | 1225.76 | 1259 | 1.027 | 0.027 |
| LT | TTGACA | 1386.09 | 1401 | 1.011 | 0.011 |
| LT | CTTACT | 1250.98 | 1259 | 1.006 | 0.006 |
| LT | CTGACC | 5266.36 | 5160 | 0.980 | −0.020 |
| LT | CTTACA | 1414.61 | 1109 | 0.784 | −0.243 |
| LT | CTGACT | 3770.17 | 2808 | 0.745 | −0.295 |
| LT | TTGACC | 1712.20 | 1235 | 0.721 | −0.327 |
| LT | CTAACC | 942.38 | 678 | 0.719 | −0.329 |
| LT | TTGACG | 562.45 | 399 | 0.709 | −0.343 |
| LT | CTGACA | 4263.32 | 3003 | 0.704 | −0.350 |
| LT | CTAACG | 309.57 | 215 | 0.695 | −0.365 |
| LT | TTAACC | 1019.22 | 687 | 0.674 | −0.394 |
| LT | CTTACC | 1747.43 | 1104 | 0.632 | −0.459 |
| LT | TTAACG | 334.81 | 164 | 0.490 | −0.714 |
| LT | CTTACG | 574.02 | 247 | 0.430 | −0.843 |
| LV | CTTGTT | 1029.60 | 1741 | 1.691 | 0.525 |
| LV | TTAGTA | 389.95 | 602 | 1.544 | 0.434 |
| LV | TTGGTA | 655.07 | 980 | 1.496 | 0.403 |
| LV | CTTGTA | 668.56 | 993 | 1.485 | 0.396 |
| LV | CTGGTG | 7859.41 | 11424 | 1.454 | 0.374 |
| LV | CTAGTA | 360.55 | 519 | 1.439 | 0.364 |
| LV | TTGGTT | 1008.84 | 1427 | 1.414 | 0.347 |
| LV | CTTGTC | 1318.22 | 1541 | 1.169 | 0.156 |
| LV | TTAGTT | 600.53 | 690 | 1.149 | 0.139 |
| LV | CTGGTC | 3972.81 | 4541 | 1.143 | 0.134 |
| LV | TTGGTG | 2555.25 | 2882 | 1.128 | 0.120 |
| LV | CTAGTT | 555.26 | 580 | 1.045 | 0.044 |
| LV | TTGGTC | 1291.64 | 1345 | 1.041 | 0.040 |
| LV | CTTGTG | 2607.83 | 2540 | 0.974 | −0.026 |
| LV | CTAGTG | 1406.38 | 1272 | 0.904 | −0.100 |
| LV | CTGGTA | 2014.87 | 1720 | 0.854 | −0.158 |
| LV | CTGGTT | 3102.98 | 2576 | 0.830 | −0.186 |
| LV | CTAGTC | 710.90 | 551 | 0.775 | −0.255 |
| LV | TTAGTG | 1521.06 | 947 | 0.623 | −0.474 |
| LV | TTAGTC | 768.87 | 416 | 0.541 | −0.614 |
| LV | CTCGTC | 1911.73 | 1013 | 0.530 | −0.635 |
| LV | CTCGTG | 3781.97 | 1691 | 0.447 | −0.805 |
| LV | CTCGTT | 1493.16 | 373 | 0.250 | −1.387 |
| LV | CTCGTA | 969.56 | 191 | 0.197 | −1.625 |
| LW | CTCTGG | 1742.64 | 2796 | 1.604 | 0.473 |
| LW | CTGTGG | 3621.43 | 3365 | 0.929 | −0.073 |
| LW | CTTTGG | 1201.63 | 1018 | 0.847 | −0.166 |
| LW | CTATGG | 648.03 | 501 | 0.773 | −0.257 |
| LW | TTATGG | 700.87 | 535 | 0.763 | −0.270 |
| LW | TTGTGG | 1177.40 | 877 | 0.745 | −0.295 |
| LY | CTCTAC | 2082.09 | 4204 | 2.019 | 0.703 |
| LY | TTATAT | 680.44 | 1022 | 1.502 | 0.407 |
| LY | CTCTAT | 1691.85 | 2487 | 1.470 | 0.385 |
| LY | CTTTAT | 1166.60 | 1591 | 1.364 | 0.310 |
| LY | CTATAT | 629.14 | 596 | 0.947 | −0.054 |
| LY | TTGTAT | 1143.08 | 1063 | 0.930 | −0.073 |
| LY | CTGTAC | 4326.84 | 3390 | 0.783 | −0.244 |
| LY | CTTTAC | 1435.69 | 1069 | 0.745 | −0.295 |
| LY | TTGTAC | 1406.74 | 1006 | 0.715 | −0.335 |
| LY | TTATAC | 837.39 | 579 | 0.691 | −0.369 |
| LY | CTGTAT | 3515.88 | 2202 | 0.626 | −0.468 |
| LY | CTATAC | 774.26 | 481 | 0.621 | −0.476 |
| MA | ATGGCG | 1645.46 | 2370 | 1.440 | 0.365 |

-continued

| AA pair | Codon pair | Expected | Observed | Observed/ Expected | CPS |
|---|---|---|---|---|---|
| MA | ATGGCA | 3503.58 | 3580 | 1.022 | 0.022 |
| MA | ATGGCT | 4002.27 | 4003 | 1.000 | 0.000 |
| MA | ATGGCC | 6085.70 | 5284 | 0.868 | −0.141 |
| MC | ATGTGT | 1386.67 | 1448 | 1.044 | 0.043 |
| MC | ATGTGC | 1646.33 | 1585 | 0.963 | −0.038 |
| MD | ATGGAT | 4467.48 | 4634 | 1.037 | 0.037 |
| MD | ATGGAC | 5046.52 | 4880 | 0.967 | −0.034 |
| ME | ATGGAG | 8054.28 | 8223 | 1.021 | 0.021 |
| ME | ATGGAA | 6022.72 | 5854 | 0.972 | −0.028 |
| MF | ATGTTT | 2565.53 | 2833 | 1.104 | 0.099 |
| MF | ATGTTC | 2936.47 | 2669 | 0.909 | −0.096 |
| MG | ATGGGC | 3467.73 | 3533 | 1.019 | 0.019 |
| MG | ATGGGT | 1655.83 | 1675 | 1.012 | 0.012 |
| MG | ATGGGA | 2557.59 | 2526 | 0.988 | −0.012 |
| MG | ATGGGG | 2496.85 | 2444 | 0.979 | −0.021 |
| MH | ATGCAT | 1465.33 | 1478 | 1.009 | 0.009 |
| MH | ATGCAC | 2020.67 | 2008 | 0.994 | −0.006 |
| MI | ATGATT | 2305.40 | 2382 | 1.033 | 0.033 |
| MI | ATGATA | 1060.28 | 1094 | 1.032 | 0.031 |
| MI | ATGATC | 2915.32 | 2805 | 0.962 | −0.039 |
| MK | ATGAAG | 6107.32 | 6423 | 1.052 | 0.050 |
| MK | ATGAAA | 4715.68 | 4400 | 0.933 | −0.069 |
| ML | ATGCTG | 5938.40 | 6536 | 1.101 | 0.096 |
| ML | ATGCTA | 1062.63 | 1122 | 1.056 | 0.054 |
| ML | ATGTTG | 1930.69 | 1922 | 0.995 | −0.005 |
| ML | ATGTTA | 1149.28 | 1134 | 0.987 | −0.013 |
| ML | ATGCTT | 1970.42 | 1887 | 0.958 | −0.043 |
| ML | ATGCTC | 2857.58 | 2308 | 0.808 | −0.214 |
| MM | ATGATG | 3925.00 | 3925 | 1.000 | 0.000 |
| MN | ATGAAT | 3249.30 | 3301 | 1.016 | 0.016 |
| MN | ATGAAC | 3578.70 | 3527 | 0.986 | −0.015 |
| MP | ATGCCC | 2676.16 | 2752 | 1.028 | 0.028 |
| MP | ATGCCA | 2313.29 | 2313 | 1.000 | 0.000 |
| MP | ATGCCT | 2396.87 | 2372 | 0.990 | −0.010 |
| MP | ATGCCG | 969.67 | 919 | 0.948 | −0.054 |
| MQ | ATGCAG | 5141.70 | 5165 | 1.005 | 0.005 |
| MQ | ATGCAA | 1841.30 | 1818 | 0.987 | −0.013 |
| MR | ATGAGG | 1626.37 | 2127 | 1.308 | 0.268 |
| MR | ATGAGA | 1656.63 | 1974 | 1.192 | 0.175 |
| MR | ATGCGG | 1642.64 | 1513 | 0.921 | −0.082 |
| MR | ATGCGT | 643.02 | 531 | 0.826 | −0.191 |
| MR | ATGCGA | 890.44 | 684 | 0.768 | −0.264 |
| MR | ATGCGC | 1501.91 | 1132 | 0.754 | −0.283 |
| MS | ATGTCG | 666.33 | 809 | 1.214 | 0.194 |
| MS | ATGTCT | 2191.95 | 2338 | 1.067 | 0.065 |
| MS | ATGTCA | 1772.07 | 1781 | 1.005 | 0.005 |
| MS | ATGTCC | 2519.77 | 2493 | 0.989 | −0.011 |
| MS | ATGAGT | 1801.10 | 1770 | 0.983 | −0.017 |
| MS | ATGAGC | 2854.78 | 2615 | 0.916 | −0.088 |
| MT | ATGACT | 2098.83 | 2195 | 1.046 | 0.045 |
| MT | ATGACC | 2931.75 | 2927 | 0.998 | −0.002 |
| MT | ATGACA | 2373.36 | 2337 | 0.985 | −0.015 |
| MT | ATGACG | 963.07 | 908 | 0.943 | −0.059 |
| MV | ATGGTG | 4813.46 | 5122 | 1.064 | 0.062 |
| MV | ATGGTT | 1900.41 | 1915 | 1.008 | 0.008 |
| MV | ATGGTA | 1234.00 | 1191 | 0.965 | −0.035 |
| MV | ATGGTC | 2433.13 | 2153 | 0.885 | −0.122 |
| MW | ATGTGG | 1876.00 | 1876 | 1.000 | 0.000 |
| MY | ATGTAC | 2354.66 | 2363 | 1.004 | 0.004 |
| MY | ATGTAT | 1913.34 | 1905 | 0.996 | −0.004 |
| NA | AATGCA | 1705.68 | 3344 | 1.961 | 0.673 |
| NA | AATGCT | 1948.47 | 3458 | 1.775 | 0.574 |
| NA | AATGCC | 2962.77 | 4259 | 1.438 | 0.363 |
| NA | AATGCG | 801.08 | 624 | 0.779 | −0.250 |
| NA | AACGCG | 882.29 | 661 | 0.749 | −0.289 |
| NA | AACGCC | 3263.12 | 1899 | 0.582 | −0.541 |
| NA | AACGCA | 1878.60 | 700 | 0.373 | −0.987 |
| NA | AACGCT | 2146.00 | 643 | 0.300 | −1.205 |
| NC | AACTGC | 1868.57 | 2826 | 1.512 | 0.414 |
| NC | AACTGT | 1573.86 | 2016 | 1.281 | 0.248 |
| NC | AATTGT | 1429.00 | 935 | 0.654 | −0.424 |
| NC | AATTGC | 1696.57 | 791 | 0.466 | −0.763 |
| ND | AATGAT | 2555.01 | 4420 | 1.730 | 0.548 |
| ND | AATGAC | 2886.18 | 4521 | 1.566 | 0.449 |
| ND | AACGAC | 3178.77 | 1654 | 0.520 | −0.653 |
| ND | AACGAT | 2814.03 | 839 | 0.298 | −1.210 |

-continued

| AA pair | Codon pair | Expected | Observed | Observed/ Expected | CPS |
|---|---|---|---|---|---|
| NE | AATGAA | 3381.19 | 7367 | 2.179 | 0.779 |
| NE | AATGAG | 4521.72 | 5796 | 1.282 | 0.248 |
| NE | AACGAG | 4980.12 | 2476 | 0.497 | −0.699 |
| NE | AACGAA | 3723.97 | 968 | 0.260 | −1.347 |
| NF | AACTTC | 3150.86 | 4259 | 1.352 | 0.301 |
| NF | AACTTT | 2752.85 | 2846 | 1.034 | 0.033 |
| NF | AATTTT | 2499.46 | 2350 | 0.940 | −0.062 |
| NF | AATTTC | 2860.84 | 1809 | 0.632 | −0.458 |
| NG | AATGGA | 2235.93 | 4484 | 2.005 | 0.696 |
| NG | AATGGT | 1447.59 | 2430 | 1.679 | 0.518 |
| NG | AATGGG | 2182.83 | 3202 | 1.467 | 0.383 |
| NG | AATGGC | 3031.62 | 4001 | 1.320 | 0.277 |
| NG | AACGGG | 2404.12 | 1508 | 0.627 | −0.466 |
| NG | AACGGC | 3338.95 | 1752 | 0.525 | −0.645 |
| NG | AACGGA | 2462.61 | 804 | 0.326 | −1.119 |
| NG | AACGGT | 1594.34 | 517 | 0.324 | −1.126 |
| NH | AACCAC | 2167.68 | 2776 | 1.281 | 0.247 |
| NH | AACCAT | 1571.93 | 1639 | 1.043 | 0.042 |
| NH | AATCAT | 1427.24 | 1456 | 1.020 | 0.020 |
| NH | AATCAC | 1968.15 | 1264 | 0.642 | −0.443 |
| NI | AACATC | 3876.27 | 5487 | 1.416 | 0.348 |
| NI | AACATT | 3065.31 | 3184 | 1.039 | 0.038 |
| NI | AATATA | 1280.01 | 1309 | 1.023 | 0.022 |
| NI | AACATA | 1409.77 | 1384 | 0.982 | −0.018 |
| NI | AATATT | 2783.16 | 2725 | 0.979 | −0.021 |
| NI | AATATC | 3519.48 | 1845 | 0.524 | −0.646 |
| NK | AACAAG | 4824.98 | 5918 | 1.227 | 0.204 |
| NK | AACAAA | 3725.54 | 4221 | 1.133 | 0.125 |
| NK | AATAAA | 3382.62 | 3607 | 1.066 | 0.064 |
| NK | AATAAG | 4380.86 | 2568 | 0.586 | −0.534 |
| NL | AATTTA | 1025.31 | 1571 | 1.532 | 0.427 |
| NL | AACCTC | 2807.78 | 3954 | 1.408 | 0.342 |
| NL | AACTTG | 1897.05 | 2429 | 1.280 | 0.247 |
| NL | AACCTG | 5834.92 | 6690 | 1.147 | 0.137 |
| NL | AATTTG | 1722.43 | 1947 | 1.130 | 0.123 |
| NL | AATCTT | 1757.88 | 1943 | 1.105 | 0.100 |
| NL | AACCTA | 1044.12 | 1135 | 1.087 | 0.083 |
| NL | AACCTT | 1936.08 | 2021 | 1.044 | 0.043 |
| NL | AACTTA | 1129.25 | 1129 | 1.000 | 0.000 |
| NL | AATCTA | 948.01 | 893 | 0.942 | −0.060 |
| NL | AATCTC | 2549.34 | 1713 | 0.672 | −0.398 |
| NL | AATCTG | 5297.84 | 2525 | 0.477 | −0.741 |
| NM | AACATG | 3351.76 | 4374 | 1.305 | 0.266 |
| NM | AATATG | 3043.24 | 2021 | 0.664 | −0.409 |
| NN | AACAAC | 3150.02 | 4430 | 1.406 | 0.341 |
| NN | AACAAT | 2860.08 | 2830 | 0.989 | −0.011 |
| NN | AATAAT | 2596.82 | 2424 | 0.933 | −0.069 |
| NN | AATAAC | 2860.08 | 1783 | 0.623 | −0.473 |
| NP | AACCCC | 2770.02 | 3474 | 1.254 | 0.226 |
| NP | AATCCA | 2174.02 | 2380 | 1.095 | 0.091 |
| NP | AACCCA | 2394.42 | 2612 | 1.091 | 0.087 |
| NP | AATCCT | 2252.58 | 2414 | 1.072 | 0.069 |
| NP | AACCCG | 1003.68 | 1048 | 1.044 | 0.043 |
| NP | AACCCT | 2480.94 | 2578 | 1.039 | 0.038 |
| NP | AATCCC | 2515.05 | 1641 | 0.652 | −0.427 |
| NP | AATCCG | 911.29 | 355 | 0.390 | −0.943 |
| NQ | AATCAA | 1516.57 | 1905 | 1.256 | 0.228 |
| NQ | AACCAA | 1670.31 | 1955 | 1.170 | 0.157 |
| NQ | AACCAG | 4664.22 | 5409 | 1.160 | 0.148 |
| NQ | AATCAG | 4234.90 | 2817 | 0.665 | −0.408 |
| NR | AACAGA | 1511.98 | 2383 | 1.576 | 0.455 |
| NR | AACCGC | 1370.77 | 1966 | 1.434 | 0.361 |
| NR | AACAGG | 1484.36 | 1903 | 1.282 | 0.248 |
| NR | AACCGA | 812.69 | 998 | 1.228 | 0.205 |
| NR | AACCGT | 586.88 | 706 | 1.203 | 0.185 |
| NR | AACCGG | 1499.21 | 1779 | 1.187 | 0.171 |
| NR | AATCGA | 737.89 | 687 | 0.931 | −0.071 |
| NR | AATCGT | 532.86 | 486 | 0.912 | −0.092 |
| NR | AATAGA | 1372.81 | 1117 | 0.814 | −0.206 |
| NR | AATCGC | 1244.60 | 602 | 0.484 | −0.726 |
| NR | AATAGG | 1347.73 | 643 | 0.477 | −0.740 |
| NR | AATCGG | 1361.22 | 593 | 0.436 | −0.831 |
| NS | AACAGC | 2917.73 | 4490 | 1.539 | 0.431 |
| NS | AACAGT | 1840.81 | 2414 | 1.311 | 0.271 |
| NS | AACTCG | 681.02 | 821 | 1.206 | 0.187 |
| NS | AATTCA | 1644.43 | 1970 | 1.198 | 0.181 |

-continued

| AA pair | Codon pair | Expected | Observed | Observed/ Expected | CPS |
|---|---|---|---|---|---|
| NS | AATTCT | 2034.08 | 2383 | 1.172 | 0.158 |
| NS | AACTCC | 2575.33 | 2818 | 1.094 | 0.090 |
| NS | AACTCA | 1811.14 | 1783 | 0.984 | −0.016 |
| NS | AACTCT | 2240.29 | 1981 | 0.884 | −0.123 |
| NS | AATAGT | 1671.38 | 1193 | 0.714 | −0.337 |
| NS | AATTCC | 2338.29 | 1655 | 0.708 | −0.346 |
| NS | AATAGC | 2649.17 | 1273 | 0.481 | −0.733 |
| NS | AATTCG | 618.33 | 241 | 0.390 | −0.942 |
| NT | AACACG | 860.22 | 1238 | 1.439 | 0.364 |
| NT | AACACA | 2119.90 | 2783 | 1.313 | 0.272 |
| NT | AACACC | 2618.65 | 3278 | 1.252 | 0.225 |
| NT | AACACT | 1874.68 | 2099 | 1.120 | 0.113 |
| NT | AATACT | 1702.13 | 1540 | 0.905 | −0.100 |
| NT | AATACA | 1924.77 | 1692 | 0.879 | −0.129 |
| NT | AATACC | 2377.62 | 1312 | 0.552 | −0.595 |
| NT | AATACG | 781.04 | 317 | 0.406 | −0.902 |
| NV | AATGTA | 927.15 | 1710 | 1.844 | 0.612 |
| NV | AATGTT | 1427.85 | 2573 | 1.802 | 0.589 |
| NV | AATGTC | 1828.10 | 2877 | 1.574 | 0.453 |
| NV | AATGTG | 3616.54 | 4314 | 1.193 | 0.176 |
| NV | AACGTG | 3983.18 | 2772 | 0.696 | −0.363 |
| NV | AACGTC | 2013.43 | 1341 | 0.666 | −0.406 |
| NV | AACGTT | 1572.60 | 509 | 0.324 | −1.128 |
| NV | AACGTA | 1021.14 | 294 | 0.288 | −1.245 |
| NW | AACTGG | 1808.22 | 2595 | 1.435 | 0.361 |
| NW | AATTGG | 1641.78 | 855 | 0.521 | −0.652 |
| NY | AACTAC | 2506.72 | 3191 | 1.273 | 0.241 |
| NY | AACTAT | 2036.89 | 2145 | 1.053 | 0.052 |
| NY | AATTAT | 1849.41 | 1795 | 0.971 | −0.030 |
| NY | AATTAC | 2275.98 | 1538 | 0.676 | −0.392 |
| PA | CCGGCG | 470.57 | 1166 | 2.478 | 0.907 |
| PA | CCGGCC | 1740.39 | 2666 | 1.532 | 0.426 |
| PA | CCAGCA | 2390.31 | 3368 | 1.409 | 0.343 |
| PA | CCAGCT | 2730.54 | 3622 | 1.326 | 0.283 |
| PA | CCTGCT | 2829.20 | 3750 | 1.325 | 0.282 |
| PA | CCTGCA | 2476.67 | 3178 | 1.283 | 0.249 |
| PA | CCAGCC | 4151.96 | 4942 | 1.190 | 0.174 |
| PA | CCCGCG | 1298.71 | 1528 | 1.177 | 0.163 |
| PA | CCTGCC | 4301.98 | 5000 | 1.162 | 0.150 |
| PA | CCAGCG | 1122.61 | 1078 | 0.960 | −0.041 |
| PA | CCTGCG | 1163.17 | 1105 | 0.950 | −0.051 |
| PA | CCGGCT | 1144.57 | 1013 | 0.885 | −0.122 |
| PA | CCGGCA | 1001.95 | 777 | 0.775 | −0.254 |
| PA | CCCGCC | 4803.25 | 2690 | 0.560 | −0.580 |
| PA | CCCGCA | 2765.26 | 846 | 0.306 | −1.184 |
| PA | CCCGCT | 3158.86 | 821 | 0.260 | −1.347 |
| PC | CCCTGC | 1550.51 | 2870 | 1.851 | 0.616 |
| PC | CCCTGT | 1305.97 | 1577 | 1.208 | 0.189 |
| PC | CCGTGC | 561.80 | 630 | 1.121 | 0.115 |
| PC | CCTTGT | 1169.67 | 1001 | 0.856 | −0.156 |
| PC | CCATGT | 1128.89 | 831 | 0.736 | −0.306 |
| PC | CCGTGT | 473.20 | 340 | 0.719 | −0.331 |
| PC | CCTTGC | 1388.69 | 937 | 0.675 | −0.393 |
| PC | CCATGC | 1340.27 | 733 | 0.547 | −0.603 |
| PD | CCAGAT | 2721.60 | 4165 | 1.530 | 0.425 |
| PD | CCTGAT | 2819.94 | 3781 | 1.341 | 0.293 |
| PD | CCGGAC | 1288.69 | 1659 | 1.287 | 0.253 |
| PD | CCAGAC | 3074.36 | 3766 | 1.225 | 0.203 |
| PD | CCTGAC | 3185.44 | 3646 | 1.145 | 0.135 |
| PD | CCGGAT | 1140.82 | 895 | 0.785 | −0.243 |
| PD | CCCGAC | 3556.62 | 2215 | 0.623 | −0.474 |
| PD | CCCGAT | 3148.53 | 809 | 0.257 | −1.359 |
| PE | CCAGAA | 3999.86 | 5699 | 1.425 | 0.354 |
| PE | CCTGAG | 5542.36 | 7122 | 1.285 | 0.251 |
| PE | CCGGAG | 2242.20 | 2870 | 1.280 | 0.247 |
| PE | CCAGAG | 5349.08 | 6777 | 1.267 | 0.237 |
| PE | CCTGAA | 4144.39 | 5108 | 1.233 | 0.209 |
| PE | CCCGAG | 6188.17 | 4149 | 0.670 | −0.400 |
| PE | CCGGAA | 1676.64 | 1032 | 0.616 | −0.485 |
| PE | CCCGAA | 4627.30 | 1013 | 0.219 | −1.519 |
| PF | CCCTTC | 2555.92 | 4301 | 1.683 | 0.520 |
| PF | CCATTT | 1930.27 | 2057 | 1.066 | 0.064 |
| PF | CCTTTT | 2000.01 | 1967 | 0.983 | −0.017 |
| PF | CCCTTT | 2233.06 | 2159 | 0.967 | −0.034 |
| PF | CCTTTC | 2289.18 | 2078 | 0.908 | −0.097 |
| PF | CCGTTC | 926.10 | 662 | 0.715 | −0.336 |

-continued

| AA pair | Codon pair | Expected | Observed | Observed/ Expected | CPS |
|---|---|---|---|---|---|
| PF | CCATTC | 2209.35 | 1290 | 0.584 | −0.538 |
| PF | CCGTTT | 809.12 | 439 | 0.543 | −0.611 |
| PG | CCTGGG | 2918.52 | 4310 | 1.477 | 0.390 |
| PG | CCTGGA | 2989.52 | 4317 | 1.444 | 0.367 |
| PG | CCGGGC | 1639.82 | 2353 | 1.435 | 0.361 |
| PG | CCGGGG | 1180.71 | 1657 | 1.403 | 0.339 |
| PG | CCTGGT | 1935.48 | 2673 | 1.381 | 0.323 |
| PG | CCAGGA | 2885.27 | 3897 | 1.351 | 0.301 |
| PG | CCAGGG | 2816.75 | 3472 | 1.233 | 0.209 |
| PG | CCAGGT | 1867.98 | 2259 | 1.209 | 0.190 |
| PG | CCTGGC | 4053.37 | 4622 | 1.140 | 0.131 |
| PG | CCAGGC | 3912.02 | 4106 | 1.050 | 0.048 |
| PG | CCGGGT | 783.01 | 661 | 0.844 | −0.169 |
| PG | CCGGGA | 1209.43 | 963 | 0.796 | −0.228 |
| PG | CCCGGG | 3258.60 | 2136 | 0.655 | −0.422 |
| PG | CCCGGC | 4525.68 | 2555 | 0.565 | −0.572 |
| PG | CCCGGA | 3337.86 | 968 | 0.290 | −1.238 |
| PG | CCCGGT | 2161.00 | 526 | 0.243 | −1.413 |
| PH | CCGCAC | 725.13 | 972 | 1.340 | 0.293 |
| PH | CCCCAC | 2001.25 | 2505 | 1.252 | 0.225 |
| PH | CCTCAT | 1299.79 | 1592 | 1.225 | 0.203 |
| PH | CCACAT | 1254.46 | 1222 | 0.974 | −0.026 |
| PH | CCCCAT | 1451.24 | 1303 | 0.898 | −0.108 |
| PH | CCTCAC | 1792.40 | 1531 | 0.854 | −0.158 |
| PH | CCACAC | 1729.89 | 1366 | 0.790 | −0.236 |
| PH | CCGCAT | 525.84 | 289 | 0.550 | −0.599 |
| PI | CCCATC | 2119.04 | 4651 | 2.195 | 0.786 |
| PI | CCCATT | 1675.71 | 2102 | 1.254 | 0.227 |
| PI | CCAATA | 666.18 | 819 | 1.229 | 0.207 |
| PI | CCCATA | 770.68 | 776 | 1.007 | 0.007 |
| PI | CCAATT | 1448.49 | 1386 | 0.957 | −0.044 |
| PI | CCTATA | 690.25 | 603 | 0.874 | −0.135 |
| PI | CCTATT | 1500.83 | 1266 | 0.844 | −0.170 |
| PI | CCAATC | 1831.71 | 939 | 0.513 | −0.668 |
| PI | CCTATC | 1897.89 | 957 | 0.504 | −0.685 |
| PI | CCGATT | 607.17 | 299 | 0.492 | −0.708 |
| PI | CCGATC | 767.80 | 342 | 0.445 | −0.809 |
| PI | CCGATA | 279.24 | 115 | 0.412 | −0.887 |
| PK | CCCAAG | 3738.47 | 6383 | 1.707 | 0.535 |
| PK | CCCAAA | 2886.60 | 3787 | 1.312 | 0.271 |
| PK | CCAAAA | 2495.20 | 2489 | 0.998 | −0.002 |
| PK | CCAAAG | 3231.55 | 3127 | 0.968 | −0.033 |
| PK | CCTAAA | 2585.35 | 1840 | 0.712 | −0.340 |
| PK | CCGAAG | 1354.58 | 940 | 0.694 | −0.365 |
| PK | CCTAAG | 3348.32 | 1660 | 0.496 | −0.702 |
| PK | CCGAAA | 1045.92 | 460 | 0.440 | −0.821 |
| PL | CCGCTG | 1824.84 | 3343 | 1.832 | 0.605 |
| PL | CCGCTC | 878.12 | 1254 | 1.428 | 0.356 |
| PL | CCTTTG | 1466.52 | 2054 | 1.401 | 0.337 |
| PL | CCTTTA | 872.97 | 1195 | 1.369 | 0.314 |
| PL | CCCTTG | 1637.40 | 2122 | 1.296 | 0.259 |
| PL | CCTCTT | 1496.70 | 1827 | 1.221 | 0.199 |
| PL | CCCCTG | 5036.31 | 5760 | 1.144 | 0.134 |
| PL | CCCCTC | 2423.49 | 2646 | 1.092 | 0.088 |
| PL | CCTCTA | 807.16 | 871 | 1.079 | 0.076 |
| PL | CCATTA | 842.53 | 826 | 0.980 | −0.020 |
| PL | CCACTT | 1444.51 | 1371 | 0.949 | −0.052 |
| PL | CCACTA | 779.01 | 729 | 0.936 | −0.066 |
| PL | CCTCTC | 2170.57 | 1934 | 0.891 | −0.115 |
| PL | CCTCTG | 4510.71 | 3745 | 0.830 | −0.186 |
| PL | CCATTG | 1415.38 | 1172 | 0.828 | −0.189 |
| PL | CCCCTT | 1671.10 | 1324 | 0.792 | −0.233 |
| PL | CCGCTA | 326.54 | 255 | 0.781 | −0.247 |
| PL | CCCCTA | 901.21 | 689 | 0.765 | −0.268 |
| PL | CCACTG | 4353.41 | 3218 | 0.739 | −0.302 |
| PL | CCCTTA | 974.69 | 709 | 0.727 | −0.318 |
| PL | CCACTC | 2094.88 | 1475 | 0.704 | −0.351 |
| PL | CCGTTG | 593.29 | 402 | 0.678 | −0.389 |
| PL | CCGCTT | 605.50 | 402 | 0.664 | −0.410 |
| PL | CCGTTA | 353.17 | 157 | 0.445 | −0.811 |
| PM | CCCATG | 2307.54 | 3923 | 1.700 | 0.531 |
| PM | CCAATG | 1994.65 | 1552 | 0.778 | −0.251 |
| PM | CCGATG | 836.10 | 520 | 0.622 | −0.475 |
| PM | CCTATG | 2066.72 | 1210 | 0.585 | −0.535 |
| PN | CCCAAC | 2313.61 | 4255 | 1.839 | 0.609 |
| PN | CCAAAT | 1815.81 | 2453 | 1.351 | 0.301 |

-continued

| AA pair | Codon pair | Expected | Observed | Observed/ Expected | CPS |
|---|---|---|---|---|---|
| PN | CCCAAT | 2100.65 | 2296 | 1.093 | 0.089 |
| PN | CCAAAC | 1999.90 | 1735 | 0.868 | −0.142 |
| PN | CCTAAT | 1881.42 | 1342 | 0.713 | −0.338 |
| PN | CCTAAC | 2072.16 | 997 | 0.481 | −0.732 |
| PN | CCGAAT | 761.14 | 340 | 0.447 | −0.806 |
| PP | CCGCCG | 608.57 | 2335 | 3.837 | 1.345 |
| PP | CCGCCC | 1679.58 | 2697 | 1.606 | 0.474 |
| PP | CCCCCG | 1679.58 | 2420 | 1.441 | 0.365 |
| PP | CCTCCA | 3588.72 | 4314 | 1.202 | 0.184 |
| PP | CCTCCT | 3718.39 | 4305 | 1.158 | 0.146 |
| PP | CCACCA | 3463.58 | 3850 | 1.112 | 0.106 |
| PP | CCACCT | 3588.72 | 3798 | 1.058 | 0.057 |
| PP | CCCCCA | 4006.89 | 4095 | 1.022 | 0.022 |
| PP | CCACCC | 4006.89 | 3595 | 0.897 | −0.108 |
| PP | CCGCCA | 1451.84 | 1280 | 0.882 | −0.126 |
| PP | CCACCG | 1451.84 | 1252 | 0.862 | −0.148 |
| PP | CCGCCT | 1504.30 | 1286 | 0.855 | −0.157 |
| PP | CCTCCC | 4151.67 | 3338 | 0.804 | −0.218 |
| PP | CCTCCG | 1504.30 | 1152 | 0.766 | −0.267 |
| PP | CCCCCT | 4151.67 | 3160 | 0.761 | −0.273 |
| PP | CCCCCC | 4635.43 | 2315 | 0.499 | −0.694 |
| PQ | CCCCAG | 5063.98 | 6421 | 1.268 | 0.237 |
| PQ | CCGCAG | 1834.86 | 2187 | 1.192 | 0.176 |
| PQ | CCTCAA | 1624.21 | 1752 | 1.079 | 0.076 |
| PQ | CCTCAG | 4535.49 | 4221 | 0.931 | −0.072 |
| PQ | CCACAA | 1567.57 | 1405 | 0.896 | −0.109 |
| PQ | CCACAG | 4377.33 | 3670 | 0.838 | −0.176 |
| PQ | CCCCAA | 1813.47 | 1497 | 0.825 | −0.192 |
| PQ | CCGCAA | 657.08 | 321 | 0.489 | −0.716 |
| PR | CCGCGC | 563.43 | 1094 | 1.942 | 0.664 |
| PR | CCGCGG | 616.23 | 1113 | 1.806 | 0.591 |
| PR | CCCAGG | 1683.86 | 2927 | 1.738 | 0.553 |
| PR | CCCCGG | 1700.71 | 2608 | 1.533 | 0.428 |
| PR | CCCCGC | 1555.00 | 1979 | 1.273 | 0.241 |
| PR | CCCCGA | 921.92 | 1166 | 1.265 | 0.235 |
| PR | CCTCGA | 825.71 | 1015 | 1.229 | 0.206 |
| PR | CCAAGA | 1482.62 | 1608 | 1.085 | 0.081 |
| PR | CCTCGT | 596.27 | 644 | 1.080 | 0.077 |
| PR | CCCAGA | 1715.19 | 1801 | 1.050 | 0.049 |
| PR | CCGAGG | 610.12 | 636 | 1.042 | 0.042 |
| PR | CCTCGG | 1523.22 | 1511 | 0.992 | −0.008 |
| PR | CCCCGT | 665.75 | 655 | 0.984 | −0.016 |
| PR | CCAAGG | 1455.54 | 1347 | 0.925 | −0.077 |
| PR | CCACGA | 796.91 | 632 | 0.793 | −0.232 |
| PR | CCGCGT | 241.23 | 191 | 0.792 | −0.233 |
| PR | CCACGT | 575.48 | 418 | 0.726 | −0.320 |
| PR | CCACGG | 1470.10 | 1040 | 0.707 | −0.346 |
| PR | CCGCGA | 334.04 | 226 | 0.677 | −0.391 |
| PR | CCTCGC | 1392.72 | 838 | 0.602 | −0.508 |
| PR | CCACGC | 1344.15 | 701 | 0.522 | −0.651 |
| PR | CCGAGA | 621.48 | 308 | 0.496 | −0.702 |
| PR | CCTAGA | 1536.19 | 692 | 0.450 | −0.797 |
| PR | CCTAGG | 1508.13 | 586 | 0.389 | −0.945 |
| PS | CCCAGC | 3196.25 | 6398 | 2.002 | 0.694 |
| PS | CCCTCG | 746.03 | 1385 | 1.856 | 0.619 |
| PS | CCGTCG | 270.31 | 483 | 1.787 | 0.580 |
| PS | CCCAGT | 2016.53 | 2743 | 1.360 | 0.308 |
| PS | CCTTCA | 1776.97 | 2263 | 1.274 | 0.242 |
| PS | CCTTCT | 2198.02 | 2711 | 1.233 | 0.210 |
| PS | CCCTCC | 2821.16 | 3353 | 1.189 | 0.173 |
| PS | CCATCA | 1715.00 | 1819 | 1.061 | 0.059 |
| PS | CCATCT | 2121.37 | 2183 | 1.029 | 0.029 |
| PS | CCTTCC | 2526.74 | 2594 | 1.027 | 0.026 |
| PS | CCGTCC | 1022.21 | 1048 | 1.025 | 0.025 |
| PS | CCCTCA | 1984.02 | 1945 | 0.980 | −0.020 |
| PS | CCAAGT | 1743.10 | 1582 | 0.908 | −0.097 |
| PS | CCCTCT | 2454.14 | 2113 | 0.861 | −0.150 |
| PS | CCTTCG | 668.17 | 552 | 0.826 | −0.191 |
| PS | CCATCC | 2438.63 | 1995 | 0.818 | −0.201 |
| PS | CCGAGC | 1158.11 | 885 | 0.764 | −0.269 |
| PS | CCATCG | 644.87 | 475 | 0.737 | −0.306 |
| PS | CCAAGC | 2762.85 | 1659 | 0.600 | −0.510 |
| PS | CCGTCT | 889.22 | 523 | 0.588 | −0.531 |
| PS | CCGAGT | 730.66 | 371 | 0.508 | −0.678 |
| PS | CCGTCA | 718.88 | 364 | 0.506 | −0.681 |
| PS | CCTAGT | 1806.08 | 860 | 0.476 | −0.742 |

-continued

| AA pair | Codon pair | Expected | Observed | Observed/ Expected | CPS |
|---|---|---|---|---|---|
| PS | CCTAGC | 2862.68 | 968 | 0.338 | −1.084 |
| PT | CCCACG | 829.55 | 1764 | 2.126 | 0.754 |
| PT | CCCACC | 2525.29 | 4586 | 1.816 | 0.597 |
| PT | CCCACA | 2044.32 | 2719 | 1.330 | 0.285 |
| PT | CCCACT | 1807.85 | 2282 | 1.262 | 0.233 |
| PT | CCAACA | 1767.12 | 1895 | 1.072 | 0.070 |
| PT | CCAACT | 1562.71 | 1593 | 1.019 | 0.019 |
| PT | CCGACG | 300.57 | 305 | 1.015 | 0.015 |
| PT | CCTACT | 1619.18 | 1252 | 0.773 | −0.257 |
| PT | CCAACC | 2182.87 | 1514 | 0.694 | −0.366 |
| PT | CCTACA | 1830.97 | 1241 | 0.678 | −0.389 |
| PT | CCGACC | 915.00 | 592 | 0.647 | −0.435 |
| PT | CCAACG | 717.06 | 463 | 0.646 | −0.437 |
| PT | CCTACC | 2261.75 | 1251 | 0.553 | −0.592 |
| PT | CCGACT | 655.05 | 342 | 0.522 | −0.650 |
| PT | CCGACA | 740.73 | 352 | 0.475 | −0.744 |
| PT | CCTACG | 742.97 | 352 | 0.474 | −0.747 |
| PV | CCTGTT | 1493.79 | 2375 | 1.590 | 0.464 |
| PV | CCTGTA | 969.97 | 1482 | 1.528 | 0.424 |
| PV | CCAGTA | 936.15 | 1352 | 1.444 | 0.368 |
| PV | CCTGTG | 3783.57 | 5362 | 1.417 | 0.349 |
| PV | CCAGTT | 1441.70 | 2038 | 1.414 | 0.346 |
| PV | CCTGTC | 1912.53 | 2666 | 1.394 | 0.332 |
| PV | CCGGTG | 1530.67 | 1911 | 1.248 | 0.222 |
| PV | CCAGTG | 3651.63 | 3787 | 1.037 | 0.036 |
| PV | CCAGTC | 1845.84 | 1863 | 1.009 | 0.009 |
| PV | CCGGTC | 773.73 | 778 | 1.006 | 0.006 |
| PV | CCCGTG | 4224.44 | 2576 | 0.610 | −0.495 |
| PV | CCGGTT | 604.32 | 351 | 0.581 | −0.543 |
| PV | CCGGTA | 392.41 | 215 | 0.548 | −0.602 |
| PV | CCCGTC | 2135.39 | 1084 | 0.508 | −0.678 |
| PV | CCCGTT | 1667.85 | 391 | 0.234 | −1.451 |
| PV | CCCGTA | 1083.00 | 216 | 0.199 | −1.612 |
| PW | CCCTGG | 1769.80 | 2753 | 1.556 | 0.442 |
| PW | CCGTGG | 641.26 | 661 | 1.031 | 0.030 |
| PW | CCATGG | 1529.83 | 1060 | 0.693 | −0.367 |
| PW | CCTTGG | 1585.10 | 1052 | 0.664 | −0.410 |
| PY | CCCTAC | 2166.25 | 3378 | 1.559 | 0.444 |
| PY | CCCTAT | 1760.24 | 2097 | 1.191 | 0.175 |
| PY | CCTTAT | 1576.54 | 1702 | 1.080 | 0.077 |
| PY | CCATAT | 1521.56 | 1513 | 0.994 | −0.006 |
| PY | CCTTAC | 1940.18 | 1485 | 0.765 | −0.267 |
| PY | CCGTAC | 784.91 | 592 | 0.754 | −0.282 |
| PY | CCGTAT | 637.80 | 429 | 0.673 | −0.397 |
| PY | CCATAC | 1872.52 | 1064 | 0.568 | −0.565 |
| QA | CAAGCA | 1597.87 | 2339 | 1.464 | 0.381 |
| QA | CAAGCT | 1825.31 | 2409 | 1.320 | 0.277 |
| QA | CAGGCG | 2095.55 | 2271 | 1.084 | 0.080 |
| QA | CAGGCC | 7750.37 | 7695 | 0.993 | −0.007 |
| QA | CAAGCC | 2775.49 | 2655 | 0.957 | −0.044 |
| QA | CAGGCT | 5097.04 | 4584 | 0.899 | −0.106 |
| QA | CAGGCA | 4461.94 | 3943 | 0.884 | −0.124 |
| QA | CAAGCG | 750.44 | 458 | 0.610 | −0.494 |
| QC | CAGTGT | 2490.13 | 2791 | 1.121 | 0.114 |
| QC | CAGTGC | 2956.40 | 3260 | 1.103 | 0.098 |
| QC | CAATGT | 891.74 | 822 | 0.922 | −0.081 |
| QC | CAATGC | 1058.72 | 524 | 0.495 | −0.703 |
| QD | CAAGAT | 2128.42 | 3326 | 1.563 | 0.446 |
| QD | CAAGAC | 2404.29 | 2506 | 1.042 | 0.041 |
| QD | CAGGAC | 6713.82 | 6642 | 0.989 | −0.011 |
| QD | CAGGAT | 5943.46 | 4716 | 0.793 | −0.231 |
| QE | CAAGAA | 3247.03 | 5286 | 1.628 | 0.487 |
| QE | CAGGAG | 12125.58 | 12556 | 1.035 | 0.035 |
| QE | CAAGAG | 4342.30 | 4206 | 0.969 | −0.032 |
| QE | CAGGAA | 9067.09 | 6734 | 0.743 | −0.297 |
| QF | CAGTTT | 3509.26 | 4032 | 1.149 | 0.139 |
| QF | CAGTTC | 4016.64 | 4205 | 1.047 | 0.046 |
| QF | CAATTT | 1256.70 | 1156 | 0.920 | −0.084 |
| QF | CAATTC | 1438.40 | 828 | 0.576 | −0.552 |
| QG | CAAGGA | 1440.03 | 2837 | 1.970 | 0.678 |
| QG | CAAGGT | 932.30 | 1506 | 1.615 | 0.480 |
| QG | CAAGGG | 1405.83 | 1700 | 1.209 | 0.190 |
| QG | CAAGGC | 1952.47 | 2192 | 1.123 | 0.116 |
| QG | CAGGGC | 5452.14 | 5605 | 1.028 | 0.028 |
| QG | CAGGGT | 2603.39 | 2292 | 0.880 | −0.127 |
| QG | CAGGGA | 4021.17 | 2871 | 0.714 | −0.337 |

-continued

| AA pair | Codon pair | Expected | Observed | Observed/ Expected | CPS |
|---|---|---|---|---|---|
| QG | CAGGGG | 3925.67 | 2730 | 0.695 | −0.363 |
| QH | CAACAT | 1067.82 | 1364 | 1.277 | 0.245 |
| QH | CAGCAC | 4111.88 | 4483 | 1.090 | 0.086 |
| QH | CAGCAT | 2981.80 | 2794 | 0.937 | −0.065 |
| QH | CAACAC | 1472.51 | 993 | 0.674 | −0.394 |
| QI | CAAATA | 656.37 | 1125 | 1.714 | 0.539 |
| QI | CAAATT | 1427.17 | 1667 | 1.168 | 0.155 |
| QI | CAGATC | 5039.60 | 5197 | 1.031 | 0.031 |
| QI | CAGATA | 1832.87 | 1802 | 0.983 | −0.017 |
| QI | CAGATT | 3985.26 | 3693 | 0.927 | −0.076 |
| QI | CAAATC | 1804.74 | 1262 | 0.699 | −0.358 |
| QK | CAGAAG | 8990.94 | 9726 | 1.082 | 0.079 |
| QK | CAAAAA | 2486.09 | 2610 | 1.050 | 0.049 |
| QK | CAGAAA | 6942.22 | 6532 | 0.941 | −0.061 |
| QK | CAAAAG | 3219.76 | 2771 | 0.861 | −0.150 |
| QL | CAGCTG | 10304.18 | 12629 | 1.226 | 0.203 |
| QL | CAACTA | 660.31 | 798 | 1.209 | 0.189 |
| QL | CAACTT | 1224.39 | 1479 | 1.208 | 0.189 |
| QL | CAGCTC | 4958.40 | 5986 | 1.207 | 0.188 |
| QL | CAGCTA | 1843.86 | 2002 | 1.086 | 0.082 |
| QL | CAGCTT | 3419.03 | 3476 | 1.017 | 0.017 |
| QL | CAATTA | 714.15 | 642 | 0.899 | −0.107 |
| QL | CAGTTG | 3350.09 | 2597 | 0.775 | −0.255 |
| QL | CAGTTA | 1994.20 | 1518 | 0.761 | −0.273 |
| QL | CAACTC | 1775.66 | 1279 | 0.720 | −0.328 |
| QL | CAACTG | 3690.04 | 2093 | 0.567 | −0.567 |
| QL | CAATTG | 1199.70 | 635 | 0.529 | −0.636 |
| QM | CAGATG | 5587.91 | 5592 | 1.001 | 0.001 |
| QM | CAAATG | 2001.09 | 1997 | 0.998 | −0.002 |
| QN | CAAAAT | 1720.47 | 2394 | 1.391 | 0.330 |
| QN | CAGAAC | 5291.34 | 5195 | 0.982 | −0.018 |
| QN | CAGAAT | 4804.30 | 4430 | 0.922 | −0.081 |
| QN | CAAAAC | 1894.89 | 1692 | 0.893 | −0.113 |
| QP | CAGCCG | 1816.66 | 2237 | 1.231 | 0.208 |
| QP | CAGCCC | 5013.75 | 6143 | 1.225 | 0.203 |
| QP | CAGCCT | 4490.51 | 4526 | 1.008 | 0.008 |
| QP | CAGCCA | 4333.91 | 4235 | 0.977 | −0.023 |
| QP | CAACCA | 1552.02 | 1441 | 0.928 | −0.074 |
| QP | CAACCT | 1608.10 | 1304 | 0.811 | −0.210 |
| QP | CAACCC | 1795.48 | 1132 | 0.630 | −0.461 |
| QP | CAACCG | 650.57 | 243 | 0.374 | −0.985 |
| QQ | CAACAA | 1545.49 | 1866 | 1.207 | 0.188 |
| QQ | CAGCAG | 12051.19 | 13131 | 1.090 | 0.086 |
| QQ | CAGCAA | 4315.66 | 4034 | 0.935 | −0.067 |
| QQ | CAACAG | 4315.66 | 3197 | 0.741 | −0.300 |
| QR | CAAAGA | 1214.45 | 1863 | 1.534 | 0.428 |
| QR | CAGAGG | 3329.32 | 4331 | 1.301 | 0.263 |
| QR | CAAAGG | 1192.27 | 1360 | 1.141 | 0.132 |
| QR | CAGAGA | 3391.27 | 3777 | 1.114 | 0.108 |
| QR | CAGCGC | 3074.54 | 3169 | 1.031 | 0.030 |
| QR | CAGCGG | 3362.63 | 3352 | 0.997 | −0.003 |
| QR | CAGCGT | 1316.32 | 1215 | 0.923 | −0.080 |
| QR | CAGCGA | 1822.82 | 1469 | 0.806 | −0.216 |
| QR | CAACGT | 471.39 | 327 | 0.694 | −0.366 |
| QR | CAACGA | 652.77 | 413 | 0.633 | −0.458 |
| QR | CAACGG | 1204.20 | 453 | 0.376 | −0.978 |
| QR | CAACGC | 1101.03 | 404 | 0.367 | −1.003 |
| QS | CAAAGT | 904.91 | 1408 | 1.556 | 0.442 |
| QS | CAGAGC | 4005.17 | 5248 | 1.310 | 0.270 |
| QS | CAGAGT | 2526.89 | 2963 | 1.173 | 0.159 |
| QS | CAAAGC | 1434.30 | 1465 | 1.021 | 0.021 |
| QS | CAGTCG | 934.84 | 923 | 0.987 | −0.013 |
| QS | CAGTCA | 2486.15 | 2379 | 0.957 | −0.044 |
| QS | CAGTCT | 3075.24 | 2806 | 0.912 | −0.092 |
| QS | CAATCA | 890.32 | 781 | 0.877 | −0.131 |
| QS | CAGTCC | 3535.16 | 3051 | 0.863 | −0.147 |
| QS | CAATCT | 1101.28 | 765 | 0.695 | −0.364 |
| QS | CAATCC | 1265.98 | 587 | 0.464 | −0.769 |
| QS | CAATCG | 334.78 | 119 | 0.355 | −1.034 |
| QT | CAAACT | 1116.05 | 1463 | 1.311 | 0.271 |
| QT | CAAACA | 1262.03 | 1602 | 1.269 | 0.239 |
| QT | CAGACG | 1430.02 | 1665 | 1.164 | 0.152 |
| QT | CAGACC | 4353.25 | 4301 | 0.988 | −0.012 |
| QT | CAGACA | 3524.12 | 3445 | 0.978 | −0.023 |
| QT | CAGACT | 3116.48 | 2792 | 0.896 | −0.110 |
| QT | CAAACC | 1558.95 | 1232 | 0.790 | −0.235 |

-continued

| AA pair | Codon pair | Expected | Observed | Observed/ Expected | CPS |
|---|---|---|---|---|---|
| QT | CAAACG | 512.11 | 373 | 0.728 | −0.317 |
| QV | CAAGTA | 657.01 | 1210 | 1.842 | 0.611 |
| QV | CAAGTT | 1011.82 | 1737 | 1.717 | 0.540 |
| QV | CAAGTC | 1295.45 | 1468 | 1.133 | 0.125 |
| QV | CAAGTG | 2562.79 | 2712 | 1.058 | 0.057 |
| QV | CAGGTG | 7156.41 | 7062 | 0.987 | −0.013 |
| QV | CAGGTC | 3617.45 | 3213 | 0.888 | −0.119 |
| QV | CAGGTT | 2825.43 | 2269 | 0.803 | −0.219 |
| QV | CAGGTA | 1834.65 | 1290 | 0.703 | −0.352 |
| QW | CAGTGG | 3057.92 | 3447 | 1.127 | 0.120 |
| QW | CAATGG | 1095.08 | 706 | 0.645 | −0.439 |
| QY | CAATAT | 1029.01 | 1120 | 1.088 | 0.085 |
| QY | CAGTAC | 3536.21 | 3820 | 1.080 | 0.077 |
| QY | CAGTAT | 2873.43 | 2979 | 1.037 | 0.036 |
| QY | CAATAC | 1266.36 | 786 | 0.621 | −0.477 |
| RA | CGGGCG | 659.18 | 1185 | 1.798 | 0.587 |
| RA | CGGGCC | 2437.97 | 3513 | 1.441 | 0.365 |
| RA | AGAGCA | 1415.51 | 1970 | 1.392 | 0.331 |
| RA | CGCGCG | 602.71 | 827 | 1.372 | 0.316 |
| RA | CGTGCC | 954.35 | 1266 | 1.327 | 0.283 |
| RA | CGAGCA | 760.84 | 970 | 1.275 | 0.243 |
| RA | CGAGCT | 869.13 | 1108 | 1.275 | 0.243 |
| RA | CGAGCC | 1321.57 | 1595 | 1.207 | 0.188 |
| RA | AGAGCT | 1616.99 | 1949 | 1.205 | 0.187 |
| RA | CGTGCT | 627.63 | 744 | 1.185 | 0.170 |
| RA | CGGGCA | 1403.55 | 1612 | 1.149 | 0.138 |
| RA | CGTGCA | 549.43 | 570 | 1.037 | 0.037 |
| RA | CGTGCG | 258.04 | 250 | 0.969 | −0.032 |
| RA | CGAGCG | 357.33 | 341 | 0.954 | −0.047 |
| RA | AGGGCC | 2413.81 | 2173 | 0.900 | −0.105 |
| RA | AGAGCC | 2458.73 | 2202 | 0.896 | −0.110 |
| RA | CGGGCT | 1603.33 | 1435 | 0.895 | −0.111 |
| RA | AGGGCA | 1389.65 | 1242 | 0.894 | −0.112 |
| RA | AGGGCT | 1587.45 | 1311 | 0.826 | −0.191 |
| RA | AGGGCG | 652.65 | 524 | 0.803 | −0.220 |
| RA | CGCGCC | 2229.09 | 1712 | 0.768 | −0.264 |
| RA | AGAGCG | 664.79 | 384 | 0.578 | −0.549 |
| RA | CGCGCA | 1283.30 | 331 | 0.258 | −1.355 |
| RA | CGCGCT | 1465.97 | 369 | 0.252 | −1.379 |
| RC | CGCTGC | 986.26 | 2873 | 2.913 | 1.069 |
| RC | CGCTGT | 830.71 | 1313 | 1.581 | 0.458 |
| RC | CGTTGT | 355.66 | 320 | 0.900 | −0.106 |
| RC | CGTTGC | 422.25 | 372 | 0.881 | −0.127 |
| RC | AGATGT | 916.29 | 806 | 0.880 | −0.128 |
| RC | CGATGT | 492.51 | 421 | 0.855 | −0.157 |
| RC | AGGTGT | 899.55 | 671 | 0.746 | −0.293 |
| RC | AGGTGC | 1067.99 | 758 | 0.710 | −0.343 |
| RC | CGATGC | 584.73 | 381 | 0.652 | −0.428 |
| RC | CGGTGC | 1078.67 | 660 | 0.612 | −0.491 |
| RC | AGATGC | 1087.86 | 642 | 0.590 | −0.527 |
| RC | CGGTGT | 908.55 | 414 | 0.456 | −0.786 |
| RD | AGAGAT | 2027.66 | 2952 | 1.456 | 0.376 |
| RD | CGGGAC | 2271.13 | 3231 | 1.423 | 0.353 |
| RD | CGAGAT | 1089.87 | 1500 | 1.376 | 0.319 |
| RD | CGAGAC | 1231.14 | 1693 | 1.375 | 0.319 |
| RD | CGTGAC | 889.05 | 1044 | 1.174 | 0.161 |
| RD | AGAGAC | 2290.48 | 2433 | 1.062 | 0.060 |
| RD | CGTGAT | 787.04 | 833 | 1.058 | 0.057 |
| RD | AGGGAC | 2248.63 | 2322 | 1.033 | 0.032 |
| RD | AGGGAT | 1990.62 | 1732 | 0.870 | −0.139 |
| RD | CGGGAT | 2010.54 | 1606 | 0.799 | −0.225 |
| RD | CGCGAC | 2076.56 | 1092 | 0.526 | −0.643 |
| RD | CGCGAT | 1838.29 | 313 | 0.170 | −1.770 |
| RE | AGAGAA | 2644.21 | 4195 | 1.586 | 0.462 |
| RE | CGGGAG | 3506.29 | 5344 | 1.524 | 0.421 |
| RE | CGAGAG | 1900.69 | 2475 | 1.302 | 0.264 |
| RE | CGAGAA | 1421.27 | 1844 | 1.297 | 0.260 |
| RE | CGTGAG | 1372.55 | 1453 | 1.059 | 0.057 |
| RE | AGGGAG | 3471.55 | 3469 | 0.999 | −0.001 |
| RE | AGAGAG | 3536.15 | 3392 | 0.959 | −0.042 |
| RE | CGTGAA | 1026.35 | 947 | 0.923 | −0.080 |
| RE | AGGGAA | 2595.91 | 2343 | 0.903 | −0.103 |
| RE | CGGGAA | 2621.88 | 2131 | 0.813 | −0.207 |
| RE | CGCGAG | 3205.89 | 1839 | 0.574 | −0.556 |
| RE | CGCGAA | 2397.25 | 268 | 0.112 | −2.191 |
| RF | CGCTTC | 1446.49 | 3411 | 2.358 | 0.858 |

-continued

| AA pair | Codon pair | Expected | Observed | Observed/ Expected | CPS |
|---|---|---|---|---|---|
| RF | CGTTTC | 619.29 | 823 | 1.329 | 0.284 |
| RF | CGTTTT | 541.07 | 705 | 1.303 | 0.265 |
| RF | AGATTT | 1393.96 | 1531 | 1.098 | 0.094 |
| RF | CGCTTT | 1263.77 | 1366 | 1.081 | 0.078 |
| RF | CGATTT | 749.26 | 772 | 1.030 | 0.030 |
| RF | AGGTTT | 1368.50 | 1295 | 0.946 | −0.055 |
| RF | AGGTTC | 1566.36 | 1192 | 0.761 | −0.273 |
| RF | CGATTC | 857.59 | 632 | 0.737 | −0.305 |
| RF | CGGTTC | 1582.03 | 951 | 0.601 | −0.509 |
| RF | AGATTC | 1595.50 | 944 | 0.592 | −0.525 |
| RF | CGGTTT | 1382.19 | 744 | 0.538 | −0.619 |
| RG | CGTGGT | 370.38 | 685 | 1.849 | 0.615 |
| RG | CGTGGG | 558.50 | 980 | 1.755 | 0.562 |
| RG | CGTGGC | 775.66 | 1315 | 1.695 | 0.528 |
| RG | CGAGGA | 792.21 | 1266 | 1.598 | 0.469 |
| RG | CGAGGG | 773.39 | 1219 | 1.576 | 0.455 |
| RG | AGAGGA | 1473.87 | 2281 | 1.548 | 0.437 |
| RG | CGAGGT | 512.89 | 789 | 1.538 | 0.431 |
| RG | CGGGGC | 1981.48 | 2952 | 1.490 | 0.399 |
| RG | CGTGGA | 572.08 | 844 | 1.475 | 0.389 |
| RG | CGAGGC | 1074.12 | 1569 | 1.461 | 0.379 |
| RG | AGAGGT | 954.21 | 1128 | 1.182 | 0.167 |
| RG | CGGGGT | 946.15 | 918 | 0.970 | −0.030 |
| RG | CGCGGC | 1811.72 | 1574 | 0.869 | −0.141 |
| RG | AGGGGC | 1961.86 | 1660 | 0.846 | −0.167 |
| RG | AGAGGC | 1998.36 | 1680 | 0.841 | −0.174 |
| RG | AGAGGG | 1438.87 | 1203 | 0.836 | −0.179 |
| RG | AGGGGT | 936.78 | 777 | 0.829 | −0.187 |
| RG | CGGGGG | 1426.72 | 1146 | 0.803 | −0.219 |
| RG | CGGGGA | 1461.42 | 1140 | 0.780 | −0.248 |
| RG | CGCGGG | 1304.48 | 904 | 0.693 | −0.367 |
| RG | AGGGGA | 1446.94 | 923 | 0.638 | −0.450 |
| RG | AGGGGG | 1412.58 | 683 | 0.484 | −0.727 |
| RG | CGCGGT | 865.09 | 248 | 0.287 | −1.249 |
| RG | CGCGGA | 1336.22 | 302 | 0.226 | −1.487 |
| RH | CGCCAC | 1288.00 | 1861 | 1.445 | 0.368 |
| RH | CGGCAC | 1408.69 | 1707 | 1.212 | 0.192 |
| RH | AGACAT | 1030.24 | 1201 | 1.166 | 0.153 |
| RH | CGTCAT | 399.89 | 447 | 1.118 | 0.111 |
| RH | AGGCAT | 1011.41 | 988 | 0.977 | −0.023 |
| RH | CGACAT | 553.75 | 530 | 0.957 | −0.044 |
| RH | AGGCAC | 1394.73 | 1292 | 0.926 | −0.077 |
| RH | AGACAC | 1420.69 | 1212 | 0.853 | −0.159 |
| RH | CGTCAC | 551.44 | 468 | 0.849 | −0.164 |
| RH | CGACAC | 763.62 | 614 | 0.804 | −0.218 |
| RH | CGCCAT | 934.02 | 728 | 0.779 | −0.249 |
| RH | CGGCAT | 1021.53 | 730 | 0.715 | −0.336 |
| RI | CGCATC | 1625.56 | 2948 | 1.814 | 0.595 |
| RI | AGAATA | 652.11 | 1175 | 1.802 | 0.589 |
| RI | AGAATT | 1417.90 | 2185 | 1.541 | 0.432 |
| RI | AGGATA | 640.20 | 804 | 1.256 | 0.228 |
| RI | CGAATA | 350.51 | 439 | 1.252 | 0.225 |
| RI | CGAATT | 762.13 | 850 | 1.115 | 0.109 |
| RI | AGGATT | 1392.00 | 1366 | 0.981 | −0.019 |
| RI | AGGATC | 1760.27 | 1662 | 0.944 | −0.057 |
| RI | CGAATC | 963.75 | 802 | 0.832 | −0.184 |
| RI | CGGATC | 1777.88 | 1479 | 0.832 | −0.184 |
| RI | AGAATC | 1793.03 | 1389 | 0.775 | −0.255 |
| RI | CGTATT | 550.36 | 408 | 0.741 | −0.299 |
| RI | CGCATT | 1285.48 | 913 | 0.710 | −0.342 |
| RI | CGGATA | 646.60 | 451 | 0.697 | −0.360 |
| RI | CGTATC | 695.96 | 440 | 0.632 | −0.459 |
| RI | CGTATA | 253.12 | 152 | 0.601 | −0.510 |
| RI | CGGATT | 1405.93 | 825 | 0.587 | −0.533 |
| RI | CGCATA | 591.21 | 276 | 0.467 | −0.762 |
| RK | AGGAAG | 3199.71 | 4856 | 1.518 | 0.417 |
| RK | AGGAAA | 2470.61 | 3737 | 1.513 | 0.414 |
| RK | AGAAAA | 2516.58 | 3482 | 1.384 | 0.325 |
| RK | CGCAAG | 2954.85 | 2981 | 1.009 | 0.009 |
| RK | CGGAAG | 3231.73 | 3225 | 0.998 | −0.002 |
| RK | AGAAAG | 3259.25 | 2909 | 0.893 | −0.114 |
| RK | CGAAAA | 1352.67 | 1189 | 0.879 | −0.129 |
| RK | CGGAAA | 2495.33 | 1834 | 0.735 | −0.308 |
| RK | CGAAAG | 1751.85 | 1265 | 0.722 | −0.326 |
| RK | CGTAAA | 976.81 | 566 | 0.579 | −0.546 |
| RK | CGCAAA | 2281.54 | 1209 | 0.530 | −0.635 |

-continued

| AA pair | Codon pair | Expected | Observed | Observed/ Expected | CPS |
|---|---|---|---|---|---|
| RK | CGTAAG | 1265.08 | 503 | 0.398 | −0.922 |
| RL | CGCCTC | 1491.12 | 2511 | 1.684 | 0.521 |
| RL | CGCCTG | 3098.73 | 4809 | 1.552 | 0.439 |
| RL | CGGCTG | 3389.08 | 5029 | 1.484 | 0.395 |
| RL | CGGCTC | 1630.84 | 2301 | 1.411 | 0.344 |
| RL | CGTTTA | 256.76 | 337 | 1.313 | 0.272 |
| RL | AGATTA | 661.49 | 862 | 1.303 | 0.265 |
| RL | CGTCTT | 440.20 | 562 | 1.277 | 0.244 |
| RL | CGTCTA | 237.40 | 296 | 1.247 | 0.221 |
| RL | CGTTTG | 431.33 | 526 | 1.219 | 0.198 |
| RL | CGTCTC | 638.40 | 723 | 1.133 | 0.124 |
| RL | AGGCTA | 600.44 | 669 | 1.114 | 0.108 |
| RL | AGACTT | 1134.11 | 1227 | 1.082 | 0.079 |
| RL | AGGCTG | 3355.51 | 3531 | 1.052 | 0.051 |
| RL | AGACTA | 611.62 | 617 | 1.009 | 0.009 |
| RL | AGGCTT | 1113.39 | 1104 | 0.992 | −0.008 |
| RL | CGACTA | 328.75 | 324 | 0.986 | −0.015 |
| RL | CGGCTA | 606.45 | 593 | 0.978 | −0.022 |
| RL | CGTCTG | 1326.68 | 1281 | 0.966 | −0.035 |
| RL | AGGCTC | 1614.68 | 1540 | 0.954 | −0.047 |
| RL | CGATTA | 355.55 | 337 | 0.948 | −0.054 |
| RL | CGACTT | 609.59 | 576 | 0.945 | −0.057 |
| RL | CGCCTA | 554.49 | 501 | 0.904 | −0.101 |
| RL | AGGTTA | 649.40 | 586 | 0.902 | −0.103 |
| RL | CGCCTT | 1028.19 | 862 | 0.838 | −0.176 |
| RL | CGCTTG | 1007.46 | 804 | 0.798 | −0.226 |
| RL | CGGCTT | 1124.53 | 866 | 0.770 | −0.261 |
| RL | AGATTG | 1111.24 | 839 | 0.755 | −0.281 |
| RL | CGACTC | 884.04 | 663 | 0.750 | −0.288 |
| RL | AGGTTG | 1090.94 | 774 | 0.709 | −0.343 |
| RL | AGACTC | 1644.73 | 1142 | 0.694 | −0.365 |
| RL | CGATTG | 597.29 | 408 | 0.683 | −0.381 |
| RL | CGACTG | 1837.15 | 1128 | 0.614 | −0.488 |
| RL | CGCTTA | 599.71 | 345 | 0.575 | −0.553 |
| RL | CGGTTG | 1101.86 | 566 | 0.514 | −0.666 |
| RL | AGACTG | 3417.95 | 1701 | 0.498 | −0.698 |
| RL | CGGTTA | 655.90 | 297 | 0.453 | −0.792 |
| RM | CGCATG | 1558.32 | 1961 | 1.258 | 0.230 |
| RM | AGGATG | 1687.45 | 1974 | 1.170 | 0.157 |
| RM | CGAATG | 923.88 | 932 | 1.009 | 0.009 |
| RM | AGAATG | 1718.85 | 1690 | 0.983 | −0.017 |
| RM | CGGATG | 1704.33 | 1374 | 0.806 | −0.215 |
| RM | CGTATG | 667.17 | 329 | 0.493 | −0.707 |
| RN | AGAAAT | 1568.88 | 2627 | 1.674 | 0.515 |
| RN | AGGAAC | 1696.37 | 2200 | 1.297 | 0.260 |
| RN | AGGAAT | 1540.22 | 1796 | 1.166 | 0.154 |
| RN | AGAAAC | 1727.93 | 1949 | 1.128 | 0.120 |
| RN | CGAAAT | 843.28 | 930 | 1.103 | 0.098 |
| RN | CGCAAC | 1566.55 | 1575 | 1.005 | 0.005 |
| RN | CGGAAC | 1713.34 | 1621 | 0.946 | −0.055 |
| RN | CGAAAC | 928.77 | 784 | 0.844 | −0.169 |
| RN | CGGAAT | 1555.63 | 1002 | 0.644 | −0.440 |
| RN | CGTAAT | 608.96 | 340 | 0.558 | −0.583 |
| RN | CGCAAT | 1422.36 | 711 | 0.500 | −0.693 |
| RN | CGTAAC | 670.70 | 308 | 0.459 | −0.778 |
| RP | CGGCCG | 587.88 | 1226 | 2.085 | 0.735 |
| RP | CGGCCC | 1622.47 | 2939 | 1.811 | 0.594 |
| RP | CGCCCG | 537.51 | 717 | 1.334 | 0.288 |
| RP | AGGCCC | 1606.39 | 1982 | 1.234 | 0.210 |
| RP | AGGCCG | 582.05 | 666 | 1.144 | 0.135 |
| RP | AGGCCT | 1438.75 | 1642 | 1.141 | 0.132 |
| RP | AGGCCA | 1388.57 | 1511 | 1.088 | 0.084 |
| RP | CGTCCT | 568.84 | 589 | 1.035 | 0.035 |
| RP | AGACCA | 1414.41 | 1387 | 0.981 | −0.020 |
| RP | CGGCCT | 1453.14 | 1390 | 0.957 | −0.044 |
| RP | AGACCT | 1465.52 | 1398 | 0.954 | −0.047 |
| RP | CGTCCC | 635.12 | 582 | 0.916 | −0.087 |
| RP | CGGCCA | 1402.47 | 1285 | 0.916 | −0.087 |
| RP | CGCCCC | 1483.46 | 1320 | 0.890 | −0.117 |
| RP | CGTCCA | 549.00 | 487 | 0.887 | −0.120 |
| RP | AGACCC | 1636.29 | 1283 | 0.784 | −0.243 |
| RP | CGACCA | 760.25 | 591 | 0.777 | −0.252 |
| RP | CGACCC | 879.51 | 671 | 0.763 | −0.271 |
| RP | CGACCT | 787.72 | 580 | 0.736 | −0.306 |
| RP | CGCCCA | 1282.31 | 887 | 0.692 | −0.369 |
| RP | CGTCCG | 230.13 | 159 | 0.691 | −0.370 |

-continued

| AA pair | Codon pair | Expected | Observed | Observed/ Expected | CPS |
|---|---|---|---|---|---|
| RP | CGCCCT | 1328.65 | 830 | 0.625 | −0.470 |
| RP | CGACCG | 318.68 | 184 | 0.577 | −0.549 |
| RP | AGACCG | 592.88 | 246 | 0.415 | −0.880 |
| RQ | AGACAA | 1054.78 | 1456 | 1.380 | 0.322 |
| RQ | CGGCAG | 2920.52 | 3950 | 1.352 | 0.302 |
| RQ | CGCCAG | 2670.31 | 3160 | 1.183 | 0.168 |
| RQ | AGGCAA | 1035.51 | 1177 | 1.137 | 0.128 |
| RQ | AGGCAG | 2891.59 | 3013 | 1.042 | 0.041 |
| RQ | CGACAA | 566.95 | 522 | 0.921 | −0.083 |
| RQ | CGTCAG | 1143.25 | 953 | 0.834 | −0.182 |
| RQ | CGTCAA | 409.41 | 327 | 0.799 | −0.225 |
| RQ | CGACAG | 1583.16 | 1249 | 0.789 | −0.237 |
| RQ | CGGCAA | 1045.87 | 763 | 0.730 | −0.315 |
| RQ | AGACAG | 2945.39 | 2062 | 0.700 | −0.357 |
| RQ | CGCCAA | 956.27 | 591 | 0.618 | −0.481 |
| RR | CGCCGC | 1172.08 | 2232 | 1.904 | 0.644 |
| RR | CGGCGG | 1402.02 | 2316 | 1.652 | 0.502 |
| RR | AGAAGA | 1426.00 | 2307 | 1.618 | 0.481 |
| RR | CGGCGC | 1281.90 | 2064 | 1.610 | 0.476 |
| RR | AGGAGG | 1374.38 | 1973 | 1.436 | 0.362 |
| RR | CGCCGG | 1281.90 | 1679 | 1.310 | 0.270 |
| RR | CGAAGA | 766.48 | 987 | 1.288 | 0.253 |
| RR | AGGAGA | 1399.95 | 1758 | 1.256 | 0.228 |
| RR | CGCAGG | 1269.20 | 1565 | 1.233 | 0.209 |
| RR | CGGAGG | 1388.13 | 1670 | 1.203 | 0.185 |
| RR | CGTCGT | 214.84 | 228 | 1.061 | 0.059 |
| RR | CGAAGG | 752.48 | 770 | 1.023 | 0.023 |
| RR | CGCCGT | 501.81 | 502 | 1.000 | 0.000 |
| RR | AGAAGG | 1399.95 | 1325 | 0.946 | −0.055 |
| RR | CGGCGT | 548.83 | 498 | 0.907 | −0.097 |
| RR | CGTCGA | 297.51 | 265 | 0.891 | −0.116 |
| RR | CGGCGA | 760.01 | 675 | 0.888 | −0.119 |
| RR | CGTCGC | 501.81 | 438 | 0.873 | −0.136 |
| RR | AGGCGG | 1388.13 | 1177 | 0.848 | −0.165 |
| RR | CGTCGG | 548.83 | 450 | 0.820 | −0.199 |
| RR | CGACGT | 297.51 | 241 | 0.810 | −0.211 |
| RR | CGCCGA | 694.89 | 547 | 0.787 | −0.239 |
| RR | AGGCGA | 752.48 | 570 | 0.757 | −0.278 |
| RR | CGGAGA | 1413.96 | 1068 | 0.755 | −0.281 |
| RR | AGACGA | 766.48 | 557 | 0.727 | −0.319 |
| RR | AGGCGT | 543.39 | 383 | 0.705 | −0.350 |
| RR | AGGCGC | 1269.20 | 889 | 0.700 | −0.356 |
| RR | AGACGT | 553.50 | 376 | 0.679 | −0.387 |
| RR | CGACGA | 411.98 | 272 | 0.660 | −0.415 |
| RR | CGCAGA | 1292.82 | 771 | 0.596 | −0.517 |
| RR | CGACGG | 760.01 | 411 | 0.541 | −0.615 |
| RR | CGACGC | 694.89 | 368 | 0.530 | −0.636 |
| RR | CGTAGA | 553.50 | 271 | 0.490 | −0.714 |
| RR | CGTAGG | 543.39 | 235 | 0.432 | −0.838 |
| RR | AGACGC | 1292.82 | 524 | 0.405 | −0.903 |
| RR | AGACGG | 1413.96 | 569 | 0.402 | −0.910 |
| RS | CGCTCG | 332.61 | 817 | 2.456 | 0.899 |
| RS | CGCAGC | 1425.00 | 2853 | 2.002 | 0.694 |
| RS | CGCTCC | 1257.78 | 2184 | 1.736 | 0.552 |
| RS | AGAAGT | 991.66 | 1532 | 1.545 | 0.435 |
| RS | CGTTCT | 468.44 | 687 | 1.467 | 0.383 |
| RS | CGAAGT | 533.02 | 728 | 1.366 | 0.312 |
| RS | CGTTCC | 538.50 | 707 | 1.313 | 0.272 |
| RS | AGGAGC | 1543.09 | 1992 | 1.291 | 0.255 |
| RS | CGTTCA | 378.71 | 471 | 1.244 | 0.218 |
| RS | CGGAGC | 1558.53 | 1856 | 1.191 | 0.175 |
| RS | AGGAGT | 973.54 | 1071 | 1.100 | 0.095 |
| RS | AGAAGC | 1571.80 | 1628 | 1.036 | 0.035 |
| RS | AGATCA | 975.67 | 1000 | 1.025 | 0.025 |
| RS | CGAAGC | 844.85 | 859 | 1.017 | 0.017 |
| RS | CGCTCA | 884.55 | 860 | 0.972 | −0.028 |
| RS | CGCAGT | 899.04 | 853 | 0.949 | −0.053 |
| RS | AGATCT | 1206.86 | 1106 | 0.916 | −0.087 |
| RS | CGCTCT | 1094.14 | 942 | 0.861 | −0.150 |
| RS | CGTTCG | 142.40 | 121 | 0.850 | −0.163 |
| RS | AGGTCA | 957.85 | 808 | 0.844 | −0.170 |
| RS | CGATCA | 524.43 | 416 | 0.793 | −0.232 |
| RS | AGGTCT | 1184.81 | 939 | 0.793 | −0.233 |
| RS | AGGTCG | 360.17 | 284 | 0.789 | −0.238 |
| RS | CGATCT | 648.69 | 497 | 0.766 | −0.266 |
| RS | AGGTCC | 1362.00 | 1036 | 0.761 | −0.274 |

-continued

| AA pair | Codon pair | Expected | Observed | Observed/ Expected | CPS |
|---|---|---|---|---|---|
| RS | CGGAGT | 983.28 | 745 | 0.758 | −0.278 |
| RS | CGTAGT | 384.91 | 278 | 0.722 | −0.325 |
| RS | CGGTCG | 363.77 | 235 | 0.646 | −0.437 |
| RS | CGATCC | 745.70 | 455 | 0.610 | −0.494 |
| RS | AGATCC | 1387.35 | 830 | 0.598 | −0.514 |
| RS | CGGTCC | 1375.63 | 821 | 0.597 | −0.516 |
| RS | CGATCG | 197.19 | 107 | 0.543 | −0.611 |
| RS | CGGTCA | 967.43 | 507 | 0.524 | −0.646 |
| RS | CGTAGC | 610.09 | 317 | 0.520 | −0.655 |
| RS | AGATCG | 366.87 | 177 | 0.482 | −0.729 |
| RS | CGGTCT | 1196.66 | 518 | 0.433 | −0.837 |
| RT | CGCACG | 450.78 | 858 | 1.903 | 0.644 |
| RT | AGAACT | 1083.61 | 1467 | 1.354 | 0.303 |
| RT | CGCACC | 1372.27 | 1821 | 1.327 | 0.283 |
| RT | AGGACG | 488.14 | 646 | 1.323 | 0.280 |
| RT | AGGACT | 1063.81 | 1389 | 1.306 | 0.267 |
| RT | AGAACA | 1225.34 | 1575 | 1.285 | 0.251 |
| RT | AGGACA | 1202.96 | 1523 | 1.266 | 0.236 |
| RT | AGGACC | 1485.98 | 1773 | 1.193 | 0.177 |
| RT | CGGACG | 493.02 | 537 | 1.089 | 0.085 |
| RT | CGAACA | 658.62 | 661 | 1.004 | 0.004 |
| RT | CGAACT | 582.44 | 556 | 0.955 | −0.046 |
| RT | CGGACC | 1500.85 | 1408 | 0.938 | −0.064 |
| RT | CGCACA | 1110.90 | 984 | 0.886 | −0.121 |
| RT | CGGACA | 1215.00 | 949 | 0.781 | −0.247 |
| RT | AGAACC | 1513.63 | 1166 | 0.770 | −0.261 |
| RT | CGTACT | 420.60 | 313 | 0.744 | −0.295 |
| RT | CGAACC | 813.58 | 599 | 0.736 | −0.306 |
| RT | CGGACT | 1074.45 | 712 | 0.663 | −0.411 |
| RT | CGCACT | 982.40 | 638 | 0.649 | −0.432 |
| RT | CGTACC | 587.52 | 361 | 0.614 | −0.487 |
| RT | AGAACG | 497.22 | 302 | 0.607 | −0.499 |
| RT | CGTACA | 475.62 | 288 | 0.606 | −0.502 |
| RT | CGAACG | 267.26 | 154 | 0.576 | −0.551 |
| RT | CGTACG | 193.00 | 79 | 0.409 | −0.893 |
| RV | CGTGTG | 889.90 | 1699 | 1.909 | 0.647 |
| RV | CGTGTC | 449.83 | 826 | 1.836 | 0.608 |
| RV | CGAGTA | 315.92 | 562 | 1.779 | 0.576 |
| RV | CGTGTA | 228.14 | 391 | 1.714 | 0.539 |
| RV | CGTGTT | 351.34 | 565 | 1.608 | 0.475 |
| RV | AGAGTT | 905.17 | 1350 | 1.491 | 0.400 |
| RV | AGAGTA | 587.76 | 876 | 1.490 | 0.399 |
| RV | CGAGTC | 622.91 | 914 | 1.467 | 0.383 |
| RV | CGAGTT | 486.53 | 681 | 1.400 | 0.336 |
| RV | CGAGTG | 1232.31 | 1576 | 1.279 | 0.246 |
| RV | CGGGTC | 1149.12 | 1310 | 1.140 | 0.131 |
| RV | AGGGTC | 1137.73 | 1221 | 1.073 | 0.071 |
| RV | CGGGTG | 2273.30 | 2328 | 1.024 | 0.024 |
| RV | AGAGTC | 1158.91 | 1154 | 0.996 | −0.004 |
| RV | CGCGTG | 2078.54 | 1725 | 0.830 | −0.186 |
| RV | AGGGTA | 577.02 | 471 | 0.816 | −0.203 |
| RV | AGAGTG | 2292.67 | 1750 | 0.763 | −0.270 |
| RV | CGGGTA | 582.79 | 438 | 0.752 | −0.286 |
| RV | AGGGTG | 2250.78 | 1658 | 0.737 | −0.306 |
| RV | CGCGTC | 1050.67 | 763 | 0.726 | −0.320 |
| RV | AGGGTT | 888.63 | 645 | 0.726 | −0.320 |
| RV | CGGGTT | 897.52 | 548 | 0.611 | −0.493 |
| RV | CGCGTA | 532.86 | 132 | 0.248 | −1.395 |
| RV | CGCGTT | 820.63 | 178 | 0.217 | −1.528 |
| RW | CGCTGG | 1038.00 | 2199 | 2.118 | 0.751 |
| RW | CGTTGG | 444.40 | 380 | 0.855 | −0.157 |
| RW | AGGTGG | 1124.01 | 876 | 0.779 | −0.249 |
| RW | CGATGG | 615.40 | 466 | 0.757 | −0.278 |
| RW | AGATGG | 1144.93 | 804 | 0.702 | −0.353 |
| RW | CGGTGG | 1135.26 | 777 | 0.684 | −0.379 |
| RY | CGCTAC | 1173.12 | 2612 | 2.227 | 0.800 |
| RY | CGCTAT | 953.25 | 1198 | 1.257 | 0.229 |
| RY | CGTTAC | 502.25 | 565 | 1.125 | 0.118 |
| RY | CGTTAT | 408.12 | 459 | 1.125 | 0.117 |
| RY | AGATAT | 1051.45 | 1018 | 0.968 | −0.032 |
| RY | AGATAC | 1293.97 | 1239 | 0.958 | −0.043 |
| RY | CGATAT | 565.15 | 509 | 0.901 | −0.105 |
| RY | CGATAC | 695.51 | 584 | 0.840 | −0.175 |
| RY | AGGTAC | 1270.33 | 1007 | 0.793 | −0.232 |
| RY | AGGTAT | 1032.24 | 769 | 0.745 | −0.294 |
| RY | CGGTAC | 1283.04 | 856 | 0.667 | −0.405 |

-continued

| AA pair | Codon pair | Expected | Observed | Observed/ Expected | CPS |
|---|---|---|---|---|---|
| RY | CGGTAT | 1042.57 | 455 | 0.436 | −0.829 |
| SA | TCGGCG | 241.39 | 778 | 3.223 | 1.170 |
| SA | TCGGCC | 892.76 | 1976 | 2.213 | 0.795 |
| SA | TCAGCA | 1366.87 | 2526 | 1.848 | 0.614 |
| SA | TCTGCA | 1690.75 | 3035 | 1.795 | 0.585 |
| SA | TCTGCT | 1931.41 | 3350 | 1.734 | 0.551 |
| SA | TCAGCT | 1561.43 | 2630 | 1.684 | 0.521 |
| SA | AGTGCT | 1587.01 | 2487 | 1.567 | 0.449 |
| SA | AGTGCA | 1389.27 | 2040 | 1.468 | 0.384 |
| SA | AGTGCC | 2413.15 | 3437 | 1.424 | 0.354 |
| SA | TCAGCC | 2374.25 | 3294 | 1.387 | 0.327 |
| SA | TCGGCT | 587.12 | 808 | 1.376 | 0.319 |
| SA | TCTGCC | 2936.83 | 3480 | 1.185 | 0.170 |
| SA | TCGGCA | 513.97 | 598 | 1.163 | 0.151 |
| SA | TCTGCG | 794.06 | 745 | 0.938 | −0.064 |
| SA | TCAGCG | 641.95 | 584 | 0.910 | −0.095 |
| SA | AGTGCG | 652.47 | 532 | 0.815 | −0.204 |
| SA | AGCGCG | 1034.18 | 802 | 0.775 | −0.254 |
| SA | AGCGCC | 3824.90 | 2428 | 0.635 | −0.454 |
| SA | TCCGCG | 912.82 | 577 | 0.632 | −0.459 |
| SA | TCCGCC | 3376.05 | 1230 | 0.364 | −1.010 |
| SA | AGCGCT | 2515.45 | 709 | 0.282 | −1.266 |
| SA | AGCGCA | 2202.02 | 601 | 0.273 | −1.299 |
| SA | TCCGCA | 1943.61 | 476 | 0.245 | −1.407 |
| SA | TCCGCT | 2220.26 | 481 | 0.217 | −1.530 |
| SC | TCCTGC | 1640.34 | 2828 | 1.724 | 0.545 |
| SC | AGCTGC | 1858.43 | 3034 | 1.633 | 0.490 |
| SC | TCCTGT | 1381.63 | 1779 | 1.288 | 0.253 |
| SC | AGCTGT | 1565.33 | 1922 | 1.228 | 0.205 |
| SC | TCGTGC | 433.77 | 361 | 0.832 | −0.184 |
| SC | TCTTGT | 1201.89 | 941 | 0.783 | −0.245 |
| SC | AGTTGT | 987.57 | 698 | 0.707 | −0.347 |
| SC | TCGTGT | 365.36 | 225 | 0.616 | −0.485 |
| SC | TCATGT | 971.65 | 584 | 0.601 | −0.509 |
| SC | TCTTGC | 1426.94 | 758 | 0.531 | −0.633 |
| SC | TCATGC | 1153.59 | 525 | 0.455 | −0.787 |
| SC | AGTTGC | 1172.49 | 504 | 0.430 | −0.844 |
| SD | TCAGAT | 1978.63 | 3706 | 1.873 | 0.628 |
| SD | AGTGAT | 2011.05 | 3683 | 1.831 | 0.605 |
| SD | AGTGAC | 2271.71 | 4040 | 1.778 | 0.576 |
| SD | TCGGAC | 840.43 | 1438 | 1.711 | 0.537 |
| SD | TCTGAT | 2447.46 | 3578 | 1.462 | 0.380 |
| SD | TCAGAC | 2235.09 | 2906 | 1.300 | 0.262 |
| SD | TCGGAT | 744.00 | 840 | 1.129 | 0.121 |
| SD | TCTGAC | 2764.69 | 2949 | 1.067 | 0.065 |
| SD | AGCGAC | 3600.71 | 2017 | 0.560 | −0.580 |
| SD | TCCGAC | 3178.17 | 1336 | 0.420 | −0.867 |
| SD | AGCGAT | 3187.56 | 920 | 0.289 | −1.243 |
| SD | TCCGAT | 2813.50 | 660 | 0.235 | −1.450 |
| SE | TCAGAA | 2420.84 | 4815 | 1.989 | 0.688 |
| SE | AGTGAA | 2460.50 | 4686 | 1.904 | 0.644 |
| SE | TCGGAG | 1217.33 | 2184 | 1.794 | 0.584 |
| SE | TCTGAA | 2994.45 | 4621 | 1.543 | 0.434 |
| SE | TCAGAG | 3237.43 | 4683 | 1.447 | 0.369 |
| SE | AGTGAG | 3290.47 | 4410 | 1.340 | 0.293 |
| SE | TCTGAG | 4004.54 | 4891 | 1.221 | 0.200 |
| SE | TCGGAA | 910.28 | 879 | 0.966 | −0.035 |
| SE | AGCGAG | 5215.47 | 2961 | 0.568 | −0.566 |
| SE | TCCGAG | 4603.44 | 2005 | 0.436 | −0.831 |
| SE | AGCGAA | 3899.95 | 847 | 0.217 | −1.527 |
| SE | TCCGAA | 3442.29 | 715 | 0.208 | −1.572 |
| SF | TCCTTC | 2645.79 | 4407 | 1.666 | 0.510 |
| SF | AGCTTC | 2997.56 | 3942 | 1.315 | 0.274 |
| SF | TCATTT | 1625.65 | 1773 | 1.091 | 0.087 |
| SF | TCCTTT | 2311.58 | 2487 | 1.076 | 0.073 |
| SF | AGTTTT | 1652.29 | 1695 | 1.026 | 0.026 |
| SF | AGCTTT | 2618.91 | 2370 | 0.905 | −0.100 |
| SF | TCTTTT | 2010.85 | 1809 | 0.900 | −0.106 |
| SF | TCTTTC | 2301.58 | 1728 | 0.751 | −0.287 |
| SF | AGTTTC | 1891.18 | 1353 | 0.715 | −0.335 |
| SF | TCGTTT | 611.27 | 342 | 0.559 | −0.581 |
| SF | TCATTC | 1860.69 | 991 | 0.533 | −0.630 |
| SF | TCGTTC | 699.65 | 330 | 0.472 | −0.751 |
| SG | AGTGGT | 1051.00 | 2094 | 1.992 | 0.689 |
| SG | TCGGGG | 586.31 | 1117 | 1.905 | 0.645 |
| SG | TCGGGC | 814.29 | 1487 | 1.826 | 0.602 |

-continued

| AA pair | Codon pair | Expected | Observed | Observed/ Expected | CPS |
|---|---|---|---|---|---|
| SG | AGTGGA | 1623.36 | 2932 | 1.806 | 0.591 |
| SG | TCAGGA | 1597.19 | 2760 | 1.728 | 0.547 |
| SG | TCTGGA | 1975.64 | 3391 | 1.716 | 0.540 |
| SG | AGTGGG | 1584.81 | 2584 | 1.630 | 0.489 |
| SG | TCTGGG | 1928.73 | 2974 | 1.542 | 0.433 |
| SG | AGTGGC | 2201.05 | 3314 | 1.506 | 0.409 |
| SG | TCTGGT | 1279.07 | 1902 | 1.487 | 0.397 |
| SG | TCAGGG | 1559.26 | 2161 | 1.386 | 0.326 |
| SG | TCAGGT | 1034.06 | 1351 | 1.307 | 0.267 |
| SG | TCGGGA | 600.57 | 684 | 1.139 | 0.130 |
| SG | TCGGGT | 388.82 | 410 | 1.054 | 0.053 |
| SG | TCTGGC | 2678.70 | 2734 | 1.021 | 0.020 |
| SG | TCAGGC | 2165.57 | 2114 | 0.976 | −0.024 |
| SG | AGCGGC | 3488.72 | 2475 | 0.709 | −0.343 |
| SG | AGCGGG | 2511.96 | 1464 | 0.583 | −0.540 |
| SG | TCCGGG | 2217.18 | 1117 | 0.504 | −0.686 |
| SG | TCCGGC | 3079.31 | 1163 | 0.378 | −0.974 |
| SG | AGCGGT | 1665.85 | 536 | 0.322 | −1.134 |
| SG | AGCGGA | 2573.06 | 663 | 0.258 | −1.356 |
| SG | TCCGGA | 2271.11 | 560 | 0.247 | −1.400 |
| SG | TCCGGT | 1470.37 | 359 | 0.244 | −1.410 |
| SH | AGCCAC | 2202.27 | 3210 | 1.458 | 0.377 |
| SH | TCTCAT | 1226.22 | 1426 | 1.163 | 0.151 |
| SH | TCCCAC | 1943.83 | 2233 | 1.149 | 0.139 |
| SH | AGTCAT | 1007.57 | 1082 | 1.074 | 0.071 |
| SH | AGCCAT | 1597.01 | 1606 | 1.006 | 0.006 |
| SH | TCGCAC | 514.03 | 512 | 0.996 | −0.004 |
| SH | TCCCAT | 1409.60 | 1349 | 0.957 | −0.044 |
| SH | TCACAT | 991.32 | 929 | 0.937 | −0.065 |
| SH | AGTCAC | 1389.42 | 1077 | 0.775 | −0.255 |
| SH | TCACAC | 1367.03 | 956 | 0.699 | −0.358 |
| SH | TCTCAC | 1690.94 | 1158 | 0.685 | −0.379 |
| SH | TCGCAT | 372.75 | 174 | 0.467 | −0.762 |
| SI | TCCATC | 2374.96 | 4526 | 1.906 | 0.645 |
| SI | AGCATC | 2690.72 | 4471 | 1.662 | 0.508 |
| SI | TCCATT | 1878.09 | 2383 | 1.269 | 0.238 |
| SI | AGCATT | 2127.79 | 2384 | 1.120 | 0.114 |
| SI | TCCATA | 863.76 | 963 | 1.115 | 0.109 |
| SI | AGTATA | 617.40 | 640 | 1.037 | 0.036 |
| SI | TCAATA | 607.45 | 618 | 1.017 | 0.017 |
| SI | AGTATT | 1342.43 | 1299 | 0.968 | −0.033 |
| SI | AGCATA | 978.60 | 943 | 0.964 | −0.037 |
| SI | TCTATA | 751.38 | 658 | 0.876 | −0.133 |
| SI | TCTATT | 1633.75 | 1215 | 0.744 | −0.296 |
| SI | TCAATT | 1320.79 | 957 | 0.725 | −0.322 |
| SI | AGTATC | 1697.59 | 924 | 0.544 | −0.608 |
| SI | TCGATA | 228.41 | 109 | 0.477 | −0.740 |
| SI | TCTATC | 2065.98 | 958 | 0.464 | −0.769 |
| SI | TCGATT | 496.64 | 185 | 0.373 | −0.988 |
| SI | TCAATC | 1670.22 | 557 | 0.333 | −1.098 |
| SI | TCGATC | 628.03 | 184 | 0.293 | −1.228 |
| SK | TCCAAG | 3563.99 | 5021 | 1.409 | 0.343 |
| SK | TCCAAA | 2751.88 | 3634 | 1.321 | 0.278 |
| SK | AGCAAG | 4037.83 | 5128 | 1.270 | 0.239 |
| SK | AGCAAA | 3117.75 | 3736 | 1.198 | 0.181 |
| SK | TCAAAA | 1935.30 | 2282 | 1.179 | 0.165 |
| SK | AGTAAA | 1967.01 | 2149 | 1.093 | 0.088 |
| SK | TCAAAG | 2506.42 | 2082 | 0.831 | −0.186 |
| SK | TCTAAA | 2393.86 | 1838 | 0.768 | −0.264 |
| SK | TCGAAG | 942.46 | 522 | 0.554 | −0.591 |
| SK | AGTAAG | 2547.49 | 1300 | 0.510 | −0.673 |
| SK | TCTAAG | 3100.32 | 1569 | 0.506 | −0.681 |
| SK | TCGAAA | 727.71 | 331 | 0.455 | −0.788 |
| SL | AGTTTA | 709.05 | 1103 | 1.556 | 0.442 |
| SL | TCGCTG | 1355.42 | 2104 | 1.552 | 0.440 |
| SL | TCCTTG | 1666.44 | 2462 | 1.477 | 0.390 |
| SL | TCTTTA | 862.92 | 1267 | 1.468 | 0.384 |
| SL | AGCCTC | 2794.39 | 4013 | 1.436 | 0.362 |
| SL | TCTTTG | 1449.64 | 2009 | 1.386 | 0.326 |
| SL | TCATTA | 697.62 | 862 | 1.236 | 0.212 |
| SL | AGCCTG | 5807.08 | 7014 | 1.208 | 0.189 |
| SL | AGTTTG | 1191.15 | 1427 | 1.198 | 0.181 |
| SL | TCGCTC | 652.23 | 777 | 1.191 | 0.175 |
| SL | TCTCTA | 797.87 | 950 | 1.191 | 0.175 |
| SL | TCTCTT | 1479.47 | 1750 | 1.183 | 0.168 |
| SL | TCCCTG | 5125.62 | 6034 | 1.177 | 0.163 |
| SL | TCCCTC | 2466.46 | 2805 | 1.137 | 0.129 |
| SL | TCCTTA | 991.98 | 1076 | 1.085 | 0.081 |
| SL | AGTCTT | 1215.66 | 1242 | 1.022 | 0.021 |
| SL | AGCCTT | 1926.85 | 1959 | 1.017 | 0.017 |
| SL | TCACTA | 645.03 | 630 | 0.977 | −0.024 |
| SL | AGCTTG | 1888.00 | 1786 | 0.946 | −0.056 |
| SL | TCACTT | 1196.06 | 1111 | 0.929 | −0.074 |
| SL | TCCCTT | 1700.73 | 1545 | 0.908 | −0.096 |
| SL | TCCCTA | 917.19 | 810 | 0.883 | −0.124 |
| SL | AGTCTA | 655.60 | 569 | 0.868 | −0.142 |
| SL | TCATTG | 1171.95 | 1015 | 0.866 | −0.144 |
| SL | AGCCTA | 1039.14 | 875 | 0.842 | −0.172 |
| SL | TCTCTC | 2145.58 | 1760 | 0.820 | −0.198 |
| SL | TCTCTG | 4458.78 | 3418 | 0.767 | −0.266 |
| SL | AGCTTA | 1123.86 | 758 | 0.674 | −0.394 |
| SL | AGTCTC | 1763.00 | 1158 | 0.657 | −0.420 |
| SL | TCGTTG | 440.67 | 280 | 0.635 | −0.454 |
| SL | TCACTC | 1734.58 | 1100 | 0.634 | −0.455 |
| SL | TCACTG | 3604.66 | 2254 | 0.625 | −0.470 |
| SL | TCGCTT | 449.74 | 279 | 0.620 | −0.477 |
| SL | TCGCTA | 242.54 | 143 | 0.590 | −0.528 |
| SL | TCGTTA | 262.32 | 140 | 0.534 | −0.628 |
| SL | AGTCTG | 3663.72 | 1808 | 0.493 | −0.706 |
| SM | TCCATG | 2282.65 | 3908 | 1.712 | 0.538 |
| SM | AGCATG | 2586.13 | 3300 | 1.276 | 0.244 |
| SM | TCAATG | 1605.31 | 1129 | 0.703 | −0.352 |
| SM | TCGATG | 603.62 | 365 | 0.605 | −0.503 |
| SM | AGTATG | 1631.61 | 966 | 0.592 | −0.524 |
| SM | TCTATG | 1985.68 | 1027 | 0.517 | −0.659 |
| SN | AGCAAC | 2539.42 | 3717 | 1.464 | 0.381 |
| SN | TCCAAC | 2241.42 | 3216 | 1.435 | 0.361 |
| SN | TCAAAT | 1431.22 | 1883 | 1.316 | 0.274 |
| SN | AGCAAT | 2305.68 | 2513 | 1.090 | 0.086 |
| SN | TCCAAT | 2035.11 | 2000 | 0.983 | −0.017 |
| SN | AGTAAT | 1454.67 | 1425 | 0.980 | −0.021 |
| SN | AGTAAC | 1602.14 | 1339 | 0.836 | −0.179 |
| SN | TCAAAC | 1576.31 | 1194 | 0.757 | −0.278 |
| SN | TCTAAT | 1770.34 | 1297 | 0.733 | −0.311 |
| SN | TCTAAC | 1949.81 | 955 | 0.490 | −0.714 |
| SN | TCGAAT | 538.16 | 258 | 0.479 | −0.735 |
| SN | TCGAAC | 592.72 | 240 | 0.405 | −0.904 |
| SP | TCGCCG | 282.21 | 549 | 1.945 | 0.665 |
| SP | TCGCCC | 778.87 | 1221 | 1.568 | 0.450 |
| SP | TCCCCG | 1067.21 | 1621 | 1.519 | 0.418 |
| SP | TCTCCA | 2214.76 | 3119 | 1.408 | 0.342 |
| SP | AGCCCC | 3336.96 | 4654 | 1.395 | 0.333 |
| SP | TCTCCT | 2294.78 | 2888 | 1.259 | 0.230 |
| SP | AGCCCG | 1209.10 | 1432 | 1.184 | 0.169 |
| SP | TCCCCA | 2545.99 | 2968 | 1.166 | 0.153 |
| SP | TCACCA | 1790.50 | 1869 | 1.044 | 0.043 |
| SP | AGCCCT | 2988.71 | 3086 | 1.033 | 0.032 |
| SP | AGTCCT | 1885.59 | 1904 | 1.010 | 0.010 |
| SP | TCACCT | 1855.20 | 1752 | 0.944 | −0.057 |
| SP | AGCCCA | 2884.48 | 2607 | 0.904 | −0.101 |
| SP | TCCCCT | 2637.98 | 2238 | 0.848 | −0.164 |
| SP | AGTCCA | 1819.84 | 1473 | 0.809 | −0.211 |
| SP | TCGCCT | 697.59 | 562 | 0.806 | −0.216 |
| SP | TCGCCA | 673.26 | 541 | 0.804 | −0.219 |
| SP | TCTCCC | 2562.18 | 2036 | 0.795 | −0.230 |
| SP | TCACCC | 2071.37 | 1568 | 0.757 | −0.278 |
| SP | AGTCCC | 2105.31 | 1534 | 0.729 | −0.317 |
| SP | TCTCCG | 928.37 | 664 | 0.715 | −0.335 |
| SP | TCCCCC | 2945.37 | 2058 | 0.699 | −0.358 |
| SP | TCACCG | 750.53 | 426 | 0.568 | −0.566 |
| SP | AGTCCG | 762.83 | 319 | 0.418 | −0.872 |
| SQ | TCCCAG | 4427.95 | 5592 | 1.263 | 0.233 |
| SQ | AGCCAG | 5016.65 | 6041 | 1.204 | 0.186 |
| SQ | TCTCAA | 1379.40 | 1644 | 1.192 | 0.175 |
| SQ | AGTCAA | 1133.44 | 1293 | 1.141 | 0.132 |
| SQ | TCACAA | 1115.16 | 1196 | 1.072 | 0.070 |
| SQ | AGCCAA | 1796.52 | 1819 | 1.013 | 0.012 |
| SQ | TCCCAA | 1585.70 | 1474 | 0.930 | −0.073 |
| SQ | TCTCAG | 3851.88 | 3430 | 0.890 | −0.116 |
| SQ | TCGCAG | 1170.92 | 1015 | 0.867 | −0.143 |
| SQ | TCACAG | 3114.02 | 2271 | 0.729 | −0.316 |
| SQ | AGTCAG | 3165.04 | 2215 | 0.700 | −0.357 |

-continued

| AA pair | Codon pair | Expected | Observed | Observed/ Expected | CPS |
|---|---|---|---|---|---|
| SQ | TCGCAA | 419.32 | 186 | 0.444 | −0.813 |
| SR | AGCCGC | 1540.23 | 2828 | 1.836 | 0.608 |
| SR | TCCAGG | 1472.14 | 2309 | 1.568 | 0.450 |
| SR | AGCCGG | 1684.56 | 2353 | 1.397 | 0.334 |
| SR | TCCCGG | 1486.87 | 1976 | 1.329 | 0.284 |
| SR | AGCAGG | 1667.87 | 2186 | 1.311 | 0.271 |
| SR | AGCCGT | 659.43 | 857 | 1.300 | 0.262 |
| SR | TCGCGC | 359.50 | 446 | 1.241 | 0.216 |
| SR | TCCAGA | 1499.54 | 1850 | 1.234 | 0.210 |
| SR | TCAAGA | 1054.57 | 1294 | 1.227 | 0.205 |
| SR | TCGCGG | 393.19 | 481 | 1.223 | 0.202 |
| SR | TCCCGC | 1359.49 | 1605 | 1.181 | 0.166 |
| SR | TCTCGA | 701.14 | 826 | 1.178 | 0.164 |
| SR | AGTCGT | 416.04 | 484 | 1.163 | 0.151 |
| SR | TCCCGA | 806.00 | 937 | 1.163 | 0.151 |
| SR | AGCAGA | 1698.90 | 1925 | 1.133 | 0.125 |
| SR | AGCCGA | 913.16 | 1020 | 1.117 | 0.111 |
| SR | TCTCGT | 506.32 | 493 | 0.974 | −0.027 |
| SR | AGTCGA | 576.12 | 553 | 0.960 | −0.041 |
| SR | TCCCGT | 582.04 | 553 | 0.950 | −0.051 |
| SR | TCAAGG | 1035.31 | 922 | 0.891 | −0.116 |
| SR | TCGAGG | 389.29 | 324 | 0.832 | −0.184 |
| SR | TCTCGG | 1293.43 | 1062 | 0.821 | −0.197 |
| SR | TCACGT | 409.33 | 323 | 0.789 | −0.237 |
| SR | AGTAGA | 1071.85 | 746 | 0.696 | −0.362 |
| SR | TCGCGT | 153.92 | 102 | 0.663 | −0.411 |
| SR | AGTCGG | 1062.80 | 675 | 0.635 | −0.454 |
| SR | AGTCGC | 971.74 | 591 | 0.608 | −0.497 |
| SR | TCACGA | 566.83 | 344 | 0.607 | −0.499 |
| SR | TCGAGA | 396.54 | 240 | 0.605 | −0.502 |
| SR | TCTAGA | 1304.45 | 750 | 0.575 | −0.553 |
| SR | TCGCGA | 213.14 | 115 | 0.540 | −0.617 |
| SR | TCTCGC | 1182.62 | 636 | 0.538 | −0.620 |
| SR | TCACGG | 1045.66 | 534 | 0.511 | −0.672 |
| SR | TCTAGG | 1280.62 | 574 | 0.448 | −0.802 |
| SR | TCACGC | 956.08 | 406 | 0.425 | −0.856 |
| SR | AGTAGG | 1052.27 | 443 | 0.421 | −0.865 |
| SS | AGCAGC | 3919.72 | 7160 | 1.827 | 0.602 |
| SS | TCGTCG | 213.54 | 376 | 1.761 | 0.566 |
| SS | TCCTCG | 807.53 | 1302 | 1.612 | 0.478 |
| SS | TCCAGC | 3459.74 | 4832 | 1.397 | 0.334 |
| SS | TCTTCA | 1868.19 | 2596 | 1.390 | 0.329 |
| SS | AGCAGT | 2472.97 | 3417 | 1.382 | 0.323 |
| SS | TCCTCC | 3053.74 | 4162 | 1.363 | 0.310 |
| SS | TCTTCT | 2310.85 | 2896 | 1.253 | 0.226 |
| SS | TCCAGT | 2182.77 | 2691 | 1.233 | 0.209 |
| SS | TCATCA | 1510.32 | 1795 | 1.188 | 0.173 |
| SS | AGCTCC | 3459.74 | 4024 | 1.163 | 0.151 |
| SS | TCATCT | 1868.19 | 2118 | 1.134 | 0.126 |
| SS | TCCTCA | 2147.58 | 2413 | 1.124 | 0.117 |
| SS | AGCTCG | 914.89 | 1001 | 1.094 | 0.090 |
| SS | TCCTCT | 2656.45 | 2744 | 1.033 | 0.032 |
| SS | TCGTCC | 807.53 | 818 | 1.013 | 0.013 |
| SS | TCTTCC | 2656.45 | 2600 | 0.979 | −0.021 |
| SS | AGTTCT | 1898.79 | 1856 | 0.977 | −0.023 |
| SS | AGTTCA | 1535.06 | 1498 | 0.976 | −0.024 |
| SS | TCAAGT | 1535.06 | 1404 | 0.915 | −0.089 |
| SS | AGCTCA | 2433.11 | 2075 | 0.853 | −0.159 |
| SS | AGCTCT | 3009.63 | 2465 | 0.819 | −0.200 |
| SS | TCTTCG | 702.47 | 556 | 0.791 | −0.234 |
| SS | TCATCC | 2147.58 | 1632 | 0.760 | −0.275 |
| SS | AGTAGT | 1560.21 | 1030 | 0.660 | −0.415 |
| SS | AGTTCC | 2182.77 | 1405 | 0.644 | −0.441 |
| SS | TCGTCT | 702.47 | 434 | 0.618 | −0.482 |
| SS | TCATCG | 567.91 | 343 | 0.604 | −0.504 |
| SS | TCGTCA | 567.91 | 313 | 0.551 | −0.596 |
| SS | TCTAGT | 1898.79 | 957 | 0.504 | −0.685 |
| SS | TCGAGC | 914.89 | 440 | 0.481 | −0.732 |
| SS | AGTAGC | 2472.97 | 1158 | 0.468 | −0.759 |
| SS | TCAAGC | 2433.11 | 1117 | 0.459 | −0.779 |
| SS | TCGAGT | 577.21 | 259 | 0.449 | −0.801 |
| SS | AGTTCG | 577.21 | 251 | 0.435 | −0.833 |
| SS | TCTAGC | 3009.63 | 899 | 0.299 | −1.208 |
| ST | TCCACG | 785.52 | 1434 | 1.826 | 0.602 |
| ST | AGCACC | 2709.18 | 4149 | 1.531 | 0.426 |
| ST | TCCACC | 2391.25 | 3527 | 1.475 | 0.389 |

-continued

| AA pair | Codon pair | Expected | Observed | Observed/ Expected | CPS |
|---|---|---|---|---|---|
| ST | AGCACG | 889.95 | 1180 | 1.326 | 0.282 |
| ST | AGCACA | 2193.18 | 2692 | 1.227 | 0.205 |
| ST | TCCACA | 1935.81 | 2329 | 1.203 | 0.185 |
| ST | TCCACT | 1711.89 | 1937 | 1.131 | 0.124 |
| ST | AGCACT | 1939.49 | 2193 | 1.131 | 0.123 |
| ST | TCAACA | 1361.39 | 1485 | 1.091 | 0.087 |
| ST | TCAACT | 1203.91 | 1270 | 1.055 | 0.053 |
| ST | TCTACT | 1489.18 | 1390 | 0.933 | −0.069 |
| ST | TCTACA | 1683.97 | 1461 | 0.868 | −0.142 |
| ST | AGTACT | 1223.64 | 1036 | 0.847 | −0.166 |
| ST | AGTACA | 1383.69 | 1061 | 0.767 | −0.266 |
| ST | TCGACG | 207.72 | 145 | 0.698 | −0.359 |
| ST | TCTACC | 2080.15 | 1218 | 0.586 | −0.535 |
| ST | TCGACC | 632.34 | 365 | 0.577 | −0.550 |
| ST | AGTACC | 1709.24 | 976 | 0.571 | −0.560 |
| ST | TCGACT | 452.69 | 240 | 0.530 | −0.635 |
| ST | TCAACC | 1681.68 | 873 | 0.519 | −0.656 |
| ST | TCAACG | 552.43 | 275 | 0.498 | −0.698 |
| ST | TCGACA | 511.90 | 236 | 0.461 | −0.774 |
| ST | TCTACG | 683.32 | 302 | 0.442 | −0.817 |
| ST | AGTACG | 561.48 | 201 | 0.358 | −1.027 |
| SV | TCGGTG | 935.47 | 1822 | 1.948 | 0.667 |
| SV | TCTGTA | 788.92 | 1398 | 1.772 | 0.572 |
| SV | TCTGTT | 1214.96 | 2136 | 1.758 | 0.564 |
| SV | TCAGTA | 637.79 | 1121 | 1.758 | 0.564 |
| SV | AGTGTT | 998.32 | 1719 | 1.722 | 0.543 |
| SV | TCAGTT | 982.23 | 1591 | 1.620 | 0.482 |
| SV | TCTGTC | 1555.54 | 2367 | 1.522 | 0.420 |
| SV | AGTGTC | 1278.17 | 1943 | 1.520 | 0.419 |
| SV | TCTGTG | 3077.33 | 4672 | 1.518 | 0.418 |
| SV | AGTGTA | 648.24 | 976 | 1.506 | 0.409 |
| SV | TCGGTC | 472.87 | 683 | 1.444 | 0.368 |
| SV | TCAGTG | 2487.84 | 2925 | 1.176 | 0.162 |
| SV | AGTGTG | 2528.60 | 2901 | 1.147 | 0.137 |
| SV | TCAGTC | 1257.56 | 1351 | 1.074 | 0.072 |
| SV | TCGGTA | 239.82 | 231 | 0.963 | −0.037 |
| SV | TCGGTT | 369.33 | 266 | 0.720 | −0.328 |
| SV | AGCGTC | 2025.93 | 1298 | 0.641 | −0.445 |
| SV | TCCGTG | 3537.57 | 2065 | 0.584 | −0.538 |
| SV | AGCGTG | 4007.89 | 2221 | 0.554 | −0.590 |
| SV | TCCGTC | 1788.18 | 829 | 0.464 | −0.769 |
| SV | AGCGTT | 1582.36 | 446 | 0.282 | −1.266 |
| SV | TCCGTA | 906.91 | 239 | 0.264 | −1.334 |
| SV | TCCGTT | 1396.67 | 329 | 0.236 | −1.446 |
| SV | AGCGTA | 1027.48 | 217 | 0.211 | −1.555 |
| SW | TCCTGG | 1756.97 | 2825 | 1.608 | 0.475 |
| SW | AGCTGG | 1990.56 | 2404 | 1.208 | 0.189 |
| SW | TCGTGG | 464.61 | 444 | 0.956 | −0.045 |
| SW | TCTTGG | 1528.39 | 1137 | 0.744 | −0.296 |
| SW | TCATGG | 1235.61 | 778 | 0.630 | −0.463 |
| SW | AGTTGG | 1255.86 | 644 | 0.513 | −0.668 |
| SY | TCCTAC | 1871.53 | 3038 | 1.623 | 0.484 |
| SY | AGCTAC | 2120.35 | 2864 | 1.351 | 0.301 |
| SY | TCCTAT | 1520.75 | 1869 | 1.229 | 0.206 |
| SY | AGCTAT | 1722.94 | 1609 | 0.934 | −0.068 |
| SY | AGTTAT | 1087.01 | 1010 | 0.929 | −0.073 |
| SY | AGTTAC | 1337.74 | 1153 | 0.862 | −0.149 |
| SY | TCATAT | 1069.49 | 897 | 0.839 | −0.176 |
| SY | TCTTAT | 1322.91 | 1100 | 0.832 | −0.185 |
| SY | TCTTAC | 1628.04 | 1204 | 0.740 | −0.302 |
| SY | TCGTAC | 494.91 | 304 | 0.614 | −0.487 |
| SY | TCGTAT | 402.15 | 204 | 0.507 | −0.679 |
| SY | TCATAC | 1316.18 | 642 | 0.488 | −0.718 |
| TA | ACGGCG | 348.71 | 734 | 2.105 | 0.744 |
| TA | ACAGCA | 1829.79 | 3283 | 1.794 | 0.585 |
| TA | ACGGCC | 1289.71 | 2090 | 1.621 | 0.483 |
| TA | ACTGCA | 1618.13 | 2557 | 1.580 | 0.458 |
| TA | ACAGCT | 2090.24 | 3295 | 1.576 | 0.455 |
| TA | ACTGCT | 1848.45 | 2764 | 1.495 | 0.402 |
| TA | ACAGCC | 3178.34 | 3912 | 1.231 | 0.208 |
| TA | ACGGCA | 742.49 | 804 | 1.083 | 0.080 |
| TA | ACTGCC | 2810.69 | 3015 | 1.073 | 0.070 |
| TA | ACGGCT | 848.18 | 804 | 0.948 | −0.053 |
| TA | ACAGCG | 859.36 | 803 | 0.934 | −0.068 |
| TA | ACTGCG | 759.96 | 623 | 0.820 | −0.199 |
| TA | ACCGCG | 1061.55 | 584 | 0.550 | −0.598 |

-continued

| AA pair | Codon pair | Expected | Observed | Observed/ Expected | CPS |
|---|---|---|---|---|---|
| TA | ACCGCC | 3926.11 | 1648 | 0.420 | −0.868 |
| TA | ACCGCA | 2260.29 | 561 | 0.248 | −1.394 |
| TA | ACCGCT | 2582.01 | 577 | 0.223 | −1.498 |
| TC | ACCTGC | 1892.82 | 3247 | 1.715 | 0.540 |
| TC | ACCTGT | 1594.30 | 1994 | 1.251 | 0.224 |
| TC | ACGTGC | 621.78 | 691 | 1.111 | 0.106 |
| TC | ACGTGT | 523.72 | 484 | 0.924 | −0.079 |
| TC | ACTTGT | 1141.35 | 1033 | 0.905 | −0.100 |
| TC | ACATGT | 1290.64 | 938 | 0.727 | −0.319 |
| TC | ACTTGC | 1355.07 | 815 | 0.601 | −0.508 |
| TC | ACATGC | 1532.31 | 750 | 0.489 | −0.714 |
| TD | ACAGAT | 2415.25 | 4195 | 1.737 | 0.552 |
| TD | ACAGAC | 2728.31 | 3765 | 1.380 | 0.322 |
| TD | ACTGAT | 2135.87 | 2913 | 1.364 | 0.310 |
| TD | ACGGAC | 1107.10 | 1446 | 1.306 | 0.267 |
| TD | ACTGAC | 2412.71 | 2615 | 1.084 | 0.081 |
| TD | ACGGAT | 980.07 | 922 | 0.941 | −0.061 |
| TD | ACCGAC | 3370.20 | 1547 | 0.459 | −0.779 |
| TD | ACCGAT | 2983.49 | 730 | 0.245 | −1.408 |
| TE | ACAGAA | 3127.33 | 5307 | 1.697 | 0.529 |
| TE | ACGGAG | 1697.07 | 2517 | 1.483 | 0.394 |
| TE | ACTGAA | 2765.58 | 4093 | 1.480 | 0.392 |
| TE | ACAGAG | 4182.23 | 5419 | 1.296 | 0.259 |
| TE | ACTGAG | 3698.46 | 4124 | 1.115 | 0.109 |
| TE | ACGGAA | 1269.01 | 1080 | 0.851 | −0.161 |
| TE | ACCGAG | 5166.20 | 2450 | 0.474 | −0.746 |
| TE | ACCGAA | 3863.10 | 779 | 0.202 | −1.601 |
| TF | ACCTTC | 3026.54 | 4955 | 1.637 | 0.493 |
| TF | ACATTT | 2140.61 | 2275 | 1.063 | 0.061 |
| TF | ACTTTT | 1893.00 | 1904 | 1.006 | 0.006 |
| TF | ACCTTT | 2644.23 | 2518 | 0.952 | −0.049 |
| TF | ACTTTC | 2166.69 | 1822 | 0.841 | −0.173 |
| TF | ACGTTT | 868.62 | 650 | 0.748 | −0.290 |
| TF | ACGTTC | 994.21 | 666 | 0.670 | −0.401 |
| TF | ACATTC | 2450.10 | 1394 | 0.569 | −0.564 |
| TG | ACTGGA | 1710.74 | 3660 | 2.139 | 0.761 |
| TG | ACTGGT | 1107.57 | 1887 | 1.704 | 0.533 |
| TG | ACAGGA | 1934.51 | 2970 | 1.535 | 0.429 |
| TG | ACGGGC | 1064.34 | 1583 | 1.487 | 0.397 |
| TG | ACTGGG | 1670.12 | 2322 | 1.390 | 0.330 |
| TG | ACGGGG | 766.35 | 1049 | 1.369 | 0.314 |
| TG | ACAGGT | 1252.44 | 1694 | 1.353 | 0.302 |
| TG | ACAGGG | 1888.57 | 2148 | 1.137 | 0.129 |
| TG | ACTGGC | 2319.53 | 2620 | 1.130 | 0.122 |
| TG | ACAGGC | 2622.93 | 2664 | 1.016 | 0.016 |
| TG | ACGGGT | 508.22 | 484 | 0.952 | −0.049 |
| TG | ACGGGA | 784.99 | 710 | 0.904 | −0.100 |
| TG | ACCGGG | 2332.90 | 1093 | 0.469 | −0.758 |
| TG | ACCGGC | 3240.03 | 1373 | 0.424 | −0.859 |
| TG | ACCGGT | 1547.11 | 355 | 0.229 | −1.472 |
| TG | ACCGGA | 2389.65 | 528 | 0.221 | −1.510 |
| TH | ACTCAT | 1054.95 | 1291 | 1.224 | 0.202 |
| TH | ACCCAC | 2032.09 | 2408 | 1.185 | 0.170 |
| TH | ACGCAC | 667.53 | 764 | 1.145 | 0.135 |
| TH | ACACAT | 1192.94 | 1186 | 0.994 | −0.006 |
| TH | ACTCAC | 1454.76 | 1384 | 0.951 | −0.050 |
| TH | ACCCAT | 1473.60 | 1287 | 0.873 | −0.135 |
| TH | ACACAC | 1645.05 | 1383 | 0.841 | −0.174 |
| TH | ACGCAT | 484.07 | 302 | 0.624 | −0.472 |
| TI | ACCATC | 2842.70 | 5915 | 2.081 | 0.733 |
| TI | ACCATT | 2247.97 | 2878 | 1.280 | 0.247 |
| TI | ACAATA | 836.96 | 980 | 1.171 | 0.158 |
| TI | ACCATA | 1033.87 | 1137 | 1.100 | 0.095 |
| TI | ACAATT | 1819.82 | 1579 | 0.868 | −0.142 |
| TI | ACTATA | 740.14 | 642 | 0.867 | −0.142 |
| TI | ACTATT | 1609.31 | 1337 | 0.831 | −0.185 |
| TI | ACGATA | 339.62 | 190 | 0.559 | −0.581 |
| TI | ACGATT | 738.45 | 389 | 0.527 | −0.641 |
| TI | ACGATC | 933.81 | 463 | 0.496 | −0.702 |
| TI | ACTATC | 2035.08 | 942 | 0.463 | −0.770 |
| TI | ACAATC | 2301.27 | 1027 | 0.446 | −0.807 |
| TK | ACCAAG | 3878.56 | 6678 | 1.722 | 0.543 |
| TK | ACCAAA | 2994.77 | 3789 | 1.265 | 0.235 |
| TK | ACAAAA | 2424.38 | 2546 | 1.050 | 0.049 |
| TK | ACAAAG | 3139.84 | 2507 | 0.798 | −0.225 |
| TK | ACTAAA | 2143.95 | 1684 | 0.785 | −0.241 |

-continued

| AA pair | Codon pair | Expected | Observed | Observed/ Expected | CPS |
|---|---|---|---|---|---|
| TK | ACGAAG | 1274.09 | 708 | 0.556 | −0.588 |
| TK | ACGAAA | 983.77 | 511 | 0.519 | −0.655 |
| TK | ACTAAG | 2776.65 | 1193 | 0.430 | −0.845 |
| TL | ACGCTG | 1815.48 | 3357 | 1.849 | 0.615 |
| TL | ACTTTA | 765.72 | 1207 | 1.576 | 0.455 |
| TL | ACTTTG | 1286.34 | 1876 | 1.458 | 0.377 |
| TL | ACATTA | 865.87 | 1115 | 1.288 | 0.253 |
| TL | ACCTTG | 1796.82 | 2257 | 1.256 | 0.228 |
| TL | ACTCTA | 707.99 | 876 | 1.237 | 0.213 |
| TL | ACGCTC | 873.61 | 1057 | 1.210 | 0.191 |
| TL | ACCCTC | 2659.44 | 3133 | 1.178 | 0.164 |
| TL | ACCCTG | 5526.65 | 6354 | 1.150 | 0.140 |
| TL | ACTCTT | 1312.81 | 1469 | 1.119 | 0.112 |
| TL | ACACTA | 800.60 | 799 | 0.998 | −0.002 |
| TL | ACGCTA | 324.87 | 307 | 0.945 | −0.057 |
| TL | ACCTTA | 1069.59 | 957 | 0.895 | −0.111 |
| TL | ACACTT | 1484.53 | 1316 | 0.886 | −0.121 |
| TL | ACGTTG | 590.25 | 505 | 0.856 | −0.156 |
| TL | ACATTG | 1454.60 | 1210 | 0.832 | −0.184 |
| TL | ACCCTT | 1833.80 | 1515 | 0.826 | −0.191 |
| TL | ACCCTA | 988.95 | 802 | 0.811 | −0.210 |
| TL | ACTCTG | 3956.51 | 3120 | 0.789 | −0.238 |
| TL | ACGTTA | 351.36 | 262 | 0.746 | −0.293 |
| TL | ACTCTC | 1903.88 | 1391 | 0.731 | −0.314 |
| TL | ACGCTT | 602.39 | 427 | 0.709 | −0.344 |
| TL | ACACTG | 4474.03 | 3013 | 0.673 | −0.395 |
| TL | ACACTC | 2152.92 | 1274 | 0.592 | −0.525 |
| TM | ACCATG | 2733.42 | 4467 | 1.634 | 0.491 |
| TM | ACAATG | 2212.81 | 1641 | 0.742 | −0.299 |
| TM | ACGATG | 897.92 | 655 | 0.729 | −0.315 |
| TM | ACTATG | 1956.85 | 1038 | 0.530 | −0.634 |
| TN | ACCAAC | 2378.62 | 4300 | 1.808 | 0.592 |
| TN | ACAAAT | 1748.34 | 2194 | 1.255 | 0.227 |
| TN | ACCAAT | 2159.68 | 2454 | 1.136 | 0.128 |
| TN | ACAAAC | 1925.59 | 1486 | 0.772 | −0.259 |
| TN | ACTAAT | 1546.11 | 1077 | 0.697 | −0.362 |
| TN | ACGAAT | 709.45 | 336 | 0.474 | −0.747 |
| TN | ACTAAC | 1702.85 | 789 | 0.463 | −0.769 |
| TN | ACGAAC | 781.37 | 316 | 0.404 | −0.905 |
| TP | ACGCCG | 349.03 | 632 | 1.811 | 0.594 |
| TP | ACGCCC | 963.29 | 1491 | 1.548 | 0.437 |
| TP | ACTCCA | 1814.66 | 2359 | 1.300 | 0.262 |
| TP | ACCCCG | 1062.52 | 1331 | 1.253 | 0.225 |
| TP | ACTCCT | 1880.23 | 2186 | 1.163 | 0.151 |
| TP | ACACCA | 2052.02 | 2361 | 1.151 | 0.140 |
| TP | ACCCCA | 2534.80 | 2784 | 1.098 | 0.094 |
| TP | ACACCT | 2126.17 | 2104 | 0.990 | −0.010 |
| TP | ACCCCT | 2626.39 | 2415 | 0.920 | −0.084 |
| TP | ACGCCA | 832.67 | 748 | 0.898 | −0.107 |
| TP | ACCCCC | 2932.43 | 2380 | 0.812 | −0.209 |
| TP | ACACCC | 2373.91 | 1922 | 0.810 | −0.211 |
| TP | ACGCCT | 862.76 | 697 | 0.808 | −0.213 |
| TP | ACTCCC | 2099.31 | 1649 | 0.785 | −0.241 |
| TP | ACTCCG | 760.66 | 538 | 0.707 | −0.346 |
| TP | ACACCG | 860.15 | 534 | 0.621 | −0.477 |
| TQ | ACTCAA | 1103.35 | 1368 | 1.240 | 0.215 |
| TQ | ACCCAG | 4303.71 | 5173 | 1.202 | 0.184 |
| TQ | ACGCAG | 1413.75 | 1518 | 1.074 | 0.071 |
| TQ | ACACAA | 1247.67 | 1328 | 1.064 | 0.062 |
| TQ | ACTCAG | 3081.01 | 2839 | 0.921 | −0.082 |
| TQ | ACCCAA | 1541.21 | 1410 | 0.915 | −0.089 |
| TQ | ACACAG | 3484.02 | 2765 | 0.794 | −0.231 |
| TQ | ACGCAA | 506.28 | 280 | 0.553 | −0.592 |
| TR | ACCAGG | 1331.08 | 2049 | 1.539 | 0.431 |
| TR | ACGCGC | 403.79 | 605 | 1.498 | 0.404 |
| TR | ACGCGG | 441.63 | 661 | 1.497 | 0.403 |
| TR | ACTCGA | 521.72 | 717 | 1.374 | 0.318 |
| TR | ACAAGA | 1097.61 | 1429 | 1.302 | 0.264 |
| TR | ACCCGC | 1229.22 | 1547 | 1.259 | 0.230 |
| TR | ACCCGG | 1344.40 | 1668 | 1.241 | 0.216 |
| TR | ACTCGT | 376.76 | 448 | 1.189 | 0.173 |
| TR | ACCAGA | 1355.85 | 1599 | 1.179 | 0.165 |
| TR | ACCCGA | 728.77 | 758 | 1.040 | 0.039 |
| TR | ACCCGT | 526.27 | 535 | 1.017 | 0.016 |
| TR | ACAAGG | 1077.56 | 1072 | 0.995 | −0.005 |
| TR | ACGAGG | 437.25 | 433 | 0.990 | −0.010 |

-continued

| AA pair | Codon pair | Expected | Observed | Observed/ Expected | CPS |
|---|---|---|---|---|---|
| TR | ACTCGG | 962.45 | 823 | 0.855 | −0.157 |
| TR | ACGCGT | 172.88 | 141 | 0.816 | −0.204 |
| TR | ACACGT | 426.04 | 329 | 0.772 | −0.258 |
| TR | ACGAGA | 445.39 | 331 | 0.743 | −0.297 |
| TR | ACACGA | 589.97 | 432 | 0.732 | −0.312 |
| TR | ACACGG | 1088.34 | 756 | 0.695 | −0.364 |
| TR | ACTCGC | 879.99 | 607 | 0.690 | −0.371 |
| TR | ACTAGA | 970.65 | 624 | 0.643 | −0.442 |
| TR | ACGCGA | 239.40 | 150 | 0.627 | −0.468 |
| TR | ACACGC | 995.10 | 498 | 0.500 | −0.692 |
| TR | ACTAGG | 952.91 | 383 | 0.402 | −0.911 |
| TS | ACCAGC | 2807.29 | 4575 | 1.630 | 0.488 |
| TS | ACCTCG | 655.24 | 1060 | 1.618 | 0.481 |
| TS | ACGTCG | 215.24 | 348 | 1.617 | 0.480 |
| TS | ACTTCA | 1247.51 | 1844 | 1.478 | 0.391 |
| TS | ACTTCT | 1543.11 | 1974 | 1.279 | 0.246 |
| TS | ACATCA | 1410.69 | 1754 | 1.243 | 0.218 |
| TS | ACCAGT | 1771.14 | 2194 | 1.239 | 0.214 |
| TS | ACCTCC | 2477.85 | 3050 | 1.231 | 0.208 |
| TS | ACCTCA | 1742.59 | 1938 | 1.112 | 0.106 |
| TS | ACATCT | 1744.95 | 1911 | 1.095 | 0.091 |
| TS | ACGTCC | 813.96 | 840 | 1.032 | 0.031 |
| TS | ACCTCT | 2155.49 | 2072 | 0.961 | −0.040 |
| TS | ACAAGT | 1433.80 | 1335 | 0.931 | −0.071 |
| TS | ACTTCC | 1773.89 | 1524 | 0.859 | −0.152 |
| TS | ACGTCA | 572.43 | 450 | 0.786 | −0.241 |
| TS | ACATCC | 2005.92 | 1570 | 0.783 | −0.245 |
| TS | ACTTCG | 469.09 | 353 | 0.753 | −0.284 |
| TS | ACGTCT | 708.07 | 527 | 0.744 | −0.295 |
| TS | ACATCG | 530.44 | 361 | 0.681 | −0.385 |
| TS | ACTAGT | 1267.95 | 725 | 0.572 | −0.559 |
| TS | ACAAGC | 2272.61 | 1275 | 0.561 | −0.578 |
| TS | ACGAGT | 581.81 | 297 | 0.510 | −0.672 |
| TS | ACGAGC | 922.18 | 469 | 0.509 | −0.676 |
| TS | ACTAGC | 2009.73 | 687 | 0.342 | −1.073 |
| TT | ACCACG | 875.88 | 1567 | 1.789 | 0.582 |
| TT | ACCACC | 2666.32 | 4767 | 1.788 | 0.581 |
| TT | ACCACA | 2158.49 | 2882 | 1.335 | 0.289 |
| TT | ACCACT | 1908.81 | 2309 | 1.210 | 0.190 |
| TT | ACAACA | 1747.38 | 1793 | 1.026 | 0.026 |
| TT | ACAACT | 1545.26 | 1567 | 1.014 | 0.014 |
| TT | ACGACG | 287.72 | 252 | 0.876 | −0.133 |
| TT | ACTACT | 1366.51 | 1065 | 0.779 | −0.249 |
| TT | ACTACA | 1545.26 | 1196 | 0.774 | −0.256 |
| TT | ACGACC | 875.88 | 575 | 0.656 | −0.421 |
| TT | ACGACA | 709.06 | 437 | 0.616 | −0.484 |
| TT | ACAACC | 2158.49 | 1310 | 0.607 | −0.499 |
| TT | ACGACT | 627.04 | 357 | 0.569 | −0.563 |
| TT | ACTACC | 1908.81 | 992 | 0.520 | −0.655 |
| TT | ACAACG | 709.06 | 365 | 0.515 | −0.664 |
| TT | ACTACG | 627.04 | 283 | 0.451 | −0.796 |
| TV | ACTGTA | 845.20 | 1425 | 1.686 | 0.522 |
| TV | ACTGTT | 1301.64 | 2058 | 1.581 | 0.458 |
| TV | ACGGTG | 1512.80 | 2306 | 1.524 | 0.422 |
| TV | ACAGTA | 955.76 | 1371 | 1.434 | 0.361 |
| TV | ACTGTC | 1666.51 | 2289 | 1.374 | 0.317 |
| TV | ACAGTT | 1471.90 | 2019 | 1.372 | 0.316 |
| TV | ACTGTG | 3296.87 | 4505 | 1.366 | 0.312 |
| TV | ACGGTC | 764.70 | 911 | 1.191 | 0.175 |
| TV | ACAGTG | 3728.11 | 4108 | 1.102 | 0.097 |
| TV | ACAGTC | 1884.50 | 1933 | 1.026 | 0.025 |
| TV | ACGGTA | 387.83 | 286 | 0.737 | −0.305 |
| TV | ACGGTT | 597.27 | 415 | 0.695 | −0.364 |
| TV | ACCGTG | 4605.23 | 2640 | 0.573 | −0.556 |
| TV | ACCGTC | 2327.87 | 1285 | 0.552 | −0.594 |
| TV | ACCGTT | 1818.19 | 496 | 0.273 | −1.299 |
| TV | ACCGTA | 1180.62 | 298 | 0.252 | −1.377 |
| TW | ACGTGG | 606.25 | 837 | 1.381 | 0.323 |
| TW | ACCTGG | 1845.52 | 2403 | 1.302 | 0.264 |
| TW | ACATGG | 1494.02 | 1089 | 0.729 | −0.316 |
| TW | ACTTGG | 1321.21 | 938 | 0.710 | −0.343 |
| TY | ACCTAC | 2130.11 | 3648 | 1.713 | 0.538 |
| TY | ACCTAT | 1730.88 | 1778 | 1.027 | 0.027 |
| TY | ACTTAC | 1524.94 | 1383 | 0.907 | −0.098 |
| TY | ACGTAC | 699.73 | 621 | 0.887 | −0.119 |
| TY | ACATAT | 1401.21 | 1136 | 0.811 | −0.210 |
| TY | ACTTAT | 1239.13 | 907 | 0.732 | −0.312 |
| TY | ACGTAT | 568.59 | 408 | 0.718 | −0.332 |
| TY | ACATAC | 1724.41 | 1138 | 0.660 | −0.416 |
| VA | GTGGCC | 6082.92 | 9316 | 1.532 | 0.426 |
| VA | GTAGCA | 897.78 | 1347 | 1.500 | 0.406 |
| VA | GTTGCT | 1579.41 | 2217 | 1.404 | 0.339 |
| VA | GTAGCT | 1025.57 | 1407 | 1.372 | 0.316 |
| VA | GTGGCT | 4000.44 | 5252 | 1.313 | 0.272 |
| VA | GTGGCG | 1644.71 | 2099 | 1.276 | 0.244 |
| VA | GTTGCA | 1382.62 | 1728 | 1.250 | 0.223 |
| VA | GTGGCA | 3501.98 | 3859 | 1.102 | 0.097 |
| VA | GTAGCC | 1559.44 | 1363 | 0.874 | −0.135 |
| VA | GTTGCC | 2401.60 | 1808 | 0.753 | −0.284 |
| VA | GTAGCG | 421.64 | 216 | 0.512 | −0.669 |
| VA | GTTGCG | 649.35 | 234 | 0.360 | −1.021 |
| VA | GTCGCG | 831.37 | 284 | 0.342 | −1.074 |
| VA | GTCGCC | 3074.82 | 992 | 0.323 | −1.131 |
| VA | GTCGCT | 2022.16 | 406 | 0.201 | −1.606 |
| VA | GTCGCA | 1770.19 | 318 | 0.180 | −1.717 |
| VC | GTCTGC | 1410.66 | 2160 | 1.531 | 0.426 |
| VC | GTCTGT | 1188.18 | 1572 | 1.323 | 0.280 |
| VC | GTTTGT | 928.03 | 942 | 1.015 | 0.015 |
| VC | GTATGT | 602.60 | 594 | 0.986 | −0.014 |
| VC | GTGTGC | 2790.71 | 2583 | 0.926 | −0.077 |
| VC | GTGTGT | 2350.57 | 1996 | 0.849 | −0.164 |
| VC | GTTTGC | 1101.80 | 830 | 0.753 | −0.283 |
| VC | GTATGC | 715.44 | 411 | 0.574 | −0.554 |
| VD | GTAGAT | 1225.65 | 1924 | 1.570 | 0.451 |
| VD | GTGGAC | 5400.58 | 7734 | 1.432 | 0.359 |
| VD | GTTGAT | 1887.55 | 2389 | 1.266 | 0.236 |
| VD | GTGGAT | 4780.91 | 5727 | 1.198 | 0.181 |
| VD | GTAGAC | 1384.52 | 1346 | 0.972 | −0.028 |
| VD | GTTGAC | 2132.21 | 1791 | 0.840 | −0.174 |
| VD | GTCGAC | 2729.91 | 602 | 0.221 | −1.512 |
| VD | GTCGAT | 2416.67 | 445 | 0.184 | −1.692 |
| VE | GTAGAA | 1456.83 | 2855 | 1.960 | 0.673 |
| VE | GTGGAG | 7599.48 | 11579 | 1.524 | 0.421 |
| VE | GTTGAA | 2243.56 | 2905 | 1.295 | 0.258 |
| VE | GTGGAA | 5682.64 | 6229 | 1.096 | 0.092 |
| VE | GTAGAG | 1948.24 | 2002 | 1.028 | 0.027 |
| VE | GTTGAG | 3000.36 | 1987 | 0.662 | −0.412 |
| VE | GTCGAG | 3841.42 | 721 | 0.188 | −1.673 |
| VE | GTCGAA | 2872.48 | 367 | 0.128 | −2.058 |
| VF | GTCTTC | 2309.08 | 4216 | 1.826 | 0.602 |
| VF | GTATTT | 1023.16 | 1512 | 1.478 | 0.391 |
| VF | GTCTTT | 2017.40 | 2238 | 1.109 | 0.104 |
| VF | GTTTTT | 1575.70 | 1706 | 1.083 | 0.079 |
| VF | GTTTTC | 1803.52 | 1604 | 0.889 | −0.117 |
| VF | GTGTTT | 3991.02 | 3257 | 0.816 | −0.203 |
| VF | GTGTTC | 4568.05 | 3205 | 0.702 | −0.354 |
| VF | GTATTC | 1171.09 | 721 | 0.616 | −0.485 |
| VG | GTTGGT | 779.74 | 1617 | 2.074 | 0.729 |
| VG | GTTGGA | 1204.37 | 2315 | 1.922 | 0.653 |
| VG | GTGGGC | 4136.07 | 5977 | 1.445 | 0.368 |
| VG | GTAGGA | 782.04 | 1089 | 1.393 | 0.331 |
| VG | GTTGGG | 1175.77 | 1510 | 1.284 | 0.250 |
| VG | GTTGGC | 1632.96 | 1794 | 1.099 | 0.094 |
| VG | GTAGGT | 506.31 | 554 | 1.094 | 0.090 |
| VG | GTGGGG | 2978.07 | 3255 | 1.093 | 0.089 |
| VG | GTGGGT | 1974.96 | 2009 | 1.017 | 0.017 |
| VG | GTAGGG | 763.47 | 683 | 0.895 | −0.111 |
| VG | GTGGGA | 3050.51 | 2599 | 0.852 | −0.160 |
| VG | GTAGGC | 1060.34 | 676 | 0.638 | −0.450 |
| VG | GTCGGG | 1505.36 | 734 | 0.488 | −0.718 |
| VG | GTCGGC | 2090.72 | 734 | 0.351 | −1.047 |
| VG | GTCGGT | 998.31 | 292 | 0.292 | −1.229 |
| VG | GTCGGA | 1541.98 | 343 | 0.222 | −1.503 |
| VH | GTTCAT | 911.79 | 1418 | 1.555 | 0.442 |
| VH | GTACAT | 592.06 | 773 | 1.306 | 0.267 |
| VH | GTCCAC | 1609.82 | 2085 | 1.295 | 0.259 |
| VH | GTCCAT | 1167.39 | 1313 | 1.125 | 0.118 |
| VH | GTTCAC | 1257.35 | 1319 | 1.049 | 0.048 |
| VH | GTGCAC | 3184.70 | 2856 | 0.897 | −0.109 |
| VH | GTACAC | 816.44 | 613 | 0.751 | −0.287 |
| VH | GTGCAT | 2309.44 | 1472 | 0.637 | −0.450 |
| VI | GTCATC | 2367.78 | 5207 | 2.199 | 0.788 |

-continued

| AA pair | Codon pair | Expected | Observed | Observed/ Expected | CPS |
|---|---|---|---|---|---|
| VI | GTCATT | 1872.41 | 2827 | 1.510 | 0.412 |
| VI | GTAATA | 436.74 | 614 | 1.406 | 0.341 |
| VI | GTAATT | 949.63 | 1074 | 1.131 | 0.123 |
| VI | GTTATT | 1462.46 | 1595 | 1.091 | 0.087 |
| VI | GTCATA | 861.15 | 904 | 1.050 | 0.049 |
| VI | GTTATA | 672.60 | 702 | 1.044 | 0.043 |
| VI | GTGATT | 3704.20 | 2742 | 0.740 | −0.301 |
| VI | GTGATC | 4684.19 | 3353 | 0.716 | −0.334 |
| VI | GTGATA | 1703.61 | 1117 | 0.656 | −0.422 |
| VI | GTTATC | 1849.37 | 1053 | 0.569 | −0.563 |
| VI | GTAATC | 1200.86 | 577 | 0.480 | −0.733 |
| VK | GTAAAA | 1288.46 | 1945 | 1.510 | 0.412 |
| VK | GTCAAG | 3290.24 | 3982 | 1.210 | 0.191 |
| VK | GTGAAG | 6509.08 | 7513 | 1.154 | 0.143 |
| VK | GTAAAG | 1668.70 | 1704 | 1.021 | 0.021 |
| VK | GTCAAA | 2540.51 | 2376 | 0.935 | −0.067 |
| VK | GTTAAA | 1984.27 | 1777 | 0.896 | −0.110 |
| VK | GTGAAA | 5025.89 | 4409 | 0.877 | −0.131 |
| VK | GTTAAG | 2569.85 | 1171 | 0.456 | −0.786 |
| VL | GTTTTA | 668.83 | 1311 | 1.960 | 0.673 |
| VL | GTTCTT | 1146.70 | 1859 | 1.621 | 0.483 |
| VL | GTTTTG | 1123.58 | 1737 | 1.546 | 0.436 |
| VL | GTATTA | 434.30 | 646 | 1.487 | 0.397 |
| VL | GTCCTC | 2129.16 | 3019 | 1.418 | 0.349 |
| VL | GTTCTA | 618.41 | 832 | 1.345 | 0.297 |
| VL | GTCCTG | 4424.65 | 5574 | 1.260 | 0.231 |
| VL | GTCCTT | 1468.14 | 1722 | 1.173 | 0.159 |
| VL | GTGCTG | 8753.31 | 10107 | 1.155 | 0.144 |
| VL | GTCTTG | 1438.54 | 1628 | 1.132 | 0.124 |
| VL | GTACTA | 401.55 | 447 | 1.113 | 0.107 |
| VL | GTCCTA | 791.76 | 874 | 1.104 | 0.099 |
| VL | GTCTTA | 856.32 | 863 | 1.008 | 0.008 |
| VL | GTATTG | 729.58 | 711 | 0.975 | −0.026 |
| VL | GTACTT | 744.59 | 693 | 0.931 | −0.072 |
| VL | GTTCTC | 1662.99 | 1501 | 0.903 | −0.102 |
| VL | GTGCTC | 4212.12 | 3765 | 0.894 | −0.112 |
| VL | GTGCTA | 1566.34 | 1286 | 0.821 | −0.197 |
| VL | GTTCTG | 3455.90 | 2350 | 0.680 | −0.386 |
| VL | GTGTTG | 2845.87 | 1910 | 0.671 | −0.399 |
| VL | GTGCTT | 2904.43 | 1933 | 0.666 | −0.407 |
| VL | GTGTTA | 1694.06 | 965 | 0.570 | −0.563 |
| VL | GTACTC | 1079.84 | 541 | 0.501 | −0.691 |
| VL | GTACTG | 2244.04 | 1121 | 0.500 | −0.694 |
| VM | GTCATG | 2149.52 | 3308 | 1.539 | 0.431 |
| VM | GTGATG | 4252.41 | 3872 | 0.911 | −0.094 |
| VM | GTAATG | 1090.17 | 935 | 0.858 | −0.154 |
| VM | GTTATG | 1678.90 | 1056 | 0.629 | −0.464 |
| VN | GTCAAC | 2052.00 | 3311 | 1.614 | 0.478 |
| VN | GTAAAT | 944.92 | 1518 | 1.606 | 0.474 |
| VN | GTCAAT | 1863.13 | 2155 | 1.157 | 0.146 |
| VN | GTTAAT | 1455.20 | 1325 | 0.911 | −0.094 |
| VN | GTGAAC | 4059.49 | 3551 | 0.875 | −0.134 |
| VN | GTGAAT | 3685.83 | 3110 | 0.844 | −0.170 |
| VN | GTAAAC | 1040.71 | 854 | 0.821 | −0.198 |
| VN | GTTAAC | 1602.73 | 880 | 0.549 | −0.600 |
| VP | GTTCCT | 1434.04 | 2257 | 1.574 | 0.454 |
| VP | GTTCCA | 1384.03 | 1911 | 1.381 | 0.323 |
| VP | GTGCCC | 4055.45 | 4998 | 1.232 | 0.209 |
| VP | GTACCT | 931.17 | 1048 | 1.125 | 0.118 |
| VP | GTCCCC | 2049.96 | 2260 | 1.102 | 0.098 |
| VP | GTCCCT | 1836.02 | 2014 | 1.097 | 0.093 |
| VP | GTACCA | 898.70 | 963 | 1.072 | 0.069 |
| VP | GTCCCG | 742.77 | 786 | 1.058 | 0.057 |
| VP | GTTCCC | 1601.13 | 1506 | 0.941 | −0.061 |
| VP | GTCCCA | 1772.00 | 1596 | 0.901 | −0.105 |
| VP | GTGCCT | 3632.21 | 3062 | 0.843 | −0.171 |
| VP | GTGCCG | 1469.43 | 1228 | 0.836 | −0.179 |
| VP | GTACCC | 1039.67 | 809 | 0.778 | −0.251 |
| VP | GTGCCA | 3505.55 | 2431 | 0.693 | −0.366 |
| VP | GTTCCG | 580.15 | 279 | 0.481 | −0.732 |
| VP | GTACCG | 376.71 | 161 | 0.427 | −0.850 |
| VQ | GTACAA | 633.37 | 1049 | 1.656 | 0.505 |
| VQ | GTTCAA | 975.42 | 1485 | 1.522 | 0.420 |
| VQ | GTCCAG | 3487.32 | 3907 | 1.120 | 0.114 |
| VQ | GTACAG | 1768.65 | 1752 | 0.991 | −0.009 |
| VQ | GTTCAG | 2723.79 | 2689 | 0.987 | −0.013 |
| VQ | GTGCAG | 6898.98 | 6734 | 0.976 | −0.024 |
| VQ | GTCCAA | 1248.85 | 1067 | 0.854 | −0.157 |
| VQ | GTGCAA | 2470.60 | 1524 | 0.617 | −0.483 |
| VR | GTTCGA | 463.33 | 867 | 1.871 | 0.627 |
| VR | GTTCGT | 334.59 | 580 | 1.733 | 0.550 |
| VR | GTCCGA | 593.21 | 805 | 1.357 | 0.305 |
| VR | GTCCGC | 1000.57 | 1332 | 1.331 | 0.286 |
| VR | GTGCGC | 1979.43 | 2543 | 1.285 | 0.251 |
| VR | GTCCGT | 428.38 | 549 | 1.282 | 0.248 |
| VR | GTCCGG | 1094.32 | 1346 | 1.230 | 0.207 |
| VR | GTACGA | 300.86 | 361 | 1.200 | 0.182 |
| VR | GTAAGA | 559.73 | 660 | 1.179 | 0.165 |
| VR | GTGCGG | 2164.91 | 2552 | 1.179 | 0.164 |
| VR | GTCAGA | 1103.65 | 1291 | 1.170 | 0.157 |
| VR | GTACGT | 217.26 | 253 | 1.165 | 0.152 |
| VR | GTCAGG | 1083.48 | 1238 | 1.143 | 0.133 |
| VR | GTGAGG | 2143.46 | 1986 | 0.927 | −0.076 |
| VR | GTGCGT | 847.46 | 761 | 0.898 | −0.108 |
| VR | GTAAGG | 549.51 | 444 | 0.808 | −0.213 |
| VR | GTTCGG | 854.73 | 650 | 0.760 | −0.274 |
| VR | GTGCGA | 1173.55 | 826 | 0.704 | −0.351 |
| VR | GTTCGC | 781.50 | 545 | 0.697 | −0.360 |
| VR | GTGAGA | 2183.35 | 1511 | 0.692 | −0.368 |
| VR | GTACGG | 555.00 | 377 | 0.679 | −0.387 |
| VR | GTTAGA | 862.01 | 556 | 0.645 | −0.438 |
| VR | GTACGC | 507.46 | 286 | 0.564 | −0.573 |
| VR | GTTAGG | 846.26 | 309 | 0.365 | −1.007 |
| VS | GTTTCT | 1206.81 | 2161 | 1.791 | 0.583 |
| VS | GTCTCC | 1776.18 | 2936 | 1.653 | 0.503 |
| VS | GTCAGC | 2012.32 | 3223 | 1.602 | 0.471 |
| VS | GTTTCA | 975.63 | 1465 | 1.502 | 0.407 |
| VS | GTCAGT | 1269.59 | 1841 | 1.450 | 0.372 |
| VS | GTATCT | 783.62 | 1093 | 1.395 | 0.333 |
| VS | GTATCA | 633.51 | 806 | 1.272 | 0.241 |
| VS | GTCTCT | 1545.10 | 1847 | 1.195 | 0.178 |
| VS | GTTTCC | 1387.29 | 1604 | 1.156 | 0.145 |
| VS | GTCTCG | 469.69 | 542 | 1.154 | 0.143 |
| VS | GTCTCA | 1249.12 | 1333 | 1.067 | 0.065 |
| VS | GTGTCC | 3513.81 | 3722 | 1.059 | 0.058 |
| VS | GTGTCG | 929.19 | 860 | 0.926 | −0.077 |
| VS | GTGTCT | 3056.67 | 2784 | 0.911 | −0.093 |
| VS | GTATCC | 900.82 | 763 | 0.847 | −0.166 |
| VS | GTAAGT | 643.89 | 499 | 0.775 | −0.255 |
| VS | GTGAGC | 3980.98 | 2901 | 0.729 | −0.316 |
| VS | GTGTCA | 2471.14 | 1710 | 0.692 | −0.368 |
| VS | GTTAGT | 991.62 | 640 | 0.645 | −0.438 |
| VS | GTATCG | 238.21 | 138 | 0.579 | −0.546 |
| VS | GTTTCG | 366.85 | 202 | 0.551 | −0.597 |
| VS | GTGAGT | 2511.63 | 1371 | 0.546 | −0.605 |
| VS | GTAAGC | 1020.58 | 514 | 0.504 | −0.686 |
| VS | GTTAGC | 1571.73 | 551 | 0.351 | −1.048 |
| VT | GTCACC | 2294.69 | 4477 | 1.951 | 0.668 |
| VT | GTCACT | 1642.76 | 2452 | 1.493 | 0.401 |
| VT | GTCACG | 753.80 | 997 | 1.323 | 0.280 |
| VT | GTAACT | 833.15 | 1046 | 1.255 | 0.228 |
| VT | GTCACA | 1857.64 | 2207 | 1.188 | 0.172 |
| VT | GTAACA | 942.13 | 1096 | 1.163 | 0.151 |
| VT | GTTACT | 1283.09 | 1208 | 0.941 | −0.060 |
| VT | GTGACC | 4539.59 | 4223 | 0.930 | −0.072 |
| VT | GTGACG | 1491.24 | 1318 | 0.884 | −0.123 |
| VT | GTGACT | 3249.88 | 2758 | 0.849 | −0.164 |
| VT | GTGACA | 3674.98 | 2947 | 0.802 | −0.221 |
| VT | GTTACA | 1450.92 | 1111 | 0.766 | −0.267 |
| VT | GTAACC | 1163.79 | 758 | 0.651 | −0.429 |
| VT | GTTACC | 1792.28 | 969 | 0.541 | −0.615 |
| VT | GTAACG | 382.30 | 191 | 0.500 | −0.694 |
| VT | GTTACG | 588.76 | 183 | 0.311 | −1.169 |
| VV | GTTGTA | 655.54 | 1109 | 1.692 | 0.526 |
| VV | GTTGTT | 1009.55 | 1701 | 1.685 | 0.522 |
| VV | GTAGTA | 425.66 | 698 | 1.640 | 0.495 |
| VV | GTGGTG | 6476.64 | 9025 | 1.393 | 0.332 |
| VV | GTGGTC | 3273.84 | 4256 | 1.300 | 0.262 |
| VV | GTAGTT | 655.54 | 800 | 1.220 | 0.199 |
| VV | GTTGTC | 1292.55 | 1561 | 1.208 | 0.189 |
| VV | GTGGTA | 1660.38 | 1777 | 1.070 | 0.068 |
| VV | GTGGTT | 2557.05 | 2613 | 1.022 | 0.022 |

-continued

| AA pair | Codon pair | Expected | Observed | Observed/ Expected | CPS |
|---|---|---|---|---|---|
| VV | GTTGTG | 2557.05 | 2261 | 0.884 | −0.123 |
| VV | GTAGTG | 1660.38 | 1161 | 0.699 | −0.358 |
| VV | GTAGTC | 839.30 | 553 | 0.659 | −0.417 |
| VV | GTCGTC | 1654.87 | 858 | 0.518 | −0.657 |
| VV | GTCGTG | 3273.84 | 1250 | 0.382 | −0.963 |
| VV | GTCGTA | 839.30 | 213 | 0.254 | −1.371 |
| VV | GTCGTT | 1292.55 | 288 | 0.223 | −1.501 |
| VW | GTCTGG | 1316.29 | 1763 | 1.339 | 0.292 |
| VW | GTGTGG | 2604.03 | 2451 | 0.941 | −0.061 |
| VW | GTATGG | 667.58 | 578 | 0.866 | −0.144 |
| VW | GTTTGG | 1028.10 | 824 | 0.801 | −0.221 |
| VY | GTCTAC | 1602.79 | 2490 | 1.554 | 0.441 |
| VY | GTTTAT | 1017.23 | 1438 | 1.414 | 0.346 |
| VY | GTATAT | 660.53 | 875 | 1.325 | 0.281 |
| VY | GTCTAT | 1302.39 | 1544 | 1.186 | 0.170 |
| VY | GTGTAC | 3170.80 | 2654 | 0.837 | −0.178 |
| VY | GTTTAC | 1251.87 | 1008 | 0.805 | −0.217 |
| VY | GTATAC | 812.88 | 582 | 0.716 | −0.334 |
| VY | GTGTAT | 2576.51 | 1804 | 0.700 | −0.356 |
| WA | TGGGCA | 1469.77 | 1535 | 1.044 | 0.043 |
| WA | TGGGCG | 690.28 | 695 | 1.007 | 0.007 |
| WA | TGGGCT | 1678.97 | 1664 | 0.991 | −0.009 |
| WA | TGGGCC | 2552.98 | 2498 | 0.978 | −0.022 |
| WC | TGGTGC | 1057.38 | 1066 | 1.008 | 0.008 |
| WC | TGGTGT | 890.62 | 882 | 0.990 | −0.010 |
| WD | TGGGAC | 2699.37 | 2807 | 1.040 | 0.039 |
| WD | TGGGAT | 2389.63 | 2282 | 0.955 | −0.046 |
| WE | TGGGAG | 3580.00 | 3650 | 1.020 | 0.019 |
| WE | TGGGAA | 2677.00 | 2607 | 0.974 | −0.026 |
| WF | TGGTTT | 1639.95 | 1735 | 1.058 | 0.056 |
| WF | TGGTTC | 1877.05 | 1782 | 0.949 | −0.052 |
| WG | TGGGGT | 955.95 | 1064 | 1.113 | 0.107 |
| WG | TGGGGC | 2002.00 | 2179 | 1.088 | 0.085 |
| WG | TGGGGA | 1476.56 | 1454 | 0.985 | −0.015 |
| WG | TGGGGG | 1441.49 | 1179 | 0.818 | −0.201 |
| WH | TGGCAT | 971.42 | 1000 | 1.029 | 0.029 |
| WH | TGGCAC | 1339.58 | 1311 | 0.979 | −0.022 |
| WI | TGGATT | 1537.91 | 1627 | 1.058 | 0.056 |
| WI | TGGATA | 707.30 | 714 | 1.009 | 0.009 |
| WI | TGGATC | 1944.78 | 1849 | 0.951 | −0.051 |
| WK | TGGAAG | 3491.83 | 3645 | 1.044 | 0.043 |
| WK | TGGAAA | 2696.17 | 2543 | 0.943 | −0.058 |
| WL | TGGCTA | 683.88 | 798 | 1.167 | 0.154 |
| WL | TGGCTG | 3821.78 | 4228 | 1.106 | 0.101 |
| WL | TGGCTT | 1268.11 | 1334 | 1.052 | 0.051 |
| WL | TGGCTC | 1839.05 | 1879 | 1.022 | 0.021 |
| WL | TGGTTG | 1242.54 | 855 | 0.688 | −0.374 |
| WL | TGGTTA | 739.64 | 501 | 0.677 | −0.390 |
| WM | TGGATG | 2335.00 | 2335 | 1.000 | 0.000 |
| WN | TGGAAT | 1978.70 | 2005 | 1.013 | 0.013 |
| WN | TGGAAC | 2179.30 | 2153 | 0.988 | −0.012 |
| WP | TGGCCC | 1302.21 | 1381 | 1.061 | 0.059 |
| WP | TGGCCG | 471.84 | 486 | 1.030 | 0.030 |
| WP | TGGCCA | 1125.64 | 1123 | 0.998 | −0.002 |
| WP | TGGCCT | 1166.31 | 1076 | 0.923 | −0.081 |
| WQ | TGGCAG | 2983.56 | 2997 | 1.005 | 0.004 |
| WQ | TGGCAA | 1068.44 | 1055 | 0.987 | −0.013 |
| WR | TGGAGG | 1198.99 | 1665 | 1.389 | 0.328 |
| WR | TGGAGA | 1221.30 | 1472 | 1.205 | 0.187 |
| WR | TGGCGG | 1210.98 | 979 | 0.808 | −0.213 |
| WR | TGGCGC | 1107.23 | 895 | 0.808 | −0.213 |
| WR | TGGCGT | 474.05 | 377 | 0.795 | −0.229 |
| WR | TGGCGA | 656.45 | 481 | 0.733 | −0.311 |
| WS | TGGAGT | 1031.75 | 1239 | 1.201 | 0.183 |
| WS | TGGAGC | 1635.35 | 1956 | 1.196 | 0.179 |
| WS | TGGTCA | 1015.12 | 898 | 0.885 | −0.123 |
| WS | TGGTCC | 1443.44 | 1271 | 0.881 | −0.127 |
| WS | TGGTCT | 1255.65 | 1076 | 0.857 | −0.154 |
| WS | TGGTCG | 381.70 | 323 | 0.846 | −0.167 |
| WT | TGGACG | 598.07 | 674 | 1.127 | 0.120 |
| WT | TGGACA | 1473.88 | 1559 | 1.058 | 0.056 |
| WT | TGGACT | 1303.39 | 1240 | 0.951 | −0.050 |
| WT | TGGACC | 1820.65 | 1723 | 0.946 | −0.055 |
| WV | TGGGTC | 1318.64 | 1378 | 1.045 | 0.044 |
| WV | TGGGTG | 2608.66 | 2633 | 1.009 | 0.009 |
| WV | TGGGTA | 668.77 | 665 | 0.994 | −0.006 |

-continued

| AA pair | Codon pair | Expected | Observed | Observed/ Expected | CPS |
|---|---|---|---|---|---|
| WV | TGGGTT | 1029.93 | 950 | 0.922 | −0.081 |
| WW | TGGTGG | 1559.00 | 1559 | 1.000 | 0.000 |
| WY | TGGTAC | 1444.91 | 1520 | 1.052 | 0.051 |
| WY | TGGTAT | 1174.09 | 1099 | 0.936 | −0.066 |
| YA | TATGCA | 1120.39 | 2249 | 2.007 | 0.697 |
| YA | TATGCT | 1279.86 | 2296 | 1.794 | 0.584 |
| YA | TATGCC | 1946.11 | 2862 | 1.471 | 0.386 |
| YA | TACGCG | 647.56 | 622 | 0.961 | −0.040 |
| YA | TATGCG | 526.19 | 482 | 0.916 | −0.088 |
| YA | TACGCC | 2395.00 | 1402 | 0.585 | −0.535 |
| YA | TACGCA | 1378.81 | 512 | 0.371 | −0.991 |
| YA | TACGCT | 1575.07 | 444 | 0.282 | −1.266 |
| YC | TACTGC | 1588.07 | 2411 | 1.518 | 0.418 |
| YC | TACTGT | 1337.61 | 1587 | 1.186 | 0.171 |
| YC | TATTGT | 1086.90 | 659 | 0.606 | −0.500 |
| YC | TATTGC | 1290.42 | 646 | 0.501 | −0.692 |
| YD | TATGAT | 2091.17 | 3707 | 1.773 | 0.572 |
| YD | TATGAC | 2362.22 | 3731 | 1.579 | 0.457 |
| YD | TACGAC | 2907.08 | 1653 | 0.569 | −0.565 |
| YD | TACGAT | 2573.52 | 843 | 0.328 | −1.116 |
| YE | TATGAA | 2515.85 | 5225 | 2.077 | 0.731 |
| YE | TATGAG | 3364.48 | 4722 | 1.403 | 0.339 |
| YE | TACGAG | 4140.53 | 2309 | 0.558 | −0.584 |
| YE | TACGAA | 3096.14 | 861 | 0.278 | −1.280 |
| YF | TACTTC | 2766.63 | 3380 | 1.222 | 0.200 |
| YF | TATTTT | 1964.12 | 2124 | 1.081 | 0.078 |
| YF | TACTTT | 2417.16 | 2201 | 0.911 | −0.094 |
| YF | TATTTC | 2248.09 | 1691 | 0.752 | −0.285 |
| YG | TATGGA | 1472.35 | 2874 | 1.952 | 0.669 |
| YG | TATGGT | 953.23 | 1665 | 1.747 | 0.558 |
| YG | TATGGG | 1437.38 | 2129 | 1.481 | 0.393 |
| YG | TATGGC | 1996.30 | 2749 | 1.377 | 0.320 |
| YG | TACGGG | 1768.93 | 1088 | 0.615 | −0.486 |
| YG | TACGGC | 2456.76 | 1484 | 0.604 | −0.504 |
| YG | TACGGT | 1173.10 | 448 | 0.382 | −0.963 |
| YG | TACGGA | 1811.96 | 633 | 0.349 | −1.052 |
| YH | TACCAC | 1862.81 | 2378 | 1.277 | 0.244 |
| YH | TACCAT | 1350.85 | 1420 | 1.051 | 0.050 |
| YH | TATCAT | 1097.67 | 1021 | 0.930 | −0.072 |
| YH | TATCAC | 1513.67 | 1006 | 0.665 | −0.409 |
| YI | TACATC | 2684.66 | 3935 | 1.466 | 0.382 |
| YI | TACATT | 2122.99 | 2162 | 1.018 | 0.018 |
| YI | TATATT | 1725.09 | 1554 | 0.901 | −0.104 |
| YI | TACATA | 976.39 | 846 | 0.866 | −0.143 |
| YI | TATATA | 793.39 | 648 | 0.817 | −0.202 |
| YI | TATATC | 2181.48 | 1339 | 0.614 | −0.488 |
| YK | TACAAG | 3508.58 | 4372 | 1.246 | 0.220 |
| YK | TACAAA | 2709.10 | 2847 | 1.051 | 0.050 |
| YK | TATAAA | 2201.34 | 2262 | 1.028 | 0.027 |
| YK | TATAAG | 2850.98 | 1789 | 0.628 | −0.466 |
| YL | TACCTG | 4522.42 | 6324 | 1.398 | 0.335 |
| YL | TATTTA | 711.20 | 966 | 1.358 | 0.306 |
| YL | TACCTC | 2176.20 | 2598 | 1.194 | 0.177 |
| YL | TACTTG | 1470.33 | 1701 | 1.157 | 0.146 |
| YL | TATTTG | 1194.75 | 1358 | 1.137 | 0.128 |
| YL | TACCTA | 809.25 | 876 | 1.082 | 0.079 |
| YL | TACCTT | 1500.58 | 1449 | 0.966 | −0.035 |
| YL | TATCTT | 1219.33 | 1166 | 0.956 | −0.045 |
| YL | TACTTA | 875.24 | 763 | 0.872 | −0.137 |
| YL | TATCTA | 657.58 | 541 | 0.823 | −0.195 |
| YL | TATCTC | 1768.32 | 1087 | 0.615 | −0.487 |
| YL | TATCTG | 3674.80 | 1751 | 0.476 | −0.741 |
| YM | TACATG | 2325.97 | 3055 | 1.313 | 0.273 |
| YM | TATATG | 1890.03 | 1161 | 0.614 | −0.487 |
| YN | TACAAC | 2442.24 | 3341 | 1.368 | 0.313 |
| YN | TACAAT | 2217.44 | 2200 | 0.992 | −0.008 |
| YN | TATAAT | 1801.83 | 1629 | 0.904 | −0.101 |
| YN | TATAAC | 1984.50 | 1276 | 0.643 | −0.442 |
| YP | TACCCG | 668.65 | 1004 | 1.502 | 0.406 |
| YP | TACCCA | 1595.15 | 1925 | 1.207 | 0.188 |
| YP | TATCCA | 1296.18 | 1438 | 1.109 | 0.104 |
| YP | TACCCC | 1845.38 | 1961 | 1.063 | 0.061 |
| YP | TATCCT | 1343.02 | 1379 | 1.027 | 0.026 |
| YP | TACCCT | 1652.79 | 1558 | 0.943 | −0.059 |
| YP | TATCCC | 1499.51 | 937 | 0.625 | −0.470 |
| YP | TATCCG | 543.32 | 242 | 0.445 | −0.809 |

-continued

| AA pair | Codon pair | Expected | Observed | Observed/ Expected | CPS |
|---|---|---|---|---|---|
| YQ | TACCAG | 3987.12 | 5013 | 1.257 | 0.229 |
| YQ | TATCAA | 1160.22 | 1179 | 1.016 | 0.016 |
| YQ | TACCAA | 1427.83 | 1397 | 0.978 | −0.022 |
| YQ | TATCAG | 3239.83 | 2226 | 0.687 | −0.375 |
| YR | TACCGC | 1307.70 | 2153 | 1.646 | 0.499 |
| YR | TACCGA | 775.30 | 990 | 1.277 | 0.244 |
| YR | TACAGA | 1442.41 | 1834 | 1.271 | 0.240 |
| YR | TACCGG | 1430.23 | 1796 | 1.256 | 0.228 |
| YR | TACAGG | 1416.06 | 1671 | 1.180 | 0.166 |
| YR | TACCGT | 559.87 | 642 | 1.147 | 0.137 |
| YR | TATCGA | 629.99 | 570 | 0.905 | −0.100 |
| YR | TATCGT | 454.94 | 383 | 0.842 | −0.172 |
| YR | TATAGA | 1172.07 | 827 | 0.706 | −0.349 |
| YR | TATCGG | 1162.17 | 629 | 0.541 | −0.614 |
| YR | TATAGG | 1150.66 | 560 | 0.487 | −0.720 |
| YR | TATCGC | 1062.60 | 509 | 0.479 | −0.736 |
| YS | TACAGC | 2204.13 | 3590 | 1.629 | 0.488 |
| YS | TACTCG | 514.46 | 783 | 1.522 | 0.420 |
| YS | TACAGT | 1390.60 | 1887 | 1.357 | 0.305 |
| YS | TATTCA | 1111.75 | 1210 | 1.088 | 0.085 |
| YS | TACTCC | 1945.47 | 2088 | 1.073 | 0.071 |
| YS | TATTCT | 1375.18 | 1466 | 1.066 | 0.064 |
| YS | TACTCA | 1368.18 | 1188 | 0.868 | −0.141 |
| YS | TATTCC | 1580.84 | 1306 | 0.826 | −0.191 |
| YS | TACTCT | 1692.37 | 1173 | 0.693 | −0.367 |
| YS | TATAGT | 1129.96 | 728 | 0.644 | −0.440 |

-continued

| AA pair | Codon pair | Expected | Observed | Observed/ Expected | CPS |
|---|---|---|---|---|---|
| YS | TATTCG | 418.04 | 229 | 0.548 | −0.602 |
| YS | TATAGC | 1791.02 | 874 | 0.488 | −0.717 |
| YT | TACACG | 697.26 | 1311 | 1.880 | 0.631 |
| YT | TACACC | 2122.58 | 2696 | 1.270 | 0.239 |
| YT | TACACA | 1718.31 | 2158 | 1.256 | 0.228 |
| YT | TACACT | 1519.54 | 1409 | 0.927 | −0.076 |
| YT | TATACT | 1234.74 | 1049 | 0.850 | −0.163 |
| YT | TATACA | 1396.25 | 1049 | 0.751 | −0.286 |
| YT | TATACC | 1724.75 | 1063 | 0.616 | −0.484 |
| YT | TATACG | 566.57 | 245 | 0.432 | −0.838 |
| YV | TATGTT | 986.79 | 1723 | 1.746 | 0.557 |
| YV | TATGTA | 640.76 | 1113 | 1.737 | 0.552 |
| YV | TATGTC | 1263.40 | 1862 | 1.474 | 0.388 |
| YV | TATGTG | 2499.39 | 3382 | 1.353 | 0.302 |
| YV | TACGTG | 3075.90 | 2279 | 0.741 | −0.300 |
| YV | TACGTC | 1554.82 | 991 | 0.637 | −0.450 |
| YV | TACGTA | 788.55 | 284 | 0.360 | −1.021 |
| YV | TACGTT | 1214.40 | 390 | 0.321 | −1.136 |
| YW | TACTGG | 1609.87 | 2212 | 1.374 | 0.318 |
| YW | TATTGG | 1308.13 | 706 | 0.540 | −0.617 |
| YY | TACTAC | 2256.03 | 2854 | 1.265 | 0.235 |
| YY | TATTAT | 1489.60 | 1459 | 0.979 | −0.021 |
| YY | TACTAT | 1833.19 | 1760 | 0.960 | −0.041 |
| YY | TATTAC | 1833.19 | 1339 | 0.730 | −0.314 |

We claim:

1. A method of making a modified viral genome comprising:

a) obtaining the nucleotide sequence of a protein encoding region of a parent virus;

b) substituting a plurality of codons of all or part of the nucleotide sequence with synonymous codons that are less frequently used in a host to obtain a mutated nucleotide sequence that i) encodes the same amino acid sequence as the protein encoding region of the parent virus, and ii) comprises a plurality of codons that are less frequently used in the host compared to the synonymous codons in the nucleotide sequence of the protein encoding region of the parent virus; and c) substituting all or part of the mutated nucleotide sequence into the sequence of the parent virus.

2. The method of claim 1, wherein the parent virus is a natural isolate, or the parent virus is a mutant of a natural isolate.

3. The method of claim 1, wherein the parent virus is a poliovirus, paramyxovirus, rhinovirus, influenza virus, severe acute respiratory syndrome (SARS) coronavirus, Human Immunodeficiency Virus (HIV), Hepatitis C Virus (HCV), infectious bronchitis virus, Ebolavirus, Marburg virus, dengue fever virus, West Nile disease virus, Epstein-Barr virus (EBV), yellow fever virus, Poxvirus, Herpes virus, Papillomavirus, or Adenovirus.

4. A method of making a modified virus comprising inserting a modified viral genome made by the method of claim 1 into a host cell, whereby modified virus is produced.

5. The method of claim 1, wherein the host is an animal.

6. The method of claim 5, wherein the animal is a human.

* * * * *

SEQUENCE LISTING

```
<160> NUMBER OF SEQ ID NOS: 42

<210> SEQ ID NO 1
<211> LENGTH: 2643
<212> TYPE: DNA
<213> ORGANISM: Human poliovirus 1

<400> SEQUENCE: 1

atgggtgctc aggtttcatc acagaaagtg ggcgcacatg aaaactcaaa tagagcgtat      60

ggtggttcta ccattaatta caccaccatt aattattata gagattcagc tagtaacgcg     120

gcttcgaaac aggacttctc tcaagaccct tccaagttca ccgagcccat caaggatgtc     180

ctgataaaaa cagccccaat gctaaactcg ccaaacatag aggcttgcgg gtatagcgat     240

agagtactgc aattaacact gggaaactcc actataacca cacaggaggc ggctaattca     300

gtagtcgctt atgggcgttg gcctgaatat ctgagggaca gcgaagccaa tccagtggac     360

cagccgacag aaccagacgt cgctgcatgc aggttttata cgctagacac cgtgtcttgg     420

acgaaagagt cgcgagggtg gtggtggaag ttgcctgatg cactgaggga catgggactc     480

tttgggcaaa atatgtacta ccactaccta ggtaggtccg ggtacaccgt gcatgtacag     540

tgtaacgcct ccaaattcca ccagggggca ctaggggtat tcgccgtacc agagatgtgt     600

ctggccgggg atagcaacac cactaccatg cacaccagct atcaaaatgc caatcctggc     660

gagaaaggag gcactttcac gggtacgttc actcctgaca acaaccagac atcacctgcc     720

cgcaggttct gcccggtgga ttacctcctt ggaaatggca cgttgttggg gaatgccttt     780

gtgttcccgc accagataat aaacctacgg accaacaact gtgctacact ggtactccct     840

tacgtgaact ccctctcgat agatagtatg gtaaagcaca ataattgggg aattgcaata     900

ttaccattgg ccccattaaa ttttgctagt gagtcctccc cagagattcc aatcaccttg     960

accatagccc ctatgtgctg tgagttcaat ggattaagaa acatcaccct gccacgctta    1020

cagggcctgc cggtcatgaa cacccctggt agcaatcaat atcttactgc agacaacttc    1080
```

```
cagtcaccgt gtgcgctgcc tgaatttgat gtgaccccac ctattgacat acccggtgaa   1140
gtaaagaaca tgatggaatt ggcagaaatc gacaccatga ttccctttga cttaagtgcc   1200
acaaaaaaga acaccatgga aatgtatagg gttcggttaa gtgacaaacc acatacagac   1260
gatcccatac tctgcctgtc actctctcca gcttcagatc ctaggttgtc acatactatg   1320
cttggagaaa tcctaaatta ctacacacac tgggcaggat ccctgaagtt cacgtttctg   1380
ttctgtggat tcatgatggc aactggcaaa ctgttggtgt catacgcgcc tcctggagcc   1440
gacccaccaa agaagcgtaa ggaggcgatg ttgggaacac atgtgatctg ggacatagga   1500
ctgcagtcct catgtactat ggtagtgcca tggattagca acaccacgta tcggcaaacc   1560
atagatgata gtttcaccga aggcggatac atcagcgtct tctaccaaac tagaatagtc   1620
gtccctcttt cgacacccag agagatggac atccttggtt ttgtgtcagc gtgtaatgac   1680
ttcagcgtgc gcttgttgcg agataccaca catatagagc aaaaagcgct agcacagggg   1740
ttaggtcaga tgcttgaaag catgattgac aacacagtcc gtgaaacggt gggggcggca   1800
acatctagag acgctctccc aaacactgaa gccagtggac caacacactc caaggaaatt   1860
ccggcactca ccgcagtgga aactggggcc acaaatccac tagtcccttc tgatacagtg   1920
caaaccagac atgttgtaca acataggtca aggtcagagt ctagcataga gtctttcttc   1980
gcgcggggtg catgcgtgac cattatgacc gtggataacc cagcttccac cacgaataag   2040
gataagctat ttgcagtgtg gaagatcact tataaagata ctgtccagtt acggaggaaa   2100
ttggagttct tcacctattc tagatttgat atggaactta cctttgtggt tactgcaaat   2160
ttcactgaga ctaacaatgg gcatgcctta aatcaagtgt accaaattat gtacgtacca   2220
ccaggcgctc cagtgcccga gaaatgggac gactacacat ggcaaacctc atcaaatcca   2280
tcaatctttt acacctacgg aacagctcca gcccggatct cggtaccgta tgttggtatt   2340
tcgaacgcct attcacactt ttacgacggt ttttccaaag taccactgaa ggaccagtcg   2400
gcagcactag gtgactccct ttatggtgca gcatctctaa atgacttcgg tattttggct   2460
gttagagtag tcaatgatca caacccgacc aaggtcacct ccaaaatcag agtgtatcta   2520
aaacccaaac acatcagagt ctggtgcccg cgtccaccga gggcagtggc gtactacggc   2580
cctggagtgg attacaagga tggtacgctt acacccctct ccaccaagga tctgaccaca   2640
tat                                                                 2643
```

<210> SEQ ID NO 2
<211> LENGTH: 7521
<212> TYPE: DNA
<213> ORGANISM: Unknown
<220> FEATURE:
<223> OTHER INFORMATION: synthetic

<400> SEQUENCE: 2

```
ttaaaacagc tctggggttg tacccacccc agaggcccac gtggcggcta gtactccggt     60
attgcggtac ccttgtacgc ctgttttata ctcccttccc gtaacttaga cgcacaaaac    120
caagttcaat agaagggggt acaaaccagt accaccacga acaagcactt ctgtttcccc    180
ggtgatgtcg tatagactgc ttgcgtggtt gaaagcgacg gatccgttat ccgcttatgt    240
acttcgagaa gcccagtacc acctcggaat cttcgatgcg ttgcgctcag cactcaaccc    300
cagagtgtag cttaggctga tgagtctgga catccctcac cggtgacggt ggtccaggct    360
gcgttggcgg cctacctatg gctaacgcca tgggacgcta gttgtgaaca aggtgtgaag    420
```

-continued

```
agcctattga gctacataag aatcctccgg cccctgaatg cggctaatcc caacctcgga    480
gcaggtggtc acaaaccagt gattggcctg tcgtaacgcg caagtccgtg gcggaaccga    540
ctactttggg tgtccgtgtt tccttttatt ttattgtggc tgcttatggt gacaatcaca    600
gattgttatc ataaagcgaa ttggattggc catccggtga aagtgagact cattatctat    660
ctgtttgctg gatccgctcc attgagtgtg tttactctaa gtacaatttc aacagttatt    720
tcaatcagac aattgtatca taatgggtgc tcaggtttcg tcgcaaaaag taggtgcgca    780
tgaaaactcg aatcgtgcgt atggttcgtc gacgataaat tatacgacga taaattatta    840
tcgtgattcg gcgtctaatg cggcttcgaa acaagatttt tcgcaagatc cgtcgaaatt    900
tacggaaccg ataaaagatg tattaataaa aacggcgccg atgttaaatt cgccgaatat    960
agaagcgtgt ggttattcgg atcgtgtatt acaattaacg ttaggtaatt cgacgataac   1020
gacgcaagaa gcggctaatt cggtagtagc gtatggtcgt tggccggagt atttacgtga   1080
ttcggaagcg aatccggtag atcaaccgac ggaaccggac gtcgcggcgt gtcgttttta   1140
tacgttagat acggtatcgt ggacgaaaga atcgcgaggt tggtggtgga aattaccgga   1200
tgcgttacgt gatatgggtt tatttggtca aaatatgtat tatcattatt taggtcgttc   1260
gggttatacg gtacatgtac aatgtaatgc gtcgaaattt catcaaggtg cgttaggtgt   1320
atttgcggta ccggaaatgt gtttagcggg tgactcgaat acgacgacga tgcatacgtc   1380
gtatcaaaat gcgaatccgg gtgaaaaagg tggtacgttt acgggtacgt ttacgccgga   1440
taataatcaa acgtcgccgg cgcgtcgttt ttgtccggta gattatttat taggtaatgg   1500
tacgttatta gggaatgcct ttgtatttcc gcatcaaata ataaatttgc gtacgaataa   1560
ttgtgcgacg ttagtattac cgtatgtaaa ttcgttatcg atagattcga tggtaaaaca   1620
taataattgg ggtatagcaa tattaccgtt agcgccgtta aattttgcgt cggaatcgtc   1680
gccggaaata ccgataacgt taacgatagc gccgatgtgt tgtgaattta atggtttgcg   1740
taatataacg ttaccgcgtt tacaaggttt accggtaatg aatacgccgg gctcgaatca   1800
gtatttaacg gcggataatt ttcaatcgcc gtgtgcgtta ccggaatttg atgtaacgcc   1860
gccgatagat ataccgggtg aagtaaaaaa tatgatggaa ttagcggaaa tagatacgat   1920
gataccgttt gatttatcgg cgacgaaaaa aaatacgatg gaaatgtatc gtgtacgttt   1980
atcggataaa ccgcatacgg atgatccgat attatgttta tcgttatcgc cggcgtcgga   2040
tcctaggtta tcgcatacga tgttaggtga gatattaaat tattatacgc attgggcggg   2100
ttcgttaaaa tttacgtttt tattttgtgg ttcgatgatg gcgacgggta aattattagt   2160
atcgtatgcg ccgccgggtg cggatccgcc gaaaaaacgt aaagaagcga tgttaggtac   2220
gcatgtaata tgggatatag gtttacaatc gtcgtgtacg atggtagtac cgtggatatc   2280
gaatacgacg tatcgtcaaa cgatagatga ttcgtttacg gaaggtggtt atatatcggt   2340
attttatcaa acgcgtatag tagtaccgtt atcgacgccg cgtgaaatgg atatattagg   2400
ttttgtatcg gcgtgtaatg atttttcggt acgtttatta cgtgatacga cgcatataga   2460
acaaaaagcg ctagcacaag gtttaggtca aatgttagaa tcgatgatag ataatacggt   2520
acgtgaaacg gtaggtgcgg ctacgtcgcg tgatgcgtta ccgaatacgg aagcgtcggg   2580
tccgacgcac tcgaaagaaa taccggcgtt aacggcggta gaaacgggtg cgacgaatcc   2640
actagtcccg tcggatacgg tacaaacgcg tcatgtagta caacatcgtt cgcgttcgga   2700
atcgtcgata gaatcgtttt ttgcgcgtgg tgcgtgtgta acgataatga cggtagataa   2760
tccggcgtcg acgacgaata aagataaatt atttgcggta tggaaaataa cgtataaaga   2820
```

tacggtacaa ttacgtcgta aattagaatt tttcacgtat tcgcgttttg atatggaatt 2880
aacgtttgta gtaacggcga attttacgga aacgaataat ggtcatgcgt taaatcaagt 2940
atatcaaata atgtacgtac cgccgggtgc gccggtaccc gaaaaatggg atgattatac 3000
gtggcaaacg tcgtcgaatc cgtcgatatt ttacacgtat ggtacggcgc cggcgcgtat 3060
atcggtaccg tatgtaggta tatctaatgc gtattcgcat ttttatgatg gtttctcgaa 3120
agtaccgtta aaagatcaat cggcggcgtt aggtgattcg ttatatggtg cggcgtcgtt 3180
aaatgatttt ggtatattag cggtacgtgt agtaaatgat cataatccga cgaaggtcac 3240
ctcgaaaata cgtgtatatt taaaaccgaa acatatacgt gtatggtgtc cgcgtccgcc 3300
gcgtgcggta gcgtattatg gtccgggtgt agattataaa gatggtacgt taacgccgtt 3360
atcgacgaaa gatttaacga cgtatggatt cggacaccaa aacaaagcgg tgtacactgc 3420
aggttacaaa atttgcaact accacttggc cactcaggat gatttgcaaa acgcagtgaa 3480
cgtcatgtgg agtagagacc tcttagtcac agaatcaaga gcccagggca ccgattcaat 3540
cgcaaggtgc aattgcaacg caggggtgta ctactgcgag tctagaagga aatactaccc 3600
agtatccttc gttggcccaa cgttccagta catggaggct aataactatt acccagctag 3660
gtaccagtcc catatgctca ttggccatgg attcgcatct ccaggggatt gtggtggcat 3720
actcagatgt caccacgggg tgatagggat cattactgct ggtggagaag ggttggttgc 3780
attttcagac attagagact tgtatgccta cgaagaagaa gccatggaac aaggcctcac 3840
caattacata gagtcacttg gggccgcatt tggaagtgga tttactcagc agattagcga 3900
caaaataaca gagttgacca atatggtgac cagtaccatc actgaaaagc tacttaagaa 3960
cttgatcaag atcatatcct cactagttat tataactagg aactatgaag acaccacaac 4020
agtgctcgct accctggccc ttcttgggtg tgatgcttca ccatggcagt ggcttagaaa 4080
gaaagcatgc gatgttctgg agatacctta tgtcatcaag caaggtgaca gttggttgaa 4140
gaagtttact gaagcatgca acgcagctaa gggactggag tgggtgtcaa acaaaatctc 4200
aaaattcatt gattggctca aggagaaaat tatcccacaa gctagagata agttggaatt 4260
tgtaacaaaa cttagacaac tagaaatgct ggaaaaccaa atctcaacta tacaccaatc 4320
atgccctagt caggaacacc aggaaattct attcaataat gtcagatggt tatccatcca 4380
gtctaagagg tttgcccctc tttacgcagt ggaagccaaa agaatacaga aactcgagca 4440
tactattaac aactacatac agttcaagag caaacaccgt attgaaccag tatgtttgct 4500
agtacatggc agccccggaa caggtaaatc tgtagcaacc aacctgattg ctagagccat 4560
agctgaaaga gaaaacacgt ccacgtactc gctacccccg gatccatcac acttcgacgg 4620
atacaaacaa cagggagtgg tgattatgga cgacctgaat caaaacccag atggtgcgga 4680
catgaagctg ttctgtcaga tggtatcaac agtggagttt ataccaccca tggcatccct 4740
ggaggagaaa ggaatcctgt ttacttcaaa ttacgttcta gcatccacaa actcaagcag 4800
aatttccccc cccactgtgg cacacagtga cgcgttagcc aggcgctttg cgttcgacat 4860
ggacattcag gtcatgaatg agtattctag agatgggaaa ttgaacatgg ccatggctac 4920
tgaaatgtgt aagaactgtc accaaccagc aaactttaag agatgctgtc ctttagtgtg 4980
tggtaaggca attcaattaa tggacaaatc ttccagagtt agatacagta ttgaccagat 5040
cactacaatg attatcaatg agagaaacag aagatccaac attggcaatt gtatggaggc 5100
tttgtttcaa ggaccactcc agtataaaga cttgaaaatt gacatcaaga cgagtccccc 5160

```
tcctgaatgt atcaatgact tgctccaagc agttgactcc caggaggtga gagattactg   5220
tgagaagaag ggttggatag ttaacatcac cagccaggtt caaacagaaa ggaacatcaa   5280
cagggcaatg acaattctac aagcggtgac aaccttcgcc gcagtggctg gagttgtcta   5340
tgtcatgtat aaactgtttg ctggacacca gggagcatac actggtttac caaacaaaaa   5400
acccaacgtg cccaccattc ggacagcaaa ggtacaagga ccagggttcg attacgcagt   5460
ggctatggct aaaagaaaca ttgttacagc aactactagc aagggagagt tcactatgtt   5520
aggagtccac gacaacgtgg ctattttacc aacccacgct tcacctggtg aaagcattgt   5580
gatcgatggc aaagaagtgg agatcttgga tgccaaagcg ctcgaagatc aagcaggaac   5640
caatcttgaa atcactataa tcactctaaa gagaaatgaa aagttcagag acattagacc   5700
acatatacct actcaaatca ctgagacaaa tgatggagtc ttgatcgtga acactagcaa   5760
gtaccccaat atgtatgttc ctgtcggtgc tgtgactgaa cagggatatc taaatctcgg   5820
tgggcgccaa actgctcgta ctctaatgta caactttcca accagagcag gacagtgtgg   5880
tggagtcatc acatgtactg ggaaagtcat cgggatgcat gttggtggga acggttcaca   5940
cgggtttgca gcggccctga agcgatcata cttcactcag agtcaaggtg aaatccagtg   6000
gatgagacct tcgaaggaag tgggatatcc aatcataaat gccccgtcca aaaccaagct   6060
tgaacccagt gctttccact atgtgtttga aggggtgaag gaaccagcag tcctcactaa   6120
aaacgatccc aggcttaaga cagactttga ggaggcaatt ttctccaagt acgtgggtaa   6180
caaaattact gaagtggatg agtacatgaa agaggcagta gaccactatg ctggccagct   6240
catgtcacta gacatcaaca tagaacaaat gtgcttggag gatgccatgt atggcactga   6300
tggtctagaa gcacttgatt tgtccaccag tgctggctac ccttatgtag caatgggaaa   6360
gaagaagaga gacatcttga acaaacaaac cagagacact aaggaaatgc aaaaactgct   6420
cgacacatat ggaatcaacc tcccactggt gacttatgta aaggatgaac ttagatccaa   6480
aacaaaggtt gagcagggga aatccagatt aattgaagct tctagtttga atgactcagt   6540
ggcaatgaga atggcttttg ggaacctata tgctgctttt cacaaaaacc caggagtgat   6600
aacaggttca gcagtggggt gcgatccaga tttgttttgg agcaaaattc cggtattgat   6660
ggaagagaag ctgtttgctt ttgactacac agggtatgat gcatctctca gccctgcttg   6720
gttcgaggca ctaaagatgg tgcttgagaa aatcggattc ggagacagag ttgactacat   6780
cgactaccta aaccactcac accacctgta caagaataaa acatactgtg tcaagggcgg   6840
tatgccatct ggctgctcag gcacttcaat ttttaactca atgattaaca acttgattat   6900
caggacactc ttactgaaaa cctacaaggg catagattta gaccacctaa aaatgattgc   6960
ctatggtgat gatgtaattg cttcctaccc ccatgaagtt gacgctagtc tcctagccca   7020
atcaggaaaa gactatggac taactatgac tccagctgac aaatcagcta catttgaaac   7080
agtcacatgg gagaatgtaa cattcttgaa gagattcttc agggcagacg agaaataccc   7140
atttcttatt catccagtaa tgccaatgaa ggaaattcat gaatcaatta gatggacaaa   7200
agatcctagg aacactcagg atcacgttcg ctctctgtgc cttttagctt ggcacaatgg   7260
cgaagaagaa tataacaaat tcctagctaa aatcaggagt gtgccaattg gaagagcttt   7320
attgctccca gagtactcaa cattgtaccg ccgttggctt gactcatttt agtaacccta   7380
cctcagtcga attggattgg gtcatactgg tgtaggggta aatttttctt taattcggag   7440
gaaaaaaaaa aaaaaaaaaa aaaaaaaaaa aaaaaaaaaa aaaaaaaaaa aaaaaaaaaa   7500
aaaaaaaaaa aaaaaaaaaa a                                             7521
```

<210> SEQ ID NO 3
<211> LENGTH: 7521
<212> TYPE: DNA
<213> ORGANISM: Unknown
<220> FEATURE:
<223> OTHER INFORMATION: synthetic

<400> SEQUENCE: 3
ttaaaacagc tctggggttg tacccacccc agaggcccac gtggcggcta gtactccggt 60
attgcggtac ccttgtacgc ctgttttata ctcccttccc gtaacttaga cgcacaaaac 120
caagttcaat agaagggggt acaaaccagt accaccacga acaagcactt ctgtttcccc 180
ggtgatgtcg tatagactgc ttgcgtggtt gaaagcgacg gatccgttat ccgcttatgt 240
acttcgagaa gcccagtacc acctcggaat cttcgatgcg ttgcgctcag cactcaaccc 300
cagagtgtag cttaggctga tgagtctgga catccctcac cggtgacggt ggtccaggct 360
gcgttggcgg cctacctatg gctaacgcca tgggacgcta gttgtgaaca aggtgtgaag 420
agcctattga gctacataag aatcctccgg cccctgaatg cggctaatcc caacctcgga 480
gcaggtggtc acaaaccagt gattggcctg tcgtaacgcg caagtccgtg gcggaaccga 540
ctactttggg tgtccgtgtt tccttttatt ttattgtggc tgcttatggt gacaatcaca 600
gattgttatc ataaagcgaa ttggattggc catccggtga aagtgagact cattatctat 660
ctgtttgctg gatccgctcc attgagtgtg tttactctaa gtacaatttc aacagttatt 720
tcaatcagac aattgtatca taatgggtgc tcaggtttcg tctcagaagg taggtgctca 780
cgaaaatagc aacagggcat acggatcatc cacaatcaac tatacaacaa tcaactacta 840
ccgggactcc gcctccaatg cagcttcgaa acaagatttt agccaggatc catctaaatt 900
tactgaacca attaaagacg tgctcatcaa gactgcacct atgttgaata gccctaacat 960
tgaagcctgt ggctactcag accgggtgct tcagctgacc ctcggtaatt caaccatcac 1020
aacgcaagaa gctgcaaaca gcgtggtggc atacggaagg tggccagagt acttaagaga 1080
ttctgaggca aaccctgtcg atcaaccaac cgagccggac gtcgcggcgt gtcgattcta 1140
caccctcgat actgtaagct ggaccaagga atcgcgaggt tggtggtgga aacttccaga 1200
cgccctacgc gatatgggtt tgttcggtca gaacatgtat tatcattatt tgggacgctc 1260
tggatataca gtccacgtgc aatgcaatgc ttcaaagttt catcagggag ctttgggtgt 1320
gttcgcggtg ccggaaatgt gcttagcagg agactcaaat acgaccacaa tgcatacttc 1380
ttaccagaac gcaaaccccg gagaaaaggg cggtacgttt accgggacct ttaccccaga 1440
taataatcaa acctccccag caagacgttt ttgtccagtt gactatttgt tgggcaacgg 1500
tacactacta gggaatgcct tcgtatttcc tcatcagatt atcaatctta gaactaataa 1560
ttgcgcaact ctcgtgttgc catatgtaaa ttctctgtcc atcgactcga tggtgaaaca 1620
taacaactgg gggatagcaa tattacctct cgcgcctctg aacttcgcgt cagaatcaag 1680
tccggaaatc ccgataacac ttactatcgc tcccatgtgt tgcgagttca acgggctcag 1740
gaatataaca ctacccaggc tgcaagggct accagttatg aatacaccag gatctaacca 1800
gtacttaacc gccgataact tccaatcccc atgcgcctta ccagagttcg atgtcacgcc 1860
gcccatcgat atccctgggg aggtgaaaaa tatgatggag cttgccgaga ttgatacaat 1920
gataccattc gatctgtccg caactaagaa aaatacaatg gagatgtacc gtgtgagact 1980
ttccgataag cctcacaccg acgacccaat tctgtgtctc agtctatctc ctgcaagtga 2040

```
ccctaggctt agccacacca tgctgggcga gatattgaac tattataccc actgggcggg   2100
cagtcttaaa ttcaccttct tattttgtgg gtcaatgatg gctacgggta agttgctagt   2160
aagctacgct ccaccaggcg cagatcctcc gaagaaaagg aaagaagcta tgcttgggac   2220
ccacgtcatt tgggatattg gtttacaatc ttcgtgcacc atggtggttc cttggatatc   2280
aaatacgacc tacagacaga caatcgacga ctcctttacg gagggtggtt atatatcagt   2340
gttttatcag acccgtattg tggtgccact gtctacccca cgggaaatgg atattctggg   2400
attcgtctcc gcctgcaacg acttctcagt caggctccta agggacacga cccacattga   2460
acagaaggcg ctagcacaag gactgggtca aatgttggag tcaatgatag ataataccgt   2520
aagggagacc gtaggagctg ccacttcacg ggatgcactg ccgaatacag aggcatcagg   2580
gcccacccat tcaaaagaga tcccagctct gacagctgta gagaccggtg caaccaaccc   2640
actagtccca tcggacactg ttcagacacg gcacgtggtg cagcacagaa gtagatccga   2700
atcctcgatt gaaagctttt tcgccagagg cgcctgtgta acaataatga cggtagacaa   2760
tcccgcaagt actaccaaca aagacaaact gttcgctgtc tggaaaataa catacaagga   2820
caccgtacaa ctgagaagaa agcttgaatt ttttacttac agcaggttcg acatggagtt   2880
aacattcgta gtgaccgcta acttcaccga aaccaataac gggcacgccc tgaaccaggt   2940
ttatcagata atgtacgtac cgccgggtgc cccccgtaccc gaaaagtggg atgattatac   3000
ttggcagact agctccaacc cttccatatt ctatacttat ggcaccgcgc cggcgagaat   3060
ttcagttcca tacgtgggaa tatcaaatgc atactctcat ttctatgatg gcttctcaaa   3120
ggtgccttta aaagaccaat cagcggccct gggagattcg ttgtacgggg ccgcctcctt   3180
gaacgatttt gggatcctag cagtgagggt ggtgaacgac cataatccaa cgaaggtcac   3240
cagtaagata cgggtctact tgaagcctaa gcatattcgt gtgtggtgtc caagacctcc   3300
acgcgccgtc gcatattatg gacccggtgt cgactataaa gacgggacct tgaccccact   3360
gagtacaaaa gacctcacaa cttacggatt cggacaccaa aacaaagcgg tgtacactgc   3420
aggttacaaa atttgcaact accacttggc cactcaggat gatttgcaaa acgcagtgaa   3480
cgtcatgtgg agtagagacc tcttagtcac agaatcaaga gcccagggca ccgattcaat   3540
cgcaaggtgc aattgcaacg caggggtgta ctactgcgag tctagaagga aatactaccc   3600
agtatccttc gttggcccaa cgttccagta catggaggct aataactatt acccagctag   3660
gtaccagtcc catatgctca ttggccatgg attcgcatct ccaggggatt gtggtggcat   3720
actcagatgt caccacgggg tgatagggat cattactgct ggtggagaag ggttggttgc   3780
attttcagac attagagact tgtatgccta cgaagaagaa gccatggaac aaggcctcac   3840
caattacata gagtcacttg ggccgcatt tggaagtgga tttactcagc agattagcga   3900
caaaataaca gagttgacca atatggtgac cagtaccatc actgaaaagc tacttaagaa   3960
cttgatcaag atcatatcct cactagttat tataactagg aactatgaag acaccacaac   4020
agtgctcgct accctggccc ttcttgggtg tgatgcttca ccatggcagt ggcttagaaa   4080
gaaagcatgc gatgttctgg agatacctta tgtcatcaag caaggtgaca gttggttgaa   4140
gaagtttact gaagcatgca acgcagctaa gggactggag tgggtgtcaa acaaaatctc   4200
aaaattcatt gattggctca aggagaaaat tatcccacaa gctagagata agttggaatt   4260
tgtaacaaaa cttagacaac tagaaatgct ggaaaaccaa atctcaacta tacaccaatc   4320
atgccctagt caggaacacc aggaaattct attcaataat gtcagatggt tatccatcca   4380
gtctaagagg tttgcccctc tttacgcagt ggaagccaaa agaatacaga aactcgagca   4440
```

```
tactattaac aactacatac agttcaagag caaacaccgt attgaaccag tatgtttgct   4500
agtacatggc agccccggaa caggtaaatc tgtagcaacc aacctgattg ctagagccat   4560
agctgaaaga gaaaacacgt ccacgtactc gctacccccg gatccatcac acttcgacgg   4620
atacaaacaa cagggagtgg tgattatgga cgacctgaat caaaacccag atggtgcgga   4680
catgaagctg ttctgtcaga tggtatcaac agtggagttt ataccaccca tggcatccct   4740
ggaggagaaa ggaatcctgt ttacttcaaa ttacgttcta gcatccacaa actcaagcag   4800
aatttccccc cccactgtgg cacacagtga cgcgttagcc aggcgctttg cgttcgacat   4860
ggacattcag gtcatgaatg agtattctag agatgggaaa ttgaacatgg ccatggctac   4920
tgaaatgtgt aagaactgtc accaaccagc aaactttaag agatgctgtc ctttagtgtg   4980
tggtaaggca attcaattaa tggacaaatc ttccagagtt agatacagta ttgaccagat   5040
cactacaatg attatcaatg agagaaacag aagatccaac attggcaatt gtatggaggc   5100
tttgtttcaa ggaccactcc agtataaaga cttgaaaatt gacatcaaga cgagtccccc   5160
tcctgaatgt atcaatgact tgctccaagc agttgactcc caggaggtga gagattactg   5220
tgagaagaag ggttggatag ttaacatcac cagccaggtt caaacagaaa ggaacatcaa   5280
cagggcaatg acaattctac aagcggtgac aaccttcgcc gcagtggctg gagttgtcta   5340
tgtcatgtat aaactgtttg ctggacacca gggagcatac actggtttac caaacaaaaa   5400
acccaacgtg cccaccattc ggacagcaaa ggtacaagga ccagggttcg attacgcagt   5460
ggctatggct aaaagaaaca ttgttacagc aactactagc aagggagagt tcactatgtt   5520
aggagtccac gacaacgtgg ctattttacc aacccacgct tcacctggtg aaagcattgt   5580
gatcgatggc aaagaagtgg agatcttgga tgccaaagcg ctcgaagatc aagcaggaac   5640
caatcttgaa atcactataa tcactctaaa gagaaatgaa aagttcagag acattagacc   5700
acatatacct actcaaatca ctgagacaaa tgatggagtc ttgatcgtga acactagcaa   5760
gtaccccaat atgtatgttc ctgtcggtgc tgtgactgaa cagggatatc taaatctcgg   5820
tgggcgccaa actgctcgta ctctaatgta caactttcca accagagcag gacagtgtgg   5880
tggagtcatc acatgtactg ggaaagtcat cgggatgcat gttggtggga acggttcaca   5940
cgggtttgca gcggccctga agcgatcata cttcactcag agtcaaggtg aaatccagtg   6000
gatgagacct tcgaaggaag tgggatatcc aatcataaat gccccgtcca aaaccaagct   6060
tgaacccagt gctttccact atgtgtttga aggggtgaag gaaccagcag tcctcactaa   6120
aaacgatccc aggcttaaga cagactttga ggaggcaatt ttctccaagt acgtgggtaa   6180
caaaattact gaagtggatg agtacatgaa agaggcagta gaccactatg ctggccagct   6240
catgtcacta gacatcaaca tagaacaaat gtgcttggag gatgccatgt atggcactga   6300
tggtctagaa gcacttgatt tgtccaccag tgctggctac ccttatgtag caatgggaaa   6360
gaagaagaga gacatcttga acaaacaaac cagagacact aaggaaatgc aaaaactgct   6420
cgacacatat ggaatcaacc tcccactggt gacttatgta aaggatgaac ttagatccaa   6480
aacaaaggtt gagcagggga aatccagatt aattgaagct tctagtttga atgactcagt   6540
ggcaatgaga atggcttttg ggaacctata tgctgctttt cacaaaaacc caggagtgat   6600
aacaggttca gcagtggggt gcgatccaga tttgttttgg agcaaaattc cggtattgat   6660
ggaagagaag ctgtttgctt ttgactacac agggtatgat gcatctctca gccctgcttg   6720
gttcgaggca ctaaagatgg tgcttgagaa aatcggattc ggagacagag ttgactacat   6780
```

cgactaccta aaccactcac accacctgta caagaataaa acatactgtg tcaagggcgg 6840
tatgccatct ggctgctcag gcacttcaat ttttaactca atgattaaca acttgattat 6900
caggacactc ttactgaaaa cctacaaggg catagattta gaccacctaa aaatgattgc 6960
ctatggtgat gatgtaattg cttcctaccc ccatgaagtt gacgctagtc tcctagccca 7020
atcaggaaaa gactatggac taactatgac tccagctgac aaatcagcta catttgaaac 7080
agtcacatgg gagaatgtaa cattcttgaa gagattcttc agggcagacg agaaataccc 7140
atttcttatt catccagtaa tgccaatgaa ggaaattcat gaatcaatta gatggacaaa 7200
agatcctagg aacactcagg atcacgttcg ctctctgtgc cttttagctt ggcacaatgg 7260
cgaagaagaa tataacaaat tcctagctaa aatcaggagt gtgccaattg gaagagcttt 7320
attgctccca gagtactcaa cattgtaccg ccgttggctt gactcatttt agtaacccta 7380
cctcagtcga attggattgg gtcatactgg tgtaggggta aatttttctt taattcggag 7440
gaaaaaaaaa aaaaaaaaaa aaaaaaaaaa aaaaaaaaaa aaaaaaaaaa aaaaaaaaaa 7500
aaaaaaaaaa aaaaaaaaaa a 7521

<210> SEQ ID NO 4
<211> LENGTH: 2643
<212> TYPE: DNA
<213> ORGANISM: Unknown
<220> FEATURE:
<223> OTHER INFORMATION: synthetic

<400> SEQUENCE: 4
atgggagctc aggtgtcatc ccaaaaagta ggcgcacacg aaaactcgaa tcgggcatac 60
ggatctagta cgattaacta tactacaatc aattactata gggactccgc ctctaacgcc 120
gcttcgaaac aggacttttc gcaagaccct agcaagttta ccgaaccgat taaggacgtg 180
ttgatcaaaa ccgcacctat gcttaactca cctaacatag aggcatgcgg atactccgat 240
agggtgttgc aactgacact cggcaatagt acgattacga cacaggaagc cgctaatagc 300
gtagtcgcat acggaaggtg gcccgaatac cttagagact ccgaagcgaa tccagtcgat 360
cagcctaccg aacctgacgt cgccgcatgt cggttttaca cactcgatac cgtgtcatgg 420
actaaggaat cgcgagggtg gtggtggaaa ctgccagacg cattgcgcga tatggggttg 480
ttcggacaga atatgtacta tcactatctc ggaagatccg ggtataccgt acacgtgcaa 540
tgtaacgcct ctaagtttca ccagggagcg ttaggcgtat tcgcagtgcc agagatgtgt 600
ctagccggag actccaatac gactactatg catacctcat accaaaacgc taacccaggc 660
gaaaaggggg ggacatttac cggaacattc acacccgata acaatcagac atcccccgct 720
agacggtttt gcccagtcga ctatctactc ggaaacggta cactgttagg gaatgccttc 780
gtattcccac accagataat taacttacgg actaacaatt gcgcaaccct agtgttgcca 840
tacgttaact cactgtcaat cgatagtatg gtgaaacata acaattgggg gatcgcaata 900
ttaccgttag cgccactgaa tttcgccagc gaatcgtcac ctgagatacc gattaccctt 960
acaatcgcac ctatgtgttg cgagttcaac ggattgcgta atataaccct accacggttg 1020
caggggttgc ccgttatgaa taccccaggg tctaaccaat accttaccgc cgataatttc 1080
caatcccctt gcgcactgcc agagttcgac gtaacccctc caatcgacat acccggcgag 1140
gttaagaata tgatggagtt agccgaaatc gatactatga taccgttcga tctatccgct 1200
acgaaaaaga atactatgga gatgtatcgc gtgagattgt ccgataagcc acataccgac 1260
gatccgatac tgtgtctgtc actgtcaccc gccagcgatc ctaggttgtc ccatacaatg 1320
ttaggcgaga tactgaatta ctatacccat tgggccggta gtctgaaatt cacatttctg 1380
ttttgcggat ctatgatggc gaccggaaag ctgttagtgt catacgctcc acccggagcc 1440
gatccaccta aaaaacgcaa ggaagcgatg ctcggtacac acgtgatatg ggatatcgga 1500
ctgcaatcgt catgtactat ggtcgtgcca tggatatcga atacgactta tagacagaca 1560
atcgacgata gctttaccga gggggggtat attagcgtat tctatcagac acgtatcgta 1620
gtgccactgt caacccctag agagatggac atactcggat tcgtatccgc atgtaacgac 1680
tttagcgtga gactgttacg cgatactacc catatcgaac agaaagcgct agcacagggg 1740
ttagggcaaa tgctagagtc aatgatcgac aatactgtac gcgaaaccgt aggcgcagcg 1800
accagtaggg acgcactacc gaataccgaa gcgagcggac ctacccactc taaagagata 1860
ccggcactaa ccgccgtcga aaccggagcg actaacccac tagtcccatc cgataccgtg 1920
caaaccagac acgtagtgca acatcggtct agatccgagt catcaatcga atccttttc 1980 gctagaggcg catgcgttac gattatgacc gtcgataacc cagcgtcaac gactaacaaa 2040
gacaaattgt tcgccgtatg gaaaattacc tataaggata ccgtgcaatt gcgacgtaaa 2100
ctagagttct ttacatactc tagattcgat atggagctta cattcgtagt gaccgctaac 2160
tttaccgaga ctaataacgg tcacgccctt aatcaggtgt atcagattat gtacgtaccg 2220
ccaggcgcac cagtgcccga aaaatgggac gactatacat ggcagactag ctctaatccg 2280
tcaattttct atacatacgg taccgcacca gctaggatta gcgtgccata cgtcggtata 2340
tcgaacgctt actcacactt ttacgacgga ttctctaaag tgccacttaa ggaccaatcc 2400
gccgcactag gcgatagcct atacggagcc gctagtctta acgatttcgg tatactcgcc 2460
gttagggtcg tgaacgacca taaccctact aaggtcacct ctaagattag ggtgtatctt 2520
aagcctaagc atattagggt gtggtgtcct agaccgccta gagccgttgc gtattacgga 2580
ccaggcgtcg actataagga cggtacattg accccactgt caacgaaaga ccttacgacg 2640
tac 2643

<210> SEQ ID NO 5
<211> LENGTH: 2643
<212> TYPE: DNA
<213> ORGANISM: Unknown
<220> FEATURE:
<223> OTHER INFORMATION: synthetic

<400> SEQUENCE: 5
atgggagctc aagtatcttc acaaaaagtt ggtgctcatg aaaattcaaa cagagcatat 60
ggttcttcaa caataaacta caccacaata aattattaca gggacagtgc ttcaaatgca 120
gcttcgaaac aagatttttc tcaagatcct tccaagttca cagagcccat caaagatgtt 180
ttaataaaaa cagcacccat gctgaacagc cccaacattg aagcatgtgg ttatagtgac 240
agagttctac agctcacgct gggaaattca acaataacaa ctcaagaagc agcaaattct 300
gtggtggcct atggtcgttg gccagagtat ctgcgggact cggaggcaaa tcctgtggac 360
cagccaacag agccggacgt cgctgcctgc cgcttctaca cgttagacac ggtctcctgg 420
accaaggagt cgcgaggctg gtggtggaaa cttccagatg ctctgcggga catgggcctc 480
tttgggcaga acatgtacta tcattatttg ggaagaagtg gctacacggt ccatgtgcag 540
tgtaatgcat ccaagtttca tcaaggtgcc ctgggcgtgt tcgcggttcc tgagatgtgt 600
ttggctgggg acagcaacac caccaccatg cacacgtcct accaaaatgc aaatccagga 660
gaaaaaggtg gcaccttcac gggcaccttc actccagaca acaaccagac ctcgccggcg 720
cgccgcttct gcccagtaga ttatcttctt ggaaatggca cgctgctggg gaatgccttt 780
gtatttcctc atcaaataat aaatttgagg accaacaact gtgccacctt ggttcttcct 840
tatgtcaaca gcctctccat tgactccatg gtgaagcaca acaactgggg aatagcaata 900
ttacctttgg cacctttaaa ttttgcctcg gagagttctc cagagatccc catcaccctc 960
accatcgcgc cgatgtgctg cgagttcaat gggctgagga acatcaccct gcccaggcta 1020
caaggtcttc ctgtcatgaa cacaccaggt tcaaatcagt atttaacagc agacaacttc 1080
cagtctccat gtgctttgcc agaatttgat gtcactccac caatagatat tccaggagaa 1140
gtaaagaaca tgatggaact agcagaaata gacaccatga ttccatttga tctttcagcc 1200
accaagaaga acaccatgga gatgtaccgt gtcaggcttt cagataaacc acacacagat 1260
gatccaattc tctgcctcag tctttctcca gcctcggacc ctaggctcag ccacaccatg 1320
ctaggagaga tattaaatta ttacacgcac tgggcaggct ccctgaagtt caccttcctc 1380
ttctgtggct ccatgatggc aactggaaaa ttattagtat catatgcgcc gccgggggca 1440
gatcctccaa agaagaggaa ggaggccatg ctaggaactc atgtaatatg ggacattggg 1500
ttgcagagca gctgcaccat ggttgttccc tggatctcca acaccaccta caggcagacc 1560
attgatgaca gcttcacaga aggtggttat atttctgtct tctaccagac aagaattgtg 1620
gtgccgctgt ccactccaag agaaatggat attcttggat ttgtatcagc ctgcaatgac 1680
ttctctgtga ggctgctgcg ggacaccact catattgagc agaaggcgct agcacaagga 1740
cttggacaaa tgctggagtc catgattgac aacactgtgc gggagactgt gggggcggcc 1800
acctcaagag atgctttgcc aaatacagag gcttcggggc caacacacag caaagaaata 1860
ccagctttga cagcagtaga aactggagca acaaatccac tagtcccttc agatactgta 1920
caaacaagac atgtggtgca gcacagatca agaagtgaaa gttcaataga atccttcttt 1980
gctcgtgggg cctgtgtcac catcatgact gtggacaacc cagcctccac caccaacaaa 2040
gataaattat ttgctgtgtg gaagatcacc tacaaagata ctgtgcagct aagaagaaaa 2100
ctagagttct tcacctactc aagatttgac atggaactaa cttttgtggt cacagccaac 2160
ttcacagaga ccaacaatgg acatgctttg aatcaagtct accagattat gtacgtacca 2220
ccaggggctc ctgtgcccga aaaatgggat gactacacgt ggcagacttc atcaaatcct 2280
tccatcttct acacatatgg aacagcgccg gccaggatat cagttcctta tgtgggcatc 2340
tcaaatgctt acagccactt ctatgatggc ttctccaaag tacctttgaa ggaccagtcg 2400
gcggcgctgg gggacagttt atatggtgca gcatctctaa atgattttgg aattttggct 2460
gtccgtgtag taaatgacca caaccccacc aaggtcacca gcaagatccg agtatattta 2520
aaaccaaagc acatccgagt gtggtgtccg agaccgccaa gagctgtagc gtattacggt 2580
cctggtgtgg actataaaga tgggactttg actcctttgt ccaccaaaga cctcaccacg 2640
tac 2643

<210> SEQ ID NO 6
<211> LENGTH: 7441
<212> TYPE: DNA
<213> ORGANISM: Unknown
<220> FEATURE:
<223> OTHER INFORMATION: synthetic

<400> SEQUENCE: 6
ttaaaacagc tctggggttg tacccacccc agaggcccac gtggcggcta gtactccggt 60

-continued

```
attgcggtac ccttgtacgc ctgttttata ctcccttccc gtaacttaga cgcacaaaac    120
caagttcaat agaagggggt acaaaccagt accaccacga acaagcactt ctgtttcccc    180
ggtgatgtcg tatagactgc ttgcgtggtt gaaagcgacg gatccgttat ccgcttatgt    240
acttcgagaa gcccagtacc acctcggaat cttcgatgcg ttgcgctcag cactcaaccc    300
cagagtgtag cttaggctga tgagtctgga catccctcac cggtgacggt ggtccaggct    360
gcgttggcgg cctacctatg gctaacgcca tgggacgcta gttgtgaaca aggtgtgaag    420
agcctattga gctacataag aatcctccgg cccctgaatg cggctaatcc caacctcgga    480
gcaggtggtc acaaaccagt gattggcctg tcgtaacgcg caagtccgtg gcggaaccga    540
ctactttggg tgtccgtgtt tccttttatt ttattgtggc tgcttatggt gacaatcaca    600
gattgttatc ataaagcgaa ttggattggc catccggtga aagtgagact cattatctat    660
ctgtttgctg gatccgctcc attgagtgtg tttactctaa gtacaatttc aacagttatt    720
tcaatcagac aattgtatca taatgggcgc gcaagtgtcg tctcaaaagg ttggagccca    780
cgagaatagt aacagagcat acggatcaag cacaataaat tatacgacga tcaattacta    840
ccgtgactcg gcatccaacg ccgctagcaa acaggacttt tctcaggatc catctaaatt    900
cacggaaccc ataaaagacg tgcttattaa gaccgcacct atgctgaatt caccgaatat    960
cgaagcctgt ggttactctg accgggtgct acagctgaca cttggcaact caacgatcac   1020
aacccaagag gccgcaaatt ccgtagtagc gtacggtagg tggccagagt acctacgtga   1080
ttcagaggct aaccctgtag atcaacctac cgaaccggac gtggcagctt gtcgtttcta   1140
cactcttgat accgtgtcct ggaccaagga aagtaggggt tggtggtgga aactccccga   1200
cgcccttagg gatatggggc tgttcggtca gaacatgtac tatcactatc tgggacgctc   1260
aggctatacg gtacacgtgc aatgcaacgc aagtaagttt catcagggcg cgctgggagt   1320
gttcgcagtt ccggaaatgt gcctagctgg cgactcaaat acaacgacta tgcatacaag   1380
ttatcagaac gcgaacccag gagaaaaggg ggaacattt acaggcacat ttaccccaga    1440
taataaccaa acctccccag cacggagatt ctgtcctgta gactacttgt tggggaacgg   1500
aaccctactt ggtaacgcat tcgtttttcc acatcaaatt atcaatctta gaactaataa   1560
ttgtgcaact ctcgtgttgc catatgtcaa ttccttgtcg atagactcca tggtcaaaca   1620
taacaactgg ggcatagcca ttctaccgct cgcaccactg aacttcgcat ccgaatcctc   1680
acccgaaatc cccataacac tcacaatcgc accaatgtgt tgcgaattta acggactgcg   1740
gaatataacc ctaccgagac tccagggttt acccgtaatg aatacgccag gatcaaatca   1800
gtacttaacc gccgataatt tccaatcccc atgcgcctta ccagaattcg acgtaacgcc   1860
tccaattgat attccaggag aggtgaaaaa tatgatggag ctcgcagaga ttgatactat   1920
gataccgttc gatctttccg ctaccaagaa aaatacgatg gagatgtacc gcgtgagact   1980
gtccgataag ccacacaccg atgacccaat actgtgttta agtttgtctc cagcttccga   2040
cccacgtctc tctcatacca tgttagggga gatacttaac tattatactc attgggccgg   2100
gtcattaaag tttaccttcc tgttttgcgg gtctatgatg gccaccggga agctgctagt   2160
tagctatgcc ccacctggtg cggatcctcc taaaaagaga aaagaagcaa tgctcggtac   2220
ccacgtaatt tgggatattg gactgcaatc gagctgcacc atggtggtgc cttggatatc   2280
taatacaacc tacagacaga caatcgacga ctcattcaca gagggtgggt atatatcggt   2340
gttttatcag acccgaatcg ttgtgccatt gtccacccct cgggaaatgg atatccttgg   2400
```

-continued

```
cttcgtgagt gcttgcaacg acttttcagt gagactacta agggacacta cgcatattga   2460
acagaaggca ctggctcaag gcctgggcca aatgctcgag tcaatgatcg ataataccgt   2520
gagagagacc gtaggtgcag cgacctcaag ggacgcgttg cctaataccg aggcgtccgg   2580
gccgactcac agtaaagaga taccagcgtt aacagcagtc gaaaccggtg cgactaatcc   2640
cttggtgcca agcgatacag tgcaaacaag gcacgtagtc cagcaccgat ccaggtcgga   2700
aagctctatc gagtcctttt ttgctagggg ggcttgtgtc actataatga cagtcgacaa   2760
tccggcatca acaaccaaca aagacaagtt attcgctgta tggaaaatta cctacaagga   2820
caccgtccaa ctgagacgga agttagaatt ctttacatac tcacggttcg acatggaatt   2880
gactttcgta gtgaccgcta actttaccga aaccaataac ggtcacgccc tgaatcaggt   2940
ataccagatc atgtacgtcc ctcctggggc accagttccg gagaaatggg atgactatac   3000
ttggcagaca tctagcaacc ctagcatttt ctacacttat ggtaccgccc ccgctagaat   3060
tagtgtgcct tacgtaggaa tttcaaacgc atatagccat ttctacgacg gattctcaaa   3120
ggtgccatta aaggatcaga gcgcggcctt gggggattcg ttgtacggag ccgcttcatt   3180
gaacgatttc gggatactag cagtcagggt cgtgaacgac cataacccta ctaaagtgac   3240
atcgaagata cgcgtctacc ttaagccaaa acacatcagg gtgtggtgtc ctaggccgcc   3300
aagagccgtc gcctattatg gtcccggtgt cgattataaa gacggaaccc tgaccccatt   3360
gtcaactaaa gacctaacca cttatggatt cggacaccaa aacaaagcgg tgtacactgc   3420
aggttacaaa atttgcaact accacttggc cactcaggat gatttgcaaa acgcagtgaa   3480
cgtcatgtgg agtagagacc tcttagtcac agaatcaaga gcccagggca ccgattcaat   3540
cgcaaggtgc aattgcaacg caggggtgta ctactgcgag tctagaagga aatactaccc   3600
agtatccttc gttggcccaa cgttccagta catggaggct aataactatt acccagctag   3660
gtaccagtcc catatgctca ttggccatgg attcgcatct ccaggggatt gtggtggcat   3720
actcagatgt caccacgggg tgatagggat cattactgct ggtggagaag ggttggttgc   3780
attttcagac attagagact tgtatgccta cgaagaagaa gccatggaac aaggcctcac   3840
caattacata gagtcacttg ggccgcatt tggaagtgga tttactcagc agattagcga   3900
caaaataaca gagttgacca atatggtgac cagtaccatc actgaaaagc tacttaagaa   3960
cttgatcaag atcatatcct cactagttat tataactagg aactatgaag acaccacaac   4020
agtgctcgct accctggccc ttcttgggtg tgatgcttca ccatggcagt ggcttagaaa   4080
gaaagcatgc gatgttctgg agatacctta tgtcatcaag caaggtgaca gttggttgaa   4140
gaagtttact gaagcatgca acgcagctaa gggactggag tgggtgtcaa acaaaatctc   4200
aaaattcatt gattggctca aggagaaaat tatcccacaa gctagagata agttggaatt   4260
tgtaacaaaa cttagacaac tagaaatgct ggaaaaccaa atctcaacta tacaccaatc   4320
atgccctagt caggaacacc aggaaattct attcaataat gtcagatggt tatccatcca   4380
gtctaagagg tttgcccctc tttacgcagt ggaagccaaa agaatacaga aactcgagca   4440
tactattaac aactacatac agttcaagag caaacaccgt attgaaccag tatgtttgct   4500
agtacatggc agccccggaa caggtaaatc tgtagcaacc aacctgattg ctagagccat   4560
agctgaaaga gaaaacacgt ccacgtactc gctacccccg gatccatcac acttcgacgg   4620
atacaaacaa cagggagtgg tgattatgga cgacctgaat caaaacccag atggtgcgga   4680
catgaagctg ttctgtcaga tggtatcaac agtggagttt ataccaccca tggcatccct   4740
ggaggagaaa ggaatcctgt ttacttcaaa ttacgttcta gcatccacaa actcaagcag   4800
```

aatttccccc cccactgtgg cacacagtga cgcgttagcc aggcgctttg cgttcgacat 4860
ggacattcag gtcatgaatg agtattctag agatgggaaa ttgaacatgg ccatggctac 4920
tgaaatgtgt aagaactgtc accaaccagc aaactttaag agatgctgtc ctttagtgtg 4980
tggtaaggca attcaattaa tggacaaatc ttccagagtt agatacagta ttgaccagat 5040
cactacaatg attatcaatg agagaaacag aagatccaac attggcaatt gtatggaggc 5100
tttgtttcaa ggaccactcc agtataaaga cttgaaaatt gacatcaaga cgagtccccc 5160
tcctgaatgt atcaatgact tgctccaagc agttgactcc caggaggtga gagattactg 5220
tgagaagaag ggttggatag ttaacatcac cagccaggtt caaacagaaa ggaacatcaa 5280
cagggcaatg acaattctac aagcggtgac aaccttcgcc gcagtggctg gagttgtcta 5340
tgtcatgtat aaactgtttg ctggacacca gggagcatac actggtttac caaacaaaaa 5400
acccaacgtg cccaccattc ggacagcaaa ggtacaagga ccagggttcg attacgcagt 5460
ggctatggct aaaagaaaca ttgttacagc aactactagc aagggagagt tcactatgtt 5520
aggagtccac gacaacgtgg ctattttacc aacccacgct tcacctggtg aaagcattgt 5580
gatcgatggc aaagaagtgg agatcttgga tgccaaagcg ctcgaagatc aagcaggaac 5640
caatcttgaa atcactataa tcactctaaa gagaaatgaa aagttcagag acattagacc 5700
acatatacct actcaaatca ctgagacaaa tgatggagtc ttgatcgtga acactagcaa 5760
gtaccccaat atgtatgttc ctgtcggtgc tgtgactgaa cagggatatc taaatctcgg 5820
tgggcgccaa actgctcgta ctctaatgta caactttcca accagagcag gacagtgtgg 5880
tggagtcatc acatgtactg ggaaagtcat cgggatgcat gttggtggga acggttcaca 5940
cgggtttgca gcggccctga agcgatcata cttcactcag agtcaaggtg aaatccagtg 6000
gatgagacct tcgaaggaag tgggatatcc aatcataaat gccccgtcca aaaccaagct 6060
tgaacccagt gctttccact atgtgtttga aggggtgaag gaaccagcag tcctcactaa 6120
aaacgatccc aggcttaaga cagactttga ggaggcaatt ttctccaagt acgtgggtaa 6180
caaaattact gaagtggatg agtacatgaa agaggcagta gaccactatg ctggccagct 6240
catgtcacta gacatcaaca tagaacaaat gtgcttggag gatgccatgt atggcactga 6300
tggtctagaa gcacttgatt tgtccaccag tgctggctac ccttatgtag caatgggaaa 6360
gaagaagaga gacatcttga acaaacaaac cagagacact aaggaaatgc aaaaactgct 6420
cgacacatat ggaatcaacc tcccactggt gacttatgta aaggatgaac ttagatccaa 6480
aacaaaggtt gagcagggga aatccagatt aattgaagct tctagtttga atgactcagt 6540
ggcaatgaga atggcttttg ggaacctata tgctgctttt cacaaaaacc caggagtgat 6600
aacaggttca gcagtggggt gcgatccaga tttgttttgg agcaaaattc cggtattgat 6660
ggaagagaag ctgtttgctt ttgactacac agggtatgat gcatctctca gccctgcttg 6720
gttcgaggca ctaaagatgg tgcttgagaa aatcggattc ggagacagag ttgactacat 6780
cgactaccta aaccactcac accacctgta caagaataaa acatactgtg tcaagggcgg 6840
tatgccatct ggctgctcag gcacttcaat ttttaactca atgattaaca acttgattat 6900
caggacactc ttactgaaaa cctacaaggg catagattta gaccacctaa aatgattgc 6960 ctatggtgat gatgtaattg cttcctaccc ccatgaagtt gacgctagtc tcctagccca 7020
atcaggaaaa gactatggac taactatgac tccagctgac aaatcagcta catttgaaac 7080
agtcacatgg gagaatgtaa cattcttgaa gagattcttc agggcagacg agaaataccc 7140

-continued

```
atttcttatt catccagtaa tgccaatgaa ggaaattcat gaatcaatta gatggacaaa   7200

agatcctagg aacactcagg atcacgttcg ctctctgtgc cttttagctt ggcacaatgg   7260

cgaagaagaa tataacaaat tcctagctaa aatcaggagt gtgccaattg gaagagcttt   7320

attgctccca gagtactcaa cattgtaccg ccgttggctt gactcatttt agtaacccta   7380

cctcagtcga attggattgg gtcatactgg tgtaggggta aatttttctt taattcggag   7440

g                                                                   7441
```

<210> SEQ ID NO 7
<211> LENGTH: 32
<212> TYPE: DNA
<213> ORGANISM: Unknown
<220> FEATURE:
<223> OTHER INFORMATION: synthetic

<400> SEQUENCE: 7

```
gcactgataa tgaactcctc tggatctact gg                                  32
```

<210> SEQ ID NO 8
<211> LENGTH: 32
<212> TYPE: DNA
<213> ORGANISM: Unknown
<220> FEATURE:
<223> OTHER INFORMATION: synthetic

<400> SEQUENCE: 8

```
ccagtagatc cagaggagtt cattatcagt gc                                  32
```

<210> SEQ ID NO 9
<211> LENGTH: 50
<212> TYPE: DNA
<213> ORGANISM: Unknown
<220> FEATURE:
<223> OTHER INFORMATION: synthetic

<400> SEQUENCE: 9

```
caagaattcc tgaccacata cggtgctcag gtttcatcac agaaagtggg                50
```

<210> SEQ ID NO 10
<211> LENGTH: 50
<212> TYPE: DNA
<213> ORGANISM: Unknown
<220> FEATURE:
<223> OTHER INFORMATION: synthetic

<400> SEQUENCE: 10

```
caagaattcc tgaccacata cggtgcgcaa gtatcgtcgc aaaaagtagg                50
```

<210> SEQ ID NO 11
<211> LENGTH: 40
<212> TYPE: DNA
<213> ORGANISM: Unknown
<220> FEATURE:
<223> OTHER INFORMATION: synthetic

<400> SEQUENCE: 11

```
ttcgaattct ccatatgtgg tcagatcctt ggtggagagg                          40
```

<210> SEQ ID NO 12
<211> LENGTH: 41
<212> TYPE: DNA
<213> ORGANISM: Unknown
<220> FEATURE:
<223> OTHER INFORMATION: synthetic

<400> SEQUENCE: 12
ttcgaattct ccatacgtcg ttaaatcttt cgtcgataac g 41

<210> SEQ ID NO 13
<211> LENGTH: 2341
<212> TYPE: DNA
<213> ORGANISM: Influenza virus

<400> SEQUENCE: 13
agcgaaagca ggcaaaccat ttgaatggat gtcaatccga ccttactttt cttaaaagtg 60
ccagcacaaa atgctataag cacaactttc ccttatactg gagaccctcc ttacagccat 120
gggacaggaa caggatacac catggatact gtcaacagga cacatcagta ctcagaaaag 180
ggaagatgga caacaaacac cgaaactgga gcaccgcaac tcaacccgat tgatgggcca 240
ctgccagaag acaatgaacc aagtggttat gcccaaacag attgtgtatt ggaagcaatg 300
gctttccttg aggaatccca tcctggtatt tttgaaaact cgtgtattga aacgatggag 360
gttgttcagc aaacacgagt agacaagctg acacaaggcc gacagaccta tgactggact 420
ctaaatagaa accaacctgc tgcaacagca ttggccaaca caatagaagt gttcagatca 480
aatggcctca cggccaatga gtctggaagg ctcatagact tccttaagga tgtaatggag 540
tcaatgaaaa aagaagaaat ggggatcaca actcattttc agagaaagag acgggtgaga 600
gacaatatga ctaagaaaat gataacacag agaacaatag gtaaaaagaa gcagagattg 660
aacaaaagga gttatctaat tagagcattg accctgaaca caatgaccaa agatgctgag 720
agagggaagc taaaacggag agcaattgca accccaggga tgcaaataag gggttttgta 780
tactttgttg agacactggc aaggagtata tgtgagaaac ttgaacaatc agggttgcca 840
gttggaggca atgagaagaa agcaaagttg gcaaatgttg taaggaagat gatgaccaat 900
tctcaggaca ccgaactttc tttcaccatc actggagata acaccaaatg gaacgaaaat 960
cagaatcctc ggatgttttt ggccatgatc acatatatga caagaaatca gcccgaatgg 1020
ttcagaaatg ttctaagtat tgctccaata atgttctcaa acaaaatggc gagactggga 1080
aaagggtata tgtttgagag caagagtatg aaacttagaa ctcaaatacc tgcagaaatg 1140
ctagcaagca tcgatttgaa atatttcaat gattcaacaa gaaagaagat tgaaaaaatc 1200
cgaccgctct taatagaggg gactgcatca ttgagccctg gaatgatgat gggcatgttc 1260
aatatgttaa gcactgtatt aggcgtctcc atcctgaatc ttggacaaaa gagatacacc 1320
aagactactt actggtggga tggtcttcaa tcctctgacg attttgctct gattgtgaat 1380
gcacccaatc atgaagggat tcaagccgga gtcgacaggt tttatcgaac ctgtaagcta 1440
cttggaatca atatgagcaa gaaaaagtct tacataaaca gaacaggtac atttgaattc 1500
acaagttttt tctatcgtta tgggtttgtt gccaatttca gcatggagct ccccagtttt 1560
ggggtgtctg ggatcaacga gtcagcggac atgagtattg gagttactgt catcaaaaac 1620
aatatgataa acaatgatct tggtccagca acagctcaaa tggcccttca gttgttcatc 1680
aaagattaca ggtacacgta ccgatgccat agaggtgaca cacaaataca aacccgaaga 1740
tcatttgaaa taaagaaact gtgggagcaa acccgttcca aagctggact gctggtctcc 1800
gacggaggcc caaatttata caacattaga aatctccaca ttcctgaagt ctgcctaaaa 1860
tgggaattga tggatgagga ttaccagggg cgtttatgca acccactgaa cccatttgtc 1920
agccataaag aaattgaatc aatgaacaat gcagtgatga tgccagcaca tggtccagcc 1980

```
aaaaacatgg agtatgatgc tgttgcaaca acacactcct ggatccccaa aagaaatcga   2040

tccatcttga atacaagtca aagaggagta cttgaagatg aacaaatgta ccaaaggtgc   2100

tgcaatttat ttgaaaaatt cttccccagc agttcataca gaagaccagt cgggatatcc   2160

agtatggtgg aggctatggt ttccagagcc cgaattgatg cacggattga tttcgaatct   2220

ggaaggataa agaaagaaga gttcactgag atcatgaaga tctgttccac cattgaagag   2280

ctcagacggc aaaaatagtg aatttagctt gtccttcatg aaaaaatgcc ttgtttctac   2340

t                                                                     2341
```

<210> SEQ ID NO 14
<211> LENGTH: 2341
<212> TYPE: DNA
<213> ORGANISM: unknown
<220> FEATURE:
<223> OTHER INFORMATION: synthetic

<400> SEQUENCE: 14

```
agcgaaagca ggcaaaccat ttgaatggat gtcaatccga ccttactttt cttaaaagtg     60

ccagcacaaa atgctataag cacaactttc ccttatactg gagaccctcc ttacagccat    120

gggacaggaa caggatacac catggatact gtcaacagga cacatcagta ctcagaaaag    180

ggaagatgga caacaaacac cgaaactgga gcaccgcaac tcaacccgat tgatgggcca    240

ctgccagaag acaatgaacc aagtggttat gcccaaacag attgtgtatt ggaagcaatg    300

gctttccttg aggaatccca tcctggtatt tttgaaaact cgtgtattga aacgatggag    360

gttgttcagc aaacacgagt agacaagctg acacaaggcc gacagaccta tgactggact    420

ctaaatagaa accaacctgc tgcaacagca ttggccaaca caatagaagt gttcagatca    480

aatggcctca cggccaatga gtctggaagg ctcatagact tccttaagga cgttatggag    540

tctatgaaaa aagaggaaat ggggattacg acacattttc aacgaaaaag acgggttagg    600

gataatatga caaaaaaaat gattacgcaa cgaacaatcg gaaagaaaaa acagagactg    660

aataagcgat catacttgat tagggcactt acacttaaca ctatgactaa ggacgccgaa    720

aggggaaagc taaagcgtag agcaattgca acacccggaa tgcaaattag gggggttcgta    780

tacttcgtcg agacactcgc tagatccata tgcgaaaagt tagagcaatc cggactgcca    840

gtcgggggga acgaaaaaaa agcgaaactc gctaacgtcg ttagaaaaat gatgactaat    900

agtcaggata ccgaactgtc atttacgatt accggcgata atactaagtg gaacgagaat    960

cagaatccta gaatgtttct cgcaatgatc acatatatga cacgtaacca acccgaatgg   1020

tttagaaacg tactgtcaat cgcaccaatt atgtttagca ataagatggc tagattgggc   1080

aaggggtata tgtttgaatc taagagtatg aaattgcgaa cacagatacc tgccgaaatg   1140

ctagcatcaa tcgatctaaa gtactttaac gatagtacac gaaaaaaaat cgaaaagatt   1200

agaccgttac tgatagaggg aaccgccagc ctatcccccg gaatgatgat ggggatgttt   1260

aatatgctta gtaccgtgtt aggcgttagc atacttaact tagggcaaaa acgttatact   1320

aagactacat attggtggga cggactgcaa tctagcgacg atttcgcact aatcgttaac   1380

gcacctaacc atgaggggat acaagccgga gtcgatagat tctatagaac atgcaaactg   1440

ttagggatta atatgtctaa aaaaaagtca tacataaata gaaccggaac atttgaattc   1500

actagctttt tttacagata cggattcgtt gctaatttta gtatggagtt acctagtttc   1560

ggagttagcg gaattaacga atccgccgat atgtcaatcg gcgtaaccgt tattaagaat   1620

aatatgatta ataacgatct agggccagca accgcacaaa tggcattgca gttgttcata   1680
```

aaggattatc gttatacata tagatgtcat agaggcgata cacagataca gactagacga 1740
tcatttgaaa tcaaaaaatt gtgggagcaa actaggtcta aagccggact gttagtgtcc 1800
gacggagggc ctaatctata caatattagg aatctgcata tacccgaagt gtgtctaaag 1860
tgggagctta tggacgaaga ctatcagggg agattgtgca atccgcttaa cccattcgtt 1920
agccataaag agatagagtc aatgaataac gccgttatga tgccagcaca cggacccgct 1980
aagaatatgg aatacgacgc agtcgcaact acacatagtt ggataccgaa acggaatcga 2040
tccatactga atacatccca aagaggcgta ctcgaagacg aacaaatgta ccaacggtgt 2100
tgcaatctat ttgaaaaatt ttttcctagt agtagctata gacgaccagt cgggatatcc 2160
agtatggtgg aggctatggt ttccagagcc cgaattgatg cacggattga tttcgaatct 2220
ggaaggataa agaaagaaga gttcactgag atcatgaaga tctgttccac cattgaagag 2280
ctcagacggc aaaaatagtg aatttagctt gtccttcatg aaaaaatgcc ttgtttctac 2340
t 2341

<210> SEQ ID NO 15
<211> LENGTH: 2341
<212> TYPE: DNA
<213> ORGANISM: unknown
<220> FEATURE:
<223> OTHER INFORMATION: synthetic

<400> SEQUENCE: 15
agcgaaagca ggcaaaccat ttgaatggat gtcaatccga ccttactttt cttaaaagtg 60
ccagcacaaa atgctataag cacaactttc ccttatactg gagaccctcc ttacagccat 120
gggacaggaa caggatacac catggatact gtcaacagga cacatcagta ctcagaaaag 180
ggaagatgga caacaaacac cgaaactgga gcaccgcaac tcaacccgat tgatgggcca 240
ctgccagaag acaatgaacc aagtggttat gcccaaacag attgtgtatt ggaagcaatg 300
gctttccttg aggaatccca tcctggtatt tttgaaaact cgtgtattga aacgatggag 360
gttgttcagc aaacacgagt agacaagctg acacaaggcc gacagaccta tgactggact 420
ctaaatagaa accaacctgc tgcaacagca ttggccaaca caatagaagt gttcagatca 480
aatggcctca cggccaatga gtctggaagg ctcatagact tccttaagga cgttatggag 540
tctatgaaaa aagaggaaat ggggattacg acacattttc aacgaaaaag acgggttagg 600
gataatatga caaaaaaaat gattacgcaa cgaacaatcg gaaagaaaaa acagagactg 660
aataagcgat catacttgat tagggcactt acacttaaca ctatgactaa ggacgccgaa 720
aggggaaagc taaagcgtag agcaattgca acacccggaa tgcaaattag gggcttcgta 780
tacttcgtcg agacactcgc tagatccata tgcgaaaagt tagagcaatc cggactgcca 840
gtcgggggga acgaaaaaaa agcgaaactc gctaacgtcg ttagaaaaat gatgactaat 900
agtcaggata ccgaactgtc atttacgatt accggcgata atactaagtg gaacgagaat 960
cagaatccta gaatgtttct cgcaatgatc acatatatga cacgtaacca acccgaatgg 1020
tttagaaacg tactgtcaat cgcaccaatt atgtttagca ataagatggc tagattgggc 1080
aaggggtata tgtttgaatc taagagtatg aaattgcgaa cacagatacc tgccgaaatg 1140
ctagcatcaa tcgatctaaa gtactttaac gatagtacac gaaaaaaaat cgaaaagatt 1200
agaccgttac tgatagaggg aaccgccagc ctatcccccg gaatgatgat ggggatgttt 1260
aatatgctta gtaccgtgtt aggcgttagc atacttaact tagggcaaaa acgttatact 1320

-continued

```
aagactacat attggtggga cggactgcaa tctagcgacg atttcgcact aatcgttaac   1380
gcacctaacc atgaggggat acaagccgga gtcgatagat tctatagaac atgcaaactg   1440
ttagggatta atatgtctaa aaaaaagtca tacataaata gaaccggaac atttgaattc   1500
acaagttttt tctatcgtta tgggtttgtt gccaatttca gcatggagct ccccagtttt   1560
ggggtgtctg ggatcaacga gtcagcggac atgagtattg gagttactgt catcaaaaac   1620
aatatgataa acaatgatct tggtccagca acagctcaaa tggcccttca gttgttcatc   1680
aaagattaca ggtacacgta ccgatgccat agaggtgaca cacaaataca aacccgaaga   1740
tcatttgaaa taaagaaact gtgggagcaa acccgttcca aagctggact gctggtctcc   1800
gacggaggcc caaatttata caacattaga aatctccaca ttcctgaagt ctgcctaaaa   1860
tgggaattga tggatgagga ttaccagggg cgtttatgca acccactgaa cccatttgtc   1920
agccataaag aaattgaatc aatgaacaat gcagtgatga tgccagcaca tggtccagcc   1980
aaaaacatgg agtatgatgc tgttgcaaca acacactcct ggatccccaa aagaaatcga   2040
tccatcttga atacaagtca aagaggagta cttgaagatg aacaaatgta ccaaaggtgc   2100
tgcaatttat ttgaaaaatt cttccccagc agttcataca gaagaccagt cgggatatcc   2160
agtatggtgg aggctatggt ttccagagcc cgaattgatg cacggattga tttcgaatct   2220
ggaaggataa agaaagaaga gttcactgag atcatgaaga tctgttccac cattgaagag   2280
ctcagacggc aaaaatagtg aatttagctt gtccttcatg aaaaaatgcc ttgtttctac   2340
t                                                                   2341
```

<210> SEQ ID NO 16
<211> LENGTH: 2341
<212> TYPE: DNA
<213> ORGANISM: Influenza virus

<400> SEQUENCE: 16

```
agcgaaagca ggtcaattat attcaatatg gaaagaataa aagaactaag aaatctaatg     60
tcgcagtctc gcacccgcga gatactcaca aaaaccaccg tggaccatat ggccataatc    120
aagaagtaca catcaggaag acaggagaag aacccagcac ttaggatgaa atggatgatg    180
gcaatgaaat atccaattac agcagacaag aggataacgg aaatgattcc tgagagaaat    240
gagcaaggac aaactttatg gagtaaaatg aatgatgcag gatcagaccg agtgatggta    300
tcacctctgg ctgtgacatg gtggaatagg aatggaccaa taacaaatac agttcattat    360
ccaaaaatct acaaaactta ttttgaaaga gtcgaaaggc taaagcatgg aacctttggc    420
cctgtccatt ttagaaacca agtcaaaata cgtcggagag ttgacataaa tcctggtcat    480
gcagatctca gtgccaagga ggcacaggat gtaatcatgg aagttgtttt ccctaacgaa    540
gtgggagcca ggatactaac atcggaatcg caactaacga taaccaaaga gaagaaagaa    600
gaactccagg attgcaaaat ttctcctttg atggttgcat acatgttgga gagagaactg    660
gtccgcaaaa cgagattcct cccagtggct ggtggaacaa gcagtgtgta cattgaagtg    720
ttgcatttga ctcaaggaac atgctgggaa cagatgtata ctccaggagg ggaagtgagg    780
aatgatgatg ttgatcaaag cttgattatt gctgctagga acatagtgag aagagctgca    840
gtatcagcag atccactagc atctttattg gagatgtgcc acagcacaca gattggtgga    900
attaggatgg tagacatcct taggcagaac ccaacagaag agcaagccgt ggatatatgc    960
aaggctgcaa tgggactgag aattagctca tccttcagtt ttggtggatt cacatttaag   1020
agaacaagcg gatcatcagt caagagagag gaagaggtgc ttacgggcaa tcttcaaaca   1080
```

ttgaagataa gagtgcatga gggatatgaa gagttcacaa tggttgggag aagagcaaca 1140
gccatactca gaaaagcaac caggagattg attcagctga tagtgagtgg gagagacgaa 1200
cagtcgattg ccgaagcaat aattgtggcc atggtatttt cacaagagga ttgtatgata 1260
aaagcagtca gaggtgatct gaatttcgtc aatagggcga atcagcgatt gaatcctatg 1320
catcaacttt taagacattt tcagaaggat gcgaaagtgc tttttcaaaa ttggggagtt 1380
gaacctatcg acaatgtgat gggaatgatt gggatattgc cagacatgac tccaagcatc 1440
gagatgtcaa tgagaggagt gagaatcagc aaaatgggtg tagatgagta ctccagcacg 1500
gagagggtag tggtgagcat tgaccgtttt ttgagaatcc gggaccaacg aggaaatgta 1560
ctactgtctc ccgaggaggt cagtgaaaca cagggaacag agaaactgac aataacttac 1620
tcatcgtcaa tgatgtggga gattaatggt cctgaatcag tgttggtcaa tacctatcaa 1680
tggatcatca gaaactggga aactgttaaa attcagtggt cccagaaccc tacaatgcta 1740
tacaataaaa tggaatttga accatttcag tctttagtac ctaaggccat tagaggccaa 1800
tacagtgggt ttgtaagaac tctgttccaa caaatgaggg atgtgcttgg gacatttgat 1860
accgcacaga taataaaact tcttcccttc gcagccgctc caccaaagca aagtagaatg 1920
cagttctcct catttactgt gaatgtgagg ggatcaggaa tgagaatact tgtaaggggc 1980
aattctcctg tattcaacta taacaaggcc acgaagagac tcacagttct cggaaaggat 2040
gctggcactt taactgaaga cccagatgaa ggcacagctg gagtggagtc cgctgttctg 2100
aggggattcc tcattctggg caaagaagac aagagatatg ggccagcact aagcatcaat 2160
gaactgagca accttgcgaa aggagagaag gctaatgtgc taattgggca aggagacgtg 2220
gtgttggtaa tgaaacggaa acgggactct agcatactta ctgacagcca gacagcgacc 2280
aaaagaattc ggatggccat caattagtgt cgaatagttt aaaaacgacc ttgtttctac 2340
t 2341

<210> SEQ ID NO 17
<211> LENGTH: 2341
<212> TYPE: DNA
<213> ORGANISM: unknown
<220> FEATURE:
<223> OTHER INFORMATION: synthetic

<400> SEQUENCE: 17
agcgaaagca ggtcaattat attcaatatg gagagaatca aagagcttag gaatcttatg 60
tcacaatcta gaactagaga gatactgact aagactacag tcgatcatat ggctataatc 120
aaaaaatata ctagcggaag acaggaaaaa aatcccgcac ttagaatgaa atggatgatg 180
gctatgaaat accctattac agccgataag cgaattaccg aaatgatacc agagagaaac 240
gaacagggac agacattgtg gtctaaaatg aacgacgccg gatccgatag agtgatggtt 300
tcgccactag ccgtaacatg gtggaataga aacggaccta ttacgaatac agtgcattac 360
cctaagatat acaaaacata tttcgaaaga gtcgagagac tgaaacacgg aacattcgga 420
ccagtgcatt ttcggaatca ggttaagatt agacgtagag tcgatattaa tccagggcat 480
gcagatctct ccgctaaaga ggcacaagac gttattatgg aggtcgtgtt tcctaacgag 540
gtcggcgcta ggatactgac tagcgaatcg caattgacaa ttacgaaaga gaaaaaagag 600
gaactccagg attgcaaaat tagcccactt atggtcgcat atatgctcga acgcgaattg 660
gttagaaaga ctagattcct accagtcgca ggcggaacgt ctagcgtgta tatcgaagtg 720

-continued

```
ttgcatctaa cacagggaac atgttgggag caaatgtata ctccaggagg cgaagtgaga    780

aacgacgacg ttgatcaatc gctaatcata gccgctagga atatagtgag aagggcagcc    840

gttagcgcag acccacttgc gtcactactc gaaatgtgcc atagtacgca aatcggaggg    900

attagaatgg tcgatatcct taggcagaat cctacagagg aacaggccgt agacatatgc    960

aaagccgcaa tgggattgcg aattagctca tcattctcat tcggagggtt tacgtttaaa   1020

cggactagcg gatctagcgt aaaacgcgaa gaggaagtgc ttactggcaa tctgcaaaca   1080

ctaaagatta gggtgcatga gggatacgaa gagtttacaa tggtcggacg tagagcaacc   1140

gctatactta gaaaagcgac taggagactg atacaattga tcgttagcgg aagggacgaa   1200

cagtcaatcg ccgaagcgat aatagtcgca atggtgtttt cgcaagagga ttgcatgatt   1260

aaggccgtta gggggggatct gaatttcgtt aatagggcta atcagagact gaatcctatg   1320

catcaattgc ttagacattt tcagaaagac gctaaagtgt tgtttcagaa ttggggagtc   1380

gaacctatcg ataacgttat gggtatgata gggatactgc cagatatgac accatcaatc   1440

gaaatgtcaa tgagaggcgt taggattagt aagatgggcg tagacgaata ctccagcact   1500

gagagagtgg tagtgtcaat cgatagattt cttaggatta gggatcagag aggcaacgta   1560

ctgctatcac ccgaagaagt tagcgaaaca cagggaaccg aaaaattgac aattacgtat   1620

agtagtagta tgatgtggga gattaacgga ccagagtcag tgttagtgaa tacatatcaa   1680

tggataatac ggaattggga gacagtgaaa atacaatggt cacagaatcc tacaatgcta   1740

tacaataaga tggagttcga accttttcaa tcgttagtgc ctaaggccat aagaggccaa   1800

tatagtgggt tcgttagaac attgtttcag caaatgagag acgtactcgg aacattcgat   1860

accgcacaga taattaagct attgccattc gcagccgcac cacctaagca atctagaatg   1920

caattttcta gctttaccgt taacgttagg ggatccggaa tgcgaatact cgttaggggg   1980

aatagtccag tgtttaatta caataaggca actaagagat tgacagtgtt aggcaaggac   2040

gcaggaacat tgaccgaaga cccagacgag ggaaccgctg gagtggaatc cgcagtgctt   2100

agggggtttc tgatactcgg aaaggaggat aagagatacg gacctgcact atcgattaac   2160

gaactatcta atctcgctaa aggcgaaaaa gcgaatgtgt taatcggaca gggagacgta   2220

gtgttagtga tgaaacggaa acgcgatagc tcaatactga cagactcaca aaccgctact   2280

aagagaattc ggatggcaat taattagtgt cgaatagttt aaaaacgacc ttgtttctac   2340

t                                                                   2341
```

<210> SEQ ID NO 18
<211> LENGTH: 2233
<212> TYPE: DNA
<213> ORGANISM: Influenza virus

<400> SEQUENCE: 18

```
agcgaaagca ggtactgatc caaaatggaa gattttgtgc gacaatgctt caatccgatg     60

attgtcgagc ttgcggaaaa aacaatgaaa gagtatgggg aggacctgaa aatcgaaaca    120

aacaaatttg cagcaatatg cactcacttg gaagtatgct tcatgtattc agattttcac    180

ttcatcaatg agcaaggcga gtcaataatc gtagaacttg gtgatccaaa tgcacttttg    240

aagcacagat ttgaaataat cgagggaaga gatcgcacaa tggcctggac agtagtaaac    300

agtatttgca acactacagg ggctgagaaa ccaaagtttc taccagattt gtatgattac    360

aaggagaata gattcatcga aattggagta acaaggagag aagttcacat atactatctg    420

gaaaaggcca ataaaattaa atctgagaaa acacacatcc acattttctc gttcactggg    480
```

```
gaagaaatgg ccacaaaggc agactacact ctcgatgaag aaagcagggc taggatcaaa    540

accagactat tcaccataag acaagaaatg gccagcagag gcctctggga ttcctttcgt    600

cagtccgaga gaggagaaga gacaattgaa gaaaggtttg aaatcacagg aacaatgcgc    660

aagcttgccg accaaagtct cccgccgaac ttctccagcc ttgaaaattt tagagcctat    720

gtggatggat tcgaaccgaa cggctacatt gagggcaagc tgtctcaaat gtccaaagaa    780

gtaaatgcta gaattgaacc tttttgaaa acaacaccac gaccacttag acttccgaat    840

gggcctccct gttctcagcg gtccaaattc ctgctgatgg atgccttaaa attaagcatt    900

gaggacccaa gtcatgaagg agagggaata ccgctatatg atgcaatcaa atgcatgaga    960

acattctttg gatggaagga acccaatgtt gttaaaccac acgaaaaggg aataaatcca   1020

aattatcttc tgtcatggaa gcaagtactg gcagaactgc aggacattga gaatgaggag   1080

aaaattccaa agactaaaaa tatgaagaaa acaagtcagc taaagtgggc acttggtgag   1140

aacatggcac cagaaaaggt agactttgac gactgtaaag atgtaggtga tttgaagcaa   1200

tatgatagtg atgaaccaga attgaggtcg ctagcaagtt ggattcagaa tgagtttaac   1260

aaggcatgcg aactgacaga ttcaagctgg atagagctcg atgagattgg agaagatgtg   1320

gctccaattg aacacattgc aagcatgaga aggaattatt tcacatcaga ggtgtctcac   1380

tgcagagcca cagaatacat aatgaagggg gtgtacatca atactgcctt gcttaatgca   1440

tcttgtgcag caatggatga tttccaatta attccaatga taagcaagtg tagaactaag   1500

gagggaaggc gaaagaccaa cttgtatggt ttcatcataa aaggaagatc ccacttaagg   1560

aatgacaccg acgtggtaaa ctttgtgagc atggagtttt ctctcactga cccaagactt   1620

gaaccacata aatgggagaa gtactgtgtt cttgagatag gagatatgct tataagaagt   1680

gccataggcc aggtttcaag gcccatgttc ttgtatgtga gaacaaatgg aacctcaaaa   1740

attaaaatga aatggggaat ggagatgagg cgttgcctcc tccagtcact tcaacaaatt   1800

gagagtatga ttgaagctga gtcctctgtc aaagagaaag acatgaccaa agagttcttt   1860

gagaacaaat cagaaacatg gcccattgga gagtccccca aaggagtgga ggaaagttcc   1920

attgggaagg tctgcaggac tttattagca aagtcggtat tcaacagctt gtatgcatct   1980

ccacaactag aaggattttc agctgaatca agaaaactgc ttcttatcgt tcaggctctt   2040

agggacaacc ttgaacctgg gacctttgat cttggggggc tatatgaagc aattgaggag   2100

tgcctgatta atgatccctg ggttttgctt aatgcttctt ggttcaactc cttccttaca   2160

catgcattga gttagttgtg gcagtgctac tatttgctat ccatactgtc caaaaaagta   2220

ccttgtttct act                                                       2233
```

<210> SEQ ID NO 19
<211> LENGTH: 2233
<212> TYPE: DNA
<213> ORGANISM: unknown
<220> FEATURE:
<223> OTHER INFORMATION: synthetic

<400> SEQUENCE: 19

```
agcgaaagca ggtactgatc caaaatggag gatttcgtta ggcaatgctt taatccaatg     60

atagtcgagt tagccgaaaa gactatgaaa gagtatggcg aagacctaaa gattgagact    120

aataaattcg ccgcaatttg cacacacctt gaggtttgct ttatgtattc cgattttcac    180

tttattaacg aacagggaga gtcaattata gtcgagttag gcgatccgaa cgcattgcta    240
```

aagcatagat ttgaaattat agagggacgc gataggacaa tggcatggac cgtagttaat 300
tcgatttgca atacaaccgg agccgaaaaa ccgaaattct tacccgatct atacgattat 360
aaagagaata ggtttatcga aatcggagtg actagacgcg aagtgcatat ttattatctc 420
gaaaaagcga ataagattaa gtccgaaaag acacacatac acatttttag ctttaccgga 480
gaggaaatgg caacaaaagc cgattataca cttgacgaag agtctagggc taggattaag 540
actagactgt ttacaattag acaggaaatg gctagtaggg ggttgtggga tagctttaga 600
caatccgaaa gaggcgaaga gacaatcgaa gagagatttg aaattaccgg aacaatgcga 660
aagcttgccg atcaatccct accccccaat ttctctagcc ttgagaattt tagggcatac 720
gttgacggat tcgaacctaa cggatatata gagggaaagc tatcgcaaat gtctaaagag 780
gttaacgcta gaatcgaacc attcctaaag acaacaccta gaccacttag actgccaaac 840
ggaccaccat gctcacagcg atctaagttt ctgcttatgg acgcactaaa gttgtcaatc 900
gaagacccat cacacgaggg agaggggata ccattgtacg acgcaattaa gtgtatgcga 960
acatttttcg gatggaaaga gcctaacgta gtgaaaccac acgaaaaagg gattaatccg 1020
aattatctgc ttagttggaa acaggtgtta gccgaattgc aggatatcga aaacgaagag 1080
aaaattccga aaactaagaa tatgaaaaaa actagccaac tgaaatgggc acttggcgag 1140
aatatggcac ccgaaaaagt cgatttcgac gattgcaaag acgtcggcga tctaaagcaa 1200
tacgatagcg acgaacccga acttagatca ctcgctagtt ggatacagaa cgagttcaat 1260
aaggcatgcg aattgaccga tagctcatgg atagagcttg acgagatagg cgaagacgta 1320
gcaccaatcg aacacatagc ctctatgaga cggaattatt ttacatccga agtgtcacat 1380
tgtagggcaa cagagtatat tatgaaaggg gtgtatatta ataccgcatt gcttaacgct 1440
agttgcgccg caatggacga tttccaactg ataccgatga tctcgaagtg tagaacaaaa 1500
gagggacgta gaaagactaa tctgtatggg ttcattatta agggaaggtc tcatttaagg 1560
aacgatacag acgtagtgaa tttcgttagt atggagttta gccttaccga tccgagactc 1620
gaaccacaca aatgggaaaa gtattgcgta ctagagatag ggatatgtt gattagatcc 1680 gcaatcggac aggtttcgag accaatgttt ttgtacgtta ggactaacgg aacctcgaag 1740
attaaaatga aatggggaat ggagatgcgt agatgcctat tgcaatccct tcagcaaatc 1800
gaatctatga tagaggccga atctagcgtt aaagagaaag atatgacaaa agagtttttt 1860
gaaaataagt ccgaaacatg gccaatcgga gagtcaccaa aaggggttga ggaatcctca 1920
atcggaaaag tttgtagaac attgctcgca aaatccgtat tcaatagtct atacgccagc 1980
ccacaactag agggattctc tgctgagtca cgaaaactgt tactgatagt gcaagccctt 2040
agggataatc tcgaacccgg aacattcgat ctaggggggt tgtacgaagc aatcgaagag 2100
tgtctgatta acgatccatg ggtactgctt aacgctagtt ggtttaattc gttccttaca 2160
cacgcactat cttagttgtg gcagtgctac tatttgctat ccatactgtc caaaaaagta 2220
ccttgtttct act 2233

<210> SEQ ID NO 20
<211> LENGTH: 1775
<212> TYPE: DNA
<213> ORGANISM: Influenza virus

<400> SEQUENCE: 20
agcaaaagca ggggaaaata aaaacaacca aaatgaaggc aaacctactg gtcctgttaa 60
gtgcacttgc agctgcagat gcagacacaa tatgtatagg ctaccatgcg aacaattcaa 120
ccgacactgt tgacacagta ctcgagaaga atgtgacagt gacacactct gttaacctgc 180
tcgaagacag ccacaacgga aaactatgta gattaaaagg aatagcccca ctacaattgg 240
ggaaatgtaa catcgccgga tggctcttgg gaaacccaga atgcgaccca ctgcttccag 300
tgagatcatg gtcctacatt gtagaaacac caaactctga gaatggaata tgttatccag 360
gagatttcat cgactatgag gagctgaggg agcaattgag ctcagtgtca tcattcgaaa 420
gattcgaaat atttcccaaa gaaagctcat ggcccaacca caacacaaac ggagtaacgg 480
cagcatgctc ccatgagggg aaaagcagtt tttacagaaa tttgctatgg ctgacggaga 540
aggagggctc atacccaaag ctgaaaaatt cttatgtgaa caaaaaaggg aaagaagtcc 600
ttgtactgtg ggtattcat cacccgccta acagtaagga acaacagaat atctatcaga 660
atgaaaatgc ttatgtctct gtagtgactt caaattataa caggagattt accccggaaa 720
tagcagaaag acccaaagta agagatcaag ctgggaggat gaactattac tggaccttgc 780
taaaacccgg agacacaata atatttgagg caaatggaaa tctaatagca ccaatgtatg 840
ctttcgcact gagtagaggc tttgggtccg gcatcatcac ctcaaacgca tcaatgcatg 900
agtgtaacac gaagtgtcaa acacccctgg gagctataaa cagcagtctc ccttaccaga 960
atatacaccc agtcacaata ggagagtgcc caaaatacgt caggagtgcc aaattgagga 1020
tggttacagg actaaggaac actccgtcca ttcaatccag aggtctattt ggagccattg 1080
ccggttttat tgaagggggga tggactggaa tgatagatgg atggtatggt tatcatcatc 1140
agaatgaaca gggatcaggc tatgcagcgg atcaaaaaag cacacaaaat gccattaacg 1200
ggattacaaa caaggtgaac actgttatcg agaaaatgaa cattcaattc acagctgtgg 1260
gtaaagaatt caacaaatta gaaaaaagga tggaaaattt aaataaaaaa gttgatgatg 1320
gatttctgga catttggaca tataatgcag aattgttagt tctactggaa aatgaaagga 1380
ctctggattt ccatgactca aatgtgaaga atctgtatga gaaagtaaaa agccaattaa 1440
agaataatgc caaagaaatc ggaaatggat gttttgagtt ctaccacaag tgtgacaatg 1500
aatgcatgga aagtgtaaga aatgggactt atgattatcc caaatattca gaagagtcaa 1560
agttgaacag ggaaaaggta gatggagtga aattggaatc aatggggatc tatcagattc 1620
tggcgatcta ctcaactgtc gccagttcac tggtgctttt ggtctccctg gggcaatca 1680 gtttctggat gtgttctaat ggatctttgc agtgcagaat atgcatctga gattagaatt 1740
tcagaaatat gaggaaaaac acccttgttt ctact 1775

<210> SEQ ID NO 21
<211> LENGTH: 1775
<212> TYPE: DNA
<213> ORGANISM: unknown
<220> FEATURE:
<223> OTHER INFORMATION: synthetic

<400> SEQUENCE: 21
agcaaaagca ggggaaaata aaaacaacca aaatgaaggc aaacctactg gtcctgttaa 60
gtgcacttgc agctgcagat gcagacacaa tatgtatagg ctaccatgcg aacaattcaa 120
ccgacactgt tgacacagta ctcgagaaga atgtgacagt gacacactct gttaacctgt 180
tagaggactc acataacgga aagctatgta ggcttaaggg aatcgcacca ctgcaattgg 240
gcaagtgtaa tatagccgga tggttgttgg ggaatcccga atgcgatcca ctgttacccg 300
ttaggtcatg gtcatatata gtcgagacac ctaatagcga aaacggaatt tgttatcccg 360

```
gcgattttat cgattacgaa gagcttagag agcaattgtc tagcgttagt tcattcgaaa    420
gattcgaaat ttttccgaaa gagtctagtt ggccaaatca taatactaac ggagtgactg    480
ccgcatgctc acacgaaggc aagtctagct tttataggaa tctgttgtgg ttgactgaga    540
aagagggatc atatccgaaa ctgaaaaact catacgtgaa caaaaaggga aaggaagtgt    600
tagtgttgtg ggggatacac catccaccaa atagtaaaga gcaacagaat atatatcaga    660
acgaaaacgc atacgttagc gtcgtaacta gtaattataa tagaaggttt acacccgaaa    720
tcgcagagag accgaaagtt agagaccaag ccggaagaat gaattattat tggacactac    780
tgaaacccgg cgatacaatt atattcgaag cgaacggaaa tctgatcgca ccgatgtatg    840
cattcgcact atctaggggg ttcggatccg gaattattac tagtaacgct agtatgcacg    900
aatgtaacac gaagtgtcag actccactag gcgcaattaa ctctagtctg ccatatcaga    960
atatacatcc cgtaacaatc ggcgaatgcc caaaatacgt tagatccgct aagcttagaa   1020
tggttaccgg actgagaaat acaccatcaa tccaatctag ggggttgttc ggagcgatag   1080
ccggatttat cgaagggggg tggacaggga tgatagacgg ttggtacgga tatcatcacc   1140
aaaacgaaca gggatccgga tacgcagccg atcagaaatc gacgcaaaac gctattaacg   1200
gaattactaa taaagtgaat accgtaatcg aaaaaatgaa tatccaattt accgcagtcg   1260
gaaaggaatt caataagctt gagaaaagaa tggagaatct gaataaaaaa gtcgacgacg   1320
gatttctaga catatggact tataacgccg aactgttagt gttgctcgaa aacgaaagaa   1380
cactagactt tcacgactca aacgttaaga atctatacga aaaagtgaaa tcccaattga   1440
aaaataacgc taaagagata gggaacggat gtttcgagtt ctatcataaa tgcgataacg   1500
aatgtatgga atccgttagg aacggaacat acgattatcc taagtatagc gaagagtcaa   1560
aactgaatag ggagaaagtc gacggagtga aactcgaatc aatggggata tatcagatac   1620
tggcaatcta tagtacagtc gccagctcac tggttctttt ggtctccctg gggggcaatca   1680
gtttctggat gtgttctaat ggatctttgc agtgcagaat atgcatctga gattagaatt   1740
tcagaaatat gaggaaaaac acccttgttt ctact                              1775
```

<210> SEQ ID NO 22
<211> LENGTH: 1565
<212> TYPE: DNA
<213> ORGANISM: Influenza virus

<400> SEQUENCE: 22

```
agcaaaagca gggtagataa tcactcactg agtgacatca aaatcatggc gtcccaaggc     60
accaaacggt cttacgaaca gatggagact gatggagaac gccagaatgc cactgaaatc    120
agagcatccg tcggaaaaat gattggtgga attggacgat tctacatcca aatgtgcacc    180
gaactcaaac tcagtgatta tgagggacgg ttgatccaaa acagcttaac aatagagaga    240
atggtgctct ctgcttttga cgaaaggaga aataaatacc tggaagaaca tcccagtgcg    300
gggaaagatc ctaagaaaac tggaggacct atatacagga gagtaaacgg aaagtggatg    360
agagaactca tcctttatga caaagaagaa ataaggcgaa tctggcgcca agctaataat    420
ggtgacgatg caacggctgg tctgactcac atgatgatct ggcattccaa tttgaatgat    480
gcaacttatc agaggacaag agctcttgtt cgcaccggaa tggatcccag gatgtgctct    540
ctgatgcaag gttcaactct ccctaggagg tctggagccg caggtgctgc agtcaaagga    600
gttggaacaa tggtgatgga attggtcagg atgatcaaac gtgggatcaa tgatcggaac    660
ttctggaggg gtgagaatgg acgaaaaaca agaattgctt atgaaagaat gtgcaacatt    720
```

```
ctcaaaggga aatttcaaac tgctgcacaa aaagcaatga tggatcaagt gagagagagc    780

cggaacccag ggaatgctga gttcgaagat ctcacttttc tagcacggtc tgcactcata    840

ttgagagggt cggttgctca caagtcctgc ctgcctgcct gtgtgtatgg acctgccgta    900

gccagtgggt acgactttga aagagaggga tactctctag tcggaataga ccctttcaga    960

ctgcttcaaa acagccaagt gtacagccta atcagaccaa atgagaatcc agcacacaag   1020

agtcaactgg tgtggatggc atgccattct gccgcatttg aagatctaag agtattaagc   1080

ttcatcaaag ggacgaaggt gctcccaaga gggaagcttt ccactagagg agttcaaatt   1140

gcttccaatg aaaatatgga gactatggaa tcaagtacac ttgaactgag aagcaggtac   1200

tgggccataa ggaccagaag tggaggaaac accaatcaac agagggcatc tgcgggccaa   1260

atcagcatac aacctacgtt ctcagtacag agaaatctcc cttttgacag aacaaccatt   1320

atggcagcat tcaatgggaa tacagaggga agaacatctg acatgaggac cgaaatcata   1380

aggatgatgg aaagtgcaag accagaagat gtgtctttcc aggggcgggg agtcttcgag   1440

ctctcggacg aaaaggcagc gagcccgatc gtgccttcct ttgacatgag taatgaagga   1500

tcttatttct tcggagacaa tgcagaggag tacgacaatt aaagaaaaat acccttgttt   1560

ctact                                                               1565


<210> SEQ ID NO 23
<211> LENGTH: 1565
<212> TYPE: DNA
<213> ORGANISM: unknown
<220> FEATURE:
<223> OTHER INFORMATION: synthetic

<400> SEQUENCE: 23

agcaaaagca gggtagataa tcactcactg agtgacatca aaatcatggc gtcccaaggc     60

accaaacggt cttacgaaca gatggagact gatggagaac gccagaatgc cactgaaatc    120

agagctagcg tcggaaaaat gatagggggga atcggaaggt tttacataca aatgtgtacc    180

gaactcaaat tgtccgatta cgaagggaga ttgatccaaa atagtctgac aatcgaaaga    240

atggtgttaa gcgcattcga cgaaagacgg aataagtatc tcgaagagca tcctagcgca    300

ggcaaggatc caaaaaaaac cggagggcca atctatagga gagtgaacgg aaagtggatg    360

cgcgaactga tactgtacga taaagaggag attagacgga tatggcgaca agcgaataac    420

ggagacgacg ctactgccgg actgacacat atgatgatat ggcactctaa tcttaacgac    480

gctacatacc aacggactag ggcactcgtt agaaccggaa tggatcctag aatgtgctca    540

cttatgcagg gatctacact ccctagacga tccggagccg caggagcagc cgttaaggga    600

gtcggaacta tggttatgga actcgttaga atgataaaaa gggggattaa cgataggaat    660

ttttggagag gcgaaaacgg acgtaaaact agaatcgcat acgaaagaat gtgcaatata    720

ctcaaaggga aattccaaac cgcagcgcaa aaagctatga tggatcaagt tagggagtct    780

aggaatccag gaaatgccga attcgaagac cttacatttc tcgctcggtc cgcactaatc    840

cttcgcggat cagtcgcaca caaatcttgc ttacccgcat gcgtatacgg acctgcagtc    900

gctagcggat acgatttcga acgcgaaggg tatagtctag taggaattga tccatttaga    960

ttgctccaaa attcgcaagt gtatagtctg attagaccta acgagaatcc tgcacacaaa   1020

tctcaactcg tatggatggc atgccatagt gccgcattcg aagaccttag agtgctatct   1080

ttcataaagg gaacgaaagt gttgcctagg ggaaagctat ctactagggg agtgcaaatc   1140
```

```
gctagtaacg agaatatgga gactatggag tctagtacac tcgaactgag atctagatat   1200

tgggctatta ggactagatc cggagggaat acgaatcagc aacgagctag cgccgggcaa   1260

atctcaatcc aacctacatt ttccgtgcaa cggaatctgc cattcgatcg gacaacgatt   1320

atggccgcat tcaatgggaa taccgaggga cggactagcg atatgagaac cgaaattatc   1380

agaatgatgg aatccgctag accagaggac gtttcgtttc aaggacgggg agtcttcgag   1440

ctctcggacg aaaaggcagc gagcccgatc gtgccttcct ttgacatgag taatgaagga   1500

tcttatttct tcggagacaa tgcagaggag tacgacaatt aaagaaaaat acccttgttt   1560

ctact                                                               1565
```

<210> SEQ ID NO 24
<211> LENGTH: 1413
<212> TYPE: DNA
<213> ORGANISM: Influenza virus

<400> SEQUENCE: 24

```
agcgaaagca ggggtttaaa atgaatccaa atcagaaaat aacaaccatt ggatcaatct     60

gtctggtagt cggactaatt agcctaatat tgcaaatagg gaatataatc tcaatatgga    120

ttagccattc aattcaaact ggaagtcaaa accatactgg aatatgcaac caaaacatca    180

ttacctataa aaatagcacc tgggtaaagg acacaacttc agtgatatta accggcaatt    240

catctctttg tcccatccgt gggtgggcta tatacagcaa agacaatagc ataagaattg    300

gttccaaagg agacgttttt gtcataagag agccctttat ttcatgttct cacttggaat    360

gcaggacctt ttttctgacc caaggtgcct tactgaatga caagcattca aatgggactg    420

ttaaggacag aagcccttat agggccttaa tgagctgccc tgtcggtgaa gctccgtccc    480

cgtacaattc aagatttgaa tcggttgctt ggtcagcaag tgcatgtcat gatggcatgg    540

gctggctaac aatcggaatt tcaggtccag ataatggagc agtggctgta ttaaaataca    600

acggcataat aactgaaacc ataaaaagtt ggaggaagaa aatattgagg acacaagagt    660

ctgaatgtgc ctgtgtaaat ggttcatgtt ttactataat gactgatggc ccgagtgatg    720

ggctggcctc gtacaaaatt ttcaagatcg aaaaggggaa ggttactaaa tcaatagagt    780

tgaatgcacc taattctcac tatgaggaat gttcctgtta ccctgatacc ggcaaagtga    840

tgtgtgtgtg cagagacaac tggcatggtt cgaaccggcc atgggtgtct ttcgatcaaa    900

acctggatta tcaaatagga tacatctgca gtggggtttt cggtgacaac ccgcgtcccg    960

aagatggaac aggcagctgt ggtccagtgt atgttgatgg agcaaacgga gtaaagggat   1020

tttcatatag gtatggtaat ggtgtttgga taggaaggac caaaagtcac agttccagac   1080

atgggtttga gatgatttgg gatcctaatg gatggacaga gactgatagt aagttctctg   1140

ttaggcaaga tgttgtggca atgactgatt ggtcagggta tagcggaagt ttcgttcaac   1200

atcctgagct aacagggcta gactgtatga ggccgtgctt ctgggttgaa ttaatcaggg   1260

gacgacctaa agaaaaaaca atctggacta gtgcgagcag catttctttt tgtggcgtga   1320

atagtgatac tgtagattgg tcttggccag acggtgctga gttgccattc agcattgaca   1380

agtagtctgt tcaaaaaact ccttgtttct act                                1413
```

<210> SEQ ID NO 25
<211> LENGTH: 1413
<212> TYPE: DNA
<213> ORGANISM: unknown
<220> FEATURE:
<223> OTHER INFORMATION: synthetic

<400> SEQUENCE: 25

```
agcgaaagca ggggtttaaa atgaatccaa atcagaaaat aacaaccatt ggatcaatct    60
gtctggtagt cggactaatt agcctaatat tgcaaatagg gaatataatc tcaatatgga   120
tttcgcattc aatccaaacc ggatcacaaa atcatacagg catatgcaat cagaatataa   180
ttacttataa aaatagtaca tgggtgaaag atactactag cgtgatacta accggcaatt   240
ctagtctatg tccgattagg gggtgggcta tatactctaa agacaatagt atacggatag   300
ggtctaaggg agacgttttc gtaattaggg aaccgtttat aagttgttca catctagagt   360
gtaggacctt ttttctgaca caaggcgcac tattaaacga taagcattct aacggtacag   420
ttaaggatag gtcaccttat agggcactta tgtcatgtcc cgtaggcgaa gcccctagtc   480
catacaatag tagatttgaa tccgttgcat ggtccgctag cgcatgtcac gacggaatgg   540
ggtggttgac tatagggatt agcggacccg ataacggagc cgttgccgta ctgaaatata   600
acggtataat taccgaaact attaagagtt ggcgtaaaaa aatattgcgt acacaagagt   660
ccgaatgcgc atgcgttaac ggatcatgtt ttacaattat gactgacgga cctagcgacg   720
ggttagcgtc atacaaaatt tttaaaatcg aaaaaggcaa ggttactaag tcaatcgagt   780
taaacgcacc taattcgcat tacgaagagt gttcatgtta tcccgatacc ggaaaggtta   840
tgtgcgtttg tagggataat tggcacggtt cgaacagacc ttgggtgtca ttcgatcaaa   900
atctagacta tcaaatcgga tatatatgta gcggagtgtt cggcgataat cctagaccag   960
aggacggtac aggcagctgt ggaccggttt acgttgacgg cgctaacggc gttaaggggt  1020
ttagttatag atacggcaat ggcgtatgga tcggtaggac taagtcacat agttctagac  1080
acggatttga aatgatatgg gatcctaacg gatggaccga aaccgactcg aagtttagcg  1140
ttaggcaaga cgtagtcgct atgaccgatt ggtccgggta tagcggatca ttcgtgcaac  1200
atccagagtt aaccggattg gattgtatgc gaccatgttt ttgggttgag ttgattaggg  1260
ggagaccgaa agagaaaact atatggacta gcgcgagcag catttctttt tgtggcgtga  1320
atagtgatac tgtagattgg tcttggccag acggtgctga gttgccattc agcattgaca  1380
agtagtctgt tcaaaaaact ccttgtttct act                                1413
```

<210> SEQ ID NO 26
<211> LENGTH: 1026
<212> TYPE: DNA
<213> ORGANISM: Influenza virus

<400> SEQUENCE: 26

```
agcgaaagca ggtagatatt gaaagatgag tcttctaacc gaggtcgaaa cgtacgtact    60
ctctatcatc ccgtcaggcc ccctcaaagc cgagatcgca cagagacttg aagatgtctt   120
tgcagggaag aacactgatc ttgaggttct catggaatgg ctaaagacaa gaccaatcct   180
gtcacctctg actaagggga ttttaggatt tgtgttcacg ctcaccgtgc ccagtgagcg   240
aggactgcag cgtagacgct ttgtccaaaa tgcccttaat gggaacgggg atccaaataa   300
catggacaaa gcagttaaac tgtataggaa gctcaagagg gagataacat tccatggggc   360
caaagaaatc tcactcagtt attctgctgg tgcacttgcc agttgtatgg gcctcatata   420
caacaggatg ggggctgtga ccactgaagt ggcatttggc ctggtatgtg caacctgtga   480
acagattgct gactcccagc atcggtctca taggcaaatg gtgacaacaa ccaatccact   540
aatcagacat gagaacagaa tggttttagc cagcactaca gctaaggcta tggagcaaat   600
```

ggctggatcg agtgagcaag cagcagaggc catggaggtt gctagtcagg ctagacaaat 660
ggtgcaagcg atgagaacca ttgggactca tcctagctcc agtgctggtc tgaaaaatga 720
tcttcttgaa aatttgcagg cctatcagaa acgaatgggg gtgcagatgc aacggttcaa 780
gtgatcctct cgctattgcc gcaaatatca ttgggatctt gcacttgaca ttgtggattc 840
ttgatcgtct ttttttcaaa tgcatttacc gtcgctttaa atacggactg aaaggagggc 900
cttctacgga aggagtgcca aagtctatga gggaagaata tcgaaaggaa cagcagagtg 960
ctgtggatgc tgacgatggt cattttgtca gcatagagct ggagtaaaaa actaccttgt 1020
ttctac 1026

<210> SEQ ID NO 27
<211> LENGTH: 890
<212> TYPE: DNA
<213> ORGANISM: Influenza virus

<400> SEQUENCE: 27
agcaaaagca gggtgacaaa gacataatgg atccaaacac tgtgtcaagc tttcaggtag 60
attgctttct ttggcatgtc cgcaaacgag ttgcagacca agaactaggt gatgccccat 120
tccttgatcg gcttcgccga gatcagaaat ccctaagagg aaggggcagc accctcggtc 180
tggacatcga gacagccaca cgtgctggaa agcagatagt ggagcggatt ctgaaagaag 240
aatccgatga ggcacttaaa atgaccatgg cctctgtacc tgcgtcgcgt tacctaactg 300
acatgactct tgaggaaatg tcaagggact ggtccatgct catacccaag cagaaagtgg 360
caggccctct ttgtatcaga atggaccagg cgatcatgga taagaacatc atactgaaag 420
cgaacttcag tgtgattttt gaccggctgg agactctaat attgctaagg gctttcaccg 480
aagagggagc aattgttggc gaaatttcac cattgccttc tcttccagga catactgctg 540
aggatgtcaa aaatgcagtt ggagtcctca tcgggggact tgaatggaat gataacacag 600
ttcgagtctc tgaaactcta cagagattcg cttggagaag cagtaatgag aatgggagac 660
ctccactcac tccaaaacag aaacgagaaa tggcgggaac aattaggtca gaagtttgaa 720
gaaataagat ggttgattga agaagtgaga cacaaactga agataacaga gaatagtttt 780
gagcaaataa catttatgca agccttacat ctattgcttg aagtggagca agagataaga 840
actttctcgt ttcagcttat ttaataataa aaaacaccct tgtttctact 890

<210> SEQ ID NO 28
<211> LENGTH: 890
<212> TYPE: DNA
<213> ORGANISM: unknown
<220> FEATURE:
<223> OTHER INFORMATION: synthetic

<400> SEQUENCE: 28
agcaaaagca gggtgacaaa gacataatgg atccaaacac tgtgtcaagc tttcaggtag 60
attgctttct ttggcatgtc cgcaaacgag ttgcagacca agaactaggt gatgccccat 120
tccttgaccg actgagacgg gatcagaaat cccttagggg caggggatcg accctaggcc 180
tagacatcga aaccgcaact agggccggaa agcagatcgt ggagcgtata ctgaaagagg 240
agtccgacga agcgcttaag atgactatgg ccagcgtacc cgctagtcgg taccttaccg 300
atatgacact cgaagagatg tcacgcgatt ggtctatgct aatccctaag cagaaagtgg 360
ccggacctct atgtatacgg atggaccagg cgattatgga caaaaacatt atccttaaag 420
cgaacttttc cgtgatattc gatcgcctag agactctgat actgttgcgt gcattcacag 480

```
aagagggagc aattgttggc gaaatttcac cattgccttc tcttccagga catactgctg    540
aggatgtcaa aaatgcagtt ggagtcctca tcgggggact tgaatggaat gataacacag    600
ttcgagtctc tgaaactcta cagagattcg cttggagaag cagtaatgag aatgggagac    660
ctccactcac tccaaaacag aaacgagaaa tggcgggaac aattaggtca gaagtttgaa    720
gaaataagat ggttgattga agaagtgaga cacaaactga agataacaga gaatagtttt    780
gagcaaataa catttatgca agccttacat ctattgcttg aagtggagca agagataaga    840
actttctcgt ttcagcttat ttaataataa aaaacaccct tgtttctact               890
```

<210> SEQ ID NO 29
<211> LENGTH: 7152
<212> TYPE: DNA
<213> ORGANISM: Human rhinovirus 89

<400> SEQUENCE: 29

```
ttaaaactgg gagtgggttg ttcccactca ctccacccat gcggtgttgt actctgttat     60
tacggtaact ttgtacgcca gtttttccca cccttcccca taatgtaact tagaagtttg    120
tacaatatga ccaataggtg acaatcatcc agactgtcaa aggtcaagca cttctgtttc    180
cccggtcaat gaggatatgc tttacccaag gcaaaaacct tagagatcgt tatccccaca    240
ctgcctacac agagcccagt accatttttg atataattgg gttggtcgct ccctgcaaac    300
ccagcagtag acctggcaga tgaggctgga cattccccac tggcgacagt ggtccagcct    360
gcgtggctgc ctgctcaccc ttcttgggtg agaagcctaa ttattgacaa ggtgtgaaga    420
gccgcgtgtg ctcagtgtgc ttcctccggc ccctgaatgt ggctaacctt aaccctgcag    480
ccgttgccca taatccaatg ggtttgcggt cgtaatgcgt aagtgcggga tgggaccaac    540
tactttgggt gtccgtgttt cctgtttttc ttttgattgc attttatggt gacaatttat    600
agtgtataga ttgtcatcat gggtgcacaa gtatctagac aaaatgttgg gacacactcc    660
acacaaaatt cagtgagcaa tggatctagc ttaaattatt tcaacatcaa ttattttaaa    720
gacgcagctt caagtggtgc ttctagattg gatttttctc aagaccctag taaatttact    780
gatcctgtta aagatgtgtt agaaaagggt attccaacac ttcaatcacc aacagttgaa    840
gcttgtggtt attcagacag actaatacag ataacccgag gagattccac tataacatcc    900
caagatactg caaatgcagt tgttgcttat ggtgtgtggc catcatactt gactccagat    960
gatgcgactg ctattgacaa acccacacaa cctgatacat catccaacag attctacacc   1020
ttggacagtc gttcttggac atctgcctca tctggatggt ggtggaaatt gcctgatgcc   1080
cttaaaaaca tgggtatatt tggtgaaaat atgttttacc attttctagg gagatctgga   1140
tacacaatac atgtacaatg taattctagc aagtttcatc agggtttatt aatagttgcc   1200
gccatcccag aacatcaatt ggcatctgca acaagtggaa atgtatcagt cgggtacaat   1260
cacacccacc caggtgagca aggtagagaa gtagtaccat cacggacatc tagtgataat   1320
aaaagaccta gtgatgacag ttggttaaat tttgatggaa cattacttgg taacttacct   1380
atttatcccc accaatacat taatctaagg actaacaatt cagctaccct tattttacct   1440
tatgtcaatg ctgtaccaat ggactctatg cttagacata ataattggag cttggttata   1500
atcccaatat gccctcttca ggtccaacct gggggacac aatccatacc tataacagta    1560
tcaattagcc ctatgttttc agaattttca gggccaagaa gtaaggttgt gtttagtacc   1620
actcagggtt taccagttat gttaacacct ggatctgggc aattcttaac aactgatgat   1680
```

-continued

```
actcaatccc catcagcgtt tccatacttc cacccgacca aggaaatatt tatacctgga   1740
caagttagga atttaattga aatgtgccaa gttgacacac tcattcctgt taacaataca   1800
caggaaaatg taagatctgt gaatatgtac actgttgatt tacgcacaca agttgattta   1860
gctaaagaag tcttttctat accagtagat attgcctcac aacctttagc cactactctc   1920
ataggagaac ttgcaagcta ttacacacac tggactggta gtctgcgctt tagctttatg   1980
ttttgtggtt ctgctagctc tactttgaaa ctattaattg catacactcc tcctggtgtt   2040
ggaaaaccta aatccaggag agaagccatg cttggtacac atttagtgtg ggatgtgggg   2100
ttgcagtcca ccgcctcact agttgtacca tgggttagtg ctagccattt tagattcact   2160
acacctgaca catattcctc agctggttat attacatgct ggtaccagac caactttgta   2220
gtacctgata gtactccaga taacgccaaa atggtgtgca tggtttctgc atgcaaagat   2280
ttttgcttaa gattagccag agatactaac ctacacacac aagaaggagt actcacacaa   2340
aacccagttg aaaattatat agatagtgta ttaaatgaag ttcttgtggt gccaaatatc   2400
caacctagca catctgtgtc aagtcatgca gcgcctgcat tggatgctgc ggaaaccgga   2460
cacaccagct ctgttcaacc tgaagatatg attgaaacta gatatgttat aactgatcaa   2520
acaagggatg aaacaagtat tgagagtttc ttaggtaggt cagggtgtat cgctatgata   2580
gaatttaata caagtagtga taaaactgaa catgataaaa ttggtaaagg attcaaaaca   2640
tggaaggtta gtcttcaaga aatggcacaa atcagaagaa aatatgaatt attcacatat   2700
acaagatttg attcagagat aacaatagtc actgcagccg cagctcaagg aaatgatagt   2760
ggacatatag tattgcaatt tatgtatgta cccccaggag cacctgtccc cgaaaaacgt   2820
gatgattaca catggcaatc aggaacaaat gcatctgtgt tctggcaaga aggacaacca   2880
taccccagat tcacaatccc ttttatgagc attgcatcag cctattacat gttttatgat   2940
ggttatgatg gtgatagtgc agcatcaaaa tacggttctg tagtcactaa tgatatggga   3000
accatatgtg ttagaatagt gacatccaac caaaaacacg attcaaatat tgtgtgccgc   3060
atttaccaca aggccaaaca tataaaagca tggtgtcctc gcccaccaag ggctgttgcc   3120
tatcaacaca cacactcaac caattacata ccatccaatg gtgaggccac aactcagatt   3180
aaaaccagac ctgatgtttt taccgttaca aacgtcggac catctagtat gtttgtacat   3240
gtgggtaact taatctatag aaatcttcat ctctttaatt ctgatcttga tgattctatt   3300
cttgtatcat actccagtga tctaatcata tatcgaacaa acactgaagg taatgatgtg   3360
atccctaatt gtgattgcac tgaatgtaca tattactgcc accacaaaga taggtatttt   3420
cctatcagag ttactgcaca tgattggtat gagattcaag aatcagaata ttacccaaaa   3480
catatccaat ataatctcct gattggagag ggtccttgtg aaccaggaga ttgtggagga   3540
aaactattgt gtaaacatgg tgttataggt atgattacag ctggaggtga aggtcacgtt   3600
gcttttattg acctgagaaa attccagtgt gctgaggagc aagggttatc tgattatgtg   3660
gaacatcttg gtcaagtctt tggtgtaggc ttcgtagaca gcatcaaaca acaggtaaac   3720
tttatcaacc ccactagtaa aattggttca aaagtgatta aatggttgtt gaggatagtt   3780
tcagctatga taataatggt aaggaatagt tctgatccac aaactgtaat tgccactctc   3840
acccttctag gttgttcagg ctcaccatgg aggtttctta aagagaaact ctgtgcgtgg   3900
ctccagctta gctatgtaca taagcagtct gattcatggc tcaagaaatt tactgaagcg   3960
tgtaacgcag cacgtgggct agagtggatt ggacaaaaga tatctaaatt tatagattgg   4020
ataaagagta tgttaccaca ggctcaattg aaaattgatt acctaaccaa attaaaacaa   4080
```

```
cttaatctct tagagaaaca aatagaaaca attagacttg cacctgctag tgttcaggag   4140
aaaattttca ttgaaataaa caccccttcat gatttatcct taaaattctt accactgtat   4200
gcatctgaag cacgtagaat taagaattta tatatcaaat gcagtaatgt tattaaaggg   4260
ggaaagagga atgaaccagt tgcagttcta atacatggtt ctcctggtac tggaaaatct   4320
cttgccactt ctgttcttgc tcgaatgcta actgttgaga ctgatatata ttctttgccc   4380
ccagatccta aatattttga tgggtatgat caacagagtg ttgttatcat ggatgatatc   4440
atgcaaaatc ctagtggtga agacatgact ttgttttgcc aaatggtatc gagtgtccct   4500
ttcatacctc ctatggcaga tcttccagat aaaggaaaac catttacatc caagtttgta   4560
cttgcaagca ctaatcacac tctactaaca ccaccaacag tatcttcatt accagcaatg   4620
gcaagaaggt tttactttga tctagacatt caagttaaga aagagtatct tttagatggc   4680
aaactagata tagcaaaaag ctttcgacca tgtgatgtta atattaaaat aggcaatgct   4740
aagtgctgtc catttatctg tggaaaagct gtagagttta aagatagaaa ttcatgtaca   4800
accttgtctt tatctcaatt gtatagtcat ataaaggaag aagataggag aagaagcagt   4860
gcagcacaag caatggaggc tatatttcaa ggtatagacc tccaatctcc tccacctcca   4920
gccatagctg acctccttag gtctgtgaaa acaccagaga tcattaagta ttgccaagat   4980
aataattgga ttgttccagc agagtgttct attgaaagag atttagggat agcaaatatg   5040
actataggta taatagctaa tgtggtctct atagtaggtg ttatctatat aatttataaa   5100
ttgttctgta cacttcaggg tccatactca ggggaaccta aacccaaaag cagagctcca   5160
gagagaagag tagttactca gggcccagag gaagagtttg gtcgctcact actcaaacat   5220
aattgctgtg ttgtgacaac cgacaaaggc aaattcacag gtcttggcat atatgaccaa   5280
gtcatggtac ttccaacaca ttctgaccca ggctctgaga tcttggtaga tggagtaaaa   5340
gttaaggtct ctgattccta tgatttgcat aaccatgagg gtgttaagct agagatcaca   5400
gttgtgaaat taattagaaa tgagaagttt aaagacatca gaaaatattt accctcacgt   5460
gaagatgact atcctgcttg taaccttgcc ttactagcta atcaagatga gccaacaata   5520
ataagtgttg gtgatgcagt atcttatggt aacatcttat tgagtggtac caatactgca   5580
cgaatgatca agtaccatta cccgacaaaa gctggatatt gtgggggtgt tttgtacaag   5640
gttggctcta ttcttggtat acatgttggt ggcaatggta gagatggatt ttctgcaatg   5700
cttctcaaat cttattttgg tgaaacccag ggtttaatca ctaaagaact tcctgtatct   5760
gtaaagaact taccatccgt acatgtttca tctaaaaccc gactacaacc tagtgttttt   5820
catgatgttt tccctggaac aaaagagcct gcagttctta gtagtaatga tccaagacta   5880
gaaactgact ttgactcagc acttttctcc aaatataaag gtaatcctgc ttgtcaagtg   5940
accccacaca tgaaaattgc tgtagcacat tatgcagcac agttatctac actagacata   6000
aatcctcaac ccctttcatt ggaagagagt gtgtttggta ttgagggatt agaagctttg   6060
gatttaaata ctagtgcagg atttccttat gtttcactgg gaataaagaa gaaagatctt   6120
atagataaaa agaccaaaga catcacaaaa cttaggaaag caattgatga atatggtatt   6180
gatttgccta tggttacttt tctgaaagat gaacttagaa agaaggaaaa aataaaagat   6240
ggaaagacta gagtcataga agctaatagt gtgaatgata ctgtgttatt cagaagtgta   6300
tttggaaatc ttttctctgc tttccacaaa aacccaggta tagtcactgg ttcagcagta   6360
gggtgtgacc ctgaagtatt ctggtcaact atacctctca tgctagatgg agaatgttta   6420
```

atggcttttg attattcaaa ctatgatggt agcctacatc ccgtttggtt taaatgtctt 6480
agtatgctct tagaagacat aggtttctcc tctcaactta ttaaccagat ctgtaactct 6540
aaacatatat acaaatctaa gtattatgaa gtggaaggag gtatgccatc tggatgtgct 6600
ggtactagta tttttaatac aataatcaac aatattatca ttagaacttt ggtactagat 6660
gcttataaga acatagatct agataaactg aaaatcttag catatgggga tgatgtcatc 6720
ttttcttata attttaaact tgacatggca gttcttgcca aagaaggaga aaaatatgga 6780
ctaacaatca cccctgctga taagtctgat gttttccaag aattgaccta taaaaatgta 6840
acttttctta aaagaggatt cagagctgat gagcgccact ctttccttat acaccctacc 6900
tttcctgtgg ctgagattca tgactccatc agatggacca aaaacccttc atgtatgcag 6960
gaacacgtgc tatctttgtg tcatttaatg tggcataatg gtagacatgc ataccaggaa 7020
ttcattaaag gtatacgcag tgtatctgcc ggtcgggcac tgtatatacc agcttatgaa 7080
gttcttgaac atgaatggta tgaaaaattt tagatataaa actgttaaat atagctagtt 7140
tattagtttt at 7152

<210> SEQ ID NO 30
<211> LENGTH: 7152
<212> TYPE: DNA
<213> ORGANISM: unknown
<220> FEATURE:
<223> OTHER INFORMATION: synthetic

<400> SEQUENCE: 30
ttaaaactgg gagtgggttg ttcccactca ctccacccat gcggtgttgt actctgttat 60
tacggtaact ttgtacgcca gtttttccca cccttcccca taatgtaact tagaagtttg 120
tacaatatga ccaataggtg acaatcatcc agactgtcaa aggtcaagca cttctgtttc 180
cccggtcaat gaggatatgc tttacccaag gcaaaaacct tagagatcgt tatccccaca 240
ctgcctacac agagcccagt accatttttg atataattgg gttggtcgct ccctgcaaac 300
ccagcagtag acctggcaga tgaggctgga cattccccac tggcgacagt ggtccagcct 360
gcgtggctgc ctgctcaccc ttcttgggtg agaagcctaa ttattgacaa ggtgtgaaga 420
gccgcgtgtg ctcagtgtgc ttcctccggc ccctgaatgt ggctaacctt aaccctgcag 480
ccgttgccca taatccaatg ggtttgcggt cgtaatgcgt aagtgcggga tgggaccaac 540
tactttgggt gtccgtgttt cctgtttttc ttttgattgc attttatggt gacaatttat 600
agtgtataga ttgtcatcat gggagcacaa gtgtctagac aaaacgtagg tacacatagt 660
acacaaaact cagtgtctaa cggatctagt cttaattatt ttaatattaa ttattttaaa 720
gacgctgcat ctagcggagc tagtagactt gattttagtc aggatccatc taaatttacc 780
gatccagtta aagacgtact cgaaaaaggt atacctacat tgcaatcacc tacagtcgaa 840
gcatgcggat actctgatag attgatacaa attactaggg gggatagtac tattactagt 900
caggataccg ctaacgccgt agtcgcatac ggagtttggc catcttatct tacacctgat 960
gacgcaaccg caatcgataa acctacacaa cctgatacta gttctaatag attctataca 1020
cttgattcta gatcatggac tagtgctagt tcaggttggt ggtggaaatt gcctgacgca 1080
cttaaaaata tgggtatatt cggtgagaat atgttttatc atttcttagg taggtcaggg 1140
tatactatac acgttcaatg taatagttct aaatttcacc aaggtctatt aatcgttgcc 1200 gctataccccg aacaccaatt agctagcgct acatcaggta acgttagcgt agggtataat 1260
catacacatc caggcgaaca gggtagggaa gtcgtaccat ctagaacatc tagcgataat 1320

```
aaacgaccat ctgacgatag ttggcttaat ttcgatggta cactattagg taatctacct   1380
atatatccac atcaatatat taatcttaga actaataatt ccgctacact tatactgcca   1440
tacgttaacg cagtgcctat ggatagtatg cttagacata ataattggtc attagtgatt   1500
ataccgatat gtccattgca agtgcaacct ggaggtacac aatctatacc tattaccgtt   1560
agtattagtc ctatgtttag cgaatttagc ggacctagat ctaaggtagt gtttagtact   1620
acacaggggt tacccgttat gcttacacct ggatcaggtc aatttttgac tactgacgat   1680
acacaatcac ctagtgcatt cccatatttt caccctacta aagagatttt tatacccggt   1740
caggttagga atctaatcga aatgtgtcaa gtcgatacac ttatacccgt taataataca   1800
caggaaaacg ttagatccgt taatatgtat accgttgatt tgcgtacaca agtcgatcta   1860
gctaaagagg ttttttcgat accagtcgat atcgctagtc aaccattagc tactacactt   1920
ataggcgaac tcgcatcata ttatacacat tggaccggat cacttagatt ttcttttatg   1980
ttttgcggat ccgctagtag tacacttaaa ctgttaatcg catatacacc tccaggagtg   2040
ggtaagccta aatctagacg cgaagctatg ttaggtacac atctagtttg ggacgtaggg   2100
ttacaatcta ccgctagttt agtcgtacca tgggttagcg catcacattt tagatttact   2160
acacctgata cttattctag tgccggatat ataacatgtt ggtatcaaac taatttcgta   2220
gtgccagata gtacacctga taacgctaaa atggtttgta tggttagcgc atgtaaagat   2280
ttttgtctta gattagctag ggatactaat ttgcatacac aagagggagt gcttacacaa   2340
aatccagtcg aaaattatat cgatagcgta cttaacgaag tgttagtcgt acctaatata   2400
caacctagta ctagtgtgtc atctcacgct gcaccagcat tagacgcagc cgaaaccgga   2460
catacatcta gtgtgcaacc tgaggatatg atagagacta gatacgttat taccgatcag   2520
actagagacg aaacatcaat cgaatcattc ttaggtaggt cagggtgtat cgctatgata   2580
gagtttaata ctagttccga taaaaccgaa cacgataaga taggtaaggg gtttaaaact   2640
tggaaagtgt cattgcagga aatggcacaa attagacgta aatacgaatt gtttacatat   2700
actagattcg atagtgagat tactatcgtt accgcagccg cagcacaagg taacgattca   2760
ggtcatatag tgttacaatt tatgtacgta ccaccaggtg caccagtacc cgaaaaacgc   2820
gatgattata catggcaatc cggtactaac gctagcgttt tttggcaaga gggacaacca   2880
tatcctagat ttactatacc ttttatgtca atcgctagtg catattatat gttttacgac   2940
ggatacgatg gcgattctgc cgcatctaaa tacggatctg tagtgactaa cgatatgggt   3000
actatatgcg ttagaatcgt tacatctaat caaaaacacg attctaatat cgtttgtaga   3060
atatatcata aagctaaaca tattaaggca tggtgtccta gaccacctag agccgttgca   3120
tatcaacata cacatagtac taattatata ccatctaacg gtgaggctac tacacaaatt   3180
aaaactagac ctgacgtttt taccgttact aacgtaggtc catctagtat gttcgtacac   3240
gtaggtaatc tgatatatag aaatttgcat ctattcaatt ccgatttaga cgattctata   3300
ctcgttagtt attctagcga tctgattata tatagaacta ataccgaagg taacgatgtg   3360
atacctaatt gcgattgtac cgaatgtact tattattgtc atcataaaga taggtatttt   3420
ccgatacgcg ttaccgcaca cgattggtac gaaatacagg aatctgagta ttatcctaaa   3480
catatacaat ataatctgtt aataggcgaa ggtccatgcg aaccaggcga ttgcggaggt   3540
aagttattgt gtaaacacgg agtgataggt atgattaccg caggggggaga gggacacgtt  3600
gcgtttatcg atttgcgaaa atttcaatgc gcagaggaac aggggttatc cgattacgtt   3660
```

```
gagcatttag ggcaagtgtt cggagtcgga ttcgttgatt caattaaaca acaggttaat   3720
tttattaatc ctacatctaa aatcggatct aaagtgataa aatggttact tagaatcgtt   3780
agcgctatga taattatggt taggaattct agcgatccac aaaccgtaat cgctacactt   3840
acactattag ggtgttcagg ttcaccttgg cgatttctta aagagaaatt atgcgcatgg   3900
ttgcaattgt catacgttca taaacaatcc gatagttggc ttaaaaaatt taccgaagca   3960
tgtaacgccg ctaggggact cgaatggata gggcaaaaaa tatctaaatt tatcgattgg   4020
attaaatcta tgttaccaca agcgcaattg aaaatcgatt atcttactaa gcttaaacaa   4080
ttgaacttac tcgaaaaaca aatcgaaact attagactcg caccagctag tgtgcaagag   4140
aaaattttta tagagattaa tacattacac gatctatcac ttaaattctt accattatac   4200
gctagcgaag ctagacggat taaaaatcta tatattaagt gttctaacgt aattaaggga   4260
ggtaagcgta acgaacccgt tgccgtactt atacacggat caccaggtac cggtaagtca   4320
ttagcgacta gcgtactcgc tagaatgctt acagtcgaaa ccgatatata ctctttacca   4380
cctgatccta aatatttcga cggatacgat caacaatccg tagtgattat ggacgatatt   4440
atgcaaaatc ctagtggtga ggatatgaca ttgttttgtc aaatggtatc tagcgtacca   4500
tttataccac ctatggccga tttacccgat aagggtaagc cttttacatc taaattcgta   4560
ctcgcatcaa ctaatcatac attgcttaca ccacctaccg ttagttcact accagctatg   4620
gctagacggt tttatttcga tctagatata caggttaaaa aagagtatct gttagacggt   4680
aagttagata tcgctaaatc ttttagacca tgcgatgtta atattaaaat cggtaacgct   4740
aaatgttgtc catttatatg cggtaaggca gtcgaattta aagataggaa ttcatgtact   4800
acactatcac tatcacaatt gtattcacat attaaggaag aggatagacg tagatctagt   4860
gccgcacaag ctatggaagc tatttttcag ggtatcgatc tgcaatcacc accaccacca   4920
gctatagccg atctacttag atccgttaaa acacctgaga taattaagta ttgtcaggat   4980
aataattgga tcgtaccagc cgaatgttca atcgaacgcg atttagggat agcgaatatg   5040
acaatcggta taatcgctaa cgtagtgtca atcgtaggcg ttatatatat tatatataaa   5100
ttgttttgta cattgcaggg accatactct ggcgaaccta aacctaaatc tagagcacct   5160
gaaagacgcg tagtgacaca gggacctgaa gaggaattcg gtaggtcatt gcttaaacat   5220
aattgttgcg tagtgactac cgataagggt aagtttaccg gattaggtat atacgatcag   5280
gttatggtgt tacctacaca ttccgatcca ggatctgaga tactcgtaga cggagttaag   5340
gttaaggtta gcgattcata cgatctacat aatcacgaag gcgttaagtt agagattacc   5400
gtagttaagc ttatacgtaa cgaaaaattt aaagatatac gaaaatatct accatcacgc   5460
gaagacgatt atcctgcatg taatctcgca ctattagcga atcaagacga acctacaatt   5520
attagcgtag gcgatgccgt atcatacggt aatatactgt tatccggtac taataccgct   5580
agaatgatta agtatcatta tcctactaaa gccggatatt gcggaggagt gttatataaa   5640
gtcggatcta tactcggtat acacgtaggc ggtaacggta gggacggatt ttccgctatg   5700
ttacttaaat cttatttcgg tgagacacag ggattgatta ctaaagagtt acccgtatcc   5760
gttaaaaatc tacctagcgt acacgttagt tctaaaacta gattgcaacc tagtgtgttt   5820
cacgacgttt ttccaggtac taaggaacct gccgtactat cttctaacga tcctagactc   5880
gaaaccgatt tcgatagtgc attattctct aaatataagg gtaatcctgc atgtcaggtt   5940
acaccacata tgaaaatcgc agtcgcacat tacgctgcac aattgtctac acttgatatt   6000
aatccacaac cactatcact tgaggaatcc gtattcggta tcgaagggtt agaggcactt   6060
```

gatcttaata ctagtgccgg attcccatac gttagtctag gtattaaaaa aaaagatcta 6120
atcgataaaa aaactaagga tattactaaa ttgcgaaaag cgatagacga atacggtatc 6180
gatctaccta tggttacatt ccttaaagac gaacttagaa aaaaagagaa aattaaagac 6240
ggtaagacta gggttatcga agctaactct gttaacgata ccgtactttt tagatccgta 6300
ttcggtaatc tattttccgc attccataaa aatccaggta tcgttaccgg atccgcagtc 6360
ggatgcgatc cagaagtgtt ttggtctact ataccactta tgttagacgg tgagtgtctt 6420
atggcattcg attattctaa ttacgatggg tcattgcatc ccgtatggtt taaatgtcta 6480
tctatgttac tcgaagatat agggtttagt tcacaattga ttaatcagat ttgtaactct 6540
aaacatatat ataaatctaa atattacgaa gtcgaagggg gtatgccatc aggttgcgca 6600
ggtacatcta tttttaatac tataattaat aatattataa ttagaacatt agtgttagac 6660
gcatataaaa atatcgatct agataagctt aagatactcg catacggaga tgacgttata 6720
ttctcatata attttaaact tgatatggcc gtactcgcta aagagggaga aaaatacgga 6780
cttacaatta cacctgccga taagtctgac gtttttcagg aattgactta taaaaacgtt 6840
acattcctta aaggggggtt tcgcgcagac gaacgacatt cttttcttat acatcctaca 6900
tttcccgttg ccgaaataca cgattcaatt agatggacta aaaatcctag ttgtatgcaa 6960
gaacacgtac ttagtctatg tcatcttatg tggcataacg gtagacacgc ttatcaggaa 7020
tttattaagg gtattagatc cgttagtgcc ggtagggcac tatatatacc cgcatacgaa 7080
gtactcgaac acgaatggta cgaaaaattt tagatataaa actgttaaat atagctagtt 7140
tattagtttt at 7152

<210> SEQ ID NO 31
<211> LENGTH: 7212
<212> TYPE: DNA
<213> ORGANISM: Human rhinovirus 14

<400> SEQUENCE: 31
ttaaaacagc ggatgggtat cccaccattc gacccattgg gtgtagtact ctggtactat 60
gtacctttgt acgcctgttt ctccccaacc acccttcctt aaaattccca cccatgaaac 120
gttagaagct tgacattaaa gtacaatagg tggcgccata tccaatggtg tctatgtaca 180
agcacttctg tttcccagga gcgaggtata ggctgtaccc actgccaaaa gcctttaacc 240
gttatccgcc aaccaactac gtaacagtta gtaccatctt gttcttgact ggacgttcga 300
tcaggtggat tttccctcca ctagtttggt cgatgaggct aggaattccc cacgggtgac 360
cgtgtcctag cctgcgtggc ggccaaccca gcttatgctg ggacgccctt ttaaggacat 420
ggtgtgaaga ctcgcatgtg cttggttgtg agtcctccgg cccctgaatg cggctaacct 480
taaccctaga gccttatgcc acgatccagt ggttgtaagg tcgtaatgag caattccggg 540
acgggaccga ctactttggg tgtccgtgtt tctcattttt cttcatattg tcttatggtc 600
acagcatata tatacatata ctgtgatcat gggcgctcag gtttctacac agaaaagtgg 660
atctcacgaa aatcaaaaca ttttgaccaa tggatcaaat cagactttca cagttataaa 720
ttactataag gatgcagcaa gtacatcatc agctggtcaa tcactgtcaa tggacccatc 780
taagtttaca gaaccagtta aagatctcat gcttaagggt gcaccagcat tgaattcacc 840
caatgttgag gcctgtggtt atagtgatag agtacaacaa atcacactcg ggaattcaac 900
aataacaaca caagaagcag ccaacgctgt tgtgtgttat gctgaatggc cagagtacct 960

-continued tccagatgtg gacgctagtg atgtcaataa aacttcaaaa ccagacactt ctgtctgtag 1020
gttttacaca ttggatagta agacatggac aacaggttct aaaggctggt gctggaaatt 1080
accagatgca ctcaaggata tgggtgtgtt cgggcaaaac atgtttttcc actcactagg 1140
aagatcaggt tacacagtac acgttcagtg caatgccaca aaattccata gcggttgtct 1200
acttgtagtt gtaataccag aacaccaact ggcttcacat gagggtggca atgtttcagt 1260
taaatacaca ttcacgcatc caggtgaacg tggtatagat ttatcatctg caaatgaagt 1320
gggagggcct gtcaaggatg tcatatacaa tatgaatggt actttattag gaaatctgct 1380
cattttccct caccagttca ttaatctaag aaccaataat acagccacaa tagtgatacc 1440
atacataaac tcagtaccca ttgattcaat gacacgtcac aacaatgtct cactgatggt 1500
catccctatt gcccctctta cagtaccaac tggagcaact ccctcactcc ctataacagt 1560
cacaatagca cctatgtgca ctgagttctc tgggataagg tccaagtcaa ttgtgccaca 1620
aggtttgcca actacaactt tgccggggtc aggacaattc ttgaccacag atgacaggca 1680
atcccccagt gcactgccaa attatgagcc aactccaaga atacacatac tagggaaagt 1740
tcataacttg ctagaaatta tacaggtaga tacactcatt cctatgaaca acacgcatac 1800
aaaagatgag gttaacagtt acctcatacc actaaatgca aacaggcaaa atgagcaggt 1860
ttttgggaca aacctgttta ttggtgatgg ggtcttcaaa actactcttc tgggtgaaat 1920
tgttcagtac tatacacatt ggtctggatc acttagattc tcttcgatgt atactggtcc 1980
tgccttgtcc agtgctaaac tcactctagc atacaccccg cctggtgctc gtggtccaca 2040
ggacaggaga gaagcaatgc taggtactca tgttgtctgg gatattggtc tgcaatccac 2100
catagtaatg acaataccat ggacatcagg ggtgcagttt agatatactg atccagatac 2160
atacaccagt gctggctttc tatcatgttg gtatcaaact tctcttatac ttccccccaga 2220 aacgaccggc caggtctact tattatcatt cataagtgca tgtccagatt ttaagcttag 2280
gctgatgaaa gatactcaaa ctatctcaca gactgttgca ctcactgaag gcttaggtga 2340
tgaattagaa gaagtcatcg ttgagaaaac gaaacagacg gtggcctcaa tctcatctgg 2400
tccaaaacac acacaaaaag tccccatact aactgcaaac gaaacagggg ccacaatgcc 2460
tgttcttcca tcagacagca tagaaaccag aactacctac atgcacttta atggttcaga 2520
aactgatgta gaatgctttt tgggtcgtgc agcttgtgtg catgtaactg aaatacaaaa 2580
caaagatgct actggaatag ataatcacag agaagcaaaa ttgttcaatg attggaaaat 2640
caacctgtcc agccttgtcc aacttagaaa gaaactggaa ctcttcactt atgttaggtt 2700
tgattctgag tataccatac tggccactgc atctcaacct gattcagcaa actattcaag 2760
caatttggtg gtccaagcca tgtatgttcc acatggtgcc ccgaaatcca aaagagtggg 2820
cgattacaca tggcaaagtg cttcaaaccc cagtgtattc ttcaaggtgg gggatacatc 2880
aaggtttagt gtgccttatg taggattggc atcagcatat aattgttttt atgatggtta 2940
ctcacatgat gatgcagaaa ctcagtatgg cataactgtt ctaaaccata tgggtagtat 3000
ggcattcaga atagtaaatg aacatgatga acacaaaact cttgtcaaga tcagagttta 3060
tcacagggca aagctcgttg aagcatggat tccaagagca cccagagcac taccctacac 3120
atcaataggg cgcacaaatt atcctaagaa tacagaacca gtaattaaga agaggaaagg 3180
tgacattaaa tcctatggtt taggacctag gtacggtggg atttatacat caaatgttaa 3240
aataatgaat taccacttga tgacaccaga agaccaccat aatctgatag caccctatcc 3300
aaatagagat ttagcaatag tctcaacagg aggacatggt gcagaaacaa taccacactg 3360
taaccgtaca tcaggtgttt actattccac atattacaga aagtattacc ccataatttg 3420
cgaaaagccc accaacatct ggattgaagg aagcccttat tacccaagta gatttcaagc 3480
aggagtgatg aaaggggttg ggccggcaga gctaggagac tgcggtggga ttttgagatg 3540
catacatggt cccattggat tgttaacagc tgaaggtagt ggatatgttt gttttgctga 3600
catacgacag ttggagtgta tcgcagagga acaggggctg agtgattaca tcacaggttt 3660
gggtagagct tttggtgtcg ggttcactga ccaaatctca acaaaagtca cagaactaca 3720
agaagtggcg aaagatttcc tcaccacaaa agttttgtcc aaagtggtca aaatggtttc 3780
agctttagtg atcatttgca gaaatcatga tgacttggtc actgttacgg ccactctagc 3840
actacttgga tgtgatggat ctccttggag atttctgaag atgtacattt ccaaacactt 3900
tcaggtgcct tacattgaaa gacaagcaaa tgatggatgg ttcagaaagt ttaatgatgc 3960
atgtaatgct gcaaagggat tggaatggat tgctaataag atttccaaac tgattgaatg 4020
gataaaaaac aaagtacttc cccaagccaa agaaaaacta gaattttgta gtaaactcaa 4080
acaacttgat atactagaga gacaaataac caccatgcat atctcgaatc caacacagga 4140
aaaacgagag cagttgttca ataacgtatt gtggttggaa caaatgtcgc aaaagtttgc 4200
cccattttat gccgttgaat caaaaagaat cagggaactc aagaacaaaa tggtaaatta 4260
tatgcaattt aaaagtaaac aaagaactga accagtgtgt gtattaatcc atggtacacc 4320
cggttctggt aaatcattaa caacatccat tgtgggacgt gcaattgcag aacacttcaa 4380
ttcagcagta tattcacttc caccagatcc caagcacttt gatggttatc agcaacagga 4440
agttgtgatt atggatgatc tgaaccaaaa tccagatgga caggatataa gcatgttttg 4500
tcaaatggtt tcttcagtgg atttcttgcc tccaatggct agtttagata acaagggcat 4560
gttattcacc agtaattttg ttctagcctc cacaaattct aacacactaa gcccccccaac 4620
aatcttgaat cctgaagctt tagtcaggag atttggtttt gacctagata tatgtttgca 4680
tactacctac acaaagaatg gaaaactcaa tgcaggcatg tcaaccaaga catgcaaaga 4740
ttgccatcaa ccatctaatt tcaagaaatg ttgcccccta gtctgtggaa aagctattag 4800
cttggtagac agaactacca acgttaggta tagtgtggat caactggtca cggctattat 4860
aagtgatttc aagagcaaaa tgcaaattac agattcccta gaaacactgt ttcaaggacc 4920
agtgtataaa gatttagaga ttgatgtttg caacacacca ccttcagaat gtatcaacga 4980
tttactgaaa tctgtagatt cagaagagat tagggaatat tgtaagaaga agaaatggat 5040
tatacctgaa attcctacca acatagaaag ggctatgaat caagccagca tgattattaa 5100
tactattctg atgtttgtca gtacattagg tattgtttat gtcatttata aattgtttgc 5160
tcaaactcaa ggaccatatt ctggtaaccc gcctcacaat aaactaaaag ccccaacttt 5220
acgcccagtt gttgtgcaag gaccaaacac agaatttgca ctatccctgt taaggaaaaa 5280
cataatgact ataacaacct caaagggaga gttcacaggg ttaggcatac atgatcgtgt 5340
ctgtgtgata cccacacacg cacagcctgg tgatgatgta ctagtgaatg gtcagaaaat 5400
tagagttaag gataagtaca aattagtaga tccagagaac attaatctag agcttacagt 5460
gttgacttta gatagaaatg aaaaattcag agatatcagg ggatttatat cagaagatct 5520
agaaggtgtg gatgccactt tggtagtaca ttcaaataac tttaccaaca ctatcttaga 5580
agttggccct gtaacaatgg caggacttat taatttgagt agcaccccca ctaacagaat 5640
gattcgttat gattatgcaa caaaaactgg gcagtgtgga ggtgtgctgt gtgctactgg 5700
taagatcttt ggtattcatg ttggcggtaa tggaagacaa ggattttcag ctcaacttaa 5760
aaaacaatat tttgtagaga aacaaggcca agtaatagct agacataagg ttagggagtt 5820
taacataaat ccagtcaaca cggcaactaa gtcaaaatta catcccagtg tattttatga 5880
tgtttttcca ggtgacaagg aacctgctgt attgagtgac aatgatccca gactggaagt 5940
taaattgact gaatcattat tctctaagta caaggggaat gtaaatacgg aacccactga 6000
aaatatgctt gtggctgtag accattatgc agggcaacta ttatcactag atatccccac 6060
ttctgaactt acactaaaag aagcattata tggagtagat ggactagaac ctatagatat 6120
tacaaccagt gcaggatttc cctatgtgag tcttgggatc aaaaagagag acattctgaa 6180
taaagagacc caggacacag aaaagatgaa gttttatcta gacaagtatg gcattgactt 6240
gcctctagtt acatatatta aggatgaatt aagaagtgtt gacaaagtcc gattagggaa 6300
aagtagatta attgaagcct ccagtttgaa tgattctgtt aacatgagaa tgaaactagg 6360
caacctttac aaagcattcc atcaaaatcc cggtgttctg actggatcag cagtgggttg 6420
tgatcctgat gtgttttggt ctgtcatccc ttgcttaatg gatgggcacc tgatggcatt 6480
tgattactct aattttgatg cctctttgtc accagtttgg tttgtctgtc tagagaaggt 6540
tttgaccaag ttaggctttg caggctcttc attaattcaa tcaatttgta atacccatca 6600
tatctttagg gatgaaatat atgtggttga aggtggcatg ccctcagggt gttcaggaac 6660
cagcatattc aattccatga tcaacaacat aatcattagg actttgatat tagatgcata 6720
taaaggaata gatttagaca aacttaaaat cttagcttac ggtgatgatt tgattgtttc 6780
ttatccttat gaactggatc cacaagtgtt ggcaactctt ggtaaaaatt atggactaac 6840
catcacaccc ccagacaaat ctgaaacttt tacaaaaatg acatgggaaa acttgacatt 6900
tttaaagaga tacttcaagc ctgatcaaca atttcccttt ttggttcacc cagttatgcc 6960
catgaaagat atacatgagt caatcagatg gacaaaggat cctaaaaaca cacaggatca 7020
cgtccgatca ttatgcatgt tagcatggca ctcaggagaa aaagagtaca atgaattcat 7080
tcagaagatc agaactactg acattggaaa atgtctaatt ctcccagaat acagcgtact 7140
taggaggcgc tggttggacc tcttttaggt taacaatata gacacttaat ttgagtagaa 7200
gtaggagttt at 7212

<210> SEQ ID NO 32
<211> LENGTH: 7212
<212> TYPE: DNA
<213> ORGANISM: unknown
<220> FEATURE:
<223> OTHER INFORMATION: synthetic

<400> SEQUENCE: 32
ttaaaacagc ggatgggtat cccaccattc gacccattgg gtgtagtact ctggtactat 60
gtacctttgt acgcctgttt ctccccaacc acccttcctt aaaattccca cccatgaaac 120
gttagaagct tgacattaaa gtacaatagg tggcgccata tccaatggtg tctatgtaca 180
agcacttctg tttcccagga gcgaggtata ggctgtaccc actgccaaaa gcctttaacc 240
gttatccgcc aaccaactac gtaacagtta gtaccatctt gttcttgact ggacgttcga 300
tcaggtggat ttccctcca ctagtttggt cgatgaggct aggaattccc cacgggtgac 360
cgtgtcctag cctgcgtggc ggccaaccca gcttatgctg ggacgccctt ttaaggacat 420
ggtgtgaaga ctcgcatgtg cttggttgtg agtcctccgg cccctgaatg cggctaacct 480
taaccctaga gccttatgcc acgatccagt ggttgtaagg tcgtaatgag caattccggg 540

```
acgggaccga ctactttggg tgtccgtgtt tctcattttt cttcatattg tcttatggtc    600
acagcatata tatacatata ctgtgatcat gggcgcacaa gtgtcaacgc aaaaatccgg    660
atcacacgaa aaccaaaaca tactgactaa cggatctaat cagactttta cagtgattaa    720
ttattataaa gacgccgcta gtactagttc agccggtcaa tcactatcta tggatccatc    780
taaatttacc gaacccgtta aggatcttat gcttaaaggc gcaccagcac ttaactcacc    840
taacgttgag gcatgcggat actctgatag agtgcaacaa attacattgg gtaatagtac    900
aattactaca caggaagccg ctaacgcagt cgtttgttac gccgaatggc ccgaatactt    960
acccgatgtc gacgcatcag acgttaataa gacatctaaa cccgatacta gcgtatgtag   1020
attctataca ctcgatagta agacttggac taccggtagt aagggatggt gttggaaatt   1080
gcctgacgca cttaaggata tgggcgtatt cggtcagaat atgtttttc actcattggg    1140
taggtcaggg tatacagtac acgttcaatg taacgctact aaatttcact cagggtgtct   1200
gttagtcgtt gtgatacccg aacaccaatt ggcatcacac gaagggggta acgttagcgt   1260
taagtataca tttacacatc caggcgaaag aggtatcgat ctatcatccg ctaacgaagt   1320
ggggggaccc gttaaagacg ttatatacaa tatgaacggt acactgttag gtaatctgtt   1380
aatttttcca catcaattta ttaatctgag aactaataat accgctacaa tcgttatacc   1440
atatattaac tcagtgccaa tcgatagtat gactagacat aataacgtta gtcttatggt   1500
gataccaatc gcaccattga cagtgccaac cggtgcaaca cctagtctac caattacggt   1560
tacaatcgca cctatgtgta ctgagttttc cggtattagg tctaaatcaa tcgtaccaca   1620
agggttacct actactacat tgcccggatc cggtcaattt ttgactactg acgataggca   1680
atcacctagc gcattgccta attacgaacc tacaccacgt atacatatac tcggtaaggt   1740
gcataatctg ttagagatta tacaggtcga tacactgata cctatgaata atacacatac   1800
aaaagacgaa gtgaattcgt atctgatacc gttaaacgct aataggcaaa acgaacaggt   1860
attcggtacg aatctgttta taggcgatgg cgtattcaaa actacactgt taggcgaaat   1920
cgttcaatac tatacacatt ggtcagggtc acttagattc tcatctatgt atacaggtcc   1980
agcactatct agcgctaaat tgacactcgc atatacacct cccggtgcta ggggaccaca   2040
ggataggaga gaggctatgt taggtacaca cgtagtgtgg gatatcggat tgcaatcgac   2100
aatcgttatg actataccat ggacatcagg cgtacaattt agatataccg atcccgatac   2160
atatacatca gccggattcc tatcatgttg gtatcagact agtctgatac tgccacccga   2220
aactaccggt caagtgtatc tattgtcatt catatccgca tgtcccgatt ttaaacttag   2280
attgatgaaa gatacacaaa caatttcgca aacagtcgca ctaaccgaag ggttaggcga   2340
cgaattagag gaagtgatag tcgaaaaaac taagcaaaca gtcgcatcaa ttagttccgg   2400
acctaaacat acacaaaaag tgccaatatt gaccgctaac gaaacaggcg caactatgcc   2460
cgtactgcca tccgattcaa tcgaaacacg aactacttat atgcatttta acggatccga   2520
aaccgatgtc gaatgctttc taggtagggc cgcatgcgta cacgttacag agatacagaa   2580
taaagacgca accggtatcg ataatcatag agaggctaaa ttgtttaacg attggaaaat   2640
taatctatct agtctagtgc aattgcgtaa aaaactcgaa ttgtttacat acgttagatt   2700
cgatagcgaa tatactatac tcgcaaccgc atcacaaccc gattccgcta attatagttc   2760
taacttagtc gttcaggcta tgtacgtacc acacggtgca cctaaatcta aaagagtcgg   2820
cgattataca tggcaatccg catctaatcc atcagtgttt tttaaggtag gcgatactag   2880
```

-continued

```
tagattctca gtgccatacg tagggttagc tagcgcatat aattgttttt acgacggata   2940
ctcacacgac gatgccgaaa cacaatacgg tattacggta ctgaatcata tggggtcaat   3000
ggcatttaga atcgttaacg aacacgacga acataaaaca ctagttaaga ttagagtgta   3060
tcatagggct aagttagtcg aagcatggat acctagagca cctagagcac taccatatac   3120
atcaatcggt aggactaatt atcctaaaaa taccgaaccc gttattaaaa aacgtaaagg   3180
cgatattaag tcatacggat tagggcctag atacggaggt atatatacat ctaacgttaa   3240
gattatgaat tatcatctta tgacaccaga ggatcatcat aacttaatcg caccataccc   3300
taatagggat ctagcaatcg ttagtacagg gggacacgga gccgaaacta taccgcattg   3360
taatagaaca tcaggcgtat actatagtac atattataga aagtattatc ctattatatg   3420
cgaaaaacct actaatattt ggatcgaagg gtcaccatat tatcctagta gattccaagc   3480
cggagtgatg aaaggcgtag gtccagccga attaggcgat tgcggaggta tactgagatg   3540
tatacacggt ccaatcggac tgttaactgc cgaagggtca ggatacgttt gtttcgccga   3600
tattaggcaa ttggagtgta tagccgaaga acagggacta tccgattata ttaccggatt   3660
gggtagggca ttcggagtgg ggtttacgga tcagattagt actaaggtta ccgaattgca   3720
ggaagtcgct aaggattttt tgactactaa agtgctatct aaagtcgtta aaatggttag   3780
cgcattagtg ataatttgta ggaatcacga cgatctagtt acggttaccg ctacactcgc   3840
actattaggg tgcgatgggt caccatggag attccttaaa atgtatatta gtaagcattt   3900
tcaagtgcca tatatcgaaa gacaggctaa cgacggatgg tttagaaaat ttaacgatgc   3960
atgtaacgcc gctaagggac tcgaatggat cgctaataag attagtaagt taatcgaatg   4020
gattaaaaat aaagtgttac cacaagctaa agagaaactc gaattttgta gtaagcttaa   4080
gcaattggat atactcgaaa gacagattac gactatgcat atatctaacc ctacacaaga   4140
gaaacgcgaa caattgttta ataacgtatt gtggttagag caaatgtcac aaaaattcgc   4200
accattttac gcagtcgaat ctaaacgtat acgcgaactg aaaaataaaa tggttaacta   4260
tatgcaattt aaatctaaac aacgaaccga acccgtatgc gtactgatac acggtacacc   4320
cggtagcggt aagtcattga ctacatcaat cgtaggtagg gctatagccg aacactttaa   4380
ctcagccgta tatagtctac cacccgatcc aaaacatttc gatgggtatc aacaacagga   4440
agtcgttatt atggacgatc tgaatcagaa tcccgatggt caggatatta gtatgttttg   4500
tcaaatggtg tcatcagtcg attttctacc acctatggca tcactcgata ataagggtat   4560
gttgtttaca tctaatttcg tactcgcatc aactaactct aatacactat caccacctac   4620
tatactgaat cccgaagcat tagtgcgtag attcggattc gatctagata tatgcttgca   4680
tacaacttat actaaaaacg gtaagcttaa cgccggtatg tcaactaaga catgtaagga   4740
ttgtcaccaa cctagtaatt ttaaaaaatg ttgtccacta gtttgcggta aggcaattag   4800
tctagtcgat agaactacta acgttaggta ttcagtcgat caattggtta ccgcaattat   4860
atccgatttt aaatctaaaa tgcaaattac cgattcactc gaaacattgt ttcagggacc   4920
agtgtataag gatcttgaga tagacgtatg caatacacca cctagtgagt gtattaacga   4980
tctgttaaaa tcagtcgata gcgaagagat acgcgaatat tgtaaaaaaa aaaaatggat   5040
tatacccgaa ataccgacta atatcgaaag agctatgaat caggctagta tgattattaa   5100
tactatactt atgttcgtta gtacattggg tatcgtttac gttatataca aattgttcgc   5160
acaaacacag ggaccatact caggtaatcc accacataat aagcttaagg cacctacact   5220
tagacccgta gtcgttcagg gacctaatac cgaattcgca ctatcactat tgcgtaaaaa   5280
```

```
tattatgaca attactacat ctaaaggcga atttacaggg ttagggatac acgatagggt   5340

atgcgttata ccgacacacg ctcaacccgg tgatgacgta ctggttaacg gtcaaaaaat   5400

tagggttaag gataagtata agttagtcga tccagagaat attaacttag agttaaccgt   5460

actgacactc gatagaaacg aaaaatttag ggatattagg gggtttatat ccgaagatct   5520

tgagggagtc gacgctacat tagtcgtaca ctctaataat tttacgaata ctatactcga   5580

agtcggaccc gttactatgg ccggattgat taatctatct agtacaccta ctaatagaat   5640

gattaggtac gattacgcta ctaagacagg gcaatgcgga ggggtgttat gcgcaaccgg   5700

taagatattc ggtatacacg tagggggtaa cggtagacag ggtttagcg cacaattgaa   5760

aaaacagtat ttcgtcgaaa aacagggtca ggtaatcgct agacataagg ttagagagtt   5820

taatattaat cccgttaata ccgctactaa gtctaaattg catccatcag tgttttacga   5880

cgtattccca ggcgataagg aaccagccgt actatccgat aacgatccta gacttgaggt   5940

taagttaacc gaatcactat tctctaagta taagggtaac gttaataccg aacctaccga   6000

aaatatgtta gtcgcagtcg atcattacgc cggtcaattg ctatcacttg atataccgac   6060

tagcgaattg acacttaaag aggcactata cggagtcgac ggactcgaac caatcgatat   6120

tactacatca gccggattcc catacgttag tctaggtatt aaaaaaaggg atatacttaa   6180

caaagagaca caggataccg aaaaaatgaa attttatcta gataaatacg gtatcgatct   6240

accattagtg acttatatta aagacgaatt gcgatcagtc gataaggtta ggttaggtaa   6300

gtctagattg atcgaagcta gttcacttaa cgatagcgtt aatatgcgta tgaaattggg   6360

taatctgtat aaggcatttc accaaaatcc cggagtgtta accggatccg cagtcggatg   6420

cgatccagac gtttttggt cagtgatacc atgtcttatg gacggacatc ttatggcatt   6480

cgattactct aatttcgatg catcactatc acccgtttgg ttcgtatgtc ttgagaaagt   6540

gttaactaag ttagggttcg caggatctag tctgatacaa tcaatttgta atacacatca   6600

tatttttaga gacgaaatat acgtagtcga agggggtatg cctagcggat gttccggtac   6660

atcaattttt aactctatga ttaacaatat tattattaga acattgatac ttgacgcata   6720

taagggtatc gatctagata agcttaagat actcgcatac ggagacgatc taatcgttag   6780

ttatccatac gaactcgatc cacaagtgtt agcgacattg ggtaagaatt acggattgac   6840

tattacacct cccgataaat ccgaaacttt tacgaaaatg acatgggaga atctgacatt   6900

tctgaaacga tattttaaac ccgatcagca atttccattc ttagtgcatc ccgttatgcc   6960

tatgaaagat atacacgaat caattagatg gactaaggat ccaaaaaata cacaggatca   7020

cgttaggtca ctatgtatgt tagcatggca ttcaggcgaa aaagagtata acgaattcat   7080

acaaaaaatt agaactaccg atatcggtaa gtgtctgata ttgcccgaat actcagtgct   7140

tagacgtaga tggttagatc tattctaggt taacaatata gacacttaat ttgagtagaa   7200

gtaggagttt at                                                         7212
```

<210> SEQ ID NO 33
<211> LENGTH: 10735
<212> TYPE: DNA
<213> ORGANISM: Dengue virus type 1

<400> SEQUENCE: 33

```
agttgttagt ctacgtggac cgacaagaac agtttcgaat cggaagcttg cttaacgtag     60

ttctaacagt tttttattag agagcagatc tctgatgaat aatcaacgta aaaaaacggg    120
```

-continued

```
tcgtccgtcg tttaatatgt taaaacgtgc gcgtaatcgt gtatcgacgg tatcgcaatt    180
agcgaaacgt ttttcgaaag gtttattatc gggtcaaggt ccgatgaaat tagtaatggc    240
gtttatagcg tttttacgtt ttttagcgat accgccgacg gcgggtatat tagcgcgttg    300
gggttcgttt aaaaaaaatg gtgcgataaa agtattacgt ggttttaaaa aagaaatatc    360
gaatatgtta aatataatga atcgtcgtaa acgttcggta acgatgttat taatgttatt    420
accgacggcg ttagcgtttc atttaacgac gcgtggtggt gaaccgcata tgatagtatc    480
gaaacaagaa cgtggtaaat cgttattatt taaaacgtcg gcgggtgtaa atatgtgtac    540
gttaatagcg atggatttag gtgaattatg tgaagatacg atgacgtata aatgtccgcg    600
tataacggaa acggaaccgg atgatgtaga ttgttggtgt aatgcgacgg aaacgtgggt    660
aacgtatggt acgtgttcgc aaacgggtga acatcgtcgt gataaacgtt cggtagcgtt    720
agcgccgcat gtaggtttag gtttagaaac gcgtacggaa acgtggatgt cgtcggaagg    780
tgcgtggaaa caaatacaaa aagtagaaac gtgggcgtta cgtcatccgg gttttacggt    840
aatagcgtta tttttagcgc atgcgatagg tacgtcgata acgcaaaaag gtataatatt    900
tatattatta atgttagtaa cgccgtcgat ggcgatgcgt tgtgtaggta taggtaatcg    960
tgattttgta gaaggtttat cgggtgcgac gtgggtagat gtagtattag aacatggttc   1020
gtgtgtaacg acgatggcga aagataaacc gacgttagat atagaattat taaaaacgga   1080
agtaacgaat ccggcggtat tacgtaaatt atgtatagaa gcgaaaatat cgaatacgac   1140
gacggattcg cgttgtccga cgcaaggtga agcgacgtta gtagaagaac aagatacgaa   1200
ttttgtatgt cgtcgtacgt ttgtagatcg tggttggggt aatggttgtg gtttatttgg   1260
taaaggttcg ttaataacgt gtgcgaaatt taaatgtgta acgaaattag aaggtaaaat   1320
agtacaatat gaaaatttaa aatattcggt aatagtaacg gtacatacgg gtgatcaaca   1380
tcaagtaggt aatgaaacga cggaacatgg tacgacggcg acgataacgc cgcaagcgcc   1440
gacgtcggaa atacaattaa cggattatgg tgcgttaacg ttagattgtt cgccgcgtac   1500
gggtttagat tttaatgaaa tggtattatt aacgatgaaa aaaaaatcgt ggttagtaca   1560
taaacaatgg tttttagatt taccgttacc gtggacgtcg ggtgcgtcga cgtcgcaaga   1620
aacgtggaat cgtcaagatt tattagtaac gtttaaaacg gcgcatgcga aaaaacaaga   1680
agtagtagta ttaggttcgc aagaaggtgc gatgcatacg gcgttaacgg gtgcgacgga   1740
aatacaaacg tcgggtacga cgacgatatt tgcgggtcat ttaaaatgtc gtttaaaaat   1800
ggataaatta atattaaaag gtatgtcgta tgtaatgtgt acgggttcgt ttaaattaga   1860
aaaagaagta gcggaaacgc aacatggtac ggtattagta caagtaaaat atgaaggtac   1920
ggatgcgccg tgtaaaatac cgttttcgtc gcaagatgaa aaaggtgtaa cgcaaaatgg   1980
tcgtttaata acggcgaatc cgatagtaac ggataaagaa aaaccggtaa atatagaagc   2040
ggaaccgccg tttggtgaat cgtatatagt agtaggtgcg ggtgaaaaag cgttaaaatt   2100
atcgtggttt aaaaaaggtt cgtcgatagg taaaatgttt gaagcgacgg cgcgtggtgc   2160
gcgtcgtatg gcgatattag gtgatacggc gtgggatttt ggttcgatag gtggtgtatt   2220
tacgtcggta ggtaaattaa tacatcaaat atttggtacg gcgtatggtg tattattttc   2280
gggtgtatcg tggacgatga aaataggtat aggtatatta ttaacgtggt taggtttaaa   2340
ttcgcgttcg acgtcgttat cgatgacgtg tatagcggta ggtatggtaa cgttatattt   2400
aggtgtaatg gtacaagcgg attcgggttg tgtaataaat tggaaaggtc gtgaattaaa   2460
atgtggttcg ggtatatttg taacgaatga agtacatacg tggacggaac aatataaatt   2520
```

tcaagcggat tcgccgaaac gtttatcggc ggcgataggt aaagcgtggg aagaaggtgt 2580
atgtggtata cgttcggcga cgcgtttaga aaatataatg tggaaacaaa tatcgaatga 2640
attaaatcat atattattag aaaatgatat gaaatttacg gtagtagtag gtgatgtatc 2700
gggtatatta gcgcaaggta aaaaaatgat acgtccgcaa ccgatggaac ataaatattc 2760
gtggaaatcg tggggtaaag cgaaaataat aggtgcggat gtacaaaata cgacgtttat 2820
aatagatggt ccgaatacgc cggaatgtcc ggataatcaa cgtgcgtgga atatatggga 2880
agtagaagat tatggttttg gtatatttac gacgaatata tggttaaaat tacgtgattc 2940
gtatacgcaa gtatgtgatc atcgtttaat gtcggcggcg ataaaagatt cgaaagcggt 3000
acatgcggat atgggttatt ggatagaatc ggaaaaaaat gaaacgtgga aattagcgcg 3060
tgcgtcgttt atagaagtaa aaacgtgtat atggccgaaa tcgcatacgt tatggtcgaa 3120
tggtgtatta gaatcggaaa tgataatacc gaaaatatat ggtggtccga tatcgcaaca 3180
taattatcgt ccgggttatt ttacgcaaac ggcgggtccg tggcatttag gtaaattaga 3240
attagatttt gatttatgtg aaggtacgac ggtagtagta gatgaacatt gtggtaatcg 3300
tggtccgtcg ttacgtacga cgacggtaac gggtaaaacg atacatgaat ggtgttgtcg 3360
ttcgtgtacg ttaccgccgt tacgttttaa aggtgaagat ggttgttggt atggtatgga 3420
aatacgtccg gtaaaagaaa aagaagaaaa tttagtaaaa tcgatggtat cggcgggttc 3480
gggtgaagta gattcgtttt cgttaggttt attatgtata tcgataatga tagaagaagt 3540
aatgcgttcg cgttggtcgc gtaaaatgtt aatgacgggt acgttagcgg tatttttatt 3600
attaacgatg ggtcaattaa cgtggaatga tttaatacgt ttatgtataa tggtaggtgc 3660
gaatgcgtcg gataaaatgg gtatgggtac gacgtattta gcgttaatgg cgacgtttcg 3720
tatgcgtccg atgtttgcgg taggtttatt atttcgtcgt ttaacgtcgc gtgaagtatt 3780
attattaacg gtaggtttat cgttagtagc gtcggtagaa ttaccgaatt cgttagaaga 3840
attaggtgat ggtttagcga tgggtataat gatgttaaaa ttattaacgg attttcaatc 3900
gcatcaatta tgggcgacgt tattatcgtt aacgtttgta aaaacgacgt tttcgttaca 3960
ttatgcgtgg aaaacgatgg cgatgatatt atcgatagta tcgttatttc cgttatgttt 4020
atcgacgacg tcgcaaaaaa cgacgtggtt accggtatta ttaggttcgt taggttgtaa 4080
accgttaacg atgtttttaa taacggaaaa taaaatatgg ggtcgtaaat cgtggccgtt 4140
aaatgaaggt ataatggcgg taggtatagt atcgatatta ttatcgtcgt tattaaaaaa 4200
tgatgtaccg ttagcgggtc cgttaatagc gggtggtatg ttaatagcgt gttatgtaat 4260
atcgggttcg tcggcggatt tatcgttaga aaaagcggcg gaagtatcgt gggaagaaga 4320
agcggaacat tcgggtgcgt cgcataatat attagtagaa gtacaagatg atggtacgat 4380
gaaaataaaa gatgaagaac gtgatgatac gttaacgata ttattaaaag cgacgttatt 4440
agcgatatcg ggtgtatatc cgatgtcgat accggcgacg ttatttgtat ggtatttttg 4500
gcaaaaaaaa aaacaacgtt cgggtgtatt atgggatacg ccgtcgccgc cggaagtaga 4560
acgtgcggta ttagatgatg gtatatatcg tatattacaa cgtggtttat taggtcgttc 4620
gcaagtaggt gtaggtgtat ttcaagaagg tgtatttcat acgatgtggc atgtaacgcg 4680
tggtgcggta ttaatgtatc aaggtaaacg tttagaaccg tcgtgggcgt cggtaaaaaa 4740
agatttaata tcgtatggtg gtggttggcg ttttcaaggt tcgtggaatg cgggtgaaga 4800
agtacaagta atagcggtag aaccgggtaa aaatccgaaa aatgtacaaa cggcgccggg 4860

```
tacgtttaaa acgccggaag gtgaagtagg tgcgatagcg ttagatttta aaccgggtac   4920
gtcgggttcg ccgatagtaa atcgtgaagg taaaatagta ggtttatatg gtaatggtgt   4980
agtaacgacg tcgggtacgt atgtatcggc gatagcgcaa gcgaaagcgt cgcaagaagg   5040
tccgttaccg gaaatagaag atgaagtatt tcgtaaacgt aatttaacga taatggattt   5100
acatccgggt tcgggtaaaa cgcgtcgtta tttaccggcg atagtacgtg aagcgataaa   5160
acgtaaatta cgtacgttag tattagcgcc gacgcgtgta gtagcgtcgg aaatggcgga   5220
agcgttaaaa ggtatgccga tacgttatca aacgacggcg gtaaaatcgg aacatacggg   5280
taaagaaata gtagatttaa tgtgtcatgc gacgtttacg atgcgtttat tatcgccggt   5340
acgtgtaccg aattataata tgataataat ggatgaagcg cattttacgg atccggcgtc   5400
gatagcggcg cgtggttata tatcgacgcg tgtaggtatg ggtgaagcgg cggcgatatt   5460
tatgacggcg acgccgccgg gttcggtaga agcgtttccg caatcgaatg cggtaataca   5520
agatgaagaa cgtgatatac cggaacgttc gtggaattcg ggttatgatt ggataacgga   5580
ttttccgggt aaaacggtat ggtttgtacc gtcgataaaa tcgggtaatg atatagcgaa   5640
ttgtttacgt aaaaatggta aacgtgtagt acaattatcg cgtaaaacgt ttgatacgga   5700
atatcaaaaa acgaaaaata atgattggga ttatgtagta acgacggata tatcggaaat   5760
gggtgcgaat tttcgtgcgg atcgtgtaat agatccgcgt cgttgtttaa aaccggtaat   5820
attaaaagat ggtccggaac gtgtaatatt agcgggtccg atgccggtaa cggtagcgtc   5880
ggcggcgcaa cgtcgtggtc gtataggtcg taatcaaaat aaagaaggtg atcaatatat   5940
atatatgggt caaccgttaa ataatgatga agatcatgcg cattggacgg aagcgaaaat   6000
gttattagat aatataaata cgccggaagg tataataccg gcgttatttg aaccggaacg   6060
tgaaaaatcg gcggcgatag atggtgaata tcgtttacgt ggtgaagcgc gtaaaacgtt   6120
tgtagaatta atgcgtcgtg gtgatttacc ggtatggtta tcgtataaag tagcgtcgga   6180
aggttttcaa tattcggatc gtcgttggtg ttttgatggt gaacgtaata atcaagtatt   6240
agaagaaaat atggatgtag aaatatggac gaaagaaggt gaacgtaaaa aattacgtcc   6300
gcgttggtta gatgcgcgta cgtattcgga tccgttagcg ttacgtgaat ttaaagaatt   6360
tgcggcgggt cgtcgttcgg tatcgggtga tttaatatta gaaataggta aattaccgca   6420
acatttaacg caacgtgcgc aaaatgcgtt agataattta gtaatgttac ataattcgga   6480
acaaggtggt aaagcgtatc gtcatgcgat ggaagaatta ccggatacga tagaaacgtt   6540
aatgttatta gcgttaatag cggtattaac gggtggtgta acgttatttt ttttatcggg   6600
tcgtggttta ggtaaaacgt cgataggttt attatgtgta atagcgtcgt cggcgttatt   6660
atggatggcg tcggtagaac cgcattggat agcggcgtcg ataatattag aatttttttt   6720
aatggtatta ttaataccgg aaccggatcg tcaacgtacg ccgcaagata atcaattagc   6780
gtatgtagta ataggtttat tatttatgat attaacggta gcggcgaatg aaatgggttt   6840
attagaaacg acgaaaaaag atttaggtat aggtcatgcg gcggcggaaa atcatcatca   6900
tgcggcgatg ttagatgtag atttacatcc ggcgtcggcg tggacgttat atgcggtagc   6960
gacgacgata ataacgccga tgatgcgtca tacgatagaa aatacgacgg cgaatatatc   7020
gttaacggcg atagcgaatc aagcggcgat attaatgggt ttagataaag gttggccgat   7080
atcgaaaatg gatataggtg taccgttatt agcgttaggt tgttattcgc aagtaaatcc   7140
gttaacgtta acggcggcgg tattaatgtt agtagcgcat tatgcgataa taggtccggg   7200
tttacaagcg aaagcgacgc gtgaagcgca aaaacgtacg gcggcgggta taatgaaaaa   7260
```

```
tccgacggta gatggtatag tagcgataga tttagatccg gtagtatatg atgcgaaatt   7320
tgaaaaacaa ttaggtcaaa taatgttatt aatattatgt acgtcgcaaa tattattaat   7380
gcgtacgacg tgggcgttat gtgaatcgat aacgttagcg acgggtccgt taacgacgtt   7440
atgggaaggt tcgccgggta aattttggaa tacgacgata gcggtatcga tggcgaatat   7500
atttcgtggt tcgtatttag cgggtgcggg tttagcgttt tcgttaatga aatcgttagg   7560
tggtggtcgt cgtggtacgg gtgcgcaagg tgaaacgtta ggtgaaaaat ggaaacgtca   7620
attaaatcaa ttatcgaaat cggaatttaa tacgtataaa cgttcgggta taatagaagt   7680
agatcgttcg gaagcgaaag aaggtttaaa acgtggtgaa acgacgaaac atgcggtatc   7740
gcgtggtacg gcgaaattac gttggtttgt agaacgtaat ttagtaaaac cggaaggtaa   7800
agtaatagat ttaggttgtg gtcgtggtgg ttggtcgtat tattgtgcgg gtttaaaaaa   7860
agtaacggaa gtaaaaggtt atacgaaagg tggtccgggt catgaagaac cgataccgat   7920
ggcgacgtat ggttggaatt tagtaaaatt atattcgggt aaagatgtat tttttacgcc   7980
gccggaaaaa tgtgatacgt tattatgtga tataggtgaa tcgtcgccga atccgacgat   8040
agaagaaggt cgtacgttac gtgtattaaa aatggtagaa ccgtggttac gtggtaatca   8100
attttgtata aaaatattaa atccgtatat gccgtcggta gtagaaacgt tagaacaaat   8160
gcaacgtaaa catggtggta tgttagtacg taatccgtta tcgcgtaatt cgacgcatga   8220
aatgtattgg gtatcgtgtg gtacgggtaa tatagtatcg gcggtaaata tgacgtcgcg   8280
tatgttatta aatcgtttta cgatggcgca tcgtaaaccg acgtatgaac gtgatgtaga   8340
tttaggtgcg ggtacgcgtc atgtagcggt agaaccggaa gtagcgaatt tagatataat   8400
aggtcaacgt atagaaaata taaaaaatga acataaatcg acgtggcatt atgatgaaga   8460
taatccgtat aaaacgtggg cgtatcatgg ttcgtatgaa gtaaaaccgt cgggttcggc   8520
gtcgtcgatg gtaaatggtg tagtacgttt attaacgaaa ccgtgggatg taataccgat   8580
ggtaacgcaa atagcgatga cggatacgac gccgtttggt caacaacgtg tatttaaaga   8640
aaaagtagat acgcgtacgc cgaaagcgaa acgtggtacg gcgcaaataa tggaagtaac   8700
ggcgcgttgg ttatggggtt ttttatcgcg taataaaaaa ccgcgtatat gtacgcgtga   8760
agaatttacg cgtaaagtac gttcgaatgc ggcgataggt gcggtatttg tagatgaaaa   8820
tcaatggaat tcggcgaaag aagcggtaga agatgaacgt tttgggatt tagtacatcg   8880
tgaacgtgaa ttacataaac aaggtaaatg tgcgacgtgt gtatataata tgatgggtaa   8940
acgtgaaaaa aaattaggtg aatttggtaa agcgaaaggt tcgcgtgcga tatggtatat   9000
gtggttaggt gcgcgttttt tagaatttga agcgttaggt tttatgaatg aagatcattg   9060
gttttcgcgt gaaaattcgt tatcgggtgt agaaggtgaa ggtttacata aattaggtta   9120
tatattacgt gatatatcga aaataccggg tggtaatatg tatgcggatg atacggcggg   9180
ttgggatacg cgtataacgg aagatgattt acaaaatgaa gcgaaaataa cggatataat   9240
ggaaccggaa catgcgttat tagcgacgtc gatatttaaa ttaacgtatc aaaataaagt   9300
agtacgtgta caacgtccgg cgaaaaatgg tacggtaatg gatgtaatat cgcgtcgtga   9360
tcaacgtggt tcgggtcaag taggtacgta tggtttaaat acgtttacga atatggaagc   9420
gcaattaata cgtcaaatgg aatcggaagg tatattttcg ccgtcggaat tagaaacgcc   9480
gaatttagcg gaacgtgtat tagattggtt aaaaaaacat ggtacggaac gtttaaaacg   9540
tatggcgata tcgggtgatg attgtgtagt aaaaccgata gatgatcgtt ttgcgacggc   9600
```

```
gttaacggcg ttaaatgata tgggtaaagt acgtaaagat ataccgcaat gggaaccgtc   9660

gaaaggttgg aatgattggc aacaagtacc gttttgttcg catcattttc atcaattaat   9720

aatgaaagat ggtcgtgaaa tagtagtacc gtgtcgtaat caagatgaat tagtaggtcg   9780

tgcgcgtgta tcgcaaggtg cgggttggtc gttacgtgaa acggcgtgtt taggtaaatc   9840

gtatgcgcaa atgtggcaat taatgtattt tcatcgtcgt gatttacgtt tagcggcgaa   9900

tgcgatatgt tcggcggtac cggtagattg ggtaccgacg tcgcgtacga cgtggtcgat   9960

acatgcgcat catcaatgga tgacgacgga agatatgtta tcggtatgga atcgtgtatg  10020

gatagaagaa aatccgtgga tggaagataa aacgcatgta tcgtcgtggg aagatgtacc  10080

gtatttaggt aaacgtgaag atcaatggtg tggttcgtta ataggtttaa cggcgcgtgc  10140

gacgtgggcg acgaatatac aagtagcgat aaatcaagta cgtcgtttaa taggtaatga  10200

aaattattta gattttatga cgtcgatgaa acgttttaaa aatgaatcgg atccggaagg  10260

tgcgttatgg taagccaact cattcacaaa ataaaggaaa ataaaaaatc aaacaaggca  10320

agaagtcagg ccggattaag ccatagcacg gtaagagcta tgctgcctgt gagccccgtc  10380

caaggacgta aaatgaagtc aggccgaaag ccacggttcg agcaagccgt gctgcctgta  10440

gctccatcgt ggggatgtaa aaacccggga ggctgcaaac catggaagct gtacgcatgg  10500

ggtagcagac tagtggttag aggagacccc tcccaagaca caacgcagca gcggggccca  10560

acaccagggg aagctgtacc ctggtggtaa ggactagagg ttagaggaga ccccccgcac  10620

aacaacaaac agcatattga cgctgggaga gaccagagat cctgctgtct ctacagcatc  10680

attccaggca cagaacgcca aaaaatggaa tggtgctgtt gaatcaacag gttct       10735
```

<210> SEQ ID NO 34
<211> LENGTH: 10735
<212> TYPE: DNA
<213> ORGANISM: Unknown
<220> FEATURE:
<223> OTHER INFORMATION: synthetic

<400> SEQUENCE: 34

```
agttgttagt ctacgtggac cgacaagaac agtttcgaat cggaagcttg cttaacgtag     60

ttctaacagt tttttattag agagcagatc tctgatgaat aaccaacgaa aaaaaaccgg    120

acgaccatca ttcaatatgc ttaaacgcgc taggaatagg gtgtcaaccg tatcgcaatt    180

ggctaagaga ttctctaagg gactgttaag cggacaggga ccaatgaaac tggttatggc    240

attcatagcg tttctgagat ttctcgcaat accgccaacc gccggaatac tcgctagatg    300

ggggtcattc aaaaaaaacg gcgcaattaa agtgcttagg gggttcaaaa aagagatatc    360

gaatatgctt aacattatga atagacgtaa gagatccgtt acaatgctat tgatgctatt    420

gccaaccgca ctagcctttc acctaacgac tagggggggg gaaccacata tgatagtgag    480

taagcaagag agaggtaagt cactattgtt caaaacatcc gccggagtga atatgtgtac    540

actaatcgct atggacttag gcgaattgtg cgaagacact atgacatata agtgtcctag    600

gattaccgaa accgaaccag acgacgtcga ttgttggtgt aacgcaaccg aaacatgggt    660

gacatacgga acatgttcgc aaaccggaga gcatagacgc gataagagat cagtcgcact    720

cgcaccacac gtcggattgg ggttagagac tagaaccgaa acatggatgt ctagcgaagg    780

cgcatggaaa cagatacaga aagtcgagac atgggccctt agacacccag ggtttaccgt    840

aatcgcacta tttctcgcac acgcaatcgg aacgtcaatt acgcaaaaag ggattatatt    900

catactgctt atgttagtga caccatctat ggctatgaga tgcgtcggaa tcggaaatag    960
```

-continued

```
ggatttcgtt gagggactat ccggagcgac atgggtcgac gtagtgctcg aacacggatc   1020
atgcgttacg actatggcca aagacaaacc gacacttgac atagagttac tgaaaaccga   1080
agtgactaac ccagccgtac tgagaaagtt gtgtatcgaa gctaagatat cgaatacgac   1140
taccgatagt aggtgtccaa cgcaaggcga agcgacacta gtcgaagagc aggatacgaa   1200
tttcgtatgt agacgtacat tcgtcgatag ggggtgggga aacggatgcg gattgttcgg   1260
taagggatca ctgattacat gcgctaaatt caaatgcgtt acgaaactcg agggtaagat   1320
agtgcaatac gagaatctga aatatagcgt aatcgttaca gtgcataccg gagaccaaca   1380
ccaagtggga aacgagacta ccgaacacgg aactaccgca acgattacgc cacaagcccc   1440
tactagcgaa atccaattga ccgattacgg cgcactaaca ctcgattgtt cacctagaac   1500
cggattggac tttaacgaaa tggtgctatt gactatgaaa aaaaaatcat ggttagtgca   1560
taagcaatgg ttcttagacc taccactacc atggactagc ggagctagta cgtcacagga   1620
gacatggaat agacaggatc tgttagtgac attcaaaacc gcacacgcta aaaaacagga   1680
ggtcgtagtg ttagggtcac aagagggagc tatgcatacc gcactaacag gcgcaaccga   1740
gatacagact agcggaacga ctacgatatt cgccggacac cttaagtgta gactgaaaat   1800
ggacaaactg atactgaaag gtatgtcata cgttatgtgt accggatcat tcaaactcga   1860
aaaagaggtc gccgaaacgc aacacggaac agtgttagtg caagtgaaat acgagggaac   1920
tgacgcacca tgtaagatac cgttttcgtc acaggacgaa aaaggcgtta cgcaaaacgg   1980
tagactgatt accgctaacc caatcgttac cgataaagag aaaccggtta atatcgaagc   2040
cgaaccacca ttcggcgaat catatatcgt agtcggagcc ggagagaaag cccttaagct   2100
atcatggttt aaaaaagggt catcaatcgg taagatgttc gaagcaaccg ctagaggcgc   2160
tagacgtatg gccatactag gcgataccgc atgggatttc ggatcaatcg gaggagtgtt   2220
tacgtcagtc ggaaaactga tacaccaaat tttcggaacc gcatacggag tgttgtttag   2280
cggagtgtca tggactatga aaatcggaat cggaatactg ttgacatggt tagggttgaa   2340
ctctagatcg actagtctat ctatgacatg tatcgcagtc ggaatggtga cactatactt   2400
aggcgtaatg gtgcaagccg atagcggatg cgttattaat tggaaaggga gagagcttaa   2460
atgcggatcc ggaatattcg ttacgaacga agtgcataca tggaccgaac agtataaatt   2520
ccaagccgat agtccgaaaa gactatctgc cgcaatcggt aaggcatggg aggagggagt   2580
gtgcggaatt aggtcagcga ctagactcga aaacattatg tggaaacaga tatctaacga   2640
actgaatcac atactgttag agaacgatat gaaatttaca gtcgtagtcg gagacgttag   2700
cggaatactc gcacagggta agaaaatgat tagaccgcaa cctatggagc ataagtatag   2760
ttggaaatca tggggaaaag cgaaaattat cggagccgac gtgcaaaata cgacattcat   2820
aatcgacgga ccgaatacgc cagagtgtcc agacaatcag agagcatgga acatatggga   2880
ggtcgaagac tacggattcg gaatttttac gactaacata tggcttaagc ttagagactc   2940
atatacacag gtatgcgatc atagattgat gtctgccgca atcaaagact ctaaagccgt   3000
acacgccgat atggggtatt ggatcgaatc cgaaaaaaac gagacatgga aactcgctag   3060
agcgtcattc atagaggtta agacatgtat ttggcctaag tcacatacat tgtggtctaa   3120
cggagtgctt gagtctgaga tgataatccc taagatatac ggcggaccga tatcgcaaca   3180
taactataga ccagggtatt ttacgcaaac agccggacca tggcatctcg gtaagcttga   3240
gttagacttc gatctatgcg aagggactac cgtagtggtc gacgaacatt gcggtaatag   3300
```

-continued

```
gggacctagt ctgagaacga ctaccgttac cggtaagact atacacgaat ggtgttgtag   3360
gtcatgtaca ctaccaccac ttagattcaa aggcgaagac ggatgttggt acggaatgga   3420
gattagacca gtgaaagaga aagaggaaaa cctagtgaaa tctatggtgt cagccggatc   3480
aggcgaagtc gactcattct cactcggact gttatgcata tcgattatga tcgaagaggt   3540
tatgcgatct agatggtcac gaaaaatgct tatgaccgga acactagccg tttttctgtt   3600
actgactatg gggcaattga catggaacga tctgattagg ttgtgtatta tggtcggagc   3660
taacgctagc gataagatgg gtatgggaac gacatactta gcccttatgg ctacatttag   3720
aatgcgacca atgttcgccg tagggttact gtttagacgg ttgactagta gggaagtgct   3780
attgttgaca gtcggactgt cactagtcgc tagcgttgag ttgcctaact cactcgaaga   3840
gttaggcgac ggactcgcaa tggggattat gatgcttaag ctattgaccg atttccaatc   3900
tcaccaattg tgggctacac tattgtcact gacattcgtt aagactacat tctcattgca   3960
ttacgcatgg aaaactatgg ctatgatact gtcaatcgtt agtctattcc cactatgtct   4020
atctacaact agtcagaaaa ctacatggtt gccagtgcta ttggggtcac tagggtgtaa   4080
accattgact atgtttctga ttaccgaaaa caaaatttgg gggagaaagt catggccact   4140
taacgaggga attatggccg tagggatagt gtcaatactg ctatctagtc tgcttaaaaa   4200
cgacgtgcca ctagccggac cactgatagc cggaggtatg ctaatcgcat gttacgtgat   4260
atccggatct agcgccgatc tgtcactcga aaaagccgcc gaagtgtcat gggaagagga   4320
agccgaacac tctggcgcat cacataacat actagtcgaa gtgcaagacg acggaactat   4380
gaaaattaaa gacgaagaga gagacgatac acttacgata ctgcttaaag cgacactgtt   4440
agcgatatcc ggagtgtatc ctatgtcaat acccgctaca ctattcgttt ggtatttttg   4500
gcaaaaaaaa aaacagagat ccggagtgtt gtgggataca cctagtccac ccgaagtcga   4560
gagagccgta ctcgacgacg gaatatatag gatactgcaa cggggattgc tcggtaggtc   4620
acaggtcgga gtgggagtgt ttcaggaggg agtgtttcac actatgtggc acgttacgag   4680
aggcgccgta ctgatgtatc agggtaagag actcgaacct agttgggcta gcgttaaaaa   4740
agacctaatc tcatacggag gggggtggag atttcagggg tcatggaacg ccggagagga   4800
agtgcaagtg atagccgtcg aacccggtaa gaaccctaaa aacgtgcaaa ccgcacccgg   4860
aacgtttaag acacccgaag gcgaagtggg cgcaatcgca ctcgacttta aacccggaac   4920
tagcggatca ccaatcgtta atagagaggg taagatagtc ggattgtacg gaaacggagt   4980
ggttacgact agcggaacat acgttagcgc aatagcgcaa gcgaaagcgt cacaagaggg   5040
accactacca gagatagagg acgaagtgtt tagaaagcgt aatctgacaa ttatggacct   5100
acatcccgga tccggtaaga ctagacggta tctgccagca atcgttaggg aggcaattaa   5160
gagaaagttg cgtacactag tgttagcccc aactagagtg gtcgctagcg aaatggccga   5220
agcccttaag ggaatgccaa ttaggtatca gactaccgcc gttaagtccg aacataccgg   5280
taaggagata gtcgacctta tgtgtcacgc tacattcaca atgagactgc tatcaccagt   5340
gagagtgcct aactataata tgataattat ggacgaagcc cattttacag acccagcctc   5400
aatcgccgct agggggtata ttagtactag ggtgggaatg ggcgaagccg ccgcaatttt   5460
tatgacagcg acaccacccg gatccgtcga agcgtttccg caatctaacg ccgttataca   5520
ggacgaagag agagacatac ccgaacggtc atggaatagc ggatacgatt ggataaccga   5580
ttttcccggt aagacagtgt ggttcgtacc gtcaattaag tccggaaacg atatcgctaa   5640
ttgtcttaga aaaaacggta agagagtggt gcaattgtct agaaagacat tcgataccga   5700
```

```
ataccaaaaa actaagaata acgattggga ttacgtagtg acaaccgaca tatccgaaat   5760
gggcgctaac tttagagccg atagggtgat agaccctaga cggtgtctga aaccagtgat   5820
actgaaagac ggaccagaga gagtgatact agccggacca atgccagtga cagtcgcatc   5880
cgccgcacaa cgtaggggac ggatagggag aaaccaaaac aaagagggag accaatacat   5940
atatatggga cagccactga ataacgacga agaccacgca cattggaccg aagcgaaaat   6000
gctattagac aatattaaca cacccgaagg gattataccc gcactattcg aacccgaacg   6060
cgaaaaatcc gccgcaatcg acggcgaata tagactgaga ggcgaagcta gaaagacatt   6120
cgttgagctt atgcgtagag gcgatctacc cgtatggttg tcatacaaag tcgctagcga   6180
agggtttcag tattccgata ggagatggtg tttcgacggc gaacggaata accaagtgct   6240
cgaagagaat atggacgttg agatatggac taaagagggc gaacgaaaaa aactgagacc   6300
tagatggtta gacgcacgta catattccga tccgttagcc cttagagagt ttaaagagtt   6360
cgcagccggt aggagatccg ttagcggaga tctgatactc gaaatcggta agctaccaca   6420
acacctaacg caacgagccc aaaacgcact agacaatctg gttatgttgc ataactccga   6480
acagggcggt aaggcatata gacacgctat ggaagagtta cccgatacaa tcgaaacact   6540
tatgctactc gcactgatag ccgtactgac aggcggagtg acactattct ttctatccgg   6600
tagggggtta ggtaagacat caatcggact gttatgcgta atcgcatcta gcgcactatt   6660
gtggatggct agcgtcgaac cacattggat agccgcatca attatactcg aattctttct   6720
tatggtgtta ctgatacccg aacccgatag gcaacgaaca ccacaggata accaattggc   6780
atacgtcgta atcggactat tgtttatgat actgacagtc gccgctaacg aaatgggatt   6840
gctcgagaca acgaaaaaag acctagggat cggacacgcc gcagccgaaa atcaccatca   6900
cgccgcaatg ttagacgtcg atctgcatcc cgctagcgca tggacactat acgcagtcgc   6960
aacgacaatt attacgccta tgatgcgaca tacaatcgag aatactaccg ctaacatatc   7020
gctaaccgct atagcgaatc aggccgcaat actgatgggg ttagacaaag ggtggccaat   7080
tagtaagatg gatatcggag tgccactgtt agccttaggg tgttatagtc aggttaaccc   7140
attgacattg accgcagccg tacttatgct agtcgcacat tacgctataa tcggaccagg   7200
actgcaagcg aaagcgacac gcgaagcgca aaaaagaacc gcagccggaa ttatgaaaaa   7260
ccctacagtc gacggaatag tcgcaatcga cttagaccca gtggtgtacg acgctaaatt   7320
cgaaaaacag ttgggacaga ttatgctact gatactgtgt acgtcacaga tactgcttat   7380
gcgaactaca tgggcactat gcgaatcaat tacactcgca accggaccat tgactacatt   7440
gtgggaggga tcacccggta agttttggaa tacgactata gccgttagta tggctaacat   7500
ttttaggggg tcatatctag ccggagccgg actcgcattc tcacttatga aatcactcgg   7560
agggggacgt agggggacag gcgcacaggg agagacacta ggcgaaaaat ggaaacgaca   7620
attgaaccaa ttgtctaaat ccgaatttaa cacttataag agatccggaa taatcgaagt   7680
cgatagatcc gaagcgaaag agggactgaa acgcggagag acaacgaaac acgccgttag   7740
taggggaacc gctaagctta gatggttcgt tgagcgtaac ttagtgaaac cagagggtaa   7800
ggtaatcgat ctcggatgcg gtaggggggg gtggtcatac tattgcgccg gactgaaaaa   7860
agtgaccgaa gtgaaagggt atactaaggg cggacccgga cacgaagagc caataccgat   7920
ggcaacatac ggatggaacc tagtgaaact gtattccggt aaggacgtat tctttacacc   7980
acccgaaaaa tgcgatacac tgttatgcga tataggcgaa tctagtccta accctacaat   8040
```

```
cgaagaggga cgtacactta gagtgcttaa aatggtcgaa ccatggttga gggggaatca   8100
gttttgtatt aagatactga atccatatat gcctagcgta gtcgagacac tcgaacagat   8160
gcaacgaaaa cacggcggaa tgctagtgag aaacccacta tctaggaatt cgacacacga   8220
aatgtattgg gtgtcatgcg gaaccggaaa catagtgtca gccgttaata tgactagtag   8280
aatgctactg aatcggttta caatggccca tagaaaaccg acatacgaaa gagacgtcga   8340
cctaggagcc ggaactagac acgttgccgt cgaacccgaa gtcgctaact tagacataat   8400
cggacagaga atcgagaata ttaaaaacga acacaaatcg acatggcatt acgacgaaga   8460
caatccgtat aagacatggg catatcacgg atcatacgaa gtgaaaccta gcggatccgc   8520
tagttctatg gttaacggag tggtgagact gttgactaag ccatgggacg tgataccgat   8580
ggtgacacaa atcgctatga ccgatacgac accattcgga cagcaaagag tgtttaaaga   8640
gaaagtcgac actagaacac ctaaagcgaa acgcggaacc gcacagatta tggaggttac   8700
cgctagatgg ttgtgggggt tcctatctag aaacaaaaaa cctaggattt gtacacgcga   8760
agagtttaca cgaaaagtga gatctaacgc cgcaatcgga gccgtattcg tagacgaaaa   8820
ccaatggaat tccgctaaag aggccgtcga agacgaacgg ttttgggact tagtgcatag   8880
ggaacgcgaa ttgcataaac agggtaagtg cgcaacatgc gtatacaata tgatgggtaa   8940
gcgcgaaaaa aagttaggcg aattcggtaa ggctaaggga tctagagcga tatggtatat   9000
gtggttaggc gctaggtttc tcgaattcga agcactcgga tttatgaacg aagaccattg   9060
gttttctaga gagaatagtc tatccggagt cgagggagag ggattgcata aactcggata   9120
tatactgaga gacatatcta agatacccgg agggaatatg tacgccgacg atacagccgg   9180
atgggataca cgaattaccg aagacgatct gcaaaacgaa gcgaaaatta ccgatattat   9240
ggaacccgaa cacgcactgt tagcgacatc tatttttaag ttgacatatc agaataaggt   9300
cgttagggtg caacgacccg ctaaaaacgg aacggttatg gacgtgatta gtaggagaga   9360
ccaacgcgga tccggacagg tcggaacata cggactgaat acgtttacga atatggaagc   9420
gcaattgatt agacagatgg agtctgaggg gatattctca cctagcgaac tcgagacacc   9480
taacctagcc gaacgggtac tcgattggtt gaaaaaacac ggaaccgaaa gactgaaaag   9540
aatggcaatt agcggagacg attgcgtagt gaaaccaatc gacgatagat tcgcaaccgc   9600
actaaccgca cttaacgata tgggtaaggt gagaaaagac ataccgcaat gggagccatc   9660
taagggatgg aacgattggc aacaggtgcc attttgctca catcactttc accaattgat   9720
tatgaaagac ggtagggaga tagtcgtgcc atgtaggaat caggacgaac tcgtaggtag   9780
ggctagagtg tcacagggag ccggatggtc acttagggaa accgcatgcc taggtaagtc   9840
atacgctcaa atgtggcaat tgatgtattt ccatagacgc gatctgagac tagccgctaa   9900
cgctatatgc tctgccgtac cagtcgattg ggtgccaact agtagaacga catggtctat   9960
acacgcacat caccaatgga tgacaaccga agacatgcta tccgtttgga atagggtgtg  10020
gatcgaagag aatccatgga tggaggataa gacacacgtg tctagttggg aggacgtgcc  10080
atatctcgga aaacgcgaag accaatggtg cggatcacta atcggattga ccgctagagc  10140
gacatgggca actaacatac aggtcgcaat taaccaagtg agacgattga tcggaaacga  10200
gaattatctc gactttatga catctatgaa aagattcaaa aacgaatccg atcccgaagg  10260
cgcactatgg taagccaact cattcacaaa ataaaggaaa ataaaaaatc aaacaaggca  10320
agaagtcagg ccggattaag ccatagcacg gtaagagcta tgctgcctgt gagccccgtc  10380
caaggacgta aaatgaagtc aggccgaaag ccacggttcg agcaagccgt gctgcctgta  10440
```

```
gctccatcgt ggggatgtaa aaacccggga ggctgcaaac catggaagct gtacgcatgg  10500

ggtagcagac tagtggttag aggagacccc tcccaagaca caacgcagca gcggggccca  10560

acaccagggg aagctgtacc ctggtggtaa ggactagagg ttagaggaga ccccccgcac  10620

aacaacaaac agcatattga cgctgggaga gaccagagat cctgctgtct ctacagcatc  10680

attccaggca cagaacgcca aaaaatggaa tggtgctgtt gaatcaacag gttct       10735


<210> SEQ ID NO 35
<211> LENGTH: 9181
<212> TYPE: DNA
<213> ORGANISM: Human immunodeficiency virus type 1

<400> SEQUENCE: 35

ggtctctctg gttagaccag atctgagcct gggagctctc tggctaacta gggaacccac     60

tgcttaagcc tcaataaagc ttgccttgag tgcttcaagt agtgtgtgcc cgtctgttgt    120

gtgactctgg taactagaga tccctcagac ccttttagtc agtgtggaaa atctctagca    180

gtggcgcccg aacagggacc tgaaagcgaa agggaaacca gaggagctct ctcgacgcag    240

gactcggctt gctgaagcgc gcacggcaag aggcgagggg cggcgactgg tgagtacgcc    300

aaaaattttg actagcggag gctagaagga gagagatggg tgcgcgtgcg tcggtattat    360

cgggtggtga attagatcgt tgggaaaaaa tacgtttacg tccgggtggt aaaaaaaaat    420

ataaattaaa acatatagta tgggcgtcgc gtgaattaga acgttttgcg gtaaatccgg    480

gtttattaga aacgtcggaa ggttgtcgtc aaatattagg tcaattacaa ccgtcgttac    540

aaacgggttc ggaagaatta cgttcgttat ataatacggt agcgacgtta tattgtgtac    600

atcaacgtat agaaataaaa gatacgaaag aagcgttaga taaaatagaa gaagaacaaa    660

ataaatcgaa aaaaaaagcg caacaagcgg cggcggatac gggtcattcg aatcaagtat    720

cgcaaaatta tccgatagta caaaatatac aaggtcaaat ggtacatcaa gcgatatcgc    780

cgcgtacgtt aaatgcgtgg gtaaaagtag tagaagaaaa agcgttttcg ccggaagtaa    840

taccgatgtt ttcggcgtta tcggaaggtg cgacgccgca agatttaaat acgatgttaa    900

atacggtagg tggtcatcaa gcggcgatgc aaatgttaaa agaaacgata aatgaagaag    960

cggcggaatg ggatcgtgta catccggtac atgcgggtcc gatagcgccg ggtcaaatgc   1020

gtgaaccgcg tggttcggat atagcgggta cgacgtcgac gttacaagaa caaataggtt   1080

ggatgacgaa taatccgccg ataccggtag gtgaaatata taaacgttgg ataatattag   1140

gtttaaataa aatagtacgt atgtattcgc cgacgtcgat attagatata cgtcaaggtc   1200

cgaaagaacc gtttcgtgat tatgtagatc gtttttataa aacgttacgt gcggaacaag   1260

cgtcgcaaga agtaaaaaat tggatgacgg aaacgttatt agtacaaaat gcgaatccgg   1320

attgtaaaac gatattaaaa gcgttaggtc cggcggcgac gttagaagaa atgatgacgg   1380

cgtgtcaagg tgtaggtggt ccgggtcata aagcgcgtgt attagcggaa gcgatgtcgc   1440

aagtaacgaa ttcggcgacg ataatgatgc aacgtggtaa ttttcgtaat caacgtaaaa   1500

tagtaaaatg ttttaattgt ggtaaagaag gtcatacggc gcgtaattgt cgtgcgccgc   1560

gtaaaaaagg ttgttggaaa tgtggtaaag aaggtcatca aatgaaagat tgtacggaac   1620

gtcaagcgaa ttttttaggg aagatctggc cttcctacaa gggaaggcca gggaattttc   1680

ttcagagcag accagagcca acagccccac cagaagagag cttcaggtct ggggtagaga   1740

caacaactcc ccctcagaag caggagccga tagacaagga actgtatcct ttaacttccc   1800
```

```
tcaggtcact ctttggcaac gacccctcgt cacaataaag ataggtggtc aattaaaaga   1860
agcgttatta gatacgggtg cggatgatac ggtattagaa gaaatgtcgt taccgggtcg   1920
ttggaaaccg aaaatgatag gtggtatagg tggttttata aaagtacgtc aatatgatca   1980
aatattaata gaaatatgtg gtcataaagc gataggtacg gtattagtag gtccgacgcc   2040
ggtaaatata ataggtcgta atttattaac gcaaataggt tgtacgttaa attttccgat   2100
atcgccgata gaaacggtac cggtaaaatt aaaaccgggt atggatggtc cgaaagtaaa   2160
acaatggccg ttaacggaag aaaaaataaa agcgttagta gaaatatgta cggaaatgga   2220
aaaagaaggt aaaatatcga aaataggtcc ggaaaatccg tataatacgc cggtatttgc   2280
gataaaaaaa aaagattcga cgaaatggcg taaattagta gattttcgtg aattaaataa   2340
acgtacgcaa gatttttggg aagtacaatt aggtataccg catccggcgg gtttaaaaaa   2400
aaaaaaatcg gtaacggtat tagatgtagg tgatgcgtat tttcggtac cgttagatga    2460
agattttcgt aaatatacgg cgtttacgat accgtcgata aataatgaaa cgccgggtat   2520
acgttatcaa tataatgtat taccgcaagg ttggaaaggt tcgccggcga tatttcaatc   2580
gtcgatgacg aaaatattag aaccgtttcg taaacaaaat ccggatatag taatatatca   2640
atatatggat gatttatatg taggttcgga tttagaaata ggtcaacatc gtacgaaaat   2700
agaagaatta cgtcaacatt tattacgttg gggtttaacg acgccggata aaaaacatca   2760
aaaagaaccg ccgtttttat ggatgggtta tgaattacat ccggataaat ggacggtaca   2820
accgatagta ttaccggaaa aagattcgtg gacggtaaat gatatacaaa aattagtagg   2880
taaattaaat tgggcgtcgc aaatatatcc gggtataaaa gtacgtcaat tatgtaaatt   2940
attacgtggt acgaaagcgt taacggaagt aataccgtta acggaagaag cggaattaga   3000
attagcggaa aatcgtgaaa tattaaaaga accggtacat ggtgtatatt atgatccgtc   3060
gaaagattta atagcggaaa tacaaaaaca aggtcaaggt caatggacgt atcaaatata   3120
tcaagaaccg tttaaaaatt taaaaacggg taaatatgcg cgtatgcgtg gtgcgcatac   3180
gaatgatgta aaacaattaa cggaagcggt acaaaaaata acgacggaat cgatagtaat   3240
atggggtaaa acgccgaaat ttaaattacc gatacaaaaa gaaacgtggg aaacgtggtg   3300
gacggaatat tggcaagcga cgtggatacc ggaatgggaa tttgtaaata cgccgccgtt   3360
agtaaaatta tggtatcaat tagaaaaaga accgatagta ggtgcggaaa cgttttatgt   3420
agatggtgcg gcgaatcgtg aaacgaaatt aggtaaagcg ggttatgtaa cgaatcgtgg   3480
tcgtcaaaaa gtagtaacgt taacggatac gacgaatcaa aaaacggaat tacaagcgat   3540
atatttagcg ttacaagatt cgggtttaga agtaaatata gtaacggatt cgcaatatgc   3600
gttaggtata atacaagcgc aaccggatca atcggaatcg gaattagtaa atcaaataat   3660
agaacaatta ataaaaaaag aaaaagtata tttagcgtgg gtaccggcgc ataaaggtat   3720
aggtggtaat gaacaagtag ataaattagt atcggcgggt atacgtaaag tattattttt   3780
agatggtata gataaagcgc aagatgaaca tgaaaaatat cattcgaatt ggcgtgcgat   3840
ggcgtcggat tttaatttac cgccggtagt agcgaaagaa atagtagcgt cgtgtgataa   3900
atgtcaatta aaaggtgaag cgatgcatgg tcaagtagat tgttcgccgg gtatatggca   3960
attagattgt acgcatttag aaggtaaagt aatattagta gcggtacatg tagcgtcggg   4020
ttatatagaa gcggaagtaa taccggcgga aacgggtcaa gaaacggcgt atttttattt   4080
aaaattagcg ggtcgttggc cggtaaaaac gatacatacg gataatggtt cgaattttac   4140
gggtgcgacg gtacgtgcgg cgtgttggtg ggcgggtata aaacaagaat ttggtatacc   4200
```

```
gtataatccg caatcgcaag gtgtagtaga atcgatgaat aaagaattaa aaaaaataat   4260
aggtcaagta cgtgatcaag cggaacattt aaaaacggcg gtacaaatgg cggtatttat   4320
acataatttt aaacgtaaag gtggtatagg tggttattcg gcgggtgaac gtatagtaga   4380
tataatagcg acggatatac aaacgaaaga attacaaaaa caaataacga aaatacaaaa   4440
ttttcgtgta tattatcgtg attcgcgtaa tccgttatgg aaaggtccgg cgaaattatt   4500
atggaaaggt gaaggtgcgg tagtaataca agataattcg gatataaaag tagtaccgcg   4560
tcgtaaagcg aaaataatac gtgattatgg aaaacagatg gcaggtgatg attgtgtggc   4620
aagtagacag gatgaggatt agaacgtgga aatcgttagt aaaacatcat atgtatgtat   4680
cgggtaaagc gcgtggttgg ttttatcgtc atcattatga atcgccgcat ccgcgtatat   4740
cgtcggaagt acatataccg ttaggtgatg cgcgtttagt aataacgacg tattggggtt   4800
tacatacggg tgaacgtgat tggcatttag gtcaaggtgt atcgatagaa tggcgtaaaa   4860
aacgttattc gacgcaagta gatccggaat tagcggatca attaatacat ttatattatt   4920
ttgattgttt ttcggattcg gcgatacgta aagcgttatt aggtcatata gtatcgccgc   4980
gttgtgaata tcaagcgggt cataataaag taggttcgtt acaatattta gcgttagcgg   5040
cgttaataac gccgaaaaaa ataaaaccgc cgttaccgtc ggtaacgaaa ttaacggaag   5100
atagatggaa caagccccag aagaccaagg gccacagagg gagccacaca atgaatggac   5160
actagagctt ttagaggagc ttaagaatga agctgttaga cattttccta ggatttggct   5220
ccatggctta gggcaacata tctatgaaac ttatggggat acttgggcag gagtggaagc   5280
cataataaga attctgcaac aactgctgtt tatccatttt cagaattggg tgtcgacata   5340
gcagaatagg cgttactcga cagaggagag caagaaatgg agccagtaga tcctagacta   5400
gagccctgga agcatccagg aagtcagcct aaaactgctt gtaccaattg ctattgtaaa   5460
aagtgttgct ttcattgcca agtttgtttc ataacaaaag ccttaggcat ctcctatggc   5520
aggaagaagc ggagacagcg acgaagagct catcagaaca gtcagactca tcaagcttct   5580
ctatcaaagc agtaagtagt acatgtaatg caacctatac caatagtagc aatagtagca   5640
ttagtagtag caataataat agcaatagtt gtgtggtcca tagtaatcat agaatatagg   5700
aaaatattaa gacaaagaaa aatagacagg ttaattgata gactaataga aagagcagaa   5760
gacagtggca atgagagtga aggagaaata tcagcacttg tggagatggg ggtggagatg   5820
gggcaccatg ctccttggga tgttgatgat ctgtagtgcg acggaaaaat tatgggtaac   5880
ggtatattat ggtgtaccgg tatggaaaga agcgacgacg acgttatttt gtgcgtcgga   5940
tgcgaaagcg tatgatacgg aagtacataa tgtatgggcg acgcatgcgt gtgtaccgac   6000
ggatccgaat ccgcaagaag tagtattagt aaatgtaacg gaaaatttta atatgtggaa   6060
aaatgatatg gtagaacaaa tgcatgaaga tataatatcg ttatgggatc aatcgttaaa   6120
accgtgtgta aaattaacgc cgttatgtgt atcgttaaaa tgtacggatt taaaaaatga   6180
tacgaatacg aattcgtcgt cgggtcgtat gataatggaa aaaggtgaaa taaaaaattg   6240
ttcgtttaat atatcgacgt cgatacgtgg taaagtacaa aaagaatatg cgttttttta   6300
taaattagat ataataccga tagataatga tacgacgtcg tataaattaa cgtcgtgtaa   6360
tacgtcggta ataacgcaag cgtgtccgaa agtatcgttt gaaccgatac cgatacatta   6420
ttgtgcgccg gcgggttttg cgatattaaa atgtaataat aaaacgttta atggtacggg   6480
tccgtgtacg aatgtatcga cggtacaatg tacgcatggt atacgtccgg tagtatcgac   6540
```

gcaattatta ttaaatggtt cgttagcgga agaagaagta gtaatacgtt cggtaaattt 6600
tacggataat gcgaaaacga taatagtaca attaaatacg tcggtagaaa taaattgtac 6660
gcgtccgaat aataatacgc gtaaacgtat acgtatacaa cgtggtccgg gtcgtgcgtt 6720
tgtaacgata ggtaaaatag gtaatatgcg tcaagcgcat tgtaatatat cgcgtgcgaa 6780
atggaataat acgttaaaac aaatagcgtc gaaattacgt gaacaatttg gtaataataa 6840
aacgataata tttaaacaat cgtcgggtgg tgatccggaa atagtaacgc attcgtttaa 6900
ttgtggtggt gaattttttt attgtaattc gacgcaatta tttaattcga cgtggtttaa 6960
ttcgacgtgg tcgacggaag gttcgaataa tacggaaggt tcggatacga taacgttacc 7020
gtgtcgtata aaacaaataa taaatatgtg gcaaaaagta ggtaaagcga tgtatgcgcc 7080
gccgatatcg ggtcaaatac gttgttcgtc gaatataacg ggtttattat taacgcgtga 7140
tggtggtaat tcgaataatg aatcggaaat atttcgtccg ggtggtggtg atatgcgtga 7200
taattggcgt tcggaattat ataaatataa agtagtaaaa atagaaccgt taggtgtagc 7260
gccgacgaaa gcgaaacgtc gtgtagtaca acgtgaaaaa cgtgcggtag gtataggtgc 7320
gttatttta ggtttttag gtgcggcggg ttcgacgatg ggtgcggcgt cgatgacgtt 7380
aacggtacaa gcgcgtcaat tattatcggg tatagtacaa caacaaaata atttattacg 7440
tgcgatagaa gcgcaacaac atttattaca attaacggta tggggtataa aacaattaca 7500
agcgcgtata ttagcggtag aacgttattt aaaagatcaa caattattag gtatatgggg 7560
ttgttcgggt aaattaatat gtacgacggc ggtaccgtgg aatgcgtcgt ggtcgaataa 7620
atcgttagaa caaatatgga atcatacgac gtggatggaa tgggatcgtg aaataaataa 7680
ttatacgtcg ttaatacatt cgttaataga agaatcgcaa aatcaacaag aaaaaaatga 7740
acaagaatta ttagaattag ataaatgggc gtcgttatgg aattggttta atataacgaa 7800
ttggttatgg tatataaaat tatttataat gatagtaggt ggtttagtag gtttacgtat 7860
agtatttgcg gtattatcga tagtaaatcg tgtacgtcaa ggttattcgc cgttatcgtt 7920
tcaaacccac ctcccaaccc cgaggggacc cgacaggccc gaaggaatag aagaagaagg 7980
tggagagaga gacagagaca gatccattcg attagtgaac ggatccttgg cacttatctg 8040
ggacgatctg cggagcctgt gcctcttcag ctaccaccgc ttgagagact tactcttgat 8100
tgtaacgagg attgtggaac ttctgggacg cagggggtgg gaagccctca aatattggtg 8160
gaatctccta cagtattgga gtcaggaact aaagaatagt gctgttagct tgctcaatgc 8220
cacagccata gcagtagctg aggggacaga tagggttata gaagtagtac aaggagcttg 8280
tagagctatt cgccacatac ctagaagaat aagacagggc ttggaaagga ttttgctata 8340
agatgggtgg taaatggtcg aaatcgtcgg taataggttg gccgacggta cgtgaacgta 8400
tgcgtcgtgc ggaaccggcg gcggatcgtg taggtgcggc gtcgcgtgat ttagaaaaac 8460
atggtgcgat aacgtcgtcg aatacggcgg cgacgaatgc ggcgtgtgcg tggttagaag 8520
cgcaagaaga agaagaagta ggttttccgg taacgccgca agtaccgtta cgtccgatga 8580
cgtataaagc ggcggtagat ttatcgcatt ttttaaaaga aaaaggtggt ttagaaggtt 8640
taatacattc gcaacgtcgt caagatatat tagatttatg gatatatcat acgcaaggtt 8700
attttccgga ttaacaaaat tatacgccgg gtccgggtgt acgttatccg ttaacgtttg 8760
gttggtgtta taaattagta ccggtagaac cggataaaat agaagaagcg aataaaggtg 8820
aaaatacgtc gttattacat ccggtatcgt tacatggtat ggatgatccg gaacgtgaag 8880
tattagaatg gcgttttgat tcgcgtttag cgtttcatca tgtagcgcgt gaattacatc 8940
cggaatattt taaaaattgt taacatcgag cttgctacaa gggactttcc gctggggact 9000
ttccagggag gcgtggcctg ggcgggactg gggagtggcg agccctcaga tcctgcatat 9060
aagcagctgc tttttgcctg tactgggtct ctctggttag accagatctg agcctgggag 9120
ctctctggct aactagggaa cccactgctt aagcctcaat aaagcttgcc ttgagtgctt 9180
c 9181

<210> SEQ ID NO 36
<211> LENGTH: 9181
<212> TYPE: DNA
<213> ORGANISM: unknown
<220> FEATURE:
<223> OTHER INFORMATION: synthetic

<400> SEQUENCE: 36
ggtctctctg gttagaccag atctgagcct gggagctctc tggctaacta gggaacccac 60
tgcttaagcc tcaataaagc ttgccttgag tgcttcaagt agtgtgtgcc cgtctgttgt 120
gtgactctgg taactagaga tccctcagac ccttttagtc agtgtggaaa atctctagca 180
gtggcgcccg aacagggacc tgaaagcgaa agggaaacca gaggagctct ctcgacgcag 240
gactcggctt gctgaagcgc gcacggcaag aggcgagggg cggcgactgg tgagtacgcc 300
aaaaattttg actagcggag gctagaagga gagagatggg agctagagct agcgtactta 360
gcggaggcga actcgataga tgggaaaaaa ttagactgag accaggggga aaaaaaaaat 420
ataaactgaa acatatagta tgggctagta gagagttaga gagattcgca gtaaacccag 480
ggttactcga aactagcgaa gggtgtagac agatactggg acaattgcaa cctagtctgc 540
aaaccggatc cgaagagctt agatcactat ataatacagt cgcaacacta tattgtgtac 600
accaacgaat cgaaattaag gatacgaaag aggcattaga caaaatcgaa gaggaacaga 660
ataagtctaa aaaaaaagcg caacaggcag cagccgatac cggacatagt aatcaggtat 720
cgcaaaatta tccaatcgta cagaatatac agggacaaat ggtacaccaa gcgatatcac 780
ctagaacact taacgcatgg gttaaggtag tcgaagagaa agcatttagt ccagaggtaa 840
tacctatgtt tagcgcatta agcgaaggcg caacaccaca ggatctgaat actatgctta 900
ataccgtagg ggggcatcaa gccgcaatgc aaatgcttaa agagacaatt aacgaagagg 960
cagccgaatg ggatagagtg catcccgtac acgcaggacc aatcgcacca ggacaaatga 1020
gagaacctag gggatccgat atagccggaa ctactagtac attgcaggaa cagatagggt 1080
ggatgactaa taatccacct atacccgtag gcgaaatata caaaagatgg ataatactgg 1140
gactgaataa gatagttaga atgtatagtc caactagtat actcgatatt agacagggac 1200
ctaaagaacc ttttagggat tacgtagata gattctataa aacacttaga gccgaacagg 1260
ctagtcaaga ggttaagaat tggatgacag agacactatt agtgcaaaac gctaatcccg 1320
attgtaaaac tatacttaag gcactaggac cagcagcaac actcgaagaa atgatgacag 1380
catgtcaggg agtagggggga ccaggacata aagctagagt gttagccgaa gctatgtcac 1440
aggtaacgaa tagcgcaaca attatgatgc aaagaggtaa ttttagaaac caacgaaaaa 1500
tcgttaagtg ttttaattgc ggaaaagagg gacataccgc tagaaattgt agggcaccta 1560
gaaaaaaagg gtgttggaaa tgcggaaaag agggacatca aatgaaagat tgtaccgaaa 1620
gacaggctaa tttttttaggg aagatctggc cttcctacaa gggaaggcca gggaattttc 1680
ttcagagcag accagagcca acagccccac cagaagagag cttcaggtct ggggtagaga 1740

```
caacaactcc ccctcagaag caggagccga tagacaagga actgtatcct ttaacttccc   1800
tcaggtcact ctttggcaac gacccctcgt cacaataaag ataggggac aattgaaaga   1860
ggcactatta gacacaggag cagacgatac agtactcgaa gaaatgtcac taccaggtag   1920
atggaaacct aaaatgatag gggggatagg ggggtttata aaggtaagac aatacgatca   1980
gatactaatc gaaatttgcg gacataaagc aatcggaaca gtgttagtcg gacctacacc   2040
cgtaaacata atcggtagga atctgttaac acagataggg tgtacattga attttccaat   2100
tagtccaatc gaaaccgtac ccgtaaaact gaaaccaggt atggacggac ctaaggttaa   2160
gcaatggcca ttaaccgaag agaaaattaa ggcattagtc gaaatttgta ccgaaatgga   2220
aaaagagggt aagattagta agataggacc agagaatcca tataatacac ccgtattcgc   2280
aattaaaaaa aaagatagta cgaaatggag aaagttagtc gattttagag agttaaacaa   2340
aagaacacaa gacttttggg aggtacagtt agggatacca catccagcag gactgaaaaa   2400
aaaaaaaagc gtaaccgtat tagacgtagg agacgcatac tttagcgtac cattagacga   2460
agactttaga aagtataccg catttacgat acctagtatt aataacgaaa caccaggaat   2520
taggtatcaa tataacgtac tgccacaggg atggaaaggg tcaccagcta tattccaatc   2580
tagtatgact aagatactcg aaccttttag aaaacagaat ccagacatag tgatatacca   2640
atatatggac gatctatacg taggtagcga tctagagata gggcaacata gaacgaaaat   2700
cgaagagctt agacagcatc tgttaagatg ggattgact acacctgaca aaaaacacca   2760
aaaagaacca ccattcttat ggatgggata cgaattgcat cccgataaat ggacagtgca   2820
acctatagtg ttacccgaaa aagactcatg gacagtaaac gatatacaaa aactggtagg   2880
taagttgaat tgggctagtc agatatatcc cggaattaag gttaggcaat tgtgtaaact   2940
gttaagggga actaaggcac taaccgaagt gataccgtta accgaagagg cagagttaga   3000
gttagccgaa aatagagaga tacttaagga acccgtacac ggagtgtatt acgatcctag   3060
taaggatctg atagccgaaa tacaaaaaca gggacaggga caatggacat atcagatata   3120
tcaggaacct tttaaaaatc tgaaaaccgg taagtacgct agaatgaggg gagcacatac   3180
aaacgacgtt aagcaattga ccgaagccgt acaaaaaatt acaaccgaat caatcgtaat   3240
ttggggtaag acacctaaat ttaaattgcc tatacaaaaa gagacatggg aaacatggtg   3300
gactgagtat tggcaagcta catggatacc cgaatgggaa ttcgtaaata caccaccatt   3360
agtgaaattg tggtatcaac tcgaaaaaga accaatcgta ggagccgaaa cattttacgt   3420
agacggagca gctaataggg aaactaagtt aggtaaggca ggatacgtta cgaatagggg   3480
gagacagaaa gtcgttacac taaccgatac aactaaccaa aaaaccgaac tgcaagcgat   3540
atacttagcg ttacaggata gcggattaga ggtaaacata gtgacagact cacaatacgc   3600
attagggatt atacaggcac aacccgatca atccgaaagc gaactagtta atcagataat   3660
cgaacaattg attaaaaaag agaaagtgta tctagcatgg gtaccagcac ataagggaat   3720
agggggaaac gaacaggtag ataagttagt tagcgcagga attagaaagg tactgttttt   3780
agacggaata gacaaagcgc aagacgaaca cgaaaaatat catagtaatt ggagagctat   3840
ggctagcgat tttaatctac cacccgtagt cgctaaagag atagtcgcat catgtgataa   3900
gtgtcaattg aaaggcgaag ctatgcacgg acaggtcgat tgtagtccag ggatatggca   3960
attggattgt acacacttag agggtaaggt aatactagtc gcagtacacg tagctagcgg   4020
atatatcgaa gccgaagtga taccagccga aaccggacag gaaaccgcat actttctgtt   4080
aaagttagcc ggtagatggc cagttaagac tatacatacc gataacggat ctaattttac   4140
```

```
aggagcaacc gttagggcag catgttggtg ggcaggaatt aaacaggaat tcggaatacc   4200
atataatcca caatcacagg gagtagtcga atctatgaat aaagagttaa aaaaaattat   4260
cggacaggtt agagaccaag ccgaacacct taaaaccgca gtgcaaatgg ccgtattcat   4320
acataatttt aaaagaaaag gggggatagg ggggtatagc gcaggcgaaa gaatcgtaga   4380
cataatcgca actgacatac agactaaaga gttacagaaa cagattacta agatacagaa   4440
ttttagagtg tattatagag actctagaaa tccattatgg aaaggaccag ctaaactgtt   4500
atggaaaggc gaaggcgcag tagtgataca ggataatagc gatattaagg tagtgcctag   4560
acgaaaagcg aaaattatta gggattatgg aaaacagatg gcaggtgatg attgtgtggc   4620
aagtagacag gatgaggatt agaacatgga aatcactagt taagcatcat atgtacgtta   4680
gcggtaaggc taggggatgg ttttatagac atcattacga atcaccacat cctagaatat   4740
ctagcgaagt gcatataccg ttaggcgacg ctagattagt gataactaca tattggggat   4800
tgcatacagg cgaaagggat tggcatctag gacagggagt gtcaatcgaa tggcgaaaaa   4860
aaagatatag tacacaggta gacccagagt tagccgatca attgatacac ctatattatt   4920
tcgattgttt tagcgatagc gcaattagaa aggcactatt agggcatata gtgtcaccta   4980
gatgcgaata tcaagccgga cataataagg tagggtcact gcaatatcta gcattagccg   5040
cactaattac acctaaaaaa attaaaccac cactacctag cgtaactaag ttaaccgaag   5100
acagatggaa caagccccag aagaccaagg gccacagagg gagccacaca atgaatggac   5160
actagagctt ttagaggagc ttaagaatga agctgttaga cattttccta ggatttggct   5220
ccatggctta gggcaacata tctatgaaac ttatggggat acttgggcag gagtggaagc   5280
cataataaga attctgcaac aactgctgtt tatccatttt cagaattggg tgtcgacata   5340
gcagaatagg cgttactcga cagaggagag caagaaatgg agccagtaga tcctagacta   5400
gagccctgga agcatccagg aagtcagcct aaaactgctt gtaccaattg ctattgtaaa   5460
aagtgttgct ttcattgcca agtttgtttc ataacaaaag ccttaggcat ctcctatggc   5520
aggaagaagc ggagacagcg acgaagagct catcagaaca gtcagactca tcaagcttct   5580
ctatcaaagc agtaagtagt acatgtaatg caacctatac caatagtagc aatagtagca   5640
ttagtagtag caataataat agcaatagtt gtgtggtcca tagtaatcat agaatatagg   5700
aaaatattaa gacaaagaaa aatagacagg ttaattgata gactaataga aagagcagaa   5760
gacagtggca atgagagtga aggagaaata tcagcacttg tggagatggg ggtggagatg   5820
gggcaccatg ctccttggga tgttgatgat ctgtagtgca accgaaaaat tgtgggttac   5880
ggtatattac ggagtacccg tatggaaaga ggcaactact acactatttt gcgctagcga   5940
cgctaaagca tacgataccg aagtgcataa cgtatgggct acacacgcat gcgtacctac   6000
cgatcctaat ccacaagagg tagtgttagt taacgtaacc gaaaatttta atatgtggaa   6060
aaacgatatg gtcgaacaaa tgcacgaaga cataattagc ttatgggacc aatcacttaa   6120
accatgtgtt aagttgacac cactatgcgt aagtcttaag tgtacagacc ttaaaaacga   6180
tactaatact aactctagta gcggaagaat gattatggaa aagggagaga taaaaaattg   6240
ttcattcaat attagtacat caattagggg taaggtacaa aaagaatacg catttttta    6300
taagttagac ataataccaa tcgataacga tacaacatca tataagttaa ctagttgtaa   6360
tactagcgta attacacagg catgtcctaa ggtatcattc gaacctatac cgatacacta   6420
ttgtgcacca gccggattcg caatactgaa atgtaataat aagacattta acggaaccgg   6480
```

-continued

```
accatgtact aacgtaagta cagtgcaatg tacacacgga attagacccg tagtgagtac   6540
gcaattactg ttaaacggat cattagccga agaggaagtg gtaattagat ccgttaattt   6600
taccgataac gctaaaacaa ttatagtgca attgaatact agcgtagaga ttaattgtac   6660
tagacctaat aataatacta gaaaacggat taggatacaa aggggaccag gtagggcatt   6720
cgtaacaatc ggtaagatag ggaatatgag acaggcacat tgtaatatta gtagggctaa   6780
atggaataat acacttaaac agatagctag taagcttaga gagcaattcg gtaataataa   6840
gacaattata ttcaaacaat ctagcggagg ggatccagaa atcgtaacac atagttttaa   6900
ttgcggaggc gaattttttt attgtaatag tacacaattg ttcaatagta catggtttaa   6960
tagtacatgg tcaaccgaag gatctaataa tacagaggga tccgatacaa ttacactacc   7020
atgtaggatt aaacagataa ttaatatgtg gcaaaaggta ggtaaggcaa tgtacgcacc   7080
acctattagc ggacaaatta gatgtagttc gaatataacc ggattactgt taactagaga   7140
cggagggaat tcgaataacg aatccgaaat ttttagacca ggggggggag atatgagaga   7200
caattggaga tccgaattgt ataagtataa agtcgttaaa atcgaaccat taggcgtagc   7260
acctacaaaa gcgaaaagac gggtagtgca acgcgaaaaa agagccgtag ggataggcgc   7320
actattctta gggtttttag gcgcagccgg atcaactatg ggagcagcta gtatgacatt   7380
gacagtgcaa gctagacaac tgttaagcgg aatagtgcaa caacagaata atctgttaag   7440
ggcaatcgaa gcacaacagc atctgttaca attgacagta tgggggatta agcaattgca   7500
ggctagaata ctcgcagtcg aacggtatct gaaagaccaa caactgttag ggatatgggg   7560
atgtagcggt aagttgatat gtacaaccgc agtaccatgg aacgctagtt ggtctaataa   7620
atcactcgaa cagatatgga atcatacaac atggatggaa tgggatagag agattaacaa   7680
ttatactagt ctgatacact cactaatcga agagtcacaa aaccaacagg aaaaaaacga   7740
acaggaactg ttagagttag acaaatgggc tagcttatgg aattggttta atattactaa   7800
ttggttatgg tatataaaac tgtttattat gatagtaggg gggttagtcg gattgagaat   7860
cgtattcgca gtactatcaa tcgttaatag ggttagacag ggatatagtc cactatcatt   7920
ccaaacccac ctcccaaccc cgaggggacc cgacaggccc gaaggaatag aagaagaagg   7980
tggagagaga gacagagaca gatccattcg attagtgaac ggatccttgg cacttatctg   8040
ggacgatctg cggagcctgt gcctcttcag ctaccaccgc ttgagagact tactcttgat   8100
tgtaacgagg attgtggaac ttctgggacg cagggggtgg gaagccctca aatattggtg   8160
gaatctccta cagtattgga gtcaggaact aaagaatagt gctgttagct tgctcaatgc   8220
cacagccata gcagtagctg aggggacaga tagggttata gaagtagtac aaggagcttg   8280
tagagctatt cgccacatac ctagaagaat aagacagggc ttggaaagga ttttgctata   8340
agatgggagg taagtggtct aaatctagcg taatcggatg gcctacagtt agggaaagaa   8400
tgcgtagagc cgaacctgca gccgataggg taggcgcagc tagtagggat ctcgaaaaac   8460
acggagcaat tactagtagt aatacagccg caactaacgc agcatgcgca tggttagagg   8520
cacaggaaga ggaagaggta gggtttcccg taacaccaca ggtaccactt agacctatga   8580
catataaagc cgcagtcgat ctatcacatt ttctgaaaga gaaagggggg ttagagggac   8640
tgatacattc acagagacga caagacatac tagacttatg gatatatcat acacagggat   8700
attttccaga ctagcaaaat tatacaccag gaccaggcgt aagatatcca ttgacattcg   8760
gatggtgtta taaactggta ccagtcgaac cagacaaaat cgaagaggct aacaaaggcg   8820
aaaatactag tctgttacat cccgtaagct tacacggaat ggacgatcca gaaagagagg   8880
```

```
tactcgaatg gagattcgat agtagactcg cattccatca cgtagctagg gaattgcatc   8940

cagagtattt taaaaattgt tgacatcgag cttgctacaa gggactttcc gctggggact   9000

ttccagggag gcgtggcctg ggcgggactg gggagtggcg agccctcaga tcctgcatat   9060

aagcagctgc tttttgcctg tactgggtct ctctggttag accagatctg agcctgggag   9120

ctctctggct aactagggaa cccactgctt aagcctcaat aaagcttgcc ttgagtgctt   9180

c                                                                   9181
```

<210> SEQ ID NO 37
<211> LENGTH: 3309
<212> TYPE: DNA
<213> ORGANISM: Rotavirus sp.

<400> SEQUENCE: 37

```
ggctaaaaaa aatggcgcaa tcgatagtag tagatggtga ttatgatgcg ttagcgtcgc     60

gttatttaaa atttgtatat gattttgaaa atgtaacgta tcaaaataat tattttgcga    120

cggataaatt taaaaaagat atagaacaat atttaaaatc gatacatgat ggtgaaaaaa    180

taacgcaatc gaaaatagat gaaaaagaaa aaatattatt agatcgtgta ccggcggaag    240

aacgttgttt aatatcgaaa ttagtatttg cgtatggtaa acatggtaat gtagaaaata    300

aattagtaaa atatggtgta aaagatgcgt tatcgcatgc gccgcaaaaa gatgcgaaac    360

cgtatgaaaa taatataata acgtcggaaa tatttaaaga aaaatcggaa tatacggata    420

tatatatgga tccgtcgata aatacgtcgt gtcaatcgaa ttgtcaagcg atgatgttta    480

cgatatcgga aatgaaatta aataatataa aaaatgcggc gcgtttagaa aaattattta    540

cgataatagc ggcgacgata aataaatatg gtatgccgcg tcataatacg cgttatcgtt    600

atgaatggga aacgatgaaa aataaaccgt atcatttagc ggcgtggata aattcgtcga    660

tagaaatgat agcgtgtgta gtagatcatc atacgtatat gatagcgcgt gaattaatag    720

taaaatcgtt tacgaatcgt acgtcgttag cgaaattagt atcgtcgccg atgacggtat    780

taacggcgat gttaccgata cgtggtacgt ttataacgac ggaaaattta gaattagaat    840

attcgaataa atcgataaat tatttaatat cgaaagaaat ggcggaagat tttatgcaag    900

cgataaaaca attacgtgat gaaggtttag aatatatacc ggattattat gaaaaatggt    960

ttaaatcgcc ggatccgtta acgtttccga atatagcgtt aatatattcg ttttcgtttc   1020

atgtaggtta tcgtaaacaa gcgttatcgg atgcggtata tgatcaaata acggtaacgt   1080

attcggataa tgtaaatatg gaaatgtata aagaatattc ggaacgtata gaaaatgaaa   1140

tatttacgat attaaaagat aaaataatac atgaagataa acgtttagaa gaatatgaat   1200

tatcggcgtt attatcgatg tcgtcggcgt cgaatggtat attacgtgaa ataaattttg   1260

gtggtcaaaa agtacgttcg acgaaaaaaa atatgcatgt aatagatgat atatatcata   1320

aaaaatatac gacggatata ccgccggtag atgcgcgtaa tccgataccg ttaggtcgtc   1380

gtgatgtacc gggtcgtcgt acgcgtgcga tatttatatt accgtatcaa tattttatag   1440

cgcaacattc gtttgcggaa ataatgttaa attatgcgaa acgtgaacgt gaatattcgg   1500

aattttattc gcaagcgaat caagtattat cgtatggtga tgtaacgcgt tatttagatt   1560

cgaattcgat attatgtttt acggatgtat cgcaatggga tgcgtcgcaa cataatacga   1620

aagtattacg tcgttcgata atacgtgcga tgaaacgttt aaaacaatta acgcataata   1680

taaatataca taaagcgata aatatatata tacaatcgca agaaaattta gaaaattcgt   1740
```

atgtattaat agataaaaaa gcgatacaat atggtgcgac ggcgtcgggt gaaaaacaaa 1800
cgaaaataat gaattcgata gcgaataaag cgttaataca aacggtatta ggtaaattaa 1860
tgacggatta tacgtttgat gtaaaaatga tacgtgtaga tggtgatgat aattatgcga 1920
tagtacgttt tccgatagcg ataacggaaa aattattatc ggaatttacg tcgaaattac 1980
gttcgtatta ttcggaaatg aatgtaaaag taaaagcgtt agcgtcgtta acgggttgtg 2040
aaatagcgaa acgttatgta gcgggtggta tgttattttt tcgtgcgggt gtaaatatat 2100
tacatcatga aaaacgtaat caagattcgg cgtatgatat ggcggcgacg ttatatgcga 2160
attatatagt aaatgcgtta cgtggtttaa cgatgtcgcg tacgtttata ttaacgaaaa 2220
tatgtcaaat gacgtcgata aaaataacgg gtacgttacg tttatttccg atgaaatcga 2280
tattagcgtt aaattcggcg tttaaagtat ttgatgaagt agattatgta ataaattatc 2340
cgatatcgaa tttatttata caattacaac gtaaattatc gtcgataaaa gcgaaatcga 2400
aaatagcgga taatatagcg aaatcgccgc aatttaaatc gtatgtagaa ttattaaata 2460
aatcgttaac gacggatgaa aatccgatag tatcggatgg tatacgttta acggaaaaag 2520
cgaaattaaa ttcgtatgcg ccgatagcgt tagaaaaacg tcgtgatcaa ttttcgataa 2580
tggtatcgtt tttacaaaat ccgacgacgt ttaaatcgga aacggtagta acgataaatg 2640
atgtattata ttttatatcg ggttttataa aaatagattc gtcgacggta ttaccgaaag 2700
aagaaaataa tacgatgccg ttattaccgg cgataataaa acgtacgtta tcgtattttg 2760
gtttacgtac gcatgattat gatataaaag gttcgtcgtc gacggtatcg aaaataataa 2820
aacaatattc ggtatatacg ccgggtatag aagaattata tgaaatagta aataaatcgg 2880
tagatacgat acgtggttat tttgcgtcgt ttaatgtacc gaaagcggat gtagatacgt 2940
atatatcgac gcaaatgtat aaacatgatc gttttaaaat attacaagcg tatatatata 3000
atttattatc ggtaaattat ggtatgtatc aattagtaga tttaaattcg gcgcgttttt 3060
ttgatcatgt aatacatacg ccgatggcga aaacgccgac ggcggtattt atgatagatt 3120
tagcgttacg tttaaaaata ataaatcatt gtatagaaaa aggtgaaata ataacggtat 3180
cggtacatgc gaataaaacg gattatttaa aattatggcg tatgttatgg aatgtaaaaa 3240
cgatgaattc gccgtattcg aaaaattcga tgtttgatga ataagagaag tggattgcat 3300
attgtggct 3309

<210> SEQ ID NO 38
<211> LENGTH: 3309
<212> TYPE: DNA
<213> ORGANISM: Unknown
<220> FEATURE:
<223> OTHER INFORMATION: synthetic

<400> SEQUENCE: 38
ggctaaaaaa aatggcacaa tcaatcgtag ttgacggaga ttatgatgca ttagctagta 60
gatatctaaa attcgtatac gatttcgaaa acgtaactta tcagaataat tatttcgcaa 120
ctgataaatt taaaaaagat atcgaacaat atcttaaatc aatacacgat ggagaaaaaa 180
ttacgcaatc taagatagac gaaaaagaaa aaatactgtt agatagagta ccagctgaag 240
aaagatgtct aatatctaag ttagtattcg catatggtaa gcatggtaac gttgagaata 300
agttagttaa gtatggagtt aaggatgcac tatcacatgc accacaaaaa gacgctaaac 360
catacgaaaa taatataatt actagcgaaa tttttaaaga aaaatccgaa tatactgata 420
tatatatgga tccatcaatt aatacatcat gtcaatctaa ttgtcaagct atgatgttta 480

```
cgatatccga aatgaaattg aataatataa aaaacgctgc tagactcgaa aaattgttta    540
caattatagc cgctacaatt aataagtatg gtatgcctag acataatact agatatagat    600
atgaatggga aactatgaaa aataaaccat atcatttagc cgcatggatt aattcgtcaa    660
tcgaaatgat agcatgcgta gtcgatcatc atacatatat gatagctaga gagttaatcg    720
ttaaatcatt tactaataga acatcattag cgaaattagt gtcatcacct atgacagtgt    780
taaccgctat gttaccaatt agaggtacat ttataactac tgaaaatctc gaactcgaat    840
attctaataa atcaattaat tatctgatat cgaaagaaat ggctgaagat tttatgcaag    900
ctataaaaca attgagagac gaaggattag agtatatacc agattattac gaaaaatggt    960
ttaaatcacc agatccatta acttttccta atatagcgtt aatatattca ttttcatttc   1020
acgtagggta tagaaaacag gcactatctg atgcagtata cgatcagatt acggttacat   1080
attcagataa cgttaatatg gaaatgtata aagagtattc agaaagaatc gaaaacgaaa   1140
tttttacgat actgaaagat aaaattatac acgaagataa acggttagag gaatacgaac   1200
tatcagcatt actatctatg tcatcagcat caaacggaat acttagagaa attaatttcg   1260
gaggacaaaa agttagatca actaaaaaaa atatgcatgt aatcgatgat atatatcata   1320
aaaaatatac tactgatata ccaccagtag acgctagaaa tccgatacca ttaggtagaa   1380
gagacgtacc aggtagacga actagagcta tttttatact accatatcaa tattttatag   1440
cgcaacattc attcgcagaa attatgctta attatgctaa aagagaacgc gaatatagcg   1500
aattttattc acaggctaat caggtactat catacggaga tgtaactaga tatctagatt   1560
ctaattcgat actatgtttt acggatgtat cacaatggga tgctagtcag cataatacta   1620
aggtacttag acgatcaatt attagagcta tgaaaagatt gaaacaattg acacataata   1680
ttaatataca taaagcgata aatatatata tacaatcaca ggaaaatctc gaaaattcat   1740
atgtgttaat cgataaaaaa gcgatacaat acggagctac tgcatcaggc gaaaaacaga   1800
ctaaaattat gaattcaatc gctaataagg cattgataca gacagtgtta ggtaagttaa   1860
tgactgatta tacattcgat gttaaaatga ttagagtaga cggagatgat aattatgcta   1920
tagttagatt tccgatagcg ataaccgaaa aactgttaag cgaatttaca tctaaattgc   1980
gatcatatta ttcagaaatg aacgttaagg ttaaggcatt agcgtcatta acgggatgtg   2040
agatagcgaa aagatatgta gccggaggta tgttattttt tagagccgga gtgaatatat   2100
tgcatcatga aaaacgtaat caggatagtg catacgatat ggcagctaca ttatacgcta   2160
attatatagt taacgcactt agagggttaa ctatgtcacg aacttttata ttgactaaga   2220
tatgtcaaat gacatcaatt aaaattacgg gaacacttag attgtttcca atgaaatcaa   2280
tactcgcact taatagtgca tttaaggtat tcgatgaggt agattatgta attaattatc   2340
ctatatctaa tctatttata caattgcaac gaaaactatc atcaattaaa gcgaaatcta   2400
agatagccga taatatagcg aaatcaccac aatttaaatc atacgttgag ttactgaata   2460
aatcattgac tactgacgaa aatccgatag tgtcagacgg aatacggtta acggaaaaag   2520
ctaaattgaa ttcatacgca ccaatcgcat tagaaaaacg tagagatcaa ttttcaatta   2580
tggtatcatt tttacagaat cctactactt ttaaatccga aacagtagtt acaattaacg   2640
atgtattgta ttttatatca ggatttataa aaatcgattc tagtacagtg ttacctaaag   2700
aggaaaataa tactatgcca ctattaccag ctataattaa acgtacacta tcatatttcg   2760
gattgcgtac acatgattat gatattaagg gatcatctag tacagtatcg aaaattataa   2820
```

```
aacagtattc agtatataca ccaggaatcg aagagttata cgaaatcgtt aataaatcag   2880

tagatacaat taggggatat tttgctagtt ttaacgtacc taaagctgat gtagatacat   2940

atatatcgac acaaatgtat aaacatgata gatttaaaat actgcaagca tatatatata   3000

atctgttatc agttaattat ggtatgtatc aattagtcga tctgaattca gctagatttt   3060

ttgatcatgt aatacataca cctatggcta aaacacctac agcagttttt atgatagatt   3120

tagcgttaag attgaaaatt ataaatcatt gtatcgaaaa aggcgaaatt ataacagtta   3180

gcgtacacgc taataaaact gattatctta agttatggcg tatgttatgg aacgttaaga   3240

ctatgaatag tccatattct aaaaattcaa tgtttgacga ataagagaag tggattgcat   3300

attgtggct                                                           3309
```

<210> SEQ ID NO 39
<211> LENGTH: 2736
<212> TYPE: DNA
<213> ORGANISM: Rotavirus sp.

<400> SEQUENCE: 39

```
ggcttaaaaa gatcagttga ggacaaatcg ttcaagatga tatcgcgtaa tcgtcgtcgt     60

aataatcaac aaaaaaatat agaaaaagaa aaacaattag aaacgataat aaataaagaa    120

gtaaaagaaa ataaagattc gatgaaagaa gataaattag tagtaacgga agaatcgaat    180

ggtgatgtaa cgacggcgaa agaacaatcg aataatataa atttacaaaa aaatgattta    240

gtaaaagaag taatgaatat acaaaatcaa acgttaaata cggtagtaac ggaaaataaa    300

gtagaaatag aagaaatagt aaaaaaatat ataccgtcgt ataatacgga ttcgttaata    360

gtaaaaaaat taacggaaat acaagaatcg tcggcgaaaa cgtataatac gttatttcgt    420

ttatttacgc cggtaaaatc gtatttatat gatataaatg gtgaaaaaaa attatcgacg    480

cgttggtatt ggaaattatt aaaagatgat ttaccggcgg gtgattattc ggtacgtcaa    540

tttttttat cgttatattt aaatgtatta gaagaaatgc cggattatat aatgttacgt    600

gatatggcgg tagataatcc gtattcggcg gaagcgggta aaatagtaga tggtaaatcg    660

aaagaaatat taatagaatt atatcaagat caaatgacgg aaggttatat acgtcgttat    720

atgtcggaat tacgtcataa aatatcgggt gaaacgaata cggcgaaata tccggcgata    780

ttacatccgg tagataatga attaaatcaa tattttttag aacatcaatt aatacaaccg    840

ttaacgacgc gtaatatagc ggaattaata ccgacgcaat tatatcatga tccgaattat    900

gtatttaata tagatgcggc gtttttaacg aattcgcgtt ttgtaccgcc gtatttaacg    960

caagatcgta taggtttaca tgatggtttt gaatcgatat gggattcgaa aacgcatgcg   1020

gattatgtat cggcgcgtcg ttttataccg gatttaacgg aattagtaga tgcggaaaaa   1080

caaataaaag aaatggcggc gcatttacaa ttagaagcga taacggtaca agtagaatcg   1140

caatttttag cgggtatatc ggcggcggcg gcgaatgaag cgtttaaatt tataataggt   1200

tcggtattat cgacgcgtac gatagcggta gaatttataa cgtcgaatta tatgtcgtta   1260

gcgtcgtgta tgtatttaat gacgataatg ccgtcggaaa tatttttacg tgaatcgtta   1320

gtagcgatgc aattagcgat aataaatacg ttaatatatc cggcgttagg tttagcgcaa   1380

atgcattatc aagcgggtga agtacgtacg ccgtttgaat tagcggaaat gcaagtagcg   1440

aatcgttcga tacgtcaatg gttacatcat tgtaatacgt tacaatttgg tcgtcaaata   1500

acggaaggta taatacattt acgttttacg aatgatataa tgacgggtcg tatagtaaat   1560

ttattttcga cgatgttagt agcgttatcg tcgcaaccgt ttgcgacgta tccgttagat   1620
```

tataaacgtt cggtacaacg tgcgttacaa ttattatcga atcgtacggc gcaaatagcg 1680
gatttaacgc gtttaatagt atataattat acgacgttat cggcgtgtat agtaatgaat 1740
atgcatttag taggtacgtt aacggtagaa cgtatacaag cgacgtcgtt aacgtcgtta 1800
atgatgttaa tatcgaataa aacggtaata ccggaaccgt cgtcgttatt ttcgtatttt 1860
tcgtcgaata taaatttttt aacgaattat aatgaacaaa tagataatgt agtagcggaa 1920
ataatggcgg cgtatcgttt aaatttatat caacaaaaaa tgttaatgtt agtaacgcgt 1980
tttgtatcga aattatatat atttgatgcg ccgaaaatac cgccggatca aatgtatcgt 2040
ttacgtaatc gtttacgtaa tataccggta gaacgtcgtc gtgcggatgt atttcgtata 2100
ataatgaata atcgtgattt aatagaaaaa acgtcggaac gtatatgtca aggtgtatta 2160
ttatcgtata cgccgatgcc gttaacgtat gtagaagatg taggtttaac gaatgtaata 2220
aatgatacga attcgtttca aataataaat atagaagaaa tagaaaaaac gggtgattat 2280
tcggcgataa cgaatgcgtt attacgtgat acgccgataa tattaaaagg tgcgataccg 2340
tatgtaacga attcgtcggt aatagatgta ttatcgaaag tagatacgac ggtatttgcg 2400
tcgatagtaa aagatcgtga tatatcgaaa ttaaaaccga taaaatttat aataaattcg 2460
gattcgtcgg aatattattt agtacataat aataaatgga cgccgacgac gacgacggcg 2520
gtatataaag cgcgttcgca acaatttgat atacaacatt cggtatcgat gttagaatcg 2580
aatttatttt ttgtagtata taatgattta tttaaatata taaaaacgac gacggtatta 2640
ccgataaatg cggtatcgta tgatggtgcg cgtataatgc aagaaacgta aatgattgta 2700
tagtatcatc ttgtgacgac ctcaaacttt gtggct 2736

<210> SEQ ID NO 40
<211> LENGTH: 2736
<212> TYPE: DNA
<213> ORGANISM: Unknown
<220> FEATURE:
<223> OTHER INFORMATION: synthetic

<400> SEQUENCE: 40
ggcttaaaaa gatcagttga ggacaaatcg ttcaagatga tatctagaaa tagacgtaga 60
aataatcagc aaaaaaatat cgaaaaagaa aaacagttag agacaattat taataaagag 120
gttaaagaga ataaggattc aatgaaagag gataagttag tggtaaccga agaatctaac 180
ggagacgtta caaccgctaa agagcaatct aataatatta atctgcaaaa aaacgattta 240
gttaaagagg ttatgaatat acagaatcag acacttaata cagtagttac cgaaaataag 300
gttgagatag aagagatagt taaaaaatat ataccgtcat ataatactga ttcattaatc 360
gttaaaaaat taaccgaaat acaggaatct agtgctaaaa cttataatac actatttaga 420
ttgtttacac cagttaaatc atacttatac gatattaatg gcgaaaaaaa actatctact 480
agatggtatt ggaaactgtt aaaagacgat ctaccagcag gtgattactc agttagacaa 540
ttttttctat cattatactt aaacgtatta gaggaaatgc cagattatat tatgcttaga 600
gatatggcag ttgataatcc atactcagct gaagcaggta agatagttga cggtaagtct 660
aaagagatat taatcgaatt gtatcaggat caaatgacag agggatatat tagacggtat 720
atgtcagaac ttagacataa aatttcaggc gaaactaata ccgctaaata tccagctata 780
ctgcatccag tagataacga attgaatcaa tattttctcg aacatcaatt gatacaacca 840
ttaactacta gaaatatagc cgaattgata ccgacacaat tgtatcatga tcctaattac 900
gtttttaata tagacgctgc atttttaact aattctagat tcgtaccacc atacttaacg 960
caagatagga tagggttaca tgacggattc gaatcaattt gggattctaa aacacatgct 1020
gattacgtat cagctagacg atttataccc gatttaaccg aattagttga cgctgaaaaa 1080
cagattaagg aaatggctgc acatttacaa ctcgaagcta ttacggtaca ggttgaatca 1140
caatttttag ccggtattag cgcagcagca gctaacgaag catttaaatt tattatagga 1200
tcagtgttat caactagaac tatagcagtc gaatttatta catctaatta tatgtcatta 1260
gctagttgta tgtatcttat gacaattatg cctagcgaaa ttttttacg cgaatcatta 1320 gtcgctatgc aattagctat tattaataca cttatatatc cagcattagg gttagcgcaa 1380
atgcattatc aggcaggtga ggttagaaca ccattcgaat tagccgaaat gcaagttgcg 1440
aatagatcaa ttagacaatg gttacatcat tgtaatacat tacaattcgg taggcaaatt 1500
accgaaggta ttatacatct tagatttact aacgatatta tgacaggtag gatagttaat 1560
ctattttcga ctatgttagt tgcgttatca tcacaaccat tcgctacata tccattagat 1620
tataaaagat cagtgcaacg agcattacaa ttgttatcta atagaaccgc tcaaatagct 1680
gatttaacta gactgatagt gtataattat actacattat ccgcatgcat agttatgaat 1740
atgcatttag tgggtacact tacagtcgaa cgtatacagg ctacatcatt aacatcatta 1800
atgatgttaa tttctaataa aacagttata cccgaaccat catcattatt ttcatatttt 1860
tcatctaata ttaatttttt aactaattat aacgaacaga tagataacgt agttgcggaa 1920
attatggctg catatagatt gaatctatat caacaaaaaa tgttaatgtt agtgactaga 1980
ttcgtaagta agttatatat attcgatgca cctaaaattc caccagatca aatgtataga 2040
cttagaaata gacttagaaa tataccagtc gaaagacgta gagcagacgt atttagaatt 2100
attatgaata atagggattt aatcgaaaaa actagcgaaa gaatttgtca gggagtgtta 2160
ctatcatata cacctatgcc attaacatac gttgaagacg taggattaac taacgtaatt 2220
aacgatacta attcgtttca aattattaat atcgaagaaa tcgaaaaaac aggtgattac 2280
tcagctatta ctaatgcact attaagggat acacctatta tacttaaggg agctatacca 2340
tacgttacga attcgtcagt gatagacgta ctatctaagg tagatactac agtattcgct 2400
agtatagtta aggataggga tatatctaag ttaaaaccaa ttaaatttat aattaattct 2460
gattctagcg aatattattt agtgcataat aataaatgga cacctactac tactactgca 2520
gtgtataaag ctagatcaca acaattcgat atacaacata gcgtatctat gctcgaatct 2580
aatctatttt tcgtagtgta taacgatcta tttaaatata ttaaaactac tacagtgtta 2640
ccaattaacg ctgtatcata cgatggagct agaattatgc aagaaacata aatgattgta 2700
tagtatcatc ttgtgacgac ctcaaacttt gtggct 2736

<210> SEQ ID NO 41
<211> LENGTH: 29751
<212> TYPE: DNA
<213> ORGANISM: Human coronavirus

<400> SEQUENCE: 41
atattaggtt tttacctacc caggaaaagc caaccaacct cgatctcttg tagatctgtt 60
ctctaaacga actttaaaat ctgtgtagct gtcgctcggc tgcatgccta gtgcacctac 120
gcagtataaa caataataaa ttttactgtc gttgacaaga aacgagtaac tcgtccctct 180
tctgcagact gcttacggtt tcgtccgtgt tgcagtcgat catcagcata cctaggtttc 240
gtccgggtgt gaccgaaagg taagatggaa tcgttagtat taggtgtaaa tgaaaaaacg 300

```
catgtacaat tatcgttacc ggtattacaa gtacgtgatg tattagtacg tggttttggt    360
gattcggtag aagaagcgtt atcggaagcg cgtgaacatt taaaaaatgg tacgtgtggt    420
ttagtagaat tagaaaaagg tgtattaccg caattagaac aaccgtatgt atttataaaa    480
cgttcggatg cgttatcgac gaatcatggt cataaagtag tagaattagt agcggaaatg    540
gatggtatac aatatggtcg ttcgggtata acgttaggtg tattagtacc gcatgtaggt    600
gaaacgccga tagcgtatcg taatgtatta ttacgtaaaa atggtaataa aggtgcgggt    660
ggtcattcgt atggtataga tttaaaatcg tatgatttag gtgatgaatt aggtacggat    720
ccgatagaag attatgaaca aaattggaat acgaaacatg gttcgggtgc gttacgtgaa    780
ttaacgcgtg aattaaatgg tggtgcggta acgcgttatg tagataataa tttttgtggt    840
ccggatggtt atccgttaga ttgtataaaa gatttttag cgcgtgcggg taaatcgatg    900
tgtacgttat cggaacaatt agattatata gaatcgaaac gtggtgtata ttgttgtcgt    960
gatcatgaac atgaaatagc gtggtttacg gaacgttcgg ataaatcgta tgaacatcaa   1020
acgccgtttg aaataaaatc ggcgaaaaaa tttgatacgt ttaaaggtga atgtccgaaa   1080
tttgtatttc cgttaaattc gaaagtaaaa gtaatacaac cgcgtgtaga aaaaaaaaaa   1140
acggaaggtt ttatgggtcg tatacgttcg gtatatccgg tagcgtcgcc gcaagaatgt   1200
aataatatgc atttatcgac gttaatgaaa tgtaatcatt gtgatgaagt atcgtggcaa   1260
acgtgtgatt ttttaaaagc gacgtgtgaa cattgtggta cggaaaattt agtaatagaa   1320
ggtccgacga cgtgtggtta tttaccgacg aatgcggtag taaaaatgcc gtgtccggcg   1380
tgtcaagatc cggaaatagg tccggaacat tcggtagcgg attatcataa tcattcgaat   1440
atagaaacgc gtttacgtaa aggtggtcgt acgcgttgtt ttggtggttg tgtatttgcg   1500
tatgtaggtt gttataataa acgtgcgtat tgggtaccgc gtgcgtcggc ggatataggt   1560
tcgggtcata cgggtataac gggtgataat gtagaaacgt taaatgaaga tttattagaa   1620
atattatcgc gtgaacgtgt aaatataaat atagtaggtg attttcattt aaatgaagaa   1680
gtagcgataa tattagcgtc gttttcggcg tcgacgtcgg cgtttataga tacgataaaa   1740
tcgttagatt ataaatcgtt taaaacgata gtagaatcgt gtggtaatta taaagtaacg   1800
aaaggtaaac cggtaaaagg tgcgtggaat ataggtcaac aacgttcggt attaacgccg   1860
ttatgtggtt ttccgtcgca agcggcgggt gtaatacgtt cgatatttgc gcgtacgtta   1920
gatgcggcga atcattcgat accggattta caacgtgcgg cggtaacgat attagatggt   1980
atatcggaac aatcgttacg tttagtagat gcgatggtat atacgtcgga tttattaacg   2040
aattcggtaa taataatggc gtatgtaacg ggtggtttag tacaacaaac gtcgcaatgg   2100
ttatcgaatt tattaggtac gacggtagaa aaattacgtc cgatatttga atggatagaa   2160
gcgaaattat cggcgggtgt agaattttta aaagatgcgt gggaaatatt aaaatttta    2220
ataacgggtg tatttgatat agtaaaaggt caaatacaag tagcgtcgga taatataaaa   2280
gattgtgtaa aatgttttat agatgtagta aataaagcgt tagaaatgtg tatagatcaa   2340
gtaacgatag cgggtgcgaa attacgttcg ttaaatttag gtgaagtatt tatagcgcaa   2400
tcgaaaggtt tatatcgtca atgtatacgt ggtaaagaac aattacaatt attaatgccg   2460
ttaaaagcgc cgaaagaagt aacgttttta gaaggtgatt cgcatgatac ggtattaacg   2520
tcggaagaag tagtattaaa aaatggtgaa ttagaagcgt tagaaacgcc ggtagattcg   2580
tttacgaatg gtgcgatagt aggtacgccg gtatgtgtaa atggtttaat gttattagaa   2640
```

```
ataaaagata aagaacaata ttgtgcgtta tcgccgggtt tattagcgac gaataatgta   2700
tttcgtttaa aggtggtgc  gccgataaaa ggtgtaacgt ttggtgaaga tacggtatgg   2760
gaagtacaag gttataaaaa tgtacgtata acgtttgaat tagatgaacg tgtagataaa   2820
gtattaaatg aaaaatgttc ggtatatacg gtagaatcgg gtacggaagt aacggaattt   2880
gcgtgtgtag tagcggaagc ggtagtaaaa acgttacaac cggtatcgga tttattaacg   2940
aatatgggta tagatttaga tgaatggtcg gtagcgacgt tttatttatt tgatgatgcg   3000
ggtgaagaaa atttttcgtc gcgtatgtat tgttcgtttt atccgccgga tgaagaagaa   3060
gaagatgatg cggaatgtga agaagaagaa atagatgaaa cgtgtgaaca tgaatatggt   3120
acggaagatg attatcaagg tttaccgtta gaatttggtg cgtcggcgga aacggtacgt   3180
gtagaagaag aagaagaaga agattggtta gatgatacga cggaacaatc ggaaatagaa   3240
ccggaaccgg aaccgacgcc ggaagaaccg gtaaatcaat ttacgggtta tttaaaatta   3300
acggataatg tagcgataaa atgtgtagat atagtaaaag aagcgcaatc ggcgaatccg   3360
atggtaatag taaatgcggc gaatatacat ttaaaacatg gtggtggtgt agcgggtgcg   3420
ttaaataaag cgacgaatgg tgcgatgcaa aaagaatcgg atgattatat aaaattaaat   3480
ggtccgttaa cggtaggtgg ttcgtgttta ttatcgggtc ataatttagc gaaaaaatgt   3540
ttacatgtag taggtccgaa tttaaatgcg ggtgaagata tacaattatt aaaagcggcg   3600
tatgaaaatt ttaattcgca agatatatta ttagcgccgt tattatcggc gggtatattt   3660
ggtgcgaaac cgttacaatc gttacaagta tgtgtacaaa cggtacgtac gcaagtatat   3720
atagcggtaa atgataaagc gttatatgaa caagtagtaa tggattattt agataattta   3780
aaaccgcgtg tagaagcgcc gaaacaagaa gaaccgccga atacggaaga ttcgaaaacg   3840
gaagaaaaat cggtagtaca aaaaccggta gatgtaaaac cgaaaataaa agcgtgtata   3900
gatgaagtaa cgacgacgtt agaagaaacg aaatttttaa cgaataaatt attattattt   3960
gcggatataa atggtaaatt atatcatgat tcgcaaaata tgttacgtgg tgaagatatg   4020
tcgtttttag aaaaagatgc gccgtatatg gtaggtgatg taataacgtc gggtgatata   4080
acgtgtgtag taataccgtc gaaaaaagcg ggtggtacga cggaaatgtt atcgcgtgcg   4140
ttaaaaaaag taccggtaga tgaatatata acgacgtatc cgggtcaagg ttgtgcgggt   4200
tatacgttag aagaagcgaa aacggcgtta aaaaaatgta aatcggcgtt ttatgtatta   4260
ccgtcggaag cgccgaatgc gaaagaagaa atattaggta cggtatcgtg gaatttacgt   4320
gaaatgttag cgcatgcgga agaaacgcgt aaattaatgc cgatatgtat ggatgtacgt   4380
gcgataatgg cgacgataca acgtaaatat aaaggtataa aaatacaaga aggtatagta   4440
gattatggtg tacgtttttt tttttatacg tcgaaagaac cggtagcgtc gataataacg   4500
aaattaaatt cgttaaatga accgttagta acgatgccga taggttatgt aacgcatggt   4560
tttaatttag aagaagcggc gcgttgtatg cgttcgttaa aagcgccggc ggtagtatcg   4620
gtatcgtcgc cggatgcggt aacgacgtat aatggttatt taacgtcgtc gtcgaaaacg   4680
tcggaagaac attttgtaga aacggtatcg ttagcgggtt cgtatcgtga ttggtcgtat   4740
tcgggtcaac gtacggaatt aggtgtagaa tttttaaaac gtggtgataa aatagtatat   4800
catacgttag aatcgccggt agaatttcat ttagatggtg aagtattatc gttagataaa   4860
ttaaaatcgt tattatcgtt acgtgaagta aaaacgataa aagtatttac gacggtagat   4920
aatacgaatt tacatacgca attagtagat atgtcgatga cgtatggtca acaatttggt   4980
ccgacgtatt tagatggtgc ggatgtaacg aaaataaaac cgcatgtaaa tcatgaaggt   5040
```

```
aaaacgtttt ttgtattacc gtcggatgat acgttacgtt cggaagcgtt tgaatattat   5100
catacgttag atgaatcgtt tttaggtcgt tatatgtcgg cgttaaatca tacgaaaaaa   5160
tggaaatttc cgcaagtagg tggtttaacg tcgataaaat gggcggataa taattgttat   5220
ttatcgtcgg tattattagc gttacaacaa ttagaagtaa aatttaatgc gccggcgtta   5280
caagaagcgt attatcgtgc gcgtgcgggt gatgcggcga atttttgtgc gttaatatta   5340
gcgtattcga ataaaacggt aggtgaatta ggtgatgtac gtgaaacgat gacgcattta   5400
ttacaacatg cgaatttaga atcggcgaaa cgtgtattaa atgtagtatg taaacattgt   5460
ggtcaaaaaa cgacgacgtt aacgggtgta gaagcggtaa tgtatatggg tacgttatcg   5520
tatgataatt taaaaacggg tgtatcgata ccgtgtgtat gtggtcgtga tgcgacgcaa   5580
tatttagtac aacaagaatc gtcgtttgta atgatgtcgg cgccgccggc ggaatataaa   5640
ttacaacaag gtacgttttt atgtgcgaat gaatatacgg gtaattatca atgtggtcat   5700
tatacgcata taacggcgaa agaaacgtta tatcgtatag atggtgcgca tttaacgaaa   5760
atgtcggaat ataaaggtcc ggtaacggat gtattttata aagaaacgtc gtatacgacg   5820
acgataaaac cggtatcgta taaattagat ggtgtaacgt atacggaaat agaaccgaaa   5880
ttagatggtt attataaaaa agataatgcg tattatacgg aacaaccgat agatttagta   5940
ccgacgcaac cgttaccgaa tgcgtcgttt gataatttta aattaacgtg ttcgaatacg   6000
aaatttgcgg atgatttaaa tcaaatgacg ggttttacga aaccggcgtc gcgtgaatta   6060
tcggtaacgt tttttccgga tttaaatggt gatgtagtag cgatagatta tcgtcattat   6120
tcggcgtcgt ttaaaaaagg tgcgaaatta ttacataaac cgatagtatg gcatataaat   6180
caagcgacga cgaaaacgac gtttaaaccg aatacgtggt gtttacgttg tttatggtcg   6240
acgaaaccgg tagatacgtc gaattcgttt gaagtattag cggtagaaga tacgcaaggt   6300
atggataatt tagcgtgtga atcgcaacaa ccgacgtcgg aagaagtagt agaaaatccg   6360
acgatacaaa aagaagtaat agaatgtgat gtaaaaacga cggaagtagt aggtaatgta   6420
atattaaaac cgtcggatga aggtgtaaaa gtaacgcaag aattaggtca tgaagattta   6480
atggcggcgt atgtagaaaa tacgtcgata acgataaaaa aaccgaatga attatcgtta   6540
gcgttaggtt taaaaacgat agcgacgcat ggtatagcgg cgataaattc ggtaccgtgg   6600
tcgaaaatat tagcgtatgt aaaaccgttt ttaggtcaag cggcgataac gacgtcgaat   6660
tgtgcgaaac gtttagcgca acgtgtattt aataattata tgccgtatgt atttacgtta   6720
ttatttcaat tatgtacgtt tacgaaatcg acgaattcgc gtatacgtgc gtcgttaccg   6780
acgacgatag cgaaaaattc ggtaaaatcg gtagcgaaat tatgtttaga tgcgggtata   6840
aattatgtaa aatcgccgaa attttcgaaa ttatttacga tagcgatgtg gttattatta   6900
ttatcgatat gtttaggttc gttaatatgt gtaacggcgg cgtttggtgt attattatcg   6960
aattttggtg cgccgtcgta ttgtaatggt gtacgtgaat tatatttaaa ttcgtcgaat   7020
gtaacgacga tggatttttg tgaaggttcg tttccgtgtt cgatatgttt atcgggttta   7080
gattcgttag attcgtatcc ggcgttagaa acgatacaag taacgatatc gtcgtataaa   7140
ttagatttaa cgatattagg tttagcggcg gaatgggtat tagcgtatat gttatttacg   7200
aaattttttt atttattagg tttatcggcg ataatgcaag tatttttgg ttattttgcg   7260
tcgcatttta tatcgaattc gtggttaatg tggtttataa tatcgatagt acaaatggcg   7320
ccggtatcgg cgatggtacg tatgtatata ttttttgcgt cgttttatta tatatggaaa   7380
```

-continued

```
tcgtatgtac atataatgga tggttgtacg tcgtcgacgt gtatgatgtg ttataaacgt   7440
aatcgtgcga cgcgtgtaga atgtacgacg atagtaaatg gtatgaaacg ttcgttttat   7500
gtatatgcga atggtggtcg tggtttttgt aaaacgcata attggaattg tttaaattgt   7560
gatacgtttt gtacgggttc gacgtttata tcggatgaag tagcgcgtga tttatcgtta   7620
caatttaaac gtccgataaa tccgacggat caatcgtcgt atatagtaga ttcggtagcg   7680
gtaaaaaatg gtgcgttaca tttatatttt gataaagcgg gtcaaaaaac gtatgaacgt   7740
catccgttat cgcattttgt aaatttagat aatttacgtg cgaataatac gaaaggttcg   7800
ttaccgataa atgtaatagt atttgatggt aaatcgaaat gtgatgaatc ggcgtcgaaa   7860
tcggcgtcgg tatattattc gcaattaatg tgtcaaccga tattattatt agatcaagcg   7920
ttagtatcgg atgtaggtga ttcgacggaa gtatcggtaa aaatgtttga tgcgtatgta   7980
gatacgtttt cggcgacgtt ttcggtaccg atggaaaaat taaaagcgtt agtagcgacg   8040
gcgcattcgg aattagcgaa aggtgtagcg ttagatggtg tattatcgac gtttgtatcg   8100
gcggcgcgtc aaggtgtagt agatacggat gtagatacga aagatgtaat agaatgttta   8160
aaattatcgc atcattcgga tttagaagta acgggtgatt cgtgtaataa ttttatgtta   8220
acgtataata aagtagaaaa tatgacgccg cgtgatttag gtgcgtgtat agattgtaat   8280
gcgcgtcata taaatgcgca agtagcgaaa tcgcataatg tatcgttaat atggaatgta   8340
aaagattata tgtcgttatc ggaacaatta cgtaaacaaa tacgttcggc ggcgaaaaaa   8400
aataatatac cgtttcgttt aacgtgtgcg acgacgcgtc aagtagtaaa tgtaataacg   8460
acgaaaatat cgttaaaagg tggtaaaata gtatcgacgt gttttaaatt aatgttaaaa   8520
gcgacgttat tatgtgtatt agcggcgtta gtatgttata tagtaatgcc ggtacatacg   8580
ttatcgatac atgatggtta tacgaatgaa ataataggtt ataaagcgat acaagatggt   8640
gtaacgcgtg atataatatc gacggatgat tgttttgcga ataaacatgc gggttttgat   8700
gcgtggtttt cgcaacgtgg tggttcgtat aaaaatgata aatcgtgtcc ggtagtagcg   8760
gcgataataa cgcgtgaaat aggttttata gtaccgggtt taccgggtac ggtattacgt   8820
gcgataaatg gtgatttttt acatttttta ccgcgtgtat tttcggcggt aggtaatata   8880
tgttatacgc cgtcgaaatt aatagaatat tcggattttg cgacgtcggc gtgtgtatta   8940
gcggcggaat gtacgatatt taaagatgcg atgggtaaac cggtaccgta ttgttatgat   9000
acgaatttat tagaaggttc gatatcgtat tcggaattac gtccggatac gcgttatgta   9060
ttaatggatg gttcgataat acaatttccg aatacgtatt tagaaggttc ggtacgtgta   9120
gtaacgacgt ttgatgcgga atattgtcgt catggtacgt gtgaacgttc ggaagtaggt   9180
atatgtttat cgacgtcggg tcgttgggta ttaaataatg aacattatcg tgcgttatcg   9240
ggtgtatttt gtggtgtaga tgcgatgaat ttaatagcga atatatttac gccgttagta   9300
caaccggtag gtgcgttaga tgtatcggcg tcggtagtag cgggtggtat aatagcgata   9360
ttagtaacgt gtgcggcgta ttattttatg aaatttcgtc gtgtatttgg tgaatataat   9420
catgtagtag cggcgaatgc gttattattt ttaatgtcgt ttacgatatt atgtttagta   9480
ccggcgtatt cgtttttacc gggtgtatat tcggtatttt atttatattt aacgttttat   9540
tttacgaatg atgtatcgtt tttagcgcat ttacaatggt ttgcgatgtt ttcgccgata   9600
gtaccgtttt ggataacggc gatatatgta ttttgtatat cgttaaaaca ttgtcattgg   9660
ttttttaata attatttacg taaacgtgta atgtttaatg gtgtaacgtt ttcgacgttt   9720
gaagaagcgg cgttatgtac gtttttatta aataaagaaa tgtatttaaa attacgttcg   9780
```

```
gaaacgttat taccgttaac gcaatataat cgttatttag cgttatataa taaatataaa   9840
tatttttcgg gtgcgttaga tacgacgtcg tatcgtgaag cggcgtgttg tcatttagcg   9900
aaagcgttaa atgatttttc gaattcgggt gcggatgtat tatatcaacc gccgcaaacg   9960
tcgataacgt cggcggtatt acaatcgggt tttcgtaaaa tggcgtttcc gtcgggtaaa  10020
gtagaaggtt gtatggtaca agtaacgtgt ggtacgacga cgttaaatgg tttatggtta  10080
gatgatacgg tatattgtcc gcgtcatgta atatgtacgg cggaagatat gttaaatccg  10140
aattatgaag atttattaat acgtaaatcg aatcattcgt ttttagtaca agcgggtaat  10200
gtacaattac gtgtaatagg tcattcgatg caaaattgtt tattacgttt aaaagtagat  10260
acgtcgaatc cgaaaacgcc gaaatataaa tttgtacgta tacaaccggg tcaaacgttt  10320
tcggtattag cgtgttataa tggttcgccg tcgggtgtat atcaatgtgc gatgcgtccg  10380
aatcatacga taaaaggttc gtttttaaat ggttcgtgtg gttcggtagg ttttaatata  10440
gattatgatt gtgtatcgtt ttgttatatg catcatatgg aattaccgac gggtgtacat  10500
gcgggtacgg atttagaagg taaattttat ggtccgtttg tagatcgtca aacggcgcaa  10560
gcggcgggta cggatacgac gataacgtta aatgtattag cgtggttata tgcggcggta  10620
ataaatggtg atcgttggtt tttaaatcgt tttacgacga cgttaaatga ttttaattta  10680
gtagcgatga aatataatta tgaaccgtta acgcaagatc atgtagatat attaggtccg  10740
ttatcggcgc aaacgggtat agcggtatta gatatgtgtg cggcgttaaa agaattatta  10800
caaaatggta tgaatggtcg tacgatatta ggttcgacga tattagaaga tgaatttacg  10860
ccgtttgatg tagtacgtca atgttcgggt gtaacgtttc aaggtaaatt taaaaaaata  10920
gtaaaaggta cgcatcattg gatgttatta acgtttttaa cgtcgttatt aatattagta  10980
caatcgacgc aatggtcgtt attttttttt gtatatgaaa atgcgttttt accgtttacg  11040
ttaggtataa tggcgatagc ggcgtgtgcg atgttattag taaaacataa acatgcgttt  11100
ttatgtttat ttttattacc gtcgttagcg acggtagcgt attttaatat ggtatatatg  11160
ccggcgtcgt gggtaatgcg tataatgacg tggttagaat tagcggatac gtcgttatcg  11220
ggttatcgtt taaaagattg tgtaatgtat gcgtcggcgt tagtattatt aatattaatg  11280
acggcgcgta cggtatatga tgatgcggcg cgtcgtgtat ggacgttaat gaatgtaata  11340
acgttagtat ataaagtata ttatggtaat gcgttagatc aagcgatatc gatgtgggcg  11400
ttagtaatat cggtaacgtc gaattattcg ggtgtagtaa cgacgataat gtttttagcg  11460
cgtgcgatag tatttgtatg tgtagaatat tatccgttat tatttataac gggtaatacg  11520
ttacaatgta taatgttagt atattgtttt ttaggttatt gttgttgttg ttattttggt  11580
ttattttgtt tattaaatcg ttattttcgt ttaacgttag gtgtatatga ttatttagta  11640
tcgacgcaag aatttcgtta tatgaattcg caaggtttat taccgccgaa atcgtcgata  11700
gatgcgttta aattaaatat aaaattatta ggtataggtg gtaaaccgtg tataaaagta  11760
gcgacggtac aatcgaaaat gtcggatgta aaatgtacgt cggtagtatt attatcggta  11820
ttacaacaat tacgtgtaga atcgtcgtcg aaattatggg cgcaatgtgt acaattacat  11880
aatgatatat tattagcgaa agatacgacg gaagcgtttg aaaaaatggt atcgttatta  11940
tcggtattat tatcgatgca aggtgcggta gatataaatc gtttatgtga agaaatgtta  12000
gataatcgtg cgacgttaca agcgatagcg tcggaatttt cgtcgttacc gtcgtatgcg  12060
gcgtatgcga cggcgcaaga agcgtatgaa caagcggtag cgaatggtga ttcggaagta  12120
```

```
gtattaaaaa aattaaaaaa atcgttaaat gtagcgaaat cggaatttga tcgtgatgcg  12180
gcgatgcaac gtaaattaga aaaaatggcg gatcaagcga tgacgcaaat gtataaacaa  12240
gcgcgttcgg aagataaacg tgcgaaagta acgtcggcga tgcaaacgat gttatttacg  12300
atgttacgta aattagataa tgatgcgtta aataatataa taaataatgc gcgtgatggt  12360
tgtgtaccgt taaatataat accgttaacg acggcggcga aattaatggt agtagtaccg  12420
gattatggta cgtataaaaa tacgtgtgat ggtaatacgt ttacgtatgc gtcggcgtta  12480
tgggaaatac aacaagtagt agatgcggat tcgaaaatag tacaattatc ggaaataaat  12540
atggataatt cgccgaattt agcgtggccg ttaatagtaa cggcgttacg tgcgaattcg  12600
gcggtaaaat tacaaaataa tgaattatcg ccggtagcgt tacgtcaaat gtcgtgtgcg  12660
gcgggtacga cgcaaacggc gtgtacggat gataatgcgt tagcgtatta taataattcg  12720
aaaggtggtc gttttgtatt agcgttatta tcggatcatc aagatttaaa atgggcgcgt  12780
tttccgaaat cggatggtac gggtacgata tatacggaat tagaaccgcc gtgtcgtttt  12840
gtaacggata cgccgaaagg tccgaaagta aaatatttat attttataaa aggtttaaat  12900
aatttaaatc gtggtatggt attaggttcg ttagcggcga cggtacgttt acaagcgggt  12960
aatgcgacgg aagtaccggc gaattcgacg gtattatcgt tttgtgcgtt tgcggtagat  13020
ccggcgaaag cgtataaaga ttatttagcg tcgggtggtc aaccgataac gaattgtgta  13080
aaaatgttat gtacgcatac gggtacgggt caagcgataa cggtaacgcc ggaagcgaat  13140
atggatcaag aatcgtttgg tggtgcgtcg tgttgtttat attgtcgttg tcatatagat  13200
catccgaatc cgaaaggttt ttgtgattta aaaggtaaat atgtacaaat accgacgacg  13260
tgtgcgaatg atccggtagg ttttacgtta cgtaatacgg tatgtacggt atgtggtatg  13320
tggaaaggtt atggttgttc gtgtgatcaa ttacgtgaac cgttaatgca atcggcggat  13380
gcgtcgacgt ttttaaatgg gtttgcggtg taagtgcggc gcgtttaacg ccgtgtggta  13440
cgggtacgtc gacggatgta gtatatcgtg cgtttgatat atataatgaa aaagtagcgg  13500
gttttgcgaa atttttaaaa acgaattgtt gtcgttttca agaaaaagat gaagaaggta  13560
atttattaga ttcgtatttt gtagtaaaac gtcatacgat gtcgaattat caacatgaag  13620
aaacgatata taatttagta aaagattgtc cggcggtagc ggtacatgat tttttaaat  13680
ttcgtgtaga tggtgatatg gtaccgcata tatcgcgtca acgtttaacg aaatatacga  13740
tggcggattt agtatatgcg ttacgtcatt ttgatgaagg taattgtgat acgttaaaag  13800
aaatattagt aacgtataat tgttgtgatg atgattattt taataaaaaa gattggtatg  13860
attttgtaga aaatccggat atattacgtg tatatgcgaa tttaggtgaa cgtgtacgtc  13920
aatcgttatt aaaaacggta caattttgtg atgcgatgcg tgatgcgggt atagtaggtg  13980
tattaacgtt agataatcaa gatttaaatg gtaattggta tgattttggt gattttgtac  14040
aagtagcgcc gggttgtggt gtaccgatag tagattcgta ttattcgtta ttaatgccga  14100
tattaacgtt aacgcgtgcg ttagcggcgg aatcgcatat ggatgcggat ttagcgaaac  14160
cgttaataaa atgggattta ttaaaatatg attttacgga agaacgttta tgtttatttg  14220
atcgttattt taaatattgg gatcaaacgt atcatccgaa ttgtataaat tgtttagatg  14280
atcgttgtat attacattgt gcgaatttta atgtattatt ttcgacggta tttccgccga  14340
cgtcgtttgg tccgttagta cgtaaaatat ttgtagatgg tgtaccgttt gtagtatcga  14400
cgggttatca ttttcgtgaa ttaggtgtag tacataatca agatgtaaat ttacattcgt  14460
cgcgtttatc gtttaaagaa ttattagtat atgcggcgga tccggcgatg catgcggcgt  14520
```

```
cgggtaattt attattagat aaacgtacga cgtgtttttc ggtagcggcg ttaacgaata  14580
atgtagcgtt tcaaacggta aaaccgggta attttaataa agatttttat gattttgcgg  14640
tatcgaaagg tttttttaaa gaaggttcgt cggtagaatt aaaacatttt ttttttgcgc  14700
aagatggtaa tgcggcgata tcggattatg attattatcg ttataattta ccgacgatgt  14760
gtgatatacg tcaattatta tttgtagtag aagtagtaga taaatatttt gattgttatg  14820
atggtggttg tataaatgcg aatcaagtaa tagtaaataa tttagataaa tcggcgggtt  14880
ttccgtttaa taaatggggt aaagcgcgtt tatattatga ttcgatgtcg tatgaagatc  14940
aagatgcgtt atttgcgtat acgaaacgta atgtaatacc gacgataacg caaatgaatt  15000
taaaatatgc gatatcggcg aaaaatcgtg cgcgtacggt agcgggtgta tcgatatgtt  15060
cgacgatgac gaatcgtcaa tttcatcaaa aattattaaa atcgatagcg gcgacgcgtg  15120
gtgcgacggt agtaataggt acgtcgaaat tttatggtgg ttggcataat atgttaaaaa  15180
cggtatattc ggatgtagaa acgccgcatt taatgggttg ggattatccg aaatgtgatc  15240
gtgcgatgcc gaatatgtta cgtataatgg cgtcgttagt attagcgcgt aaacataata  15300
cgtgttgtaa tttatcgcat cgtttttatc gtttagcgaa tgaatgtgcg caagtattat  15360
cggaaatggt aatgtgtggt ggttcgttat atgtaaaacc gggtggtacg tcgtcgggtg  15420
atgcgacgac ggcgtatgcg aattcggtat ttaatatatg tcaagcggta acggcgaatg  15480
taaatgcgtt attatcgacg gatggtaata aaatagcgga taaatatgta cgtaatttac  15540
aacatcgttt atatgaatgt ttatatcgta atcgtgatgt agatcatgaa tttgtagatg  15600
aattttatgc gtatttacgt aaacattttt cgatgatgat attatcggat gatgcggtag  15660
tatgttataa ttcgaattat gcggcgcaag gtttagtagc gtcgataaaa aattttaaag  15720
cggtattata ttatcaaaat aatgtattta tgtcggaagc gaaatgttgg acggaaacgg  15780
atttaacgaa aggtccgcat gaattttgtt cgcaacatac gatgttagta aaacaaggtg  15840
atgattatgt atatttaccg tatccggatc cgtcgcgtat attaggtgcg ggttgttttg  15900
tagatgatat agtaaaaacg gatggtacgt taatgataga acgttttgta tcgttagcga  15960
tagatgcgta tccgttaacg aaacatccga atcaagaata tgcggatgta tttcatttat  16020
atttacaata tatacgtaaa ttacatgatg aattaacggg tcatatgtta gatatgtatt  16080
cggtaatgtt aacgaatgat aatacgtcgc gttattggga accggaattt tatgaagcga  16140
tgtatacgcc gcatacggta ttacaagcgg taggtgcgtg tgtattatgt aattcgcaaa  16200
cgtcgttacg ttgtggtgcg tgtatacgtc gtccgttttt atgttgtaaa tgttgttatg  16260
atcatgtaat atcgacgtcg cataaattag tattatcggt aaatccgtat gtatgtaatg  16320
cgccgggttg tgatgtaacg gatgtaacgc aattatattt aggtggtatg tcgtattatt  16380
gtaaatcgca taaaccgccg atatcgtttc cgttatgtgc gaatggtcaa gtatttggtt  16440
tatataaaaa tacgtgtgta ggttcggata atgtaacgga ttttaatgcg atagcgacgt  16500
gtgattggac gaatgcgggt gattatatat tagcgaatac gtgtacggaa cgtttaaaat  16560
tatttgcggc ggaaacgtta aaagcgacgg aagaaacgtt taaattatcg tatggtatag  16620
cgacggtacg tgaagtatta tcggatcgtg aattacattt atcgtgggaa gtaggtaaac  16680
cgcgtccgcc gttaaatcgt aattatgtat ttacgggtta tcgtgtaacg aaaaattcga  16740
aagtacaaat aggtgaatat acgtttgaaa aaggtgatta tggtgatgcg gtagtatatc  16800
gtggtacgac gacgtataaa ttaaatgtag gtgattattt tgtattaacg tcgcatacgg  16860
```

```
taatgccgtt atcggcgccg acgttagtac cgcaagaaca ttatgtacgt ataacgggtt  16920
tatatccgac gttaaatata tcggatgaat tttcgtcgaa tgtagcgaat tatcaaaaag  16980
taggtatgca aaaatattcg acgttacaag gtccgccggg tacgggtaaa tcgcattttg  17040
cgataggttt agcgttatat tatccgtcgg cgcgtatagt atatacggcg tgttcgcatg  17100
cggcggtaga tgcgttatgt gaaaaagcgt taaaatattt accgatagat aaatgttcgc  17160
gtataatacc ggcgcgtgcg cgtgtagaat gttttgataa atttaaagta aattcgacgt  17220
tagaacaata tgtattttgt acggtaaatg cgttaccgga aacgacggcg gatatagtag  17280
tatttgatga aatatcgatg gcgacgaatt atgatttatc ggtagtaaat gcgcgtttac  17340
gtgcgaaaca ttatgtatat ataggtgatc cggcgcaatt accggcgccg cgtacgttat  17400
taacgaaagg tacgttagaa ccggaatatt ttaattcggt atgtcgttta atgaaaacga  17460
taggtccgga tatgttttta ggtacgtgtc gtcgttgtcc ggcggaaata gtagatacgg  17520
tatcggcgtt agtatatgat aataaattaa aagcgcataa agataaatcg gcgcaatgtt  17580
ttaaaatgtt ttataaaggt gtaataacgc atgatgtatc gtcggcgata aatcgtccgc  17640
aaataggtgt agtacgtgaa tttttaacgc gtaatccggc gtggcgtaaa gcggtattta  17700
tatcgccgta taattcgcaa aatgcggtag cgtcgaaaat attaggttta ccgacgcaaa  17760
cggtagattc gtcgcaaggt tcggaatatg attatgtaat atttacgcaa acgacggaaa  17820
cggcgcattc gtgtaatgta aatcgtttta atgtagcgat aacgcgtgcg aaaataggta  17880
tattatgtat aatgtcggat cgtgatttat atgataaatt acaatttacg tcgttagaaa  17940
taccgcgtcg taatgtagcg acgttacaag cggaaaatgt aacgggttta tttaaagatt  18000
gttcgaaaat aataacgggt ttacatccga cgcaagcgcc gacgcattta tcggtagata  18060
taaaatttaa aacggaaggt ttatgtgtag atataccggg tataccgaaa gatatgacgt  18120
atcgtcgttt aatatcgatg atgggtttta aaatgaatta tcaagtaaat ggttatccga  18180
atatgtttat aacgcgtgaa gaagcgatac gtcatgtacg tgcgtggata ggttttgatg  18240
tagaaggttg tcatgcgacg cgtgatgcgg taggtacgaa tttaccgtta caattaggtt  18300
tttcgacggg tgtaaattta gtagcggtac cgacgggtta tgtagatacg gaaaataata  18360
cggaatttac gcgtgtaaat gcgaaaccgc cgccgggtga tcaatttaaa catttaatac  18420
cgttaatgta taaaggttta ccgtggaatg tagtacgtat aaaaatagta caaatgttat  18480
cggatacgtt aaaaggttta tcggatcgtg tagtatttgt attatgggcg catggttttg  18540
aattaacgtc gatgaaatat tttgtaaaaa taggtccgga acgtacgtgt tgtttatgtg  18600
ataaacgtgc gacgtgtttt tcgacgtcgt cggatacgta tgcgtgttgg aatcattcgg  18660
taggttttga ttatgtatat aatccgttta tgatagatgt acaacaatgg ggttttacgg  18720
gtaatttaca atcgaatcat gatcaacatt gtcaagtaca tggtaatgcg catgtagcgt  18780
cgtgtgatgc gataatgacg cgttgtttag cggtacatga atgttttgta aaacgtgtag  18840
attggtcggt agaatatccg ataataggtg atgaattacg tgtaaattcg gcgtgtcgta  18900
aagtacaaca tatggtagta aaatcggcgt tattagcgga taaatttccg gtattacatg  18960
atataggtaa tccgaaagcg ataaaatgtg taccgcaagc ggaagtagaa tggaaatttt  19020
atgatgcgca accgtgttcg gataaagcgt ataaaataga agaattattt tattcgtatg  19080
cgacgcatca tgataaattt acggatggtg tatgtttatt ttggaattgt aatgtagatc  19140
gttatccggc gaatgcgata gtatgtcgtt ttgatacgcg tgtattatcg aatttaaatt  19200
taccgggttg tgatggtggt tcgttatatg taaataaaca tgcgtttcat acgccggcgt  19260
```

ttgataaatc ggcgtttacg aatttaaaac aattaccgtt tttttattat tcggattcgc 19320
cgtgtgaatc gcatggtaaa caagtagtat cggatataga ttatgtaccg ttaaaatcgg 19380
cgacgtgtat aacgcgttgt aatttaggtg gtgcggtatg tcgtcatcat gcgaatgaat 19440
atcgtcaata tttagatgcg tataatatga tgatatcggc gggtttttcg ttatggatat 19500
ataaacaatt tgatacgtat aatttatgga atacgtttac gcgtttacaa tcgttagaaa 19560
atgtagcgta taatgtagta aataaaggtc attttgatgg tcatgcgggt gaagcgccgg 19620
tatcgataat aaataatgcg gtatatacga aagtagatgg tatagatgta gaaatatttg 19680
aaaataaaac gacgttaccg gtaaatgtag cgtttgaatt atgggcgaaa cgtaatataa 19740
aaccggtacc ggaaataaaa atattaaata atttaggtgt agatatagcg gcgaatacgg 19800
taatatggga ttataaacgt gaagcgccgg cgcatgtatc gacgataggt gtatgtacga 19860
tgacggatat agcgaaaaaa ccgacggaat cggcgtgttc gtcgttaacg gtattatttg 19920
atggtcgtgt agaaggtcaa gtagatttat ttcgtaatgc gcgtaatggt gtattaataa 19980
cggaaggttc ggtaaaaggt ttaacgccgt cgaaaggtcc ggcgcaagcg tcggtaaatg 20040
gtgtaacgtt aataggtgaa tcggtaaaaa cgcaatttaa ttattttaaa aaagtagatg 20100
gtataataca acaattaccg gaaacgtatt ttacgcaatc gcgtgattta gaagatttta 20160
aaccgcgttc gcaaatggaa acggattttt tagaattagc gatggatgaa tttatacaac 20220
gttataaatt agaaggttat gcgtttgaac atatagtata tggtgatttt tcgcatggtc 20280
aattaggtgg tttacattta atgataggtt tagcgaaacg ttcgcaagat tcgccgttaa 20340
aattagaaga ttttataccg atggattcga cggtaaaaaa ttattttata acggatgcgc 20400
aaacgggttc gtcgaaatgt gtatgttcgg taatagattt attattagat gattttgtag 20460
aaataataaa atcgcaagat ttatcggtaa tatcgaaagt agtaaaagta acgatagatt 20520
atgcggaaat atcgtttatg ttatggtgta aagatggtca tgtagaaacg ttttatccga 20580
aattacaagc gtcgcaagcg tggcaaccgg gtgtagcgat gccgaattta tataaaatgc 20640
aacgtatgtt attagaaaaa tgtgatttac aaaattatgg tgaaaatgcg gtaataccga 20700
aaggtataat gatgaatgta gcgaaatata cgcaattatg tcaatattta aatacgttaa 20760
cgttagcggt accgtataat atgcgtgtaa tacattttgg tgcgggttcg gataaaggtg 20820
tagcgccggg tacggcggta ttacgtcaat ggttaccgac gggtacgtta ttagtagatt 20880
cggatttaaa tgattttgta tcggatgcgg attcgacgtt aataggtgat tgtgcgacgg 20940
tacatacggc gaataaatgg gatttaataa tatcggatat gtatgatccg cgtacgaaac 21000
atgtaacgaa agaaaatgat tcgaaagaag gtttttttac gtatttatgt ggttttataa 21060
aacaaaaatt agcgttaggt ggttcgatag cggtaaaaat aacggaacat tcgtggaatg 21120
cggatttata taaattaatg ggtcattttt cgtggtggac ggcgtttgta acgaatgtaa 21180
atgcgtcgtc gtcggaagcg tttttaatag gtgcgaatta tttaggtaaa ccgaaagaac 21240
aaatagatgg ttatacgatg catgcgaatt atatattttg gcgtaatacg aatccgatac 21300
aattatcgtc gtattcgtta tttgatatgt cgaaatttcc gttaaaatta cgtggtacgg 21360
cggtaatgtc gttaaaagaa aatcaaataa atgatatgat atattcgtta ttagaaaaag 21420
gtcgtttaat aatacgtgaa aataatcgtg tagtagtatc gtcggatata ttagtaaata 21480
attaaacgaa catgtttata tttttattat ttttaacgtt aacgtcgggt tcggatttag 21540
atcgttgtac gacgtttgat gatgtacaag cgccgaatta tacgcaacat acgtcgtcga 21600
tgcgtggtgt atattatccg gatgaaatat ttcgttcgga tacgttatat ttaacgcaag 21660
atttattttt accgttttat tcgaatgtaa cgggttttca tacgataaat catacgtttg 21720
gtaatccggt aataccgttt aaagatggta tatattttgc ggcgacggaa aaatcgaatg 21780
tagtacgtgg ttgggtattt ggttcgacga tgaataataa atcgcaatcg gtaataataa 21840
taaataattc gacgaatgta gtaatacgtg cgtgtaattt tgaattatgt gataatccgt 21900
tttttgcggt atcgaaaccg atgggtacgc aaacgcatac gatgatattt gataatgcgt 21960
ttaattgtac gtttgaatat atatcggatg cgttttcgtt agatgtatcg gaaaaatcgg 22020
gtaattttaa acatttacgt gaatttgtat ttaaaaataa agatggtttt ttatatgtat 22080
ataaaggtta tcaaccgata gatgtagtac gtgatttacc gtcgggtttt aatacgttaa 22140
aaccgatatt taaattaccg ttaggtataa atataacgaa ttttcgtgcg atattaacgg 22200
cgttttcgcc ggcgcaagat atatggggta cgtcggcggc ggcgtatttt gtaggttatt 22260
taaaaccgac gacgtttatg ttaaaatatg atgaaaatgg tacgataacg gatgcggtag 22320
attgttcgca aaatccgtta gcggaattaa aatgttcggt aaaatcgttt gaaatagata 22380
aaggtatata tcaaacgtcg aattttcgtg tagtaccgtc gggtgatgta gtacgttttc 22440
cgaatataac gaatttatgt ccgtttggtg aagtatttaa tgcgacgaaa tttccgtcgg 22500
tatatgcgtg ggaacgtaaa aaaatatcga attgtgtagc ggattattcg gtattatata 22560
attcgacgtt tttttcgacg tttaaatgtt atggtgtatc ggcgacgaaa ttaaatgatt 22620
tatgtttttc gaatgtatat gcggattcgt ttgtagtaaa aggtgatgat gtacgtcaaa 22680
tagcgccggg tcaaacgggt gtaatagcgg attataatta taaattaccg gatgatttta 22740
tgggttgtgt attagcgtgg aatacgcgta atatagatgc gacgtcgacg ggtaattata 22800
attataaata tcgttattta cgtcatggta aattacgtcc gtttgaacgt gatatatcga 22860
atgtaccgtt ttcgccggat ggtaaaccgt gtacgccgcc ggcgttaaat tgttattggc 22920
cgttaaatga ttatggtttt tatacgacga cgggtatagg ttatcaaccg tatcgtgtag 22980
tagtattatc gtttgaatta ttaaatgcgc cggcgacggt atgtggtccg aaattatcga 23040
cggatttaat aaaaaatcaa tgtgtaaatt ttaattttaa tggtttaacg ggtacgggtg 23100
tattaacgcc gtcgtcgaaa cgttttcaac cgtttcaaca atttggtcgt gatgtatcgg 23160
attttacgga ttcggtacgt gatccgaaaa cgtcggaaat attagatata tcgccgtgtg 23220
cgtttggtgg tgtatcggta ataacgccgg gtacgaatgc gtcgtcggaa gtagcggtat 23280
tatatcaaga tgtaaattgt acggatgtat cgacggcgat acatgcggat caattaacgc 23340
cggcgtggcg tatatattcg acgggtaata atgtatttca aacgcaagcg ggttgtttaa 23400
taggtgcgga acatgtagat acgtcgtatg aatgtgatat accgataggt gcgggtatat 23460
gtgcgtcgta tcatacggta tcgttattac gttcgacgtc gcaaaaatcg atagtagcgt 23520
atacgatgtc gttaggtgcg gattcgtcga tagcgtattc gaataatacg atagcgatac 23580
cgacgaattt ttcgatatcg ataacgacgg aagtaatgcc ggtatcgatg gcgaaaacgt 23640
cggtagattg taatatgtat atatgtggtg attcgacgga atgtgcgaat ttattattac 23700
aatatggttc gttttgtacg caattaaatc gtgcgttatc gggtatagcg gcggaacaag 23760
atcgtaatac gcgtgaagta tttgcgcaag taaaacaaat gtataaaacg ccgacgttaa 23820
aatattttgg tggttttaat ttttcgcaaa tattaccgga tccgttaaaa ccgacgaaac 23880
gttcgtttat agaagattta ttatttaata aagtaacgtt agcggatgcg ggttttatga 23940
aacaatatgg tgaatgttta ggtgatataa atgcgcgtga tttaatatgt gcgcaaaaat 24000

```
ttaatggttt aacggtatta ccgccgttat taacggatga tatgatagcg gcgtatacgg  24060
cggcgttagt atcgggtacg gcgacggcgg gttggacgtt tggtgcgggt gcggcgttac  24120
aaataccgtt tgcgatgcaa atggcgtatc gttttaatgg tataggtgta acgcaaaatg  24180
tattatatga aaatcaaaaa caaatagcga atcaatttaa taaagcgata tcgcaaatac  24240
aagaatcgtt aacgacgacg tcgacggcgt taggtaaatt acaagatgta gtaaatcaaa  24300
atgcgcaagc gttaaatacg ttagtaaaac aattatcgtc gaattttggt gcgatatcgt  24360
cggtattaaa tgatatatta tcgcgtttag ataaagtaga agcggaagta caaatagatc  24420
gtttaataac gggtcgttta caatcgttac aaacgtatgt aacgcaacaa ttaatacgtg  24480
cggcggaaat acgtgcgtcg gcgaatttag cggcgacgaa aatgtcggaa tgtgtattag  24540
gtcaatcgaa acgtgtagat ttttgtggta aaggttatca tttaatgtcg tttccgcaag  24600
cggcgccgca tggtgtagta tttttacatg taacgtatgt accgtcgcaa gaacgtaatt  24660
ttacgacggc gccggcgata tgtcatgaag gtaaagcgta ttttccgcgt gaaggtgtat  24720
ttgtatttaa tggtacgtcg tggtttataa cgcaacgtaa tttttttcg ccgcaaataa  24780
taacgacgga taatacgttt gtatcgggta attgtgatgt agtaataggt ataataaata  24840
atacggtata tgatccgtta caaccggaat tagattcgtt taaagaagaa ttagataaat  24900
attttaaaaa tcatacgtcg ccggatgtag atttaggtga tatatcgggt ataaatgcgt  24960
cggtagtaaa tatacaaaaa gaaatagatc gtttaaatga agtagcgaaa aatttaaatg  25020
aatcgttaat agatttacaa gaattaggta aatatgaaca atatataaaa tggccgtggt  25080
atgtatggtt aggttttata gcgggtttaa tagcgatagt aatggtaacg atattattat  25140
gttgtatgac gtcgtgttgt tcgtgtttaa aaggtgcgtg ttcgtgtggt tcgtgttgta  25200
aatttgatga agatgattcg gaaccggtat taaaaggtgt aaaattacat tatacgtaaa  25260
cgaacttatg gatttgttta tgagattttt tactcttaga tcaattactg cacagccagt  25320
aaaaattgac aatgcttctc ctgcaagtac tgttcatgct acagcaacga taccgctaca  25380
agcctcactc cctttcggat ggcttgttat tggcgttgca tttcttgctg tttttcagag  25440
cgctaccaaa ataattgcgc tcaataaaag atggcagcta gccctttata agggcttcca  25500
gttcatttgc aatttactgc tgctatttgt taccatctat tcacatcttt tgcttgtcgc  25560
tgcaggtatg gaggcgcaat tttgtacct ctatgccttg atatattttc tacaatgcat  25620
caacgcatgt agaattatta tgagatgttg gctttgttgg aagtgcaaat ccaagaaccc  25680
attactttat gatgccaact actttgtttg ctggcacaca cataactatg actactgtat  25740
accatataac agtgtcacag atacaattgt cgttactgaa ggtgacggca tttcaacacc  25800
aaaactcaaa gaagactacc aaattggtgg ttattctgag gataggcact caggtgttaa  25860
agactatgtc gttgtacatg gctatttcac cgaagtttac taccagcttg agtctacaca  25920
aattactaca gacactggta ttgaaaatgc tacattcttc atctttaaca agcttgttaa  25980
agacccaccg aatgtgcaaa tacacacaat cgacggctct tcaggagttg ctaatccagc  26040
aatggatcca atttatgatg agccgacgac gactactagc gtgcctttgt aagcacaaga  26100
aagtgagtac gaacttatgt actcattcgt ttcggaagaa acaggtacgt taatagttaa  26160
tagcgtactt ctttttcttg ctttcgtggt attcttgcta gtcacactag ccatccttac  26220
tgcgcttcga ttgtgtgcgt actgctgcaa tattgttaac gtgagtttag taaaaccaac  26280
ggtttacgtc tactcgcgtg ttaaaaatct gaactcttct gaaggagttc ctgatcttct  26340
```

-continued

```
ggtctaaacg aactaactat tattattatt ctgtttggaa ctttaacatt gcttatcatg  26400
gcggataatg gtacgataac ggtagaagaa ttaaaacaat tattagaaca atggaattta  26460
gtaataggtt ttttattttt agcgtggata atgttattac aatttgcgta ttcgaatcgt  26520
aatcgttttt tatatataat aaaattagta tttttatggt tattatggcc ggtaacgtta  26580
gcgtgttttg tattagcggc ggtatatcgt ataaattggg taacgggtgg tatagcgata  26640
gcgatggcgt gtatagtagg tttaatgtgg ttatcgtatt ttgtagcgtc gtttcgttta  26700
tttgcgcgta cgcgttcgat gtggtcgttt aatccggaaa cgaatatatt attaaatgta  26760
ccgttacgtg gtacgatagt aacgcgtccg ttaatggaat cggaattagt aataggtgcg  26820
gtaataatac gtggtcattt acgtatggcg ggtcattcgt taggtcgttg tgatataaaa  26880
gatttaccga aagaaataac ggtagcgacg tcgcgtacgt tatcgtatta taaattaggt  26940
gcgtcgcaac gtgtaggtac ggattcgggt tttgcggcgt ataatcgtta tcgtataggt  27000
aattataaat taaatacgga tcatgcgggt tcgaatgata atatagcgtt attagtacaa  27060
taagtgacaa cagatgtttc atcttgttga cttccaggtt acaatagcag agatattgat  27120
tatcattatg aggactttca ggattgctat ttggaatctt gacgttataa taagttcaat  27180
agtgagacaa ttatttaagc ctctaactaa gaagaattat tcggagttag atgatgaaga  27240
acctatggag ttagattatc cataaaacga acatgaaaat tattctcttc ctgacattga  27300
ttgtatttac atcttgcgag ctatatcact atcaggagtg tgttagaggt acgactgtac  27360
tactaaaaga accttgccca tcaggaacat acgagggcaa ttcaccattt caccctcttg  27420
ctgacaataa atttgcacta acttgcacta gcacacactt tgcttttgct tgtgctgacg  27480
gtactcgaca tacctatcag ctgcgtgcaa gatcagtttc accaaaactt ttcatcagac  27540
aagaggaggt tcaacaagag ctctactcgc cactttttct cattgttgct gctctagtat  27600
ttttaatact ttgcttcacc attaagagaa agacagaatg aatgagctca ctttaattga  27660
cttctatttg tgctttttag cctttctgct attccttgtt ttaataatgc ttattatatt  27720
ttggttttca ctcgaaatcc aggatctaga agaaccttgt accaaagtct aaacgaacat  27780
gaaacttctc attgttttga cttgtatttc tctatgcagt tgcatatgca ctgtagtaca  27840
gcgctgtgca tctaataaac ctcatgtgct tgaagatcct tgtaaggtac aacactaggg  27900
gtaatactta tagcactgct tggctttgtg ctctaggaaa ggttttacct tttcatagat  27960
ggcacactat ggttcaaaca tgcacaccta atgttactat caactgtcaa gatccagctg  28020
gtggtgcgct tatagctagg tgttggtacc ttcatgaagg tcaccaaact gctgcattta  28080
gagacgtact tgttgtttta aataaacgaa caaattaaaa tgtctgataa tggaccccaa  28140
tcaaaccaac gtagtgcccc ccgcattaca tttggtggac ccacagattc aactgacaat  28200
aaccagaatg gaggacgcaa tggggcaagg ccaaaacagc gccgaccccca aggtttaccc  28260
aataatactg cgtcttggtt cacagctctc actcagcatg gcaaggagga acttagattc  28320
cctcgaggcc agggcgttcc aatcaacacc aatagtggtc cagatgacca aattggctac  28380
taccgaagag ctacccgacg agttcgtggt ggtgacggca aaatgaaaga gctcagcccc  28440
agatggtact tctattacct aggaactggc ccagaagctt cacttcccta cggcgctaac  28500
aaagaaggca tcgtatgggt tgcaactgag ggagccttga atacacccaa agaccacatt  28560
ggcacccgca atcctaataa caatgctgcc accgtgctac aacttcctca aggaacaaca  28620
ttgccaaaag gcttctacgc agagggaagc agaggcggca gtcaagcctc ttctcgctcc  28680
tcatcacgta gtcgcggtaa ttcaagaaat tcaactcctg gcagcagtag gggaaattct  28740
```

cctgctcgaa tggctagcgg aggtggtgaa actgccctcg cgctattgct gctagacaga 28800
ttgaaccagc ttgagagcaa agtttctggt aaaggccaac aacaacaagg ccaaactgtc 28860
actaagaaat ctgctgctga ggcatctaaa aagcctcgcc aaaaacgtac tgccacaaaa 28920
cagtacaacg tcactcaagc atttgggaga cgtggtccag aacaaaccca aggaaatttc 28980
ggggaccaag acctaatcag acaaggaact gattacaaac attggccgca aattgcacaa 29040
tttgctccaa gtgcctctgc attctttgga atgtcacgca ttggcatgga agtcacacct 29100
tcgggaacat ggctgactta tcatggagcc attaaattgg atgacaaaga tccacaattc 29160
aaagacaacg tcatactgct gaacaagcac attgacgcat acaaaacatt cccaccaaca 29220
gagcctaaaa aggacaaaaa gaaaaagact gatgaagctc agcctttgcc gcagagacaa 29280
aagaagcagc ccactgtgac tcttcttcct gcggctgaca tggatgattt ctccagacaa 29340
cttcaaaatt ccatgagtgg agcttctgct gattcaactc aggcataaac actcatgatg 29400
accacacaag gcagatgggc tatgtaaacg ttttcgcaat tccgtttacg atacatagtc 29460
tactcttgtg cagaatgaat tctcgtaact aaacagcaca agtaggttta gttaacttta 29520
atctcacata gcaatcttta atcaatgtgt aacattaggg aggacttgaa agagccacca 29580
cattttcatc gaggccacgc ggagtacgat cgagggtaca gtgaataatg ctagggagag 29640
ctgcctatat ggaagagccc taatgtgtaa aattaatttt agtagtgcta tccccatgtg 29700
attttaatag cttcttagga gaatgacaaa aaaaaaaaaa aaaaaaaaaa a 29751

<210> SEQ ID NO 42
<211> LENGTH: 29751
<212> TYPE: DNA
<213> ORGANISM: Unknown
<220> FEATURE:
<223> OTHER INFORMATION: synthetic

<400> SEQUENCE: 42
atattaggtt tttacctacc caggaaaagc caaccaacct cgatctcttg tagatctgtt 60
ctctaaacga actttaaaat ctgtgtagct gtcgctcggc tgcatgccta gtgcacctac 120
gcagtataaa caataataaa ttttactgtc gttgacaaga aacgagtaac tcgtccctct 180
tctgcagact gcttacggtt tcgtccgtgt tgcagtcgat catcagcata cctaggtttc 240
gtccgggtgt gaccgaaagg taagatggag tcattagtgt taggcgttaa cgaaaaaact 300
cacgttcaat tgtcactacc agtgttacag gttagagacg tactcgttag gggttcggt 360 gattcagtcg aagaggcact atccgaagct agagagcatc ttaaaaacgg tacatgcgga 420
ttagtcgaac tcgaaaaagg cgtactacca caattggagc aaccatacgt ttttattaaa 480
cggtctgacg cacttagtac taatcacggt cataaggtag tcgagttagt cgccgaaatg 540
gacggtattc aatacggtag gtcaggtatt acactcggag tgttagtgcc acacgtaggc 600
gaaacaccta tcgcttatcg taacgttcta ttgcgtaaaa acggtaataa gggcgcaggc 660
ggacattcat acggtatcga tcttaagtca tacgatttag gcgacgaact cggtacggat 720
ccaatcgaag attacgaaca gaattggaat actaaacacg gatctggcgc attacgcgaa 780
cttacacgcg aacttaacgg aggcgcagtg actagatacg tcgataataa tttttgcggt 840
ccagacggat atccactcga ttgtattaag gattttctcg ctagggcagg taagtctatg 900
tgtacactta gcgaacaact cgattatatc gaatctaaaa gaggcgtata ttgttgtcgc 960
gatcacgaac acgaaatcgc ttggtttact gagcgatctg ataagtcata cgaacatcag 1020

```
actccattcg aaattaagtc tgctaaaaaa ttcgatactt ttaaaggcga atgtcctaaa   1080
ttcgtttttc cacttaactc taaggttaag gttattcaac ctagagtcga aaaaaaaaaa   1140
actgagggtt ttatgggtag gattaggtca gtgtatccag tcgctagtcc acaagagtgt   1200
aataatatgc atctatctac acttatgaaa tgtaatcatt gtgacgaagt gtcatggcaa   1260
acatgcgatt tccttaaggc tacatgcgaa cattgcggta ccgaaaatct cgtaatcgag   1320
ggacctacta catgcggata cttacctact aacgcagtcg ttaaaatgcc atgtccagct   1380
tgtcaggatc cagagatagg tccagagcat agcgttgccg attatcataa tcattctaat   1440
atcgaaacta gattgcgtaa aggcggtagg acacgttgtt tcggcggatg cgtattcgca   1500
tacgtaggtt gttataataa gagagcgtat tgggtgccta gagctagtgc cgatatcggt   1560
agcggacata ccggtattac aggcgataac gttgagacac ttaacgagga tctgttagag   1620
attctatcac gcgaacgcgt taatattaac atagtcggcg attttcatct taacgaagag   1680
gtcgctatta tactcgctag tttttccgct agtacatccg cttttatcga tactattaag   1740
tctcttgact ataagtcttt taaaactatc gttgagtcat gcggtaatta taaggttact   1800
aagggtaagc cagtgaaagg cgcatggaat atcggtcagc aacgttcagt gcttacacca   1860
ctatgcggtt ttcctagtca agccgcaggc gtaattagat ctattttcgc acgtacactt   1920
gacgctgcta atcattctat tcccgatctg caacgtgctg ccgttacgat actcgacggt   1980
attagcgaac agtcacttag actcgttgac gctatggtgt atacatccga tctgttaacg   2040
aatagtgtga ttattatggc ttacgttaca ggcggattag tgcaacagac tagtcaatgg   2100
ttgtctaatc tgttaggtac tacagtcgaa aaattgcgac ctattttcga atggattgag   2160
gctaaattgt ctgccggagt cgaattcctt aaagacgctt gggagatact taaatttctg   2220
attaccggcg tattcgatat cgttaagggt cagattcagg tcgctagcga taatattaag   2280
gattgcgtta agtgttttat cgacgtagtg aataaggcac tcgaaatgtg tatcgatcag   2340
gttacaattg ccggagctaa gcttagatca cttaacttag gcgaagtgtt tatcgctcaa   2400
tctaagggat tgtatcgtca atgtatacgc ggtaaggagc aattgcaatt gcttatgcca   2460
cttaaggctc ctaaagaggt tacattcctt gagggcgatt cacacgatac agtgcttact   2520
agcgaagagg ttgtgcttaa aaacggcgaa ctcgaagcac ttgagacacc agtcgattct   2580
tttactaacg gcgcaatcgt aggtacaccc gtatgcgtta acggtcttat gttgcttgag   2640
attaaggata aagagcaata ttgcgcactt agtccaggtc tgttagcgac taataacgtt   2700
tttagactta agggaggcgc acctattaaa ggcgttacat tcggtgagga tacagtttgg   2760
gaagtgcaag ggtataaaaa cgttaggatt acattcgaac tcgacgaacg tgtcgataag   2820
gtacttaacg aaaagtgtag cgtatataca gtcgaatccg gtactgaggt tactgagttc   2880
gcatgcgtag tcgctgaggc agtcgttaag acattgcaac cggttagcga tctgttaact   2940
aatatgggta tcgatcttga cgaatggtca gtcgctactt tttatctatt cgatgacgct   3000
ggcgaagaga atttttcgtc acgtatgtat tgttcttttt accctcctga cgaagaggaa   3060
gaggacgacg ctgaatgcga agaggaagag atagacgaaa catgcgaaca cgaatacggt   3120
acggaagacg attatcaggg attgccactc gaattcggcg ctagcgctga gactgttaga   3180
gtcgaagagg aagaggaaga ggattggtta gacgatacta ctgagcaatc cgaaatcgaa   3240
cccgaacccg aacctacacc tgaggaaccc gttaatcaat ttacagggta tcttaagctt   3300
accgataacg ttgcgattaa atgcgttgat atcgttaaag aggctcaatc cgctaatcct   3360
atggtaatcg ttaacgctgc taatatacat cttaagcatg gcggaggcgt tgcaggcgca   3420
```

```
cttaataagg ctactaacgg cgctatgcaa aaagagtctg acgattatat taagcttaac   3480
ggtccactta ccgtaggcgg atcatgtcta ttgtcaggtc ataatctcgc taaaaaatgt   3540
cttcacgtag tcggacctaa tcttaacgct ggcgaagaca tacaattgct taaagccgca   3600
tacgagaatt ttaattcgca agacatattg ctcgcaccac tgttatccgc aggtattttc   3660
ggagctaaac cattgcaatc attgcaggta tgcgttcaga cagtgcgtac acaggtatat   3720
atcgcagtta acgataaggc actatacgaa caggtcgtta tggattatct cgataatctt   3780
aagcctagag tcgaagctcc taaacaggaa gagccaccta atactgagga ttctaagact   3840
gaggaaaaat ccgttgtgca aaaaccagtc gacgttaagc ctaaaattaa ggcatgtatt   3900
gacgaagtga ctactacact tgaggagact aagtttctta ctaataagtt actgttattc   3960
gctgatatta acggtaagtt gtatcacgat tcacagaata tgcttagagg cgaagatatg   4020
tcttttctcg aaaaagacgc tccatatatg gtaggcgacg ttattacatc tggcgatatt   4080
acatgcgtag tgatacctag taaaaaagcc ggaggtacta ccgaaatgct atcacgtgca   4140
cttaaaaaag tgccagtcga cgaatacatt actacttatc ccggtcaggg atgcgcaggt   4200
tatacactcg aagaggctaa aaccgcactt aaaaaatgta aatccgcttt ttacgttctg   4260
ccatctgagg cacctaacgc taaagaggag atactcggta cagtgtcatg gaatttacgc   4320
gaaatgcttg cgcatgccga agagacacgt aagcttatgc ctatttgtat ggacgttagg   4380
gctattatgg ctactattca acgtaagtat aagggtatta agattcaaga gggtatagtc   4440
gattacggag tgagattttt tttttataca tctaaagagc cagtcgctag tattattact   4500
aagcttaact cacttaacga accattagtg actatgccta tcggatacgt tacacacggt   4560
tttaatctcg aagaggccgc tagatgtatg cgatcactta aggcaccagc cgtagtgtca   4620
gtgtcatcac ctgacgccgt tactacttat aacggatacc ttacatctag ttctaagact   4680
agtgaggaac atttcgttga gacagtgtca cttgccggtt catatcgcga ttggtcttat   4740
tcaggtcaac gtactgagtt aggcgttgag tttcttaaac gcggagataa gatagtgtat   4800
catacacttg agtcaccagt cgagtttcac ttagacggcg aagtgcttag tctcgataag   4860
cttaagtctc tattgtcact tagagaggtt aagactatta aagtgtttac tacagtcgat   4920
aatactaatc tgcatacaca gttagtcgat atgtctatga catacggtca gcaattcgga   4980
cctacttatc ttgacggtgc agacgttact aagattaagc ctcacgttaa tcacgaaggt   5040
aagacttttt tcgtattgcc atctgacgat acacttagat ccgaagcatt cgaatactat   5100
catacacttg acgaatcttt tctcggtagg tatatgtcag cacttaacca tacaaaaaaa   5160
tggaaattcc cacaggtagg cggacttaca tctattaaat gggccgataa taattgttat   5220
ctgtcatcag tgttactcgc attgcagcaa ctcgaagtga aatttaacgc tcctgcattg   5280
caagaggcat actatagggc tagagccggt gacgctgcta atttttgcgc acttatactc   5340
gcatactcta ataaaaccgt aggcgaactc ggtgacgtta gagagactat gacacatcta   5400
ttgcaacacg ctaatctcga atccgctaaa agagtgctta acgtagtgtg taaacattgc   5460
ggtcagaaaa ctactacact taccggagtc gaagccgtta tgtatatggg tacactatca   5520
tacgataatc ttaaaaccgg agtgtcaatt ccatgcgtat gcggtaggga cgctacacaa   5580
tacttagtgc aacaagagtc tagtttcgtt atgatgtcag ctccacctgc cgaatacaaa   5640
ttgcaacagg gtacattctt atgcgctaac gagtataccg gtaattatca atgcggtcat   5700
tatacacata ttaccgctaa agagacattg tatcgtatag acggtgcaca tcttactaaa   5760
```

```
atgtctgagt ataagggtcc agttactgac gttttttaca aagagactag ttatactact   5820
actattaaac cggttagtta taagttagac ggagtgactt ataccgaaat cgaacctaag   5880
ttagacggat actataaaaa agataacgct tattataccg aacagccaat cgatttagtg   5940
cctacacaac cattgcctaa cgctagtttc gataatttta agcttacatg ttctaatact   6000
aaattcgcag acgatcttaa tcagatgacc ggttttacta agcctgctag tagagagtta   6060
tccgttactt tttttcccga tcttaacggt gacgtagtcg caatcgatta tcgtcattac   6120
tctgctagtt ttaaaaaagg cgctaagcta ttgcataaac ctatcgtttg gcatattaat   6180
caggctacta ctaagactac ttttaaacct aatacttggt gtcttagatg tctttggtct   6240
actaagccag tcgatacatc taattcattc gaagtgcttg cagtcgagga tacacagggt   6300
atggataatc tcgcatgcga atcgcaacaa cctacatccg aagaggtagt cgagaatcct   6360
acaattcaga aagaggtaat cgaatgcgac gttaagacta ccgaagtggt aggtaacgtt   6420
atacttaaac cgtctgacga aggcgttaag gttacgcaag agttaggcca tgaggatctt   6480
atggccgcat acgttgagaa tacatctatt actattaaaa aacctaacga actatcactc   6540
gcattaggtc ttaagactat cgctacacac ggtatagccg ctattaattc ggttccatgg   6600
tctaagatac tcgcatacgt taagcctttt ctcggtcaag ccgctattac tacatctaat   6660
tgcgctaaac gacttgcgca acgcgttttt aataattata tgccatacgt tttacattg   6720
ctttttcaat tgtgtacttt tactaagtct actaactcac gtatacgcgc tagtctacct   6780
actactatcg ctaaaaattc cgttaaatcc gttgcgaaat tgtgtcttga cgcaggtatt   6840
aattacgtta agtcacctaa attttctaaa ttgtttacaa tcgctatgtg gttactgtta   6900
ttgtctattt gtctcggttc attgatttgc gttaccgctg cattcggagt gttactatct   6960
aatttcggcg cacctagtta ttgtaacgga gtgagagagt tgtatctgaa tagttctaac   7020
gttactacta tggatttttg cgaaggatct tttccatgtt caatttgtct atctggtctc   7080
gattcactcg attcatatcc cgctctcgaa actattcagg ttacgattag ttcttataaa   7140
ctcgatctta ctatactcgg tctagccgct gaatgggtgt tagcgtatat gctttttact   7200
aagtttttt acttactcgg tctatccgct attatgcaag tgtttttcgg atatttcgct   7260
agtcatttta tttctaatag ttggcttatg tggtttatta tttcgattgt gcaaatggca   7320
ccagttagcg ctatggtacg tatgtatatt tttttcgcta gtttttacta tatttggaaa   7380
tcatacgttc atattatgga cggatgtaca tctagtacat gtatgatgtg ttataaacgt   7440
aatcgcgcta ctagagtcga gtgtactact atcgttaacg gtatgaaacg atctttttac   7500
gtttacgcta acggaggtag gggttttgt aagactcata attggaattg tcttaattgc   7560
gatacttttt gtaccggtag tactttttatt tctgacgaag tcgcacgcga tctatcattg   7620
caatttaaac gtccaattaa ccctaccgat caatctagtt atatagtcga tagcgttgcg   7680
gttaaaaacg gcgcattgca tctatatttc gataaagccg gtcagaaaac atacgaacgt   7740
catccactat cacatttcgt taacttagac aatcttaggg ctaataatac taagggtagt   7800
ctgccaatta acgtaatcgt attcgacggt aagtctaaat gcgacgaatc cgctagtaag   7860
tctgctagtg tgtattactc tcagcttatg tgtcaaccta tactgttact cgatcaggca   7920
ttagtgtcag acgtaggcga tagtactgag gttagcgtta aaatgttcga cgcttacgtc   7980
gatactttta gcgctacatt ctcagtgcct atggagaaac ttaaggcatt agtcgctacc   8040
gctcattctg agttagcgaa aggcgttgcg ttagacggag tgctatctac attcgtatct   8100
gccgctagac agggcgtagt cgatactgac gtcgatacta aagacgtaat cgaatgtctt   8160
```

```
aagctatcac atcattccga tcttgaggtt acaggcgatt catgtaataa ttttatgctt   8220
acatataata aggtcgagaa tatgacacct agagacttag gcgcatgtat cgattgtaac   8280
gctagacata ttaacgctca ggttgcgaaa tcacataacg tatcattgat ttggaacgtt   8340
aaagactata tgtcactatc tgagcaattg cgtaaacaga tacgatccgc tgctaaaaaa   8400
aataatatac cgtttagact tacatgcgct actactagac aggtcgttaa cgttattact   8460
actaagatta gtcttaaggg aggtaagatc gttagtacat gttttaagct tatgcttaag   8520
gctacactgt tatgcgtact cgctgcactc gtatgttata tcgttatgcc agtgcataca   8580
ctatctattc acgacggata tactaacgaa attatcggat ataaggctat tcaagacgga   8640
gtgacacgcg atattattag tactgacgat tgtttcgcta ataaacacgc tggattcgac   8700
gcttggtttt cgcaacgcgg agggtcatat aaaaacgata agtcatgtcc agtcgttgcc   8760
gctattatta cacgcgaaat cggattcata gtgccagggt tacccggtac agtgttgcgt   8820
gctattaacg gcgatttttt gcattttctg ccacgcgttt ttagcgcagt cggtaatatt   8880
tgttatacac ctagtaagtt aatcgaatac tctgatttcg ctactagcgc atgcgtactt   8940
gccgctgagt gtactatttt taaagacgct atgggtaagc cagtgccata ttgttacgat   9000
actaatctgt tagagggatc tatttcatac tctgagttgc gacctgatac taggtacgta   9060
cttatggacg gatctattat tcaattccct aatacttatc ttgagggatc cgttagagtc   9120
gttactacat tcgacgctga gtattgtaga cacggtacat gcgaacgatc tgaggtcggt   9180
atttgtctat ctacatctgg tagatgggta cttaataacg aacattatcg cgcactatct   9240
ggcgtttttt gcggcgtaga cgctatgaat cttatcgcta atatttttac accattagtg   9300
caaccagtcg gcgcacttga cgtatccgct agcgtagtcg caggcggtat tatcgctata   9360
ctcgttacat gcgctgcata ctattttatg aaatttcgta gggtattcgg tgagtataat   9420
cacgtagtcg ctgctaacgc tctattattc cttatgtctt ttacgatact gtgtctcgta   9480
cctgcatact cttttctgcc aggcgtatac tctgtgtttt atctgtatct tacattttac   9540
tttactaacg acgtttcgtt tctcgcacat ctgcaatggt tcgctatgtt ttcacctata   9600
gtgccatttt ggattaccgc tatttacgtt ttttgtattt cgcttaagca ttgtcattgg   9660
ttttttaata attatttgcg taaacgcgtt atgtttaacg gagtgacttt ttcgacattc   9720
gaagaggccg cactttgtac ttttctgctt aataaagaga tgtatcttaa gttacggtct   9780
gagacactgt taccacttac acaatacaat aggtatctcg cactatataa taagtataag   9840
tatttttcag gcgcactcga tactacatct tatcgcgaag ccgcatgttg tcatctcgct   9900
aaagcgctta acgatttttc taactctggc gcagacgtac tgtatcaacc tccacaaaca   9960
tctattacgt ctgccgtact gcaatccggt tttcgtaaaa tggcttttcc atcaggtaag  10020
gtcgagggat gtatggtgca agttacatgc ggtactacta cacttaacgg tctatggtta  10080
gacgatacgg tttattgtcc tagacacgtt atttgtactg ccgaagatat gcttaaccct  10140
aattacgaag acttactgat acgtaaatct aatcactctt ttttagtgca agccggtaac  10200
gttcaattgc gcgttatcgg tcattctatg caaaattgtc tgttacgtct taaagtcgat  10260
acatctaatc ctaaaactcc taagtataaa ttcgttagga ttcaacccgg tcagacattc  10320
tcagtactcg catgttataa cggttcacct agcggagtgt atcaatgcgc tatgcgacct  10380
aatcatacaa ttaagggatc ttttcttaac ggttcatgcg gatcagtcgg ttttaatatc  10440
gattacgatt gcgttagttt ttgttatatg catcatatgg agttacctac aggcgtacac  10500
```

```
gctggtactg atcttgaggg taagttttac ggtccattcg ttgatcgtca aaccgctcaa  10560
gccgcaggta ccgatactac tattacactt aacgtactcg catggttata cgctgccgtt  10620
attaacggcg atagatggtt tcttaataga tttactacta cacttaacga ttttaactta  10680
gtcgctatga aatataatta cgaaccactt acacaggatc acgtcgatat actcggtcca  10740
cttagtgcgc aaaccggtat agccgtactc gatatgtgcg ctgcacttaa agagttactg  10800
caaaacggta tgaacggtag gactatactc ggtagtacta tactcgaaga cgaatttaca  10860
ccattcgacg tcgttagaca gtgttcaggc gttacatttc agggtaagtt taaaaaaatc  10920
gttaagggta cacatcattg gatgttgctt acattcctta ctagtctatt gatactcgta  10980
caatctacac aatggtcatt gtttttttc gtatacgaaa acgctttttt gccttttaca  11040
ctcggtatta tggctatagc cgcatgcgct atgttgttag tgaaacataa acacgcattc  11100
ttatgtctat tcctattgcc tagtctcgct acagtcgcat actttaatat ggtgtatatg  11160
cctgctagtt gggttatgcg tattatgact tggcttgagt tagccgatac atctctatct  11220
ggttatagac ttaaggattg cgttatgtac gctagtgcat tagtgttact gatacttatg  11280
actgcacgta cagtttacga cgacgctgct agacgcgttt ggacacttat gaacgttatt  11340
acacttgtgt ataaagtgta ttacggtaac gctctcgatc aggctattag tatgtgggca  11400
ttagtgatat ccgttacgtc taattactct ggagtcgtta cgactattat gtttctcgct  11460
agggctatcg tattcgtatg cgttgagtat tatccactat tgtttattac cggtaataca  11520
ttgcaatgta ttatgttagt gtattgtttt ttagggtatt gttgttgttg ttatttcgga  11580
ttgttttgtc tacttaatag gtattttaga cttacattag gcgtatacga ttatctcgtt  11640
agtacgcaag agtttagata tatgaattca cagggactgt taccacctaa atcttcaatc  11700
gacgctttta agcttaacat taagttactc ggtataggcg gtaagccttg tattaaggtt  11760
gcgacagtgc aatctaaaat gtctgacgtt aagtgtacta gtgtcgtact gttatcagtg  11820
ttacagcaat tgcgagtcga atctagttct aaattgtggg ctcaatgcgt tcaattgcat  11880
aacgatatct tactcgctaa ggatactact gaggcattcg aaaaaatggt tagtctgtta  11940
agcgtactgt tatctatgca aggcgcagtc gatattaatc gattatgcga agagatgtta  12000
gacaataggg ctacattgca ggctattgcg tcagagtttt ctagtctgcc atcatacgct  12060
gcatacgcta ccgctcaaga ggcatacgaa caggcagtcg ctaacggcga ttctgaggta  12120
gtgcttaaaa aacttaaaaa atcacttaac gttgcgaaat ctgagttcga tagagacgct  12180
gctatgcaac gtaaactcga aaaaatggcc gatcaggcta tgacacaaat gtataaacag  12240
gctagatctg aggataagcg tgctaaggtt acatccgcta tgcaaactat gttgtttact  12300
atgttgcgta aactcgataa cgacgcactt aacaatatta ttaataacgc tagagacgga  12360
tgcgtaccac ttaatattat accgcttact actgccgcta agcttatggt agtcgttccc  12420
gattacggta cttataagaa tacatgcgac ggtaatactt ttacatacgc tagtgcattg  12480
tgggagattc aacaggtcgt tgacgctgat tctaaaatcg ttcaattgtc tgagattaat  12540
atggataact cacctaatct cgcatggcca ttaatcgtta cagcgttacg cgctaactct  12600
gccgttaagt tacagaataa cgaattgtca ccagtcgcat tgcgtcaaat gtcatgcgct  12660
gccggtacta cacaaaccgc ttgtactgac gataacgctc tcgcatacta taataactct  12720
aaaggcggta gattcgtact cgcactatta tccgatcatc aggatcttaa atgggctaga  12780
ttccctaagt ctgacggtac aggtacaatt tataccgaac tcgaaccacc atgtagattc  12840
gttaccgata cacctaaggg acctaaggtt aagtatctat actttattaa gggactgaat  12900
```

aatctgaata ggggtatggt gttagggtca ctcgcagcta ccgttagatt gcaagccggt 12960
aacgctactg aggttcccgc taactcaacc gtacttagtt tttgcgcatt cgcagtcgat 13020
ccagctaagg cttataagga ttacttagct agcggaggtc aacctattac taattgcgtt 13080
aaaatgctat gtacacatac cggtacaggt caggctatta cggttacacc tgaggctaat 13140
atggatcagg agtcattcgg aggcgcatca tgttgtctat attgtagatg tcatatcgat 13200
catcctaatc ctaagggttt ttgcgatctt aagggtaagt acgttcagat tcctactaca 13260
tgcgctaacg atccagtcgg ttttacattg cgtaataccg tttgtacagt atgcggtatg 13320
tggaaaggtt acggatgttc atgcgatcag ttacgcgaac cacttatgca atccgctgac 13380
gctagtacat tccttaatgg gtttgcggtg taagtgccgc tagattgact ccatgcggta 13440
caggtactag tactgacgta gtgtatcgcg cattcgatat ttataacgaa aaggttgccg 13500
gattcgctaa attccttaag actaattgtt gtagatttca ggaaaaagac gaagagggta 13560
atctgttaga ctcatatttc gtagtgaaac gtcatactat gtctaattat caacacgaag 13620
agactattta taatctcgtt aaggattgtc cagccgttgc ggtacacgat tttttaaat 13680
ttagagtcga cggtgatatg gtgccacata tttctagaca gagattgact aagtatacta 13740
tggccgatct agtttacgct cttagacatt tcgacgaagg taattgcgat acacttaaag 13800
agatactcgt tacatataat tgttgcgacg acgattactt taataaaaaa gattggtacg 13860
atttcgttga gaatcccgat atacttaggg tttacgctaa cttaggcgaa cgcgttagac 13920
agtcattgct taagacagtg caattttgcg acgctatgcg tgacgcaggt atagtcggcg 13980
tacttacact cgataatcag gatcttaacg gtaattggta cgatttcggc gatttcgttc 14040
aggtcgcacc aggttgcgga gtgcctatag tcgattcata ctattcattg cttatgccta 14100
tacttacact tacacgtgca cttgccgctg agtcacatat ggacgctgat ctcgctaaac 14160
cattgattaa atgggatcta cttaaatacg attttactga ggaacgattg tgtctattcg 14220
ataggtattt taagtattgg gatcagactt atcatcctaa ttgtattaat tgtcttgacg 14280
atagatgtat actgcattgc gctaatttta acgtattgtt ctcaaccgta ttcccaccta 14340
catcattcgg tccactcgta cgtaagattt tcgttgacgg cgtaccattc gtagtgtcaa 14400
ccggttatca ttttagagag ttaggcgtag tgcataatca ggacgttaat ctgcattcta 14460
gtagactatc ttttaaagag ttgttagtgt acgctgccga tccagctatg catgccgcta 14520
gcggtaatct gttactcgat aagcgtacta catgttttag cgttgccgca cttactaata 14580
acgttgcgtt tcagactgtt aaacccggta attttaataa ggatttttac gatttcgcag 14640
tgagtaaggg ttttttttaaa gagggatcta gcgttgagct taagcatttt tttttcgctc 14700
aagacggtaa cgctgctatt agcgattacg attactatag atataatctg ccaactatgt 14760
gcgatatacg tcaattgttg ttcgtcgttg aggtagtcga taagtatttc gattgttacg 14820
acggaggttg tattaacgct aatcaggtaa tcgttaataa tctcgataag tctgccggat 14880
tcccattcaa taaatggggt aaggctagat tgtattacga ttctatgtca tacgaggatc 14940
aggacgctct attcgcatat actaagcgta acgttatacc gacaattacg caaatgaatc 15000
ttaaatacgc tattagcgct aaaaatcgtg cacgtacagt cgcaggcgta tcaatttgta 15060
gtactatgac taatcgtcaa tttcaccaaa aattgcttaa gtctattgcc gctactagag 15120
gcgctacagt cgttatcggt acatctaaat tttacggagg ttggcataat atgcttaaga 15180
cagtgtattc tgacgttgag actccacatc ttatgggttg ggattaccct aaatgcgata 15240

-continued

```
gggctatgcc taatatgttg cgtattatgg ctagtctcgt actcgcacgt aaacataata  15300
catgttgtaa tctatcacat agattctata gactcgctaa cgaatgcgct caagtgctta  15360
gcgaaatggt tatgtgtggc ggatcacttt acgttaagcc tggcggtaca tctagcggag  15420
acgctactac cgcttacgct aattccgttt ttaatatttg tcaagccgtt accgctaacg  15480
ttaacgctct attgtctact gacggtaata agattgccga taaatacgta cgtaatctgc  15540
aacatagatt gtacgaatgt ctgtatcgta atcgcgatgt cgatcacgaa ttcgttgacg  15600
aattttacgc ttacttacgt aaacattttt ctatgatgat tctatctgac gacgcagtcg  15660
tttgttataa ctctaattac gctgcacagg ggttagtcgc tagtattaag aattttaaag  15720
ccgtactgta ttatcagaat aacgttttta tgtctgaggc taagtgttgg accgaaaccg  15780
atctgactaa gggtccacac gaattttgtt cacagcatac tatgctcgtt aaacagggtg  15840
acgattacgt ttatctacca tatcccgatc cgtcacgtat attaggcgca ggttgtttcg  15900
ttgacgatat cgttaagact gacggtacac ttatgattga gagattcgtt agtctcgcaa  15960
tcgacgctta tccattgact aagcatccta atcaggaata cgctgacgtt tttcacttat  16020
acttacagta tatacgtaaa ttgcacgacg aacttacagg gcatatgctt gatatgtatt  16080
cggttatgct tactaacgat aatactagta ggtattggga acctgagttt tacgaagcta  16140
tgtatacacc acataccgta ctgcaagccg taggcgcatg cgtactatgt aattcacaga  16200
ctagtcttag atgtggcgca tgtatacgta gaccattctt atgttgtaag tgttgttacg  16260
atcacgttat tagtacatca cataagttag tgttatccgt taacccatac gtttgtaacg  16320
ctccaggttg cgacgttact gacgttacgc aattgtactt aggcggtatg tcatactatt  16380
gtaaatcaca taaacctcct attagttttc cgttatgcgc taacggtcag gtattcggtc  16440
tatataagaa tacatgcgta gggtctgata acgttaccga ttttaacgct atcgctacat  16500
gcgattggac taacgctggc gattatatac tcgctaatac atgtactgag cgacttaagt  16560
tattcgcagc cgaaacactt aaggctaccg aagagacttt taaattgtca tacggtatcg  16620
ctaccgtacg cgaagtgctt agcgatagag agttgcatct atcatgggag gtcggtaagc  16680
ctagaccacc acttaatcgt aattacgttt ttacagggta tcgggttact aagaattcga  16740
aagtgcaaat tggcgaatat acattcgaaa aaggcgatta cggtgacgcc gtagtgtata  16800
gaggtactac tacttataag cttaacgtag gcgattattt cgtacttaca tcacataccg  16860
ttatgccatt atccgctcct acattagtgc cacaagagca ttacgttagg attaccggat  16920
tgtatcctac acttaatatt tctgacgaat tttcatctaa cgttgcgaat tatcagaaag  16980
tgggtatgca aaaatactct acattgcagg gacctcccgg taccggtaag tctcatttcg  17040
caatcggact cgcattgtat tatcctagtg ctaggattgt gtataccgct tgttcacacg  17100
ctgcagtcga cgctctatgc gaaaaagctc ttaagtatct accaatcgat aagtgttcac  17160
gtattatacc cgctagggct agagtcgaat gtttcgataa gtttaaagtg aattcgacac  17220
tcgaacaata cgtttttgt acggttaacg ctctaccaga gactactgcc gatatcgtag  17280
tgttcgacga aatttctatg gctactaatt acgatctatc agtcgttaac gctagactta  17340
gggctaagca ttacgtttat ataggcgatc cagcgcaatt gcctgcacca cgtacattgt  17400
tgactaaggg tacactcgaa cctgagtatt ttaattcagt gtgtagactt atgaaaacta  17460
tcggacctga tatgtttctc ggtacatgtc gtagatgtcc tgccgaaata gtcgatacag  17520
ttagcgcact cgtatacgat aataagctta aggcacataa ggataagtct gcgcaatgtt  17580
ttaaaatgtt ttacaaaggc gtaattacac acgacgttag ttccgctatt aatagaccac  17640
```

```
agataggcgt agtgagagag tttcttacac gtaatcccgc ttggcgtaaa gccgttttta  17700
ttagtccata taactctcaa aacgcagtcg ctagtaagat actcggattg cctacacaga  17760
cagtcgattc tagtcagggt agcgaatacg attacgttat ttttacgcaa actaccgaaa  17820
ccgctcattc atgtaacgtt aatagattta acgttgcgat tactagggct aaaatcggta  17880
ttctatgtat tatgtctgat cgcgatctat acgataagtt gcaatttaca tcacttgaga  17940
tacctagacg taacgttgcg acattgcaag ccgaaaacgt taccggattg tttaaggatt  18000
gttctaagat tattaccgga ttgcatccta cacaggcacc tacacatcta tcagtcgata  18060
ttaagtttaa gactgagggt ctatgcgttg acatacccgg tatacctaag gatatgactt  18120
atcgtagatt gattagtatg atgggtttta aaatgaatta tcaggttaac ggttatccta  18180
atatgtttat tacacgcgaa gaggctatta gacacgttag ggcttggata gggttcgacg  18240
ttgagggatg tcacgctaca cgtgacgcag tcggtactaa tctgccattg caattagggt  18300
tttcgacagg cgttaatctg gttgccgtac ctaccggata cgtcgatact gagaataata  18360
ctgagtttac tagggttaac gctaaacctc cacctggcga tcaatttaaa catctgattc  18420
cacttatgta taagggattg ccttggaacg tagtgcgtat taagattgtg caaatgctta  18480
gcgatacact taagggattg tctgataggg ttgtgttcgt actttgggct cacggattcg  18540
aattgacatc tatgaaatat ttcgttaaaa tcggacctga gcgtacatgt tgtctatgcg  18600
ataagcgtgc tacatgtttt agtacatcta gcgatacata cgcttgttgg aatcattcag  18660
tcggattcga ttacgtttat aatcctttta tgattgacgt tcagcaatgg gggtttaccg  18720
gtaatctgca atctaatcac gatcagcatt gtcaggtaca cggtaacgct cacgttgcgt  18780
catgcgacgc tattatgact agatgtcttg ccgtacacga atgtttcgtt aagagagtcg  18840
attggtcagt cgaataccct attataggcg acgaacttag ggttaattcc gcttgtcgta  18900
aagtgcaaca tatggtcgtt aagtctgctc tattagccga taagtttccc gtattgcacg  18960
atatcggtaa tcctaaagcg attaaatgcg taccacaagc cgaagtcgaa tggaaatttt  19020
acgacgctca accatgttct gataaggcat acaaaatcga agagttgttt tactcatacg  19080
ctacacatca cgataagttt actgacggcg tatgtctgtt ttggaattgt aacgttgata  19140
ggtatcccgc taacgctatc gtttgtagat tcgatactag ggttctatct aatctgaatc  19200
tgccaggttg cgatggcgga tcactatacg ttaataaaca cgcttttcat acacctgcat  19260
tcgataaatc cgcttttacg aatcttaagc aattgccttt tttttattac tctgatagtc  19320
catgcgaatc tcacggtaag caagtcgtta gcgatatcga ttacgttcca cttaaatccg  19380
ctacatgtat tacacgttgt aatctcggag gcgcagtttg tagacatcac gctaacgaat  19440
atcgtcaata cttagacgct tataatatga tgattagtgc cggtttttca ttgtggattt  19500
ataagcaatt cgatacttat aatctatgga atacttttac tagattgcaa tctctcgaaa  19560
acgttgcgta taacgtcgtt aataagggtc atttcgacgg tcacgctggc gaagctcccg  19620
tatcaattat taataacgca gtgtatacta aggtcgacgg tattgacgtc gagattttcg  19680
aaaataagac tacattaccc gttaacgttg cattcgaatt gtgggctaaa cgtaatatta  19740
aaccagtgcc agagattaag atacttaata acttaggcgt tgatatcgct gctaataccg  19800
ttatttggga ttataaacgc gaagctcctg cacatgtgtc aactataggc gtatgtacta  19860
tgactgatat cgctaaaaaa cctaccgaat ccgcttgttc atcacttaca gtgttattcg  19920
acggtagggt tgagggtcag gtcgatctgt ttcgtaacgc acgtaacggc gtactgatta  19980
```

-continued

```
ctgagggatc ggttaaggga ttgacaccta gtaagggacc tgctcaagct agcgttaacg  20040
gagtgacact tataggcgaa tcagttaaga ctcaatttaa ttactttaaa aaagtcgacg  20100
gtattattca acagttacca gagacttatt ttacacaatc acgcgatctt gaggatttta  20160
aacctagatc tcaaatggag actgattttc tcgaactcgc tatggacgaa tttattcaac  20220
gatataagct tgagggatac gcattcgaac atatcgttta cggcgatttt tcacacggtc  20280
agttaggcgg attgcatctt atgatcggtc tagctaaacg atcacaggat agtccactta  20340
agcttgagga ttttatacct atggattcaa ccgttaagaa ttactttatt accgatgcgc  20400
aaaccggttc atctaaatgc gtttgtagcg taatcgattt actgttagac gatttcgttg  20460
agattattaa gtctcaggat ctatcagtga ttagtaaggt agtgaaagtg acaatcgatt  20520
acgctgagat ttcttttatg ctttggtgta aagacggtca cgttgagact ttttacccta  20580
aattgcaggc tagtcaggca tggcaacctg gagtcgctat gcctaatttg tataaaatgc  20640
aacgtatgtt actcgaaaaa tgcgatctgc aaaattacgg tgagaacgca gtgataccta  20700
agggtattat gatgaacgtc gctaagtata cacaattgtg tcaataccct aatacactta  20760
cacttgccgt accatataat atgcgagtga tacatttcgg agccggatct gataagggcg  20820
ttgcgccagg tactgccgta ttgcgtcaat ggttgcctac cggtacactg ttagtcgatt  20880
ccgatcttaa cgatttcgta tctgacgctg atagtacact tataggcgat tgcgctacag  20940
tgcataccgc taataaatgg gatctgatta ttagcgatat gtacgatcca cgtactaaac  21000
acgttacgaa agagaacgat tctaaagagg gtttttttac atatctatgc ggttttatta  21060
aacagaaact cgcattaggc ggatctattg ccgttaagat tactgagcat agttggaacg  21120
ctgatctgta taagcttatg ggtcatttta gttggtggac cgcattcgtt actaacgtta  21180
acgctagttc tagcgaagca ttcttaatcg gcgctaatta tctcggtaag cctaaagagc  21240
aaatcgacgg atatactatg cacgctaatt atatttttg gcgtaatact aatcctattc  21300
aattgtctag ttattcattg ttcgatatgt ctaaatttcc acttaagtta cgcggtactg  21360
ccgttatgtc acttaaagag aatcagatta acgatatgat ttactcttta ctcgaaaagg  21420
gtaggttgat tatacgcgaa aataataggg tagtcgttag ttctgacata ctcgttaata  21480
attaaacgaa catgtttatt tttctgttat tccttacact tacatccggt tcagatctcg  21540
atagatgtac tacattcgac gacgttcagg cacctaatta tacacagcat acatctagta  21600
tgagaggcgt atactatcct gacgaaattt ttagatccga tacattgtat cttacacagg  21660
atctattctt acctttttac tctaacgtta cagggtttca tacaattaat catacattcg  21720
gtaatcccgt tataccgttt aaagacggta tttatttcgc agctaccgaa aaatctaacg  21780
tagtgagagg ttgggtattc ggtagtacta tgaataataa gtctcaatca gtgattatta  21840
ttaataattc gactaacgta gtgatacgcg catgtaattt cgaattgtgc gataatcctt  21900
ttttcgcagt gtctaaacct atgggtacac agactcatac tatgattttc gataacgctt  21960
ttaattgtac attcgaatat atttctgacg ctttttcact tgacgtatcc gaaaaatctg  22020
gtaattttaa acacttacgc gaattcgttt ttaaaaataa agacggtttt ttgtacgttt  22080
ataagggata ccaacctatc gacgtcgtta gggatctgcc atcaggtttt aatacactta  22140
agcctatttt taagttaccg ttaggcatta atattactaa ttttagagct atacttaccg  22200
cttttagtcc agctcaggat atttggggta ctagcgctgc cgcatatttc gtcggatatc  22260
ttaaacctac tacttttatg cttaaatacg acgaaaacgg tacaattact gacgcagtcg  22320
attgttcaca gaatccatta gccgaactta agtgttcagt taagtcattc gaaatcgata  22380
```

agggtattta tcagactagt aattttagag tcgtacctag cggtgacgta gtgagattcc 22440
ctaatattac gaatctatgt ccattcggcg aagtgtttaa cgctactaaa ttccctagcg 22500
tatacgcttg ggagcgtaaa aaaattagta attgcgttgc cgattactct gtgttgtata 22560
attcgacttt ttttagtact tttaagtgtt acggagtgtc agctactaag cttaacgatc 22620
tatgtttttc taacgtatac gctgattcat tcgtagtgaa aggcgatgac gttaggcaaa 22680
tcgctcccgg tcagactggc gtaatcgctg attataatta taagttacct gacgatttta 22740
tgggttgcgt actcgcatgg aatacacgta atatcgacgc tactagtacc ggtaattata 22800
attataagta tagatatctt agacacggta agcttagacc attcgaacgc gatatttcta 22860
acgtaccatt ctcacctgac ggtaagcctt gtacacctcc tgcacttaat tgttattggc 22920
cacttaacga ttacggtttt tacactacta ccggtatagg gtatcaacct tatagggtag 22980
tcgttctatc attcgaattg cttaacgctc cagctaccgt atgcggacct aaattgtcaa 23040
ccgatctgat taagaatcaa tgcgttaatt ttaattttaa cggtcttacc ggtacaggcg 23100
tacttacacc tagttctaaa cggtttcaac cttttcagca attcggtagg gacgttagcg 23160
attttaccga tagcgttagg gatcctaaaa ctagtgagat actcgatatt agtccatgcg 23220
cattcggagg cgtaagtgtg attactcccg gtactaacgc tagttctgag gttgccgtac 23280
tgtatcagga cgttaattgt actgacgtat caaccgctat acacgctgat caattgacac 23340
ctgcatggcg tatatactct accggtaata acgtttttca gacacaagcc ggttgtctga 23400
taggcgcaga gcatgtcgat acatcatacg aatgcgatat accgataggc gcaggtattt 23460
gcgctagtta tcatacagtg tcattgctta gatctactag tcagaaatca atcgttgcgt 23520
atactatgtc attaggcgct gatagttcaa tcgcatactc taataatact atcgctatac 23580
ctactaattt ttcaatttcg attactactg aggttatgcc agtgtctatg gctaagacta 23640
gtgtcgattg taatatgtat atttgtggcg attcaaccga atgcgctaat ctgttattgc 23700
aatacggatc tttttgtacg caattgaatc gtgcactatc aggtatagcc gctgaacagg 23760
atcgtaatac tagagaggta ttcgcacagg ttaaacagat gtataagact cctacactta 23820
agtatttcgg agggtttaat ttttcacaga ttttacccga tccacttaaa cctactaaac 23880
gatcttttat tgaggatctg ttattcaata aggttacact cgcagacgca ggttttatga 23940
aacaatacgg cgaatgttta ggcgatatta acgctaggga tctgatttgc gctcaaaaat 24000
ttaacggtct tacagtgtta ccaccactat tgactgacga tatgatagcc gcatatactg 24060
ccgcattagt gtcaggtacc gctaccgcag gttggacatt cggtgccggt gccgcattgc 24120
agattccatt cgctatgcaa atggcttata gatttaacgg tataggcgtt acgcaaaacg 24180
tactttacga gaatcagaaa caaatcgcta accaatttaa taaggctatt agtcagattc 24240
aagagtcact tactactact agtaccgcac tcggtaagtt gcaagacgtc gttaatcaga 24300
acgctcaggc acttaataca ctcgttaagc aattgtctag taatttcgga gctattagtt 24360
cagtgcttaa cgatattcta tctagactcg ataaggtcga agccgaagtg caaatcgata 24420
gattgattac cggtaggttg caatctctgc aaacatacgt tacgcaacaa ttgatacgcg 24480
ctgctgagat tagggctagc gctaatctcg cagctactaa aatgtctgag tgcgtactcg 24540
gtcaatctaa aagagtcgat ttttgcggta aggggtatca tcttatgtct tttccacaag 24600
ccgcaccaca cggagtggtt tttttacacg ttacatacgt acctagtcag gaacgtaatt 24660
ttactaccgc tccagctatt tgtcacgaag gtaaggcata ctttccacgc gaaggcgtat 24720

```
tcgtttttaa cggtacatca tggtttatta cgcaacgtaa ttttttagt ccacaaatta  24780
ttactactga taatacattc gttagcggta attgcgatgt cgttatcggt attattaata  24840
ataccgttta cgatccattg caacctgagt tagactcttt taaagaggaa ctcgataagt  24900
attttaaaaa tcatacatca cctgacgttg acttaggcga tatttcaggt attaacgctt  24960
cagtcgttaa tattcagaaa gagattgata gacttaacga agtcgctaaa aatcttaacg  25020
aatcacttat cgatctgcaa gagttaggta agtacgaaca gtatattaaa tggccttggt  25080
acgtttggtt agggtttata gccggtctaa tcgctatcgt tatggttacg atactgttat  25140
gttgtatgac atcatgttgt tcatgtctta aaggcgcatg ttcatgcgga tcatgttgta  25200
aattcgacga agacgattct gagccagtgc ttaagggagt gaaattgcat tatacataaa  25260
cgaacttatg gatttgttta tgagattttt tactcttaga tcaattactg cacagccagt  25320
aaaaattgac aatgcttctc ctgcaagtac tgttcatgct acagcaacga taccgctaca  25380
agcctcactc cctttcggat ggcttgttat tggcgttgca tttcttgctg tttttcagag  25440
cgctaccaaa ataattgcgc tcaataaaag atggcagcta gccctttata agggcttcca  25500
gttcatttgc aatttactgc tgctatttgt taccatctat tcacatcttt tgcttgtcgc  25560
tgcaggtatg gaggcgcaat tttgtacct ctatgccttg atatattttc tacaatgcat  25620
caacgcatgt agaattatta tgagatgttg gctttgttgg aagtgcaaat ccaagaaccc  25680
attactttat gatgccaact actttgtttg ctggcacaca cataactatg actactgtat  25740
accatataac agtgtcacag atacaattgt cgttactgaa ggtgacggca tttcaacacc  25800
aaaactcaaa gaagactacc aaattggtgg ttattctgag gataggcact caggtgttaa  25860
agactatgtc gttgtacatg gctatttcac cgaagtttac taccagcttg agtctacaca  25920
aattactaca gacactggta ttgaaaatgc tacattcttc atctttaaca agcttgttaa  25980
agacccaccg aatgtgcaaa tacacacaat cgacggctct tcaggagttg ctaatccagc  26040
aatggatcca atttatgatg agccgacgac gactactagc gtgcctttgt aagcacaaga  26100
aagtgagtac gaacttatgt actcattcgt ttcggaagaa acaggtacgt taatagttaa  26160
tagcgtactt ctttttcttg ctttcgtggt attcttgcta gtcacactag ccatccttac  26220
tgcgcttcga ttgtgtgcgt actgctgcaa tattgttaac gtgagtttag taaaaccaac  26280
ggtttacgtc tactcgcgtg ttaaaaatct gaactcttct gaaggagttc ctgatcttct  26340
ggtctaaacg aactaactat tattattatt ctgtttggaa ctttaacatt gcttatcatg  26400
gccgataacg gtacaattac cgttgaggaa cttaaacagt tactcgaaca atggaatctc  26460
gtaatcggtt ttctgtttct cgcatggatt atgctattgc aattcgcata ctctaatcgt  26520
aatcggtttt tgtatattat taaactcgta ttcttatggt tattgtggcc agttacactc  26580
gcatgtttcg tactcgcagc cgtttatcgt attaattggg ttacaggcgg tatcgctatc  26640
gctatggctt gtatagtcgg acttatgtgg ttgtcttatt tcgttgcgtc atttagattg  26700
ttcgcacgta ctagatctat gtggtctttt aatcccgaaa ctaatatact gcttaacgta  26760
ccacttagag gtacaatcgt tactagacca cttatggagt ctgagttagt gataggcgca  26820
gtgattatta gggggcattt gcgtatggcc ggtcatagtc taggtagatg cgatattaag  26880
gatctaccta aagagattac cgttgcgact agtcgtacac tatcttatta taagttaggc  26940
gctagtcaac gtgtcggtac tgatagcgga ttcgcagctt ataataggta tcgtatcggt  27000
aattataagc ttaataccga tcacgctgga tctaacgata atatcgcatt actcgtacag  27060
taagtgacaa cagatgtttc atcttgttga cttccaggtt acaatagcag agatattgat  27120
```

tatcattatg aggactttca ggattgctat ttggaatctt gacgttataa taagttcaat 27180
agtgagacaa ttatttaagc ctctaactaa gaagaattat tcggagttag atgatgaaga 27240
acctatggag ttagattatc cataaaacga acatgaaaat tattctcttc ctgacattga 27300
ttgtatttac atcttgcgag ctatatcact atcaggagtg tgttagaggt acgactgtac 27360
tactaaaaga accttgccca tcaggaacat acgagggcaa ttcaccattt caccctcttg 27420
ctgacaataa atttgcacta acttgcacta gcacacactt tgcttttgct tgtgctgacg 27480
gtactcgaca tacctatcag ctgcgtgcaa gatcagtttc accaaaactt ttcatcagac 27540
aagaggaggt tcaacaagag ctctactcgc cactttttct cattgttgct gctctagtat 27600
ttttaatact ttgcttcacc attaagagaa agacagaatg aatgagctca ctttaattga 27660
cttctatttg tgctttttag cctttctgct attccttgtt ttaataatgc ttattatatt 27720
ttggttttca ctcgaaatcc aggatctaga agaaccttgt accaaagtct aaacgaacat 27780
gaaacttctc attgttttga cttgtatttc tctatgcagt tgcatatgca ctgtagtaca 27840
gcgctgtgca tctaataaac ctcatgtgct tgaagatcct tgtaaggtac aacactaggg 27900
gtaatactta tagcactgct tggctttgtg ctctaggaaa ggttttacct tttcatagat 27960
ggcacactat ggttcaaaca tgcacaccta atgttactat caactgtcaa gatccagctg 28020
gtggtgcgct tatagctagg tgttggtacc ttcatgaagg tcaccaaact gctgcattta 28080
gagacgtact tgttgtttta aataaacgaa caaattaaaa tgtctgataa tggaccccaa 28140
tcaaaccaac gtagtgcccc ccgcattaca tttggtggac ccacagattc aactgacaat 28200
aaccagaatg gaggacgcaa tggggcaagg ccaaaacagc gccgacccca aggtttaccc 28260
aataatactg cgtcttggtt cacagctctc actcagcatg gcaaggagga acttagattc 28320
cctcgaggcc agggcgttcc aatcaacacc aatagtggtc cagatgacca aattggctac 28380
taccgaagag ctacccgacg agttcgtggt ggtgacggca aaatgaaaga gctcagcccc 28440
agatggtact tctattacct aggaactggc ccagaagctt cacttcccta cggcgctaac 28500
aaagaaggca tcgtatgggt tgcaactgag ggagccttga atacacccaa agaccacatt 28560
ggcacccgca atcctaataa caatgctgcc accgtgctac aacttcctca aggaacaaca 28620
ttgccaaaag gcttctacgc agagggaagc agaggcggca gtcaagcctc ttctcgctcc 28680
tcatcacgta gtcgcggtaa ttcaagaaat tcaactcctg gcagcagtag gggaaattct 28740
cctgctcgaa tggctagcgg aggtggtgaa actgccctcg cgctattgct gctagacaga 28800
ttgaaccagc ttgagagcaa agtttctggt aaaggccaac aacaacaagg ccaaactgtc 28860
actaagaaat ctgctgctga ggcatctaaa aagcctcgcc aaaaacgtac tgccacaaaa 28920
cagtacaacg tcactcaagc atttgggaga cgtggtccag aacaaaccca aggaaatttc 28980
ggggaccaag acctaatcag acaaggaact gattacaaac attggccgca aattgcacaa 29040
tttgctccaa gtgcctctgc attctttgga atgtcacgca ttggcatgga agtcacacct 29100
tcgggaacat ggctgactta tcatggagcc attaaattgg atgacaaaga tccacaattc 29160
aaagacaacg tcatactgct gaacaagcac attgacgcat acaaaacatt cccaccaaca 29220
gagcctaaaa aggacaaaaa gaaaaagact gatgaagctc agcctttgcc gcagagacaa 29280
aagaagcagc ccactgtgac tcttcttcct gcggctgaca tggatgattt ctccagacaa 29340
cttcaaaatt ccatgagtgg agcttctgct gattcaactc aggcataaac actcatgatg 29400
accacacaag gcagatgggc tatgtaaacg ttttcgcaat tccgtttacg atacatagtc 29460

-continued

```
tactcttgtg cagaatgaat tctcgtaact aaacagcaca agtaggttta gttaacttta  29520

atctcacata gcaatcttta atcaatgtgt aacattaggg aggacttgaa agagccacca  29580

cattttcatc gaggccacgc ggagtacgat cgagggtaca gtgaataatg ctagggagag  29640

ctgcctatat ggaagagccc taatgtgtaa aattaatttt agtagtgcta tccccatgtg  29700

attttaatag cttcttagga gaatgacaaa aaaaaaaaaa aaaaaaaaaa a           29751
```